United States Patent
Bowen et al.

(10) Patent No.: US 12,188,062 B2
(45) Date of Patent: Jan. 7, 2025

(54) DNA MODIFYING ENZYMES AND ACTIVE FRAGMENTS AND VARIANTS THEREOF AND METHODS OF USE

(71) Applicant: Life Edit Therapeutics, Inc., Durham, NC (US)

(72) Inventors: Tyson D. Bowen, Morrisville, NC (US); Alexandra Briner Crawley, Cary, NC (US); Tedd D. Elich, Durham, NC (US)

(73) Assignee: Life Edit Therapeutics, Inc., Durham, NC (US)

( * ) Notice: Subject to any disclaimer, the term of this patent is extended or adjusted under 35 U.S.C. 154(b) by 0 days.

(21) Appl. No.: 18/627,839

(22) Filed: Apr. 5, 2024

(65) Prior Publication Data

US 2024/0336906 A1 Oct. 10, 2024

Related U.S. Application Data

(60) Division of application No. 17/929,162, filed on Sep. 1, 2022, now Pat. No. 11,981,940, which is a continuation of application No. 17/851,880, filed on Jun. 28, 2022, which is a continuation of application No. PCT/US2021/049853, filed on Sep. 10, 2021.

(60) Provisional application No. 63/146,840, filed on Feb. 8, 2021, provisional application No. 63/077,089, filed on Sep. 11, 2020.

(51) Int. Cl.
*C12N 9/22* (2006.01)
*C12N 15/63* (2006.01)

(52) U.S. Cl.
CPC ............... *C12N 9/22* (2013.01); *C12N 15/63* (2013.01); *C12N 2310/20* (2017.05); *C12N 2800/80* (2013.01)

(58) Field of Classification Search
CPC ...... C12N 9/22; C12N 15/63; C12N 2310/20; C12N 2800/80
See application file for complete search history.

(56) References Cited

FOREIGN PATENT DOCUMENTS

CA 3 125 175 A1 7/2020

OTHER PUBLICATIONS

Database Uniprot, A0A0H3CQ57, "Full-tRNA-specific adenosine deaminase," 2015, 1 page.
Database Uniprot, A0A4R0HT86, "Full=tRNA-specific adenosine deaminase," 2019, 1 page.
Gaudelli, N., et al., "Programmable base editing of A•T to G•C in genomic DNA without DNA cleavage," *Nature*, 2017, vol. 551, pp. 464-471.
Richter, M., et al., "Phage-assisted evolution of an adenine base editor with improved Cas domain compatibility and activity," *Nature BioTechnology*, 2020, vol. 38, pp. 883-891.
Sadowski, M., et anan., "The sequence structure relationship and protein function prediction," *Current Opinion in Structural Biology*, 2009, vol. 19, pp. 357-362.
Seffernick, J., et al., "Melamine Deaminase and Atrazine Chlorohydrolase: 98 Percent Identical but Functionally Different," *Journal of Bacteriology*, 2001, vol. 183(8), pp. 2405-2410.
Singh, R., et al., "Protein Engineering Approaches in the Post-Genomic Era," *Current Protein and Peptide Science*, 2018, vol. 19, pp. 5-15.
Tang, S., et anan., "Identification of *Dehalobacter* reductive dehalogenases that catalyse dichlorination of chloroform, 1,1,1-trichloroethane and 1,1-dichlo9roetehane," *Phil0s Trans R Soc Long B. Biol Sci*, 2013, vol. 368(1616), pp. 1-10.
Wiltkowski, A., et al., "Conversion of a β-Ketoacyl Synthase to a Malonyl Decarboxylase by Replacement of the Active-Site Cysteine wiht Glutamine," *Biochemistry*, 1999, vol. 38, pp. 11643-11650.

*Primary Examiner* — Delia M Ramirez
(74) *Attorney, Agent, or Firm* — Womble Bond Dickinson (US) LLP

(57) ABSTRACT

Compositions and methods comprising novel deaminase polypeptides for targeted editing of nucleic acids are provided. Compositions comprise deaminase polypeptides. Also provided are fusion proteins comprising a DNA-binding polypeptide and a deaminase of the invention. The fusion proteins include RNA-guided nucleases fused to deaminases, optionally in complex with guide RNAs. Compositions also include nucleic acid molecules encoding the deaminases or the fusion proteins. Vectors and host cells comprising the nucleic acid molecules encoding the deaminases or the fusion proteins are also provided.

20 Claims, No Drawings
Specification includes a Sequence Listing.

SEQUENCE LISTING

```
Sequence total quantity: 564
SEQ ID NO: 1          moltype = AA  length = 169
FEATURE               Location/Qualifiers
REGION                1..169
                      note = source = /note="Description of Artificial Sequence:
                      Syntheticpolypeptide"
REGION                1..169
                      note = source = /note="APG09982 protein sequence"
source                1..169
                      mol_type = protein
                      organism = synthetic construct
```

```
SEQUENCE: 1
MSDLELNHEY WMRHALQLAK RARDEGEVPV GAVLVLNNQV IGEGWNRAIG LHDPTAHAEI    60
MALRQGGLVL QNYRLYDTTL YSTFEPCVMC SGAMVHSRIG TLVFGVRNEK TGAAGSLMDV   120
LRHPGMNHQV QIIDGVLAPE CSGLLCRFFR MPRRVFNQQK AESTSSPGD               169

SEQ ID NO: 2           moltype = AA   length = 164
FEATURE                Location/Qualifiers
REGION                 1..164
                       note = source = /note="Description of Artificial Sequence:
                         Syntheticpolypeptide"
REGION                 1..164
                       note = source = /note="APG03724 protein sequence"
source                 1..164
                       mol_type = protein
                       organism = synthetic construct
SEQUENCE: 2
MSNPELTHEH WMRYALTLAK RAREEGEVPV GAVLVLNNQV IGEGWNRAIG LHDPTAHAEI    60
MALRQGGLVL QNYRLYDTTL YSTFEPCVMC AGAMVHSRIG QLVFGVRNAK TGAAGSLMDV   120
LHHPGMNHRI EFTEGVLRDE CAAMLCRFFR QPRRVFNALK TGNA                    164

SEQ ID NO: 3           moltype = AA   length = 169
FEATURE                Location/Qualifiers
REGION                 1..169
                       note = source = /note="Description of Artificial Sequence:
                         Syntheticpolypeptide"
REGION                 1..169
                       note = source = /note="APG09949 protein sequence"
source                 1..169
                       mol_type = protein
                       organism = synthetic construct
SEQUENCE: 3
MSIPELNHDV WMRHALTLAK RAREEGEVPV GAVLVLNGQV IGEGWNRAIG LHDPTAHAEI    60
MALRQGGLVL QNYRLYDTTL YSTFEPCVMC AGAMVHSRIG QLVFGVRNAK TGAAGSLIDV   120
LHHPGMNHRV AITEGVLREE CAAMLCRFFR QPRRVFNALK KPAGDPTAF               169

SEQ ID NO: 4           moltype = AA   length = 172
FEATURE                Location/Qualifiers
REGION                 1..172
                       note = source = /note="Description of Artificial Sequence:
                         Syntheticpolypeptide"
REGION                 1..172
                       note = source = /note="APG08196 protein sequence"
source                 1..172
                       mol_type = protein
                       organism = synthetic construct
SEQUENCE: 4
MSNPELNHEY WMRYALTLAK RARDEGEVPV GAVLVLNDQV IGEGWNRAIG LHDPTAHAEI    60
MALRQGGLVL QNYRLYDTTL YSTFEPCVMC AGAMVHSRIG RLVFGVRNAK TGAAGSLLDV   120
LHHPGMNHHI EMEEGVLRDE CAAMLCRFFR QPRRVFNALK KSPPDSPNLQ AR           172

SEQ ID NO: 5           moltype = AA   length = 169
FEATURE                Location/Qualifiers
REGION                 1..169
                       note = source = /note="Description of Artificial Sequence:
                         Syntheticpolypeptide"
REGION                 1..169
                       note = source = /note="APG06333 protein sequence"
source                 1..169
                       mol_type = protein
                       organism = synthetic construct
SEQUENCE: 5
MSNPELTHDH WMRHALTLAQ RARNEGEVPV GAVLVLNGQV IGEGWNRAIG LHDPTAHAEI    60
MALRQGGLVL QNYRLYDTVL YSTFEPCVMC AGAMVHSRIG QLVFGVRNAK TGAAGSLIDV   120
LHHPGMNHRV EIIEGVLRDE CAAMLCRFFR HPRRVFNALK KNAGTSPTQ               169

SEQ ID NO: 6           moltype = AA   length = 166
FEATURE                Location/Qualifiers
REGION                 1..166
                       note = source = /note="Description of Artificial Sequence:
                         Syntheticpolypeptide"
REGION                 1..166
                       note = source = /note="APG06489 protein sequence"
source                 1..166
                       mol_type = protein
                       organism = synthetic construct
SEQUENCE: 6
MSDTELNHEY WMRHALMLAK RARDEGEVPV GAVLVLKNQV IGEGWNRAIG LHDPTAHAEI    60
MALRQGGLVL QNYRLYDTTL YSTFEPCVMC AGAMVHSRIG NLVFGVRNAK TGAAGSLIDV   120
LHHPGMNHRV EIAEGVLADE CSAMLCRFFR HPRRVFNALK QAAKHD                  166
```

```
SEQ ID NO: 7               moltype = AA   length = 171
FEATURE                    Location/Qualifiers
REGION                     1..171
                           note = source = /note="Description of Artificial Sequence:
                             Syntheticpolypeptide"
REGION                     1..171
                           note = source = /note="APG08449 protein sequence"
source                     1..171
                           mol_type = protein
                           organism = synthetic construct
SEQUENCE: 7
MSDIELNHEY WMRHALMLAK RAREEGEVPV GAVLVLNNQV IGEGWNRAIG LHDPTAHAEI    60
MALRQGGLVL QNYRLYDTTL YSTFEPCVMC AGAMVHSRIG HLVFGVRNAK TGAAGSLIDV   120
LHHPGMNHRI EFTEGVLADE CSGMLCRFFR YPRRVFNTLK QAAKANPPAA Q            171

SEQ ID NO: 8               moltype = AA   length = 173
FEATURE                    Location/Qualifiers
REGION                     1..173
                           note = source = /note="Description of Artificial Sequence:
                             Syntheticpolypeptide"
REGION                     1..173
                           note = source = /note="APG05174 protein sequence"
source                     1..173
                           mol_type = protein
                           organism = synthetic construct
SEQUENCE: 8
MSIPELNHDV WMRHALTLAK RAREEGEVPV GAVLVLNGQV IGEGWNRAIG LHDPTAHAEI    60
MALRQGGLVL QNYRLYDTTL YSTFEPCVMC AGAMVHSRIG QLVFGVRNAK TGAAGSLMDV   120
LHHPGMNHRV EITEGVLRDE CAAMLCRFFR QPRRVFNALK KPAGDPSALQ NNR          173

SEQ ID NO: 9               moltype = AA   length = 168
FEATURE                    Location/Qualifiers
REGION                     1..168
                           note = source = /note="Description of Artificial Sequence:
                             Syntheticpolypeptide"
REGION                     1..168
                           note = source = /note="APG09102 protein sequence"
source                     1..168
                           mol_type = protein
                           organism = synthetic construct
SEQUENCE: 9
MSNPEFTHEY WMRHALTLAR RARDEGEVPV GAVLVLNNQV IGEGWNRAIG LHDPTAHAEI    60
MALRQGGLVL QNYRLYDTTL YSTFEPCVMC SGAMVHSRIG TLVFGVRNEK TGAAGSLMDV   120
LGHPGMNHQV KTIGGVLAPE CSGLLCRFFR MPRRVFNQQK AELKSSGD                168

SEQ ID NO: 10              moltype = AA   length = 167
FEATURE                    Location/Qualifiers
REGION                     1..167
                           note = source = /note="Description of Artificial Sequence:
                             Syntheticpolypeptide"
REGION                     1..167
                           note = source = /note="APG05723 protein sequence"
source                     1..167
                           mol_type = protein
                           organism = synthetic construct
SEQUENCE: 10
MSDAELTHEY WMRHALTLAQ RARDEGEVPV GAVLVLNNQV IGEGWNRAIG LHDPTAHAEI    60
MALRQGGLVQ QNYRLYDTTL YSTFEPCVMC AGAMVHSRIG RLIFGVRNAK TGAAGSLIDV   120
LHHPGMNHRV EVVEGILRDE CAGMLCRFFR QPRRVFNALK KGATDVL                 167

SEQ ID NO: 11              moltype = DNA   length = 507
FEATURE                    Location/Qualifiers
misc_feature               1..507
                           note = source = /note="Description of Artificial Sequence:
                             Syntheticpolynucleotide"
misc_feature               1..507
                           note = source = /note="mammalian codon optimized APG09982"
source                     1..507
                           mol_type = other DNA
                           organism = synthetic construct
SEQUENCE: 11
atgagcgacc tggaactgaa tcacgagtac tggatgagac acgccctgca gctggccaag    60
cgggagagag atgagggcga ggtgcccgtg ggcgctgtgc tggtcctgaa caaccaggtg   120
atcggcgaag ctggaacaga agccattgga ctgcatgacc caacagccca cgccgaaatc   180
atggccctgc ggcagggcgg cctggtgctg caaaattacc ggctgtacga caccacccty   240
tatagccact tcgagccctg cgtgatgtgc tctggtgcta tggtcacag cagaatcgga   300
accctgtgt ttggcgtgcg gaacgagaag accggcgccg ctggcagcct gatggacgtg   360
ctgaggcatc ctggaatgaa ccaccaggtt cagatcatcg acggcgtgct cgcccctgag   420
```

```
tgttctggcc tgctgtgccg gttcttcaga atgcctagaa gagtgttcaa ccagcagaaa    480
gccgaatcca ccagcagccc tggcgac                                        507
```

| SEQ ID NO: 12 | moltype = DNA length = 492 |
|---|---|
| FEATURE | Location/Qualifiers |
| misc_feature | 1..492 |
| | note = source = /note="Description of Artificial Sequence: Syntheticpolynucleotide" |
| misc_feature | 1..492 |
| | note = source = /note="mammalian codon optimized APG03724" |
| source | 1..492 |
| | mol_type = other DNA |
| | organism = synthetic construct |

SEQUENCE: 12
```
atgagcaacc ccgagctgac ccacgagcac tggatgcggt acgccctgac actggccaag    60
cgggccagag aggaaggaga agtgccagtg ggcgccgtgc tggtcctcaa caaccaggtg    120
atcggcgaag gctggaatag agccatcggc ctgcatgatc ctacagccca cgccgaaatc    180
atggccctga cacagggcgg cctggtgctg cagaattaca gactgtatga caccaccctg    240
tactccacct tcgagccttg tgtgatgtgc gccggagcta tggtgcactc tagaatcggc    300
cagctggttt tcggcgtgcg gaacgctaaa accggcgctg ctggcagcct gatggacgtg    360
ctgcataccc ccggcatgaa ccacagaatc gagttcaccg agggagtgct gcgcgacgag    420
tgcgccgcca tgcgtgccg gttcttccgg caacctagaa gggtgtttaa cgccctgaag    480
acaggcaacg cc                                                        492
```

| SEQ ID NO: 13 | moltype = DNA length = 507 |
|---|---|
| FEATURE | Location/Qualifiers |
| misc_feature | 1..507 |
| | note = source = /note="Description of Artificial Sequence: Syntheticpolynucleotide" |
| misc_feature | 1..507 |
| | note = source = /note="mammalian codon optimizedAPG09949" |
| source | 1..507 |
| | mol_type = other DNA |
| | organism = synthetic construct |

SEQUENCE: 13
```
atgagcatcc ccgagctgaa tcacgatgtt tggatgcggc acgccctgac cctggccaaa    60
agagccagag aggaaggcga ggtgcctgtg ggtgccgtgc tggtgctgaa cggccaggtg    120
atcggagaag gctggaatag agccattgga ctgcatgatc ctacagccca cgctgaaatc    180
atggccctga cacagggcgg cctggtcctc cagaactaca gactgtacga caccaccctg    240
tactctacct tcgagccttg cgtgatgtgc gccggcgcca tggtgcactc cagaatcggc    300
cagctggtgt tcggcgtgcg gaacgccaag acaggcgctg ctggcagcct gatcgacgtg    360
ctgcataccc ctggcatgaa ccacaggtg gccatcaccg agggagtgct gcgggaagag    420
tgcgccgcca tgctgtgtag attcttcaga caacctagac gggtcttcaa cgccctgaag    480
aagccagctg gcgaccccac agccttt                                        507
```

| SEQ ID NO: 14 | moltype = DNA length = 516 |
|---|---|
| FEATURE | Location/Qualifiers |
| misc_feature | 1..516 |
| | note = source = /note="Description of Artificial Sequence: Syntheticpolynucleotide" |
| misc_feature | 1..516 |
| | note = source = /note="mammalian codon optimized APG08196" |
| source | 1..516 |
| | mol_type = other DNA |
| | organism = synthetic construct |

SEQUENCE: 14
```
atgagcaacc ccgagctgaa tcacgagtac tggatgcggt acgccctgac actggccaag    60
cgggctcggg acgagggcga agtgcccgtg ggagccgtgc tggtgctgaa cgaccaggtg    120
atcggagaag gatggaatag agccatcggc ctgcatgacc ccaccgccca cgccgagatc    180
atggccctgc gccagggcgg cctggttctc cagaactaca ggctgtacga cacaaccctg    240
tattccacct tcgagccttg tgtgatgtgc gccggcgcca tggtgcacag cagaatcggc    300
agactggtct ttggcgtgcg gaacgccaag accggcgctg ctggcagcct gctggacgtg    360
ctgcataccc tggcatgaa ccaccacatc gagatggaag aaggcgtgct gagagatgag    420
tgcgccgcta tgctgtgccg gttcttcaga caacctagaa gagtgttcaa cgccctgaag    480
aaatctccac ctgatagccc taatctgcag gccaga                              516
```

| SEQ ID NO: 15 | moltype = DNA length = 507 |
|---|---|
| FEATURE | Location/Qualifiers |
| misc_feature | 1..507 |
| | note = source = /note="Description of Artificial Sequence: Syntheticpolynucleotide" |
| misc_feature | 1..507 |
| | note = source = /note=" mammalian codon optimized APG06333" |
| source | 1..507 |
| | mol_type = other DNA |
| | organism = synthetic construct |

SEQUENCE: 15
```
atgagcaacc ctgagctgac acacgaccac tggatgcggc acgctctgac cctggcccag    60
cgcgctagaa acgagggaga agtgcctgtg ggcgccgtgc tggttctgaa cggccaagtg    120
```

```
atcggagagg gctggaatcg ggccatcggc ctgcatgacc ctacagccca cgccgagatt    180
atggccctga gacagggcgg cctggtgctg cagaactaca gactgtacga caccgtgctc    240
tacagcacct tcgagccttg cgtgatgtgc gccggcgcta tggtccactc tagaatcggc    300
cagctggtct ttggcgtgcg gaatgccaag acaggcgccg ccggcagcct gatcgacgtg    360
cttcatcacc ccggaatgaa ccacagagtg gaaatcatcg agggcgtgct gcgggatgaa    420
tgtgccgcta tgctgtgccg gttcttcaga cacccaagaa gggtgttcaa cgccctgaaa    480
aagaacgccg gcaccagccc cacccag                                       507

SEQ ID NO: 16           moltype = DNA   length = 498
FEATURE                 Location/Qualifiers
misc_feature            1..498
                        note = source = /note="Description of Artificial Sequence:
                        Syntheticpolynucleotide"
misc_feature            1..498
                        note = source = /note="mammalian codon optimized APG06489"
source                  1..498
                        mol_type = other DNA
                        organism = synthetic construct
SEQUENCE: 16
atgagcgaca ccgagctgaa ccacgagtac tggatgcggc acgccctgat gctggctaag    60
cgggccagag atgagggcga agtgccccgtg ggcgccgtgc tggtcctgaa gaaccaggtt    120
atcggagaag gctggaatag agccatcggc ctgcatgacc ctacagccca cgccgagatt    180
atggccctga gacaaggcgg cctggtgctg cagaactaca gactgtacga cacaaccctg    240
tattccacct tcgagccttg tgtgatgtgc gccggcgcca tggtgcactc tagaatcggc    300
aatctggtgt tcggcgtgcg gaacgccaag accggcgctg ctggcagcct gatcgacgtg    360
ctccatcacc ctggaatgaa ccacagagtg gaaatcgccg aaggagtgct ggccgacgaa    420
tgcagcgcca tgctgtgccg gttcttcaga cacccaaggc gggtgttttaa cgccctgaaa    480
caggccgcta agcacgac                                                 498

SEQ ID NO: 17           moltype = DNA   length = 513
FEATURE                 Location/Qualifiers
misc_feature            1..513
                        note = source = /note="Description of Artificial Sequence:
                        Syntheticpolynucleotide"
misc_feature            1..513
                        note = source = /note="mammalian codon optimized APG08449"
source                  1..513
                        mol_type = other DNA
                        organism = synthetic construct
SEQUENCE: 17
atgtctgata tcgagctgaa tcacgagtac tggatgcggc acgccctgat gctggccaag    60
cgggccagag aggaaggcga agtgccagtg ggcgccgtgc tggtgctgaa caaccaggtg    120
atcggagaag gctggaatag agccatcggc ctgcatgatc ctaccgccca cgccgagatc    180
atggccctga gacagggcgg actggtgctg cagaactacc ggctgtacga caccaccctg    240
tacagcacat tcgagccttg tgtgatgtgc gccggagcca tggtgcacag cagaatcggc    300
cacctggttt ttggcgtgcg gaacgccaag accggcgctg ctggcagcct gatcgacgtc    360
ctgcatcacc ctggcatgaa ccacagaatt gaattccacag agggcgtgct cgccgacgag    420
tgctccggca tgctgtgccg gttcttcaga tatcctagaa gggtgttcaa cacccctgaag    480
caggccgcta agccaacccc cccgccgct caa                                 513

SEQ ID NO: 18           moltype = DNA   length = 519
FEATURE                 Location/Qualifiers
misc_feature            1..519
                        note = source = /note="Description of Artificial Sequence:
                        Syntheticpolynucleotide"
misc_feature            1..519
                        note = source = /note="mammalian codon optimized APG05174"
source                  1..519
                        mol_type = other DNA
                        organism = synthetic construct
SEQUENCE: 18
atgtctatcc ctgagctgaa ccacgatgtg tggatgcggc acgccctgac actggccaag    60
cgggccagag aagagggaga agtgccagtg ggcgccgtgc tggtgctgaa tggccaggtg    120
atcggcgaag gctggaacag agccatcggc ctgcatgacc ctaccgccca cgccgagatt    180
atggccctgc ggcagggcgg actggtcctg caaaattaca gactgtacga caccacactg    240
tacagcacct ttgagccttg tgtgatgtgc gccggcgcta tggtgcacag cagaatcgga    300
cagctggttt tcggagtgcg gaacgccaaa accggcgccg ctggctccct gatcgacgtg    360
ctgcatcacc ccggcatgaa ccatagagtg aaggcgtcct cagagatgga                420
tgcgctgcta tgctgtgccg gttcttcaga cagcctagac gcgtgttcaa cgccctgaag    480
aagcctgccg gcgaccccag cgccctgcag aacaaccgg                          519

SEQ ID NO: 19           moltype = DNA   length = 504
FEATURE                 Location/Qualifiers
misc_feature            1..504
                        note = source = /note="Description of Artificial Sequence:
                        Syntheticpolynucleotide"
misc_feature            1..504
                        note = source = /note="mammalian codon optimized APG09102"
```

| | | |
|---|---|---|
| source | 1..504<br>mol_type = other DNA<br>organism = synthetic construct | |

SEQUENCE: 19

```
atgagcaacc cgaattcac ccacgagtac tggatgcggc acgccctgac actggctaga   60
agggcccggg acgagggcga ggtgccagtg ggcgccgtgc tggtgctgaa caaccaggtg  120
atcggagaag gctggaatag agccatcggc ctgcatgatc ctacagccca cgccgaaatc  180
atggccctga cagggcgg cctggtgctg cagaactacc ggctgtacga caccacactg  240
tatagcacct tcgagccttg cgtgatgtgt agcggagcta tggtgcacag cagaatcggc  300
accctggttt tcggcgtgcg gaacgagaag accggccgcg ctggctctct gatgacgtg   360
ctcggccacc ccggcatgaa ccaccaggtc aagaccatcg gcggagtgct ggcccctgaa  420
tgtagcggcc tgctgtgccg gttcttcaga atgcctagaa gagtgtttaa tcaacagaaa  480
gccgagctga agtcttccgg agat                                          504
```

| | | |
|---|---|---|
| SEQ ID NO: 20<br>FEATURE<br>misc_feature | moltype = DNA length = 501<br>Location/Qualifiers<br>1..501<br>note = source = /note="Description of Artificial Sequence:<br>Syntheticpolynucleotide" | |
| misc_feature | 1..501<br>note = source = /note="mammalian codon optimized APG05723" | |
| source | 1..501<br>mol_type = other DNA<br>organism = synthetic construct | |

SEQUENCE: 20

```
atgagcgacg ccgagctgac acacgagtac tggatgcggc acgccctgac cctggcccag   60
cgcgccagag atgagggaga agtgcctgtg ggcgccgtgc tggtgctgaa caaccaggtg  120
atcggcgaag gctggaatag agccatcgga ctgcatgacc ccaccgccca cgctgaaatc  180
atggccctga cagggcgg cctggtccag cagaactaca gactgtacga caccaccctg  240
tattccacct tcgagccttg tgtgatgtgc gccggagcta tggtgcacag cagaatcggc  300
agactgattt tcggcgtgcg gaacgccaag acaggcgccg ctggatctct gatcgacgtg  360
ctccatcacc ccggcatgaa ccacagagtt gaggtggtgg aaggcatcct gcgggacgag  420
tgcgccggca tgctgtgccg gttcttcaga caacctaggc gggtctttaa cgccctgaag  480
aaaggcgcta cagatgtgct g                                             501
```

| | | |
|---|---|---|
| SEQ ID NO: 21<br>FEATURE<br>misc_feature | moltype = DNA length = 25<br>Location/Qualifiers<br>1..25<br>note = source = /note="Description of Artificial Sequence:<br>Syntheticoligonucleotide" | |
| misc_feature | 1..25<br>note = source = /note="SGN000930 target sequence" | |
| source | 1..25<br>mol_type = other DNA<br>organism = synthetic construct | |

SEQUENCE: 21

```
gaacaactca aatggaaatg aatat                                          25
```

| | | |
|---|---|---|
| SEQ ID NO: 22<br>FEATURE<br>misc_feature | moltype = DNA length = 20<br>Location/Qualifiers<br>1..20<br>note = source = /note="Description of Artificial Sequence:<br>Syntheticoligonucleotide" | |
| misc_feature | 1..20<br>note = source = /note="SGN000186 target sequence" | |
| source | 1..20<br>mol_type = other DNA<br>organism = synthetic construct | |

SEQUENCE: 22

```
ggacagtgcg catctccctg                                                20
```

| | | |
|---|---|---|
| SEQ ID NO: 23<br>FEATURE<br>misc_feature | moltype = DNA length = 20<br>Location/Qualifiers<br>1..20<br>note = source = /note="Description of Artificial Sequence:<br>Syntheticoligonucleotide" | |
| misc_feature | 1..20<br>note = source = /note="SGN000194 target sequence" | |
| source | 1..20<br>mol_type = other DNA<br>organism = synthetic construct | |

SEQUENCE: 23

```
gccgcacagc attcaggtcg                                                20
```

| | | |
|---|---|---|
| SEQ ID NO: 24<br>FEATURE<br>misc_feature | moltype = DNA length = 20<br>Location/Qualifiers<br>1..20<br>note = source = /note="Description of Artificial Sequence:<br>Syntheticoligonucleotide" | |

```
misc_feature           1..20
                       note = source = /note="SGN000143 target sequence"
source                 1..20
                       mol_type = other DNA
                       organism = synthetic construct
SEQUENCE: 24
catggcagta cattagagca                                                   20

SEQ ID NO: 25          moltype = DNA  length = 20
FEATURE                Location/Qualifiers
misc_feature           1..20
                       note = source = /note="Description of Artificial Sequence:
                       Syntheticoligonucleotide"
misc_feature           1..20
                       note = source = /note="SGN000139 target sequence"
source                 1..20
                       mol_type = other DNA
                       organism = synthetic construct
SEQUENCE: 25
aggttttaat ggcccagcct                                                   20

SEQ ID NO: 26          moltype = RNA  length = 135
FEATURE                Location/Qualifiers
misc_feature           1..135
                       note = source = /note="Description of Artificial Sequence:
                       Syntheticpolynucleotide"
misc_feature           1..135
                       note = source = /note="SGN000930 sgRNA sequence"
source                 1..135
                       mol_type = other RNA
                       organism = synthetic construct
SEQUENCE: 26
gaacaactca aatggaaatg aatatgtcat agttccatga aagccaaaag tggctttgat       60
gtttctatga taagggtttc ggcccgtggc gtcggggatc gcctgcccat tccgatgggc      120
ttctccccat ttatt                                                       135

SEQ ID NO: 27          moltype = RNA  length = 130
FEATURE                Location/Qualifiers
misc_feature           1..130
                       note = source = /note="Description of Artificial Sequence:
                       Syntheticpolynucleotide"
misc_feature           1..130
                       note = source = /note="SGN000186 sgRNA sequence"
source                 1..130
                       mol_type = other RNA
                       organism = synthetic construct
SEQUENCE: 27
ggacagtgcg catctccctg gtcatagttc cattaaagcc aaaagtggct ttgatgtttc       60
tatgataagg gtttcgaccc gtggcgtcgg ggatcgcctg cccattgaaa tgggcttctc      120
cccatttatt                                                             130

SEQ ID NO: 28          moltype = RNA  length = 130
FEATURE                Location/Qualifiers
misc_feature           1..130
                       note = source = /note="Description of Artificial Sequence:
                       Syntheticpolynucleotide"
misc_feature           1..130
                       note = source = /note="SGN000194 sgRNA sequence"
source                 1..130
                       mol_type = other RNA
                       organism = synthetic construct
SEQUENCE: 28
gccgcacagc attcaggtcg gtcatagttc cattaaagcc aaaagtggct ttgatgtttc       60
tatgataagg gtttcgaccc gtggcgtcgg ggatcgcctg cccattgaaa tgggcttctc      120
cccatttatt                                                             130

SEQ ID NO: 29          moltype = RNA  length = 130
FEATURE                Location/Qualifiers
misc_feature           1..130
                       note = source = /note="Description of Artificial Sequence:
                       Syntheticpolynucleotide"
misc_feature           1..130
                       note = source = /note="SGN000143 sgRNA sequence"
source                 1..130
                       mol_type = other RNA
                       organism = synthetic construct
SEQUENCE: 29
catggcagta cattagagca gtcatagttc cattaaagcc aaaagtggct ttgatgtttc       60
tatgataagg gtttcgaccc gtggcgtcgg ggatcgcctg cccattgaaa tgggcttctc      120
```

```
cccatttatt                                                              130

SEQ ID NO: 30            moltype = RNA  length = 130
FEATURE                  Location/Qualifiers
misc_feature             1..130
                         note = source = /note="Description of Artificial Sequence:
                           Syntheticpolynucleotide"
misc_feature             1..130
                         note = source = /note="SGN000139 sgRNA sequence"
source                   1..130
                         mol_type = other RNA
                         organism = synthetic construct
SEQUENCE: 30
aggttttaat ggcccagcct gtcatagttc cattaaagcc aaaagtggct ttgatgtttc    60
tatgataagg gtttcgaccc gtggcgtcgg ggatcgcctg cccattgaaa tgggcttctc   120
cccatttatt                                                          130

SEQ ID NO: 31            moltype = DNA  length = 20
FEATURE                  Location/Qualifiers
misc_feature             1..20
                         note = source = /note="Description of Artificial Sequence:
                           Syntheticoligonucleotide"
misc_feature             1..20
                         note = source = /note="SGN000930 FWD primer"
source                   1..20
                         mol_type = other DNA
                         organism = synthetic construct
SEQUENCE: 31
gacagccaag aggttttgcc                                                    20

SEQ ID NO: 32            moltype = DNA  length = 20
FEATURE                  Location/Qualifiers
misc_feature             1..20
                         note = source = /note="Description of Artificial Sequence:
                           Syntheticoligonucleotide"
misc_feature             1..20
                         note = source = /note="SGN000930 REV primer"
source                   1..20
                         mol_type = other DNA
                         organism = synthetic construct
SEQUENCE: 32
ctgtcccttg cagcttctgt                                                    20

SEQ ID NO: 33            moltype = DNA  length = 20
FEATURE                  Location/Qualifiers
misc_feature             1..20
                         note = source = /note="Description of Artificial Sequence:
                           Syntheticoligonucleotide"
misc_feature             1..20
                         note = source = /note="SGN000186 FWD primer"
source                   1..20
                         mol_type = other DNA
                         organism = synthetic construct
SEQUENCE: 33
tggcccctat gtggagatca                                                    20

SEQ ID NO: 34            moltype = DNA  length = 20
FEATURE                  Location/Qualifiers
misc_feature             1..20
                         note = source = /note="Description of Artificial Sequence:
                           Syntheticoligonucleotide"
misc_feature             1..20
                         note = source = /note="SGN000186 REV primer"
source                   1..20
                         mol_type = other DNA
                         organism = synthetic construct
SEQUENCE: 34
ggcagagctc agcctcatag                                                    20

SEQ ID NO: 35            moltype = DNA  length = 20
FEATURE                  Location/Qualifiers
misc_feature             1..20
                         note = source = /note="Description of Artificial Sequence:
                           Syntheticoligonucleotide"
misc_feature             1..20
                         note = source = /note="SGN000194 FWD primer"
source                   1..20
                         mol_type = other DNA
                         organism = synthetic construct
```

```
SEQUENCE: 35
atgacattca ggccacagtg                                                    20

SEQ ID NO: 36           moltype = DNA  length = 20
FEATURE                 Location/Qualifiers
misc_feature            1..20
                        note = source = /note="Description of Artificial Sequence:
                          Syntheticoligonucleotide"
misc_feature            1..20
                        note = source = /note="SGN000194 REV primer"
source                  1..20
                        mol_type = other DNA
                        organism = synthetic construct
SEQUENCE: 36
cttcctccta ttcaggccca                                                    20

SEQ ID NO: 37           moltype = DNA  length = 19
FEATURE                 Location/Qualifiers
misc_feature            1..19
                        note = source = /note="Description of Artificial Sequence:
                          Syntheticoligonucleotide"
misc_feature            1..19
                        note = source = /note="SGN000143 FWD primer"
source                  1..19
                        mol_type = other DNA
                        organism = synthetic construct
SEQUENCE: 37
acatttgacg agcagcgaa                                                     19

SEQ ID NO: 38           moltype = DNA  length = 22
FEATURE                 Location/Qualifiers
misc_feature            1..22
                        note = source = /note="Description of Artificial Sequence:
                          Syntheticoligonucleotide"
misc_feature            1..22
                        note = source = /note="SGN000143 REV primer"
source                  1..22
                        mol_type = other DNA
                        organism = synthetic construct
SEQUENCE: 38
agggcccctg gagaggtttt aa                                                 22

SEQ ID NO: 39           moltype = DNA  length = 20
FEATURE                 Location/Qualifiers
misc_feature            1..20
                        note = source = /note="Description of Artificial Sequence:
                          Syntheticoligonucleotide"
misc_feature            1..20
                        note = source = /note="SGN000139 FWD primer"
source                  1..20
                        mol_type = other DNA
                        organism = synthetic construct
SEQUENCE: 39
cttgtagctg gaggtccatc                                                    20

SEQ ID NO: 40           moltype = DNA  length = 20
FEATURE                 Location/Qualifiers
misc_feature            1..20
                        note = source = /note="Description of Artificial Sequence:
                          Syntheticoligonucleotide"
misc_feature            1..20
                        note = source = /note="SGN000139 REV primer"
source                  1..20
                        mol_type = other DNA
                        organism = synthetic construct
SEQUENCE: 40
tgttggcaaa tctagtctcg                                                    20

SEQ ID NO: 41           moltype = AA  length = 1071
FEATURE                 Location/Qualifiers
REGION                  1..1071
                        note = source = /note="Bacillus sp. APG07433.1"
source                  1..1071
                        mol_type = protein
                        organism = Bacillus sp.
SEQUENCE: 41
MRELDYRIGL DIGTNSIGWG VIELSWNKDR ERYEKVRIVD QGVRMFDRAE MPKTGASLAE   60
PRRIARSSRR RLNRKSQRKK NIRNLLVQHG VITQEELDSL YPLSKKSMDI WGIRLDGLDR  120
LLNHFEWARL LIHLAQRRGF KSNRKSELKD TETGKVLSSI QLNEKRLSLY RTVGEMWMKD  180
```

```
PDFSKYDRKR NSPNEYVFSV SRAELEKEIV TLFAAQRRFQ SPYASKDLQE TYLQIWTHQL  240
PFASGNAILN KVGYCSLLKG KERRIPKATY TFQYFSALDQ VNRTRLGPDF QPFTKEQREI  300
ILNNMFQRTD YYKKKTIPEV TYYDIRKWLE LDETIQFKGL NYDPNEELKK IEKKPFINLK  360
AFYEINKVVA NYSERTNETF STLDYDGIGY ALTVYKTDKD IRSYLKSSHN LPKRCYDDQL  420
IEELLSLSYT KFGHLSLKAI NHVLSIMQKG NTYKEAVDQL GYDTSGLKKE KRSKFLPPIS  480
DEITNPIVKR ALTQARKVVN AIIRRHGSPH SVHIELAREL SKNHDERTKI VSAQDENYKK  540
NKGAISILSE HGILNPTGYD IVRYKLWKEQ GERCAYSLKE IPADTFFNEL KKERNGAPIL  600
EVDHILPYSQ SFIDSYHNKV LVYSDENRKK GNRIPYTYFL ETNKDWEAFE RYVRSNKFFS  660
KKKREYLLKR AYLPRESELI KERHLNDTRY ASTFLKNFIE QNLQFKEAED NPRKRRVQTV  720
NGVITAHFRK RWGLEKDRQE TYLHHAMDAI IVACTDHHMV TRVTEYYQIK ESNKSVKKPY  780
FPMPWEGFRD ELLSHLASQP IAKKISEELK AGYQSLDYIF VSRMPKRSIT GAAHKQTIMR  840
KGGIDKKGKT IIIERLHLKD IKFDENGDFK MVGKEQDMAT YEAIKQRYLE HGKNSKKAFE  900
TPLYKPSKKG TGNLIKRVKV EGQAKSFVRE VNGGVAQNGD LVRVDLFEKD DKYYMVPIYV  960
PDTVCSELPK KVVASSKGYE QWLTLDNSFT FKFSLYPYDL VRLVKGDEDR FLYFGTLDID 1020
SDRLNFKDVN KPSKKNEYRY SLKTIEDLEK YEVGVLGDLR LVRKETRRNF H          1071

SEQ ID NO: 42          moltype = AA  length = 1071
FEATURE                Location/Qualifiers
REGION                 1..1071
                       note = source = /note="Description of Artificial Sequence:
                        Syntheticpolypeptide"
REGION                 1..1071
                       note = source = /note="nAPG07433.1"
source                 1..1071
                       mol_type = protein
                       organism = synthetic construct
SEQUENCE: 42
MRELDYRIGL AIGTNSIGWG VIELSWNKDR ERYEKVRIVD QGVRMFDRAE MPKTGASLAE   60
PRRIARSSRR RLNRKSQRKK NIRNLLVQHG VITQEELDSL YPLSKKSMDI WGIRLDGLDR  120
LLNHFEWARL LIHLAQRRGF KSNRKSELKD TETGKVLSSI QLNEKRLSLY RTVGEMWMKD  180
PDFSKYDRKR NSPNEYVFSV SRAELEKEIV TLFAAQRRFQ SPYASKDLQE TYLQIWTHQL  240
PFASGNAILN KVGYCSLLKG KERRIPKATY TFQYFSALDQ VNRTRLGPDF QPFTKEQREI  300
ILNNMFQRTD YYKKKTIPEV TYYDIRKWLE LDETIQFKGL NYDPNEELKK IEKKPFINLK  360
AFYEINKVVA NYSERTNETF STLDYDGIGY ALTVYKTDKD IRSYLKSSHN LPKRCYDDQL  420
IEELLSLSYT KFGHLSLKAI NHVLSIMQKG NTYKEAVDQL GYDTSGLKKE KRSKFLPPIS  480
DEITNPIVKR ALTQARKVVN AIIRRHGSPH SVHIELAREL SKNHDERTKI VSAQDENYKK  540
NKGAISILSE HGILNPTGYD IVRYKLWKEQ GERCAYSLKE IPADTFFNEL KKERNGAPIL  600
EVDHILPYSQ SFIDSYHNKV LVYSDENRKK GNRIPYTYFL ETNKDWEAFE RYVRSNKFFS  660
KKKREYLLKR AYLPRESELI KERHLNDTRY ASTFLKNFIE QNLQFKEAED NPRKRRVQTV  720
NGVITAHFRK RWGLEKDRQE TYLHHAMDAI IVACTDHHMV TRVTEYYQIK ESNKSVKKPY  780
FPMPWEGFRD ELLSHLASQP IAKKISEELK AGYQSLDYIF VSRMPKRSIT GAAHKQTIMR  840
KGGIDKKGKT IIIERLHLKD IKFDENGDFK MVGKEQDMAT YEAIKQRYLE HGKNSKKAFE  900
TPLYKPSKKG TGNLIKRVKV EGQAKSFVRE VNGGVAQNGD LVRVDLFEKD DKYYMVPIYV  960
PDTVCSELPK KVVASSKGYE QWLTLDNSFT FKFSLYPYDL VRLVKGDEDR FLYFGTLDID 1020
SDRLNFKDVN KPSKKNEYRY SLKTIEDLEK YEVGVLGDLR LVRKETRRNF H          1071

SEQ ID NO: 43          moltype = AA  length = 7
FEATURE                Location/Qualifiers
REGION                 1..7
                       note = source = /note="Description of Artificial Sequence:
                        Syntheticpeptide"
REGION                 1..7
                       note = source = /note="SV40 NLS"
source                 1..7
                       mol_type = protein
                       organism = synthetic construct
SEQUENCE: 43
PKKKRKV                                                              7

SEQ ID NO: 44          moltype = AA  length = 22
FEATURE                Location/Qualifiers
REGION                 1..22
                       note = source = /note="Description of Artificial Sequence:
                        Syntheticpeptide"
REGION                 1..22
                       note = source = /note="3X Flag tag"
source                 1..22
                       mol_type = protein
                       organism = synthetic construct
SEQUENCE: 44
DYKDHDGDYK DHDIDYKDDD DK                                            22

SEQ ID NO: 45          moltype = AA  length = 16
FEATURE                Location/Qualifiers
REGION                 1..16
                       note = source = /note="Description of Artificial Sequence:
                        Syntheticpeptide"
REGION                 1..16
                       note = source = /note="peptide linker"
```

```
source                  1..16
                        mol_type = protein
                        organism = synthetic construct
SEQUENCE: 45
SGSETPGTSE SATPES                                                           16

SEQ ID NO: 46           moltype = AA   length = 16
FEATURE                 Location/Qualifiers
REGION                  1..16
                        note = source = /note="Description of Artificial Sequence:
                         Syntheticpeptide"
REGION                  1..16
                        note = source = /note="Nucleoplasmin NLS"
source                  1..16
                        mol_type = protein
                        organism = synthetic construct
SEQUENCE: 46
KRPAATKKAG QAKKKK                                                           16

SEQ ID NO: 47           moltype = DNA   length = 723
FEATURE                 Location/Qualifiers
misc_feature            1..723
                        note = source = /note="Description of Artificial Sequence:
                         Syntheticpolynucleotide"
misc_feature            1..723
                        note = source = /note="GFP-stop coding sequence"
source                  1..723
                        mol_type = other DNA
                        organism = synthetic construct
SEQUENCE: 47
atggtgtcta agggcgagga actgttcacc ggcgtggtgc ccatcctggt ggaactggac    60
ggggatgtga acggccacaa gttcagcgtg tccggcgagg gagagggcga cgccacatac   120
ggcaagctga ccctgaaatt catctgcacc acaggaaagc tccccgtgcc ttgacctacc   180
ctggtcacca ccctgactta cggcgtgcaa tgtttcagcc gctaccccga ccacatgaaa   240
cagcacgact ttttcaaaag cgccatgcct gagggctacg tgcaagaggc gaccatcttc   300
ttcaaggacg acggaaatta caagaccaga gccgaggtga agttcgaggg cgacaccctg   360
gtgaatagaa tcgagctgaa gggcatcgac ttcaaggaag atggcaacat cctgggccac   420
aagctggaat acaactacaa cagccacaac gtgtacatca tggccgacaa gcagaagaac   480
ggcatcaagg tgaacttcaa gatcagacac aacatcgagg acggcagcgt gcaactggcc   540
gatcattacc agcagaacac ccctatcggc gatggtcctg tgctgctgcc tgacaaccac   600
tacctgagca cccagagcgc cctgtctaaa gatcctaacg agaagcggga ccacatggtc   660
ctgctggaat tcgtgaccgc cgctggcata acactcggca tggacgagct gtacaagtaa   720
tga                                                                        723

SEQ ID NO: 48           moltype = RNA   length = 141
FEATURE                 Location/Qualifiers
misc_feature            1..141
                        note = source = /note="Description of Artificial Sequence:
                         Syntheticpolynucleotide"
misc_feature            1..141
                        note = source = /note="GFP-stop guide RNA"
source                  1..141
                        mol_type = other RNA
                        organism = synthetic construct
SEQUENCE: 48
ggctccccgt gccttgacct accctggtca tagttccatg aaagccaaaa gtggctttga    60
tgtttctatg ataagggttt cggcccgtgg cgtcggggat cgcctgccca ttccgatggg   120
cttctcccca tttattttt t                                                     141

SEQ ID NO: 49           moltype = AA   length = 9
FEATURE                 Location/Qualifiers
REGION                  1..9
                        note = source = /note="Description of Artificial Sequence:
                         Syntheticpeptide"
REGION                  1..9
                        note = source = /note="meganuclease motif"
source                  1..9
                        mol_type = protein
                        organism = synthetic construct
SEQUENCE: 49
LAGLIDADG                                                                    9

SEQ ID NO: 50           moltype = DNA   length = 318
FEATURE                 Location/Qualifiers
misc_feature            1..318
                        note = source = /note="Homo sapiens Human RNA pol III U6
                         promoter"
```

| source | 1..318 |
| --- | --- |
| | mol_type = genomic DNA |
| | organism = Homo sapiens |

SEQUENCE: 50

```
tgtacaaaaa agcaggcttt aaaggaacca attcagtcga ctggatccgg taccaaggtc   60
gggcaggaag agggcctatt tcccatgatt ccttcatatt tgcatatacg atacaaggct  120
gttagagaga taattagaat taatttgact gtaaacacaa agatattagt acaaaatacg  180
tgacgtagaa agtaataatt tcttgggtag tttgcagttt taaaattatg tttttaaatg  240
gactatcata tgcttaccgt aacttgaaag tatttcgatt tcttggcttt atatatcttg  300
tggaaaggac gaaacacc                                                318
```

| SEQ ID NO: 51 | moltype = DNA length = 32701 |
| --- | --- |
| FEATURE | Location/Qualifiers |
| misc_feature | 1..32701 |
| | note = source = /note="Homo sapiens CFTR gene" |
| source | 1..32701 |
| | mol_type = genomic DNA |
| | organism = Homo sapiens |

SEQUENCE: 51

```
aattggaagc aaatgacatc acagcaggtc agagaaaaag ggttgagcgg caggcaccca   60
gagtagtagg tctttggcat taggagcttg agcccagacg gccctagcag ggaccccagc  120
gcccgagaga ccatgcagag gtcgcctctg gaaaaggcca gcgttgtctc caaacttttt  180
ttcaggtgag aaggtggcca accgagcttc ggaaagacac gtgcccacga aagaggaggg  240
cgtgtgtatg ggtgggttt ggggtaaagg aataagcagt ttttaaaaag atgcgctatc  300
attcattgtt ttgaaagaaa atgtgggtat tgtagaataa aacagaaagc attaagaaga  360
gatggaagaa tgaactgaag ctgattgaat agagagccaa atctacttgc aactgaaaag  420
ttagaatctc aagactcaag tacgctacta tgcacttgtt ttatttcatt tttctaagaa  480
actaaaaata cttgttaata agtacctaag tatggtttat tggttttccc ccttcatgcc  540
ttggacactt gattgtcttc ttggcacata caggtgccat gcctgcatat agtaagtgct  600
cagaaaacat ttcttgactg aattcagcca acaaaaattt tgggtaggt agaaaatata  660
tgcttaaagt atttattgtt atgagactgg atatatctag tatttgtcac aggtaaatga  720
ttcttcaaaa attgaaagca aatttgttga aatatttatt tgaaaaaag ttacttcaca  780
agctataaat tttaaaagcc ataggaatag ataccgaagt tatatccaac tgacatttaa  840
taaattgtat tcatagccta atgtgatgag ccacagaagc ttgcaaactt taatgagatt  900
ttttaaaata gcatctaagt tcggaatctt aggcaaagtg ttgttagatg tagcacttca  960
tatttgaagt gttctttgga tattgcatct actttgttcc tgttattata ctggtgtgaa 1020
tgaatgaata ggtactgctc tctcttggga cattacttga cacataatta cccaatgaat 1080
aagcatactg aggtatcaaa aaagtcaaat atgttataaa tagctcatat atgtgtgtag 1140
gggggaagga atttagcttt cacatctctc ttatgtttag ttctctgcat gtgcagttaa 1200
tcctggaact ccggtgctaa ggagagactg ttggcccttg aaggagagct cctccctgtg 1260
gatgagagag aaggacttta ctctttggaa ttatctttt gtgttgatgt tatccacctt 1320
ttgttactcc acctataaaa tcggcttatc tattgatctg ttttcctagt ccttataaag 1380
tcaaaatgtt aatggcata aattatagac tttttttagc agagaacttt gaggaaccta 1440
aatgccaacc agtctaaaaa tgcagttttc agaagaatga atatttcatg gatagttcta 1500
aatactaatg aactttaaaa tagcttacta ttgatctgtc aaagtgggtt tttatataat 1560
tttctttta caaatcacct gacacattta atataggtta aaaatgcta tcaggctggt 1620
ttgcaaagaa aatgtattac aaaggctgct aagtgtgtta agagcatact catttcgttt 1680
ctccaaaata tttcataagg tgctttaaga ataggtatgt ttttaaaagt taagttccta 1740
ctatttatag gaactgacaa tcacctaaaa taccaatgat tacaaacttc cttctggcct 1800
tctgactgc aattctaaaa gtgtaaaaaa catatttct gcattaagtt aggcagtatt 1860
gctagttttt caaagtggta ggctttggag tcagattatt ttgattcaga tcctacatgt 1920
actgtttagt agctctgttg cctgaggcag gtccttaac atctctgtgt gtgacttgac 1980
cttttaaaatt tggagactgt catagggtt aatcccttga gaaatgaat gtgaaaagtt 2040
agcctaatgt taactgctat tattatggat taccatattt tcacattcat cacagtacat 2100
gcaccttgtt aatataagat gctcaattca tctttgaagt attttgtg actctcaatc 2160
tggatatgca atgagtgggc ctgtatgaga atttaattta tgaaaaattg tgtttcacat 2220
ggccttacca gatatacagg aaacacgtca catgttccta ttgtatgttg taaatgcct 2280
tagaatttaa cttctgaat aggatccctt cagtttgaga gtcataaaag agtaaaatta 2340
ttatggtatg agttatagat tgtattgaat atctctttat atgtctaggt tttgtcattg 2400
gaaaaccaaa aagtttgaa aaaaatcta agttatttct tactttctta attttgtgtg 2460
gatttcacat caagtataaa atttgaagaa catctgaact atcataatcc atatatatat 2520
ataaaataaa cataatctaa gagagaattt caccatgaaa aattcaggta gttcatgact 2580
atcagagcaa acaagtacat taaattgaaa cttttatgaa aataacattt atgaaatagg 2640
aagctatttt taaactagaa gtgatatatt agcatatat ttataattca tacaagtg 2700
ggattgattt ataaatggtc accaacagag attgtgctat ttaatttggg aaaattttt 2760
aaatttacat tttctcacaa cttttaaggt agttattcag tttgttcctc tctgtctctt 2820
ctctcatgcc ctgaatttt catatttcgt ttagttgtaa gagtgtatat caaaccgtgt 2880
gtcacatgac ataacttgaa ttttcgtcgt gatatctgtg ctatgtctag gtctatactg 2940
aggaactgtg ggaacccac agaatccaag tatacagag cactgatttc ttacaaggga 3000
tgtgggggtct cctgtaaact ctgcagttag tctcaagtaa gaccaaagag taaaatattg 3060
ttaggatcta aggtggaaat tcagcaaaga atcacatagt ctaagtctcg agtttaacag 3120
taagataatt tgagatactt ttgtaattat taaacacaaa gtaatgagag attttaaaac 3180
aaacaaatac acctgaattt atatatcaga ataggtatgg tggttcaaaa tagctatcta 3240
ataaaaacca cactcctatt ctaaacattt gcctttgatc aaaataattt tgggtctctt 3300
attatgaaat tgcctttcta aataatacat aaatttcttc tcataagtat atattagcca 3360
cattatttta ttgttattgt tttatattca tagcttgctt tagattaaaa attatattac 3420
ccagactggt ctcttggact tgcttccaag tgactttga ctgtatcaca aaatcaaatt 3480
cactctgaaa atataaagat ttttcatcat aatttccttt gttaacagcc aagtgctacc 3540
taattttagg tgttttcatt aaaaaaaaat gcattgcaaa ctttaaagac aattctttg 3600
```

```
tttgtttgtt tttaaaagac agagtctcac tctgttgccc aggctagagt gcagtgacac 3660
aatcataact cactgcaacc tccacctcct gggctcaagt gagccttcca tcttgcctca 3720
cgagtagctg ggtcttcagg tgtacaggtg tgtaccacca tgcctggcta acttttttt  3780
tttttaagtt atatagagac agtatctcac tatgttgccc aggctgctct tggagctcct 3840
ggcctcaagt tatcctccca ctcagtctcc caaagtgctg ggattacagg cgtaagccac 3900
ctcaccctgt cagcctaaag acagtgctta atgaagagaa atataagtgc tttgagcaat 3960
ggaagtataa ttaaaattat actatgaaag atttataaag atgaccattt tgaatgggac 4020
cacacttatt tggttatata aattatgata cactattaaa aattcatcat gatgattttg 4080
tatttacatt ttatttacat gtttgcaatt tgtgaggaaa gctaaaatta tggctaagcc 4140
ataaatattt ttgcagtttg ttgagggtgt ttgtaaaagt gttgccaagg aagaccagtt 4200
ggctacccaa acaagggttt agtctaggtc tgatcaatac atacacatta tctcaggttt 4260
gtctatcaga aaaaccttag gttatccaaa tcaaataaaa atagatgcat aaaacaaagg 4320
ccaatatgtg ttgaacaatt atattgtgat atacaactgc caagcattcc cgattaccat 4380
gactccattt agtcagtcca tgggcaaatg ccatcaatga ggacagccca gggtttccat 4440
attctctctt ggctttacat cctataggaa ttggaggggc ccacctctgg gataggagcc 4500
cttctgtctt gaacaatgtt gtctgaacac taacaaatgt tgactttcta caccagtccc 4560
tcaatagtct tttctattta tccttttgct gaccatgttt tgttattaca cagttgagat 4620
ttttcagctg ggaatctgtg ttaattttgt attaattttg attagcttaa ctctcagagt 4680
tctaaaagta cctcctgtac ctgatatatg acaaaaatta taattacatt tatttatata 4740
taaaatatct ttgtatatgt aaaatatctt tgtatatata attatataat tgtttctttt 4800
aattttgcaa atttttaaaaa gttctccttt gttttgaagt ttattcctat agtttttat  4860
atgctagtta aattattaat cacttgattc aagtaatatt cttatatact tataaggaat 4920
agtgtagttt taatatttaa ttccttgcta aagagagaag tggaatctat ttttcttagc 4980
tacttcatca atatttatg tttgatgtga cagtcaaaat atccctcaga gctaactgtt 5040
acactaggga aatcacggtt ttccagtttt ccatttatgt gttatgggag ggagtggaac 5100
ttagtgtaat aatattcaat acataaatgt taacacttgt ttaaaggtcc ttgagtgagt 5160
actgctataa aatgcattat tattgctagt gtcatttcac aagagcctat aatttcagtg 5220
tgatagagct acaatataag tatagtattg caaaaccatc aggaagggtg ttaactattt 5280
agcatgcagt tatgtgttgg ttgtcaaaac gttaaaaaca tctctgactc agcagcaatt 5340
ttggcaattt tgatcctgag gcatctgtgt agggcatctt cctggagaaa aacctctgag 5400
atgcaatgag gtcaaagggg gaaaacagac tatgataaag atcaagttgt ttggagatct 5460
tgtagaaaga ttaatttaca aatatgtcaa gtgcattatc atggaggaaa acattgctat 5520
ttctgttggt tctcttcaga gctctagaat caatttacca catagttgtt tcagtgtgaa 5580
attagcatta cagagtggct ttacggcttt actgtatgggc agtgtgtcag caaagagctt 5640
aggcttcttt tagcaagaag cttgtaaaaa tttaatttac tcttagattg cttgatgtag 5700
agaattacat tcctacagag ctctgaaaaa tcttttttca gagttttca cagctgtatt 5760
caagttgcaa ggcttgtcaa ctttgctatt tttctgtgca gctctgttaa cttattatta 5820
tcttttgaca taaattatga ttccaaattg taaagctctg gatgtcaggg cctttctaa  5880
tttgtttagt atgatattca gaccatttca agactcttcc gtggaacaat ttaataaaga 5940
tttttttgtg atgttaatga gttcatggtg atcaaccta gagacctgtg tctattgtag 6000
atcgatgaca ttcaacagtc ctgcagtgct ggcatcattt tgataaaaag gggtcaaagc 6060
aagtgggact gtgggcagat ttttaatgct tagaacaatt attccatcga agtttctgg  6120
tgtccctttct gccttagcct ttgtaggata gcatgcttgc taatttcttg ctcatgggt  6180
aaggaaatga agattttgc taggtccgta ggattattag gactactcag gcctgaagct 6240
atgcctggat atagccagaa aactctccca tagcttgctc caaggagctg agatacagca 6300
gtacttcctt tgtaggtcat gattctgggt aacctgaag atgacctcat tcatattctg 6360
tattctatgt gagacgttaa gaaggtagag gtggccaaga aggaaattgt tgctgccttt 6420
atggaacaaa ttatctgaaa cccagctttc tcgagggctt cattgaagta ctcaactggg 6480
gcacttaacc cagtctaagg ctggtcaagg aaggcttgct gggggaagtg tctttttgtat 6540
tcacacctaa aggaggttat tcaattgaaa ttatccaaag agggtaggga tgggctagga 6600
aaaatttaaa caggtagtgt ggaggactga caggataagt aagcatggca ccttcaaaat 6660
atcctgagaa gttccctatg acgggaacat aaaaatatgtg acagagattt gtgggagatg 6720
ggtctggaaa ctctagcagg ggccagatcg taagggggcc ttgtaggctt tgtaggcttt 6780
gtttgggctt tatcatactg gaagtgaaaaa gccatggctt ttaaacagga gagggacata 6840
atcagttcat atactgttgc agttttgtaa aagaaaagat gagctgaaag agtggccatg 6900
gtggaggtgg gtgggtgggg ggggagggg cggggagaga gagagagaga gagagattg  6960
aaaagacattt aggaggtaaa atcaactggt ttggtaatca attagtagtt gaaggtgaag 7020
gaaagagaag agttaaggat aacatctata tttgttgatt tggataatag aggggacagt 7080
ggtgctgctt attgaatgag aaaatttaat cggagaagaa ggctggagc aggagtgcag 7140
acctatgtga ctctacttct ctcaaaacca gaaacgaaa tgatgtatat ggctcaggt  7200
taggtaaatat ggttatttga aaatgtatta aagtgattta gagcttagtc ttaggtaaga 7260
gatataagat gtctgaggtg acagttttat aaatatgtag agtgcccact tgttggcct  7320
tattgtggca tagtgtgacc tgagagtgtt aggaagaagc agctgagttc tagggacagt 7380
actgtttaaa ttctacttag aaattatact ctataaaccc ctataacctc ggcctcaggt 7440
tgtctgaacc tcctgataac ttcactcctt taggcagtgc ttttcacatc acgggacaca 7500
acatatgaga gatcatagaa attcaatgtg gtatgaaaat ctgcttggga cttcagatat 7560
tgtctccagt gattgaataa aaataggagc tcacctacta tgatgaggtt tctgtgtgtg 7620
ttaaaagaag gttttcatta cttttgaaaa ggttatgtat ccttgttttta tgttaaaact 7680
ttgagctttg ttaaatgc agagttctct ttcttagcgt ggactacaga ggtgcaacta 7740
cctcctacct gacttcacat ctactcccaa atgcctagtg aaggcttaat aatttcaaaa 7800
agggactcta gaatttcatt tgataccagt cagacaaatgt tgtgaaaatt aagcataata 7860
ggcagaatcc caggggtact gacagctgta ttaagaggta attcaagggc taaaccttag 7920
agtccagcat tggttatggg tgtgacaaga aaatgaagcc tatgttggct gggattagca 7980
accacagttc tagaggaagc aaggtggaga aactatatag ggggctccct ttgtacgttt 8040
tatttatttt aaacatctct ataaactcta gaaattaaaa caacaatacc aacacaaaag 8100
catcacttttt tcgaccaaag accattgcta tactttttg tgtaaagggc tagatagtaa 8160
atattttcag ctttgtggc cacataagtc tctgcaatag acaatatgca aacaaataag 8220
catggctgtg tttcaattaa actttattat gaacattaaa atttgaattt catataactt 8280
ttacatgttg caaaatattc tttatttaaa ttctattgca atatgcttta aagagatacag 8340
```

```
tttttagtct ttcttagttt aaaataaaat ctagaaaaaa ttttaagtct tctataactt    8400
tttttcggta actgaataat tttaaaagta agtgaaacat ttagacatgc aaaatggact    8460
tttcagaaga agaaaatggt agcttaacag ttattagatt attgtccaga ataattttg     8520
acttataagt ctctgttgac catttcattg cctcttttt tggaatatgc atctttaat     8580
gtgtccttca aggcaaaggc tctatcttat ctatcttgtg tcttgcattt tcccagggca    8640
atgttttca caatttttt aaaaaacaat actgtaatca attttcaaat aaaattttcc     8700
atgggaccgc agtgtataca aatagcagtg acaataaaag ataataactc tcccataaat    8760
acaaagaaac agttaaccta gtgctctaaa gtaaaggcta cagtgatttt gtataacatt    8820
tatatgtaat tttcttgatc ctacatggtt gtgttttca cagtgttatg tttctgaaat    8880
cgagatgcct tttataattg atgtcaaaag aaacttgtca gccacaaggc ccaggaataa    8940
gttgtaatat gggaacttag caatacataa aggtatatat actcctgtga cctcagctga    9000
attatttgca ttggttgcat cccacaaggt tgactcttaa ataaatttag tttgttgctt    9060
gaaatttctt gggataaatt actttgtgat gtagtttga aaaaaaaaca ggtaatattt     9120
agtctgaagt ttgtctgaca tactaagcaa tgtaattaaa gtagaagtcg cctaagctca    9180
gcactttatt atgccttgaa attatactgc ctgtcctaca ggtgaaggtg ttatgaatgc    9240
agtttgtcac tgtaactcta ttcatagctc tgaaaggctg agagtgactc agaagaatat    9300
ttttgctctg aatatgaaga acgcttagac taaaacttgt ta attcgatgc tgaagaagaa    9360
agtggtaggt gattgcatga ataagtatgt aatattgtta atttctaaaa actgtgtata    9420
gttaatgtag tgcttctttt tggaaaggct attgttaaat tgatggtaaa ttctataacc    9480
aatatcacct taaagcaagt acgcatgata aagtattata aaaccatgat aatatcatat    9540
gtggcttatt attgttccct gagtgttgta caactctgtt atgctgtgat gaaacctcat    9600
gcaaacaggt atgtcaaaga tatgatgggc tgttaactga gcttggccca catatggtgt    9660
agtgacatgc tcactaatgc agtgcagaga taaccaataa cagatcataa caggtttaaa    9720
tatgtgcaag gagatgtcag cagaagcttt cctacatagt gaatactaaa caagcctgac    9780
agcccaggat catgttcgga tcaatctagt gtgctaaaat taacatatag tcctacattt    9840
gagaatgtgt gattttcttg gttcctgtct ataaaataat attttaaaat acatacattt    9900
caaatcagaa gttggtgaat tcactgaaat atttctagag aacactaggt attggggctc    9960
atagtgtgaa aaccactgac ttaattcttc ccccatcttg gttgttcctg atcttccctt   10020
gtgtccccat tccagccatt tgtatcctta gaaaatgatc tcatattcta cttcatcttt   10080
atcttcattg tcaactgtca ggtagcaata tatgatggaa gaagcatgta ctttggaatc   10140
agacagacct ggctgaaatc ctaactctgt cacttattaa caatgtgatc ttaggcaatt   10200
tacttaatct ctctgaacct cagctactct cgtcagtaca atgagttatc cttatcttta   10260
catggcacag tattattatg atatcaaaaa ttcattgagt atttactctg catattagtc   10320
aaggttctcc agagaagtag aaccaatgat acacacacac acacacacac acacacacac   10380
acacacacac acaatttatt ataaggaatt gacttacatg attatgatgg ctaacaagtc   10440
caaaatctgc agtatgggtc agctggcagg aaacccagga gagtcaatgt tccagtttga   10500
gtctgaaggc agtctgttgg ggaatttcgt ccttctctgg gaggccagcc tttttgttct   10560
atacaggcct tcaaccgatt ggatgaagtt caccttattat agtgagggca atctgcttta   10620
accaaagttt actgatttaa atgttaatct catccaaaaa cacccaccca gttgacacat   10680
aaaattaacc atcactctct gtaagcactt tctatgcatt aagtgatagc aaataatgcc   10740
agacataggc cgtcttaat aaatggtaag cactgttatc agcaacaaca ggattattat   10800
aattagcacc tttcatcttt tctgtctggg ctctgagaaa gtacctctct tctctaaatt   10860
tatccctcct ttcctatgaa ttagacccag tgcttctct gaattatgaa ggtcacactc   10920
ctacaaatgc cccttcccaa ttgcacatct gtcggctttc tttgccattg actttatct    10980
ctagctttta aatttacagg catatgtcag ttaacaatgg gaatgcgttc tgggtaatat   11040
gtccttaggc aattttatcg ttgtgagaat actatagagt ataactacac aagcctagat   11100
gtcgtatagc ctactacaca cctaggacat atgacatgt cttttgcttc taggctacaa   11160
acctgtacgg cttgttacta tactgaatac tgcaggcagt tgtgacacag tggtatttgc   11220
atatcggaac atgtctaaac acagaaaagg tgcactaaaa atactatgta gtgatctcat   11280
gggaccacca ttgtatatgc agtctgctgt agactgaaat gtcatgcagt gcataactgt   11340
atcttaaata ctcaaagtat caccttttgtt tgtttgtccc cttgtgtgca tcatcctaac   11400
gtggaattttc tctgttgatt agggccagcg tattagtttg ctagggctac cataacaaaa   11460
taccacaat ttggtggctt aaataacagg aatttattat cttatggttt tgaagactag   11520
aagtacaaga tcaaggtgtt ggcaggtttt tcttctaagg gccatgagga agagtctatt   11580
ccatgccttt cccctacctt ctggtggttt gctagaaatc cttggcattc cttgacttac   11640
agaggcatca ccctgatctc tgttttcatc ttcacatggc attctccctg tgagcctgtc   11700
tctgtgtcca aacttcttta ctattaata aaggacacca gtcatattgg attagggtct   11760
actttagtga cctcattgga atgttattac ctctgtaaag atcctatctc taaataaggt   11820
cacatcccta ggtaccgggg gttaggactc aaacatacct tttttggggg aaacacaatt   11880
caacctataa caattgataa cactctttag gagcagaatg cgatatggaa gtaatttgag   11940
accataaagt atatacatgt agggagttaa tctatgaaac ctattgaaag ccatatatac   12000
ctcatgtata gtggtccata aatagcatgg agacattgca gaggatgtta agtgatatga   12060
tacaggaaca atccaagaag gtcataagaa aaaggaccct ttgctcttga gaggactgaa   12120
gaatgacttt ccatttatga aattttggta catgtccact aaaaatagga tgaaggccaa   12180
acttaggaag aatatttga taatggaaa ggttgcatat aaaaacattt tattgaggac    12240
aattaaataa tgttggctgg aagttttagg atgatcatct ttaggactca gaaaagaga    12300
agaaacatta ttaagaatt gtccctgaac aagtataggc accctcacat ttgcattgca    12360
tttactatag aattgaaaaa tgttttgacc tttttttttt ggcttttaat atatttgacc    12420
aagagtaaca gctaagcaat acctatttgc aatcagtgtc atcatgtgg ctccaaacat    12480
atcatgtttg tgtaattaat tgattgaccc attaatttgt tcaatttctg ctctgttcca   12540
ggcactgaac aacatgatgg agataaaaga taaatattac acctgccttg tcctcaagaa   12600
gttagtcttc tgagggaaag aaattagcaa acaaattgta atctcagtta tgtgccatgt   12660
tccatgctgg gcacaggga tacagtagtt taaaaaaaac acaagatcta taaggtgttt   12720
cttcttgtgg aaccttcagt ctagggtgct tggaaacatg ggcgttggc agacaagtaa   12780
atacacattt tgtggtaaag gctcaggtag aagaagtaca ggatagaata gagcacacca   12840
tggggaatta atctagactt cagagaggct cacacataca taattttatgt gtgactattt   12900
caatgcattt gaggttttctt ggaaatagag ttaggttttt attttaagga agttaccatt   12960
tttttttca gtgtgatgtg gttgaaccaa agaatgccat gcccagtgat ggtaatagga   13020
taatcttttt aaaaattaag agccacctaa taaatcaata gtttcattca gcgggagctc   13080
```

```
ctgcagagtt caaaaagaag agaatctggc acagcgtttc ctttaaagtt cattttccta   13140
gagtgtgaat ggaagcaaga gattataaca ttttgaggtc aaaaaaattc tgaaatgcct   13200
ataaaaatta ttttctccaa attatcatca tttgtgcttt taatgacctg attgcaaaga   13260
tgaacatttt gaattcttaa attgcttatt aggattggtt aatgaatcaa ttatctatta   13320
ctgtatgttt tgctattgga aaaaatagca acttaagtgt tttgcagacc tttacttagg   13380
tatatgttgc ttttatgaaa aaaagatgt aaatattaag taaaagggat ttaaagcaag   13440
gcttttgagg tagagtctta ttaattcctt ggtaaacctt gagccaattg ttgtctatgt   13500
tctctgcctc tgtcttgctc cttccttctg ggattcactg tgggaatgcg ggattgttaa   13560
tctggggatg ctgtccaatc ctgcctctct caagctttgc tattgatctc cctcccagtg   13620
ataataaagc ttgaagaaaa tgaaagtagc gttagtattg gtcctcaaac tcaagaacag   13680
gatgaaactt aaatcttgag tcatacaatt gtgtctacat actgctcccc aaaaagagaa   13740
gtaaagaaga tgctaacttt ccctttaat ttgcagtact tagcaatttg ttttcttgag   13800
ggttaagtaa taacagtgga agaaaaaagg gttaaaatgc caccaagaac ccaattccat   13860
gtttagtttg aaagtgggaa atcagctgcc actgggaagt ctgaatccaa tgccatgatg   13920
ttctttgaat ccttctgaga aataatcatg tgtagccata acatacctgt ataacagagc   13980
agaaacata aacaaatgaa ggtgaaggga agattaagac agaagagaaa aattccagaa   14040
tcgactgatc atttttatct gtttagatga tttcaggcag aatcctagag accaactta   14100
tcacaactga attttaaaaa tcaccagctt tgtcattgtg atgcagcatc agtttcagta   14160
ttatccttgg agtattaatt cttaatcatc ttcatcttag aacatttttg aggtcacttc   14220
tagtctctat ttcaccagtg aagaaacaaa aatcccaaa ctatatcagg tggaattaca   14280
cagtatttt tttttaattt tggggaaagt cgattcaagg cagtaacttg caagctagtg   14340
ttagaaagga tttaataaat agtggttttt ctgtacacat agtgagaggt cattacatca   14400
tttggttgtt gaaagtcata aggatgtcta gcatgcgctt tgcctgtagt ggttcatgcc   14460
aggcagattc ctgactccta taacccagag cttatcagag catttatgtc cccaaagaga   14520
aatgtcacct ccatctttca ataaacactt tagcaaagaa aaatcaagta cttaattcc   14580
aaatcttgag ttaattccag aataacaatg atggctcgga aaatatggct ttttctgtc   14640
aaaggacaga gaaacctagt agagagtatt tactttgggt cctagtgatg gtatctgaac   14700
aagctaggtg aacaaagagc ctcaataagg gattttgagg tctagaaaaa gagaggaaat   14760
accaaataaa tggaataatt ataaaataaa taccagcaaa gttaaatcaa tatatcatgt   14820
gggagatatc cttatatcac tcatgtgatt tctattttgt tcctatatta ggcaaggag   14880
aggtggaact tgttttcctt tttccctctc agctacgaat ggacatactt aaaactgttt   14940
ctctgcttct gttctctaaa atgtgattgt ctaacagtaa ccgtgatgac gttttgacag   15000
ttgcacaagt ttctttcttt aagctttaaa aatgccagcc agtaacccag tggcatttct   15060
actataaat cttaaggcca atccatttcc cctttcctt attttcttgg tttcaaatat   15120
attttattg ccaatggaaa taaaaatcct aaattagaga gcaatggcat cccttgtctt   15180
gtgaataaag agctcctaaa tgtgaactta tacaggatgc agcaatttat agggtagtta   15240
atcattcttc tttctagcca gttgttccag ctacagtttt gtggctcttg ttagtggctt   15300
cattcccaga tagaataaaa atcaaaccaa aatcctggaa aggcactctg aggatgcttc   15360
tctaaagtag atgggcatca actataaatc acaatgcttt gtttcctctg ttatgtttca   15420
agatgggtgg gatttttttt gtagcattac ttattattgc ctctcaagtg cttgagtctt   15480
tgaaatccaa gtcatgtgag tgaattagat acagctgtta gaagtggcct ttcaatgcca   15540
atggtacaca ttccttggtt tctttacgat actattgctc ttacaacttt tatctgaagt   15600
cataaattca tagttgtccc agaagttaag ttccttgctt ctagaggaca gaaaacaaac   15660
aatttacaca actcatggtg catgtcacca gtccttagat ctcatgaaat atgcatgaaa   15720
tcttaaatca cttgctgtag ccacccagcc attgacatat ttgaaagact ttagtgtatc   15780
aaagtcacta taatgaaaat tttgatttca ccagttctag gagtgaaaaa tcaaatgttt   15840
agtaaaactt tctaaaatta acactgacag ttgatttctg tatactgttg ttcttaataa   15900
tagcttatt gagatataat tcatattcaa aacaacttac ccatttaaag catacaatcc   15960
aatgattttt tagtatcttc aaagagttgc ctatcaccat aaccaatttt agaacacttt   16020
catcactgta aaaagaaact ccattcctat tagcagtcat tccttattcc aaatcccct   16080
gctcgcccta gacaactaca aatgtacttt ccatctctat agatttgcct gttctggaaa   16140
ttttatgtaa atagaacaaa gtgttctttt gtgactggct tatttcactt agcatttttt   16200
ttcaaagatt catccctgtt gtagcgtgta tcagtgcatc attctttttt attttttag   16260
agacagggcc ttgctctgtt gcccaggttg gaatgtgcag tggcatgatc atgggtcact   16320
atagctttga agtcataggc gaaagcggtc ctcccacctc agtctcccga gtagctgaga   16380
ctacaggctt gcaccacatg actgtctaat ttataatttt ctttagagac agggtcttgt   16440
tatgttgtct aggctgctct caaactccag ggctcaagtg gtcctcctcc cacagcatcc   16500
taaagtgctg ggattatagg tgtgagccac agcacctggc ttgcatcatt ctttttattg   16560
ttgaataata tcccacttgt aagaatatgt attttattta tccttttccc agttaataga   16620
tatttcgatt gttcctaatt cttgtctatt ataaataatg gtgctatgaa catttgtgta   16680
caagtttttg tgcagacatc cattttcctt tcttttgggc atataacctac gagtgtaatg   16740
gatgggccat atagtaactt tatgtttaat attttgagga ttttttcaaac tgttttccaa   16800
agtggctgca tcattttaaa ttccttccac cattgtgtga gtgtttcaat ttctccacat   16860
atttgcaaca cttactatta tctactctta aaaattacag ccatcctact gggcatgaag   16920
tggtatttca ttgtgagttt ttttttttctt tttcttttttt tctttttttg ctaatgtttg   16980
tggatttttct tttcatttttc ttgatggtgt cctttgaagc acaaaagtat ttaatttga   17040
taatttccaa tttatttttt gttattgctg tttgtgcttc tggtgttgta tcaagtgta   17100
tgctacttta aaaaattagt tgtaatatgg caaattggat agctgtag gctttggtgt   17160
cacaatccta attttaaaat tctgactctg cccttgacaa attaactaat taagcttcct   17220
tagcctcagt ttctcaactg taagttggag atattaccaa gacctacctc ttgaattgtt   17280
gtggggatca gatgaaataa tgtatgtgaa atatttagaa ttatgcaagt ctgtggtaat   17340
gaatactaat gttagctatc attattgtta taatcccaat aataaattct ggtgctttga   17400
aaattaaacc aaagccaagc agttgatatg aagaagcatg taataatgta cagacataat   17460
tataaga caacattgaa tttggctctc atgaacatca ggaatagtgg tcatgtagt   17520
tattatctcc agcaggaact gtagctgaga gatcttcaga gctttttcca aggcgatatc   17580
actgggaaat aatagagaca aggttacaag ctagggctgt gttttcttct taaaatcttt   17640
agttcagttt ttttcaataa cagatttgta gtaggcatca ggtgactggg gattcgtatt   17700
cttcaagttg aaatattacc ttgttgagaa agaaccatg tgtgagacaa ccatgttgag   17760
aaagaaaaag tgattttata gaaaattaat attgatagtg agcattatat gaaaatcatg   17820
```

```
aagttagaac atatttggcc agaaaattta cattaatagt tacccatagc aattaatgca  17880
ttataattac acatacettt tctttaatga aaaagaattc tttccttcca aagttatgca  17940
tgctattgtt aaacattaga gaatatagag aagcaaaaaa gaaaatatct tttttgatat  18000
tttcttaaca tacgtctgtt cctaataatg tttatagttt agaagcattg catgaaatgg  18060
gtagatcaat tttctattta atgtttggat tcattagtca cgaagttagc aaattaattt  18120
ccattagggt gcctgtatgg ttgtaaatcc tggacctgca gaagattttt cagtattggt  18180
ttgtagtctt ttgtttagca gcaaataatt agttctccag agcttctgaa attaattgac  18240
cactttaatg gtgtttacct acctagagaa agaaaaagaa cttctccaag tcccttggta  18300
aaattaagcc tcatgaacaa ttaactcaaa tatacacaag gcttgtcttt agcgagcata  18360
tactccctaa agttgattaa gctgaccaag tgattactgc ttataaattc accattttat  18420
ggagaagaag caaacactgc taaatacctt gtggaatcag aggagggaa attagtaact   18480
tgaccccaat actgcgattt taaattgaat tcttgaagcc tacaagtttt acacaggact  18540
ttagagagct ggatagtatc actttgtcaa gtcctacttt tactatgatt ctttgagaaa  18600
aatacatctg actaaataac tctgaatcta aattggataa aataaatgtg acattcaaaa  18660
tgttatttat gattttagaa aaatatcctt atagacacta gatgagtttt agtctcaaat  18720
caatcctccc tatcatagtc acttatcaaa ataactaaag caaagtggta gagctgtgct  18780
ctagaagttt gggatttatg atcacaatct tttccaatga gtcccctctt tcctctgcct  18840
gtcttcaaca tttgttttt ttttttttg gttaggacta tccagattgt gtggcctatt   18900
tcaaactcat ggcaaataca ttggatgatc agaaatttc taatgtattt gaatttgtct   18960
acacaaacta gagtaattgc tattaattcc tcaagtgtta attatttcat gcaaaaagga  19020
aaaaggctat tagtctttaa gtgtattagt atgtcaatat ttgggagaag tgtcatgcaa  19080
ttagtggttt gaatttccta tttttatttta ttgcatttta ttttatttgc ctagtcaaat  19140
aaaaagtaat gttaaataca tggaagcatg attgttttct acactaaaaa tcattttgac  19200
ttgaaaagat ctgatatcca tgaccttcat ctgaagtttt ggcagatgaa aatgtcagat   19260
gcgtcttttg gattaataaa aggcaaaagt cagatcgaaa aatgagtata agctttaatt  19320
atatgacttt aggaggatat gttatgaaaa tcaaagcttt aatagtgatt ataattggaa  19380
agttcttttt ttataaggaa ttacaagtca ctctatacaa aaattggaat ttttgtccta  19440
agaaatgaaa tttactatag tttcatctgt gtgtgtgtgt gtgtgtgtgt gtgtgtgtgt  19500
ttaaaaaatc aagtgatagg gcttttcctc aataaaatct gaaatctctt atagttaagt  19560
gaacagaaca gtgtatctag gatgctagac tttttttttca aagttagttt aaaacttata  19620
catagtaaaa tctgtatgcc ttagggatct ctgtttgcta tcccatagtg aatgattaat  19680
tagtttctgt tagaaatagt cagaactagg ctgggtgtgg tggtggctca tgcctgtaat  19740
tccaggactt gggaggcca aggcaggagg atctcttaag cccaggaatt tgcaaccagc   19800
ttgggcaggc tggtgagatc ctatctctac aaaaacaaac aaacaaacaa aggacaataa  19860
gaaagaaaga aatagccaga gctttgaaca aaatttctaa gtagaccaat gtaaagtct   19920
gtcgtcaata tgtagtggct atgaatggag gttatgaatg aaagagaagg ataagatgaa   19980
ctagaggtga gaggggaaga cagcaggccc aagtgaaagg cagagccgag tttattgctt  20040
tttggttatt ccaggtgtgt ctgctttgtc tcatgaaaca cctggatgat cactgatttc  20100
tagtggaaga aatgctgaaa agtccttact gtgcatttaa acattctagg tttaatatac  20160
tcagggtttt tcaaaagaaa gggtggctgg agttttgcac taactaatat ttcataaagt  20220
gtctaagtat agatgtctgg ttttttttg tatttctaag actggcttga ggtaggcatg   20280
gagaattctt tgatgggaca taattttctt ccttcttt ttttttttt tttttttt      20340
tgagacggag ttttgctctt gttgcccagg ctggagtgca atggcacaat tcggctcac   20400
tgcaacctcc gcctcccagg ttcaagcaat tctcccacct cagcctcccg cgtagctggg  20460
attacaggca gtgtgcccca tgcctggcta attttttttg tatttttagt agagatgggg  20520
tttctccatg ttggtcaggc tggtctcgaa ctccttacct caggtgatcc acccacctcg  20580
gcctcccaaa gtgctgggat tacaggcgtg agccaccgcg cccggcctga tgggacatat  20640
ttttcattca attttattga tttaacctca caaaataaaa tatttcctta agtgactct   20700
gtggtcattg ttgggcagca taagcttaat ggattttagt tatcataatt taccttaaac  20760
ccaatttgta tttcaggata taaatagagg tttattgtag tgaatcttcc aggaaatact  20820
aagtgatact aataattata gatggtgaac ttaagtcttt atattactga attttgtttgg  20880
tttgatgatg ctaggctatg gcattcttgc taatcaaaac gatgtgtcat ggtgtaacat  20940
aacttattaa aatgggcaca gataacacag gaagcttttt ataaaagcag ctcacaaatt  21000
gtgttacttt gaactgaact ggccatttat gggaaaggtc actgggttgt aaataaggac  21060
caaaagagtt acgtttatat ttttttaaaag agattgagga gatttatttt tacatttctt  21120
gaaaatgcct tattttggta tggtattgac agatagtgaa attctgctca tttgtaaata  21180
tagtgtcata ttttaataat ttcaaacata ttgaaaatgc agaatttatt aatagtggga  21240
gcacattttc ctttttacta aatgttctac aggttctttt ctttccatcc acacacagtg  21300
ccattaccct cattctaagc ctttcaaaca tctggcagta agtgatctgc tgcacttagc  21360
tctttccagc tgagctgatt tttaaatttt cagaaaattt gtgagctaat tgttaaacat  21420
ggccattatt aaaaattaaa ttatttcaac ttataattaa ataaattata ttaaaacaaa  21480
agtattaaaa actcaaaagt tggctgggcg cactggctca cgtctgtaat cccagcactt  21540
tgggagaccg aggcaggtgg attgcctgaa gtcaggggtt cgagaccaac ctgaccaaca  21600
tggagaaacc ctgtctctac taaaaatata aaaaaatagc cgggcatggt ggtgcatgcc  21660
tgtaatccca gctactcagg aggctgaggc aggagaattc cttgaaccca ggaggtggag  21720
gttgtggtga gctgagattg cgccattgcg ctccagcctg gcaacaaga gtgaaactct   21780
gtctcaaaaa aaaaaaaaaa aaaaaaaag aaacaaaaaa aaaaaaaaaa caaaaagcaa   21840
acaaacaaaa aaacaaaaat tatcacttcc taattatttt gcatttttact attatctatg  21900
ctattaacgt tatttgcctt cattgtattt gaaaggtgga ctatattcta ttgcactttc  21960
attgtactat attctaatat gcaactgtgt atccttccc aactctgtgt tcaatgactt   22020
tatatttggt tgctttaaaa tgatgacgat gagagtattt atatcataga aattggcaaa  22080
tgccgtaagt cagtttttgt ttttgttttt gttttccgga gaggggattg ttaaatattt  22140
gcctgcatgc aacaccacta catgcagtct gctatctttt gttcttcctg ctttcaggct  22200
cctctcccag ctgtctgtct agcacaaccc agcataccaa attttcttaa ataggaaag   22260
ttgaacatgg taaagaaatg aatgaagtca aaagaatgtg gaaagaccta ggctttgcca  22320
tttagtaaag tttagcatct ctaagcctcc atctctttat caataaaatt gagcaatgat  22380
cccttttagt tctacccatt taagaagatt ttcaaatgaa aaccacaacc tgctcatgtt  22440
tatgaaggca ctttggaaag cgctaaatac acgggttttt attagtagta aacacttact  22500
tcaccttttt cacttcttga ctttagtttta caagggctca taatctaaat tatatcataa  22560
```

```
attgctgtcc cagatttttt tacagcctaa ttgccacctg tatgttcgac tttccttctg   22620
ttctttatgt tagatactgg gatagtatgc accaggtggg tgtgccatca ctttctcaga   22680
tgatgtccac tgaagacctt gcatgatcat ggcattcatt ttcctgctgt attcagactg   22740
gcctcaacta ttttctttat tgctctccag gaaaaattac aaatgaatca gactgggcaa   22800
tgaagggtaa acctaattat cgctctttgt taaagacagc tcttgttaaa atgcggatat   22860
tgcaaattaa tggaaaaaat atgacatagt aaaccatact cacttattaa tatcttagta   22920
aggaataatt gatgaagtta cttaacctta gagccctaat tcagttaagt tttaatgaag   22980
gacaagttgt agagatatcg agaacccagg gcaggtgcct actgaagaag ttccagacca   23040
aggaagtata aagaaggacc tgggtgggag cagtgagatt ggatatggag gccactggca   23100
aagttttgcc ccagaacagt gtcaaaatgt ttgcatttgg catagcccct tctcttttg    23160
ttctgaatgg ctttgctaga atatcttttc tataatgaat ttatcctgct tctcagatat   23220
tgctaaagca ctcccttttg aattttggtg ctttaacatg cattttgata cattaccaaa   23280
taaggtctga atgcacacaa ttttagaact ctccagagaa aagaaagatg ctgagggaaa   23340
aagcataggt ttgggactca ctaaatccca gttcaattcc tttctttaat aaatatattc   23400
aattttacct gagaaagctc tcgtgctctc gaatttatt tagaaatttc tctttgtaca    23460
tgattgattt cacaatcctt cttctgcctc ctcttctact ttcttcttc tagattttcc    23520
tatctttatg aagattattc tgccttatcc tcaacgttga gaaacaatat ttttgaaaat   23580
cactacggta tcctgcatag tgatttccca tgccaacttt actaatttcc attataaatt   23640
attatttatt gatgcctaga gggcagatga gtgtagctgc tatggagtga ggagacaaaa   23700
cataagaaag ttatgatcct accctcaggt aatgattcag acatgataat taagtcaaca   23760
aattgataga aactaatcac taactctctg gctatagtca ttctttcaat gaatagctca   23820
ttactgagta tgcatgctac agtaacaaaa ttatataagg ctgttgatta aatgttgatt   23880
aagtgcatgt cttattcaga gttttttat atttgaaatg gaagaggctg gacttcagta   23940
atttgctata aactgctagt atatgattat ttgggggcag ttatttta aagaataatt     24000
taaatatgga atgtttagca gtttgttttt tccctgggaa aaaccatact attattccct   24060
cccaatccct ttgacaaagt gacagtcaca ttagttcaga atattgtg ttttatacag     24120
gtgtagcctg taagagatga agcctggtat ttatagaaat tgacttattt tattctcata   24180
tttacatgtg cataatttc catatgccag aaaagttgaa tagtatcaga ttccaaatct    24240
gtatggagac caaatcaagt gaatatctgt tcctcctctc tttattttag ctggaccaga   24300
ccaattttga ggaaaggata cagacagcgc ctggaattgt cagacatata ccaaatccct   24360
tctgttgatt ctgctgacaa tctatctgaa aaattggaaa ggtatgttca tgtacattgt   24420
ttagttgaag agagaaattc atattattaa ttatttagag aagagaaagc aaacatatta   24480
taagtttaat tcttatattt aaaaatagga gccaagtatg tggctaatg cctgtaatcc     24540
caactatttg ggaggccaag atgagaggat tgcttgagac caggagtttg ataccagcc    24600
gggcaacata gcaagatgtt atctctacac aaaataaaaa agttagctgg gaatggtagt   24660
gcatgcttgt attcccagct actcaggagg ctgaagcagg agggttactt gagcccagga   24720
gtttgaggtt gcagtgagct atgattgtgc cactgcactc cagcttgggt gacacagcaa   24780
aaccctctct ctctaaaaaa aaaaaaaaa aggaacatct cattttcaca ctgaaatgtt    24840
gactgaaatc attaaacaat aaaatcataa aagaaaata atcagtttcc taagaaatga   24900
ttttttttcc tgaaaaatac acatttggtt tcagagaatt tgtcttatta gagaccatga   24960
gatggatttt gtgaaaacta aagtaacacc attatgaagt aaatcgtgta tatttgcttt   25020
caaacccttt atatttgaat acaaatgtac tccctgggaa gtcttaaggt aatggctact   25080
ggttatcaaa caaatgtaaa aattgtatat ttttgagtac cttgtacatg ccaggtagaa   25140
tatctcctct cagccactct gagtggaaag catcattatc tctattttac agaaaagcaa   25200
actgaggctc agagagataa tatactttgc cagttcaatga atgatggagc catgattcca   25260
gctgaggtct gtattgcctt gctctctagg aatggtagtc cccccataa agaatctctc    25320
agtttccttt ccaatcaaaa ggttaggatc cttttgattg ccagtgacag aaacccaatt   25380
tactagctta agtaaataaa aggaacgaat ttattggctc atgaagcctg aactatgtga   25440
agacctaggt ggagaactgg ccttaggaac tcaatgggac caaggactca aatgccacct   25500
ggtggcattt gccttatgct ggttttattt tctcagaccg gaccagcttt ctacataaag   25560
tgggtccctg gttagaactc tttgctccta tcttaagga ccacgaaaga aggagccctt    25620
tgtccttggc taaatgtgaa aaatcccaga gactcttgag tcatagtgct taccccttgg   25680
gccactcata gtctagaatg aactaggctg agtctcgtgc caacagcaca ggcctgatgc   25740
cagataaaag ggtgagtgaa ggggggataaa aaataagaca tagctactaa attattgcac   25800
caaagtaaaa acattgagtt gacttgcaat ttgtttccttt taattaaatt catttccttt   25860
ttttggcatt ttgaaggcaa agtaagatat taaactttat ttttattgat tttattcaaa   25920
gaattaagct agtgggagta gcagattcac acttctaaga tcaagggcca gcttctatta   25980
ttgaacactt ggtgtgtgca aatgccatga ggtagggata ctttgttttg ttttttattt   26040
tttattgggt tcgatctctt ttgtttatga tgtatcccca agtgcctaga ataggggctg   26100
gcatatggta tatactcaat aaatattttgt tgaatgaatc catgatgaga tgtgaaatga   26160
ctagcattac atagaaacct gtagcattgc tggagagata aaatatataa acataatcca   26220
ttgcaggtat attgacaagt tcaaaataat ataatgggta ttgaatatct aaatgttgt    26280
tgttgttgtt gctgttgttt ttgagacaga gtcttgctct gttgcccagg ctggagtgta   26340
atggtgcaat tttggctcac tgcaaacttc gtctcctggg ttcaagtgat tctcctgcct   26400
cagcctctcg agtagctggg tttacaggca ctcgccacaa tgcctggcta attttttgtat  26460
tttagtagat gtggagtttc gccatgttgg ccaggctggt cttgaactcc tgacctcaag   26520
tgatctgccc accttggcct cccaaaatgc tgggattata ggtgtgagcc actatgccca   26580
gctttgaata tctaagtttt aattggatgc tgagggaatg attaatcaga gtagggctgg   26640
gttaattgaa aaatgtgata catttgtatt tatggccaga tagaagaacat gaatctgaat   26700
ttgcagaatt atctggctta acattttttt cttccagtt ttcactgtat ccccatgtt     26760
gattcaattt aaaaaatata cctatttac ttcaattcaa caatgctatg ccagtacaaa    26820
cccatacgtt ctattatttt tgttttgttt tgtttttgta tctccaccct gttacttctt   26880
ttcttataaa attggtattt gaatttatt gaaatatttt ggagagtga cataccattt     26940
ttggtacttt gtacctctgc accctggga agtgaccctg gcttcacatt tcataactgc    27000
cttgtgacca tggccctcaa gtggttgcca gatgggtgaa gaacattaac ctatctggct   27060
caattttgtg accatggatt gaatcctcta cataactgca gtgtgcaaac cacacatccg   27120
ttccaagatt gtagtcagga tatgaacttt ttaagaataa aacttcttcc cttctgatct   27180
gggcctggta tgtggtccta ctagaaccac atcacctact cttggtgcta acaatttgtg   27240
gcaccaagtt gttcaagttt cacccattaa agaaatttccc cgaccttgcc ttctcctcag   27300
```

```
gtaactaccc cattctattt tttctttcat agctaacatt ctctgctctc ctggtctctc   27360
tacttcactt tcatttacat ctcagctcct gaagtatggt ttccaccatg ttcctaaaac   27420
tacattgccc agggtcacta gagacctctt atgaaatata acaacacctt tctacattac   27480
ttccgtgtgg accactttt cacattgaac ccatttgtt ggtttatgta cacacccctt   27540
ccttgcgttt cccatctgat ccatttctcc tttgatggag aaggtgagtc tgctccatat   27600
ttagcttctt actctgagta accaaatgtt atggatggga ggttagctct gtgtgtgaga   27660
gaaaggtgga gaagcatgtg gggagggaaa tagatgggaa aaggtaatta ggctttatag   27720
aagggctctc attagcaagc ttctagggga tgccaagatc catgcttaga gattgccagg   27780
cttgtcttca aatctcagct gtgtattact cctttatgtt ttttgtttgt ttgtgttgtt   27840
tgttttgag acagagtctc gctgtgtcac ccaggctgga gtgtagtggt gtgatctcag   27900
ctcactgcaa actctgcctc ctgggttcaa gcgaatctca gtcctgag tagctgggac   27960
tacaggcatg caccaccagg cctggctaat ttttgtagag acggggtttt gctatgctgg   28020
ccaggctggt cttgaactcc tgacctcaag tgatctgccc gccttggcct cccaaagtgt   28080
tgggattagt ggcgtgagcc actgcccggg cctattactc ctttagagtg atttagagcc   28140
atgtttactt atggtaactt gacagtaatg gaataaccac ctgatgaaac gtaaagcctt   28200
tgtctaattg tttacctagt tcttccttgt ggttcatgaa atttttcatc tctgtacagt   28260
ttgaaaatta agatgataat atttagagat attttattcc tttgtgaaga gaaaaaaggc   28320
tttcattaac agaaatcagt ggcaataact taataaatac aatcagctgg tgttcctata   28380
gtatttaaaa gaaaacagaa agtttactag atttcagcca gttttcagac tatttaatgt   28440
ctattcttac tataatagaa aatatataat ttgatcttgt tctcatttt caaagacctt   28500
taatacatga ttttagtagt tgaaaatgaa gtttaatgat agtttatgcc tctactttta   28560
aaaacaaagt ctaacagatt tttctcatgt taaatcacag aaaaagccac ctgacatttt   28620
aacttgtttt tgatttgaca gtgaaatctt ataaatctgc cacagttcta aaccaataaa   28680
gatcaaggta taagggaaaa atgtagaatg tttgtgtgtt tattttttcc accttgttct   28740
aagcacagca atgagcattc gtaaaagcct tactttattt gtccacccct tcattgttt   28800
tttagaagcc caacactttt cttttaacaca tacaatgtgg cctttttcatg aaatcaattc   28860
cctgcacagt gatatatggc agagcattga attctgccaa atatctggct gagtgttttgg   28920
tgttgtatgg tctccatgag attttgtctc tataatactt gggttaatct ccttggatat   28980
acttgtgtga atcaaactat gttaagggaa ataggacaac taaaatattt gcacatgcaa   29040
cttattggtc ccacttttta ttcttttgca gagaatggga tagagagctg gcttcaaaga   29100
aaaatcctaa actcattaat gcccttcggc gatgttttt ctggagattt atgttctatg   29160
gaatcttttt atatttaggg gtaaggatct catttgtaca ttcattatgt atcacataac   29220
tatattcatt tttgtgatta tgaaaagact acgaaatctg gtgaataggt gtaaaaatat   29280
aaaggatgaa tccaactcca aacactaaga aaccacctaa aactctagta aggataagta   29340
aaaatccttt ggaactaaaa tgtcctggaa cacgggtggc aatttacaat ctcaatgggc   29400
tcagcaaaat aaaattgctt cttaaaaaat tattttctgt tatgattcca aatcacatta   29460
tcttactagt acatgagatt actggtgcct ttattttgct gtattcaaca ggagagtgtc   29520
aggagacaat gtcagcagaa ttaggtcaaa tgcagctaat tacatatatg aatgtttgta   29580
atattttgaa atcatatctg catggtgaat tgtttcaaag aaaaacacta aaaatttaaa   29640
gtatagcagc tttaaatact aaataaataa tactaaaaat ttaaagttct cttgcaaatt   29700
atttttcttaa tcttacat ctcatcagtg tgaaaagttg cacacctgaa aatccaggct   29760
ttgtggtgtt taagtgcctt gtatgttccc cagttgctgt ccaatgtgac tctgatttat   29820
tattttctac atcatgaaag cattatttga atccttggtt gtaacctata aaaggagaca   29880
gattcaagac ttgttttaatc ttcttgttaa agctgtgcac aatatttgct ttggggcgtt   29940
tacttatcat atggattgac ttgtgtttat attggtctt atgcctcagg gagttaaaca   30000
gtgtctccca gagaaatgcc atttgtgtta cattgcttga aaaatttcag ttcatacacc   30060
cccatgaaaa atacattaa aacttatctt aacaagatg agtacactta ggcccagaat   30120
gttctctaat gctcttgata atttcctaga agaaattttt ctgactttg aaataatga   30180
tccataaatat atattcttat ggaaatctga aaccatttgg gcatttgggg gtaaaagta   30240
ttttattagt aaatttaaat gaggtagctg gataattaaa ttacttttaa gttacctttg   30300
agatgatttt tctcaatcag agcaccaccc agagctttga gaaacaattt tattcacagc   30360
ttctgattct atttgatgta attttttagaa aataagtttt gctggttgct ttgaatcagg   30420
gtatggagta cagttcactc tgatcctatc atataaatca tgtaagtata aacattttc   30480
aataagtgat tgttggattg aagtgaatga tattcaagt aattgttatg tcatggccaa   30540
gatttcagtg aaactcaaaa tttctcctgg ttgtgttctc cattgcatgc tgcttctatt   30600
gattaaccta agcactactg agtagaagct ggaagagggg tctaattaga aggccccttt   30660
ctatgctctg cttggcttgt aaaataattt atttctctag atcccaccaa catagtagtt   30720
tcatgtatgc aaaaacaccc acctaaatgt caaagtttgt atgatacatg gacatatcta   30780
tagaattttt tttggtctgg tgcatgccaa aaaataaaca tgatatagaa gaatttaata   30840
tttattgagt acctaatctg ttccagttca atatgaaggt ctttatgcag attatttac   30900
ttaatttttcc tagtaactcc atggagcaaa aattatctct aatttatata acaggaagtt   30960
gagcgtgagg caaattaagt aactttccca aagttacaca tatggtaagt ttgagagata   31020
tcccagtctc tttagctcca aagcctttga cccctttcacc ataccagatt atgattgcta   31080
ttaatatata attataatta taatgattgt atttaggtac tcaacagaat ggtgactcta   31140
gtaaccagcc ttggttctgc tgagcttctc tgcgtcttct caggagacac aggctacaga   31200
gcttgaaggc tgaggattct tccagggtca cttcaggggc aaatctgaaa ctttcttcag   31260
gacaggaatc aacgagatct tctcacttac ttatacctgg gggaggaact gtatgaaatc   31320
caccaagaa ccagtcatgc taagggccaa acctatagac aaaaaaaggg ataggagaat   31380
ggagtatgta tggagaaaga ctaaattgtt cttaaacttc tcaagcttaa aaatatccta   31440
gcaaaagaga tcgtaaaagc ccttcatggc gtattaatta ccatgcatg ggggtgagtg   31500
gaaaggtact cctgagcccg aggctacagc tttggaacta gcagcaccctt tgaagggaa   31560
agcgtgtttc catcatctca actcctactg ataaccaatg gaatattggt gagtaaagga   31620
tcctgggga agagcagct gaaatgtgta ggtgagaagg cagagagaag aatatttata   31680
aaaatggaa tcaaagtgtg atgaggctgc aggttttca ccctttgtcat agagaaaaaa   31740
ccacgctgac accatgcagt tttaaatagt gagaaatttg caaattgtta gatcttaaat   31800
aattttagata aacatagtgg ccatttgat tattgcagtt tttcaggat atctgatctc   31860
ttgatttcat tcttttttgtc tcttataaga ataaagggg gggagaaaat ttagccatta   31920
tagtatttct ctacatttc tctgtccttt tacataactt acaccagtgc cttcctattt   31980
atggtattat ttatgggtat ttcttctttt ctttcactga gcaaggataa atgagccagg   32040
```

```
                                         -continued
gattcttgaa actactgtaa cacttctctt agaaatagat ggtcatactt tcagaatctc   32100
tacacattct tagtccctct aaacaatgat agttgtggca taaaaatatt tgcttggttt   32160
caggactgat agagaaaagt actataaaat ttgctgttaa ctgtgaaagg ttaaaaaaaa   32220
ggaggtgcca tcatgaagga gctaatcttt ctgaagtact gctgtagttt taaatattat   32280
tagctatgac ttctcaccat taactatgca ctttgctttt cttcatctga ctcagcagcc   32340
agatagatgc aacattgtct ttaacatttta agactcctag caagtccggg cacgggggct   32400
cacacctgta atcccagcac tttgggaggc cgaggtgggc aaatcacaag gtcaggagtt   32460
tgagaccagc ctggccaata tggtgaaacc ctgtctctac taaaagtaca aaaatcagcc   32520
aggtgtggtg gcgtggtggc gggcacctgt ggtcccagct acttgggagg ctgaggcagg   32580
agaatagctt gaacctggga ggcagaggtt gcagtgagct gagatcgcac cactgcactc   32640
cagcctgggt gacagagcga gactccatct caaaaaaaaa aaaaaaaaa aagactccta   32700
g                                                                   32701

SEQ ID NO: 52              moltype = AA   length = 1060
FEATURE                    Location/Qualifiers
REGION                     1..1060
                           note = source = /note="Description of Artificial Sequence:
                           Syntheticpolypeptide"
REGION                     1..1060
                           note = source = /note="nAPG00969"
source                     1..1060
                           mol_type = protein
                           organism = synthetic construct
SEQUENCE: 52
MKQTSYSLGL AIGIASVGYG LIDNDENIVD AGVRLFPEAN SKNNDGRRKS RGSKRLIRRK   60
RHRIARVKHL LKESGIDVSY ENTVLTNPYE IRCKGLTLPL TNHELSIALL HLAKRRGVHN   120
VKSMDQEKVK GNELSTKEQL TINDNLLEEK FICELQLERL NKEGIVRSHS NRFKTADYIK   180
EIKNLLETQA KQNTLVTEEF IEKYIEIFSG RRKYYEGPGG ESKYGWKGDI EKWYEGLMGK   240
CTYFPKELRC VKHAYSAALF NLLNDLNNLS INREEDTKLS QYEKEQIIEK IFKVRKTPTL   300
TQIAKLLKVD PTNIKGFRTK ANGTPDFLSI KIYHDLKGII DDKQLLDDIA FLDNVAQILT   360
VWQDSQSIQE KLKTLNKNLD DKTIKEISEL KKYTQTHSLS LKLINVLLPE LWETTKNQMT   420
ILSELKLKPR KIDLHNCNEI PVNMINDLIV SPVVRRSLTQ SIEMINQIIK DYGHPREIVI   480
ELAREKNSEE KKNFIKSLNE KNKQINDEVI EKLNASNHRD NKGMFNKVKL WILQDGHCLY   540
SLKPIRLEDL LNNPNHYEID HIIPKSVSFD DSMSNKVLVY QIENSKKGNR TPYQYLTSAD   600
KTITYEKFKA NITQLAKSNH KISKKKLDYL LEERDINRFH IKKEFINRNL VDTRYATRSL   660
INLLKYYFSE KDINVKVKSI NGSFTDYLRK LWNFPKDREF YHKHHAEDAL IIAMANKIFT   720
TRKIPFKEQNS VFSDEQILDG EVTNILSDDQ FQAEFTEKFY KVQAIKKYDK YKYSHRVDKK   780
PNRQLFDDTL YSTREFEGEE YYIGKIKDIY NLKDKRLKKI FTKSPEKILM YQHDSQTFKK   840
LKQIMRSYED EVNPLAKYHK ETGEYLRKEC KKGNGPIVKS LKYRVTKLGV HKDITHKYEN   900
SKNKVVILSL KPFRMDVFKE NGVYKFITIR YCDLKETVNS YTISEHLYKA KLKAKDIKSM   960
DSFKWSFYKN DLLEYNGELC TFKGVNDDKK NKIEVNWVEK NFAIYAEKKN LKSKQLVKSI   1020
TKSTVKSLLK YTTDILGNRY PVRNEKLKLM IRKQTFRGDL                        1060

SEQ ID NO: 53              moltype = AA   length = 1092
FEATURE                    Location/Qualifiers
REGION                     1..1092
                           note = source = /note="Description of Artificial Sequence:
                           Syntheticpolypeptide"
REGION                     1..1092
                           note = source = /note="nAPG06646"
source                     1..1092
                           mol_type = protein
                           organism = synthetic construct
SEQUENCE: 53
MRYSIGLAIG TTSIGNAVIN KDLQRFEHLG VRIFDAAENP KDGSSLSAPR RLARSSRRRL   60
RRRKHRVERT KQLLINKGLL TKTQVKNLYN SKNINLDIWD IRVSGIDRKL FNNEFARVLI   120
HFSKNRGFKS NRKSELKEDD NGAILSAVKE NRELMDEKGY RTIAEMLVSD EKYEGTKRNK   180
GGDYSHVVAR SDIENEICLL FQKQREYGHP FATEENEEAF LSIWSSQRPF STKDDIVKKI   240
GNCTLEPKEK RAPKSTYTFE RFRALDKLNR LRILSTTAPS RPLTNEERKS ILSSLFSKKE   300
VKYKELRKLL KLTDDQRFNE IYYSPDETIE KTENRTFLSL ESQYKIKKII EKTESKNMQS   360
SYHPIDYDTI GYALTVFKDD KDIQHYLQNS YIDSKGKAIP NMANREYNLE LIEELLGLSF   420
AKFGHLSLKA LNNILPYMEE GEPYHIACEM ASYQFSQRLS KEKHRLLPPI PVDEIPNPVV   480
VRALTQVRKV LNSIIKKYGP PSDIYIELAR EMSKPFKERK SLEREFNENR QINEKAKAHI   540
SELYRIPNDP RPHDILKFKL WNEQNGICPY SLKPISIEYL FNIGYAEVDH IIPYSRSFDD   600
SNGNKVLVLT RENQNKLNRT PYEWFGHEEN RWEDFVSFIR TMKVGKKKKN MLLKNFDEE   660
QEEQILSRNL NDTRYITRYI KSFIEDNLEF RTEENKEQYV HTVNGAYTSL MRKRWGLNKD   720
RRGNDLHHAV DAAIIAVSLP FKNKVNAYFK RQETGLSKLL NNKKDIFPEP WRNFIKELEA   780
RMIQDPEKMK RALESLELET YGEIPLNKLK PIFVSRMPKD SIKGQIHEET IRRVRGFTEE   840
GFLVTVKKTR LDQIPFDKNG DFPMYGKETD IKTYMAIKQR YLEYGQDKQK AFAVPLRKPS   900
KNPKNAPIVR SVKIEGKANR VVMLDDKAAA DNASIVRTEV FRHKKTGEYY LTPVYVADIL   960
SNKIPDRLIT IKKSYSDWDR ITDEHEYLFS LYNNDLVKII LPKEKETKKY TGGNHLWQEG   1020
FFYFKGVDSS NAGIKIINHL NSFEARIGTK RLIAFEKYQV NPLGEINKVH GEKRPGELLN   1080
KEEIKENRKN IS                                                      1092

SEQ ID NO: 54              moltype = AA   length = 1108
FEATURE                    Location/Qualifiers
REGION                     1..1108
                           note = source = /note="Description of Artificial Sequence:
                           Syntheticpolypeptide"
```

| | | |
|---|---|---|
| REGION | 1..1108 | |
| | note = source = /note="nAPG09748" | |
| source | 1..1108 | |
| | mol_type = protein | |
| | organism = synthetic construct | |

SEQUENCE: 54

```
MAIRSIKLKL KTRTGPEAQN LRKGIWRTHR LLNEGVAYYM KMLLLFRQES TGGQTKKELQ    60
EELVRHIREQ QQKNRADKNT QALPLDKAFA ALRQLYELLV PSSIGQSGDA QIISRKFLSP   120
LVDPNSEGGK GTSKAGAKPT WQKKKEANDP TWEQDYEKWK KRREEDPTAS VITTLEEYGI   180
RPIFPLYTNT VADIAWLPLQ SNQFVRTWDR DMLQQAIERL LSWESWNKRV QEEYSKLQEK   240
MTQLNEQLEG GQEWISLLEQ YEEQREQELI ENMTAANDKY RITKRQMKGW NELYEQWSTV   300
LPNASHEQYR EALKRVQQRL RGRFGDAHFF QYLMKEEHHL IWKGNPQRIH YFVARNELKK   360
RLEEAKQNAT MTLPDARKHP LWVRFDARGG NLQDYYLTAE ADNPRSRRFV TFSQLIWPNE   420
SGWMEKQDVE VELALSKQFY QQVTLQKNDK GKQEIEFKDK GSGSTFSGHL GGAKLQLERG   480
DLEKEEKDFE GGEIGSVYLN IVIDFEPLQE VKNGRLQSPY GQVLQLVRRP NEFPKVTTYK   540
SEELVEWIKS STKDSAGVES LESGFRVMSI ALGLRTAAAT SIFSVEESND ANAAGFSYWI   600
EGTPLVAVHK RSYMLKLPGE QVEKQVREKR DERQDQQRRV RFQIRILSQV IRMAKKQNRE   660
RADELDHLSQ ALEKQKSLLD QTDRTFWNGI VCDLTDALRE KEGGWEQAVV QIHRKAEEHV   720
GKVVQAWRKR FDADERKGIA GLSMWSIEEL DSLRKLLISW SRRTRNPREI NCFEQGHTSH   780
QRLLTHIQNV KEDRLKQLSH AIVMTALGYV YDEKKLEWFA KYPACQVILF ENLSQYRSNM   840
DRSTKENSTL MKWAHRSIPK YVHMQAEPYG IQIGDVRAEY SSRFHAKTGT PGIRCKMVSG   900
HDLQGRRFEN LQKRLISEQF LTEEQVKQLR PGDIVPDDSG EGKEVVFLQA               960
DINAAQNLQK RFWQRYNELF KVSCRVLIRG EEEYLIPKTK SVQAKLGKGL FVKKTDTVMK  1020
DVYVWDSQAK LKGKTTFTEE SESPEQLEDF QEIIEEAEEA KGTYRTLFRD PSGVFFPEFV  1080
WSTQKDFWSE VKRRLYGKLR ERFLMKTR                                    1108
```

| | | |
|---|---|---|
| SEQ ID NO: 55 | moltype = AA length = 1150 | |
| FEATURE | Location/Qualifiers | |
| REGION | 1..1150 | |
| | note = source = /note="Description of Artificial Sequence: Syntheticpolypeptide" | |
| REGION | 1..1150 | |
| | note = source = /note="nAPG09882" | |
| source | 1..1150 | |
| | mol_type = protein | |
| | organism = synthetic construct | |

SEQUENCE: 55

```
MYSIGLALGI SSVGWSVIDE RTGNVIDLGI RLFSAKNSEK NLERRTNRGG RRLIRRKTNR    60
LKDAKKILAA VGFYEDKSLK NSCPYQLRVK GLTEPLSKGE IYKVTLHILK KRGISYLDED   120
DTEAAKESQD YKEQVRENAQ LLTKYTPGQI QLQRLKENNR VKTGINAQGN YQLNVFKVSA   180
YANELATILK TQQAFYPNEL TDDWIALFVQ PGIAEEAGLI YRKRPYYHGP GNEANNSPYG   240
RWSDFKKTGQ PATNIFDKLI GKDFQGELRA SGLSLSAQQY NLLNDLTNLK IDGEIPLSPE   300
QKEYILAELM TKEFTRFGVN DVVKLLGVKK ERLSGWRLDK KGKPEIHTLK GYRNWRKIFA   360
ESGIDLATLP TETIDCLAKV LTLNTEREGI ENTLAFELSE LAESVKLLVL DRYKELSQSV   420
STQAWHRFSL KTLHLLIPEL MNATSEQNTL LEQFQLKSDV RKRYSEYKKL PTKDVLTEIY   480
NPTVNKTVSQ AFKVIDALLV KYGKEQIRYI TIEMPRDDNE EDEKKRIKEL HAKNSQRKND   540
SQSYFMQKSG WSQEKFQTTI QKNRRFLAKL LYYYEQDGIC AYTGLSISPE LLVSDSTEID   600
HIIPISISLD DSINNKVLVL SKANQVKGQQ TPYDAWMDGS FKKINGKFSN WDDYQKWVES   660
CHFSHKKENN LLETRNIFDS EQVEKFLARN LNDTRYASRL VLNTLQSFFA NQETKVRVVN   720
GSFTHTLRKK WGADLDKTRE THHHHAVDAT LCAVTPFVKV SRYHYAVKEE TGEKVMREID   780
FETGEIVDEM SYREFKKSKK YERKTYQVKW PNFREQLKPV NLHPRIKFSH QVDRKANRKL   840
SDATIYSVRE KTEVKTLKSG KQKITTDEYT IGKIKDIYTV DGWEAFKKKQ DKLLMKDLDE   900
KTYERLLSIA ETTPDFQEVE EKNGKVKRVK RSPPAVYCEE NDIPAIRKYA KKNNGPLIRS   960
LKYYDGKLNK HINITKDSQG RPVEKTKNGR KVTLQSLKPY RYDIYQDLET KAYYTVQLYY  1020
SDLRFVEGKY GITEKEYMKK VAEQTKGQVV RFCFSLQKND GLEIEWKDSQ CYDVRFYNFQ  1080
SANSINFKGL EQEMMPAENQ FKQKPYNNGA INLNIAKYGK EGKKLRKFNT DILGKKHYLY  1140
YEKEPKNIIK                                                        1150
```

| | | |
|---|---|---|
| SEQ ID NO: 56 | moltype = AA length = 1068 | |
| FEATURE | Location/Qualifiers | |
| REGION | 1..1068 | |
| | note = source = /note="Description of Artificial Sequence: Syntheticpolypeptide" | |
| REGION | 1..1068 | |
| | note = source = /note="nAPG03850" | |
| source | 1..1068 | |
| | mol_type = protein | |
| | organism = synthetic construct | |

SEQUENCE: 56

```
MKYVLGLAIG IASCGWAVIN QEKHRIEDLG VRIFDKAENP KDGKSLATPR RDARSTRRTL    60
RRKKHRMQRI KILLVKHGLL SKTEIDHLYE SATEIDVWYL RLNALERRLN PKEFARVLIH   120
LAKRRGFKSN RKETTLSENG QILENISENL QIMEQQNYRT VGEMILKDKK FENHKRNKDG   180
TYIGTVTRQQ LKEEIQMIFN AQRLYKNDYA TEEFESSYLE IWASQRPYAS KDQIEKMIGY   240
CTLEPKEKRV PKASWSFQYF VALQTINNLR LINKDRIEEL SFEEKNQIMN LALEKSIVKY   300
IDIRKLLSIP NEFHFNNLLY SADTVDTAVE NKKCIEFKEY HSINKLYKQI YGKSVPNLLP   360
IDYDTIACGL TIFKDDKDIL AYLQNKYVNA KGKPISNLAK KTYDDTFIQA LLTLNFSKMG   420
HLSFKALKNI IPFLEEGLSY DKACEKAGYN FKGTSHAEKT KYLPVIPQNT NPVVHRALSQ   480
TRKVINAIIK KYGSPSAIHI ETARELSKTF QERKEIDSMY QDNSKKNEHA IHKLKELGLI   540
NPSGINIVKF KLWNEQDGRC MYSGKYIEPH RLFEEGYTEV DHILPYSRSL DDSYNNKALT   600
```

```
LGIENQRKGN KTPYEYIGKT SIWHEFETRV QSNKRINKKK QQKLLLQYFS YTREQEFIKR   660
NLNDTRYATI YLSTLIQQHL IFSESSRKKK VHTVSGIITS HLRSRWGFNK DRKEGHIHHA   720
LDAVIVAVTS DHMIQRVTKY YKLKELNRNL QAKRMQFPEP WEGFRLELEA RISPNTQQYL   780
KRILFKNYAD VNLSEIKPIF VSRMPKRSIT GELHQETIRK LIGYNEKGKV LTAIKTKLED   840
IPFDANGDFP MYGKETDLYT YNAIKERYLS HKKDKRKSFQ DPLYKPTKSG EIGPLIKSIK   900
IMDTRTIVNP VNQGKGVVYN SKIARTDVFK KDEKYYLIPI YTIDLLKNIL PQKAITAGKG   960
YEDWTTIDPS FTFLFSLFPN DLIQIVPSKN KTIKARTTVS KKEVLLPSLT GYFKGVHSGT  1020
AGITVETHDG SVIANVGSKQ LLLFEKYQVD VLGHYTKIKE EKRIGMVI              1068

SEQ ID NO: 57           moltype = AA  length = 1081
FEATURE                 Location/Qualifiers
REGION                  1..1081
                        note = source = /note="Description of Artificial Sequence:
                         Syntheticpolypeptide"
REGION                  1..1081
                        note = source = /note="nAPG07553"
source                  1..1081
                        mol_type = protein
                        organism = synthetic construct
SEQUENCE: 57
MQYVLGLAIG IASCGWAVIN QEKERIEDLG VRIFDKAENP KDGKSLAAPR RDARSTRRTL    60
RRKKHRMQRI KILLVKHGLL SQTELDHLYE SATEVDVWNL RLDAIERKLN PKEFTRVLIH   120
LAKRRGFKSN SKETTLSENG QILESISENQ QIMEQKNYKT IGEMILKDKK FENHKRNKDG   180
TYIGTVTRQQ LQDEIQIIFN AQRLYKNNYA TKEFESSYLE IWASQRPYAS KDQIEKMIGY   240
CTLEQKEKRV PRASWSFQYF VALHTINNLR LISKDRIEEL SFKEKKQIMN LALEKPIVKY   300
IDIRKLLSIP NELHFNSLLY SADTVDTTVE NRKCIELKEY HSINKVYKQI YGKNALNLLP   360
IDYDTIAYGL TIFKDDKDIL EHLKNKYVNA KGKPINNLAK KTYDDTFIQA LLTLNFSKMG   420
HLSFKALKNI IPFLEEGLSY DKACEKAGYN FKGTSYTEQT KYLPVIPQNT NPVVHRALSQ   480
TKKVINAIIK KYGSPNAIHI ETARELSKTF QERKEIDSMY QDNSKKNEHA IHKLKELGNI   540
NPSGINIVKF KLWNEQDGKC MYSGKYIEPH RLFEEGYTEV DHILPYSRSL DDSYNNKTLT   600
LGIENQRKGN KTPYEYMGNT SIWDEYEIRV QSNKKINKKK QQKLLLQHFS YAREQEFIER   660
NLNDTRYATI YLSSLIQQHL IFSESSRKKK VHTVSGIITS HLRSRWGFNK DRKEGHIHHA   720
LDAVIVAVTS DHMIQRVTKY YKLKELNRNL QAKRMPFPEP WEGFRLELEA RISPNTQQYL   780
KGLRFKNYAD VNLCEIKPIF VSKMPKRSIT GELHQETIRK FIGYNEKGKV LTAIKTKLED   840
IPFDANGDFP MYGKETDLYT YNSIKERYLS HKKDKRKSFQ EPLYKPTKSG GIGPLIKSIK   900
IMDTRTIVNP VNQGKGVVYN SKIARTDVFK KDDKYYLIPI YTIDLMKNIL PQKAITAGKG   960
YEDWITIDHS FTFLFSLFPN DLIKIVPSKN KEIKARTSSS KKEILLPSLI GYFKSVHSGT  1020
AGITVESHDG RFIANVGSKQ LLLFEKYQVD VLGHYTKIKE EKRIGMATCN DNKKSTAFGS  1080
L                                                                 1081

SEQ ID NO: 58           moltype = AA  length = 1150
FEATURE                 Location/Qualifiers
REGION                  1..1150
                        note = source = /note="Description of Artificial Sequence:
                         Syntheticpolypeptide"
REGION                  1..1150
                        note = source = /note="nAPG05586"
source                  1..1150
                        mol_type = protein
                        organism = synthetic construct
SEQUENCE: 58
MYSIGLALGI SSVGWSVIDE ETGKIVDLGV RLFSAKNSEK NLERRTSRGA RRLIRRKTNR    60
LKDAKKLLEA IGFYEDKALK NVCPYQLRVK GLTEGLTKGE LYKVVLHIVK KRGISYLDED   120
DAEAAKESQD YKEQVRKNAQ LLTKYTPGQI QLQRLKENNR VKTGINGQGH YQLNVFKVSA   180
YADELATILK TQQALYPNEL TDDWIALFVQ PGIAENAGLI YRKRPYYHGP GNEANNSPYG   240
RWSDFQKTGQ PAANIFDKLI GKDFQGELRA SGLSLSAQQY NLLNDLTNLK IDGEVSLSPE   300
QKEFILTELM TKEFARFGVN DIAKLLGVKK EQLSGWRLDK KGKPEIHTLK GYRNWRKIFA   360
EAGIDLATLP TETIDCLAKV LTLNTEREGV ENTLAFELPE LAEPVKSLVL DHYKELSQSI   420
STQAWHRFSL KTLHLLIPEL IKSTSEQNTL LEQPQLKAGV RKRYSDYKKL PTKEVLAEIY   480
NPTVNKTVSQ AFKVMDALLE KYGKDQIHYI TVEMPRDDNE EEERKRIKEL QTKNSQRKND   540
SQQYFLQKSG WSQEKFQATI HKNRRFLAKL LYYFEQDGVC AYTGNPISPE LLVSDSTEID   600
HIIPISISLD DSINNKVLVL SHANQVKGQQ TPYDARMAGA FNKINGKFSN WDEYQKWVES   660
RPFSRKKVNN LLETRNIFDS EQVQKFLSRN LNDTRYASRL VLNTLQSFFE NQDTIVRVVN   720
GSFTHTLRKK WGADLDKTRE THHHHAVDAT LCAVTPFVKV SRYHYAVNEE TGEKFMREID   780
VETGEILDEI PYREYKKAKH YERKTYQVKW SNFREQLKPI TIHPKIKFSH QVDRKANRKL   840
SDATIYSVRE KTEVKTLKSG KEKITTDEYT IGKIKDIYTV DGWEAFKKKQ DKLLMKEFDE   900
KTYELLVTIA ATTPDFQEVE EKNGKVKRVK RSPFAVYCEE NGIPAIRKYA KKNNGPVIRS   960
LKYYDGLNK HINITKDEKG RPVEQTKNGR KVTLQSLKPY RYDIYQDLET KAYYTVQLYY  1020
SDLRFVEGEY GITEKEYMKK VAEQTKGQVV RFCFSLQKND GLEIEWKDSQ RYDVRFYNFQ  1080
SANSINFKGL EQEMIPAENQ FKQKPYNNGA INLNIAKYGK EGKKLRKFNT DILGKHHHLS  1140
YEKEPKNIIK                                                        1150

SEQ ID NO: 59           moltype = AA  length = 1052
FEATURE                 Location/Qualifiers
REGION                  1..1052
                        note = source = /note="Description of Artificial Sequence:
                         Syntheticpolypeptide"
REGION                  1..1052
                        note = source = /note="nAPG01604"
```

```
source                  1..1052
                        mol_type = protein
                        organism = synthetic construct
SEQUENCE: 59
MVTKYILGLA IGITSVGYGI INYEDKTIID AGVRLFPEAN VENNEGRRSK RGARRLKRRR    60
IHRLDRIKQL LSEYNLVDLD NIPQSPSPYE IRVKGLREEL SKDELVIALL HIAKRRGIHN   120
VEAVDETQDE GNELSTKEQL AKNNNLLKDK YVCELLLERL KDGKVRGEKN RFKTTDIIKE   180
VKQLLETQKE AHQLDDDFIN RYIDLIETRR EYFEGPGKGS PFGWGGDLKK WYETLMGHCT   240
YFPNELRSVK YSYSADLFNA LNDLNNLVIQ REGNSKLEYH EKYHIIENVF KQKKKPTLKQ   300
IANEIGVSPD DIKGFRINKS GKETFTEFKL YHDLKKVLID QSILENVQLL DQIAEILTIY   360
QDKESIINEL NQLSEIINEQ DKESISNLSG YNGTHRLSLK CINLVIEELW HTSRNQMEIF   420
TYLNIKPKKI DLAKTNKIPK NMIDEFILSP VVKRTFGQAI NVINKVIEKY GVPEDIIIEL   480
ARESNSKDKQ KFINSLQKKN ETTRKRINEI IGQYGNQNAK RLVEKIRLHD EQEGKCLYSL   540
ESIPLEDLIN NPQYYEVDHI IPRSVSFDNS YQNKVLVKQT ENSKKSNRTP YQYFNSGETK   600
LSYNQFKQHV LNLSKSKDRI SKKKKEYLLE ERDINKYEVQ KEFINRNLVD TRYATRELTN   660
YLKAYFSAND MDVKVKTING SFTDYLRKVW KFKKERNHGY KHHAEDALII ANADFLFKEN   720
KKLKKANAIL EQPSLDNGKS DATVENDNEY VETFSIPKQV NDIKEFRDFK FSHRVDKKPN   780
RQLINDTLYS TRKIENHTFI VSPITNIYSK DNDELKKKFN KNPEKFLMYQ HDPKTFEKLE   840
VIMKQYANEK NPLAKYHEET GEYLTKYSKK NNGPIVKTIK VLGDKVGKHL DVTHKYKYSN   900
SKIVKKTINP YRFDVYLTDK GYKFITISYL DVLKKDNYYY ILKEKYEELK IKKSISDTDQ   960
FIGSFYYNDL IKINDQIFKV VGVNNDLLNR IELDLLDISY KEYCKINNIK TNRIIKGITK  1020
KITNIEKFST DVLGNLYKAH SNHPQLIFKQ RD                                1052

SEQ ID NO: 60           moltype = AA  length = 1072
FEATURE                 Location/Qualifiers
REGION                  1..1072
                        note = source = /note="Bacillus sp. APG08290.1"
source                  1..1072
                        mol_type = protein
                        organism = Bacillus sp.
SEQUENCE: 60
MSELDYRIGL DIGTNSIGWG VIELFWNKDR ERYEKVRIVD KGVRMFDKAE IPNKGASLAE    60
PRRIARSSRR RLNRKSQRKK EIRNLLVQHG MITQEELDLL YPLSKKSIDI WDIRLDGLDR   120
LLNHLEWARL LIHLAQRRGF KSNRKSELKD AETGKVLSSI QVNEKRLFLY RTVGEMWIKD   180
AEFSKYDRRR NSPNEYVFSV SRADLEKEIV TLFEAQRKFQ SSYASKNLQE TYLQIWAHQL   240
PFASGNAILN KVGYCSLLKG KERRIPKATY TFQYFSALDQ VNRTRLGPDF QPFTQEQKEI   300
ILDKMFQRTD YYKKKTIPEV SYYDIRKWLE LDETIQFKGL NYDPNEELKK IEKKPFINLK   360
AFYEIKKVVA NYAERTNEAF STLDYDAIAY ALTVYKTDLD IRSYLKKSNN LSKRCYDDQL   420
IEEELFTLSYT KFGHLSFKAI NHVLPIMQEG RTYQEAIHQL GYDTTNLKKE NRSMFLPLIP   480
DEITNPIVKR AITQARKVVN AIIRRYGSPN SVHIELAREL SKSHDERKKI MTAHDENYKK   540
NKGAISILIE NGILNPTGYD IVRYKLWKEQ GERCAYSLKE IPPDTFFNEL KKERNGSPIL   600
EVDHILPYSQ SFIDSYHNKV LVYSDENRNK GNRIPYTYFL ETNKDWEAFE RYVRSNKLFS   660
KKKREYLLKK TYLPRESELI KERHLNDTRY ASTFLKNFIE QNLQFKEVEV NLRKKRVQTV   720
NGVITAHLRK RWGLEKNRQE TYLHHAMDAI IVACTDHHMV TRITEYYQIK ESNKSVKKPY   780
FPMPWEGFRD ELLSHLASQP IAKKISEELK AGYQSSDYIF VSRMPKRSVT GAAHDQTIRR   840
KGGIDKKGKT IIIKRVRLKD IKFDENGDFK MVGKEQDLAT YEAIKQRYLE HRKNSKKAFE   900
TPLYKPSKKG TGNLIKRVKI EGQTKAFVRE VNGGVAQNSD DKYYMVPIYV               960
PDTVCSELPK KVVKSGKGYE QWLTLDNSFT FKSSLYPYDL VRLVKGNEDR FLYFGTLDID  1020
SDRLNFKDVN KPSKQNEYRY SLKTIENLEK YEVGVLGDLR LVKQETRRIF NR          1072

SEQ ID NO: 61           moltype = AA  length = 1072
FEATURE                 Location/Qualifiers
REGION                  1..1072
                        note = source = /note="Description of Artificial Sequence:
                        Syntheticpolypeptide"
REGION                  1..1072
                        note = source = /note="nAPG08290.1"
source                  1..1072
                        mol_type = protein
                        organism = synthetic construct
SEQUENCE: 61
MSELDYRIGL AIGTNSIGWG VIELFWNKDR ERYEKVRIVD KGVRMFDKAE IPNKGASLAE    60
PRRIARSSRR RLNRKSQRKK EIRNLLVQHG MITQEELDLL YPLSKKSIDI WDIRLDGLDR   120
LLNHLEWARL LIHLAQRRGF KSNRKSELKD AETGKVLSSI QVNEKRLFLY RTVGEMWIKD   180
AEFSKYDRRR NSPNEYVFSV SRADLEKEIV TLFEAQRKFQ SSYASKNLQE TYLQIWAHQL   240
PFASGNAILN KVGYCSLLKG KERRIPKATY TFQYFSALDQ VNRTRLGPDF QPFTQEQKEI   300
ILDKMFQRTD YYKKKTIPEV SYYDIRKWLE LDETIQFKGL NYDPNEELKK IEKKPFINLK   360
AFYEIKKVVA NYAERTNEAF STLDYDAIAY ALTVYKTDLD IRSYLKKSNN LSKRCYDDQL   420
IEEELFTLSYT KFGHLSFKAI NHVLPIMQEG RTYQEAIHQL GYDTTNLKKE NRSMFLPLIP   480
DEITNPIVKR AITQARKVVN AIIRRYGSPN SVHIELAREL SKSHDERKKI MTAHDENYKK   540
NKGAISILIE NGILNPTGYD IVRYKLWKEQ GERCAYSLKE IPPDTFFNEL KKERNGSPIL   600
EVDHILPYSQ SFIDSYHNKV LVYSDENRNK GNRIPYTYFL ETNKDWEAFE RYVRSNKLFS   660
KKKREYLLKK TYLPRESELI KERHLNDTRY ASTFLKNFIE QNLQFKEVEV NLRKKRVQTV   720
NGVITAHLRK RWGLEKNRQE TYLHHAMDAI IVACTDHHMV TRITEYYQIK ESNKSVKKPY   780
FPMPWEGFRD ELLSHLASQP IAKKISEELK AGYQSSDYIF VSRMPKRSVT GAAHDQTIRR   840
KGGIDKKGKT IIIKRVRLKD IKFDENGDFK MVGKEQDLAT YEAIKQRYLE HRKNSKKAFE   900
TPLYKPSKKG TGNLIKRVKI EGQTKAFVRE VNGGVAQNSD LVRVDLFEKD DKYYMVPIYV   960
PDTVCSELPK KVVKSGKGYE QWLTLDNSFT FKSSLYPYDL VRLVKGNEDR FLYFGTLDID  1020
SDRLNFKDVN KPSKQNEYRY SLKTIENLEK YEVGVLGDLR LVKQETRRIF NR          1072
```

```
SEQ ID NO: 62           moltype = DNA   length = 65
FEATURE                 Location/Qualifiers
misc_feature            1..65
                        note = source = /note="Description of Artificial Sequence:
                          Syntheticoligonucleotide"
misc_feature            1..65
                        note = source = /note="CF E60X nAPG06646 Target 1"
source                  1..65
                        mol_type = other DNA
                        organism = synthetic construct
SEQUENCE: 62
aatgagttta ggattttttct ttgaagccag ctatctatcc cattctctgc aaaagaataa    60
aaagt                                                                 65

SEQ ID NO: 63           moltype = DNA   length = 65
FEATURE                 Location/Qualifiers
misc_feature            1..65
                        note = source = /note="Description of Artificial Sequence:
                          Syntheticoligonucleotide"
misc_feature            1..65
                        note = source = /note="CF E60X nAPG06646 Target 2"
source                  1..65
                        mol_type = other DNA
                        organism = synthetic construct
SEQUENCE: 63
attaatgagt ttaggatttt tctttgaagc cagctatcta tcccattctc tgcaaaagaa    60
taaaa                                                                 65

SEQ ID NO: 64           moltype = DNA   length = 65
FEATURE                 Location/Qualifiers
misc_feature            1..65
                        note = source = /note="Description of Artificial Sequence:
                          Syntheticoligonucleotide"
misc_feature            1..65
                        note = source = /note="CF E60X nAPG06646 Target 3"
source                  1..65
                        mol_type = other DNA
                        organism = synthetic construct
SEQUENCE: 64
gcattaatga gtttaggatt tttctttgaa gccagctatc tatcccattc tctgcaaaag    60
aataa                                                                 65

SEQ ID NO: 65           moltype = DNA   length = 65
FEATURE                 Location/Qualifiers
misc_feature            1..65
                        note = source = /note="Description of Artificial Sequence:
                          Syntheticoligonucleotide"
misc_feature            1..65
                        note = source = /note="CF E60X nAPG06646 Target 4"
source                  1..65
                        mol_type = other DNA
                        organism = synthetic construct
SEQUENCE: 65
aagggcatta atgagtttag gattttttctt tgaagccagc tatctatccc attctctgca    60
aaaga                                                                 65

SEQ ID NO: 66           moltype = DNA   length = 65
FEATURE                 Location/Qualifiers
misc_feature            1..65
                        note = source = /note="Description of Artificial Sequence:
                          Syntheticoligonucleotide"
misc_feature            1..65
                        note = source = /note="CF E60X nAPG06646 Target 5"
source                  1..65
                        mol_type = other DNA
                        organism = synthetic construct
SEQUENCE: 66
gaagggcatt aatgagttta ggattttttct ttgaagccag ctatctatcc cattctctgc    60
aaaag                                                                 65

SEQ ID NO: 67           moltype = DNA   length = 65
FEATURE                 Location/Qualifiers
misc_feature            1..65
                        note = source = /note="Description of Artificial Sequence:
                          Syntheticoligonucleotide"
misc_feature            1..65
                        note = source = /note="CF E60X nAPG06646 Target 6"
```

```
                        source          1..65
                                        mol_type = other DNA
                                        organism = synthetic construct
SEQUENCE: 67
cgaagggcat taatgagttt aggattttc tttgaagcca gctatctatc ccattctctg    60
caaaa                                                               65

SEQ ID NO: 68           moltype = DNA   length = 65
FEATURE                 Location/Qualifiers
misc_feature            1..65
                        note = source = /note="Description of Artificial Sequence:
                         Syntheticoligonucleotide"
misc_feature            1..65
                        note = source = /note="CF E60X nAPG09882 Target 1"
source                  1..65
                        mol_type = other DNA
                        organism = synthetic construct
SEQUENCE: 68
gagtttagga ttttctttg aagccagcta tctatcccat tctctgcaaa agaataaaaa    60
gtggg                                                               65

SEQ ID NO: 69           moltype = DNA   length = 65
FEATURE                 Location/Qualifiers
misc_feature            1..65
                        note = source = /note="Description of Artificial Sequence:
                         Syntheticoligonucleotide"
misc_feature            1..65
                        note = source = /note="CF E60X nAPG09882 Target 2"
source                  1..65
                        mol_type = other DNA
                        organism = synthetic construct
SEQUENCE: 69
tgagtttagg attttctttt gaagccagct atctatccca ttctctgcaa agaataaaa    60
agtgg                                                               65

SEQ ID NO: 70           moltype = DNA   length = 65
FEATURE                 Location/Qualifiers
misc_feature            1..65
                        note = source = /note="Description of Artificial Sequence:
                         Syntheticoligonucleotide"
misc_feature            1..65
                        note = source = /note="CF E60X nAPG09882 Target 3"
source                  1..65
                        mol_type = other DNA
                        organism = synthetic construct
SEQUENCE: 70
atgagtttag gattttctt tgaagccagc tatctatccc attctctgca aagaataaa    60
aagtg                                                               65

SEQ ID NO: 71           moltype = DNA   length = 65
FEATURE                 Location/Qualifiers
misc_feature            1..65
                        note = source = /note="Description of Artificial Sequence:
                         Syntheticoligonucleotide"
misc_feature            1..65
                        note = source = /note="CF E60X nAPG09882 Target 4"
source                  1..65
                        mol_type = other DNA
                        organism = synthetic construct
SEQUENCE: 71
agggcattaa tgagtttagg attttctttt gaagccagct atctatccca ttctctgcaa    60
aagaa                                                               65

SEQ ID NO: 72           moltype = DNA   length = 65
FEATURE                 Location/Qualifiers
misc_feature            1..65
                        note = source = /note="Description of Artificial Sequence:
                         Syntheticoligonucleotide"
misc_feature            1..65
                        note = source = /note="CF E60X nAPG00969 Target 1"
source                  1..65
                        mol_type = other DNA
                        organism = synthetic construct
SEQUENCE: 72
gtttaggatt ttctttgaa gccagctatc tatcccattc tctgcaaaag aataaaaagt    60
gggac                                                               65

SEQ ID NO: 73           moltype = DNA   length = 65
FEATURE                 Location/Qualifiers
```

| | |
|---|---|
| misc_feature | 1..65<br>note = source = /note="Description of Artificial Sequence: Syntheticoligonucleotide" |
| misc_feature | 1..65<br>note = source = /note="CF E60X nAPG00969 Target 2" |
| source | 1..65<br>mol_type = other DNA<br>organism = synthetic construct |

SEQUENCE: 73
agtttaggat ttttctttga agccagctat ctatcccatt ctctgcaaaa gaataaaaag 60
tggga 65

| | |
|---|---|
| SEQ ID NO: 74 | moltype = DNA length = 60 |
| FEATURE | Location/Qualifiers |
| misc_feature | 1..60<br>note = source = /note="Description of Artificial Sequence: Syntheticoligonucleotide" |
| misc_feature | 1..60<br>note = source = /note="CF E60X nAPG03850 Target 1" |
| source | 1..60<br>mol_type = other DNA<br>organism = synthetic construct |

SEQUENCE: 74
ggattttct ttgaagccag ctatctatcc cattctctgc aaaagaataa aaagtgggac 60

| | |
|---|---|
| SEQ ID NO: 75 | moltype = DNA length = 60 |
| FEATURE | Location/Qualifiers |
| misc_feature | 1..60<br>note = source = /note="Description of Artificial Sequence: Syntheticoligonucleotide" |
| misc_feature | 1..60<br>note = source = /note="CF E60X nAPG03850 Target 2" |
| source | 1..60<br>mol_type = other DNA<br>organism = synthetic construct |

SEQUENCE: 75
agtttaggat ttttctttga agccagctat ctatcccatt ctctgcaaaa gaataaaaag 60

| | |
|---|---|
| SEQ ID NO: 76 | moltype = DNA length = 65 |
| FEATURE | Location/Qualifiers |
| misc_feature | 1..65<br>note = source = /note="Description of Artificial Sequence: Syntheticoligonucleotide" |
| misc_feature | 1..65<br>note = source = /note="CF E60X nAPG07433.1 Target 1" |
| source | 1..65<br>mol_type = other DNA<br>organism = synthetic construct |

SEQUENCE: 76
gaagggcatt aatgagttta ggattttct ttgaagccag ctatctatcc cattctctgc 60
aaaag 65

| | |
|---|---|
| SEQ ID NO: 77 | moltype = DNA length = 60 |
| FEATURE | Location/Qualifiers |
| misc_feature | 1..60<br>note = source = /note="Description of Artificial Sequence: Syntheticoligonucleotide" |
| misc_feature | 1..60<br>note = source = /note="CF E60X nAPG09748Target 1" |
| source | 1..60<br>mol_type = other DNA<br>organism = synthetic construct |

SEQUENCE: 77
gtcccacttt ttattctttt gcagagaatg ggatagatag ctggcttcaa agaaaaatcc 60

| | |
|---|---|
| SEQ ID NO: 78 | moltype = DNA length = 60 |
| FEATURE | Location/Qualifiers |
| misc_feature | 1..60<br>note = source = /note="Description of Artificial Sequence: Syntheticoligonucleotide" |
| misc_feature | 1..60<br>note = source = /note="CF E60X nAPG07553 Target 1" |
| source | 1..60<br>mol_type = other DNA<br>organism = synthetic construct |

SEQUENCE: 78
agtttaggat ttttctttga agccagctat ctatcccatt ctctgcaaaa gaataaaaag 60

| | |
|---|---|
| SEQ ID NO: 79 | moltype = DNA length = 60 |

```
FEATURE                 Location/Qualifiers
misc_feature            1..60
                        note = source = /note="Description of Artificial Sequence:
                        Syntheticoligonucleotide"
misc_feature            1..60
                        note = source = /note="CF E60X nAPG05586 Target 1"
source                  1..60
                        mol_type = other DNA
                        organism = synthetic construct
SEQUENCE: 79
tttaggattt ttctttgaag ccagctatct atcccattct ctgcaaaaga ataaaaagtg   60

SEQ ID NO: 80           moltype = DNA  length = 25
FEATURE                 Location/Qualifiers
misc_feature            1..25
                        note = source = /note="Description of Artificial Sequence:
                        Syntheticoligonucleotide"
misc_feature            1..25
                        note = source = /note="CF E60X nAPG06646 Target 1"
source                  1..25
                        mol_type = other DNA
                        organism = synthetic construct
SEQUENCE: 80
ttgaagccag ctatctatcc cattc                                        25

SEQ ID NO: 81           moltype = DNA  length = 25
FEATURE                 Location/Qualifiers
misc_feature            1..25
                        note = source = /note="Description of Artificial Sequence:
                        Syntheticoligonucleotide"
misc_feature            1..25
                        note = source = /note="CF E60X nAPG06646 Target 2"
source                  1..25
                        mol_type = other DNA
                        organism = synthetic construct
SEQUENCE: 81
tctttgaagc cagctatcta tccca                                        25

SEQ ID NO: 82           moltype = DNA  length = 25
FEATURE                 Location/Qualifiers
misc_feature            1..25
                        note = source = /note="Description of Artificial Sequence:
                        Syntheticoligonucleotide"
misc_feature            1..25
                        note = source = /note="CF E60X nAPG06646 Target 3"
source                  1..25
                        mol_type = other DNA
                        organism = synthetic construct
SEQUENCE: 82
tttctttgaa gccagctatc tatcc                                        25

SEQ ID NO: 83           moltype = DNA  length = 25
FEATURE                 Location/Qualifiers
misc_feature            1..25
                        note = source = /note="Description of Artificial Sequence:
                        Syntheticoligonucleotide"
misc_feature            1..25
                        note = source = /note="CF E60X nAPG06646 Target 4"
source                  1..25
                        mol_type = other DNA
                        organism = synthetic construct
SEQUENCE: 83
gatttttctt tgaagccagc tatct                                        25

SEQ ID NO: 84           moltype = DNA  length = 25
FEATURE                 Location/Qualifiers
misc_feature            1..25
                        note = source = /note="Description of Artificial Sequence:
                        Syntheticoligonucleotide"
misc_feature            1..25
                        note = source = /note="CF E60X nAPG06646 Target 5"
source                  1..25
                        mol_type = other DNA
                        organism = synthetic construct
SEQUENCE: 84
ggattttctt tgaagccag ctatc                                         25

SEQ ID NO: 85           moltype = DNA  length = 25
FEATURE                 Location/Qualifiers
```

```
misc_feature            1..25
                        note = source = /note="Description of Artificial Sequence:
                           Syntheticoligonucleotide"
misc_feature            1..25
                        note = source = /note="CF E60X nAPG06646 Target 6"
source                  1..25
                        mol_type = other DNA
                        organism = synthetic construct
SEQUENCE: 85
aggatttttc tttgaagcca gctat                                              25

SEQ ID NO: 86           moltype = DNA  length = 25
FEATURE                 Location/Qualifiers
misc_feature            1..25
                        note = source = /note="Description of Artificial Sequence:
                           Syntheticoligonucleotide"
misc_feature            1..25
                        note = source = /note="CF E60X nAPG09882 Target 1"
source                  1..25
                        mol_type = other DNA
                        organism = synthetic construct
SEQUENCE: 86
aagccagcta tctatcccat tctct                                              25

SEQ ID NO: 87           moltype = DNA  length = 25
FEATURE                 Location/Qualifiers
misc_feature            1..25
                        note = source = /note="Description of Artificial Sequence:
                           Syntheticoligonucleotide"
misc_feature            1..25
                        note = source = /note="CF E60X nAPG09882 Target 2"
source                  1..25
                        mol_type = other DNA
                        organism = synthetic construct
SEQUENCE: 87
gaagccagct atctatccca ttctc                                              25

SEQ ID NO: 88           moltype = DNA  length = 25
FEATURE                 Location/Qualifiers
misc_feature            1..25
                        note = source = /note="Description of Artificial Sequence:
                           Syntheticoligonucleotide"
misc_feature            1..25
                        note = source = /note="CF E60X nAPG09882 Target 3"
source                  1..25
                        mol_type = other DNA
                        organism = synthetic construct
SEQUENCE: 88
tgaagccagc tatctatccc attct                                              25

SEQ ID NO: 89           moltype = DNA  length = 25
FEATURE                 Location/Qualifiers
misc_feature            1..25
                        note = source = /note="Description of Artificial Sequence:
                           Syntheticoligonucleotide"
misc_feature            1..25
                        note = source = /note="CF E60X nAPG09882 Target 4"
source                  1..25
                        mol_type = other DNA
                        organism = synthetic construct
SEQUENCE: 89
atttttcttt gaagccagct atcta                                              25

SEQ ID NO: 90           moltype = DNA  length = 25
FEATURE                 Location/Qualifiers
misc_feature            1..25
                        note = source = /note="Description of Artificial Sequence:
                           Syntheticoligonucleotide"
misc_feature            1..25
                        note = source = /note="CF E60X nAPG00969 Target 1"
source                  1..25
                        mol_type = other DNA
                        organism = synthetic construct
SEQUENCE: 90
gccagctatc tatcccattc tctgc                                              25

SEQ ID NO: 91           moltype = DNA  length = 25
FEATURE                 Location/Qualifiers
```

```
misc_feature         1..25
                     note = source = /note="Description of Artificial Sequence:
                        Syntheticoligonucleotide"
misc_feature         1..25
                     note = source = /note="CF E60X nAPG00969 Target 2"
source               1..25
                     mol_type = other DNA
                     organism = synthetic construct
SEQUENCE: 91
agccagctat ctatcccatt ctctg                                              25

SEQ ID NO: 92        moltype = DNA   length = 20
FEATURE              Location/Qualifiers
misc_feature         1..20
                     note = source = /note="Description of Artificial Sequence:
                        Syntheticoligonucleotide"
misc_feature         1..20
                     note = source = /note="CF E60X nAPG03850 Target 1"
source               1..20
                     mol_type = other DNA
                     organism = synthetic construct
SEQUENCE: 92
ctatctatcc cattctctgc                                                    20

SEQ ID NO: 93        moltype = DNA   length = 20
FEATURE              Location/Qualifiers
misc_feature         1..20
                     note = source = /note="Description of Artificial Sequence:
                        Syntheticoligonucleotide"
misc_feature         1..20
                     note = source = /note="CF E60X nAPG03850 Target 2"
source               1..20
                     mol_type = other DNA
                     organism = synthetic construct
SEQUENCE: 93
agccagctat ctatcccatt                                                    20

SEQ ID NO: 94        moltype = DNA   length = 25
FEATURE              Location/Qualifiers
misc_feature         1..25
                     note = source = /note="Description of Artificial Sequence:
                        Syntheticoligonucleotide"
misc_feature         1..25
                     note = source = /note="CF E60X nAPG07433.1 Target 1"
source               1..25
                     mol_type = other DNA
                     organism = synthetic construct
SEQUENCE: 94
ggatttttct ttgaagccag ctatc                                              25

SEQ ID NO: 95        moltype = DNA   length = 20
FEATURE              Location/Qualifiers
misc_feature         1..20
                     note = source = /note="Description of Artificial Sequence:
                        Syntheticoligonucleotide"
misc_feature         1..20
                     note = source = /note="CF E60X nAPG09748Target 1"
source               1..20
                     mol_type = other DNA
                     organism = synthetic construct
SEQUENCE: 95
gcagagaatg ggatagatag                                                    20

SEQ ID NO: 96        moltype = DNA   length = 20
FEATURE              Location/Qualifiers
misc_feature         1..20
                     note = source = /note="Description of Artificial Sequence:
                        Syntheticoligonucleotide"
misc_feature         1..20
                     note = source = /note="CF E60X nAPG07553 Target 1"
source               1..20
                     mol_type = other DNA
                     organism = synthetic construct
SEQUENCE: 96
agccagctat ctatcccatt                                                    20
```

```
SEQ ID NO: 97              moltype = DNA   length = 20
FEATURE                    Location/Qualifiers
misc_feature               1..20
                           note = source = /note="Description of Artificial Sequence:
                             Syntheticoligonucleotide"
misc_feature               1..20
                           note = source = /note="CF E60X nAPG05586 Target 1"
source                     1..20
                           mol_type = other DNA
                           organism = synthetic construct
SEQUENCE: 97
ccagctatct atcccattct                                                       20

SEQ ID NO: 98              moltype = RNA   length = 164
FEATURE                    Location/Qualifiers
misc_feature               1..164
                           note = source = /note="Description of Artificial Sequence:
                             Syntheticpolynucleotide"
misc_feature               1..164
                           note = source = /note="CF E60X nAPG06646 Target 1 sgRNA"
source                     1..164
                           mol_type = other RNA
                           organism = synthetic construct
SEQUENCE: 98
ttgaagccag ctatctatcc cattcgccat aattcctctg taaaacttaa agaaggttta           60
tagagttatt atggtaaggc aatatgccgt ggcgttgggg atcgcctatg tccggtttta          120
ccggatctcc ctaaaggtga ctaactttgg ttagtcacct tttt                           164

SEQ ID NO: 99              moltype = RNA   length = 164
FEATURE                    Location/Qualifiers
misc_feature               1..164
                           note = source = /note="Description of Artificial Sequence:
                             Syntheticpolynucleotide"
misc_feature               1..164
                           note = source = /note="CF E60X nAPG06646 Target 2 sgRNA"
source                     1..164
                           mol_type = other RNA
                           organism = synthetic construct
SEQUENCE: 99
tctttgaagc cagctatcta tcccagccat aattcctctg taaaacttaa agaaggttta           60
tagagttatt atggtaaggc aatatgccgt ggcgttgggg atcgcctatg tccggtttta          120
ccggatctcc ctaaaggtga ctaactttgg ttagtcacct tttt                           164

SEQ ID NO: 100             moltype = RNA   length = 164
FEATURE                    Location/Qualifiers
misc_feature               1..164
                           note = source = /note="Description of Artificial Sequence:
                             Syntheticpolynucleotide"
misc_feature               1..164
                           note = source = /note="CF E60X nAPG06646 Target 3 sgRNA"
source                     1..164
                           mol_type = other RNA
                           organism = synthetic construct
SEQUENCE: 100
tttctttgaa gccagctatc tatccgccat aattcctctg taaaacttaa agaaggttta           60
tagagttatt atggtaaggc aatatgccgt ggcgttgggg atcgcctatg tccggtttta          120
ccggatctcc ctaaaggtga ctaactttgg ttagtcacct tttt                           164

SEQ ID NO: 101             moltype = RNA   length = 164
FEATURE                    Location/Qualifiers
misc_feature               1..164
                           note = source = /note="Description of Artificial Sequence:
                             Syntheticpolynucleotide"
misc_feature               1..164
                           note = source = /note="CF E60X nAPG06646 Target 4 sgRNA"
source                     1..164
                           mol_type = other RNA
                           organism = synthetic construct
SEQUENCE: 101
gattttctt tgaagccagc tatctgccat aattcctctg taaaacttaa agaaggttta            60
tagagttatt atggtaaggc aatatgccgt ggcgttgggg atcgcctatg tccggtttta          120
ccggatctcc ctaaaggtga ctaactttgg ttagtcacct tttt                           164

SEQ ID NO: 102             moltype = RNA   length = 164
FEATURE                    Location/Qualifiers
misc_feature               1..164
                           note = source = /note="Description of Artificial Sequence:
                             Syntheticpolynucleotide"
```

```
misc_feature            1..164
                        note = source = /note="CF E60X nAPG06646 Target 5 sgRNA"
source                  1..164
                        mol_type = other RNA
                        organism = synthetic construct
SEQUENCE: 102
ggattttct  ttgaagccag  ctatcgccat  aattcctctg  taaaacttaa  agaaggttta   60
tagagttatt atggtaaggc aatatgccgt ggcgttgggg atcgcctatg tccggtttta  120
ccggatctcc ctaaaggtga ctaactttgg ttagtcacct tttt                    164

SEQ ID NO: 103          moltype = RNA   length = 164
FEATURE                 Location/Qualifiers
misc_feature            1..164
                        note = source = /note="Description of Artificial Sequence:
                        Syntheticpolynucleotide"
misc_feature            1..164
                        note = source = /note="CF E60X nAPG06646 Target 6 sgRNA"
source                  1..164
                        mol_type = other RNA
                        organism = synthetic construct
SEQUENCE: 103
aggatttttc tttgaagcca gctatgccat aattcctctg taaaacttaa agaaggttta   60
tagagttatt atggtaaggc aatatgccgt ggcgttgggg atcgcctatg tccggtttta  120
ccggatctcc ctaaaggtga ctaactttgg ttagtcacct tttt                    164

SEQ ID NO: 104          moltype = RNA   length = 118
FEATURE                 Location/Qualifiers
misc_feature            1..118
                        note = source = /note="Description of Artificial Sequence:
                        Syntheticpolynucleotide"
misc_feature            1..118
                        note = source = /note="CF E60X nAPG09882 Target 1 sgRNA"
source                  1..118
                        mol_type = other RNA
                        organism = synthetic construct
SEQUENCE: 104
aagccagcta tctatcccat tctctgtttt tgtactctca ataaaaagtt attgagaatc   60
tacaaaaata aggcattttg ccgaatttac cgccctacat atgtagggcg gttttttt    118

SEQ ID NO: 105          moltype = RNA   length = 118
FEATURE                 Location/Qualifiers
misc_feature            1..118
                        note = source = /note="Description of Artificial Sequence:
                        Syntheticpolynucleotide"
misc_feature            1..118
                        note = source = /note="CF E60X nAPG09882 Target 2 sgRNA"
source                  1..118
                        mol_type = other RNA
                        organism = synthetic construct
SEQUENCE: 105
gaagccagct atctatccca ttctctgttt tgtactctca ataaaaagtt attgagaatc   60
tacaaaaata aggcattttg ccgaatttac cgccctacat atgtagggcg gttttttt    118

SEQ ID NO: 106          moltype = RNA   length = 118
FEATURE                 Location/Qualifiers
misc_feature            1..118
                        note = source = /note="Description of Artificial Sequence:
                        Syntheticpolynucleotide"
misc_feature            1..118
                        note = source = /note="CF E60X nAPG09882 Target 3 sgRNA"
source                  1..118
                        mol_type = other RNA
                        organism = synthetic construct
SEQUENCE: 106
tgaagccagc tatctatccc attctgtttt tgtactctca ataaaaagtt attgagaatc   60
tacaaaaata aggcattttg ccgaatttac cgccctacat atgtagggcg gttttttt    118

SEQ ID NO: 107          moltype = RNA   length = 118
FEATURE                 Location/Qualifiers
misc_feature            1..118
                        note = source = /note="Description of Artificial Sequence:
                        Syntheticpolynucleotide"
misc_feature            1..118
                        note = source = /note="CF E60X nAPG09882 Target 4 sgRNA"
source                  1..118
                        mol_type = other RNA
                        organism = synthetic construct
```

```
SEQUENCE: 107
attttttcttt gaagccagct atctagtttt tgtactctca ataaaaagtt attgagaatc   60
tacaaaaata aggcattttg ccgaatttac cgccctacat atgtagggcg gttttttt    118

SEQ ID NO: 108         moltype = RNA   length = 118
FEATURE                Location/Qualifiers
misc_feature           1..118
                       note = source = /note="Description of Artificial Sequence:
                       Syntheticpolynucleotide"
misc_feature           1..118
                       note = source = /note="CF E60X nAPG00969 Target 1 sgRNA"
source                 1..118
                       mol_type = other RNA
                       organism = synthetic construct
SEQUENCE: 108
gccagctatc tatcccattc tctgcgtttt agtactctgt gaaagcacag aatctactaa   60
aataaggcat aatgccgtat ttaatcccat cataattctg atgggatttt ttatattt    118

SEQ ID NO: 109         moltype = RNA   length = 118
FEATURE                Location/Qualifiers
misc_feature           1..118
                       note = source = /note="Description of Artificial Sequence:
                       Syntheticpolynucleotide"
misc_feature           1..118
                       note = source = /note="CF E60X nAPG00969 Target 2 sgRNA"
source                 1..118
                       mol_type = other RNA
                       organism = synthetic construct
SEQUENCE: 109
agccagctat ctatcccatt ctctggtttt agtactctgt gaaagcacag aatctactaa   60
aataaggcat aatgccgtat ttaatcccat cataattctg atgggatttt ttatattt    118

SEQ ID NO: 110         moltype = RNA   length = 163
FEATURE                Location/Qualifiers
misc_feature           1..163
                       note = source = /note="Description of Artificial Sequence:
                       Syntheticpolynucleotide"
misc_feature           1..163
                       note = source = /note="CF E60X nAPG03850 Target 1 sgRNA"
source                 1..163
                       mol_type = other RNA
                       organism = synthetic construct
SEQUENCE: 110
ctatctatcc cattctctgc gctatagttc cataagaaaa aagtttctta agttactata   60
gtaagggcaa tgacccgtgg cgtttgggga tcgccttatc ctggtatgga tattctcccc  120
atgtgaaaag cacctaagca tagcgctatg gtgcttttat ttt                    163

SEQ ID NO: 111         moltype = RNA   length = 163
FEATURE                Location/Qualifiers
misc_feature           1..163
                       note = source = /note="Description of Artificial Sequence:
                       Syntheticpolynucleotide"
misc_feature           1..163
                       note = source = /note="CF E60X nAPG03850 Target 2 sgRNA"
source                 1..163
                       mol_type = other RNA
                       organism = synthetic construct
SEQUENCE: 111
agccagctat ctatcccatt gctatagttc cataagaaaa aagtttctta agttactata   60
gtaagggcaa tgacccgtgg cgtttgggga tcgccttatc ctggtatgga tattctcccc  120
atgtgaaaag cacctaagca tagcgctatg gtgcttttat ttt                    163

SEQ ID NO: 112         moltype = RNA   length = 135
FEATURE                Location/Qualifiers
misc_feature           1..135
                       note = source = /note="Description of Artificial Sequence:
                       Syntheticpolynucleotide"
misc_feature           1..135
                       note = source = /note="CF E60X nAPG07433.1 Target 1 sgRNA"
source                 1..135
                       mol_type = other RNA
                       organism = synthetic construct
SEQUENCE: 112
ggattttct tgaagccag ctatcgtcat agttccatta aagccaaaag tggctttgat     60
gtttctatga taagggtttc gacccgtggc gtcgggatc gcctgcccat tgaaatgggc   120
ttctccccat ttatt                                                   135

SEQ ID NO: 113         moltype = RNA   length = 135
FEATURE                Location/Qualifiers
```

| | | |
|---|---|---|
| misc_feature | 1..135 | |
| | note = source = /note="Description of Artificial Sequence: Syntheticpolynucleotide" | |
| misc_feature | 1..135 | |
| | note = source = /note="CF E60X nAPG09748Target 1 sgRNA" | |
| source | 1..135 | |
| | mol_type = other RNA | |
| | organism = synthetic construct | |

SEQUENCE: 113

```
cgacggttag aggccgtatg tcgatttgct ttaatttcgt gcgtgtgcat tgtcgtcctc    60
cattacaggg cggctaccac gaatagccac gaagtaaaag cttcgtggct agcacgcaga   120
gaatgggata gatag                                                    135
```

| | | |
|---|---|---|
| SEQ ID NO: 114 | moltype = RNA  length = 151 | |
| FEATURE | Location/Qualifiers | |
| misc_feature | 1..151 | |
| | note = source = /note="Description of Artificial Sequence: Syntheticpolynucleotide" | |
| misc_feature | 1..151 | |
| | note = source = /note="CF E60X nAPG07553 Target 1 sgRNA" | |
| source | 1..151 | |
| | mol_type = other RNA | |
| | organism = synthetic construct | |

SEQUENCE: 114

```
agccagctat ctatcccatt gctatagttc cataagaaag cttaagttac tatagtaagg    60
gcaatgaccc gtggcgtttg gggatcgcct catccattac ggatattctc cccatgtgaa   120
aagcacctaa gcataaggct aaggtgcttt t                                  151
```

| | | |
|---|---|---|
| SEQ ID NO: 115 | moltype = RNA  length = 110 | |
| FEATURE | Location/Qualifiers | |
| misc_feature | 1..110 | |
| | note = source = /note="Description of Artificial Sequence: Syntheticpolynucleotide" | |
| misc_feature | 1..110 | |
| | note = source = /note="CF E60X nAPG05586 Target 1 sgRNA" | |
| source | 1..110 | |
| | mol_type = other RNA | |
| | organism = synthetic construct | |

SEQUENCE: 115

```
ccagctatct atcccattct gttattgtac tctcaataaa aagttattga gaatctacaa    60
taataaggca tcttgccgaa tttaccgccc tacatatgta gggcggtttt              110
```

| | | |
|---|---|---|
| SEQ ID NO: 116 | moltype = DNA  length = 65 | |
| FEATURE | Location/Qualifiers | |
| misc_feature | 1..65 | |
| | note = source = /note="Description of Artificial Sequence: Syntheticoligonucleotide" | |
| misc_feature | 1..65 | |
| | note = source = /note="CF G542X nAPG06646 Target 1" | |
| source | 1..65 | |
| | mol_type = other DNA | |
| | organism = synthetic construct | |

SEQUENCE: 116

```
cgttgacctc cactcagtgt gattccacct tctcaaagaa ctatattgtc tttctctgca    60
aactt                                                                65
```

| | | |
|---|---|---|
| SEQ ID NO: 117 | moltype = DNA  length = 65 | |
| FEATURE | Location/Qualifiers | |
| misc_feature | 1..65 | |
| | note = source = /note="Description of Artificial Sequence: Syntheticoligonucleotide" | |
| misc_feature | 1..65 | |
| | note = source = /note="CF G542X nAPG06646 Target 2" | |
| source | 1..65 | |
| | mol_type = other DNA | |
| | organism = synthetic construct | |

SEQUENCE: 117

```
gacctccact cagtgtgatt ccaccttctc aaagaactat attgtctttc tctgcaaact    60
tggag                                                                65
```

| | | |
|---|---|---|
| SEQ ID NO: 118 | moltype = DNA  length = 65 | |
| FEATURE | Location/Qualifiers | |
| misc_feature | 1..65 | |
| | note = source = /note="Description of Artificial Sequence: Syntheticoligonucleotide" | |
| misc_feature | 1..65 | |
| | note = source = /note="CF G542X nAPG06646 Target 3" | |

```
source                  1..65
                        mol_type = other DNA
                        organism = synthetic construct
SEQUENCE: 118
cctccactca gtgtgattcc accttctcaa agaactatat tgtctttctc tgcaaacttg    60
gagat                                                                65

SEQ ID NO: 119          moltype = DNA  length = 65
FEATURE                 Location/Qualifiers
misc_feature            1..65
                        note = source = /note="Description of Artificial Sequence:
                         Syntheticoligonucleotide"
misc_feature            1..65
                        note = source = /note="CF G542X nAPG06646 Target 4"
source                  1..65
                        mol_type = other DNA
                        organism = synthetic construct
SEQUENCE: 119
ccactcagtg tgattccacc ttctcaaaga actatattgt ctttctctgc aaacttggag    60
atgtc                                                                65

SEQ ID NO: 120          moltype = DNA  length = 65
FEATURE                 Location/Qualifiers
misc_feature            1..65
                        note = source = /note="Description of Artificial Sequence:
                         Syntheticoligonucleotide"
misc_feature            1..65
                        note = source = /note="CF G542X nAPG09882 Target 1"
source                  1..65
                        mol_type = other DNA
                        organism = synthetic construct
SEQUENCE: 120
tcttgctcgt tgacctccac tcagtgtgat tccaccttct caaagaacta tattgtcttt    60
ctctg                                                                65

SEQ ID NO: 121          moltype = DNA  length = 65
FEATURE                 Location/Qualifiers
misc_feature            1..65
                        note = source = /note="Description of Artificial Sequence:
                         Syntheticoligonucleotide"
misc_feature            1..65
                        note = source = /note="CF G542X nAPG09882 Target 2"
source                  1..65
                        mol_type = other DNA
                        organism = synthetic construct
SEQUENCE: 121
ttgctcgttg acctccactc agtgtgattc caccttctca agaactata ttgtctttct    60
ctgca                                                                65

SEQ ID NO: 122          moltype = DNA  length = 65
FEATURE                 Location/Qualifiers
misc_feature            1..65
                        note = source = /note="Description of Artificial Sequence:
                         Syntheticoligonucleotide"
misc_feature            1..65
                        note = source = /note="CF G542X nAPG09882 Target 3"
source                  1..65
                        mol_type = other DNA
                        organism = synthetic construct
SEQUENCE: 122
cactcagtgt gattccacct tctcaaagaa ctatattgtc tttctctgca aacttggaga    60
tgtcc                                                                65

SEQ ID NO: 123          moltype = DNA  length = 60
FEATURE                 Location/Qualifiers
misc_feature            1..60
                        note = source = /note="Description of Artificial Sequence:
                         Syntheticoligonucleotide"
misc_feature            1..60
                        note = source = /note="CF G542X nAPG03850 Target 1"
source                  1..60
                        mol_type = other DNA
                        organism = synthetic construct
SEQUENCE: 123
tgacctccac tcagtgtgat tccaccttct caaagaacta tattgtcttt ctctgcaaac    60
```

```
SEQ ID NO: 124          moltype = DNA  length = 60
FEATURE                 Location/Qualifiers
misc_feature            1..60
                        note = source = /note="Description of Artificial Sequence:
                          Syntheticoligonucleotide"
misc_feature            1..60
                        note = source = /note="CF G542X nAPG03850 Target 2"
source                  1..60
                        mol_type = other DNA
                        organism = synthetic construct
SEQUENCE: 124
tcagtgtgat tccaccttct caaagaacta tattgtcttt ctctgcaaac ttggagatgt    60

SEQ ID NO: 125          moltype = DNA  length = 60
FEATURE                 Location/Qualifiers
misc_feature            1..60
                        note = source = /note="Description of Artificial Sequence:
                          Syntheticoligonucleotide"
misc_feature            1..60
                        note = source = /note="CF G542X nAPG09748 Target 1"
source                  1..60
                        mol_type = other DNA
                        organism = synthetic construct
SEQUENCE: 125
agagaaagac aatatagttc tttgagaagg tggaatcaca ctgagtggag gtcaacgagc    60

SEQ ID NO: 126          moltype = DNA  length = 60
FEATURE                 Location/Qualifiers
misc_feature            1..60
                        note = source = /note="Description of Artificial Sequence:
                          Syntheticoligonucleotide"
misc_feature            1..60
                        note = source = /note="CF G542X nAPG07553 Target 1"
source                  1..60
                        mol_type = other DNA
                        organism = synthetic construct
SEQUENCE: 126
tcagtgtgat tccaccttct caaagaacta tattgtcttt ctctgcaaac ttggagatgt    60

SEQ ID NO: 127          moltype = DNA  length = 60
FEATURE                 Location/Qualifiers
misc_feature            1..60
                        note = source = /note="Description of Artificial Sequence:
                          Syntheticoligonucleotide"
misc_feature            1..60
                        note = source = /note="CF G542X nAPG05586 Target 1"
source                  1..60
                        mol_type = other DNA
                        organism = synthetic construct
SEQUENCE: 127
cgttgacctc cactcagtgt gattccacct tctcaaagaa ctatattgtc tttctctgca    60

SEQ ID NO: 128          moltype = DNA  length = 25
FEATURE                 Location/Qualifiers
misc_feature            1..25
                        note = source = /note="Description of Artificial Sequence:
                          Syntheticoligonucleotide"
misc_feature            1..25
                        note = source = /note="CF G542X nAPG06646 Target 1"
source                  1..25
                        mol_type = other DNA
                        organism = synthetic construct
SEQUENCE: 128
gattccacct tctcaaagaa ctata                                          25

SEQ ID NO: 129          moltype = DNA  length = 25
FEATURE                 Location/Qualifiers
misc_feature            1..25
                        note = source = /note="Description of Artificial Sequence:
                          Syntheticoligonucleotide"
misc_feature            1..25
                        note = source = /note="CF G542X nAPG06646 Target 2"
source                  1..25
                        mol_type = other DNA
                        organism = synthetic construct
SEQUENCE: 129
ccaccttctc aaagaactat attgt                                          25
```

-continued

```
SEQ ID NO: 130           moltype = DNA  length = 25
FEATURE                  Location/Qualifiers
misc_feature             1..25
                         note = source = /note="Description of Artificial Sequence:
                         Syntheticoligonucleotide"
misc_feature             1..25
                         note = source = /note="CF G542X nAPG06646 Target 3"
source                   1..25
                         mol_type = other DNA
                         organism = synthetic construct
SEQUENCE: 130
accttctcaa agaactatat tgtct                                               25

SEQ ID NO: 131           moltype = DNA  length = 25
FEATURE                  Location/Qualifiers
misc_feature             1..25
                         note = source = /note="Description of Artificial Sequence:
                         Syntheticoligonucleotide"
misc_feature             1..25
                         note = source = /note="CF G542X nAPG06646 Target 4"
source                   1..25
                         mol_type = other DNA
                         organism = synthetic construct
SEQUENCE: 131
ttctcaaaga actatattgt ctttc                                               25

SEQ ID NO: 132           moltype = DNA  length = 25
FEATURE                  Location/Qualifiers
misc_feature             1..25
                         note = source = /note="Description of Artificial Sequence:
                         Syntheticoligonucleotide"
misc_feature             1..25
                         note = source = /note="CF G542X nAPG09882 Target 1"
source                   1..25
                         mol_type = other DNA
                         organism = synthetic construct
SEQUENCE: 132
tcagtgtgat tccaccttct caaag                                               25

SEQ ID NO: 133           moltype = DNA  length = 25
FEATURE                  Location/Qualifiers
misc_feature             1..25
                         note = source = /note="Description of Artificial Sequence:
                         Syntheticoligonucleotide"
misc_feature             1..25
                         note = source = /note="CF G542X nAPG09882 Target 2"
source                   1..25
                         mol_type = other DNA
                         organism = synthetic construct
SEQUENCE: 133
agtgtgattc caccttctca aagaa                                               25

SEQ ID NO: 134           moltype = DNA  length = 25
FEATURE                  Location/Qualifiers
misc_feature             1..25
                         note = source = /note="Description of Artificial Sequence:
                         Syntheticoligonucleotide"
misc_feature             1..25
                         note = source = /note="CF G542X nAPG09882 Target 3"
source                   1..25
                         mol_type = other DNA
                         organism = synthetic construct
SEQUENCE: 134
tctcaaagaa ctatattgtc tttct                                               25

SEQ ID NO: 135           moltype = DNA  length = 20
FEATURE                  Location/Qualifiers
misc_feature             1..20
                         note = source = /note="Description of Artificial Sequence:
                         Syntheticoligonucleotide"
misc_feature             1..20
                         note = source = /note="CF G542X nAPG03850 Target 1"
source                   1..20
                         mol_type = other DNA
                         organism = synthetic construct
SEQUENCE: 135
tccaccttct caaagaacta                                                     20

SEQ ID NO: 136           moltype = DNA  length = 20
```

```
FEATURE               Location/Qualifiers
misc_feature          1..20
                      note = source = /note="Description of Artificial Sequence:
                        Syntheticoligonucleotide"
misc_feature          1..20
                      note = source = /note="CF G542X nAPG03850 Target 2"
source                1..20
                      mol_type = other DNA
                      organism = synthetic construct
SEQUENCE: 136
caaagaacta tattgtcttt                                                    20

SEQ ID NO: 137        moltype = DNA  length = 20
FEATURE               Location/Qualifiers
misc_feature          1..20
                      note = source = /note="Description of Artificial Sequence:
                        Syntheticoligonucleotide"
misc_feature          1..20
                      note = source = /note="CF G542X nAPG09748 Target 1"
source                1..20
                      mol_type = other DNA
                      organism = synthetic construct
SEQUENCE: 137
tttgagaagg tggaatcaca                                                    20

SEQ ID NO: 138        moltype = DNA  length = 20
FEATURE               Location/Qualifiers
misc_feature          1..20
                      note = source = /note="Description of Artificial Sequence:
                        Syntheticoligonucleotide"
misc_feature          1..20
                      note = source = /note="CF G542X nAPG07553 Target 1"
source                1..20
                      mol_type = other DNA
                      organism = synthetic construct
SEQUENCE: 138
caaagaacta tattgtcttt                                                    20

SEQ ID NO: 139        moltype = DNA  length = 20
FEATURE               Location/Qualifiers
misc_feature          1..20
                      note = source = /note="Description of Artificial Sequence:
                        Syntheticoligonucleotide"
misc_feature          1..20
                      note = source = /note="CF G542X nAPG05586 Target 1"
source                1..20
                      mol_type = other DNA
                      organism = synthetic construct
SEQUENCE: 139
gattccacct tctcaaagaa                                                    20

SEQ ID NO: 140        moltype = RNA  length = 164
FEATURE               Location/Qualifiers
misc_feature          1..164
                      note = source = /note="Description of Artificial Sequence:
                        Syntheticpolynucleotide"
misc_feature          1..164
                      note = source = /note="CF G542X nAPG06646 Target 1 sgRNA"
source                1..164
                      mol_type = other RNA
                      organism = synthetic construct
SEQUENCE: 140
gattccacct tctcaaagaa ctatagccat aattcctctg taaaacttaa agaaggttta        60
tagagttatt atggtaaggc aatatgccgt ggcgttgggg atcgcctatg tccggtttta       120
ccggatctcc ctaaaggtga ctaactttgg ttagtcacct tttt                        164

SEQ ID NO: 141        moltype = RNA  length = 164
FEATURE               Location/Qualifiers
misc_feature          1..164
                      note = source = /note="Description of Artificial Sequence:
                        Syntheticpolynucleotide"
misc_feature          1..164
                      note = source = /note="CF G542X nAPG06646 Target 2 sgRNA"
source                1..164
                      mol_type = other RNA
                      organism = synthetic construct
```

-continued

```
SEQUENCE: 141
ccaccttctc aaagaactat attgtgccat aattcctctg taaaacttaa agaaggttta    60
tagagttatt atggtaaggc aatatgccgt ggcgttgggg atcgcctatg tccggtttta   120
ccggatctcc ctaaaggtga ctaactttgg ttagtcacct tttt                    164

SEQ ID NO: 142          moltype = RNA   length = 164
FEATURE                 Location/Qualifiers
misc_feature            1..164
                        note = source = /note="Description of Artificial Sequence:
                           Syntheticpolynucleotide"
misc_feature            1..164
                        note = source = /note="CF G542X nAPG06646 Target 3 sgRNA"
source                  1..164
                        mol_type = other RNA
                        organism = synthetic construct
SEQUENCE: 142
accttctcaa agaactatat tgtctgccat aattcctctg taaaacttaa agaaggttta    60
tagagttatt atggtaaggc aatatgccgt ggcgttgggg atcgcctatg tccggtttta   120
ccggatctcc ctaaaggtga ctaactttgg ttagtcacct tttt                    164

SEQ ID NO: 143          moltype = RNA   length = 164
FEATURE                 Location/Qualifiers
misc_feature            1..164
                        note = source = /note="Description of Artificial Sequence:
                           Syntheticpolynucleotide"
misc_feature            1..164
                        note = source = /note="CF G542X nAPG06646 Target 4 sgRNA"
source                  1..164
                        mol_type = other RNA
                        organism = synthetic construct
SEQUENCE: 143
ttctcaaaga actatattgt ctttcgccat aattcctctg taaaacttaa agaaggttta    60
tagagttatt atggtaaggc aatatgccgt ggcgttgggg atcgcctatg tccggtttta   120
ccggatctcc ctaaaggtga ctaactttgg ttagtcacct tttt                    164

SEQ ID NO: 144          moltype = RNA   length = 118
FEATURE                 Location/Qualifiers
misc_feature            1..118
                        note = source = /note="Description of Artificial Sequence:
                           Syntheticpolynucleotide"
misc_feature            1..118
                        note = source = /note="CF G542X nAPG09882 Target 1 sgRNA"
source                  1..118
                        mol_type = other RNA
                        organism = synthetic construct
SEQUENCE: 144
tcagtgtgat tccaccttct caaaggtttt tgtactctca ataaaaagtt attgagaatc    60
tacaaaaata aggcattttg ccgaatttac cgccctacat atgtagggcg gttttttt    118

SEQ ID NO: 145          moltype = RNA   length = 118
FEATURE                 Location/Qualifiers
misc_feature            1..118
                        note = source = /note="Description of Artificial Sequence:
                           Syntheticpolynucleotide"
misc_feature            1..118
                        note = source = /note="CF G542X nAPG09882 Target 2 sgRNA"
source                  1..118
                        mol_type = other RNA
                        organism = synthetic construct
SEQUENCE: 145
agtgtgattc caccttctca aagaagtttt tgtactctca ataaaaagtt attgagaatc    60
tacaaaaata aggcattttg ccgaatttac cgccctacat atgtagggcg gttttttt    118

SEQ ID NO: 146          moltype = RNA   length = 118
FEATURE                 Location/Qualifiers
misc_feature            1..118
                        note = source = /note="Description of Artificial Sequence:
                           Syntheticpolynucleotide"
misc_feature            1..118
                        note = source = /note="CF G542X nAPG09882 Target 3 sgRNA"
source                  1..118
                        mol_type = other RNA
                        organism = synthetic construct
SEQUENCE: 146
tctcaaagaa ctatattgtc tttctgtttt tgtactctca ataaaaagtt attgagaatc    60
tacaaaaata aggcattttg ccgaatttac cgccctacat atgtagggcg gttttttt    118

SEQ ID NO: 147          moltype = RNA   length = 163
FEATURE                 Location/Qualifiers
```

```
misc_feature               1..163
                           note = source = /note="Description of Artificial Sequence:
                              Syntheticpolynucleotide"
misc_feature               1..163
                           note = source = /note="CF G542X nAPG03850 Target 1 sgRNA"
source                     1..163
                           mol_type = other RNA
                           organism = synthetic construct
SEQUENCE: 147
tccaccttct caaagaacta gctatagttc cataagaaaa aagtttctta agttactata    60
gtaagggcaa tgacccgtgg cgtttgggga tcgccttatc ctggtatgga tattctcccc   120
atgtgaaaag cacctaagca tagcgctatg gtgcttttat ttt                     163

SEQ ID NO: 148             moltype = RNA  length = 163
FEATURE                    Location/Qualifiers
misc_feature               1..163
                           note = source = /note="Description of Artificial Sequence:
                              Syntheticpolynucleotide"
misc_feature               1..163
                           note = source = /note="CF G542X nAPG03850 Target 2 sgRNA"
source                     1..163
                           mol_type = other RNA
                           organism = synthetic construct
SEQUENCE: 148
caaagaacta tattgtcttt gctatagttc cataagaaaa aagtttctta agttactata    60
gtaagggcaa tgacccgtgg cgtttgggga tcgccttatc ctggtatgga tattctcccc   120
atgtgaaaag cacctaagca tagcgctatg gtgcttttat ttt                     163

SEQ ID NO: 149             moltype = RNA  length = 135
FEATURE                    Location/Qualifiers
misc_feature               1..135
                           note = source = /note="Description of Artificial Sequence:
                              Syntheticpolynucleotide"
misc_feature               1..135
                           note = source = /note="CF G542X nAPG09748 Target 1 sgRNA"
source                     1..135
                           mol_type = other RNA
                           organism = synthetic construct
SEQUENCE: 149
cgacggttag aggccgtatg tcgatttgct ttaatttcgt gcgtgtgcat tgtcgtcctc    60
cattacaggg cggctaccac gaatagccac gaagtaaaag cttcgtggct agcactttga   120
gaaggtggaa tcaca                                                    135

SEQ ID NO: 150             moltype = RNA  length = 151
FEATURE                    Location/Qualifiers
misc_feature               1..151
                           note = source = /note="Description of Artificial Sequence:
                              Syntheticpolynucleotide"
misc_feature               1..151
                           note = source = /note="CF G542X nAPG07553 Target 1 sgRNA"
source                     1..151
                           mol_type = other RNA
                           organism = synthetic construct
SEQUENCE: 150
caaagaacta tattgtcttt gctatagttc cataagaaag cttaagttac tatagtaagg    60
gcaatgaccc gtggcgtttg gggatcgcct catccattac ggatattctc cccatgtgaa   120
aagcacctaa gcataaggct aaggtgcttt t                                  151

SEQ ID NO: 151             moltype = RNA  length = 110
FEATURE                    Location/Qualifiers
misc_feature               1..110
                           note = source = /note="Description of Artificial Sequence:
                              Syntheticpolynucleotide"
misc_feature               1..110
                           note = source = /note="CF G542X nAPG05586 Target 1 sgRNA"
source                     1..110
                           mol_type = other RNA
                           organism = synthetic construct
SEQUENCE: 151
gattccacct tctcaaagaa gttattgtac tctcaataaa aagttattga gaatctacaa    60
taataaggca tcttgccgaa tttaccgccc tacatatgta gggcggtttt              110

SEQ ID NO: 152             moltype = DNA  length = 65
FEATURE                    Location/Qualifiers
misc_feature               1..65
                           note = source = /note="Description of Artificial Sequence:
                              Syntheticoligonucleotide"
```

```
misc_feature            1..65
                        note = source = /note="CF Q493X nAPG09882 Target 1"
source                  1..65
                        mol_type = other DNA
                        organism = synthetic construct
SEQUENCE: 152
gatatttctt ttaatggtgc caggcataat ccaggaaaac taagaacaga atgaaattct      60
tccac                                                                 65

SEQ ID NO: 153          moltype = DNA  length = 65
FEATURE                 Location/Qualifiers
misc_feature            1..65
                        note = source = /note="Description of Artificial Sequence:
                         Syntheticoligonucleotide"
misc_feature            1..65
                        note = source = /note="CF Q493X nAPG09882 Target 2"
source                  1..65
                        mol_type = other DNA
                        organism = synthetic construct
SEQUENCE: 153
atattttctt taatggtgcc aggcataatc caggaaaact aagaacagaa tgaaattctt      60
ccact                                                                 65

SEQ ID NO: 154          moltype = DNA  length = 65
FEATURE                 Location/Qualifiers
misc_feature            1..65
                        note = source = /note="Description of Artificial Sequence:
                         Syntheticoligonucleotide"
misc_feature            1..65
                        note = source = /note="CF Q493X nAPG09882 Target 3"
source                  1..65
                        mol_type = other DNA
                        organism = synthetic construct
SEQUENCE: 154
ttttctttaa tggtgccagg cataatccag gaaaactaag aacagaatga aattcttcca      60
ctgtg                                                                 65

SEQ ID NO: 155          moltype = DNA  length = 65
FEATURE                 Location/Qualifiers
misc_feature            1..65
                        note = source = /note="Description of Artificial Sequence:
                         Syntheticoligonucleotide"
misc_feature            1..65
                        note = source = /note="CF Q493X nAPG09882 Target 4"
source                  1..65
                        mol_type = other DNA
                        organism = synthetic construct
SEQUENCE: 155
tttctttaat ggtgccaggc ataatccagg aaaactaaga acagaatgaa attcttccac      60
tgtgc                                                                 65

SEQ ID NO: 156          moltype = DNA  length = 65
FEATURE                 Location/Qualifiers
misc_feature            1..65
                        note = source = /note="Description of Artificial Sequence:
                         Syntheticoligonucleotide"
misc_feature            1..65
                        note = source = /note="CF Q493X nAPG09882 Target 5"
source                  1..65
                        mol_type = other DNA
                        organism = synthetic construct
SEQUENCE: 156
ttctttaatg gtgccaggca taatccagga aaactaagaa cagaatgaaa ttcttccact      60
gtgct                                                                 65

SEQ ID NO: 157          moltype = DNA  length = 60
FEATURE                 Location/Qualifiers
misc_feature            1..60
                        note = source = /note="Description of Artificial Sequence:
                         Syntheticoligonucleotide"
misc_feature            1..60
                        note = source = /note="CF Q493X nAPG09748 Target 1"
source                  1..60
                        mol_type = other DNA
                        organism = synthetic construct
SEQUENCE: 157
taagcacagt ggaagaattt cattctgttc ttagttttcc tggattatgc ctggcaccat      60

SEQ ID NO: 158          moltype = DNA  length = 60
```

```
FEATURE                 Location/Qualifiers
misc_feature            1..60
                        note = source = /note="Description of Artificial Sequence:
                        Syntheticoligonucleotide"
misc_feature            1..60
                        note = source = /note="CF Q493X nAPG09748 Target 2"
source                  1..60
                        mol_type = other DNA
                        organism = synthetic construct
SEQUENCE: 158
aagcacagtg gaagaatttc attctgttct tagttttcct ggattatgcc tggcaccatt    60

SEQ ID NO: 159          moltype = DNA   length = 60
FEATURE                 Location/Qualifiers
misc_feature            1..60
                        note = source = /note="Description of Artificial Sequence:
                        Syntheticoligonucleotide"
misc_feature            1..60
                        note = source = /note="CF Q493X nAPG09748 Target 3"
source                  1..60
                        mol_type = other DNA
                        organism = synthetic construct
SEQUENCE: 159
acagtggaag aatttcattc tgttcttagt tttcctggat tatgcctggc accattaaag    60

SEQ ID NO: 160          moltype = DNA   length = 60
FEATURE                 Location/Qualifiers
misc_feature            1..60
                        note = source = /note="Description of Artificial Sequence:
                        Syntheticoligonucleotide"
misc_feature            1..60
                        note = source = /note="CF Q493X nAPG09748 Target 4"
source                  1..60
                        mol_type = other DNA
                        organism = synthetic construct
SEQUENCE: 160
ggaagaattt cattctgttc ttagttttcc tggattatgc ctggcaccat taaagaaaat    60

SEQ ID NO: 161          moltype = DNA   length = 65
FEATURE                 Location/Qualifiers
misc_feature            1..65
                        note = source = /note="Description of Artificial Sequence:
                        Syntheticoligonucleotide"
misc_feature            1..65
                        note = source = /note="CF Q493X nAPG00969 Target 1"
source                  1..65
                        mol_type = other DNA
                        organism = synthetic construct
SEQUENCE: 161
gatattttct ttaatggtgc caggcataat ccaggaaaac taagaacaga atgaaattct    60
tccac                                                                65

SEQ ID NO: 162          moltype = DNA   length = 65
FEATURE                 Location/Qualifiers
misc_feature            1..65
                        note = source = /note="Description of Artificial Sequence:
                        Syntheticoligonucleotide"
misc_feature            1..65
                        note = source = /note="CF Q493X nAPG00969 Target 2"
source                  1..65
                        mol_type = other DNA
                        organism = synthetic construct
SEQUENCE: 162
ttctttaatg gtgccaggca taatccagga aaactaagaa cagaatgaaa ttcttccact    60
gtgct                                                                65

SEQ ID NO: 163          moltype = DNA   length = 65
FEATURE                 Location/Qualifiers
misc_feature            1..65
                        note = source = /note="Description of Artificial Sequence:
                        Syntheticoligonucleotide"
misc_feature            1..65
                        note = source = /note="CF Q493X nAPG06646 Target 1"
source                  1..65
                        mol_type = other DNA
                        organism = synthetic construct
SEQUENCE: 163
tttaatggtg ccaggcataa tccaggaaaa ctaagaacag aatgaaattc ttccactgtg    60
cttaa                                                                65
```

```
SEQ ID NO: 164          moltype = DNA   length = 65
FEATURE                 Location/Qualifiers
misc_feature            1..65
                        note = source = /note="Description of Artificial Sequence:
                        Syntheticoligonucleotide"
misc_feature            1..65
                        note = source = /note="CF Q493X nAPG06646 Target 2"
source                  1..65
                        mol_type = other DNA
                        organism = synthetic construct
SEQUENCE: 164
aatggtgcca ggcataatcc aggaaaacta agaacagaat gaaattcttc cactgtgctt   60
aattt                                                               65

SEQ ID NO: 165          moltype = DNA   length = 60
FEATURE                 Location/Qualifiers
misc_feature            1..60
                        note = source = /note="Description of Artificial Sequence:
                        Syntheticoligonucleotide"
misc_feature            1..60
                        note = source = /note="CF Q493X nAPG01604 Target 1"
source                  1..60
                        mol_type = other DNA
                        organism = synthetic construct
SEQUENCE: 165
ttctttaatg gtgccaggca taatccagga aaactaagaa cagaatgaaa ttcttccact   60

SEQ ID NO: 166          moltype = DNA   length = 60
FEATURE                 Location/Qualifiers
misc_feature            1..60
                        note = source = /note="Description of Artificial Sequence:
                        Syntheticoligonucleotide"
misc_feature            1..60
                        note = source = /note="CF Q493X nAPG01604 Target 2"
source                  1..60
                        mol_type = other DNA
                        organism = synthetic construct
SEQUENCE: 166
ttaatggtgc caggcataat ccaggaaaac taagaacaga atgaaattct tccactgtgc   60

SEQ ID NO: 167          moltype = DNA   length = 60
FEATURE                 Location/Qualifiers
misc_feature            1..60
                        note = source = /note="Description of Artificial Sequence:
                        Syntheticoligonucleotide"
misc_feature            1..60
                        note = source = /note="CF Q493X nAPG03850 Target 1"
source                  1..60
                        mol_type = other DNA
                        organism = synthetic construct
SEQUENCE: 167
ctttaatggt gccaggcata atccaggaaa actaagaaca gaatgaaatt cttccactgt   60

SEQ ID NO: 168          moltype = DNA   length = 60
FEATURE                 Location/Qualifiers
misc_feature            1..60
                        note = source = /note="Description of Artificial Sequence:
                        Syntheticoligonucleotide"
misc_feature            1..60
                        note = source = /note="CF Q493X nAPG07553 Target 1"
source                  1..60
                        mol_type = other DNA
                        organism = synthetic construct
SEQUENCE: 168
ctttaatggt gccaggcata atccaggaaa actaagaaca gaatgaaatt cttccactgt   60

SEQ ID NO: 169          moltype = DNA   length = 25
FEATURE                 Location/Qualifiers
misc_feature            1..25
                        note = source = /note="Description of Artificial Sequence:
                        Syntheticoligonucleotide"
misc_feature            1..25
                        note = source = /note="CF Q493X nAPG09882 Target 1"
source                  1..25
                        mol_type = other DNA
                        organism = synthetic construct
SEQUENCE: 169
caggcataat ccaggaaaac taaga                                         25
```

```
SEQ ID NO: 170          moltype = DNA  length = 25
FEATURE                 Location/Qualifiers
misc_feature            1..25
                        note = source = /note="Description of Artificial Sequence:
                          Syntheticoligonucleotide"
misc_feature            1..25
                        note = source = /note="CF Q493X nAPG09882 Target 2"
source                  1..25
                        mol_type = other DNA
                        organism = synthetic construct
SEQUENCE: 170
aggcataatc caggaaaact aagaa                                                25

SEQ ID NO: 171          moltype = DNA  length = 25
FEATURE                 Location/Qualifiers
misc_feature            1..25
                        note = source = /note="Description of Artificial Sequence:
                          Syntheticoligonucleotide"
misc_feature            1..25
                        note = source = /note="CF Q493X nAPG09882 Target 3"
source                  1..25
                        mol_type = other DNA
                        organism = synthetic construct
SEQUENCE: 171
cataatccag gaaaactaag aacag                                                25

SEQ ID NO: 172          moltype = DNA  length = 25
FEATURE                 Location/Qualifiers
misc_feature            1..25
                        note = source = /note="Description of Artificial Sequence:
                          Syntheticoligonucleotide"
misc_feature            1..25
                        note = source = /note="CF Q493X nAPG09882 Target 4"
source                  1..25
                        mol_type = other DNA
                        organism = synthetic construct
SEQUENCE: 172
ataatccagg aaaactaaga acaga                                                25

SEQ ID NO: 173          moltype = DNA  length = 25
FEATURE                 Location/Qualifiers
misc_feature            1..25
                        note = source = /note="Description of Artificial Sequence:
                          Syntheticoligonucleotide"
misc_feature            1..25
                        note = source = /note="CF Q493X nAPG09882 Target 5"
source                  1..25
                        mol_type = other DNA
                        organism = synthetic construct
SEQUENCE: 173
taatccagga aaactaagaa cagaa                                                25

SEQ ID NO: 174          moltype = DNA  length = 20
FEATURE                 Location/Qualifiers
misc_feature            1..20
                        note = source = /note="Description of Artificial Sequence:
                          Syntheticoligonucleotide"
misc_feature            1..20
                        note = source = /note="CF Q493X nAPG09748 Target 1"
source                  1..20
                        mol_type = other DNA
                        organism = synthetic construct
SEQUENCE: 174
cattctgttc ttagttttcc                                                      20

SEQ ID NO: 175          moltype = DNA  length = 20
FEATURE                 Location/Qualifiers
misc_feature            1..20
                        note = source = /note="Description of Artificial Sequence:
                          Syntheticoligonucleotide"
misc_feature            1..20
                        note = source = /note="CF Q493X nAPG09748 Target 2"
source                  1..20
                        mol_type = other DNA
                        organism = synthetic construct
SEQUENCE: 175
attctgttct tagttttcct                                                      20
```

```
SEQ ID NO: 176           moltype = DNA   length = 20
FEATURE                  Location/Qualifiers
misc_feature             1..20
                         note = source = /note="Description of Artificial Sequence:
                         Syntheticoligonucleotide"
misc_feature             1..20
                         note = source = /note="CF Q493X nAPG09748 Target 3"
source                   1..20
                         mol_type = other DNA
                         organism = synthetic construct
SEQUENCE: 176
tgttcttagt tttcctggat                                                         20

SEQ ID NO: 177           moltype = DNA   length = 20
FEATURE                  Location/Qualifiers
misc_feature             1..20
                         note = source = /note="Description of Artificial Sequence:
                         Syntheticoligonucleotide"
misc_feature             1..20
                         note = source = /note="CF Q493X nAPG09748 Target 4"
source                   1..20
                         mol_type = other DNA
                         organism = synthetic construct
SEQUENCE: 177
ttagttttcc tggattatgc                                                         20

SEQ ID NO: 178           moltype = DNA   length = 25
FEATURE                  Location/Qualifiers
misc_feature             1..25
                         note = source = /note="Description of Artificial Sequence:
                         Syntheticoligonucleotide"
misc_feature             1..25
                         note = source = /note="CF Q493X nAPG00969 Target 1"
source                   1..25
                         mol_type = other DNA
                         organism = synthetic construct
SEQUENCE: 178
caggcataat ccaggaaaac taaga                                                   25

SEQ ID NO: 179           moltype = DNA   length = 25
FEATURE                  Location/Qualifiers
misc_feature             1..25
                         note = source = /note="Description of Artificial Sequence:
                         Syntheticoligonucleotide"
misc_feature             1..25
                         note = source = /note="CF Q493X nAPG00969 Target 2"
source                   1..25
                         mol_type = other DNA
                         organism = synthetic construct
SEQUENCE: 179
taatccagga aaactaagaa cagaa                                                   25

SEQ ID NO: 180           moltype = DNA   length = 25
FEATURE                  Location/Qualifiers
misc_feature             1..25
                         note = source = /note="Description of Artificial Sequence:
                         Syntheticoligonucleotide"
misc_feature             1..25
                         note = source = /note="CF Q493X nAPG06646 Target 1"
source                   1..25
                         mol_type = other DNA
                         organism = synthetic construct
SEQUENCE: 180
tccaggaaaa ctaagaacag aatga                                                   25

SEQ ID NO: 181           moltype = DNA   length = 25
FEATURE                  Location/Qualifiers
misc_feature             1..25
                         note = source = /note="Description of Artificial Sequence:
                         Syntheticoligonucleotide"
misc_feature             1..25
                         note = source = /note="CF Q493X nAPG06646 Target 2"
source                   1..25
                         mol_type = other DNA
                         organism = synthetic construct
SEQUENCE: 181
aggaaaacta agaacagaat gaaat                                                   25

SEQ ID NO: 182           moltype = DNA   length = 20
```

```
FEATURE                 Location/Qualifiers
misc_feature            1..20
                        note = source = /note="Description of Artificial Sequence:
                        Syntheticoligonucleotide"
misc_feature            1..20
                        note = source = /note="CF Q493X nAPG01604 Target 1"
source                  1..20
                        mol_type = other DNA
                        organism = synthetic construct
SEQUENCE: 182
taatccagga aaactaagaa                                                20

SEQ ID NO: 183          moltype = DNA  length = 20
FEATURE                 Location/Qualifiers
misc_feature            1..20
                        note = source = /note="Description of Artificial Sequence:
                        Syntheticoligonucleotide"
misc_feature            1..20
                        note = source = /note="CF Q493X nAPG01604 Target 2"
source                  1..20
                        mol_type = other DNA
                        organism = synthetic construct
SEQUENCE: 183
ccaggaaaac taagaacaga                                                20

SEQ ID NO: 184          moltype = DNA  length = 20
FEATURE                 Location/Qualifiers
misc_feature            1..20
                        note = source = /note="Description of Artificial Sequence:
                        Syntheticoligonucleotide"
misc_feature            1..20
                        note = source = /note="CF Q493X nAPG03850 Target 1"
source                  1..20
                        mol_type = other DNA
                        organism = synthetic construct
SEQUENCE: 184
atccaggaaa actaagaaca                                                20

SEQ ID NO: 185          moltype = DNA  length = 20
FEATURE                 Location/Qualifiers
misc_feature            1..20
                        note = source = /note="Description of Artificial Sequence:
                        Syntheticoligonucleotide"
misc_feature            1..20
                        note = source = /note="CF Q493X nAPG07553 Target 1"
source                  1..20
                        mol_type = other DNA
                        organism = synthetic construct
SEQUENCE: 185
atccaggaaa actaagaaca                                                20

SEQ ID NO: 186          moltype = RNA  length = 118
FEATURE                 Location/Qualifiers
misc_feature            1..118
                        note = source = /note="Description of Artificial Sequence:
                        Syntheticpolynucleotide"
misc_feature            1..118
                        note = source = /note="CF Q493X nAPG09882 Target 1 sgRNA"
source                  1..118
                        mol_type = other RNA
                        organism = synthetic construct
SEQUENCE: 186
caggcataat ccaggaaaac taagagtttt tgtactctca ataaaaagtt attgagaatc     60
tacaaaaata aggcattttg ccgaatttac cgccctacat atgtagggcg gttttttt     118

SEQ ID NO: 187          moltype = RNA  length = 118
FEATURE                 Location/Qualifiers
misc_feature            1..118
                        note = source = /note="Description of Artificial Sequence:
                        Syntheticpolynucleotide"
misc_feature            1..118
                        note = source = /note="CF Q493X nAPG09882 Target 2 sgRNA"
source                  1..118
                        mol_type = other RNA
                        organism = synthetic construct
SEQUENCE: 187
aggcataatc caggaaaact aagaagtttt tgtactctca ataaaaagtt attgagaatc     60
tacaaaaata aggcattttg ccgaatttac cgccctacat atgtagggcg gttttttt     118
```

| SEQ ID NO: 188 | moltype = RNA  length = 118 |
| --- | --- |
| FEATURE | Location/Qualifiers |
| misc_feature | 1..118 |
| | note = source = /note="Description of Artificial Sequence: Syntheticpolynucleotide" |
| misc_feature | 1..118 |
| | note = source = /note="CF Q493X nAPG09882 Target 3 sgRNA" |
| source | 1..118 |
| | mol_type = other RNA |
| | organism = synthetic construct |

SEQUENCE: 188

```
cataatccag gaaaactaag aacaggtttt tgtactctca ataaaaagtt attgagaatc   60
tacaaaaata aggcattttg ccgaatttac cgccctacat atgtagggcg gttttttt   118
```

| SEQ ID NO: 189 | moltype = RNA  length = 118 |
| --- | --- |
| FEATURE | Location/Qualifiers |
| misc_feature | 1..118 |
| | note = source = /note="Description of Artificial Sequence: Syntheticpolynucleotide" |
| misc_feature | 1..118 |
| | note = source = /note="CF Q493X nAPG09882 Target 4 sgRNA" |
| source | 1..118 |
| | mol_type = other RNA |
| | organism = synthetic construct |

SEQUENCE: 189

```
ataatccagg aaaactaaga acagagtttt tgtactctca ataaaaagtt attgagaatc   60
tacaaaaata aggcattttg ccgaatttac cgccctacat atgtagggcg gttttttt   118
```

| SEQ ID NO: 190 | moltype = RNA  length = 118 |
| --- | --- |
| FEATURE | Location/Qualifiers |
| misc_feature | 1..118 |
| | note = source = /note="Description of Artificial Sequence: Syntheticpolynucleotide" |
| misc_feature | 1..118 |
| | note = source = /note="CF Q493X nAPG09882 Target 5 sgRNA" |
| source | 1..118 |
| | mol_type = other RNA |
| | organism = synthetic construct |

SEQUENCE: 190

```
taatccagga aaactaagaa cagagttttt gtactctca ataaaaagtt attgagaatc   60
tacaaaaata aggcattttg ccgaatttac cgccctacat atgtagggcg gttttttt   118
```

| SEQ ID NO: 191 | moltype = RNA  length = 135 |
| --- | --- |
| FEATURE | Location/Qualifiers |
| misc_feature | 1..135 |
| | note = source = /note="Description of Artificial Sequence: Syntheticpolynucleotide" |
| misc_feature | 1..135 |
| | note = source = /note="CF Q493X nAPG09748 Target 1 sgRNA" |
| source | 1..135 |
| | mol_type = other RNA |
| | organism = synthetic construct |

SEQUENCE: 191

```
cgacggttag aggccgtatg tcgatttgct ttaatttcgt gcgtgtgcat tgtcgtcctc   60
cattacaggg cggctaccac gaatagccac gaagtaaaag cttcgtggct agcaccattc  120
tgttcttagt tttcc                                                   135
```

| SEQ ID NO: 192 | moltype = RNA  length = 135 |
| --- | --- |
| FEATURE | Location/Qualifiers |
| misc_feature | 1..135 |
| | note = source = /note="Description of Artificial Sequence: Syntheticpolynucleotide" |
| misc_feature | 1..135 |
| | note = source = /note="CF Q493X nAPG09748 Target 2 sgRNA" |
| source | 1..135 |
| | mol_type = other RNA |
| | organism = synthetic construct |

SEQUENCE: 192

```
cgacggttag aggccgtatg tcgatttgct ttaatttcgt gcgtgtgcat tgtcgtcctc   60
cattacaggg cggctaccac gaatagccac gaagtaaaag cttcgtggct agcacattct  120
gttcttagtt ttcct                                                   135
```

| SEQ ID NO: 193 | moltype = RNA  length = 135 |
| --- | --- |
| FEATURE | Location/Qualifiers |
| misc_feature | 1..135 |
| | note = source = /note="Description of Artificial Sequence: Syntheticpolynucleotide" |
| misc_feature | 1..135 |
| | note = source = /note="CF Q493X nAPG09748 Target 3 sgRNA" |

```
source              1..135
                    mol_type = other RNA
                    organism = synthetic construct
SEQUENCE: 193
cgacggttag aggccgtatg tcgatttgct ttaatttcgt gcgtgtgcat tgtcgtcctc    60
cattacaggg cggctaccac gaatagccac gaagtaaaag cttcgtggct agcactgttc   120
ttagttttcc tggat                                                   135

SEQ ID NO: 194          moltype = RNA  length = 135
FEATURE                 Location/Qualifiers
misc_feature            1..135
                        note = source = /note="Description of Artificial Sequence:
                        Syntheticpolynucleotide"
misc_feature            1..135
                        note = source = /note="CF Q493X nAPG09748 Target 4 sgRNA"
source                  1..135
                        mol_type = other RNA
                        organism = synthetic construct
SEQUENCE: 194
cgacggttag aggccgtatg tcgatttgct ttaatttcgt gcgtgtgcat tgtcgtcctc    60
cattacaggg cggctaccac gaatagccac gaagtaaaag cttcgtggct agcacttagt   120
tttcctggat tatgc                                                   135

SEQ ID NO: 195          moltype = RNA  length = 118
FEATURE                 Location/Qualifiers
misc_feature            1..118
                        note = source = /note="Description of Artificial Sequence:
                        Syntheticpolynucleotide"
misc_feature            1..118
                        note = source = /note="CF Q493X nAPG00969 Target 1 sgRNA"
source                  1..118
                        mol_type = other RNA
                        organism = synthetic construct
SEQUENCE: 195
caggcataat ccaggaaaac taagagtttt agtactctgt gaaagcacag aatctactaa    60
aataaggcat aatgccgtat ttaatcccat cataattctg atgggatttt ttatattt    118

SEQ ID NO: 196          moltype = RNA  length = 118
FEATURE                 Location/Qualifiers
misc_feature            1..118
                        note = source = /note="Description of Artificial Sequence:
                        Syntheticpolynucleotide"
misc_feature            1..118
                        note = source = /note="CF Q493X nAPG00969 Target 2 sgRNA"
source                  1..118
                        mol_type = other RNA
                        organism = synthetic construct
SEQUENCE: 196
taatccagga aaactaagaa cagaagtttt agtactctgt gaaagcacag aatctactaa    60
aataaggcat aatgccgtat ttaatcccat cataattctg atgggatttt ttatattt    118

SEQ ID NO: 197          moltype = RNA  length = 164
FEATURE                 Location/Qualifiers
misc_feature            1..164
                        note = source = /note="Description of Artificial Sequence:
                        Syntheticpolynucleotide"
misc_feature            1..164
                        note = source = /note="CF Q493X nAPG06646 Target 1 sgRNA"
source                  1..164
                        mol_type = other RNA
                        organism = synthetic construct
SEQUENCE: 197
tccaggaaaa ctaagaacag aatgagccat aattcctctg taaaacttaa agaaggttta    60
tagagttatt atggtaaggc aatatgccgt ggcgttgggg atcgcctatg tccggtttta   120
ccggatctcc ctaaaggtga ctaactttgg ttagtcacct tttt                    164

SEQ ID NO: 198          moltype = RNA  length = 164
FEATURE                 Location/Qualifiers
misc_feature            1..164
                        note = source = /note="Description of Artificial Sequence:
                        Syntheticpolynucleotide"
misc_feature            1..164
                        note = source = /note="CF Q493X nAPG06646 Target 2 sgRNA"
source                  1..164
                        mol_type = other RNA
                        organism = synthetic construct
```

```
SEQUENCE: 198
aggaaaacta agaacagaat gaaatgccat aattcctctg taaaacttaa agaaggttta    60
tagagttatt atggtaaggc aatatgccgt ggcgttgggg atcgcctatg tccggtttta   120
ccggatctcc ctaaaggtga ctaactttgg ttagtcacct tttt                    164

SEQ ID NO: 199            moltype = RNA   length = 105
FEATURE                   Location/Qualifiers
misc_feature              1..105
                          note = source = /note="Description of Artificial Sequence:
                          Syntheticpolynucleotide"
misc_feature              1..105
                          note = source = /note="CF Q493X nAPG01604 Target 1 sgRNA"
source                    1..105
                          mol_type = other RNA
                          organism = synthetic construct
SEQUENCE: 199
taatccagga aaactaagaa gttttagtac tctgtaaaaa gttacagaat ctactaaaac    60
aaggcaaaat gccgtgttta tctcgtcaac ttgttggcga gattt                   105

SEQ ID NO: 200            moltype = RNA   length = 105
FEATURE                   Location/Qualifiers
misc_feature              1..105
                          note = source = /note="Description of Artificial Sequence:
                          Syntheticpolynucleotide"
misc_feature              1..105
                          note = source = /note="CF Q493X nAPG01604 Target 2 sgRNA"
source                    1..105
                          mol_type = other RNA
                          organism = synthetic construct
SEQUENCE: 200
ccaggaaaac taagaacaga gttttagtac tctgtaaaaa gttacagaat ctactaaaac    60
aaggcaaaat gccgtgttta tctcgtcaac ttgttggcga gattt                   105

SEQ ID NO: 201            moltype = RNA   length = 163
FEATURE                   Location/Qualifiers
misc_feature              1..163
                          note = source = /note="Description of Artificial Sequence:
                          Syntheticpolynucleotide"
misc_feature              1..163
                          note = source = /note="CF Q493X nAPG03850 Target 1 sgRNA"
source                    1..163
                          mol_type = other RNA
                          organism = synthetic construct
SEQUENCE: 201
atccaggaaa actaagaaca gctatagttc cataagaaaa aagtttctta agttactata    60
gtaagggcaa tgacccgtgg cgtttgggga tcgccttatc ctggtatgga tattctcccc   120
atgtgaaaag cacctaagca tagcgctatg gtgcttttat ttt                     163

SEQ ID NO: 202            moltype = RNA   length = 151
FEATURE                   Location/Qualifiers
misc_feature              1..151
                          note = source = /note="Description of Artificial Sequence:
                          Syntheticpolynucleotide"
misc_feature              1..151
                          note = source = /note="CF Q493X nAPG07553 Target 1 sgRNA"
source                    1..151
                          mol_type = other RNA
                          organism = synthetic construct
SEQUENCE: 202
atccaggaaa actaagaaca gctatagttc cataagaaag cttaagttac tatagtaagg    60
gcaatgaccc gtggcgtttg gggatcgcct catccattac ggatattctc cccatgtgaa   120
aagcacctaa gcataaggct aaggtgcttt t                                  151

SEQ ID NO: 203            moltype = DNA   length = 65
FEATURE                   Location/Qualifiers
misc_feature              1..65
                          note = source = /note="Description of Artificial Sequence:
                          Syntheticoligonucleotide"
misc_feature              1..65
                          note = source = /note="CF R553X nAPG06646 Target 1"
source                    1..65
                          mol_type = other DNA
                          organism = synthetic construct
SEQUENCE: 203
ccaataatta gttattcacc ttgctaaaga aattcttgct cattgacctc cactcagtgt    60
gattc                                                               65

SEQ ID NO: 204            moltype = DNA   length = 65
FEATURE                   Location/Qualifiers
```

-continued

```
misc_feature            1..65
                        note = source = /note="Description of Artificial Sequence:
                        Syntheticoligonucleotide"
misc_feature            1..65
                        note = source = /note="CF R553X nAPG06646 Target 2"
source                  1..65
                        mol_type = other DNA
                        organism = synthetic construct
SEQUENCE: 204
caataattag ttattcacct tgctaaagaa attcttgctc attgacctcc actcagtgtg    60
attcc                                                                65

SEQ ID NO: 205          moltype = DNA  length = 65
FEATURE                 Location/Qualifiers
misc_feature            1..65
                        note = source = /note="Description of Artificial Sequence:
                        Syntheticoligonucleotide"
misc_feature            1..65
                        note = source = /note="CF R553X nAPG06646 Target 3"
source                  1..65
                        mol_type = other DNA
                        organism = synthetic construct
SEQUENCE: 205
ataattagtt attcaccttg ctaaagaaat tcttgctcat tgacctccac tcagtgtgat    60
tccac                                                                65

SEQ ID NO: 206          moltype = DNA  length = 65
FEATURE                 Location/Qualifiers
misc_feature            1..65
                        note = source = /note="Description of Artificial Sequence:
                        Syntheticoligonucleotide"
misc_feature            1..65
                        note = source = /note="CF R553X nAPG06646 Target 4"
source                  1..65
                        mol_type = other DNA
                        organism = synthetic construct
SEQUENCE: 206
aattagttat tcaccttgct aaagaaattc ttgctcattg acctccactc agtgtgattc    60
cacct                                                                65

SEQ ID NO: 207          moltype = DNA  length = 65
FEATURE                 Location/Qualifiers
misc_feature            1..65
                        note = source = /note="Description of Artificial Sequence:
                        Syntheticoligonucleotide"
misc_feature            1..65
                        note = source = /note="CF R553X nAPG06646 Target 5"
source                  1..65
                        mol_type = other DNA
                        organism = synthetic construct
SEQUENCE: 207
tcaccttgct aaagaaattc ttgctcattg acctccactc agtgtgattc caccttctcc    60
aagaa                                                                65

SEQ ID NO: 208          moltype = DNA  length = 65
FEATURE                 Location/Qualifiers
misc_feature            1..65
                        note = source = /note="Description of Artificial Sequence:
                        Syntheticoligonucleotide"
misc_feature            1..65
                        note = source = /note="CF R553X nAPG06646 Target 6"
source                  1..65
                        mol_type = other DNA
                        organism = synthetic construct
SEQUENCE: 208
caccttgcta aagaaattct tgctcattga cctccactca gtgtgattcc accttctcca    60
agaac                                                                65

SEQ ID NO: 209          moltype = DNA  length = 65
FEATURE                 Location/Qualifiers
misc_feature            1..65
                        note = source = /note="Description of Artificial Sequence:
                        Syntheticoligonucleotide"
misc_feature            1..65
                        note = source = /note="CF R553X nAPG06646 Target 7"
source                  1..65
                        mol_type = other DNA
                        organism = synthetic construct
```

```
SEQUENCE: 209
ccttgctaaa gaaattcttg ctcattgacc tccactcagt gtgattccac cttctccaag    60
aacta                                                                65

SEQ ID NO: 210           moltype = DNA   length = 65
FEATURE                  Location/Qualifiers
misc_feature             1..65
                         note = source = /note="Description of Artificial Sequence:
                             Syntheticoligonucleotide"
misc_feature             1..65
                         note = source = /note="CF R553X nAPG07433.1 Target 1"
source                   1..65
                         mol_type = other DNA
                         organism = synthetic construct
SEQUENCE: 210
ccaataatta gttattcacc ttgctaaaga aattcttgct cattgacctc cactcagtgt    60
gattc                                                                65

SEQ ID NO: 211           moltype = DNA   length = 65
FEATURE                  Location/Qualifiers
misc_feature             1..65
                         note = source = /note="Description of Artificial Sequence:
                             Syntheticoligonucleotide"
misc_feature             1..65
                         note = source = /note="CF R553X nAPG07433.1 Target 2"
source                   1..65
                         mol_type = other DNA
                         organism = synthetic construct
SEQUENCE: 211
tcaccttgct aaagaaattc ttgctcattg acctccactc agtgtgattc caccttctcc    60
aagaa                                                                65

SEQ ID NO: 212           moltype = DNA   length = 65
FEATURE                  Location/Qualifiers
misc_feature             1..65
                         note = source = /note="Description of Artificial Sequence:
                             Syntheticoligonucleotide"
misc_feature             1..65
                         note = source = /note="CF R553X nAPG07433.1 Target 3"
source                   1..65
                         mol_type = other DNA
                         organism = synthetic construct
SEQUENCE: 212
ccttgctaaa gaaattcttg ctcattgacc tccactcagt gtgattccac cttctccaag    60
aacta                                                                65

SEQ ID NO: 213           moltype = DNA   length = 65
FEATURE                  Location/Qualifiers
misc_feature             1..65
                         note = source = /note="Description of Artificial Sequence:
                             Syntheticoligonucleotide"
misc_feature             1..65
                         note = source = /note="CF R553X nAPG09882 Target 1"
source                   1..65
                         mol_type = other DNA
                         organism = synthetic construct
SEQUENCE: 213
aataattagt tattcacctt gctaaagaaa ttcttgctca ttgacctcca ctcagtgtga    60
ttcca                                                                65

SEQ ID NO: 214           moltype = DNA   length = 65
FEATURE                  Location/Qualifiers
misc_feature             1..65
                         note = source = /note="Description of Artificial Sequence:
                             Syntheticoligonucleotide"
misc_feature             1..65
                         note = source = /note="CF R553X nAPG09882 Target 2"
source                   1..65
                         mol_type = other DNA
                         organism = synthetic construct
SEQUENCE: 214
attagttatt caccttgcta aagaaattct tgctcattga cctccactca gtgtgattcc    60
acctt                                                                65

SEQ ID NO: 215           moltype = DNA   length = 65
FEATURE                  Location/Qualifiers
misc_feature             1..65
                         note = source = /note="Description of Artificial Sequence:
                             Syntheticoligonucleotide"
```

```
misc_feature            1..65
                        note = source = /note="CF R553X nAPG09882 Target 3"
source                  1..65
                        mol_type = other DNA
                        organism = synthetic construct
SEQUENCE: 215
tattcacctt gctaaagaaa ttcttgctca ttgacctcca ctcagtgtga ttccaccttc   60
tccaa                                                               65

SEQ ID NO: 216          moltype = DNA  length = 60
FEATURE                 Location/Qualifiers
misc_feature            1..60
                        note = source = /note="Description of Artificial Sequence:
                         Syntheticoligonucleotide"
misc_feature            1..60
                        note = source = /note="CF R553X nAPG03850 Target 1"
source                  1..60
                        mol_type = other DNA
                        organism = synthetic construct
SEQUENCE: 216
tattcacctt gctaaagaaa ttcttgctca ttgacctcca ctcagtgtga ttccaccttc   60

SEQ ID NO: 217          moltype = DNA  length = 60
FEATURE                 Location/Qualifiers
misc_feature            1..60
                        note = source = /note="Description of Artificial Sequence:
                         Syntheticoligonucleotide"
misc_feature            1..60
                        note = source = /note="CF R553X nAPG03850 Target 2"
source                  1..60
                        mol_type = other DNA
                        organism = synthetic construct
SEQUENCE: 217
ttcaccttgc taaagaaatt cttgctcatt gacctccact cagtgtgatt ccaccttctc   60

SEQ ID NO: 218          moltype = DNA  length = 60
FEATURE                 Location/Qualifiers
misc_feature            1..60
                        note = source = /note="Description of Artificial Sequence:
                         Syntheticoligonucleotide"
misc_feature            1..60
                        note = source = /note="CF R553X nAPG03850 Target 3"
source                  1..60
                        mol_type = other DNA
                        organism = synthetic construct
SEQUENCE: 218
caccttgcta aagaaattct tgctcattga cctccactca gtgtgattcc accttctcca   60

SEQ ID NO: 219          moltype = DNA  length = 25
FEATURE                 Location/Qualifiers
misc_feature            1..25
                        note = source = /note="Description of Artificial Sequence:
                         Syntheticoligonucleotide"
misc_feature            1..25
                        note = source = /note="CF R553X nAPG06646 Target 1"
source                  1..25
                        mol_type = other DNA
                        organism = synthetic construct
SEQUENCE: 219
ttgctaaaga aattcttgct cattg                                         25

SEQ ID NO: 220          moltype = DNA  length = 25
FEATURE                 Location/Qualifiers
misc_feature            1..25
                        note = source = /note="Description of Artificial Sequence:
                         Syntheticoligonucleotide"
misc_feature            1..25
                        note = source = /note="CF R553X nAPG06646 Target 2"
source                  1..25
                        mol_type = other DNA
                        organism = synthetic construct
SEQUENCE: 220
tgctaaagaa attcttgctc attga                                         25

SEQ ID NO: 221          moltype = DNA  length = 25
FEATURE                 Location/Qualifiers
misc_feature            1..25
                        note = source = /note="Description of Artificial Sequence:
                         Syntheticoligonucleotide"
```

```
misc_feature           1..25
                       note = source = /note="CF R553X nAPG06646 Target 3"
source                 1..25
                       mol_type = other DNA
                       organism = synthetic construct
SEQUENCE: 221
ctaaagaaat tcttgctcat tgacc                                              25

SEQ ID NO: 222         moltype = DNA  length = 25
FEATURE                Location/Qualifiers
misc_feature           1..25
                       note = source = /note="Description of Artificial Sequence:
                        Syntheticoligonucleotide"
misc_feature           1..25
                       note = source = /note="CF R553X nAPG06646 Target 4"
source                 1..25
                       mol_type = other DNA
                       organism = synthetic construct
SEQUENCE: 222
aaagaaattc ttgctcattg acctc                                              25

SEQ ID NO: 223         moltype = DNA  length = 25
FEATURE                Location/Qualifiers
misc_feature           1..25
                       note = source = /note="Description of Artificial Sequence:
                        Syntheticoligonucleotide"
misc_feature           1..25
                       note = source = /note="CF R553X nAPG06646 Target 5"
source                 1..25
                       mol_type = other DNA
                       organism = synthetic construct
SEQUENCE: 223
ttgctcattg acctccactc agtgt                                              25

SEQ ID NO: 224         moltype = DNA  length = 25
FEATURE                Location/Qualifiers
misc_feature           1..25
                       note = source = /note="Description of Artificial Sequence:
                        Syntheticoligonucleotide"
misc_feature           1..25
                       note = source = /note="CF R553X nAPG06646 Target 6"
source                 1..25
                       mol_type = other DNA
                       organism = synthetic construct
SEQUENCE: 224
tgctcattga cctccactca gtgtg                                              25

SEQ ID NO: 225         moltype = DNA  length = 25
FEATURE                Location/Qualifiers
misc_feature           1..25
                       note = source = /note="Description of Artificial Sequence:
                        Syntheticoligonucleotide"
misc_feature           1..25
                       note = source = /note="CF R553X nAPG06646 Target 7"
source                 1..25
                       mol_type = other DNA
                       organism = synthetic construct
SEQUENCE: 225
ctcattgacc tccactcagt gtgat                                              25

SEQ ID NO: 226         moltype = DNA  length = 25
FEATURE                Location/Qualifiers
misc_feature           1..25
                       note = source = /note="Description of Artificial Sequence:
                        Syntheticoligonucleotide"
misc_feature           1..25
                       note = source = /note="CF R553X nAPG07433.1 Target 1"
source                 1..25
                       mol_type = other DNA
                       organism = synthetic construct
SEQUENCE: 226
ttgctaaaga aattcttgct cattg                                              25

SEQ ID NO: 227         moltype = DNA  length = 25
FEATURE                Location/Qualifiers
misc_feature           1..25
                       note = source = /note="Description of Artificial Sequence:
                        Syntheticoligonucleotide"
```

```
misc_feature           1..25
                       note = source = /note="CF R553X nAPG07433.1 Target 2"
source                 1..25
                       mol_type = other DNA
                       organism = synthetic construct
SEQUENCE: 227
ttgctcattg acctccactc agtgt                                              25

SEQ ID NO: 228         moltype = DNA  length = 25
FEATURE                Location/Qualifiers
misc_feature           1..25
                       note = source = /note="Description of Artificial Sequence:
                        Syntheticoligonucleotide"
misc_feature           1..25
                       note = source = /note="CF R553X nAPG07433.1 Target 3"
source                 1..25
                       mol_type = other DNA
                       organism = synthetic construct
SEQUENCE: 228
ctcattgacc tccactcagt gtgat                                              25

SEQ ID NO: 229         moltype = DNA  length = 25
FEATURE                Location/Qualifiers
misc_feature           1..25
                       note = source = /note="Description of Artificial Sequence:
                        Syntheticoligonucleotide"
misc_feature           1..25
                       note = source = /note="CF R553X nAPG09882 Target 1"
source                 1..25
                       mol_type = other DNA
                       organism = synthetic construct
SEQUENCE: 229
gctaaagaaa ttcttgctca ttgac                                              25

SEQ ID NO: 230         moltype = DNA  length = 25
FEATURE                Location/Qualifiers
misc_feature           1..25
                       note = source = /note="Description of Artificial Sequence:
                        Syntheticoligonucleotide"
misc_feature           1..25
                       note = source = /note="CF R553X nAPG09882 Target 2"
source                 1..25
                       mol_type = other DNA
                       organism = synthetic construct
SEQUENCE: 230
aagaaattct tgctcattga cctcc                                              25

SEQ ID NO: 231         moltype = DNA  length = 25
FEATURE                Location/Qualifiers
misc_feature           1..25
                       note = source = /note="Description of Artificial Sequence:
                        Syntheticoligonucleotide"
misc_feature           1..25
                       note = source = /note="CF R553X nAPG09882 Target 3"
source                 1..25
                       mol_type = other DNA
                       organism = synthetic construct
SEQUENCE: 231
ttcttgctca ttgacctcca ctcag                                              25

SEQ ID NO: 232         moltype = DNA  length = 20
FEATURE                Location/Qualifiers
misc_feature           1..20
                       note = source = /note="Description of Artificial Sequence:
                        Syntheticoligonucleotide"
misc_feature           1..20
                       note = source = /note="CF R553X nAPG03850 Target 1"
source                 1..20
                       mol_type = other DNA
                       organism = synthetic construct
SEQUENCE: 232
ttcttgctca ttgacctcca                                                    20

SEQ ID NO: 233         moltype = DNA  length = 20
FEATURE                Location/Qualifiers
misc_feature           1..20
                       note = source = /note="Description of Artificial Sequence:
                        Syntheticoligonucleotide"
```

```
misc_feature         1..20
                     note = source = /note="CF R553X nAPG03850 Target 2"
source               1..20
                     mol_type = other DNA
                     organism = synthetic construct
SEQUENCE: 233
cttgctcatt gacctccact                                                20

SEQ ID NO: 234       moltype = DNA  length = 20
FEATURE              Location/Qualifiers
misc_feature         1..20
                     note = source = /note="Description of Artificial Sequence:
                     Syntheticoligonucleotide"
misc_feature         1..20
                     note = source = /note="CF R553X nAPG03850 Target 3"
source               1..20
                     mol_type = other DNA
                     organism = synthetic construct
SEQUENCE: 234
tgctcattga cctccactca                                                20

SEQ ID NO: 235       moltype = RNA  length = 164
FEATURE              Location/Qualifiers
misc_feature         1..164
                     note = source = /note="Description of Artificial Sequence:
                     Syntheticpolynucleotide"
misc_feature         1..164
                     note = source = /note="CF R553X nAPG06646 Target 1 sgRNA"
source               1..164
                     mol_type = other RNA
                     organism = synthetic construct
SEQUENCE: 235
ttgctaaaga aattcttgct cattggccat aattcctctg taaaacttaa agaaggttta   60
tagagttatt atggtaaggc aatatgccgt ggcgttgggg atcgcctatg tccggtttta  120
ccggatctcc ctaaaggtga ctaactttgg ttagtcacct tttt                   164

SEQ ID NO: 236       moltype = RNA  length = 164
FEATURE              Location/Qualifiers
misc_feature         1..164
                     note = source = /note="Description of Artificial Sequence:
                     Syntheticpolynucleotide"
misc_feature         1..164
                     note = source = /note="CF R553X nAPG06646 Target 2 sgRNA"
source               1..164
                     mol_type = other RNA
                     organism = synthetic construct
SEQUENCE: 236
tgctaaagaa attcttgctc attgagccat aattcctctg taaaacttaa agaaggttta   60
tagagttatt atggtaaggc aatatgccgt ggcgttgggg atcgcctatg tccggtttta  120
ccggatctcc ctaaaggtga ctaactttgg ttagtcacct tttt                   164

SEQ ID NO: 237       moltype = RNA  length = 164
FEATURE              Location/Qualifiers
misc_feature         1..164
                     note = source = /note="Description of Artificial Sequence:
                     Syntheticpolynucleotide"
misc_feature         1..164
                     note = source = /note="CF R553X nAPG06646 Target 3 sgRNA"
source               1..164
                     mol_type = other RNA
                     organism = synthetic construct
SEQUENCE: 237
ctaaagaaat tcttgctcat tgaccgccat aattcctctg taaaacttaa agaaggttta   60
tagagttatt atggtaaggc aatatgccgt ggcgttgggg atcgcctatg tccggtttta  120
ccggatctcc ctaaaggtga ctaactttgg ttagtcacct tttt                   164

SEQ ID NO: 238       moltype = RNA  length = 164
FEATURE              Location/Qualifiers
misc_feature         1..164
                     note = source = /note="Description of Artificial Sequence:
                     Syntheticpolynucleotide"
misc_feature         1..164
                     note = source = /note="CF R553X nAPG06646 Target 4 sgRNA"
source               1..164
                     mol_type = other RNA
                     organism = synthetic construct
```

-continued

```
SEQUENCE: 238
aaagaaattc ttgctcattg acctcgccat aattcctctg taaaacttaa agaaggttta    60
tagagttatt atggtaaggc aatatgccgt ggcgttgggg atcgcctatg tccggtttta   120
ccggatctcc ctaaaggtga ctaactttgg ttagtcacct tttt                    164

SEQ ID NO: 239          moltype = RNA   length = 164
FEATURE                 Location/Qualifiers
misc_feature            1..164
                        note = source = /note="Description of Artificial Sequence:
                          Syntheticpolynucleotide"
misc_feature            1..164
                        note = source = /note="CF R553X nAPG06646 Target 5 sgRNA"
source                  1..164
                        mol_type = other RNA
                        organism = synthetic construct
SEQUENCE: 239
ttgctcattg acctccactc agtgtgccat aattcctctg taaaacttaa agaaggttta    60
tagagttatt atggtaaggc aatatgccgt ggcgttgggg atcgcctatg tccggtttta   120
ccggatctcc ctaaaggtga ctaactttgg ttagtcacct tttt                    164

SEQ ID NO: 240          moltype = RNA   length = 164
FEATURE                 Location/Qualifiers
misc_feature            1..164
                        note = source = /note="Description of Artificial Sequence:
                          Syntheticpolynucleotide"
misc_feature            1..164
                        note = source = /note="CF R553X nAPG06646 Target 6 sgRNA"
source                  1..164
                        mol_type = other RNA
                        organism = synthetic construct
SEQUENCE: 240
tgctcattga cctccactca gtgtggccat aattcctctg taaaacttaa agaaggttta    60
tagagttatt atggtaaggc aatatgccgt ggcgttgggg atcgcctatg tccggtttta   120
ccggatctcc ctaaaggtga ctaactttgg ttagtcacct tttt                    164

SEQ ID NO: 241          moltype = RNA   length = 164
FEATURE                 Location/Qualifiers
misc_feature            1..164
                        note = source = /note="Description of Artificial Sequence:
                          Syntheticpolynucleotide"
misc_feature            1..164
                        note = source = /note="CF R553X nAPG06646 Target 7 sgRNA"
source                  1..164
                        mol_type = other RNA
                        organism = synthetic construct
SEQUENCE: 241
ctcattgacc tccactcagt gtgatgccat aattcctctg taaaacttaa agaaggttta    60
tagagttatt atggtaaggc aatatgccgt ggcgttgggg atcgcctatg tccggtttta   120
ccggatctcc ctaaaggtga ctaactttgg ttagtcacct tttt                    164

SEQ ID NO: 242          moltype = RNA   length = 135
FEATURE                 Location/Qualifiers
misc_feature            1..135
                        note = source = /note="Description of Artificial Sequence:
                          Syntheticpolynucleotide"
misc_feature            1..135
                        note = source = /note="CF R553X nAPG07433.1 Target 1 sgRNA"
source                  1..135
                        mol_type = other RNA
                        organism = synthetic construct
SEQUENCE: 242
ttgctaaaga aattcttgct cattggtcat agtccatta aagccaaaag tggctttgat     60
gtttctatga taagggtttc gaccgtgggc gtcgggatc gcctgccat tgaaatgggc    120
ttctccccat ttatt                                                    135

SEQ ID NO: 243          moltype = RNA   length = 135
FEATURE                 Location/Qualifiers
misc_feature            1..135
                        note = source = /note="Description of Artificial Sequence:
                          Syntheticpolynucleotide"
misc_feature            1..135
                        note = source = /note="CF R553X nAPG07433.1 Target 2 sgRNA"
source                  1..135
                        mol_type = other RNA
                        organism = synthetic construct
SEQUENCE: 243
ttgctcattg acctccactc agtgtgtcat agtccatta aagccaaaag tggctttgat     60
gtttctatga taagggtttc gaccgtgggc gtcgggatc gcctgccat tgaaatgggc    120
ttctccccat ttatt                                                    135
```

```
SEQ ID NO: 244          moltype = RNA   length = 135
FEATURE                 Location/Qualifiers
misc_feature            1..135
                        note = source = /note="Description of Artificial Sequence:
                         Syntheticpolynucleotide"
misc_feature            1..135
                        note = source = /note="CF R553X nAPG07433.1 Target 3 sgRNA"
source                  1..135
                        mol_type = other RNA
                        organism = synthetic construct
SEQUENCE: 244
ctcattgacc tccactcagt gtgatgtcat agttccatta aagccaaaag tggctttgat   60
gtttctatga taagggtttc gacccgtggc gtcgggatc gcctgcccat tgaaatgggc  120
ttctccccat ttatt                                                  135

SEQ ID NO: 245          moltype = RNA   length = 118
FEATURE                 Location/Qualifiers
misc_feature            1..118
                        note = source = /note="Description of Artificial Sequence:
                         Syntheticpolynucleotide"
misc_feature            1..118
                        note = source = /note="CF R553X nAPG09882 Target 1 sgRNA"
source                  1..118
                        mol_type = other RNA
                        organism = synthetic construct
SEQUENCE: 245
gctaaagaaa ttcttgctca ttgacgtttt tgtactctca ataaaaagtt attgagaatc   60
tacaaaaata aggcattttg ccgaatttac cgccctacat atgtagggcg gttttttt   118

SEQ ID NO: 246          moltype = RNA   length = 118
FEATURE                 Location/Qualifiers
misc_feature            1..118
                        note = source = /note="Description of Artificial Sequence:
                         Syntheticpolynucleotide"
misc_feature            1..118
                        note = source = /note="CF R553X nAPG09882 Target 2 sgRNA"
source                  1..118
                        mol_type = other RNA
                        organism = synthetic construct
SEQUENCE: 246
aagaaattct tgctcattga cctccgtttt tgtactctca ataaaaagtt attgagaatc   60
tacaaaaata aggcattttg ccgaatttac cgccctacat atgtagggcg gttttttt   118

SEQ ID NO: 247          moltype = RNA   length = 118
FEATURE                 Location/Qualifiers
misc_feature            1..118
                        note = source = /note="Description of Artificial Sequence:
                         Syntheticpolynucleotide"
misc_feature            1..118
                        note = source = /note="CF R553X nAPG09882 Target 3 sgRNA"
source                  1..118
                        mol_type = other RNA
                        organism = synthetic construct
SEQUENCE: 247
ttcttgctca ttgacctcca ctcaggtttt tgtactctca ataaaaagtt attgagaatc   60
tacaaaaata aggcattttg ccgaatttac cgccctacat atgtagggcg gttttttt   118

SEQ ID NO: 248          moltype = RNA   length = 163
FEATURE                 Location/Qualifiers
misc_feature            1..163
                        note = source = /note="Description of Artificial Sequence:
                         Syntheticpolynucleotide"
misc_feature            1..163
                        note = source = /note="CF R553X nAPG03850 Target 1 sgRNA"
source                  1..163
                        mol_type = other RNA
                        organism = synthetic construct
SEQUENCE: 248
ttcttgctca ttgacctcca gctatagttc cataagaaaa aagtttctta agttactata   60
gtaagggcaa tgacccgtgg cgtttgggga tcgcccttatc ctggtatgga tattctcccc  120
atgtgaaaag cacctaagca tagcgctatg gtgcttttat ttt                   163

SEQ ID NO: 249          moltype = RNA   length = 163
FEATURE                 Location/Qualifiers
misc_feature            1..163
                        note = source = /note="Description of Artificial Sequence:
                         Syntheticpolynucleotide"
```

```
misc_feature            1..163
                        note = source = /note="CF R553X nAPG03850 Target 2 sgRNA"
source                  1..163
                        mol_type = other RNA
                        organism = synthetic construct
SEQUENCE: 249
cttgctcatt gacctccact gctatagttc cataagaaaa aagtttctta agttactata    60
gtaagggcaa tgacccgtgg cgtttgggga tcgcccttatc ctggtatgga tattctcccc   120
atgtgaaaag cacctaagca tagcgctatg gtgcttttat ttt                      163

SEQ ID NO: 250          moltype = RNA  length = 163
FEATURE                 Location/Qualifiers
misc_feature            1..163
                        note = source = /note="Description of Artificial Sequence:
                          Syntheticpolynucleotide"
misc_feature            1..163
                        note = source = /note="CF R553X nAPG03850 Target 3 sgRNA"
source                  1..163
                        mol_type = other RNA
                        organism = synthetic construct
SEQUENCE: 250
tgctcattga cctccactca gctatagttc cataagaaaa aagtttctta agttactata    60
gtaagggcaa tgacccgtgg cgtttgggga tcgcccttatc ctggtatgga tattctcccc   120
atgtgaaaag cacctaagca tagcgctatg gtgcttttat ttt                      163

SEQ ID NO: 251          moltype = DNA  length = 65
FEATURE                 Location/Qualifiers
misc_feature            1..65
                        note = source = /note="Description of Artificial Sequence:
                          Syntheticoligonucleotide"
misc_feature            1..65
                        note = source = /note="CF R1162X nAPG09882 Target 1"
source                  1..65
                        mol_type = other DNA
                        organism = synthetic construct
SEQUENCE: 251
ggtttaccttt ctgttggcat gtcaatgaac ttaaagactc agctcacaga tcgcatctga   60
aataa                                                                 65

SEQ ID NO: 252          moltype = DNA  length = 65
FEATURE                 Location/Qualifiers
misc_feature            1..65
                        note = source = /note="Description of Artificial Sequence:
                          Syntheticoligonucleotide"
misc_feature            1..65
                        note = source = /note="CF R1162X nAPG09882 Target 2"
source                  1..65
                        mol_type = other DNA
                        organism = synthetic construct
SEQUENCE: 252
accttctgtt ggcatgtcaa tgaacttaaa gactcagctc acagatcgca tctgaaataa    60
aaata                                                                 65

SEQ ID NO: 253          moltype = DNA  length = 65
FEATURE                 Location/Qualifiers
misc_feature            1..65
                        note = source = /note="Description of Artificial Sequence:
                          Syntheticoligonucleotide"
misc_feature            1..65
                        note = source = /note="CF R1162X nAPG09882 Target 3"
source                  1..65
                        mol_type = other DNA
                        organism = synthetic construct
SEQUENCE: 253
ctgttggcat gtcaatgaac ttaaagactc agctcacaga tcgcatctga aataaaaata    60
acaac                                                                 65

SEQ ID NO: 254          moltype = DNA  length = 65
FEATURE                 Location/Qualifiers
misc_feature            1..65
                        note = source = /note="Description of Artificial Sequence:
                          Syntheticoligonucleotide"
misc_feature            1..65
                        note = source = /note="CF R1162X nAPG09882 Target 4"
source                  1..65
                        mol_type = other DNA
                        organism = synthetic construct
```

```
SEQUENCE: 254
tgttggcatg tcaatgaact taaagactca gctcacagat cgcatctgaa ataaaaataa    60
caaca                                                                65

SEQ ID NO: 255          moltype = DNA  length = 65
FEATURE                 Location/Qualifiers
misc_feature            1..65
                        note = source = /note="Description of Artificial Sequence:
                         Syntheticoligonucleotide"
misc_feature            1..65
                        note = source = /note="CF R1162X nAPG09882 Target 5"
source                  1..65
                        mol_type = other DNA
                        organism = synthetic construct
SEQUENCE: 255
gttggcatgt caatgaactt aaagactcag ctcacagatc gcatctgaaa taaaataac    60
aacat                                                                65

SEQ ID NO: 256          moltype = DNA  length = 65
FEATURE                 Location/Qualifiers
misc_feature            1..65
                        note = source = /note="Description of Artificial Sequence:
                         Syntheticoligonucleotide"
misc_feature            1..65
                        note = source = /note="CF R1162X nAPG06646 Target 1"
source                  1..65
                        mol_type = other DNA
                        organism = synthetic construct
SEQUENCE: 256
tttaccttct gttggcatgt caatgaactt aaagactcag ctcacagatc gcatctgaaa    60
taaaa                                                                65

SEQ ID NO: 257          moltype = DNA  length = 65
FEATURE                 Location/Qualifiers
misc_feature            1..65
                        note = source = /note="Description of Artificial Sequence:
                         Syntheticoligonucleotide"
misc_feature            1..65
                        note = source = /note="CF R1162X nAPG06646 Target 2"
source                  1..65
                        mol_type = other DNA
                        organism = synthetic construct
SEQUENCE: 257
taccttctgt tggcatgtca atgaacttaa agactcagct cacagatcgc atctgaaata    60
aaaat                                                                65

SEQ ID NO: 258          moltype = DNA  length = 60
FEATURE                 Location/Qualifiers
misc_feature            1..60
                        note = source = /note="Description of Artificial Sequence:
                         Syntheticoligonucleotide"
misc_feature            1..60
                        note = source = /note="CF R1162X nAPG06646 Target 3"
source                  1..60
                        mol_type = other DNA
                        organism = synthetic construct
SEQUENCE: 258
tggcatgtca atgaacttaa agactcagct cacagatcgc atctgaaata aaaataacaa    60

SEQ ID NO: 259          moltype = DNA  length = 60
FEATURE                 Location/Qualifiers
misc_feature            1..60
                        note = source = /note="Description of Artificial Sequence:
                         Syntheticoligonucleotide"
misc_feature            1..60
                        note = source = /note="CF R1162X nAPG03850 Target 1"
source                  1..60
                        mol_type = other DNA
                        organism = synthetic construct
SEQUENCE: 259
taccttctgt tggcatgtca atgaacttaa agactcagct cacagatcgc atctgaaata    60

SEQ ID NO: 260          moltype = DNA  length = 60
FEATURE                 Location/Qualifiers
misc_feature            1..60
                        note = source = /note="Description of Artificial Sequence:
                         Syntheticoligonucleotide"
misc_feature            1..60
                        note = source = /note="CF R1162X nAPG03850 Target 2"
```

```
source                  1..60
                        mol_type = other DNA
                        organism = synthetic construct
SEQUENCE: 260
ttctgttggc atgtcaatga acttaaagac tcagctcaca gatcgcatct gaaataaaaa   60

SEQ ID NO: 261          moltype = DNA  length = 60
FEATURE                 Location/Qualifiers
misc_feature            1..60
                        note = source = /note="Description of Artificial Sequence:
                        Syntheticoligonucleotide"
misc_feature            1..60
                        note = source = /note="CF R1162X nAPG03850 Target 3"
source                  1..60
                        mol_type = other DNA
                        organism = synthetic construct
SEQUENCE: 261
tggcatgtca atgaacttaa agactcagct cacagatcgc atctgaaata aaataacaa    60

SEQ ID NO: 262          moltype = DNA  length = 60
FEATURE                 Location/Qualifiers
misc_feature            1..60
                        note = source = /note="Description of Artificial Sequence:
                        Syntheticoligonucleotide"
misc_feature            1..60
                        note = source = /note="CF R1162X nAPG05586 Target 1"
source                  1..60
                        mol_type = other DNA
                        organism = synthetic construct
SEQUENCE: 262
ttaccttctg ttggcatgtc aatgaactta aagactcagc tcacagatcg catctgaaat   60

SEQ ID NO: 263          moltype = DNA  length = 60
FEATURE                 Location/Qualifiers
misc_feature            1..60
                        note = source = /note="Description of Artificial Sequence:
                        Syntheticoligonucleotide"
misc_feature            1..60
                        note = source = /note="CF R1162X nAPG05586 Target 2"
source                  1..60
                        mol_type = other DNA
                        organism = synthetic construct
SEQUENCE: 263
ctgttggcat gtcaatgaac ttaaagactc agctcacaga tcgcatctga aataaaaata   60

SEQ ID NO: 264          moltype = DNA  length = 60
FEATURE                 Location/Qualifiers
misc_feature            1..60
                        note = source = /note="Description of Artificial Sequence:
                        Syntheticoligonucleotide"
misc_feature            1..60
                        note = source = /note="CF R1162X nAPG05586 Target 3"
source                  1..60
                        mol_type = other DNA
                        organism = synthetic construct
SEQUENCE: 264
tgtcaatgaa cttaaagact cagctcacag atcgcatctg aaataaaaat aacaacattt   60

SEQ ID NO: 265          moltype = DNA  length = 65
FEATURE                 Location/Qualifiers
misc_feature            1..65
                        note = source = /note="Description of Artificial Sequence:
                        Syntheticoligonucleotide"
misc_feature            1..65
                        note = source = /note="CF R1162X nAPG00969 Target 1"
source                  1..65
                        mol_type = other DNA
                        organism = synthetic construct
SEQUENCE: 265
ggtttacctt ctgttggcat gtcaatgaac ttaaagactc agctcacaga tcgcatctga   60
aataa                                                               65

SEQ ID NO: 266          moltype = DNA  length = 65
FEATURE                 Location/Qualifiers
misc_feature            1..65
                        note = source = /note="Description of Artificial Sequence:
                        Syntheticoligonucleotide"
misc_feature            1..65
                        note = source = /note="CF R1162X nAPG00969 Target 2"
```

```
source                  1..65
                        mol_type = other DNA
                        organism = synthetic construct
SEQUENCE: 266
gttggcatgt caatgaactt aaagactcag ctcacagatc gcatctgaaa taaaataac    60
aacat                                                               65

SEQ ID NO: 267          moltype = DNA  length = 60
FEATURE                 Location/Qualifiers
misc_feature            1..60
                        note = source = /note="Description of Artificial Sequence:
                         Syntheticoligonucleotide"
misc_feature            1..60
                        note = source = /note="CF R1162X nAPG07553 Target 1"
source                  1..60
                        mol_type = other DNA
                        organism = synthetic construct
SEQUENCE: 267
tggcatgtca atgaacttaa agactcagct cacagatcgc atctgaaata aaaataacaa   60

SEQ ID NO: 268          moltype = DNA  length = 60
FEATURE                 Location/Qualifiers
misc_feature            1..60
                        note = source = /note="Description of Artificial Sequence:
                         Syntheticoligonucleotide"
misc_feature            1..60
                        note = source = /note="CF R1162X nAPG01604 Target 1"
source                  1..60
                        mol_type = other DNA
                        organism = synthetic construct
SEQUENCE: 268
gcatgtcaat gaacttaaag actcagctca cagatcgcat ctgaaataaa aataacaaca   60

SEQ ID NO: 269          moltype = DNA  length = 25
FEATURE                 Location/Qualifiers
misc_feature            1..25
                        note = source = /note="Description of Artificial Sequence:
                         Syntheticoligonucleotide"
misc_feature            1..25
                        note = source = /note="CF R1162X nAPG09882 Target 1"
source                  1..25
                        mol_type = other DNA
                        organism = synthetic construct
SEQUENCE: 269
gtcaatgaac ttaaagactc agctc                                         25

SEQ ID NO: 270          moltype = DNA  length = 25
FEATURE                 Location/Qualifiers
misc_feature            1..25
                        note = source = /note="Description of Artificial Sequence:
                         Syntheticoligonucleotide"
misc_feature            1..25
                        note = source = /note="CF R1162X nAPG09882 Target 2"
source                  1..25
                        mol_type = other DNA
                        organism = synthetic construct
SEQUENCE: 270
tgaacttaaa gactcagctc acaga                                         25

SEQ ID NO: 271          moltype = DNA  length = 25
FEATURE                 Location/Qualifiers
misc_feature            1..25
                        note = source = /note="Description of Artificial Sequence:
                         Syntheticoligonucleotide"
misc_feature            1..25
                        note = source = /note="CF R1162X nAPG09882 Target 3"
source                  1..25
                        mol_type = other DNA
                        organism = synthetic construct
SEQUENCE: 271
ttaaagactc agctcacaga tcgca                                         25

SEQ ID NO: 272          moltype = DNA  length = 25
FEATURE                 Location/Qualifiers
misc_feature            1..25
                        note = source = /note="Description of Artificial Sequence:
                         Syntheticoligonucleotide"
misc_feature            1..25
                        note = source = /note="CF R1162X nAPG09882 Target 4"
```

```
source                    1..25
                          mol_type = other DNA
                          organism = synthetic construct
SEQUENCE: 272
taaagactca gctcacagat cgcat                                              25

SEQ ID NO: 273            moltype = DNA   length = 25
FEATURE                   Location/Qualifiers
misc_feature              1..25
                          note = source = /note="Description of Artificial Sequence:
                          Syntheticoligonucleotide"
misc_feature              1..25
                          note = source = /note="CF R1162X nAPG09882 Target 5"
source                    1..25
                          mol_type = other DNA
                          organism = synthetic construct
SEQUENCE: 273
aaagactcag ctcacagatc gcatc                                              25

SEQ ID NO: 274            moltype = DNA   length = 25
FEATURE                   Location/Qualifiers
misc_feature              1..25
                          note = source = /note="Description of Artificial Sequence:
                          Syntheticoligonucleotide"
misc_feature              1..25
                          note = source = /note="CF R1162X nAPG06646 Target 1"
source                    1..25
                          mol_type = other DNA
                          organism = synthetic construct
SEQUENCE: 274
caatgaactt aaagactcag ctcac                                              25

SEQ ID NO: 275            moltype = DNA   length = 25
FEATURE                   Location/Qualifiers
misc_feature              1..25
                          note = source = /note="Description of Artificial Sequence:
                          Syntheticoligonucleotide"
misc_feature              1..25
                          note = source = /note="CF R1162X nAPG06646 Target 2"
source                    1..25
                          mol_type = other DNA
                          organism = synthetic construct
SEQUENCE: 275
atgaacttaa agactcagct cacag                                              25

SEQ ID NO: 276            moltype = DNA   length = 25
FEATURE                   Location/Qualifiers
misc_feature              1..25
                          note = source = /note="Description of Artificial Sequence:
                          Syntheticoligonucleotide"
misc_feature              1..25
                          note = source = /note="CF R1162X nAPG06646 Target 3"
source                    1..25
                          mol_type = other DNA
                          organism = synthetic construct
SEQUENCE: 276
aacttaaaga ctcagctcac agatc                                              25

SEQ ID NO: 277            moltype = DNA   length = 20
FEATURE                   Location/Qualifiers
misc_feature              1..20
                          note = source = /note="Description of Artificial Sequence:
                          Syntheticoligonucleotide"
misc_feature              1..20
                          note = source = /note="CF R1162X nAPG03850 Target 1"
source                    1..20
                          mol_type = other DNA
                          organism = synthetic construct
SEQUENCE: 277
atgaacttaa agactcagct                                                    20

SEQ ID NO: 278            moltype = DNA   length = 20
FEATURE                   Location/Qualifiers
misc_feature              1..20
                          note = source = /note="Description of Artificial Sequence:
                          Syntheticoligonucleotide"
misc_feature              1..20
                          note = source = /note="CF R1162X nAPG03850 Target 2"
```

```
source                          1..20
                                mol_type = other DNA
                                organism = synthetic construct
SEQUENCE: 278
acttaaagac tcagctcaca                                                        20

SEQ ID NO: 279                  moltype = DNA  length = 20
FEATURE                         Location/Qualifiers
misc_feature                    1..20
                                note = source = /note="Description of Artificial Sequence:
                                Syntheticoligonucleotide"
misc_feature                    1..20
                                note = source = /note="CF R1162X nAPG03850 Target 3"
source                          1..20
                                mol_type = other DNA
                                organism = synthetic construct
SEQUENCE: 279
agactcagct cacagatcgc                                                        20

SEQ ID NO: 280                  moltype = DNA  length = 20
FEATURE                         Location/Qualifiers
misc_feature                    1..20
                                note = source = /note="Description of Artificial Sequence:
                                Syntheticoligonucleotide"
misc_feature                    1..20
                                note = source = /note="CF R1162X nAPG05586 Target 1"
source                          1..20
                                mol_type = other DNA
                                organism = synthetic construct
SEQUENCE: 280
aatgaactta aagactcagc                                                        20

SEQ ID NO: 281                  moltype = DNA  length = 20
FEATURE                         Location/Qualifiers
misc_feature                    1..20
                                note = source = /note="Description of Artificial Sequence:
                                Syntheticoligonucleotide"
misc_feature                    1..20
                                note = source = /note="CF R1162X nAPG05586 Target 2"
source                          1..20
                                mol_type = other DNA
                                organism = synthetic construct
SEQUENCE: 281
ttaaagactc agctcacaga                                                        20

SEQ ID NO: 282                  moltype = DNA  length = 20
FEATURE                         Location/Qualifiers
misc_feature                    1..20
                                note = source = /note="Description of Artificial Sequence:
                                Syntheticoligonucleotide"
misc_feature                    1..20
                                note = source = /note="CF R1162X nAPG05586 Target 3"
source                          1..20
                                mol_type = other DNA
                                organism = synthetic construct
SEQUENCE: 282
cagctcacag atcgcatctg                                                        20

SEQ ID NO: 283                  moltype = DNA  length = 25
FEATURE                         Location/Qualifiers
misc_feature                    1..25
                                note = source = /note="Description of Artificial Sequence:
                                Syntheticoligonucleotide"
misc_feature                    1..25
                                note = source = /note="CF R1162X nAPG00969 Target 1"
source                          1..25
                                mol_type = other DNA
                                organism = synthetic construct
SEQUENCE: 283
gtcaatgaac ttaaagactc agctc                                                  25

SEQ ID NO: 284                  moltype = DNA  length = 25
FEATURE                         Location/Qualifiers
misc_feature                    1..25
                                note = source = /note="Description of Artificial Sequence:
                                Syntheticoligonucleotide"
misc_feature                    1..25
                                note = source = /note="CF R1162X nAPG00969 Target 2"
```

```
source                  1..25
                        mol_type = other DNA
                        organism = synthetic construct
SEQUENCE: 284
aaagactcag ctcacagatc gcatc                                             25

SEQ ID NO: 285          moltype = DNA  length = 20
FEATURE                 Location/Qualifiers
misc_feature            1..20
                        note = source = /note="Description of Artificial Sequence:
                        Syntheticoligonucleotide"
misc_feature            1..20
                        note = source = /note="CF R1162X nAPG07553 Target 1"
source                  1..20
                        mol_type = other DNA
                        organism = synthetic construct
SEQUENCE: 285
agactcagct cacagatcgc                                                   20

SEQ ID NO: 286          moltype = DNA  length = 20
FEATURE                 Location/Qualifiers
misc_feature            1..20
                        note = source = /note="Description of Artificial Sequence:
                        Syntheticoligonucleotide"
misc_feature            1..20
                        note = source = /note="CF R1162X nAPG01604 Target 1"
source                  1..20
                        mol_type = other DNA
                        organism = synthetic construct
SEQUENCE: 286
actcagctca cagatcgcat                                                   20

SEQ ID NO: 287          moltype = RNA  length = 118
FEATURE                 Location/Qualifiers
misc_feature            1..118
                        note = source = /note="Description of Artificial Sequence:
                        Syntheticpolynucleotide"
misc_feature            1..118
                        note = source = /note="CF R1162X nAPG09882 Target 1 sgRNA"
source                  1..118
                        mol_type = other RNA
                        organism = synthetic construct
SEQUENCE: 287
gtcaatgaac ttaaagactc agctcgtttt tgtactctca ataaaaagtt attgagaatc       60
tacaaaaata aggcattttg ccgaatttac cgccctacat atgtagggcg gttttttt       118

SEQ ID NO: 288          moltype = RNA  length = 118
FEATURE                 Location/Qualifiers
misc_feature            1..118
                        note = source = /note="Description of Artificial Sequence:
                        Syntheticpolynucleotide"
misc_feature            1..118
                        note = source = /note="CF R1162X nAPG09882 Target 2 sgRNA"
source                  1..118
                        mol_type = other RNA
                        organism = synthetic construct
SEQUENCE: 288
tgaacttaaa gactcagctc acagagtttt tgtactctca ataaaaagtt attgagaatc       60
tacaaaaata aggcattttg ccgaatttac cgccctacat atgtagggcg gttttttt       118

SEQ ID NO: 289          moltype = RNA  length = 118
FEATURE                 Location/Qualifiers
misc_feature            1..118
                        note = source = /note="Description of Artificial Sequence:
                        Syntheticpolynucleotide"
misc_feature            1..118
                        note = source = /note="CF R1162X nAPG09882 Target 3 sgRNA"
source                  1..118
                        mol_type = other RNA
                        organism = synthetic construct
SEQUENCE: 289
ttaaagactc agctcacaga tcgcagtttt tgtactctca ataaaaagtt attgagaatc       60
tacaaaaata aggcattttg ccgaatttac cgccctacat atgtagggcg gttttttt       118

SEQ ID NO: 290          moltype = RNA  length = 118
FEATURE                 Location/Qualifiers
misc_feature            1..118
                        note = source = /note="Description of Artificial Sequence:
                        Syntheticpolynucleotide"
```

```
misc_feature           1..118
                       note = source = /note="CF R1162X nAPG09882 Target 4 sgRNA"
source                 1..118
                       mol_type = other RNA
                       organism = synthetic construct
SEQUENCE: 290
taaagactca gctcacagat cgcatgtttt tgtactctca ataaaaagtt attgagaatc    60
tacaaaaata aggcattttg ccgaatttac cgccctacat atgtagggcg gttttttt    118

SEQ ID NO: 291         moltype = RNA   length = 118
FEATURE                Location/Qualifiers
misc_feature           1..118
                       note = source = /note="Description of Artificial Sequence:
                         Syntheticpolynucleotide"
misc_feature           1..118
                       note = source = /note="CF R1162X nAPG09882 Target 5 sgRNA"
source                 1..118
                       mol_type = other RNA
                       organism = synthetic construct
SEQUENCE: 291
aaagactcag ctcacagatc gcatcgtttt tgtactctca ataaaaagtt attgagaatc    60
tacaaaaata aggcattttg ccgaatttac cgccctacat atgtagggcg gttttttt    118

SEQ ID NO: 292         moltype = RNA   length = 164
FEATURE                Location/Qualifiers
misc_feature           1..164
                       note = source = /note="Description of Artificial Sequence:
                         Syntheticpolynucleotide"
misc_feature           1..164
                       note = source = /note="CF R1162X nAPG06646 Target 1 sgRNA"
source                 1..164
                       mol_type = other RNA
                       organism = synthetic construct
SEQUENCE: 292
caatgaactt aaagactcag ctcacgccat aattcctctg taaaacttaa agaaggttta    60
tagagttatt atggtaaggc aatatgccgt ggcgttgggg atcgcctatg tccggtttta   120
ccggatctcc ctaaaggtga ctaactttgg ttagtcacct tttt                    164

SEQ ID NO: 293         moltype = RNA   length = 164
FEATURE                Location/Qualifiers
misc_feature           1..164
                       note = source = /note="Description of Artificial Sequence:
                         Syntheticpolynucleotide"
misc_feature           1..164
                       note = source = /note="CF R1162X nAPG06646 Target 2 sgRNA"
source                 1..164
                       mol_type = other RNA
                       organism = synthetic construct
SEQUENCE: 293
atgaacttaa agactcagct cacaggccat aattcctctg taaaacttaa agaaggttta    60
tagagttatt atggtaaggc aatatgccgt ggcgttgggg atcgcctatg tccggtttta   120
ccggatctcc ctaaaggtga ctaactttgg ttagtcacct tttt                    164

SEQ ID NO: 294         moltype = RNA   length = 164
FEATURE                Location/Qualifiers
misc_feature           1..164
                       note = source = /note="Description of Artificial Sequence:
                         Syntheticpolynucleotide"
misc_feature           1..164
                       note = source = /note="CF R1162X nAPG06646 Target 3 sgRNA"
source                 1..164
                       mol_type = other RNA
                       organism = synthetic construct
SEQUENCE: 294
aacttaaaga ctcagctcac agatcgccat aattcctctg taaaacttaa agaaggttta    60
tagagttatt atggtaaggc aatatgccgt ggcgttgggg atcgcctatg tccggtttta   120
ccggatctcc ctaaaggtga ctaactttgg ttagtcacct tttt                    164

SEQ ID NO: 295         moltype = RNA   length = 163
FEATURE                Location/Qualifiers
misc_feature           1..163
                       note = source = /note="Description of Artificial Sequence:
                         Syntheticpolynucleotide"
misc_feature           1..163
                       note = source = /note="CF R1162X nAPG03850 Target 1 sgRNA"
source                 1..163
                       mol_type = other RNA
                       organism = synthetic construct
```

-continued

```
SEQUENCE: 295
atgaacttaa agactcagct gctatagttc cataagaaaa aagtttctta agttactata    60
gtaagggcaa tgacccgtgg cgtttgggga tcgccttatc ctggtatgga tattctcccc   120
atgtgaaaag caccctaagca tagcgctatg gtgcttttat ttt                    163

SEQ ID NO: 296          moltype = RNA   length = 163
FEATURE                 Location/Qualifiers
misc_feature            1..163
                        note = source = /note="Description of Artificial Sequence:
                           Syntheticpolynucleotide"
misc_feature            1..163
                        note = source = /note="CF R1162X nAPG03850 Target 2 sgRNA"
source                  1..163
                        mol_type = other RNA
                        organism = synthetic construct
SEQUENCE: 296
acttaaagac tcagctcaca gctatagttc cataagaaaa aagtttctta agttactata    60
gtaagggcaa tgacccgtgg cgtttgggga tcgccttatc ctggtatgga tattctcccc   120
atgtgaaaag caccctaagca tagcgctatg gtgcttttat ttt                    163

SEQ ID NO: 297          moltype = RNA   length = 163
FEATURE                 Location/Qualifiers
misc_feature            1..163
                        note = source = /note="Description of Artificial Sequence:
                           Syntheticpolynucleotide"
misc_feature            1..163
                        note = source = /note="CF R1162X nAPG03850 Target 3 sgRNA"
source                  1..163
                        mol_type = other RNA
                        organism = synthetic construct
SEQUENCE: 297
agactcagct cacagatcgc gctatagttc cataagaaaa aagtttctta agttactata    60
gtaagggcaa tgacccgtgg cgtttgggga tcgccttatc ctggtatgga tattctcccc   120
atgtgaaaag caccctaagca tagcgctatg gtgcttttat ttt                    163

SEQ ID NO: 298          moltype = RNA   length = 110
FEATURE                 Location/Qualifiers
misc_feature            1..110
                        note = source = /note="Description of Artificial Sequence:
                           Syntheticpolynucleotide"
misc_feature            1..110
                        note = source = /note="CF R1162X nAPG05586 Target 1 sgRNA"
source                  1..110
                        mol_type = other RNA
                        organism = synthetic construct
SEQUENCE: 298
aatgaactta aagactcagc gttattgtac tctcaataaa aagttattga gaatctacaa    60
taataaggca tcttgccgaa tttaccgccc tacatatgta gggcggtttt              110

SEQ ID NO: 299          moltype = RNA   length = 110
FEATURE                 Location/Qualifiers
misc_feature            1..110
                        note = source = /note="Description of Artificial Sequence:
                           Syntheticpolynucleotide"
misc_feature            1..110
                        note = source = /note="CF R1162X nAPG05586 Target 2 sgRNA"
source                  1..110
                        mol_type = other RNA
                        organism = synthetic construct
SEQUENCE: 299
ttaaagactc agctcacaga gttattgtac tctcaataaa aagttattga gaatctacaa    60
taataaggca tcttgccgaa tttaccgccc tacatatgta gggcggtttt              110

SEQ ID NO: 300          moltype = RNA   length = 110
FEATURE                 Location/Qualifiers
misc_feature            1..110
                        note = source = /note="Description of Artificial Sequence:
                           Syntheticpolynucleotide"
misc_feature            1..110
                        note = source = /note="CF R1162X nAPG05586 Target 3 sgRNA"
source                  1..110
                        mol_type = other RNA
                        organism = synthetic construct
SEQUENCE: 300
cagctcacag atcgcatctg gttattgtac tctcaataaa aagttattga gaatctacaa    60
taataaggca tcttgccgaa tttaccgccc tacatatgta gggcggtttt              110

SEQ ID NO: 301          moltype = RNA   length = 118
FEATURE                 Location/Qualifiers
```

| | |
|---|---|
| misc_feature | 1..118 |
| | note = source = /note="Description of Artificial Sequence: Syntheticpolynucleotide" |
| misc_feature | 1..118 |
| | note = source = /note="CF R1162X nAPG00969 Target 1 sgRNA" |
| source | 1..118 |
| | mol_type = other RNA |
| | organism = synthetic construct |

SEQUENCE: 301
```
gtcaatgaac ttaaagactc agctcgtttt agtactctgt gaaagcacag aatctactaa   60
aataaggcat aatgccgtat ttaatcccat cataattctg atgggatttt ttatattt    118
```

| | |
|---|---|
| SEQ ID NO: 302 | moltype = RNA   length = 118 |
| FEATURE | Location/Qualifiers |
| misc_feature | 1..118 |
| | note = source = /note="Description of Artificial Sequence: Syntheticpolynucleotide" |
| misc_feature | 1..118 |
| | note = source = /note="CF R1162X nAPG00969 Target 2 sgRNA" |
| source | 1..118 |
| | mol_type = other RNA |
| | organism = synthetic construct |

SEQUENCE: 302
```
aaagactcag ctcacagatc gcatcgtttt agtactctgt gaaagcacag aatctactaa   60
aataaggcat aatgccgtat ttaatcccat cataattctg atgggatttt ttatattt    118
```

| | |
|---|---|
| SEQ ID NO: 303 | moltype = RNA   length = 151 |
| FEATURE | Location/Qualifiers |
| misc_feature | 1..151 |
| | note = source = /note="Description of Artificial Sequence: Syntheticpolynucleotide" |
| misc_feature | 1..151 |
| | note = source = /note="CF R1162X nAPG07553 Target 1 sgRNA" |
| source | 1..151 |
| | mol_type = other RNA |
| | organism = synthetic construct |

SEQUENCE: 303
```
agactcagct cacagatcgc gctatagttc cataagaaag cttaagttac tatagtaagg   60
gcaatgaccc gtggcgtttg gggatcgcct catccattac ggatattctc cccatgtgaa  120
aagcacctaa gcataaggct aaggtgcttt t                                 151
```

| | |
|---|---|
| SEQ ID NO: 304 | moltype = RNA   length = 105 |
| FEATURE | Location/Qualifiers |
| misc_feature | 1..105 |
| | note = source = /note="Description of Artificial Sequence: Syntheticpolynucleotide" |
| misc_feature | 1..105 |
| | note = source = /note="CF R1162X nAPG01604 Target 1 sgRNA" |
| source | 1..105 |
| | mol_type = other RNA |
| | organism = synthetic construct |

SEQUENCE: 304
```
actcagctca cagatcgcat gttttagtac tctgtaaaaa gttacagaat ctactaaaac   60
aaggcaaaat gccgtgttta tctcgtcaac ttgttggcga gattt                  105
```

| | |
|---|---|
| SEQ ID NO: 305 | moltype = DNA   length = 65 |
| FEATURE | Location/Qualifiers |
| misc_feature | 1..65 |
| | note = source = /note="Description of Artificial Sequence: Syntheticoligonucleotide" |
| misc_feature | 1..65 |
| | note = source = /note="CF W1282X nAPG09882 Target 1" |
| source | 1..65 |
| | mol_type = other DNA |
| | organism = synthetic construct |

SEQUENCE: 305
```
gtgtgtcttg ggattcaata actttgcaac agtgaaggaa agcctttgga gtgataccac   60
aggtg                                                               65
```

| | |
|---|---|
| SEQ ID NO: 306 | moltype = DNA   length = 65 |
| FEATURE | Location/Qualifiers |
| misc_feature | 1..65 |
| | note = source = /note="Description of Artificial Sequence: Syntheticoligonucleotide" |
| misc_feature | 1..65 |
| | note = source = /note="CF W1282X nAPG09882 Target 2" |
| source | 1..65 |
| | mol_type = other DNA |
| | organism = synthetic construct |

```
SEQUENCE: 306
gtcttgggat tcaataactt tgcaacagtg aaggaaagcc tttggagtga taccacaggt    60
gagca                                                                65

SEQ ID NO: 307          moltype = DNA   length = 65
FEATURE                 Location/Qualifiers
misc_feature            1..65
                        note = source = /note="Description of Artificial Sequence:
                        Syntheticoligonucleotide"
misc_feature            1..65
                        note = source = /note="CF W1282X nAPG09882 Target 3"
source                  1..65
                        mol_type = other DNA
                        organism = synthetic construct
SEQUENCE: 307
cttgggattc aataactttg caacagtgaa ggaaagcctt tggagtgata ccacaggtga    60
gcaaa                                                                65

SEQ ID NO: 308          moltype = DNA   length = 65
FEATURE                 Location/Qualifiers
misc_feature            1..65
                        note = source = /note="Description of Artificial Sequence:
                        Syntheticoligonucleotide"
misc_feature            1..65
                        note = source = /note="CF W1282X nAPG09882 Target 4"
source                  1..65
                        mol_type = other DNA
                        organism = synthetic construct
SEQUENCE: 308
gggattcaat aactttgcaa cagtgaagga aagcctttgg agtgatacca caggtgagca    60
aaagg                                                                65

SEQ ID NO: 309          moltype = DNA   length = 65
FEATURE                 Location/Qualifiers
misc_feature            1..65
                        note = source = /note="Description of Artificial Sequence:
                        Syntheticoligonucleotide"
misc_feature            1..65
                        note = source = /note="CF W1282X nAPG09882 Target 5"
source                  1..65
                        mol_type = other DNA
                        organism = synthetic construct
SEQUENCE: 309
gattcaataa ctttgcaaca gtgaaggaaa gcctttggag tgataccaca ggtgagcaaa    60
aggac                                                                65

SEQ ID NO: 310          moltype = DNA   length = 65
FEATURE                 Location/Qualifiers
misc_feature            1..65
                        note = source = /note="Description of Artificial Sequence:
                        Syntheticoligonucleotide"
misc_feature            1..65
                        note = source = /note="CF W1282X nAPG06646 Target 1"
source                  1..65
                        mol_type = other DNA
                        organism = synthetic construct
SEQUENCE: 310
tcgatggtgt gtcttgggat tcaataactt tgcaacagtg aaggaaagcc tttggagtga    60
tacca                                                                65

SEQ ID NO: 311          moltype = DNA   length = 65
FEATURE                 Location/Qualifiers
misc_feature            1..65
                        note = source = /note="Description of Artificial Sequence:
                        Syntheticoligonucleotide"
misc_feature            1..65
                        note = source = /note="CF W1282X nAPG06646 Target 2"
source                  1..65
                        mol_type = other DNA
                        organism = synthetic construct
SEQUENCE: 311
ttgggattca ataactttgc aacagtgaag gaaagccttt ggagtgatac cacaggtgag    60
caaaa                                                                65

SEQ ID NO: 312          moltype = DNA   length = 65
FEATURE                 Location/Qualifiers
misc_feature            1..65
                        note = source = /note="Description of Artificial Sequence:
                        Syntheticoligonucleotide"
```

```
misc_feature              1..65
                          note = source = /note="CF W1282X nAPG06646 Target 3"
source                    1..65
                          mol_type = other DNA
                          organism = synthetic construct
SEQUENCE: 312
tgggattcaa taactttgca acagtgaagg aaagcctttg gagtgatacc acaggtgagc    60
aaaag                                                                65

SEQ ID NO: 313            moltype = DNA  length = 65
FEATURE                   Location/Qualifiers
misc_feature              1..65
                          note = source = /note="Description of Artificial Sequence:
                           Syntheticoligonucleotide"
misc_feature              1..65
                          note = source = /note="CF W1282X nAPG06646 Target 4"
source                    1..65
                          mol_type = other DNA
                          organism = synthetic construct
SEQUENCE: 313
ggattcaata actttgcaac agtgaaggaa agcctttgga gtgataccac aggtgagcaa    60
aagga                                                                65

SEQ ID NO: 314            moltype = DNA  length = 60
FEATURE                   Location/Qualifiers
misc_feature              1..60
                          note = source = /note="Description of Artificial Sequence:
                           Syntheticoligonucleotide"
misc_feature              1..60
                          note = source = /note="CF W1282X nAPG03850 Target 1"
source                    1..60
                          mol_type = other DNA
                          organism = synthetic construct
SEQUENCE: 314
tgtcttggga ttcaataact tgcaacagt gaaggaaagc ctttggagtg ataccacagg    60

SEQ ID NO: 315            moltype = DNA  length = 60
FEATURE                   Location/Qualifiers
misc_feature              1..60
                          note = source = /note="Description of Artificial Sequence:
                           Syntheticoligonucleotide"
misc_feature              1..60
                          note = source = /note="CF W1282X nAPG03850 Target 2"
source                    1..60
                          mol_type = other DNA
                          organism = synthetic construct
SEQUENCE: 315
gtcttgggat tcaataactt tgcaacagtg aaggaaagcc tttggagtga taccacaggt    60

SEQ ID NO: 316            moltype = DNA  length = 60
FEATURE                   Location/Qualifiers
misc_feature              1..60
                          note = source = /note="Description of Artificial Sequence:
                           Syntheticoligonucleotide"
misc_feature              1..60
                          note = source = /note="CF W1282X nAPG03850 Target 3"
source                    1..60
                          mol_type = other DNA
                          organism = synthetic construct
SEQUENCE: 316
cttgggattc aataactttg caacagtgaa ggaaagcctt tggagtgata ccacaggtga    60

SEQ ID NO: 317            moltype = DNA  length = 60
FEATURE                   Location/Qualifiers
misc_feature              1..60
                          note = source = /note="Description of Artificial Sequence:
                           Syntheticoligonucleotide"
misc_feature              1..60
                          note = source = /note="CF W1282X nAPG03850 Target 4"
source                    1..60
                          mol_type = other DNA
                          organism = synthetic construct
SEQUENCE: 317
tgggattcaa taactttgca acagtgaagg aaagcctttg gagtgatacc acaggtgagc    60

SEQ ID NO: 318            moltype = DNA  length = 60
FEATURE                   Location/Qualifiers
```

| | |
|---|---|
| misc_feature | 1..60 |
| | note = source = /note="Description of Artificial Sequence: Syntheticoligonucleotide" |
| misc_feature | 1..60 |
| | note = source = /note="CF W1282X nAPG07553 Target 1" |
| source | 1..60 |
| | mol_type = other DNA |
| | organism = synthetic construct |

SEQUENCE: 318
cttgggattc aataactttg caacagtgaa ggaaagcctt tggagtgata ccacaggtga 60

| | |
|---|---|
| SEQ ID NO: 319 | moltype = DNA length = 60 |
| FEATURE | Location/Qualifiers |
| misc_feature | 1..60 |
| | note = source = /note="Description of Artificial Sequence: Syntheticoligonucleotide" |
| misc_feature | 1..60 |
| | note = source = /note="CF W1282X nAPG07553 Target 2" |
| source | 1..60 |
| | mol_type = other DNA |
| | organism = synthetic construct |

SEQUENCE: 319
tgggattcaa taactttgca acagtgaagg aaagcctttg gagtgatacc acaggtgagc 60

| | |
|---|---|
| SEQ ID NO: 320 | moltype = DNA length = 60 |
| FEATURE | Location/Qualifiers |
| misc_feature | 1..60 |
| | note = source = /note="Description of Artificial Sequence: Syntheticoligonucleotide" |
| misc_feature | 1..60 |
| | note = source = /note="CF W1282X nAPG01604 Target 1" |
| source | 1..60 |
| | mol_type = other DNA |
| | organism = synthetic construct |

SEQUENCE: 320
tcttgggatt caataacttt gcaacagtga aggaaagcct ttggagtgat accacaggtg 60

| | |
|---|---|
| SEQ ID NO: 321 | moltype = DNA length = 60 |
| FEATURE | Location/Qualifiers |
| misc_feature | 1..60 |
| | note = source = /note="Description of Artificial Sequence: Syntheticoligonucleotide" |
| misc_feature | 1..60 |
| | note = source = /note="CF W1282X nAPG01604 Target 2" |
| source | 1..60 |
| | mol_type = other DNA |
| | organism = synthetic construct |

SEQUENCE: 321
cttgggattc aataactttg caacagtgaa ggaaagcctt tggagtgata ccacaggtga 60

| | |
|---|---|
| SEQ ID NO: 322 | moltype = DNA length = 65 |
| FEATURE | Location/Qualifiers |
| misc_feature | 1..65 |
| | note = source = /note="Description of Artificial Sequence: Syntheticoligonucleotide" |
| misc_feature | 1..65 |
| | note = source = /note="CF W1282X nAPG07433.1 Target 1" |
| source | 1..65 |
| | mol_type = other DNA |
| | organism = synthetic construct |

SEQUENCE: 322
ttgggattca ataactttgc aacagtgaag gaaagccttt ggagtgatac cacaggtgag 60
caaaa                                                              65

| | |
|---|---|
| SEQ ID NO: 323 | moltype = DNA length = 60 |
| FEATURE | Location/Qualifiers |
| misc_feature | 1..60 |
| | note = source = /note="Description of Artificial Sequence: Syntheticoligonucleotide" |
| misc_feature | 1..60 |
| | note = source = /note="CF W1282X nAPG09748 Target 1" |
| source | 1..60 |
| | mol_type = other DNA |
| | organism = synthetic construct |

SEQUENCE: 323
gtatcactcc aaaggctttc cttcactgtt gcaaagttat tgaatcccaa gacacaccat 60

| | |
|---|---|
| SEQ ID NO: 324 | moltype = DNA length = 60 |
| FEATURE | Location/Qualifiers |

```
misc_feature            1..60
                        note = source = /note="Description of Artificial Sequence:
                        Syntheticoligonucleotide"
misc_feature            1..60
                        note = source = /note="CF W1282X nAPG05586 Target 1"
source                  1..60
                        mol_type = other DNA
                        organism = synthetic construct
SEQUENCE: 324
gattcaataa ctttgcaaca gtgaaggaaa gcctttggag tgataccaca ggtgagcaaa   60

SEQ ID NO: 325          moltype = DNA  length = 25
FEATURE                 Location/Qualifiers
misc_feature            1..25
                        note = source = /note="Description of Artificial Sequence:
                        Syntheticoligonucleotide"
misc_feature            1..25
                        note = source = /note="CF W1282X nAPG09882 Target 1"
source                  1..25
                        mol_type = other DNA
                        organism = synthetic construct
SEQUENCE: 325
actttgcaac agtgaaggaa agcct                                         25

SEQ ID NO: 326          moltype = DNA  length = 25
FEATURE                 Location/Qualifiers
misc_feature            1..25
                        note = source = /note="Description of Artificial Sequence:
                        Syntheticoligonucleotide"
misc_feature            1..25
                        note = source = /note="CF W1282X nAPG09882 Target 2"
source                  1..25
                        mol_type = other DNA
                        organism = synthetic construct
SEQUENCE: 326
tgcaacagtg aaggaaagcc tttgg                                         25

SEQ ID NO: 327          moltype = DNA  length = 25
FEATURE                 Location/Qualifiers
misc_feature            1..25
                        note = source = /note="Description of Artificial Sequence:
                        Syntheticoligonucleotide"
misc_feature            1..25
                        note = source = /note="CF W1282X nAPG09882 Target 3"
source                  1..25
                        mol_type = other DNA
                        organism = synthetic construct
SEQUENCE: 327
caacagtgaa ggaaagcctt tggag                                         25

SEQ ID NO: 328          moltype = DNA  length = 25
FEATURE                 Location/Qualifiers
misc_feature            1..25
                        note = source = /note="Description of Artificial Sequence:
                        Syntheticoligonucleotide"
misc_feature            1..25
                        note = source = /note="CF W1282X nAPG09882 Target 4"
source                  1..25
                        mol_type = other DNA
                        organism = synthetic construct
SEQUENCE: 328
cagtgaagga aagcctttgg agtga                                         25

SEQ ID NO: 329          moltype = DNA  length = 25
FEATURE                 Location/Qualifiers
misc_feature            1..25
                        note = source = /note="Description of Artificial Sequence:
                        Syntheticoligonucleotide"
misc_feature            1..25
                        note = source = /note="CF W1282X nAPG09882 Target 5"
source                  1..25
                        mol_type = other DNA
                        organism = synthetic construct
SEQUENCE: 329
gtgaaggaaa gcctttggag tgata                                         25
```

```
SEQ ID NO: 330           moltype = DNA  length = 25
FEATURE                  Location/Qualifiers
misc_feature             1..25
                         note = source = /note="Description of Artificial Sequence:
                           Syntheticoligonucleotide"
misc_feature             1..25
                         note = source = /note="CF W1282X nAPG06646 Target 1"
source                   1..25
                         mol_type = other DNA
                         organism = synthetic construct
SEQUENCE: 330
tcaataactt tgcaacagtg aagga                                              25

SEQ ID NO: 331           moltype = DNA  length = 25
FEATURE                  Location/Qualifiers
misc_feature             1..25
                         note = source = /note="Description of Artificial Sequence:
                           Syntheticoligonucleotide"
misc_feature             1..25
                         note = source = /note="CF W1282X nAPG06646 Target 2"
source                   1..25
                         mol_type = other DNA
                         organism = synthetic construct
SEQUENCE: 331
aacagtgaag gaaagccttt ggagt                                              25

SEQ ID NO: 332           moltype = DNA  length = 25
FEATURE                  Location/Qualifiers
misc_feature             1..25
                         note = source = /note="Description of Artificial Sequence:
                           Syntheticoligonucleotide"
misc_feature             1..25
                         note = source = /note="CF W1282X nAPG06646 Target 3"
source                   1..25
                         mol_type = other DNA
                         organism = synthetic construct
SEQUENCE: 332
acagtgaagg aaagcctttg gagtg                                              25

SEQ ID NO: 333           moltype = DNA  length = 25
FEATURE                  Location/Qualifiers
misc_feature             1..25
                         note = source = /note="Description of Artificial Sequence:
                           Syntheticoligonucleotide"
misc_feature             1..25
                         note = source = /note="CF W1282X nAPG06646 Target 4"
source                   1..25
                         mol_type = other DNA
                         organism = synthetic construct
SEQUENCE: 333
agtgaaggaa agcctttgga gtgat                                              25

SEQ ID NO: 334           moltype = DNA  length = 20
FEATURE                  Location/Qualifiers
misc_feature             1..20
                         note = source = /note="Description of Artificial Sequence:
                           Syntheticoligonucleotide"
misc_feature             1..20
                         note = source = /note="CF W1282X nAPG03850 Target 1"
source                   1..20
                         mol_type = other DNA
                         organism = synthetic construct
SEQUENCE: 334
ttgcaacagt gaaggaaagc                                                    20

SEQ ID NO: 335           moltype = DNA  length = 20
FEATURE                  Location/Qualifiers
misc_feature             1..20
                         note = source = /note="Description of Artificial Sequence:
                           Syntheticoligonucleotide"
misc_feature             1..20
                         note = source = /note="CF W1282X nAPG03850 Target 2"
source                   1..20
                         mol_type = other DNA
                         organism = synthetic construct
SEQUENCE: 335
tgcaacagtg aaggaaagcc                                                    20
```

-continued

```
SEQ ID NO: 336            moltype = DNA   length = 20
FEATURE                   Location/Qualifiers
misc_feature              1..20
                          note = source = /note="Description of Artificial Sequence:
                          Syntheticoligonucleotide"
misc_feature              1..20
                          note = source = /note="CF W1282X nAPG03850 Target 3"
source                    1..20
                          mol_type = other DNA
                          organism = synthetic construct
SEQUENCE: 336
caacagtgaa ggaaagcctt                                                       20

SEQ ID NO: 337            moltype = DNA   length = 20
FEATURE                   Location/Qualifiers
misc_feature              1..20
                          note = source = /note="Description of Artificial Sequence:
                          Syntheticoligonucleotide"
misc_feature              1..20
                          note = source = /note="CF W1282X nAPG03850 Target 4"
source                    1..20
                          mol_type = other DNA
                          organism = synthetic construct
SEQUENCE: 337
acagtgaagg aaagcctttg                                                       20

SEQ ID NO: 338            moltype = DNA   length = 20
FEATURE                   Location/Qualifiers
misc_feature              1..20
                          note = source = /note="Description of Artificial Sequence:
                          Syntheticoligonucleotide"
misc_feature              1..20
                          note = source = /note="CF W1282X nAPG07553 Target 1"
source                    1..20
                          mol_type = other DNA
                          organism = synthetic construct
SEQUENCE: 338
caacagtgaa ggaaagcctt                                                       20

SEQ ID NO: 339            moltype = DNA   length = 20
FEATURE                   Location/Qualifiers
misc_feature              1..20
                          note = source = /note="Description of Artificial Sequence:
                          Syntheticoligonucleotide"
misc_feature              1..20
                          note = source = /note="CF W1282X nAPG07553 Target 2"
source                    1..20
                          mol_type = other DNA
                          organism = synthetic construct
SEQUENCE: 339
acagtgaagg aaagcctttg                                                       20

SEQ ID NO: 340            moltype = DNA   length = 20
FEATURE                   Location/Qualifiers
misc_feature              1..20
                          note = source = /note="Description of Artificial Sequence:
                          Syntheticoligonucleotide"
misc_feature              1..20
                          note = source = /note="CF W1282X nAPG01604 Target 1"
source                    1..20
                          mol_type = other DNA
                          organism = synthetic construct
SEQUENCE: 340
gcaacagtga aggaaagcct                                                       20

SEQ ID NO: 341            moltype = DNA   length = 20
FEATURE                   Location/Qualifiers
misc_feature              1..20
                          note = source = /note="Description of Artificial Sequence:
                          Syntheticoligonucleotide"
misc_feature              1..20
                          note = source = /note="CF W1282X nAPG01604 Target 2"
source                    1..20
                          mol_type = other DNA
                          organism = synthetic construct
SEQUENCE: 341
caacagtgaa ggaaagcctt                                                       20

SEQ ID NO: 342            moltype = DNA   length = 25
```

```
FEATURE                 Location/Qualifiers
misc_feature            1..25
                        note = source = /note="Description of Artificial Sequence:
                         Syntheticoligonucleotide"
misc_feature            1..25
                        note = source = /note="CF W1282X nAPG07433.1 Target 1"
source                  1..25
                        mol_type = other DNA
                        organism = synthetic construct
SEQUENCE: 342
aacagtgaag gaaagccttt ggagt                                              25

SEQ ID NO: 343          moltype = DNA  length = 20
FEATURE                 Location/Qualifiers
misc_feature            1..20
                        note = source = /note="Description of Artificial Sequence:
                         Syntheticoligonucleotide"
misc_feature            1..20
                        note = source = /note="CF W1282X nAPG09748 Target 1"
source                  1..20
                        mol_type = other DNA
                        organism = synthetic construct
SEQUENCE: 343
cttcactgtt gcaaagttat                                                    20

SEQ ID NO: 344          moltype = DNA  length = 20
FEATURE                 Location/Qualifiers
misc_feature            1..20
                        note = source = /note="Description of Artificial Sequence:
                         Syntheticoligonucleotide"
misc_feature            1..20
                        note = source = /note="CF W1282X nAPG05586 Target 1"
source                  1..20
                        mol_type = other DNA
                        organism = synthetic construct
SEQUENCE: 344
gtgaaggaaa gcctttggag                                                    20

SEQ ID NO: 345          moltype = RNA  length = 118
FEATURE                 Location/Qualifiers
misc_feature            1..118
                        note = source = /note="Description of Artificial Sequence:
                         Syntheticpolynucleotide"
misc_feature            1..118
                        note = source = /note="CF W1282X nAPG09882 Target 1 sgRNA"
source                  1..118
                        mol_type = other RNA
                        organism = synthetic construct
SEQUENCE: 345
actttgcaac agtgaaggaa agcctgtttt tgtactctca ataaaaagtt attgagaatc    60
tacaaaaata aggcattttg ccgaatttac cgccctacat atgtagggcg gttttttt     118

SEQ ID NO: 346          moltype = RNA  length = 118
FEATURE                 Location/Qualifiers
misc_feature            1..118
                        note = source = /note="Description of Artificial Sequence:
                         Syntheticpolynucleotide"
misc_feature            1..118
                        note = source = /note="CF W1282X nAPG09882 Target 2 sgRNA"
source                  1..118
                        mol_type = other RNA
                        organism = synthetic construct
SEQUENCE: 346
tgcaacagtg aaggaaagcc tttgggtttt tgtactctca ataaaaagtt attgagaatc    60
tacaaaaata aggcattttg ccgaatttac cgccctacat atgtagggcg gttttttt     118

SEQ ID NO: 347          moltype = RNA  length = 118
FEATURE                 Location/Qualifiers
misc_feature            1..118
                        note = source = /note="Description of Artificial Sequence:
                         Syntheticpolynucleotide"
misc_feature            1..118
                        note = source = /note="CF W1282X nAPG09882 Target 3 sgRNA"
source                  1..118
                        mol_type = other RNA
                        organism = synthetic construct
SEQUENCE: 347
caacagtgaa ggaaagcctt tggaggtttt tgtactctca ataaaaagtt attgagaatc    60
tacaaaaata aggcattttg ccgaatttac cgccctacat atgtagggcg gttttttt     118
```

```
SEQ ID NO: 348          moltype = RNA   length = 118
FEATURE                 Location/Qualifiers
misc_feature            1..118
                        note = source = /note="Description of Artificial Sequence:
                         Syntheticpolynucleotide"
misc_feature            1..118
                        note = source = /note="CF W1282X nAPG09882 Target 4 sgRNA"
source                  1..118
                        mol_type = other RNA
                        organism = synthetic construct
SEQUENCE: 348
cagtgaagga aagcctttgg agtgagtttt tgtactctca ataaaaagtt attgagaatc   60
tacaaaaata aggcatttg ccgaatttac cgccctacat atgtagggcg gttttttt    118

SEQ ID NO: 349          moltype = RNA   length = 118
FEATURE                 Location/Qualifiers
misc_feature            1..118
                        note = source = /note="Description of Artificial Sequence:
                         Syntheticpolynucleotide"
misc_feature            1..118
                        note = source = /note="CF W1282X nAPG09882 Target 5 sgRNA"
source                  1..118
                        mol_type = other RNA
                        organism = synthetic construct
SEQUENCE: 349
gtgaaggaaa gcctttggag tgatagtttt tgtactctca ataaaaagtt attgagaatc   60
tacaaaaata aggcatttg ccgaatttac cgccctacat atgtagggcg gttttttt    118

SEQ ID NO: 350          moltype = RNA   length = 164
FEATURE                 Location/Qualifiers
misc_feature            1..164
                        note = source = /note="Description of Artificial Sequence:
                         Syntheticpolynucleotide"
misc_feature            1..164
                        note = source = /note="CF W1282X nAPG06646 Target 1 sgRNA"
source                  1..164
                        mol_type = other RNA
                        organism = synthetic construct
SEQUENCE: 350
tcaataactt tgcaacagtg aaggagccat aattcctctg taaaacttaa agaaggttta   60
tagagttatt atggtaaggc aatatgccgt ggcgttgggg atcgcctatg tccggtttta  120
ccggatctcc ctaaaggtga ctaactttgg ttagtcacct tttt                   164

SEQ ID NO: 351          moltype = RNA   length = 164
FEATURE                 Location/Qualifiers
misc_feature            1..164
                        note = source = /note="Description of Artificial Sequence:
                         Syntheticpolynucleotide"
misc_feature            1..164
                        note = source = /note="CF W1282X nAPG06646 Target 2 sgRNA"
source                  1..164
                        mol_type = other RNA
                        organism = synthetic construct
SEQUENCE: 351
aacagtgaag gaaagccttt ggagtgccat aattcctctg taaaacttaa agaaggttta   60
tagagttatt atggtaaggc aatatgccgt ggcgttgggg atcgcctatg tccggtttta  120
ccggatctcc ctaaaggtga ctaactttgg ttagtcacct tttt                   164

SEQ ID NO: 352          moltype = RNA   length = 164
FEATURE                 Location/Qualifiers
misc_feature            1..164
                        note = source = /note="Description of Artificial Sequence:
                         Syntheticpolynucleotide"
misc_feature            1..164
                        note = source = /note="CF W1282X nAPG06646 Target 3 sgRNA"
source                  1..164
                        mol_type = other RNA
                        organism = synthetic construct
SEQUENCE: 352
acagtgaagg aaagcctttg gagtggccat aattcctctg taaaacttaa agaaggttta   60
tagagttatt atggtaaggc aatatgccgt ggcgttgggg atcgcctatg tccggtttta  120
ccggatctcc ctaaaggtga ctaactttgg ttagtcacct tttt                   164

SEQ ID NO: 353          moltype = RNA   length = 164
FEATURE                 Location/Qualifiers
misc_feature            1..164
                        note = source = /note="Description of Artificial Sequence:
                         Syntheticpolynucleotide"
```

| | |
|---|---|
| misc_feature | 1..164<br>note = source = /note="CF W1282X nAPG06646 Target 4 sgRNA" |
| source | 1..164<br>mol_type = other RNA<br>organism = synthetic construct |

SEQUENCE: 353
```
agtgaaggaa agcctttgga gtgatgccat aattcctctg taaaacttaa agaaggttta   60
tagagttatt atggtaaggc aatatgccgt ggcgttgggg atcgccatg tccggtttta   120
ccggatctcc ctaaaggtga ctaactttgg ttagtcacct tttt                   164
```

| | |
|---|---|
| SEQ ID NO: 354 | moltype = RNA  length = 163 |
| FEATURE | Location/Qualifiers |
| misc_feature | 1..163<br>note = source = /note="Description of Artificial Sequence: Syntheticpolynucleotide" |
| misc_feature | 1..163<br>note = source = /note="CF W1282X nAPG03850 Target 1 sgRNA" |
| source | 1..163<br>mol_type = other RNA<br>organism = synthetic construct |

SEQUENCE: 354
```
ttgcaacagt gaaggaaagc gctatagttc cataagaaaa aagtttctta agttactata   60
gtaagggcaa tgacccgtgg cgtttgggga tcgccttatc ctggtatgga tattctcccc   120
atgtgaaaag cacctaagca tagcgctatg gtgctttat ttt                     163
```

| | |
|---|---|
| SEQ ID NO: 355 | moltype = RNA  length = 163 |
| FEATURE | Location/Qualifiers |
| misc_feature | 1..163<br>note = source = /note="Description of Artificial Sequence: Syntheticpolynucleotide" |
| misc_feature | 1..163<br>note = source = /note="CF W1282X nAPG03850 Target 2 sgRNA" |
| source | 1..163<br>mol_type = other RNA<br>organism = synthetic construct |

SEQUENCE: 355
```
tgcaacagtg aaggaaagcc gctatagttc cataagaaaa aagtttctta agttactata   60
gtaagggcaa tgacccgtgg cgtttgggga tcgccttatc ctggtatgga tattctcccc   120
atgtgaaaag cacctaagca tagcgctatg gtgctttat ttt                     163
```

| | |
|---|---|
| SEQ ID NO: 356 | moltype = RNA  length = 163 |
| FEATURE | Location/Qualifiers |
| misc_feature | 1..163<br>note = source = /note="Description of Artificial Sequence: Syntheticpolynucleotide" |
| misc_feature | 1..163<br>note = source = /note="CF W1282X nAPG03850 Target 3 sgRNA" |
| source | 1..163<br>mol_type = other RNA<br>organism = synthetic construct |

SEQUENCE: 356
```
caacagtgaa ggaaagcctt gctatagttc cataagaaaa aagtttctta agttactata   60
gtaagggcaa tgacccgtgg cgtttgggga tcgccttatc ctggtatgga tattctcccc   120
atgtgaaaag cacctaagca tagcgctatg gtgctttat ttt                     163
```

| | |
|---|---|
| SEQ ID NO: 357 | moltype = RNA  length = 163 |
| FEATURE | Location/Qualifiers |
| misc_feature | 1..163<br>note = source = /note="Description of Artificial Sequence: Syntheticpolynucleotide" |
| misc_feature | 1..163<br>note = source = /note="CF W1282X nAPG03850 Target 4 sgRNA" |
| source | 1..163<br>mol_type = other RNA<br>organism = synthetic construct |

SEQUENCE: 357
```
acagtgaagg aaagcctttg gctatagttc cataagaaaa aagtttctta agttactata   60
gtaagggcaa tgacccgtgg cgtttgggga tcgccttatc ctggtatgga tattctcccc   120
atgtgaaaag cacctaagca tagcgctatg gtgctttat ttt                     163
```

| | |
|---|---|
| SEQ ID NO: 358 | moltype = RNA  length = 151 |
| FEATURE | Location/Qualifiers |
| misc_feature | 1..151<br>note = source = /note="Description of Artificial Sequence: Syntheticpolynucleotide" |

```
misc_feature            1..151
                        note = source = /note="CF W1282X nAPG07553 Target 1 sgRNA"
source                  1..151
                        mol_type = other RNA
                        organism = synthetic construct
SEQUENCE: 358
caacagtgaa ggaaagcctt gctatagttc cataagaaag cttaagttac tatagtaagg    60
gcaatgaccc gtggcgtttg gggatcgcct catccattac ggatattctc cccatgtgaa   120
aagcacctaa gcataaggct aaggtgcttt t                                  151

SEQ ID NO: 359          moltype = RNA   length = 151
FEATURE                 Location/Qualifiers
misc_feature            1..151
                        note = source = /note="Description of Artificial Sequence:
                           Syntheticpolynucleotide"
misc_feature            1..151
                        note = source = /note="CF W1282X nAPG07553 Target 2 sgRNA"
source                  1..151
                        mol_type = other RNA
                        organism = synthetic construct
SEQUENCE: 359
acagtgaagg aaaagccttt gctatagttc cataagaaag cttaagttac tatagtaagg    60
gcaatgaccc gtggcgtttg gggatcgcct catccattac ggatattctc cccatgtgaa   120
aagcacctaa gcataaggct aaggtgcttt t                                  151

SEQ ID NO: 360          moltype = RNA   length = 105
FEATURE                 Location/Qualifiers
misc_feature            1..105
                        note = source = /note="Description of Artificial Sequence:
                           Syntheticpolynucleotide"
misc_feature            1..105
                        note = source = /note="CF W1282X nAPG01604 Target 1 sgRNA"
source                  1..105
                        mol_type = other RNA
                        organism = synthetic construct
SEQUENCE: 360
gcaacagtga aggaaagcct gttttagtac tctgtaaaaa gttacagaat ctactaaaac    60
aaggcaaaat gccgtgttta tctcgtcaac ttgttggcga gattt                   105

SEQ ID NO: 361          moltype = RNA   length = 105
FEATURE                 Location/Qualifiers
misc_feature            1..105
                        note = source = /note="Description of Artificial Sequence:
                           Syntheticpolynucleotide"
misc_feature            1..105
                        note = source = /note="CF W1282X nAPG01604 Target 2 sgRNA"
source                  1..105
                        mol_type = other RNA
                        organism = synthetic construct
SEQUENCE: 361
caacagtgaa ggaaagcctt gttttagtac tctgtaaaaa gttacagaat ctactaaaac    60
aaggcaaaat gccgtgttta tctcgtcaac ttgttggcga gattt                   105

SEQ ID NO: 362          moltype = RNA   length = 135
FEATURE                 Location/Qualifiers
misc_feature            1..135
                        note = source = /note="Description of Artificial Sequence:
                           Syntheticpolynucleotide"
misc_feature            1..135
                        note = source = /note="CF W1282X nAPG07433.1 Target 1 sgRNA"
source                  1..135
                        mol_type = other RNA
                        organism = synthetic construct
SEQUENCE: 362
aacagtgaag gaaagccttt ggagtgtcat agttccatta aagccaaaag tggctttgat    60
gtttctatga taagggtttc gacccgtggc gtcggggatc gcctgcccat tgaaatgggc   120
ttctccccat ttatt                                                    135

SEQ ID NO: 363          moltype = RNA   length = 135
FEATURE                 Location/Qualifiers
misc_feature            1..135
                        note = source = /note="Description of Artificial Sequence:
                           Syntheticpolynucleotide"
misc_feature            1..135
                        note = source = /note="CF W1282X nAPG09748 Target 1 sgRNA"
source                  1..135
                        mol_type = other RNA
                        organism = synthetic construct
```

```
SEQUENCE: 363
cgacggttag aggccgtatg tcgatttgct ttaatttcgt gcgtgtgcat tgtcgtcctc    60
cattacaggg cggctaccac gaatagccac gaagtaaaag cttcgtggct agcaccttca   120
ctgttgcaaa gttat                                                   135

SEQ ID NO: 364          moltype = RNA  length = 110
FEATURE                 Location/Qualifiers
misc_feature            1..110
                        note = source = /note="Description of Artificial Sequence:
                         Syntheticpolynucleotide"
misc_feature            1..110
                        note = source = /note="CF W1282X nAPG05586 Target 1 sgRNA"
source                  1..110
                        mol_type = other RNA
                        organism = synthetic construct
SEQUENCE: 364
gtgaaggaaa gcctttggag gttattgtac tctcaataaa aagttattga gaatctacaa    60
taataaggca tcttgccgaa tttaccgccc tacatatgta gggcggtttt              110

SEQ ID NO: 365          moltype = AA  length = 8
FEATURE                 Location/Qualifiers
REGION                  1..8
                        note = source = /note="Description of Artificial Sequence:
                         Syntheticpeptide"
REGION                  1..8
                        note = source = /note="APG07433.1 deleted motif"
source                  1..8
                        mol_type = protein
                        organism = synthetic construct
SEQUENCE: 365
LKKERNGA                                                              8

SEQ ID NO: 366          moltype = AA  length = 1063
FEATURE                 Location/Qualifiers
REGION                  1..1063
                        note = source = /note="Description of Artificial Sequence:
                         Syntheticpolypeptide"
REGION                  1..1063
                        note = source = /note="APG07433.1 engineered deletion"
source                  1..1063
                        mol_type = protein
                        organism = synthetic construct
SEQUENCE: 366
MRELDYRIGL DIGTNSIGWG VIELSWNKDR ERYEKVRIVD QGVRMFDRAE MPKTGASLAE    60
PRRIARSSRR RLNRKSQRKK NIRNLLVQHG VITQEELDSL YPLSKKSMDI WGIRLDGLDR   120
LLNHFEWARL LIHLAQRRGF KSNRKSELKD TETGKVLSSI QLNEKRLSLY RTVGEMWMKD   180
PDFSKYDRKR NSPNEYVFSV SRAELEKEIV TLFAAQRRFQ SPYASKDLQE TYLQIWTHQL   240
PFASGNAILN KVGYCSLLKG KERRIPKATY TFQYFSALDQ VNRTRLGPDF QPFTKEQREI   300
ILNNMFQRTD YYKKKTIPEV TYYDIRKWLE LDETIQFKGL NYDPNEELKK IEKKPFINLK   360
AFYEINKVVA NYSERTNETF STLDYDGIGY ALTVYKTDKD IRSYLKSSHN LPKRCYDDQL   420
IEELLSLSYT KFGHLSLKAI NHVLSIMQKG NTYKEAVDQL GYDTSGLKKE KRSKFLPPIS   480
DEITNPIVKR ALTQARKVVN AIIRRHGSPH SVHIELAREL SKNHDERTKI VSAQDENYKK   540
NKGAISILSE HGILNPTGYD IVRYKLWKEQ GERCAYSLKE IPADTFFNEP ILEVDHILPY   600
SQSFIDSYHN KVLVYSDENR KKGNRIPYTY FLETNKDWEA FERYVRSNKF FSKKKREYLL   660
KRAYLPRESE LIKERHLNDT RYASTFLKNF IEQNLQFEKL EDNPRKRRVQ TVNGVITAHF   720
RKRWGLEKDR QETYLHHAMD AIIVACTDHH MVTRVTEYYQ IKESNKSVKK PYFPMPWEGF   780
RDELLSHLAS QPIAKKISEE LKAGYQSLDY IFVSRMPKRS ITGAAHKQTI MRKGGIDKKG   840
KTIIIERLHL KDIKFDENGD FKMVGKEQDM ATYEAIKQRY LEHGKNSKKA FETPLYKPSK   900
KGTGNLIKRV KVEGQAKSFV REVNGGVAQN GDLVRVDLFE KDDKYYMVGP YVPDTVCSEL   960
PKKVVASSKG YEQWLTLDNS FTFKFSLYPY DLVRLVKGDE DRFLYFGTLD IDSDRLNFKD  1020
VNKPSKKNEY RYSLKTIEDL EKYEVGVLGD LRLVRKETRR NFH                   1063

SEQ ID NO: 367          moltype = AA  length = 8
FEATURE                 Location/Qualifiers
REGION                  1..8
                        note = source = /note="Description of Artificial Sequence:
                         Syntheticpeptide"
REGION                  1..8
                        note = source = /note="APG08290.1 deleted motif"
source                  1..8
                        mol_type = protein
                        organism = synthetic construct
SEQUENCE: 367
LKKERNGS                                                              8

SEQ ID NO: 368          moltype = AA  length = 1064
FEATURE                 Location/Qualifiers
REGION                  1..1064
                        note = source = /note="Description of Artificial Sequence:
                         Syntheticpolypeptide"
```

```
REGION                  1..1064
                        note = source = /note="APG08290.1 engineered deletion"
source                  1..1064
                        mol_type = protein
                        organism = synthetic construct
SEQUENCE: 368
MSELDYRIGL DIGTNSIGWG VIELFWNKDR ERYEKVRIVD KGVRMFDKAE IPNKGASLAE    60
PRRIARSSRR RLNRKSQRKK EIRNLLVQHG MITQEELDLL YPLSKKSIDI WDIRLDGLDR   120
LLNHLEWARL LIHLAQRRGF KSNRKSELKD AETGKVLSSI QVNEKRLFLY RTVGEMWIKD   180
AEFSKYDRRR NSPNEYVFSV SRADLEKEIV TLFEAQRKFQ SSYASKNLQE TYLQIWAHQL   240
PPFASGNAILN KVGYCSLLKG KERRIPKATY TFQYFSALDQ VNRTRLGPDF QPFTQEQKEI   300
ILDKMFQRTD YYKKKTIPEV SYYDIRKWLE LDETIQFKGL NYDPNEELKK IEKKPFINLK   360
APYEIKKVVA NYAERTNEAF STLDYDAIAY ALTVYKTDKD IRSYLKKSNN LSKRCYDDQL   420
IEELFTLSYT KFGHLSFKAI NHVLPIMQEG RTYQEAIHQL GYDTTNLKKE NRSMFLPLIP   480
DEITNPIVKR AITQARKVVN AIIRRYGSPN SVHIELAREL SKSHDERKKI MTAHDENYKK   540
NKGAISILIE NGILNPTGYD IVRYKLWKEQ GERCAYSLKE IPPDTFFNEP ILEVDHILPY   600
SQSFIDSYHN KVLVYSDENR NKGNRIPYTY FLETNKDWEA FERYVRSNKL FSKKKREYLL   660
KKTYLPRESE LIKERHLNDT RYASTFLKNF IEQNLQFKEV EVNLRKKRVQ TVNGVITAHL   720
RKRWGLEKNR QETYLHHAMD AIIVACTDHH MVTRITEYYQ IKESNKSVKK PYFPMPWEGF   780
RDELLSHLAS QPIAKKISEE LKAGYQSSDY IFVSRMPKRS VTGAAHDQTI RRKGGIDKKG   840
KTIIIKRVRL KDIKFDENGD FKMVGKEQDL ATYEAIKQRY LEHRKNSKKA FETPLYKPSK   900
KGTGNLIKRV KIEGQTKAFV REVNGGVAQN SDLVRVDLFE KDDKYYMVPI YVPDTVCSEL   960
PKKVVKSGKG YEQWLTLDNS FTFKSSLYPY DLVRLVKGNE DRFLYFGTLD IDSDRLNFKD  1020
VNKPSKQNEY RYSLKTIENL EKYEVGVLGD LRLVKQETRR IFNR                  1064

SEQ ID NO: 369          moltype = DNA   length = 20
FEATURE                 Location/Qualifiers
misc_feature            1..20
                        note = source = /note="Description of Artificial Sequence:
                         Syntheticoligonucleotide"
misc_feature            1..20
                        note = source = /note="SGN000139 target sequence"
source                  1..20
                        mol_type = other DNA
                        organism = synthetic construct
SEQUENCE: 369
aggttttaat ggcccagcct                                                 20

SEQ ID NO: 370          moltype = DNA   length = 20
FEATURE                 Location/Qualifiers
misc_feature            1..20
                        note = source = /note="Description of Artificial Sequence:
                         Syntheticoligonucleotide"
misc_feature            1..20
                        note = source = /note="SGN000143 target sequence"
source                  1..20
                        mol_type = other DNA
                        organism = synthetic construct
SEQUENCE: 370
catggcagta cattagagca                                                 20

SEQ ID NO: 371          moltype = DNA   length = 20
FEATURE                 Location/Qualifiers
misc_feature            1..20
                        note = source = /note="Description of Artificial Sequence:
                         Syntheticoligonucleotide"
misc_feature            1..20
                        note = source = /note="SGN000169 target sequence"
source                  1..20
                        mol_type = other DNA
                        organism = synthetic construct
SEQUENCE: 371
cacatctcga gcaagacgtt                                                 20

SEQ ID NO: 372          moltype = DNA   length = 20
FEATURE                 Location/Qualifiers
misc_feature            1..20
                        note = source = /note="Description of Artificial Sequence:
                         Syntheticoligonucleotide"
misc_feature            1..20
                        note = source = /note="SGN000173 target sequence"
source                  1..20
                        mol_type = other DNA
                        organism = synthetic construct
SEQUENCE: 372
cttctatagc ctccttcccc                                                 20

SEQ ID NO: 373          moltype = DNA   length = 20
FEATURE                 Location/Qualifiers
```

```
misc_feature          1..20
                      note = source = /note="Description of Artificial Sequence:
                        Syntheticoligonucleotide"
misc_feature          1..20
                      note = source = /note="SGN000186 target sequence"
source                1..20
                      mol_type = other DNA
                      organism = synthetic construct
SEQUENCE: 373
ggacagtgcg catctccctg                                                    20

SEQ ID NO: 374        moltype = DNA  length = 20
FEATURE               Location/Qualifiers
misc_feature          1..20
                      note = source = /note="Description of Artificial Sequence:
                        Syntheticoligonucleotide"
misc_feature          1..20
                      note = source = /note="SGN000194 target sequence"
source                1..20
                      mol_type = other DNA
                      organism = synthetic construct
SEQUENCE: 374
gccgcacagc attcaggtcg                                                    20

SEQ ID NO: 375        moltype = DNA  length = 25
FEATURE               Location/Qualifiers
misc_feature          1..25
                      note = source = /note="Description of Artificial Sequence:
                        Syntheticoligonucleotide"
misc_feature          1..25
                      note = source = /note="SGN000926 target sequence"
source                1..25
                      mol_type = other DNA
                      organism = synthetic construct
SEQUENCE: 375
agagccatca ccatcacatc cctaa                                              25

SEQ ID NO: 376        moltype = DNA  length = 25
FEATURE               Location/Qualifiers
misc_feature          1..25
                      note = source = /note="Description of Artificial Sequence:
                        Syntheticoligonucleotide"
misc_feature          1..25
                      note = source = /note="SGN000927 target sequence"
source                1..25
                      mol_type = other DNA
                      organism = synthetic construct
SEQUENCE: 376
ggccaaaatc cagctgcctt ccttg                                              25

SEQ ID NO: 377        moltype = DNA  length = 25
FEATURE               Location/Qualifiers
misc_feature          1..25
                      note = source = /note="Description of Artificial Sequence:
                        Syntheticoligonucleotide"
misc_feature          1..25
                      note = source = /note="SGN000928 target sequence"
source                1..25
                      mol_type = other DNA
                      organism = synthetic construct
SEQUENCE: 377
gcttctactc ttggcttaca accca                                              25

SEQ ID NO: 378        moltype = DNA  length = 25
FEATURE               Location/Qualifiers
misc_feature          1..25
                      note = source = /note="Description of Artificial Sequence:
                        Syntheticoligonucleotide"
misc_feature          1..25
                      note = source = /note="SGN000929 target sequence"
source                1..25
                      mol_type = other DNA
                      organism = synthetic construct
SEQUENCE: 378
atctggaggg aacttacagc atatg                                              25

SEQ ID NO: 379        moltype = DNA  length = 25
FEATURE               Location/Qualifiers
```

```
misc_feature          1..25
                      note = source = /note="Description of Artificial Sequence:
                        Syntheticoligonucleotide"
misc_feature          1..25
                      note = source = /note="SGN000930 target sequence"
source                1..25
                      mol_type = other DNA
                      organism = synthetic construct
SEQUENCE: 379
gaacaactca aatggaaatg aatat                                          25

SEQ ID NO: 380        moltype = DNA  length = 25
FEATURE               Location/Qualifiers
misc_feature          1..25
                      note = source = /note="Description of Artificial Sequence:
                        Syntheticoligonucleotide"
misc_feature          1..25
                      note = source = /note="SGN000931 target sequence"
source                1..25
                      mol_type = other DNA
                      organism = synthetic construct
SEQUENCE: 380
tcctgttcca tcaccatcaa aaaaa                                          25

SEQ ID NO: 381        moltype = DNA  length = 25
FEATURE               Location/Qualifiers
misc_feature          1..25
                      note = source = /note="Description of Artificial Sequence:
                        Syntheticoligonucleotide"
misc_feature          1..25
                      note = source = /note="SGN000935 target sequence"
source                1..25
                      mol_type = other DNA
                      organism = synthetic construct
SEQUENCE: 381
tgttggttac ctccctgcca ccacc                                          25

SEQ ID NO: 382        moltype = DNA  length = 25
FEATURE               Location/Qualifiers
misc_feature          1..25
                      note = source = /note="Description of Artificial Sequence:
                        Syntheticoligonucleotide"
misc_feature          1..25
                      note = source = /note="SGN001101 target sequence"
source                1..25
                      mol_type = other DNA
                      organism = synthetic construct
SEQUENCE: 382
atattttctt taatggtgcc aggca                                          25

SEQ ID NO: 383        moltype = RNA  length = 130
FEATURE               Location/Qualifiers
misc_feature          1..130
                      note = source = /note="Description of Artificial Sequence:
                        Syntheticpolynucleotide"
misc_feature          1..130
                      note = source = /note="SGN000139 sgRNA"
source                1..130
                      mol_type = other RNA
                      organism = synthetic construct
SEQUENCE: 383
aggttttaat ggcccagcct gtcatagttc cattaaagcc aaaagtggct ttgatgtttc    60
tatgataagg gtttcgaccc gtggcgtcgg ggatcgcctg cccattgaaa tgggcttctc   120
cccatttatt                                                         130

SEQ ID NO: 384        moltype = RNA  length = 130
FEATURE               Location/Qualifiers
misc_feature          1..130
                      note = source = /note="Description of Artificial Sequence:
                        Syntheticpolynucleotide"
misc_feature          1..130
                      note = source = /note="SGN000143 sgRNA"
source                1..130
                      mol_type = other RNA
                      organism = synthetic construct
SEQUENCE: 384
catggcagta cattagagca gtcatagttc cattaaagcc aaaagtggct ttgatgtttc    60
tatgataagg gtttcgaccc gtggcgtcgg ggatcgcctg cccattgaaa tgggcttctc   120
cccatttatt                                                         130
```

| | | |
|---|---|---|
| SEQ ID NO: 385 | moltype = RNA length = 130 | |
| FEATURE | Location/Qualifiers | |
| misc_feature | 1..130 | |
| | note = source = /note="Description of Artificial Sequence: Syntheticpolynucleotide" | |
| misc_feature | 1..130 | |
| | note = source = /note="SGN000169 sgRNA" | |
| source | 1..130 | |
| | mol_type = other RNA | |
| | organism = synthetic construct | |
| SEQUENCE: 385 | | |
| cacatctcga gcaagacgtt gtcatagttc cattaaagcc aaaagtggct ttgatgtttc | | 60 |
| tatgataagg gtttcgaccc gtggcgtcgg ggatcgcctg cccattgaaa tgggcttctc | | 120 |
| cccatttatt | | 130 |
| | | |
| SEQ ID NO: 386 | moltype = RNA length = 130 | |
| FEATURE | Location/Qualifiers | |
| misc_feature | 1..130 | |
| | note = source = /note="Description of Artificial Sequence: Syntheticpolynucleotide" | |
| misc_feature | 1..130 | |
| | note = source = /note="SGN000173 sgRNA" | |
| source | 1..130 | |
| | mol_type = other RNA | |
| | organism = synthetic construct | |
| SEQUENCE: 386 | | |
| cttctatagc ctccttcccc gtcatagttc cattaaagcc aaaagtggct ttgatgtttc | | 60 |
| tatgataagg gtttcgaccc gtggcgtcgg ggatcgcctg cccattgaaa tgggcttctc | | 120 |
| cccatttatt | | 130 |
| | | |
| SEQ ID NO: 387 | moltype = RNA length = 130 | |
| FEATURE | Location/Qualifiers | |
| misc_feature | 1..130 | |
| | note = source = /note="Description of Artificial Sequence: Syntheticpolynucleotide" | |
| misc_feature | 1..130 | |
| | note = source = /note="SGN000186 sgRNA" | |
| source | 1..130 | |
| | mol_type = other RNA | |
| | organism = synthetic construct | |
| SEQUENCE: 387 | | |
| ggacagtgcg catctccctg gtcatagttc cattaaagcc aaaagtggct ttgatgtttc | | 60 |
| tatgataagg gtttcgaccc gtggcgtcgg ggatcgcctg cccattgaaa tgggcttctc | | 120 |
| cccatttatt | | 130 |
| | | |
| SEQ ID NO: 388 | moltype = RNA length = 130 | |
| FEATURE | Location/Qualifiers | |
| misc_feature | 1..130 | |
| | note = source = /note="Description of Artificial Sequence: Syntheticpolynucleotide" | |
| misc_feature | 1..130 | |
| | note = source = /note="SGN000194 sgRNA" | |
| source | 1..130 | |
| | mol_type = other RNA | |
| | organism = synthetic construct | |
| SEQUENCE: 388 | | |
| gccgcacagc attcaggtcg gtcatagttc cattaaagcc aaaagtggct ttgatgtttc | | 60 |
| tatgataagg gtttcgaccc gtggcgtcgg ggatcgcctg cccattgaaa tgggcttctc | | 120 |
| cccatttatt | | 130 |
| | | |
| SEQ ID NO: 389 | moltype = RNA length = 135 | |
| FEATURE | Location/Qualifiers | |
| misc_feature | 1..135 | |
| | note = source = /note="Description of Artificial Sequence: Syntheticpolynucleotide" | |
| misc_feature | 1..135 | |
| | note = source = /note="SGN000926 sgRNA" | |
| source | 1..135 | |
| | mol_type = other RNA | |
| | organism = synthetic construct | |
| SEQUENCE: 389 | | |
| agagccatca ccatcacatc cctaagtcat agttccatga aagccaaaag tggctttgat | | 60 |
| gtttctatga taagggtttc ggcccgtggc gtcggggatc gcctgccat tccgatgggc | | 120 |
| ttctccccat ttatt | | 135 |

```
SEQ ID NO: 390          moltype = RNA  length = 135
FEATURE                 Location/Qualifiers
misc_feature            1..135
                        note = source = /note="Description of Artificial Sequence:
                         Syntheticpolynucleotide"
misc_feature            1..135
                        note = source = /note="SGN000927 sgRNA"
source                  1..135
                        mol_type = other RNA
                        organism = synthetic construct
SEQUENCE: 390
ggccaaaatc cagctgcctt ccttggtcat agttccatga aagccaaaag tggctttgat    60
gtttctatga taagggtttc ggcccgtggc gtcgggatc gcctgcccat tccgatgggc    120
ttctccccat ttatt                                                    135

SEQ ID NO: 391          moltype = RNA  length = 135
FEATURE                 Location/Qualifiers
misc_feature            1..135
                        note = source = /note="Description of Artificial Sequence:
                         Syntheticpolynucleotide"
misc_feature            1..135
                        note = source = /note="SGN000928 sgRNA"
source                  1..135
                        mol_type = other RNA
                        organism = synthetic construct
SEQUENCE: 391
gcttctactc ttggcttaca acccagtcat agttccatga aagccaaaag tggctttgat    60
gtttctatga taagggtttc ggcccgtggc gtcgggatc gcctgcccat tccgatgggc    120
ttctccccat ttatt                                                    135

SEQ ID NO: 392          moltype = RNA  length = 135
FEATURE                 Location/Qualifiers
misc_feature            1..135
                        note = source = /note="Description of Artificial Sequence:
                         Syntheticpolynucleotide"
misc_feature            1..135
                        note = source = /note="SGN000929 sgRNA"
source                  1..135
                        mol_type = other RNA
                        organism = synthetic construct
SEQUENCE: 392
atctggaggg aacttacagc atatggtcat agttccatga aagccaaaag tggctttgat    60
gtttctatga taagggtttc ggcccgtggc gtcgggatc gcctgcccat tccgatgggc    120
ttctccccat ttatt                                                    135

SEQ ID NO: 393          moltype = RNA  length = 135
FEATURE                 Location/Qualifiers
misc_feature            1..135
                        note = source = /note="Description of Artificial Sequence:
                         Syntheticpolynucleotide"
misc_feature            1..135
                        note = source = /note="SGN000930 sgRNA"
source                  1..135
                        mol_type = other RNA
                        organism = synthetic construct
SEQUENCE: 393
gaacaactca aatggaaatg aatatgtcat agttccatga aagccaaaag tggctttgat    60
gtttctatga taagggtttc ggcccgtggc gtcgggatc gcctgcccat tccgatgggc    120
ttctccccat ttatt                                                    135

SEQ ID NO: 394          moltype = RNA  length = 135
FEATURE                 Location/Qualifiers
misc_feature            1..135
                        note = source = /note="Description of Artificial Sequence:
                         Syntheticpolynucleotide"
misc_feature            1..135
                        note = source = /note="SGN000931 sgRNA"
source                  1..135
                        mol_type = other RNA
                        organism = synthetic construct
SEQUENCE: 394
tcctgttcca tcaccatcaa aaaaagtcat agttccatga aagccaaaag tggctttgat    60
gtttctatga taagggtttc ggcccgtggc gtcgggatc gcctgcccat tccgatgggc    120
ttctccccat ttatt                                                    135

SEQ ID NO: 395          moltype = RNA  length = 135
FEATURE                 Location/Qualifiers
```

-continued

```
misc_feature           1..135
                       note = source = /note="Description of Artificial Sequence:
                        Syntheticpolynucleotide"
misc_feature           1..135
                       note = source = /note="SGN000935 sgRNA"
source                 1..135
                       mol_type = other RNA
                       organism = synthetic construct
SEQUENCE: 395
tgttggttac ctccctgcca ccaccgtcat agttccatga aagccaaaag tggctttgat    60
gtttctatga taagggtttc ggcccgtggc gtcgggatc gcctgccat tccgatgggc    120
ttctccccat ttatt                                                    135

SEQ ID NO: 396         moltype = RNA  length = 130
FEATURE                Location/Qualifiers
misc_feature           1..130
                       note = source = /note="Description of Artificial Sequence:
                        Syntheticpolynucleotide"
misc_feature           1..130
                       note = source = /note="SGN001101 sgRNA"
source                 1..130
                       mol_type = other RNA
                       organism = synthetic construct
SEQUENCE: 396
atattttctt taatggtgcc aggcagtcat agttccatta aagccaaaag tggctttgat    60
gtttctatga taagggtttc gacccgtggc gtcgggatc gcctgccat tgaaatgggc    120
ttctccccat                                                          130

SEQ ID NO: 397         moltype = AA  length = 1063
FEATURE                Location/Qualifiers
REGION                 1..1063
                       note = source = /note="Description of Artificial Sequence:
                        Syntheticpolypeptide"
REGION                 1..1063
                       note = source = /note="nAPG07433.1-del"
source                 1..1063
                       mol_type = protein
                       organism = synthetic construct
SEQUENCE: 397
MRELDYRIGL AIGTNSIGWG VIELSWNKDR ERYEKVRIVD QGVRMFDRAE MPKTGASLAE    60
PRRIARSSRR RLNRKSQRKK NIRNLLVQHG VITQEELDSL YPLSKKSMDI WGIRLDGLDR    120
LLNHFEWARL LIHLAQRRGF KSNRKSELKD TETGKVLSSI QLNEKRLSLY RTVGEMWMKD    180
PDFSKYDRKR NSPNEYVFSV SRAELEKEIV TLFAAQRRFQ SPYASKDLQE TYLQIWTHQL    240
PFASGNAILN KVGYCSLLKG KERRIPKATY TFQYFSALDQ VNRTRLGPDF QPFTKEQREI    300
ILNNMFQRTD YYKKKTIPEV TYYDIRKWLE LDETIQFKGL NYDPNEELKK IEKKPFINLK    360
AFYEINKVVA NYSERTNETF STLDYDGIGY ALTVYKTDKD IRSYLKSSHN LPKRCYDDQL    420
IEELLSLSYT KFGHLSLKAI NHVLSIMQKG NTYKEAVDQL GYDTSGLKKE KRSKFLPPIS    480
DEITNPIVKR ALTQARKVVN AIIRRHGSPH SVHIELAREL SKNHDERTKI VSAQDENYKK    540
NKGAISILSE HGILNPTGYD IVRYKLWKEQ GERCAYSLKE IPADTFFNEP ILEVDHILPY    600
SQSFIDSYHN KVLVYSDENR KKGNRIPTY FLETNKDWEA FERYVRSNKF FSKKKREYLL    660
KRAYLPRESE LIKERHLNDT RYASTFLKNF IEQNLQFRLE EDNPRKRRVQ TVNGVITAHF    720
RKRWGLEKDR QETYLHHAMD AIIVACTDHH MVTRVTEYYQ IKESNKSVKK PYFPMPWEGF    780
RDELLSHLAS QPIAKKISEE LKAGYQSLDY IFVSRMPKRS ITGAAHKQTI MRKGGIDKKG    840
KTIIIERLHL KDIKFDENGD FKMVGKEQDM ATYEAIKQRY LEHGKNSKKA FETPLYKPSK    900
KGTGNLIKRV KVEGQAKSFV REVNGGVAQN GDLVRVDLFE KDDKYYMVPI YVPDTVCSEL    960
PKKVVASSKG YEQWLTLDNS FTFKFSLYPY DLVRLVKGDE DRFLYFGTLD IDSDRLNFKD    1020
VNKPSKKNEY RYSLKTIEDL EKYEVGVLGD LRLVRKETRR NFH                    1063

SEQ ID NO: 398         moltype = AA  length = 1064
FEATURE                Location/Qualifiers
REGION                 1..1064
                       note = source = /note="Description of Artificial Sequence:
                        Syntheticpolypeptide"
REGION                 1..1064
                       note = source = /note="nAPG08290.1-del"
source                 1..1064
                       mol_type = protein
                       organism = synthetic construct
SEQUENCE: 398
MSELDYRIGL AIGTNSIGWG VIELFWNKDR ERYEKVRIVD KGVRMFDKAE IPNKGASLAE    60
PRRIARSSRR RLNRKSQRKK EIRNLLVQHG MITQEELDLL YPLSKKSIDI WDIRLDGLDR    120
LLNHLEWARL LIHLAQRRGF KSNRKSELKD AETGKVLSSI ENKRLFLY RTVGEMWIKD      180
AEFSKYDRRR NSPNEYVFSV SRADLEKEIV TLFEAQRKFQ SSYASKNLQE TYLQIWAHQL    240
PFASGNAILN KVGYCSLLKG KERRIPKATY TFQYFSALDQ VNRTRLGPDF QPFTQEQKEI    300
ILDKMFQRTD YYKKKTIPEV SYYDIRKWLE LDETIQFKGL NYDPNEELKK IEKKPFINLK    360
AFYEIKKVVA NYAERTNEAF STLDYDAIAY ALTVYKTDKD IRSYLKKSNN LSKRCYDDQL    420
IEELFTLSYT KFGHLSFKAI NHVLPIMQEG RTYQEAIHQL GYDTTNLKKE NRSMFLPLIP    480
DEITNPIVKR AITQARKVVN AIIRRYGSPN SVHIELAREL SKSHDERKKI MTAHDENYKK    540
NKGAISILIE NGILNPTGYD IVRYKLWKEQ GERCAYSLKE IPPDTFFNEP ILEVDHILPY    600
SQSFIDSYHN KVLVYSDENR NKGNRIPTY FLETNKDWEA FERYVRSNKL FSKKKREYLL     660
```

-continued

```
KKTYLPRESE LIKERHLNDT RYASTFLKNF IEQNLQFKEV EVNLRKKRVQ TVNGVITAHL    720
RKRWGLEKNR QETYLHHAMD AIIVACTDHH MVTRITEYYQ IKESNKSVKK PYFPMPWEGF    780
RDELLSHLAS QPIAKKISEE LKAGYQSSDY IFVSRMPKRS VTGAAHDQTI RRKGGIDKKG    840
KTIIIKRVRL KDIKFDENGD FKMVGKEQDL ATYEAIKQRY LEHRKNSKKA FETPLYKPSK    900
KGTGNLIKRV KIEGQTKAFV REVNGGVAQN SDLVRVDLFE KDDKYYMVPI YVPDTVCSEL    960
PKKVVKSGKG YEQWLTLDNS FTFKSSLYPY DLVRLVKGNE DRFLYFGTLD IDSDRLNFKD   1020
VNKPSKQNEY RYSLKTIENL EKYEVGVLGD LRLVKQETRR IFNR                   1064

SEQ ID NO: 399            moltype = AA  length = 169
FEATURE                   Location/Qualifiers
REGION                    1..169
                          note = source = /note="Description of Artificial Sequence:
                           Syntheticpolypeptide"
REGION                    1..169
                          note = source = /note="LPG50140 protein sequence"
source                    1..169
                          mol_type = protein
                          organism = synthetic construct
SEQUENCE: 399
MSDLELNHEY WMRHALQLAK RARDEGEVPV GAVLVLNNQV IGEGWNRAIG LHDPTAHAEI     60
MALRQGGLVL QNYRLIDTTL YVTFEPCVMC SGAMVHSRIG TLVFGVRNSK RGAAGSLMNV    120
LNYPGMNHQV QIIDGVLAPE CSGLLCDFYR MPRQVFNQQK AESTSINGD               169

SEQ ID NO: 400            moltype = AA  length = 164
FEATURE                   Location/Qualifiers
REGION                    1..164
                          note = source = /note="Description of Artificial Sequence:
                           Syntheticpolypeptide"
REGION                    1..164
                          note = source = /note="LPG50141 protein sequence"
source                    1..164
                          mol_type = protein
                          organism = synthetic construct
SEQUENCE: 400
MSNPELTHEH WMRYALTLAK RAREEGEVPV GAVLVLNNQV IGEGWNRAIG LHDPTAHAEI     60
MALRQGGLVL QNYRLIDTTL YVTFEPCVMC AGAMVHSRIG QLVFGVRNSK RGAAGSLMNV    120
LNYPGMNHRI EFTEGVLRDE CAAMLCDFYR QPRQVFNALK TGNA                    164

SEQ ID NO: 401            moltype = AA  length = 169
FEATURE                   Location/Qualifiers
REGION                    1..169
                          note = source = /note="Description of Artificial Sequence:
                           Syntheticpolypeptide"
REGION                    1..169
                          note = source = /note="LPG50142 protein sequence"
source                    1..169
                          mol_type = protein
                          organism = synthetic construct
SEQUENCE: 401
MSIPELNHDV WMRHALTLAK RAREEGEVPV GAVLVLNGQV IGEGWNRAIG LHDPTAHAEI     60
MALRQGGLVL QNYRLIDTTL YVTFEPCVMC AGAMVHSRIG QLVFGVRNSK RGAAGSLINV    120
LNYPGMNHRV AITEGVLREE CAAMLCDFYR QPRQVFNALK KPAGDINAF               169

SEQ ID NO: 402            moltype = AA  length = 172
FEATURE                   Location/Qualifiers
REGION                    1..172
                          note = source = /note="Description of Artificial Sequence:
                           Syntheticpolypeptide"
REGION                    1..172
                          note = source = /note="LPG50143 protein sequence"
source                    1..172
                          mol_type = protein
                          organism = synthetic construct
SEQUENCE: 402
MSNPELNHEY WMRYALTLAK RARDEGEVPV GAVLVLNDQV IGEGWNRAIG LHDPTAHAEI     60
MALRQGGLVL QNYRLIDTTL YVTFEPCVMC AGAMVHSRIG RLVFGVRNSK RGAAGSLLNV    120
LNYPGMNHHI EMEEGVLRDE CAAMLCDFYR QPRQVFNALK KSPPDINNLQ AR           172

SEQ ID NO: 403            moltype = AA  length = 169
FEATURE                   Location/Qualifiers
REGION                    1..169
                          note = source = /note="Description of Artificial Sequence:
                           Syntheticpolypeptide"
REGION                    1..169
                          note = source = /note="LPG50144 protein sequence"
source                    1..169
                          mol_type = protein
                          organism = synthetic construct
```

```
SEQUENCE: 403
MSNPELTHDH WMRHALTLAQ RARNEGEVPV GAVLVLNGQV IGEGWNRAIG LHDPTAHAEI    60
MALRQGGLVL QNYRLIDTVL YVTFEPCVMC AGAMVHSRIG QLVFGVRNSK RGAAGSLINV   120
LNYPGMNHRV EIIEGVLRDE CAAMLCDFYR HPRQVFNALK KNAGTINTQ              169

SEQ ID NO: 404          moltype = AA   length = 166
FEATURE                 Location/Qualifiers
REGION                  1..166
                        note = source = /note="Description of Artificial Sequence:
                          Syntheticpolypeptide"
REGION                  1..166
                        note = source = /note="LPG50145 protein sequence"
source                  1..166
                        mol_type = protein
                        organism = synthetic construct
SEQUENCE: 404
MSDTELNHEY WMRHALMLAK RARDEGEVPV GAVLVLKNQV IGEGWNRAIG LHDPTAHAEI    60
MALRQGGLVL QNYRLIDTTL YVTFEPCVMC AGAMVHSRIG NLVFGVRNSK RGAAGSLINV   120
LNYPGMNHRV EIAEGVLADE CSAMLCDFYR HPRQVFNALK QAAKHI                 166

SEQ ID NO: 405          moltype = AA   length = 171
FEATURE                 Location/Qualifiers
REGION                  1..171
                        note = source = /note="Description of Artificial Sequence:
                          Syntheticpolypeptide"
REGION                  1..171
                        note = source = /note="LPG50146 protein sequence"
source                  1..171
                        mol_type = protein
                        organism = synthetic construct
SEQUENCE: 405
MSDIELNHEY WMRHALMLAK RAREEGEVPV GAVLVLNNQV IGEGWNRAIG LHDPTAHAEI    60
MALRQGGLVL QNYRLIDTTL YVTFEPCVMC AGAMVHSRIG HLVFGVRNSK RGAAGSLINV   120
LNYPGMNHRI EFTEGVLADE CSGMLCDFYR YPRQVFNTLK QAAKAINPAA Q           171

SEQ ID NO: 406          moltype = AA   length = 173
FEATURE                 Location/Qualifiers
REGION                  1..173
                        note = source = /note="Description of Artificial Sequence:
                          Syntheticpolypeptide"
REGION                  1..173
                        note = source = /note="LPG50147 protein sequence"
source                  1..173
                        mol_type = protein
                        organism = synthetic construct
SEQUENCE: 406
MSIPELNHDV WMRHALTLAK RAREEGEVPV GAVLVLNGQV IGEGWNRAIG LHDPTAHAEI    60
MALRQGGLVL QNYRLIDTTL YVTFEPCVMC AGAMVHSRIG QLVFGVRNSK RGAAGSLMNV   120
LNYPGMNHRV EITEGVLRDE CAAMLCDFYR QPRQVFNALK KPAGDINALQ NNR         173

SEQ ID NO: 407          moltype = AA   length = 168
FEATURE                 Location/Qualifiers
REGION                  1..168
                        note = source = /note="Description of Artificial Sequence:
                          Syntheticpolypeptide"
REGION                  1..168
                        note = source = /note="LPG50148 protein sequence"
source                  1..168
                        mol_type = protein
                        organism = synthetic construct
SEQUENCE: 407
MSNPEFTHEY WMRHALTLAR RARDEGEVPV GAVLVLNNQV IGEGWNRAIG LHDPTAHAEI    60
MALRQGGLVL QNYRLIDTTL YVTFEPCVMC SGAMVHSRIG TLVFGVRNSK RGAAGSLMNV   120
LNYPGMNHQV KTIGGVQAPE CSGLLCDFYR MPRQVFNQQK AELKSIND              168

SEQ ID NO: 408          moltype = AA   length = 167
FEATURE                 Location/Qualifiers
REGION                  1..167
                        note = source = /note="Description of Artificial Sequence:
                          Syntheticpolypeptide"
REGION                  1..167
                        note = source = /note="LPG50149 protein sequence"
source                  1..167
                        mol_type = protein
                        organism = synthetic construct
SEQUENCE: 408
MSDAELTHEY WMRHALTLAQ RARDEGEVPV GAVLVLNNQV IGEGWNRAIG LHDPTAHAEI    60
MALRQGGLVQ QNYRLIDTTL YVTFEPCVMC AGAMVHSRIG RLIFGVRNSK RGAAGSLINV   120
LNYPGMNHRV EVVEGILRDE CAGMLCDFYR QPRQVFNALK KGATDIN                167
```

| | |
|---|---|
| SEQ ID NO: 409 | moltype = AA  length = 167 |
| FEATURE | Location/Qualifiers |
| REGION | 1..167 |
| | note = source = /note="Description of Artificial Sequence: Syntheticpolypeptide" |
| REGION | 1..167 |
| | note = source = /note="LPG50150 protein sequence" |
| source | 1..167 |
| | mol_type = protein |
| | organism = synthetic construct |

SEQUENCE: 409
```
MSDAELTHEY WMRHALTLAQ RARDEGEVPV GAVLVLNNQV IGEGWNRAIG LHDPTAHAEI   60
MALRQGGLVQ QNYRLLDTTL YVTFEPCVMC AGAMVHSRIG RLIFGVRNSK RGAAGSLINV  120
LNYPGMNHRV EVVEGILRDE CAGMLCAFYR QPRAVKNALK KGATDVL                167
```

| | |
|---|---|
| SEQ ID NO: 410 | moltype = AA  length = 169 |
| FEATURE | Location/Qualifiers |
| REGION | 1..169 |
| | note = source = /note="Description of Artificial Sequence: Syntheticpolypeptide" |
| REGION | 1..169 |
| | note = source = /note="LPG50151 protein sequence" |
| source | 1..169 |
| | mol_type = protein |
| | organism = synthetic construct |

SEQUENCE: 410
```
MSDLELNHEY WMRHALQLAQ RARDEGEVPV GAVLVYNNQV IGEGWNRAIG LHDPTAHAEI   60
MALRQGGLVL QNYRLLDTTL YVTFEPCVMC SGAMVHSRIG TLVFGVRNEK RGAAGSLMNV  120
LRYPGMNHQV QIIDGVLAPE CSGLLCDFYR MPRQQKNQQK AESTSSPGD              169
```

| | |
|---|---|
| SEQ ID NO: 411 | moltype = AA  length = 167 |
| FEATURE | Location/Qualifiers |
| REGION | 1..167 |
| | note = source = /note="Description of Artificial Sequence: Syntheticpolypeptide" |
| REGION | 1..167 |
| | note = source = /note="LPG50152 protein sequence" |
| source | 1..167 |
| | mol_type = protein |
| | organism = synthetic construct |

SEQUENCE: 411
```
MSDNELNHEY WMRHALGLAK RAREEGEVPV GAVLVLNNQV IGEGWNRAIG LHDPTAHAEI   60
MALRQGGLVL QNYRLTDTTL YVTFEPCVMC AGAMVHSRIG TLVFGVRNSK RGAAGSLMNV  120
LNYPGMNHRV EIVEGILSES CAAMLCDFYR QPRAVKNALK KAADPAA                167
```

| | |
|---|---|
| SEQ ID NO: 412 | moltype = AA  length = 164 |
| FEATURE | Location/Qualifiers |
| REGION | 1..164 |
| | note = source = /note="Description of Artificial Sequence: Syntheticpolypeptide" |
| REGION | 1..164 |
| | note = source = /note="LPG50153 protein sequence" |
| source | 1..164 |
| | mol_type = protein |
| | organism = synthetic construct |

SEQUENCE: 412
```
MSDTEFTHEH WMRHALTLAQ RARDEGEVPV GAVLVLNNQV IGEGWNRAIG LHDPTAHAEI   60
MALRQGGLVL QNYRLLDTTL YVTFEPCVMC AGAMVHSRIG HLVFGVRNSK RGAIGSLMNV  120
LGYPGMNHQV QVSEGVLATE CSAMLCDFYR APRLVKNALK EKAR                   164
```

| | |
|---|---|
| SEQ ID NO: 413 | moltype = AA  length = 171 |
| FEATURE | Location/Qualifiers |
| REGION | 1..171 |
| | note = source = /note="Description of Artificial Sequence: Syntheticpolypeptide" |
| REGION | 1..171 |
| | note = source = /note="LPG50154 protein sequence" |
| source | 1..171 |
| | mol_type = protein |
| | organism = synthetic construct |

SEQUENCE: 413
```
MSESEFTHEH WMRHALTLAR RAREEGEVPV GAVLVLNNQV IGEGWNRAIG LHDPTAHAEI   60
MALRQGGLVL QNYRLLDSTL YVTFEPCVMC AGAMVHGRIG NLVFGVRNSK RGAIGSLMNV  120
VGYPGMNHQI NVIEGVLAEE CSAMLCDFYR APRLVKNALK EKARNGNNPN K           171
```

| | |
|---|---|
| SEQ ID NO: 414 | moltype = AA  length = 164 |
| FEATURE | Location/Qualifiers |

```
REGION                        1..164
                              note = source = /note="Description of Artificial Sequence:
                                  Syntheticpolypeptide"
REGION                        1..164
                              note = source = /note="LPG50155 protein sequence"
source                        1..164
                              mol_type = protein
                              organism = synthetic construct
SEQUENCE: 414
MSNPELTHEH WMRYALTLAK RAREEGEVPV GAVLVLNNQV IGEGWNRAIG LHDPTAHAEI    60
MALRQGGLVL QNYRLIDTTL YVTFEPCVMC AGAMVHSRIG QLVFGVRNSK RGAAGSLMNV   120
LNYPGMNHRI EFTEGVLRDE CAAMLCDFYR QPRLVKNALK TGNA                    164

SEQ ID NO: 415                moltype = AA  length = 166
FEATURE                       Location/Qualifiers
REGION                        1..166
                              note = source = /note="Description of Artificial Sequence:
                                  Syntheticpolypeptide"
REGION                        1..166
                              note = source = /note="LPG50156 protein sequence"
source                        1..166
                              mol_type = protein
                              organism = synthetic construct
SEQUENCE: 415
MSDPELNHEY WMRHALQLAK RAREEGEVPV GAVLVLNNQV IGEGWNRAIG LHDPTAHAEI    60
MALRQGGLVL QNYRLLDTTL YVTFEPCVMC SGAMIHSRIG TVVFGVRNEK RGAAGSLLNV   120
LRYPGMNHQV NVLGGVLAPA CSEMLCEFYR MPRQQKNRQK AESKLS                  166

SEQ ID NO: 416                moltype = AA  length = 166
FEATURE                       Location/Qualifiers
REGION                        1..166
                              note = source = /note="Description of Artificial Sequence:
                                  Syntheticpolypeptide"
REGION                        1..166
                              note = source = /note="LPG50157 protein sequence"
source                        1..166
                              mol_type = protein
                              organism = synthetic construct
SEQUENCE: 416
MSDNELNHEH WMRHALTLAQ RAREEGEVPV GAVLVLQNQV IGEGWNRAIG LHDPTAHAEI    60
MALRQGGMVL QNYRLIDTTL YVTFEPCVMC AGAMVHSRIG QLVFGVRNSK RGAAGSLINV   120
LNYPGMNHRV EITEGVLADD CSSMLCDFYR HPREQKNALK RAAHSN                  166

SEQ ID NO: 417                moltype = AA  length = 168
FEATURE                       Location/Qualifiers
REGION                        1..168
                              note = source = /note="Description of Artificial Sequence:
                                  Syntheticpolypeptide"
REGION                        1..168
                              note = source = /note="LPG50158 protein sequence"
source                        1..168
                              mol_type = protein
                              organism = synthetic construct
SEQUENCE: 417
MSNPEHNHEY WMRHALTLAQ RARDEGEVPV GAVLVYNNQV IGEGWNRAIG LHDPTAHAEI    60
MALRQGGLVL QNYRLLDTTL YVTFEPCVMC SGAMVHSRIG TLVFGVRNEK RGAAGSLMNV   120
LGYPGMNHQV QTIGGVLAPE CSGLLCDFYR MPRQQKNQQK AELNQPGD                168

SEQ ID NO: 418                moltype = AA  length = 168
FEATURE                       Location/Qualifiers
REGION                        1..168
                              note = source = /note="Description of Artificial Sequence:
                                  Syntheticpolypeptide"
REGION                        1..168
                              note = source = /note="LPG50159 protein sequence"
source                        1..168
                              mol_type = protein
                              organism = synthetic construct
SEQUENCE: 418
MSDLELNHEY WMRHALSLAK RARDEGEVPV GAVLVLNNQV IGEGWNRAIG LHDPTAHAEI    60
MALRQGGLVL QNYRLLDTTL YVTFEPCVMC SGAMVHSRIG TLVYGVRNEK RGAAGSLMNV   120
LGYPGMNHQV QIIGGVLAPD CSGLLCDFYR MPRQQKNQQK AELKSSGD                168

SEQ ID NO: 419                moltype = AA  length = 166
FEATURE                       Location/Qualifiers
REGION                        1..166
                              note = source = /note="Description of Artificial Sequence:
                                  Syntheticpolypeptide"
```

```
REGION                    1..166
                          note = source = /note="LPG50160 protein sequence"
source                    1..166
                          mol_type = protein
                          organism = synthetic construct
SEQUENCE: 419
MSDHEFNDEY WMRHALTLAK RAREEGEVPV GAVLVLNNQV IGEGWNRAIG LHDPTAHAEI    60
MALRQGGLVL QNYRLIDATL YVTFEPCVMC AGAMVHSRIS RLVFGVRNSK RGAAGSLINV   120
LNYPGMNHRV EITEGILAES CSAMLCDFYR WPREVKNALK KARQEE                 166

SEQ ID NO: 420            moltype = AA  length = 166
FEATURE                   Location/Qualifiers
REGION                    1..166
                          note = source = /note="Description of Artificial Sequence:
                             Syntheticpolypeptide"
REGION                    1..166
                          note = source = /note="LPG50161 protein sequence"
source                    1..166
                          mol_type = protein
                          organism = synthetic construct
SEQUENCE: 420
MSQTELTHEY WMRHALTLAQ RARDEGEVPV GAVLVLNNQV IGEGWNRAIG LHDPTAHAEI    60
MALRQGGLVL QNYRLLDTTL YVTFEPCVMC AGAMVHGRIG TLVFGVRNSK RGAVGSLMNI   120
TGYPGMNHQV QVIEGILATE CSAMLCAFYR QPRLVKNALK EAAKTA                 166

SEQ ID NO: 421            moltype = AA  length = 167
FEATURE                   Location/Qualifiers
REGION                    1..167
                          note = source = /note="Description of Artificial Sequence:
                             Syntheticpolypeptide"
REGION                    1..167
                          note = source = /note="LPG50162 protein sequence"
source                    1..167
                          mol_type = protein
                          organism = synthetic construct
SEQUENCE: 421
MSNPELNHDY WMRHALSLAK RAREEGEVPV GAVLVRNNEV IGEGWNRAIG LHDPTAHAEI    60
MALRQGGMVL QNYRLIDTTL YVTFEPCVMC AGAMVHSRIG QLVFGVRNSK RGAAGSLMNV   120
LNYPGMNHRV EIVEGVLRDE CAGMLCDFYR QPRLVKNAQK KGAEPLI                167

SEQ ID NO: 422            moltype = AA  length = 172
FEATURE                   Location/Qualifiers
REGION                    1..172
                          note = source = /note="Description of Artificial Sequence:
                             Syntheticpolypeptide"
REGION                    1..172
                          note = source = /note="LPG50163 protein sequence"
source                    1..172
                          mol_type = protein
                          organism = synthetic construct
SEQUENCE: 422
MSNPELNHEY WMRYALTLAK RARDEGEVPV GAVLVYNDQV IGEGWNRAIG LHDPTAHAEI    60
MALRQGGLVL QNYRLIDTTL YVTFEPCVMC AGAMVHSRIG RLVFGVRNSK RGAAGSLLNV   120
LNYPGMNHHI EMEEGVLRDE CAAMLCDFYR QPRMVKNALK KSPPDSPNLQ AR          172

SEQ ID NO: 423            moltype = AA  length = 168
FEATURE                   Location/Qualifiers
REGION                    1..168
                          note = source = /note="Description of Artificial Sequence:
                             Syntheticpolypeptide"
REGION                    1..168
                          note = source = /note="LPG50164 protein sequence"
source                    1..168
                          mol_type = protein
                          organism = synthetic construct
SEQUENCE: 423
MSNPEFTHEY WMRHALTLAR RARDEGEVPV GAVLVLNNQV IGEGWNRAIG LHDPTAHAEI    60
MALRQGGLVL QNYRLLDTTL YVTFEPCVMC SGAMVHSRIG TLVFGVRNEK RGAAGSLMNV   120
LGYPGMNHQV KTIGGVLAPE CSGLLCDFYR MPRQQKNQQK AELKSSGD               168

SEQ ID NO: 424            moltype = AA  length = 165
FEATURE                   Location/Qualifiers
REGION                    1..165
                          note = source = /note="Description of Artificial Sequence:
                             Syntheticpolypeptide"
REGION                    1..165
                          note = source = /note="LPG50165 protein sequence"
source                    1..165
                          mol_type = protein
                          organism = synthetic construct
```

```
SEQUENCE: 424
MSDNEFNHEY WMRHALTLAQ RARDEGEVPV GAVLVLDNQV IGEGWNRAIG LHDPTAHAEI    60
MALRQGGMVL QNYRLINATL YVTFEPCVMC AGAMVHSRIG HVVFGVRNSK RGAAGSLMNV   120
LNYPGMNHRV EVTEGVLREQ CAGMLCDFYR EPREQFNALR KAQKA                  165

SEQ ID NO: 425          moltype = AA  length = 170
FEATURE                 Location/Qualifiers
REGION                  1..170
                        note = source = /note="Description of Artificial Sequence:
                          Syntheticpolypeptide"
REGION                  1..170
                        note = source = /note="LPG50166 protein sequence"
source                  1..170
                        mol_type = protein
                        organism = synthetic construct
SEQUENCE: 425
MSDNELNHEY WMRHALTLAQ RARDEGEVPV GAVLVLNNQV IGEGWNRAIG LHDPTAHAEI    60
MALRQGGMVL QNYRLIDATL YVTFEPCIMC AGAMVHSRIG QVVFGVRNSK RGAAGSLINI   120
LNYPGMNHRV DVTEGVLSER CANMLCDFYR EPRLQFNAQR KAEKAGNAAA              170

SEQ ID NO: 426          moltype = AA  length = 169
FEATURE                 Location/Qualifiers
REGION                  1..169
                        note = source = /note="Description of Artificial Sequence:
                          Syntheticpolypeptide"
REGION                  1..169
                        note = source = /note="LPG50167 protein sequence"
source                  1..169
                        mol_type = protein
                        organism = synthetic construct
SEQUENCE: 426
MSNPELTHDH WMRHALTLAQ RARNEGEVPV GAVLVLNGQV IGEGWNRAIG LHDPTAHAEI    60
MALRQGGLVL QNYRLIDTVL YVTFEPCVMC AGAMVHSRIG QLVFGVRNSK RGAAGSLINV   120
LNYPGMNHRV EIIEGVLRDE CAAMLCDFYR HPRLVKNALK KNAGTSPTQ               169

SEQ ID NO: 427          moltype = AA  length = 166
FEATURE                 Location/Qualifiers
REGION                  1..166
                        note = source = /note="Description of Artificial Sequence:
                          Syntheticpolypeptide"
REGION                  1..166
                        note = source = /note="LPG50168 protein sequence"
source                  1..166
                        mol_type = protein
                        organism = synthetic construct
SEQUENCE: 427
MSDTELNHEY WMRHALMLAK RARDEGEVPV GAVLVLKNQV IGEGWNRAIG LHDPTAHAEI    60
MALRQGGLVL QNYRLIDTTL YVTFEPCVMC AGAMVHSRIG NLVFGVRNSK RGAAGSLINV   120
LNYPGMNHRV EIAEGVLADE CSAMLCDFYR HPRQQQNALK QAAKHD                  166

SEQ ID NO: 428          moltype = AA  length = 171
FEATURE                 Location/Qualifiers
REGION                  1..171
                        note = source = /note="Description of Artificial Sequence:
                          Syntheticpolypeptide"
REGION                  1..171
                        note = source = /note="LPG50169 protein sequence"
source                  1..171
                        mol_type = protein
                        organism = synthetic construct
SEQUENCE: 428
MSDIELNHEY WMRHALMLAK RAREEGEVPV GAVLVLNNQV IGEGWNRAIG LHDPTAHAEI    60
MALRQGGLVL QNYRLIDTTL YVTFEPCVMC AGAMVHSRIG HLVFGVRNSK RGAAGSLINV   120
LNYPGMNHRI EFTEGVLADE CSGMLCDFYR YPRQQQNTLK QAAKANPPAA Q            171

SEQ ID NO: 429          moltype = AA  length = 165
FEATURE                 Location/Qualifiers
REGION                  1..165
                        note = source = /note="Description of Artificial Sequence:
                          Syntheticpolypeptide"
REGION                  1..165
                        note = source = /note="LPG50170 protein sequence"
source                  1..165
                        mol_type = protein
                        organism = synthetic construct
SEQUENCE: 429
MSDNELNHER WMRHALTLAQ RARDEGEVPV GAVLVYQNQV IGEGWNRAIG LHDPTAHAEI    60
MALRQGGLVL QNYRLIDTTL YVTFEPCVMC AGAMVHSRIG QLVFGVRNSK RGAAGSLINV   120
LNYPGMNHRV AITEGVLAES CSAMLCDFYR HPREQKNALR RAAQS                   165
```

```
SEQ ID NO: 430          moltype = AA   length = 166
FEATURE                 Location/Qualifiers
REGION                  1..166
                        note = source = /note="Description of Artificial Sequence:
                         Syntheticpolypeptide"
REGION                  1..166
                        note = source = /note="LPG50171 protein sequence"
source                  1..166
                        mol_type = protein
                        organism = synthetic construct
SEQUENCE: 430
MSDLELNDEY WMRHALTLAK RAREEGEVPV GAVLVLNNQV IGEGWNRAIG LHDPTAHAEI   60
MALRQGGLVL QNYRLIDATL YVTFEPCVMC AGAMVHSRIA RLVFGVRNSK RGAAGSLMNV  120
LNYPGMNHRV EISEGVLAES CSAMLCDFYR WPREVKNALK KAREQN                166

SEQ ID NO: 431          moltype = AA   length = 169
FEATURE                 Location/Qualifiers
REGION                  1..169
                        note = source = /note="Description of Artificial Sequence:
                         Syntheticpolypeptide"
REGION                  1..169
                        note = source = /note="LPG50172 protein sequence"
source                  1..169
                        mol_type = protein
                        organism = synthetic construct
SEQUENCE: 431
MSDLELDHEY WMRHALLLAK RARDEGEVPV GAVLVLNNQV IGEGWNRAIG LHDPTAHAEI   60
MALRQGGLVL QNYRLLDTTL YVTFEPCVMC SGAMVHSRIG TLVYGVRNEK RGAAGSLMNV  120
LGYPGMNHQV QVIDGVLAPE CSGLLCDFYR MPRQQKNQQK AESTSSRGD             169

SEQ ID NO: 432          moltype = AA   length = 162
FEATURE                 Location/Qualifiers
REGION                  1..162
                        note = source = /note="Description of Artificial Sequence:
                         Syntheticpolypeptide"
REGION                  1..162
                        note = source = /note="LPG50173 protein sequence"
source                  1..162
                        mol_type = protein
                        organism = synthetic construct
SEQUENCE: 432
MSDTELTHEY WMRHALMLAQ RARDEGEVPV GAVLVLNNRV IGEGWNRAIG LHDPTAHAEI   60
MALRQGGLVL QNYRLLDTTL YVTFEPCVMC AGAMVHGRIG TLVFGVRNLK RGAAGSLMNV  120
LNYPGMNHRV EIVEGTLSDE CSGMLCEFYR QPRLAFNAQK QA                    162

SEQ ID NO: 433          moltype = AA   length = 173
FEATURE                 Location/Qualifiers
REGION                  1..173
                        note = source = /note="Description of Artificial Sequence:
                         Syntheticpolypeptide"
REGION                  1..173
                        note = source = /note="LPG50174 protein sequence"
source                  1..173
                        mol_type = protein
                        organism = synthetic construct
SEQUENCE: 433
MSIPELNHDV WMRHALTLAK RAREEGEVPV GAVLVLNGQV IGEGWNRAIG LHDPTAHAEI   60
MALRQGGLVL QNYRLIDTTL YVTFEPCVMC AGAMVHSRIG QLVFGVRNSK RGAAGSLMNV  120
LNYPGMNHRV EITEGVLRDE CAAMLCDFYR QPRLVKNALK KPAGDPSALQ NNR         173

SEQ ID NO: 434          moltype = AA   length = 166
FEATURE                 Location/Qualifiers
REGION                  1..166
                        note = source = /note="Description of Artificial Sequence:
                         Syntheticpolypeptide"
REGION                  1..166
                        note = source = /note="LPG50175 protein sequence"
source                  1..166
                        mol_type = protein
                        organism = synthetic construct
SEQUENCE: 434
MSDLELNDEY WMRHALTLAK RAREEGEVPV GAVLVLNNQV IGEGWNRAIG LHDPTAHAEI   60
MALRQGGLVL QNYRLIDATL YVTFEPCVMC AGAMVHSRIA RLVFGVRNSK RGAAGSLMNV  120
LNYPGMNHRV EISEGVLAGS CSAMLCDFYR WPREVKNALK KAREQN                166

SEQ ID NO: 435          moltype = AA   length = 153
FEATURE                 Location/Qualifiers
```

```
REGION                      1..153
                            note = source = /note="Description of Artificial Sequence:
                                Syntheticpolypeptide"
REGION                      1..153
                            note = source = /note="LPG50176 protein sequence"
source                      1..153
                            mol_type = protein
                            organism = synthetic construct
SEQUENCE: 435
MSDIEQNHEY WMRHALVLAK RAREEGEVPV GAVLVLNNQV IGEGWNRAIG LHDPTAHAEI    60
MALRQGGLVL QNYRLIDTTL YVTFEPCVMC AGAMVHGRIG SLVFGVRNSK RGAAGSLINV   120
LNYPGMNHRV EMTEGVLADE CSAMLCDFYR HPR                                153

SEQ ID NO: 436              moltype = AA   length = 168
FEATURE                     Location/Qualifiers
REGION                      1..168
                            note = source = /note="Description of Artificial Sequence:
                                Syntheticpolypeptide"
REGION                      1..168
                            note = source = /note="LPG50177 protein sequence"
source                      1..168
                            mol_type = protein
                            organism = synthetic construct
SEQUENCE: 436
MCNPERDHEY WMRHALTLAQ RARDEGEVPV GAVLVLNNQV IGEGWNRAIG LHDPTAHAEI    60
MALRQGGMVL QNYRLLDTTL YVTFEPCVMC SGAMVHSRIG TLVFGVRNEK RGAAGSLLNV   120
LGYPGMNHQV KTIGGVLAPA CSALLCDFYR MPRQQKNQQK AELKLSND                168

SEQ ID NO: 437              moltype = AA   length = 162
FEATURE                     Location/Qualifiers
REGION                      1..162
                            note = source = /note="Description of Artificial Sequence:
                                Syntheticpolypeptide"
REGION                      1..162
                            note = source = /note="LPG50178 protein sequence"
source                      1..162
                            mol_type = protein
                            organism = synthetic construct
SEQUENCE: 437
MSAIELNHEY WMRHALGLAQ RARDEGEVPV GAVLVYQNV IGEGWNRAIG LHDPTAHAEI     60
MALRQGGLVL QNYRLIDTTL YVTFEPCVMC AGAMVHSRIG RVVFGVRNSK RGAAGSLMNV   120
LNYPGMNHRV EVTEGVLAGE CSAMLCDFYR APRAQFNAQK RP                      162

SEQ ID NO: 438              moltype = AA   length = 169
FEATURE                     Location/Qualifiers
REGION                      1..169
                            note = source = /note="Description of Artificial Sequence:
                                Syntheticpolypeptide"
REGION                      1..169
                            note = source = /note="LPG50179 protein sequence"
source                      1..169
                            mol_type = protein
                            organism = synthetic construct
SEQUENCE: 438
MSNPELNHEY WMRYALTLAK RAREEGEVPV GAVLVLNERV IGEGWNRAIG LHDPTAHAEI    60
MALRQGGMVL QNYRLIDTTL YVTFEPCVMC AGAMVHSRIG HLVFGVRNSK RGAAGSLMNV   120
LNYPGMNHRV AITEGVLRDE CAAMLCDFYR QPRQVKNALK KTLSDSQEQ               169

SEQ ID NO: 439              moltype = AA   length = 168
FEATURE                     Location/Qualifiers
REGION                      1..168
                            note = source = /note="Description of Artificial Sequence:
                                Syntheticpolypeptide"
REGION                      1..168
                            note = source = /note="LPG50180 protein sequence"
source                      1..168
                            mol_type = protein
                            organism = synthetic construct
SEQUENCE: 439
MSNPEHDHEY WMRHALNLAQ RARDEGEVPV GAVLVLNNQV IGEGWNRAIG LHDPTAHAEI    60
MALRQGGLVL QNYRLLDTTL YVTFEPCVMC SGAMVHSRIG TLVYGVRNEK RGAAGSLMNV   120
LGYPGMNHQV NVIGGVLAQD CSARLCDFYR MPRQQKNQQR AELKAQGD                168

SEQ ID NO: 440              moltype = AA   length = 168
FEATURE                     Location/Qualifiers
REGION                      1..168
                            note = source = /note="Description of Artificial Sequence:
                                Syntheticpolypeptide"
REGION                      1..168
                            note = source = /note="LPG50181 protein sequence"
```

```
source                     1..168
                           mol_type = protein
                           organism = synthetic construct
SEQUENCE: 440
MSDPELNHEY WMRHALQLAQ RARDEGEVPV GAVLVLNNQV IGEGWNRAIG LHDPTAHAEI    60
MALRQGGLVL QNYRLLDTTL YVTFEPCVMC SGAMIHSRIG TVVYGVRNEK RGAAGSLLNV   120
LSYPGMNHQV KVIGEVLAPA CSAMLCDFYR MPRQQKNQQK AEWKLSGE                168

SEQ ID NO: 441             moltype = AA   length = 171
FEATURE                    Location/Qualifiers
REGION                     1..171
                           note = source = /note="Description of Artificial Sequence:
                             Syntheticpolypeptide"
REGION                     1..171
                           note = source = /note="LPG50182 protein sequence"
source                     1..171
                           mol_type = protein
                           organism = synthetic construct
SEQUENCE: 441
MSNPELNHEY WMRYALTLAK RARDEGEVPV GAVLVYHDQV IGEGWNRAIG LHDPTAHAEI    60
MALRQGGLVL QNYRLIDTTL YVTFEPCVMC AGAMVHSRIG RLVFGVRNSK RGAAGSLLNV   120
LNYPGMNHQI DMEEGVLRDE CAAMLCDFYR LPRIVKNALK QSPPDSTNLH A            171

SEQ ID NO: 442             moltype = AA   length = 32
FEATURE                    Location/Qualifiers
REGION                     1..32
                           note = source = /note="Description of Artificial Sequence:
                             Syntheticpolypeptide"
REGION                     1..32
                           note = source = /note="L32 Linker sequence"
source                     1..32
                           mol_type = protein
                           organism = synthetic construct
SEQUENCE: 442
SGGSSGGSSG SETPGTSESA TPESSGGSSG GS                                  32

SEQ ID NO: 443             moltype = DNA   length = 507
FEATURE                    Location/Qualifiers
misc_feature               1..507
                           note = source = /note="Description of Artificial Sequence:
                             Syntheticpolynucleotide"
misc_feature               1..507
                           note = source = /note="Mammalian codon optimized LPG50140"
source                     1..507
                           mol_type = other DNA
                           organism = synthetic construct
SEQUENCE: 443
atgtctgatc tggaactgaa tcacgagtac tggatgcggc acgccctgca actggccaag    60
cgggccagag atgagggcga ggtgccagtg ggcgccgtgc tggtgctgaa caaccaggtc   120
atcggagaag gctggaacag agccatcggc ctgcatgacc ccacagccca tgccgaaatc   180
atggccctga cagggcgg actggtgctg cagaactata ggctgattga caccaccctg    240
tacgtgacct tcgagccttg tgtgatgtgc tccggcgcta tggtgcacag cagaatcggc   300
acactggtct ttggcgttag aaacagcaag cgcggagctg ctggcagcct gatgaatgtg   360
ctgaactacc ccggcatgaa ccaccaggtg caaatcatcg acggcgtgct cgcccctgaa   420
tgcagcggac tgctgtgcga cttctaccgg atgcctagac aggtgttcaa ccagcagaaa   480
gccgagagca cctctatcaa cggcgac                                      507

SEQ ID NO: 444             moltype = DNA   length = 492
FEATURE                    Location/Qualifiers
misc_feature               1..492
                           note = source = /note="Description of Artificial Sequence:
                             Syntheticpolynucleotide"
misc_feature               1..492
                           note = source = /note="Mammalian codon optimized LPG50141"
source                     1..492
                           mol_type = other DNA
                           organism = synthetic construct
SEQUENCE: 444
atgtccaacc ccgagctgac ccacgagcac tggatgagat acgccctgac actggccaag    60
cgggccagag aggaaggcga agtgccagtg ggcgccgtgc tggtgctgaa caaccaggtg   120
atcggagaag gctggaatag agccattgga ctgcatgatc ctacagccca cgccgaaatc   180
atggccctga cagggcgg cctggtgctg cagaactata gactgatcga caccaccctg    240
tacgtgacat tcgagccttg tgtgatgtgc gccggcgcca tggtgcacag cagaatcggc   300
cagctgtct ttggcgtgcg gaacagcaaa cggggcgctg caggctctct gatgaatgtg    360
ctcaactacc ccggcatgaa ccacagaatc gagttcaccg agggagttct gcgggacgag   420
tgcgctgcta tgctgtgcga cttctaccgc cagcctagac aagtgttcaa cgccctgaag   480
accggcaacg cc                                                       492

SEQ ID NO: 445             moltype = DNA   length = 507
```

```
FEATURE              Location/Qualifiers
misc_feature         1..507
                     note = source = /note="Description of Artificial Sequence:
                     Syntheticpolynucleotide"
misc_feature         1..507
                     note = source = /note="Mammalian codon optimized LPG50142"
source               1..507
                     mol_type = other DNA
                     organism = synthetic construct
SEQUENCE: 445
atgagcatcc ccgagctgaa ccacgacgtg tggatgcggc acgctcttac actggccaag    60
cgggccagag aagaaggcga agtgccagtg ggcgccgtgc tggttctgaa cggccaggtg   120
atcggcgagg gctggaacag agccattgga ctgcatgacc ctaccgccca cgccgagatc   180
atggccctga cagggcgg actggtgctg cagaactatc gcctgatcga caccaccctg    240
tacgtgacct tcgagccttg cgtgatgtgc gccggcgcta tggtgcacag cagaatcggc   300
cagctggtgt tcggcgtgcg gaactccaag aggggcgccg ctggatctct gatcaacgtg   360
ctgaattacc ccggcatgaa ccatagagtc gccatcacag agggagtgct cagagaggaa   420
tgtgccgcca tgctgtgcga cttctacaga caacctagac aggtctttaa cgccctgaag   480
aaacctgctg gcgatatcaa tgccttc                                       507

SEQ ID NO: 446       moltype = DNA  length = 516
FEATURE              Location/Qualifiers
misc_feature         1..516
                     note = source = /note="Description of Artificial Sequence:
                     Syntheticpolynucleotide"
misc_feature         1..516
                     note = source = /note="Mammalian codon optimized LPG50143"
source               1..516
                     mol_type = other DNA
                     organism = synthetic construct
SEQUENCE: 446
atgagcaacc ccgagctgaa tcacgagtac tggatgcggt acgccctgac actggccaag    60
cgggccagag atgaaggcga agtgcctgtg ggcgccgtgc tggtgctgaa cgaccaggtg   120
atcggagaag gctggaatag agccattggc ctgcatgacc ccaccgccca cgccgagatc   180
atggccctga cagggcgg actggttctg cagaactacc gcctgatcga caccaccctg    240
tacgtgacat tcgagccttg tgtgatgtgc gccggcgcca tggtgcattc tagaatcggc   300
agactggtgt tcggcgtgcg gaacagcaag aggggcgctg ctggcagcct gctgaacgtg   360
ctcaattatc ctggaatgaa ccaccacatc gagatggaag agggcgtgct gcgggacgag   420
tgcgccgcta tgctgtgcga cttctacaga cagcctagac aggtctttaa cgccctgaag   480
aaatccccac ctgatatcaa caacctgcaa gctaga                             516

SEQ ID NO: 447       moltype = DNA  length = 507
FEATURE              Location/Qualifiers
misc_feature         1..507
                     note = source = /note="Description of Artificial Sequence:
                     Syntheticpolynucleotide"
misc_feature         1..507
                     note = source = /note="Mammalian codon optimized LPG50144"
source               1..507
                     mol_type = other DNA
                     organism = synthetic construct
SEQUENCE: 447
atgagcaacc ctgagctgac acacgaccac tggatgagac acgccctgac cctggcccag    60
cgggccagaa acgagggcga agtgcccgtg ggcgctgtgc tggtgctgaa tggccaagtg   120
atcggagaag gctgaacag agccatcggc ctgcatgacc caacagccca cgccgagatc    180
atggccctgc ggcagggcgg actggtcctg cagaactatc ggctgatcga caccgtgctg   240
tacgtgacct tcgagccttg tgtgatgtgc gccggcgcca tggtgcactc tagaatcgga   300
cagctggtct ttggcgtgcg gaatagcaag cgcggcgccg ctggctccct gatcaacgtg   360
cttaattacc ccggcatgaa ccacagagtg gaaattatcg agggcgttct gagagatgag   420
tgcgcagcta tgctgtgcga cttctacaga catcctagac aggtgttcaa cgccctgaaa   480
aagaacgccg gaaccatcaa cacccag                                       507

SEQ ID NO: 448       moltype = DNA  length = 498
FEATURE              Location/Qualifiers
misc_feature         1..498
                     note = source = /note="Description of Artificial Sequence:
                     Syntheticpolynucleotide"
misc_feature         1..498
                     note = source = /note="Mammalian codon optimized LPG50145"
source               1..498
                     mol_type = other DNA
                     organism = synthetic construct
SEQUENCE: 448
atgagcgaca ccgagctgaa ccacgagtac tggatgcggc acgccctgat gctggctaag    60
cgggccagag atgagggcga agtgcctgtg ggcgccgtgc tggtcctgaa aaaccaggtg   120
atcggagaag gctggaatag agccatcggc ctgcatgacc ccaccgccca cgctgaaatc   180
atggccctga cagggagg cctggtgctc cagaactata gactgattga taccacactg     240
tacgtgacat tcgagccttg tgtgatgtgc gccggcgcca tggtgcactc tagaatcggc   300
aacctggtct ttggcgtgcg gaacagcaag aggggcgctg ctggcagcct gatcaacgtg   360
```

```
ctgaattacc ccggcatgaa ccacagagtg gaaatcgccg agggagttct ggccgacgag   420
tgctccgcca tgctgtgcga cttctaccgg catcctagac aagtgttcaa cgccctgaag   480
caggccgcca agcacatc                                                 498

SEQ ID NO: 449          moltype = DNA  length = 513
FEATURE                 Location/Qualifiers
misc_feature            1..513
                        note = source = /note="Description of Artificial Sequence:
                        Syntheticpolynucleotide"
misc_feature            1..513
                        note = source = /note="Mammalian codon optimized LPG50146"
source                  1..513
                        mol_type = other DNA
                        organism = synthetic construct
SEQUENCE: 449
atgagcgaca tcgagctgaa tcacgagtac tggatgcggc acgccctgat gctggccaaa   60
agagccagag aggaaggaga agtgccagtg gcgccgtgc tggtgctgaa caaccaggtg    120
atcggcgaag gctggaaccg ggccattggc ctgcatgatc ctaccgccca cgccgagatc   180
atggccctga cagggcgg actggtgctc cagaactata gactgatcga cacaacactg     240
tacgtgacct tcgagccttg tgtgatgtgc gccggcgcca tggtgcacag cagaatcggc   300
cacctggtct ttggcgttag aaactctaag cgcggagctg ctggctccct gatcaatgtg   360
ctgaactacc ccggcatgaa ccaccggatc gaattcaccg agggcgtgct ggctgatgaa   420
tgcagcggca tgctgtgcga cttctacaga taccctagac aagtgttcaa cacccctgaag  480
caggccgcta aggccatcaa ccccgccgcc cag                                513

SEQ ID NO: 450          moltype = DNA  length = 519
FEATURE                 Location/Qualifiers
misc_feature            1..519
                        note = source = /note="Description of Artificial Sequence:
                        Syntheticpolynucleotide"
misc_feature            1..519
                        note = source = /note="Mammalian codon optimized LPG50147"
source                  1..519
                        mol_type = other DNA
                        organism = synthetic construct
SEQUENCE: 450
atgagcatcc ctgagctgaa tcacgatgtg tggatgcggc acgccctgac actggctaag   60
agaccagggg aagagggcga agtgccagtg ggagccgtgc tggtgctgaa cggccaggtg   120
atcggagaag gctggaaccg ggccatcggc ctgcatgacc ccaccgccca cgccgagatt   180
atggccctga cagggcgg actggtgcctt caaaattata gactgatcga caccaccctg    240
tacgtgacat tcgagccttg tgtgatgtgc gccggagcca tggtgcactc tagaatcggc   300
cagctggtgt tcggcgtgcg caacagcaag cggggcgctg ctggctccct gatgaacgtg   360
ctgaactacc ccggcatgaa tcatagagtg gaaatcaccg agggcgttct cagagatgag   420
tgcgccgcta tgctgtgcga cttctaccgg cagcctagac aggtctttaa cgccctgaag   480
aaacctgccg gcgacatcaa cgccctgcag aacaacaga                         519

SEQ ID NO: 451          moltype = DNA  length = 504
FEATURE                 Location/Qualifiers
misc_feature            1..504
                        note = source = /note="Description of Artificial Sequence:
                        Syntheticpolynucleotide"
misc_feature            1..504
                        note = source = /note="Mammalian codon optimized LPG50148"
source                  1..504
                        mol_type = other DNA
                        organism = synthetic construct
SEQUENCE: 451
atgagcaacc ccgagttcac acacgagtac tggatgcggc acgccctgac actggcccgc   60
agagccagag atgagggcga agtgcctgtg gcgccgtgc tggtcctgaa caaccaggtg    120
atcggcgaag gctggaaccg ggccattgga ctgcatgacc ccaccgccca cgccgaaatc   180
atggccctga cagggcgg actggtgctg cagaactacc ggctgatcga caccaccctg     240
tacgtgacat tcgagccatg tgtgatgtgt agcggcgcta tggtccattc tagaatcggc   300
accctggttt tcggcgtgcg gaacagcaag agaggagctg ctggcagcct gatgaacgtg   360
ctgaattatc ctggaatgaa tcaccaggtg aagaccatcg gcggcgtgct cgcccctgaa   420
tgcagcggcc tgctgtgcga cttctacaga atgcctagac aagtgtttaa ccagcagaaa   480
gccgagctga agtccatcaa cgac                                         504

SEQ ID NO: 452          moltype = DNA  length = 501
FEATURE                 Location/Qualifiers
misc_feature            1..501
                        note = source = /note="Description of Artificial Sequence:
                        Syntheticpolynucleotide"
misc_feature            1..501
                        note = source = /note="Mammalian codon optimized LPG50149"
source                  1..501
                        mol_type = other DNA
                        organism = synthetic construct
```

```
SEQUENCE: 452
atgagcgacg ccgagctgac ccacgagtac tggatgagac acgccctgac actggcccag    60
cgcgccagag atgagggaga agtgccagtg ggcgccgtgc tggttctgaa caaccaggtg   120
atcggcgagg gctggaatag agccatcggc ctgcatgacc ccaccgccca tgctgaaatc   180
atggccctgc ggcagggcgg cctggtgcaa cagaactaca gactgatcga caccaccctg   240
tacgtgacat tcgagccttg tgtgatgtgc gccggagcta tggtgcactc caggatcgga   300
agactgatct tcggcgtgcg gaacagcaag cggggcgcag ctggatctct gattaacgtg   360
ctgaattatc ctggcatgaa ccacagagtg gaagtggtgg aaggcatcct gagagatgag   420
tgcgccggca tgctgtgcga cttctaccgg caacctagac aggtctttaa cgccctcaag   480
aaaggcgcca ccgacatcaa c                                             501

SEQ ID NO: 453           moltype = DNA  length = 501
FEATURE                  Location/Qualifiers
misc_feature             1..501
                         note = source = /note="Description of Artificial Sequence:
                           Syntheticpolynucleotide"
misc_feature             1..501
                         note = source = /note="Mammalian codon optimized LPG50150"
source                   1..501
                         mol_type = other DNA
                         organism = synthetic construct
SEQUENCE: 453
atgagcgacg ccgagctgac ccacgagtac tggatgagac acgccctgac actggcccag    60
agagctaggg atgagggaga agtccccgtg ggtgctgttc tggtgctcaa caaccaggtg   120
atcggagagg gctggaatag agccatcggc ctgcatgatc ctacagccca cgccgaaatc   180
atggccctga gacagggcgg actggtccag cagaactatc ggctgctgga caccaccctg   240
tacgtgacct tcgagccatg tgtgatgtgc gccggcgcca tggtgcactc tagaatcgga   300
agactgatct tcggcgtgcg gaacagcaag cggggcgccg ctggctccct gattaacgtg   360
ctgaattacc ctggcatgaa ccacagagtg gaagtggtgg aaggcatcct gcgggacgag   420
tgcgccggca tgctgtgcgc ttttttaccgc caacctagac ccgtgaagaa cgccctgaaa   480
aagggcgcca ccgacgtgct g                                             501

SEQ ID NO: 454           moltype = DNA  length = 507
FEATURE                  Location/Qualifiers
misc_feature             1..507
                         note = source = /note="Description of Artificial Sequence:
                           Syntheticpolynucleotide"
misc_feature             1..507
                         note = source = /note="Mammalian codon optimized LPG50151"
source                   1..507
                         mol_type = other DNA
                         organism = synthetic construct
SEQUENCE: 454
atgagcgacc tggaactgaa ccacgagtac tggatgagac acgccctgca actggcccag    60
agggccagag atgagggaga agtgccagtg ggcgccgtgc tggtctacaa caaccaggtt   120
atcggcgaag gctggaatag agccattggc ctgcatgacc ccaccgccca tgctgaaatc   180
atggccctgc ggcagggcgg actggtgctc cagaactacc ggctgctgga caccaccctg   240
tatgtgacct ttgagccttg tgtgatgtgc tccggcgcca tggtgcacag cagaatcgga   300
acactggtgt tcggcgtgcg gaacgagaag cggggcgctg ctggcagcct gatgaacgtg   360
ctgagatacc ccggcatgaa tcaccaggtg caaatcatcg acggcgtgct ggcccctgaa   420
tgcagcggcc tgctgtgcga cttctacaga atgcctagac agcagaaaaa ccagcaaaag   480
gccgagtcta catctagccc tggagat                                       507

SEQ ID NO: 455           moltype = DNA  length = 501
FEATURE                  Location/Qualifiers
misc_feature             1..501
                         note = source = /note="Description of Artificial Sequence:
                           Syntheticpolynucleotide"
misc_feature             1..501
                         note = source = /note="Mammalian codon optimized LPG50152"
source                   1..501
                         mol_type = other DNA
                         organism = synthetic construct
SEQUENCE: 455
atgagcgaca acgagctgaa ccacgagtac tggatgcggc acgccctggg cctcgccaaa    60
agagccagag aggaaggcga ggtgcccgtg ggcgctgttc tggtcctgaa caaccaggtg   120
atcggagaag gctggaacag ggccatcggc ctgcatgacc aaacagccca cgccgagatc   180
atggctctga cagggcgg cctggtgctg cagaactata gactgacaga taccaccctg   240
tacgtgacct ttgagccttg tgtgatgtgc gccggagcaa tggtccacag cagaatcggc   300
accctggtgt tcggcgtgcg gaacagcaag cggggcgccg ccggctctct gatgaacgtg   360
ctgaattacc ccggcatgaa tcatagagtg gaaattgtgg aaggaatcct gagcgagtcc   420
tgcgccgcca tgctgtgcga cttctaccgg caacctagag ccgtgaagaa cgccctgaag   480
aaggccgctg atcctgccgc t                                             501

SEQ ID NO: 456           moltype = DNA  length = 492
FEATURE                  Location/Qualifiers
misc_feature             1..492
                         note = source = /note="Description of Artificial Sequence:
                           Syntheticpolynucleotide"
```

```
misc_feature           1..492
                       note = source = /note="Mammalian codon optimized LPG50153"
source                 1..492
                       mol_type = other DNA
                       organism = synthetic construct
SEQUENCE: 456
atgagcgata cagaattcac ccacgagcac tggatgagac acgccctgac actggctcaa    60
agagcccggg acgagggcga agtgccagtg ggagccgtgc tcgtgctgaa caaccaggtt   120
atcggcgaag gctggaatag agccatcggc ctgcatgacc ctaccgccca cgccgagatc   180
atggccctga cacagggcgg cctggtcctg cagaactata ggctgctgga caccaccctg   240
tacgtgacat ttgagccttg tgtgatgtgc gccggcgcaa tggtgcacag cagaatcgga   300
catctggtgt tcggcgtgcg gaacagcaag cggggcgcca tcggatctct gatgaacgtg   360
ctgggctacc ccggcatgaa tcaccaggtc caggtgtccg agggcgtgct ggccaccgaa   420
tgcagcgcta tgctgtgcga cttctaccgg gctcctagac tggtgaaaaa cgccctgaag   480
gaaaaggcca ga                                                       492

SEQ ID NO: 457          moltype = DNA  length = 513
FEATURE                 Location/Qualifiers
misc_feature            1..513
                        note = source = /note="Description of Artificial Sequence:
                        Syntheticpolynucleotide"
misc_feature            1..513
                        note = source = /note="Mammalian codon optimized LPG50154"
source                  1..513
                        mol_type = other DNA
                        organism = synthetic construct
SEQUENCE: 457
atgagcgagt ccgagttcac ccacgagcac tggatgcggc acgccctgac actggccaga    60
agagccagag aggaaggcga ggtgccagtg ggagctgtgc tggtgctgaa caaccaggtg   120
atcggagaag gctggaacag agccatcggc ctgcatgatc ctaccgccca cgccgagatc   180
atggccctga cagggcgg cctcgtcctg cagaactacc ggctgctgga cagcaccctg    240
tatgtgacat tcgagccctg tgtgatgtgc gccggcgcta tggtgcacgg cagaatcgga   300
aatctggtct ttggcgtgcg gaacagcaag cggggcgcca ttggatctct gatgaatgtg   360
gtgggctacc ccggcatgaa ccaccaaatc aacgtgatcg agggcgttct tgcagaagaa   420
tgcagcgcca tgctgtgcga cttctacaga gcccctagac tggtgaaaaa cgccctgaag   480
gaaaaggcca gaaacgcaa caatcctaac aag                                 513

SEQ ID NO: 458          moltype = DNA  length = 492
FEATURE                 Location/Qualifiers
misc_feature            1..492
                        note = source = /note="Description of Artificial Sequence:
                        Syntheticpolynucleotide"
misc_feature            1..492
                        note = source = /note="Mammalian codon optimized LPG50155"
source                  1..492
                        mol_type = other DNA
                        organism = synthetic construct
SEQUENCE: 458
atgagcaacc ccgagctgac acacgagcac tggatgagat acgccctgac actggccaag    60
cgggccagag aggaaggcga agtgccagtg ggcgccgtgc tggttctgaa caaccaggtg   120
atcggcgaag gctggaacag agccatcggc ctgcatgatc ctaccgccca cgccgaaatc   180
atggccctga cagggcgg actggtgctc cagaactata gactgatcga caccaccctg    240
tacgtgacct tcgagccttg tgtgatgtgc gccggagcta tggtgcactc cagaattggc   300
cagctggtgt tcggcgtgcg gaacagcaag aggggcgctg ctggctctct gatgaatgtg   360
ctgaattacc ccggcatgaa ccacagaatc gagtttacag agggagtgct gcgggacgag   420
tgcgccgcta tgctgtgcga cttctaccgg caacctagac tggtcaagaa cgccctgaaa   480
accggcaacg cc                                                        492

SEQ ID NO: 459          moltype = DNA  length = 498
FEATURE                 Location/Qualifiers
misc_feature            1..498
                        note = source = /note="Description of Artificial Sequence:
                        Syntheticpolynucleotide"
misc_feature            1..498
                        note = source = /note="Mammalian codon optimized LPG50156"
source                  1..498
                        mol_type = other DNA
                        organism = synthetic construct
SEQUENCE: 459
atgagcgatc tgagctgaa tcatgaatat tggatgagac acgccctgca gctggctaaa     60
agagccagag aggaaggcga agtgcccgtg ggagccgtgc tcgtgctgaa caaccaggtt   120
atcggcgagg ctggaacag agccatcggc ctgcatgacc ccaccgccca cgccgaaatc    180
atggccctgc ggcagggagg cctggtgctg cagaactacc ggctgctgga caccacactg   240
tacgtgacct tcgagccttg cgtgatgtgt agcggagcta tgatccactc tagaatcggc   300
acagtggtct ttggcgtgcg gaacgagaag cgcggcgccg ccggcagcct gctgaatgtg   360
ctgagatacc caggcatgaa ccaccaggtg aacgtgctgg gcgcgtcct ggccctgct    420
tgttccgaga tgctgtgcga attctacaga atgcctagac agcagaagaa ccggcaaaag   480
gccgagagca agctgagc                                                 498
```

```
SEQ ID NO: 460          moltype = DNA   length = 498
FEATURE                 Location/Qualifiers
misc_feature            1..498
                        note = source = /note="Description of Artificial Sequence:
                        Syntheticpolynucleotide"
misc_feature            1..498
                        note = source = /note="Mammalian codon optimized LPG50157"
source                  1..498
                        mol_type = other DNA
                        organism = synthetic construct
SEQUENCE: 460
atgagcgaca acgagctgaa tcacgagcac tggatgcggc acgccctgac actggcccag    60
cgcgccagag aggaaggcga ggtgcctgtg ggcgccgtgc tggtgctgca aaaccaggtg   120
atcggagaag gctggaatag agccatcggc ctgcatgacc ccaccgccca tgccgagatc   180
atggccctga cagggcggc atggtgctg cagaactacc ggctgatcga caccaccctg    240
tacgtgacct tcgagccatg tgtgatgtgc gccggcgcca tggtccactc tagaatcgga   300
cagctggtct ttggcgtgcg gaacagcaag cggggcgctg ctggcagcct gattaacgtg   360
ctgaactatc ctggaatgaa ccacagagtg gaaatcacag agggagtgct ggctgatgat   420
tgcagcagca tgctgtgcga cttctacaga cacccctag aacagaagaa cgccctcaaa    480
agagccgctc actccaac                                                 498

SEQ ID NO: 461          moltype = DNA   length = 504
FEATURE                 Location/Qualifiers
misc_feature            1..504
                        note = source = /note="Description of Artificial Sequence:
                        Syntheticpolynucleotide"
misc_feature            1..504
                        note = source = /note="Mammalian codon optimized LPG50158"
source                  1..504
                        mol_type = other DNA
                        organism = synthetic construct
SEQUENCE: 461
atgagcaacc ccgagcacaa ccacgagtac tggatgcggc acgccctgac cctggcccag    60
agggccagag atgagggaga agtgccagtg ggcgccgtgc tggtctacaa caaccaggtt   120
atcggcgaag gctggaacag agccatcgga cttcatgatc ctaccgccca cgctgaaatc   180
atggccctga cagggcggg cctggtgctg cagaactacc ggctgctgga cacaaccctg    240
tatgtgacct ttgagccttg tgtgatgtgt agcggcgcta tggtcactc tagaatcgga    300
acactggtgt cggcgtgcg caacgagaag cggggcgccg ctggcagcct gatgaacgtg    360
ctgggctacc ccggcatgaa tcaccaggtg caaaccatcg gcggagtgct cgcccctgag   420
tgctccggcc tgctgtgcga cttctacaga atgcctagac aacagaaaaa ccagcagaag   480
gccgaactga atcaacctgg cgac                                          504

SEQ ID NO: 462          moltype = DNA   length = 504
FEATURE                 Location/Qualifiers
misc_feature            1..504
                        note = source = /note="Description of Artificial Sequence:
                        Syntheticpolynucleotide"
misc_feature            1..504
                        note = source = /note="Mammalian codon optimized LPG50159"
source                  1..504
                        mol_type = other DNA
                        organism = synthetic construct
SEQUENCE: 462
atgagcgacc tggaactgaa tcacgagtac tggatgagac acgccctgag cctggctaag    60
agagccagag atgagggcga agtgcccgtg ggcgccgtgc tggtgctgaa caaccaggtt   120
atcggcgagg gatggaaccg ggccattggc ctgcatgacc ccaccgccca cgctgaaatc   180
atggccctga gcagggcgg actggtgctc cagaactaca gactgctgga cacaccctg    240
tacgtgacat tcgagccatg tgtgatgtgc tctggcgcta tggtgcattc tagaatcgga   300
acactggtct acggcgtgcg gaacgagaag cggggcgccg ccggcagcct gatgaatgtg   360
ctgggctatc ctggcatgaa ccaccaggtg caaatcatcg gcggcgtgct ggcccctgac   420
tgcagcggcc tgctgtgcga cttctaccgc atgcctagac aacagaaaaa ccagcagaag   480
gccgagctga agtccagcgg agat                                          504

SEQ ID NO: 463          moltype = DNA   length = 498
FEATURE                 Location/Qualifiers
misc_feature            1..498
                        note = source = /note="Description of Artificial Sequence:
                        Syntheticpolynucleotide"
misc_feature            1..498
                        note = source = /note="Mammalian codon optimized LPG50160"
source                  1..498
                        mol_type = other DNA
                        organism = synthetic construct
SEQUENCE: 463
atgtctgatc acgagttcaa cgatgagtac tggatgcggc acgccctgac cctggctaaa    60
agagccaggg aagagggcga ggtgcctgtg ggcgccgtgc tggtgctgaa caaccaggtg   120
atcggagaag gatggaatag agccatcggc ctgcatgacc ccaccgccca tgctgaaatc   180
atggccctga acaaggagg cctggtcctc cagaactatc gcctgatcga cgccacactg    240
tacgtgacct ttgagccttg tgtgatgtgc gccggcgcca tggtgcacag cagaatcagc   300
```

```
cggctggttt tcggcgtgcg aacagcaag cggggcgctg ctggcagcct gattaacgtg    360
ctgaattacc ccggcatgaa ccacagagtg gaaatcacag agggcatcct ggccgagtcc    420
tgcagcgcca tgctgtgcga cttctacaga tggcctagag aggtgaagaa cgccctgaag    480
aaggccagac aggaggaa                                                  498
```

| SEQ ID NO: 464 | moltype = DNA length = 498 |
|---|---|
| FEATURE | Location/Qualifiers |
| misc_feature | 1..498 |
| | note = source = /note="Description of Artificial Sequence: Syntheticpolynucleotide" |
| misc_feature | 1..498 |
| | note = source = /note="Mammalian codon optimized LPG50161" |
| source | 1..498 |
| | mol_type = other DNA |
| | organism = synthetic construct |

```
SEQUENCE: 464
atgagccaga ccgaactgac ccacgagtat tggatgcggc acgccctgac actggcccaa    60
agagccagag acgagggcga agtgccagtg ggcgccgtgc tggtgctgaa caaccaggtc   120
atcggcgaag gctggaatag ggccattgga ctgcatgatc ctaccgccca cgccgagatc   180
atggccctga cagggcgg cctggtcctc cagaactacc ggctgctgga caccaccctg    240
tacgtgacct tcgagccttg tgtgatgtgc gccggagcta tggtgcacgg cagaatcgga   300
acactggtgt tcggcgtgcg gaacagcaaa gaggccgctg ttggatctct gatgaatatc   360
acaggctacc ccggcatgaa ccaccagtg caagtgatcg agggcatcct ggctacagag    420
tgctccgcca tgctgtgcgc ttttttaccgc cagcctagcg tggtgaagaa cgccctgaag   480
gaagccgcca agaccgcc                                                 498
```

| SEQ ID NO: 465 | moltype = DNA length = 501 |
|---|---|
| FEATURE | Location/Qualifiers |
| misc_feature | 1..501 |
| | note = source = /note="Description of Artificial Sequence: Syntheticpolynucleotide" |
| misc_feature | 1..501 |
| | note = source = /note="Mammalian codon optimized LPG50162" |
| source | 1..501 |
| | mol_type = other DNA |
| | organism = synthetic construct |

```
SEQUENCE: 465
atgagcaacc ccgagctgaa ccatgattac tggatgcggc acgccctgag cctggccaag    60
cgggccagag aggaaggcga agtgccagtg ggcgccgtgc tggtgcggaa caacgaggtg   120
atcggcgagg gatggaacag agccatcggc ctgcatgacc ctacagccca cgccgagatc   180
atggccctga cagggcgg catggtcctc cagaactata gactgatcga caccaccctg    240
tacgtgacct tcgagccttg tgtgatgtgc gccggcgcca tggtgcacag cagaatcggc   300
cagctggtct ttggcgttag aaattctaag cgcggagctg ctggttccct gatgaacgtg   360
ctgaattacc ccggcatgaa ccacagagtg gaaatcgtgg aaggcgtgct gcgggacgag    420
tgcgccggaa tgctgtgcga cttctacagg caacctagac tggtgaagaa cgcccagaaa   480
aagggcgctg aacctctgat t                                             501
```

| SEQ ID NO: 466 | moltype = DNA length = 516 |
|---|---|
| FEATURE | Location/Qualifiers |
| misc_feature | 1..516 |
| | note = source = /note="Description of Artificial Sequence: Syntheticpolynucleotide" |
| misc_feature | 1..516 |
| | note = source = /note="Mammalian codon optimized LPG50163" |
| source | 1..516 |
| | mol_type = other DNA |
| | organism = synthetic construct |

```
SEQUENCE: 466
atgagcaacc ccgagctgaa tcacgagtac tggatgagat acgccctgac cctggccaag    60
agagccagag acgaaggaga ggtgcctgtg ggcgctgttc tggtgtacaa cgaccaggtg   120
atcggcgaag gctggaaccg ggccatcggc ctgcatgacc ccaccgccca cgccgagatt   180
atggccctgc gccagggcgg cctggtgctg cagaactacc ggctgatcga cacaaccctg    240
tacgtgacat ttgagccctg cgtgatgtgc gccggagcaa tggtgcacag cagaatcggc   300
agactggtgt tcggcgtgcg gaacagcaag cggggcgctg ctggctctct gctgaacgtg   360
ctcaattatc ctggaatgaa ccatcacatc gagatggaag aaggcgtgct gagagatgag    420
tgcgccgcca tgctgtgtga tttctacaga caacctagaa tggtcaagaa cgcccttaaa    480
aagtccccac ctgacagccc taatctgcag gccaga                             516
```

| SEQ ID NO: 467 | moltype = DNA length = 504 |
|---|---|
| FEATURE | Location/Qualifiers |
| misc_feature | 1..504 |
| | note = source = /note="Description of Artificial Sequence: Syntheticpolynucleotide" |
| misc_feature | 1..504 |
| | note = source = /note="Mammalian codon optimized LPG50164" |
| source | 1..504 |
| | mol_type = other DNA |
| | organism = synthetic construct |

```
SEQUENCE: 467
atgagcaacc ccgaattcac ccacgagtac tggatgagac acgccctgac cctggctaga    60
cgcgcccggg acgagggcga ggtgccagtg ggcgctgtgc tggtcctcaa caaccaggtg   120
atcggcgaag gctggaatag agccatcggc ctgcatgatc ctacagccca cgctgaaatc   180
atggccctga gacagggcgg cctggtgctg cagaactacc ggctgctgga caccaccctg   240
tacgtgacat ttgagccttg tgtgatgtgt agcggcgcca tggtgcactc tagaatcgga   300
acactggtgt tcggcgtgcg gaacgagaag cggggcgccg ccggcagcct gatgaatgtg   360
ctgggatatc ccggcatgaa ccaccaggtt aagaccatcg gaggcgtgct ggcccctgaa   420
tgcagcggac tgctgtgcga cttctacaga atgcctagac agcaaaagaa ccagcagaaa   480
gccgagctga agtccagcgg cgat                                          504

SEQ ID NO: 468         moltype = DNA   length = 495
FEATURE                Location/Qualifiers
misc_feature           1..495
                       note = source = /note="Description of Artificial Sequence:
                        Syntheticpolynucleotide"
misc_feature           1..495
                       note = source = /note="Mammalian codon optimized LPG50165"
source                 1..495
                       mol_type = other DNA
                       organism = synthetic construct
SEQUENCE: 468
atgagcgaca acgagttcaa ccacgagtac tggatgagac acgccctgac cctggcccag    60
cgcgccagag atgagggcga ggtgcctgtg ggcgccgtgc tggtcctcga taaccaggtg   120
atcggagaag gctggaatag agccatcggc ctgcatgacc ctaccgccca cgccgagatc   180
atggccctga ggcagggcgg catggtcctg cagaactata gactgatcaa cgctacactg   240
tacgtgacct tcgagccttg cgtgatgtgc gccggcgcta tggttcattc tagaatcgga   300
cacgtggtgt tcggcgtgcg gaacagcaag cggggcgccg ctggcagcct gatgaacgtg   360
ctgaactacc ccggcatgaa tcacagagtg gaagtgacag agggagtgct gcgggaacag   420
tgtgccggca tgctgtgcga cttctaccgg gaaccaagag aacaatttaa cgccctgaga   480
aaggctcaga aagcc                                                    495

SEQ ID NO: 469         moltype = DNA   length = 510
FEATURE                Location/Qualifiers
misc_feature           1..510
                       note = source = /note="Description of Artificial Sequence:
                        Syntheticpolynucleotide"
misc_feature           1..510
                       note = source = /note="Mammalian codon optimized LPG50166"
source                 1..510
                       mol_type = other DNA
                       organism = synthetic construct
SEQUENCE: 469
atgagcgaca acgagctgaa tcacgagtac tggatgagac acgccctgac cctggcccag    60
cgggccagag atgagggaga agtgcccgtg ggcgccgtgc tcgtgctgaa caaccaggtt   120
atcggcgaag gctggaatag agccatcggc ctgcatgatc ctaccgccca cgctgaaatc   180
atggccctga gacagggcgg aatggtcctg cagaactata gactgatcaa cgccacactg   240
tacgtgacat tcgagccatg tatcatgtgc gccggcgcca tggtgcactc tagaatcgga   300
caggtggtgt tcggcgtgcg caacagcaag cggggcgctg ccggctccct gattaacatc   360
ctgaactacc ctggcatgaa ccacagagtg gacgtgaccg agggcgtgct gagcgagcgg   420
tgcgccaaca tgctgtgcga cttctaccgg gaacctagac tgcaatttaa cgcccagaga   480
aaggccgaga agccggaaaa tgccgctgct                                    510

SEQ ID NO: 470         moltype = DNA   length = 507
FEATURE                Location/Qualifiers
misc_feature           1..507
                       note = source = /note="Description of Artificial Sequence:
                        Syntheticpolynucleotide"
misc_feature           1..507
                       note = source = /note="Mammalian codon optimized LPG50167"
source                 1..507
                       mol_type = other DNA
                       organism = synthetic construct
SEQUENCE: 470
atgagcaacc ccgagctgac ccacgaccac tggatgcggc acgccctgac cctggcccag    60
agagccagaa acgagggaga agtgcctgtg ggcgctgttc tggtgctgaa cggccaagtg   120
atcggcgaag gctggaacag agccatcggc ctgcatgacc ctaccgccca cgccgagatc   180
atggccctgc ggcagggcgg actggtcctc cagaactacc ggctgatcga caccgtgctg   240
tacgtgacct ttgagccttg tgtgatgtgc gctggcgcca tggtccattc tagaatcgga   300
cagctggtgt tcggcgtgcg caatagcaag cggggtgccg ccggcagcct gattaacgtg   360
ctgaactatc ctggcatgaa ccacagagtg gaaatcatcg agggcgtgct gagagatgag   420
tgcgcagcta tgctgtgcga cttctacaga caccccagac tggtgaagaa cgccctgaaa   480
agaatgccg gaacatcccc aacacag                                        507

SEQ ID NO: 471         moltype = DNA   length = 498
FEATURE                Location/Qualifiers
misc_feature           1..498
                       note = source = /note="Description of Artificial Sequence:
                        Syntheticpolynucleotide"
```

```
misc_feature           1..498
                       note = source = /note="Mammalian codon optimized LPG50168"
source                 1..498
                       mol_type = other DNA
                       organism = synthetic construct
SEQUENCE: 471
atgagcgaca cagagctgaa ccacgagtac tggatgcggc acgccctgat gctggctaaa    60
cgcgccagag atgagggaga agtgccagtg ggcgccgtgc tggtgctgaa gaaccaggtg   120
atcggcgaag gctggaacag agccatcgga ctgcatgacc ctacagccca cgctgaaatc   180
atggccctga cacagggcgg cctggtcctc cagaactata gactgatcga caccaccctg   240
tacgtgacct ttgagccttg tgtgatgtgc gccggcgcta tggtgcactc tagaatcgga   300
aatctggttt tcggcgtgcg gaacagcaag cggggcgccg ctggctccct gattaacgtg   360
ctgaattacc ccggcatgaa ccacagagtg gaaatcgccg agggcgtgct ggccgacgaa   420
tgcagcgcca tgctgtgcga cttctaccgg catcctagac agcagcaaaa cgccctgaag   480
caggccgcca agcacgat                                                 498

SEQ ID NO: 472           moltype = DNA  length = 513
FEATURE                  Location/Qualifiers
misc_feature             1..513
                         note = source = /note="Description of Artificial Sequence:
                         Syntheticpolynucleotide"
misc_feature             1..513
                         note = source = /note="Mammalian codon optimized LPG50169"
source                   1..513
                         mol_type = other DNA
                         organism = synthetic construct
SEQUENCE: 472
atgagcgaca tcgagctgaa tcacgagtac tggatgagac acgccctgat gctggccaag    60
agagccagag aggaaggcga agtgcctgtg ggcgccgtgc tggtgctgaa caaccaggtg   120
atcggagaag gatgaaccg gccatcggc ctgcatgatc ctacagccca cgccgagatc   180
atggccctga ggcagggcgg actggtcctc cagaactaca gactgatcga caccaccctg   240
tacgtgacct ttgagccatg tgtgatgtgc gccggcgcca tggtgcacag cagaatcggc   300
cacctggttt tcggcgtgcg gaacagcaag cggggcgctg ctggctccct gattaacgtg   360
ctgaactatc ctggcatgaa ccacagaatc gaattcaccg agggcgtgct ggctgatgag   420
tgctctggca tgctgtgcga cttctacaga taccctagac agcagcaaaa tacactgaag   480
caggccgcta aagccaaccc ccccgccgcc cag                                513

SEQ ID NO: 473           moltype = DNA  length = 495
FEATURE                  Location/Qualifiers
misc_feature             1..495
                         note = source = /note="Description of Artificial Sequence:
                         Syntheticpolynucleotide"
misc_feature             1..495
                         note = source = /note="Mammalian codon optimized LPG50170"
source                   1..495
                         mol_type = other DNA
                         organism = synthetic construct
SEQUENCE: 473
atgagcgaca acgagctgaa ccacgagaga tggatgcggc atgccctgac cctggctcaa    60
agagccagag atgagggcga ggtgccagtg ggcgctgtgc tggtctacca gaaccaggtg   120
atcggcgaag gctggaacag agccattggc ctgcatgacc ctaccgccca cgccgagatc   180
atggccctga cacagggcgg actggttctg cagaattacc ggctgatcga cacaaccctg   240
tacgtgacct ttgagccttg tgtgatgtgc gccggcgcca tggtgcactc tagaatcgga   300
cagctggtgt tcggcgtgcg gaacagcaag cggggcgccg ccggcagcct gatcaacgtg   360
ctcaattatc ctggcatgaa ccacagagtg gccatcacag aaggagtgct ggccgaatcc   420
tgcagcgcca tgctgtgcga cttctacaga caccccagag aacagaagaa cgccctgagg   480
cgggctgctc agagc                                                    495

SEQ ID NO: 474           moltype = DNA  length = 498
FEATURE                  Location/Qualifiers
misc_feature             1..498
                         note = source = /note="Description of Artificial Sequence:
                         Syntheticpolynucleotide"
misc_feature             1..498
                         note = source = /note="Mammalian codon optimized LPG50171"
source                   1..498
                         mol_type = other DNA
                         organism = synthetic construct
SEQUENCE: 474
atgagcgatc tggaactgaa cgacgagtac tggatgcggc acgctctgac cctggccaag    60
cgggccagag aagagggaga agtccccgtg ggcgccgtgc tcgttctgaa caaccaggtg   120
atcggcgagg gctggaacag agccattgga ctgcatgaac ctaccgccca cgccgagatc   180
atggccctga cacagggcgg cctggtcctc caaaattata gactgatcga cgccaccctg   240
tacgtgacat ttgagccttg tgtgatgtgc gccggcgcta tggtgcacag cagaatcgcc   300
aggctggtgt tcggcgtgcg gaacagcaag cgcggcgccg ctggatctct gatgaacgtg   360
ctgaattacc caggcatgaa ccacagagtg gaaatcagcg agggcgtgct ggctgagtcc   420
tgcagcgcca tgctgtgcga cttctacaga tggcctagag aggtgaagaa cgccctgaaa   480
aaggcccggg aacagaac                                                 498

SEQ ID NO: 475           moltype = DNA  length = 507
```

```
FEATURE              Location/Qualifiers
misc_feature         1..507
                     note = source = /note="Description of Artificial Sequence:
                     Syntheticpolynucleotide"
misc_feature         1..507
                     note = source = /note="Mammalian codon optimized LPG50172"
source               1..507
                     mol_type = other DNA
                     organism = synthetic construct
SEQUENCE: 475
atgagcgacc tggaactgga tcacgagtac tggatgcggc acgccctgct gctggctaaa    60
agagccagag atgagggcga agtgcccgtg ggcgccgtgc tggtgctcaa caaccaggtc   120
atcggagaag gctggaatag agccatcggc ctgcatgacc aacagcccca tgccgaaatc   180
atggccctga ggcagggcgg cctggtgctg cagaactaca gactgctgga caccacctg   240
tatgtgacct tcgagccttg tgtgatgtgc tctggcgcta tggtgcactc tagaatcgga   300
accctggtct acggcgtgcg gaacgagaag cggggcgccg ctggctccct gatgaacgtg   360
ctgggctacc ccgtatgaa tcaccaggtg caagtgatcg acggcgtgct ggcccctgaa   420
tgcagcggac tgctgtgcga cttctaccgg atgcctagac agcaaaagaa ccagcagaag   480
gccgagagca ccagcagcag aggcgac                                      507

SEQ ID NO: 476       moltype = DNA  length = 486
FEATURE              Location/Qualifiers
misc_feature         1..486
                     note = source = /note="Description of Artificial Sequence:
                     Syntheticpolynucleotide"
misc_feature         1..486
                     note = source = /note="Mammalian codon optimized LPG50173"
source               1..486
                     mol_type = other DNA
                     organism = synthetic construct
SEQUENCE: 476
atgagcgaca ccgagctgac ccacgagtac tggatgcggc acgccctgat gctggctcaa    60
agagccagag atgaaggcga agtgccagtg ggagccgtgc tggtcctgaa caaccgggtg   120
atcggcgagg gctggaacag agcctatcgga ctgcatgatc ctacagccca cgccgagatc   180
atggccctga gacagggcgg cctggtgctg cagaactacc gcctgctgga caccacctg   240
tacgttacat ttgagccttg tgtgatgtgc gccggcgcta tggtgcacgg cagaatcggc   300
acactggtgt tcgccgtgcg gaacctgaag cggggcgccg ccggatctct gatgaatgtg   360
ctgaattatc ctggcatgaa ccacagagtg gaaatcgtgg aaggaaccct ctccgacgaa   420
tgcagcggca tgctgtgcga gttctacaga cagcccgcac tggcctcaa cgcccagaag   480
caggcc                                                             486

SEQ ID NO: 477       moltype = DNA  length = 519
FEATURE              Location/Qualifiers
misc_feature         1..519
                     note = source = /note="Description of Artificial Sequence:
                     Syntheticpolynucleotide"
misc_feature         1..519
                     note = source = /note="Mammalian codon optimized LPG50174"
source               1..519
                     mol_type = other DNA
                     organism = synthetic construct
SEQUENCE: 477
atgtctatcc ccgagctgaa tcacgatgtg tggatgagac acgctctgac actggccaag    60
agggctagag aggaaggcga agtgccagtg ggcgccgtgc tggttctgaa cggccaagtg   120
atcggagaag gatgaacag agccatcggc ctgcatgacc ccaccgccca cgccgagatt   180
atggccctgc gccagggcgg cctggtgctc cagaactaca gactgatcga cacaaccctg   240
tacgtgacct tcgagccttg tgtgatgtgc gccggcgcta tggtgcacag cagaatcggc   300
cagctggtct ttggcgtgcg gaacagcaag cggggcgccg ctggttccct gatgaacgtg   360
cttaattatc ctggcatgaa ccatagagtg gaaatcaccg agggagtgct gagagatgag   420
tgcgccgcca tgctgtgcga cttctaccgg agcctagac tggtcaagaa cgccctgaag   480
aaacctgccg gcgaccctag cgccctgcag aacaaccgg                         519

SEQ ID NO: 478       moltype = DNA  length = 498
FEATURE              Location/Qualifiers
misc_feature         1..498
                     note = source = /note="Description of Artificial Sequence:
                     Syntheticpolynucleotide"
misc_feature         1..498
                     note = source = /note="Mammalian codon optimized LPG50175"
source               1..498
                     mol_type = other DNA
                     organism = synthetic construct
SEQUENCE: 478
atgagcgatc tggaactgaa tgatgagtac tggatgcggc acgccctgac actggccaag    60
agagccagag aagagggcga agtgcctgtc ggcgccgtgc tggtgctgaa caaccaggtg   120
atcggcgagg gctggaaccg ggccatcgga ctgcatgacc ccaccgccca tgccgagatt   180
atggccctga gacaggggcg cctggttctg caaaattatc gcctgatcga cgccaccctg   240
tacgtgacct tcgagccttg tgtgatgtgc gccggagcta tggtgcacag cagaatcgcc   300
aggctggtct ttggcgtgcg gaacagcaag cggggcgctg ctggctccct gatgaacgtg   360
```

```
ctgaactacc caggcatgaa ccacagagtg gaaatcagcg agggagtgct cgctggctct    420
tgcagcgcca tgctgtgcga cttctacaga tggcctagag aagtgaagaa cgccctgaag    480
aaagccagag agcagaac                                                  498

SEQ ID NO: 479          moltype = DNA   length = 459
FEATURE                 Location/Qualifiers
misc_feature            1..459
                        note = source = /note="Description of Artificial Sequence:
                        Syntheticpolynucleotide"
misc_feature            1..459
                        note = source = /note="Mammalian codon optimized LPG50176"
source                  1..459
                        mol_type = other DNA
                        organism = synthetic construct
SEQUENCE: 479
atgagcgaca tcgagcagaa ccacgagtac tggatgcggc acgccctggt tctggccaag    60
cgggccagag aggaaggcga agtgccagtg ggcgccgtgc tggtgctgaa caaccaggtg    120
atcggcgagg gctgaacag ggccatcggc ctccatgatc ctaccgccca cgccgaaatc    180
atggccctga caggggcgg actggtcctg caaaattacc ggctgatcga cacaaccctg    240
tacgtgacat cgagcctg tgtgatgtgc gccggcgcta tggtgcacgg cagaatcggc    300
agcctggtct ttggcgtgcg gaacagcaag agaggcgccg ctggctctct gattaacgtg    360
ctgaattatc ctggaatgaa ccacagagtg gaaatgaccg agggcgtgct ggctgatgaa    420
tgcagcgcca tgctgtgcga cttctacaga caccccaga                          459

SEQ ID NO: 480          moltype = DNA   length = 504
FEATURE                 Location/Qualifiers
misc_feature            1..504
                        note = source = /note="Description of Artificial Sequence:
                        Syntheticpolynucleotide"
misc_feature            1..504
                        note = source = /note="Mammalian codon optimized LPG50177"
source                  1..504
                        mol_type = other DNA
                        organism = synthetic construct
SEQUENCE: 480
atgtgcaacc tgagagaga tcacgagtac tggatgcggc acgccctgac actggcccag    60
cgggccagag atgagggcga agtgcctgtg ggcgccgtgc tggtgctgaa caaccaggtt    120
atcggcgaag gatggaatag agccatcggc ctgcatgacc ccaccgccca tgccgaaatc    180
atggccctga cacagggcgg catggtgctg cagaactaca gactgctgga caccaccctg    240
tacgtgacct ttgagccctg cgtgatgtgt tccggcgcca tggtccactc tagaatcggt    300
acactggtgt tcgccgtgcg gaacgagaag cggggcgctg ctggcagcct gctgaatgtg    360
ctgggatatc ctggcatgaa ccaccaggtg aagaccatcg gaggcgtgct cgccccagct    420
tgcagcgccc tgctgtgcga cttctaccgc atgcctagac aacagaaaaa ccagcagaag    480
gccgagctga agctgagcaa cgac                                           504

SEQ ID NO: 481          moltype = DNA   length = 486
FEATURE                 Location/Qualifiers
misc_feature            1..486
                        note = source = /note="Description of Artificial Sequence:
                        Syntheticpolynucleotide"
misc_feature            1..486
                        note = source = /note="Mammalian codon optimized LPG50178"
source                  1..486
                        mol_type = other DNA
                        organism = synthetic construct
SEQUENCE: 481
atgagcgcca tcgagctgaa ccacgagtac tggatgcggc acgccctggg cctggctcag    60
cgcgctagag atgagggcga ggtccccgtg ggcgccgtgc tggtctacca gaaccaggtg    120
atcggcgaag gatggaaccg ggccattggc ctgcatgacc ccacagccca cgccgaaatc    180
atggccctga cagggcgg actggtgctg cagaattacc ggctgatcga caccaccctg    240
tacgtgacat cgagccatg tgtgatgtgc gccggcgcta tggtgcactc tagaatcggt    300
agagtggtgt tcggcgttag aaacagcaag cggggcgccg ccggcagcct gatgaacgtg    360
ctcaattatc ctggcatgaa ccatagagtg gaagtgaccg agggcgtgct ggccggagaa    420
tgctccgcca tgctgtgcga cttctacaga gcccctaggg ctcaatttaa cgcccagaag    480
agacct                                                               486

SEQ ID NO: 482          moltype = DNA   length = 507
FEATURE                 Location/Qualifiers
misc_feature            1..507
                        note = source = /note="Description of Artificial Sequence:
                        Syntheticpolynucleotide"
misc_feature            1..507
                        note = source = /note="Mammalian codon optimized LPG50179"
source                  1..507
                        mol_type = other DNA
                        organism = synthetic construct
SEQUENCE: 482
atgagcaacc tgagctgaa ccacgagtac tggatgaggt acgccctgac cctggccaag    60
cgggccagag aggaaggcga agtgccagtg ggcgccgtgc tggttctgaa cgaacgggtg    120
```

```
atcggagaag gatggaacag agccatcggc ctgcatgacc ccaccgccca cgccgagatc    180
atggccctca gacagggcgg catggtcctg cagaactatc ggctgatcga caccaccctg    240
tacgtgacat ttgagccttg cgtgatgtgc gccggcgcta tggtgcactc tagaatcggc    300
cacctggtgt tcggcgtgcg gaacagcaag agaggagctg ctggttccct gatgaacgtg    360
ctgaattacc ccggcatgaa tcatagagtg gccattacag agggcgtgct gagagatgaa    420
tgtgccgcta tgctgtgcga cttctaccgc cagcctagac aagtgaagaa cgccctgaaa    480
aagaccctga gcgatagcca ggagcag                                        507
```

| SEQ ID NO: 483 | moltype = DNA length = 504 |
|---|---|
| FEATURE | Location/Qualifiers |
| misc_feature | 1..504 |
| | note = source = /note="Description of Artificial Sequence: Syntheticpolynucleotide" |
| misc_feature | 1..504 |
| | note = source = /note="Mammalian codon optimized LPG50180" |
| source | 1..504 |
| | mol_type = other DNA |
| | organism = synthetic construct |

SEQUENCE: 483
```
atgtccaatc ctgagcacga ccacgagtac tggatgcggc acgccctgaa cctggcccag     60
cgggccagag atgagggcga ggtgcccgtg ggcgccgtgc tggtgctcaa caaccaggtc    120
atcggagaag gctgaaccg cgccatcggc ctgcatgacc caacagccca tgctgaaatc    180
atggccctga cagggcgg cctggtgctg cagaactacc ggctgctgga tacaaccctg    240
tacgtgacct tcgagccctg cgtgatgtgt agcggcgcta tggtgcacag ccggatcggc    300
accctggtct acgcgttag aaacgagaaa agaggcgccg ccggcagcct gatgaacgtg    360
ctgggatatc ctggaatgaa tcaccaggtg aacgtgatcg gcgagtgct ggctcaggac    420
tgttctgcca gactgtgcga cttctacaga atgcctagac agcaaagaa ccagcagaga    480
gccgaactga aggcccaagg cgac                                           504
```

| SEQ ID NO: 484 | moltype = DNA length = 504 |
|---|---|
| FEATURE | Location/Qualifiers |
| misc_feature | 1..504 |
| | note = source = /note="Description of Artificial Sequence: Syntheticpolynucleotide" |
| misc_feature | 1..504 |
| | note = source = /note="Mammalian codon optimized LPG50181" |
| source | 1..504 |
| | mol_type = other DNA |
| | organism = synthetic construct |

SEQUENCE: 484
```
atgagcgacc ccgagctgaa tcacgagtat tggatgagac acgccctgca actggcccag     60
agagccagag atgagggcga agtgcccagtg ggcgccgtgc tggtcctgaa caaccaggtg    120
attggagaag gctggaacag ggccatcgga ctgcatgatc ctacagccca cgccgaaatc    180
atggccctga cagggcgg cctggtgctg cagaactacc ggctgctgga caccaccctg    240
tacgtgacct tcgagccttg cgtgatgtgc tctggcgcca tgatccacag cagaatcgga    300
acagtggtgt acggcgtgcg gaacgagaag cggggcgctg ctggcagcct gctgaatgtg    360
ctctcctacc ccggcatgaa ccaccaggtt aaggtgatcg gcgaagtgct ggcccctgct    420
tgtagcgcca tgctgtgcga cttctacaga atgcctagac agcagaaaaa ccagcaaaag    480
gccgagtggga agctgagcgg cgag                                          504
```

| SEQ ID NO: 485 | moltype = DNA length = 513 |
|---|---|
| FEATURE | Location/Qualifiers |
| misc_feature | 1..513 |
| | note = source = /note="Description of Artificial Sequence: Syntheticpolynucleotide" |
| misc_feature | 1..513 |
| | note = source = /note="Mammalian codon optimized LPG50182" |
| source | 1..513 |
| | mol_type = other DNA |
| | organism = synthetic construct |

SEQUENCE: 485
```
atgagcaacc ccgagctgaa ccacgagtac tggatggagat acgccctgac actggccaaa     60
agagccagag acgagggaga agtgcccgtg ggcgctgtgc tggtctacca cgaccaagtg    120
atcggagaag gctggaacag agccatcgga ctgcatgatc ctaccgccca cgccgagatc    180
atggccctcc ggcagggagg cctggtgctg cagaactata gactgatcga ccaccacactg    240
tacgtgacct ttgagccttg tgtgatgtgc gccggcgcca tggtgcacag cagaattggc    300
agactggttt tcggcgtgcg caactctaag cggggcgccg ctggcagcct gctgaacgtg    360
ctgaattacc ctggcatgaa ccaccagatc gatatggaaa aggcgtgct gcgggatgag    420
tgcgccgcca tgctgtgcga cttctaccgg ctgcctagaa tcgtgaagaa tgcactgaag    480
cagtcccctc cagacagcac caacctgcat gcc                                 513
```

| SEQ ID NO: 486 | moltype = DNA length = 3213 |
|---|---|
| FEATURE | Location/Qualifiers |
| misc_feature | 1..3213 |
| | note = source = /note="Description of Artificial Sequence: Syntheticpolynucleotide" |
| misc_feature | 1..3213 |
| | note = source = /note="Mammalian codon optimized nAPG07433.1" |

```
source                  1..3213
                        mol_type = other DNA
                        organism = synthetic construct
SEQUENCE: 486
atgagagagc tggactacag aattggcctg gccatcggca ccaacagcat cggatggggc      60
gtgatcgagc tgtcctggaa caaagaccgg gagagatacg agaaggtcag aatcgtggat     120
caaggcgtga gaatgttcga cagagccgag atgcccaaga caggcgccag cttagctgaa     180
cccagaagaa tcgccagatc cagcagacgg agactgaatc gcaagtccca gagaaagaaa     240
aacatccgga acctgctggt gcaacaccgg cgtgatcacac aggaggaact ggatagcctg     300
tacccctga gcaaaaagag catggacatc tggggcattc ggctcgacgg cctggacaga     360
ctcctcaatc atttcgagtg ggccagactg ctgatccacc tggctcagag acggggcttt     420
aagtccaaca gaaagagtga actgaaagat acagagacag gcaaggtgct gagcagcatc     480
caactgaacg agaaacggct gagcttgtat agaaccgtgg gcgagatgtg gatgaaggac     540
cccgacttct ctaaatacga taggaagaga aatagcccca acgaatacgt gttcagcgtg     600
tctagagccg agctggaaaa ggaaatcgtg accctgttcg ccgcccagcg gagattccag     660
agcccttacg ccagcaaaga tctgcaggag acatatctgc agatctggac ccaccaactg     720
cctttcgcca gcggcaatgc catcctgaac aaggtcggat actgctccct gttgaaaggc     780
aaagaaagaa ggattcccaa ggctacatac accttccaat acttctctgc tctggaccag     840
gtgaatcgga ccagactggg acctgatttc cagcccttca ccaaggagca acgggaaatt     900
atcttgaaca acatgttcca gaggacagat tactacaaga gaaaaccat cccccgaggtg     960
acctactatg acatacggaa gtggctgaaa ttggacgaga caattcagtt caagggcctg    1020
aactacgacc ctaacgagga actgaagaag atcgagaaga gccttttat caatctgaag    1080
gccttctacg agatcaacaa ggtggtggcc aactacagcg aaagaaccaa cgagaccttc    1140
tccaccctgg actacgacgg catcggctac gccctgaccg tgtacaaaac cgacaaggat    1200
atccgcagct acctgaagag cagtcacaac ctacctaaga gatgctacga cgaccaactg    1260
atcgaggaac tgctgagcct gagctacaca aagttcggcc acctgtccct gaaagccatc    1320
aaccacgtgc tgtctatcat gcagaagggc aatacctaca ggaagccgt ggaccaactg    1380
ggctacgaca ccagcggcct taagaaggag aagaggtcca agttcctgcc acctatttct    1440
gatgaaatca cgaatccaat cgtgaaaagg gccctgaccc aggccagaaa agtggtgaac    1500
gccataatta gaagacacgg atctcctcac tccgtgcaca tcagctggc cagagagctg    1560
agcaagaacc acgacgagcg gacaaagatc gtcagcgccc aggatgaaaa ctacaagaaa    1620
aacaagggcg ctatcagcat cctgtctgag cacggcatcc tgaacccttac aggctacgac    1680
atcgtgagat acaaactgtg gaaggagcag ggcgaacggt gcgcctacag cctgaaggaa    1740
atccctgccg atacattttt caacgcgctg aagaaggaac gcaacggcgc ccctatcctt    1800
gaagtggacc acatcctgcc ctacagccag tccttcatcg actcctacca caacaaggtc    1860
ctggtgtaca gcgacgaaaa ccggaaaaag gcaacagaa tcccttatac ctacttcctg    1920
gaaaccaaca aggattggga ggcctttgag cggtacgtgc ggagcaacaa attcttctcc    1980
aagaaaaagc gagagtacct tctgaagcgg gcttatctgc ctagaaatc tgagctgatc    2040
aagaacgcc acctgaacga caccagatac gcctctacct tcctgaagaa cttcatcgag    2100
cagaacctgc agttcaagga agccgaggac aaccccagaa aaagacgggt gcaaaccgtg    2160
aacggcgtta tcaccgccca cttcagaaag cggtgggggcc tggagaagga ccggcaggag    2220
acataacctcc atcacgctat ggacgccatc atcgtggctt gtacagacca ccacatggtc    2280
accagatga ccgagtacta tcagatcaga gaaagcaaca gagcgtgaa gaagcctat    2340
tttcctatgc cttgggaagg cttccggac gagctgctga gcccacttggc ttctcagcct    2400
atcgccaaga aaatcagcga ggaactgaag gccggctacc agagcctgga ctacatcttc    2460
gtgtccagaa tgcctaagag aagcattaca ggcgctgctc ataagcagac catcatgcgg    2520
aagggaggaa ttgacaagaa gggcaaaaca atcatcatcg aacggctgca cctgaaggat    2580
atcaagttcg acgagaacgg agatttcaag atggtgggca aggaacagga catgccacca    2640
tacgaagcta ttaaaacagag ataccctggag cacggcaaga atagcaagaa ggcccttgag    2700
accccctctgt acaagcccag caaaaagggc acagtaacc tgatcaagcg ggtgaaggtg    2760
gaaggacagg ccaagagctt tgtgagggaa gtgaacggcg agtggccca aaatggcgat    2820
ctggttagag ttgatttgtt tgagaaggat gataagtact acatggtccc catctacgtg    2880
ccagacaccg tgtgtagcga gctgcccaaa aaggtggtcg ccagctctaa gggctatgag    2940
cagtggctga cactggataa cagcttcacc tttaagttca gcctgtaccc ttatgatctg    3000
gtgcggctga tcaagggaga tgaggatcgg ttcctgtact ttggcacccct ggacatcgac    3060
agcgacagac ttaacttcaa ggacgtgaac aagccaagca gaagaacga gtaccggtac    3120
agcttgaaaa ccatccgaga cttggagaag tacgaggtgg cgtgctggg cgatctaaga    3180
ctggtccgga aggaaactcg aagaaacttc cac                                 3213

SEQ ID NO: 487          moltype = DNA  length = 96
FEATURE                 Location/Qualifiers
misc_feature            1..96
                        note = source = /note="Description of Artificial Sequence:
                        Syntheticoligonucleotide"
misc_feature            1..96
                        note = source = /note="Codon optimized linker"
source                  1..96
                        mol_type = other DNA
                        organism = synthetic construct
SEQUENCE: 487
tccggcgggt cttccggcgg ctctagtggg agtgagacgc caggaacgtc tgaatctgct      60
actcccgaat ctagcggcgg atccagtggc ggtagt                                96

SEQ ID NO: 488          moltype = AA   length = 1323
FEATURE                 Location/Qualifiers
REGION                  1..1323
                        note = source = /note="Description of Artificial Sequence:
                        Syntheticpolypeptide"
```

```
REGION                  1..1323
                        note = source = /note="LPG50140-nAPG07433.1 protein
                        sequence"
source                  1..1323
                        mol_type = protein
                        organism = synthetic construct
SEQUENCE: 488
MAPKKKRKVD YKDHDGDYKD HDIDYKDDDD KMSDLELNHE YWMRHALQLA KRARDEGEVP    60
VGAVLVLNNQ VIGEGWNRAI GLHDPTAHAE IMALRQGGLV LQNYRLIDTT LYVTFEPCVM   120
CSGAMVHSRI GTLVFGVRNS KRGAAGSLMN VLNYPGMNHQ VQIIDGVLAP ECSGLLCDFY   180
RMPRQVFNQQ KAESTSINGD SGGSSGGSSG SETPGSSESA TPESSGGSSG GSMRELDYRI   240
GLAIGTNSIG WGVIELSWNK DRERYEKVRI VDQGVRMFDR AEMPKTGASL AEPRRIARSS   300
RRRLNRKSQR KKNIRNLLVQ HGVITQEELD SLYPLSKKSM DIWGIRLDGL DRLLNHFEWA   360
RLLIHLAQRR GFKSNRKSEL KDTETGKVLS SIQLNEKRLS LYRTVGEMWM KDPDFSKYDR   420
KRNSPNEYVF SVSRAELEKE IVTLFAAQRR FQSPYASKDL QETYLQIWTH QLPFASGNAI   480
LNKVGYCSLL KGKERRIPKA TYTFQYFSAL DQVNRTRLGP DFQPFTKEQR EIILNNMFQR   540
TDYYKKKTIP EVTYYDIRKW LELDETIQFK GLNYDPNEEL KKIEKKPFIN LKAFYEINKV   600
VANYSERTNE TFSTLDYDGI GYALTVYKTD KDIRSYLKSS HNLPKRCYDD QLIEELLSLS   660
YTKFGHLSLK AINHVLSIMQ KGNTYKEAVD QLGYDTSGLK KEKRSKFLPP ISDEITNPIV   720
KRALTQARKV VNAIIRRHGS PHSVHIELAR ELSKNHDERT KIVSAQDENY KKNKGAISIL   780
SEHGILNPTG YDIVRYKLWK EQGERCAYSL KEIPADTFFN ELKKERNGAP ILEVDHILPY   840
SQSFIDSYHN KVLVYSDENR KKGNRIPYTY FLETNKDWEA FERYVRSNKF FSKKKREYLL   900
KRAYLPRESE LIKERHLNDT RYASTFLKNF IEQNLQFKEA EDNPRKRRVQ TVNGVITAHF   960
RKRWGLEKDR QETYLHHAMD AIIVACTDHH MVTRVTEYYQ IKESNKSVKK PYFPMPWEGF  1020
RDELLSHLAS QPIAKKISEE LKAGYQSLDY IFVSRMPKRS ITGAAHKQTI MRKGGIDKKG  1080
KTIIIERLHL KDIKFDENGD FKMVGKEQDM ATYEAIKQRY LEHGKNSKKA FETPLYKPSK  1140
KGTGNLIKRV KVEGQAKSFV REVNGGVAQN GDLVRVDLFE KDDKYYMVPI YVPDTVCSEL  1200
PKKVVASSKG YEQWLTLDNS FTFKFSLYPY DLVRLVKGDE DRFLYFGTLD IDSDRLNFKD  1260
VNKPSKKNEY RYSLKTIEDL EKYEVGVLGD LRLVRKETRR NFHSGGSKRP AATKKAGQAK  1320
KKK                                                               1323

SEQ ID NO: 489          moltype = AA  length = 1318
FEATURE                 Location/Qualifiers
REGION                  1..1318
                        note = source = /note="Description of Artificial Sequence:
                        Syntheticpolypeptide"
REGION                  1..1318
                        note = source = /note="LPG50141-nAPG07433.1protein sequence"
source                  1..1318
                        mol_type = protein
                        organism = synthetic construct
SEQUENCE: 489
MAPKKKRKVD YKDHDGDYKD HDIDYKDDDD KMSNPELTHE HWMRYALTLA KRAREEGEVP    60
VGAVLVLNNQ VIGEGWNRAI GLHDPTAHAE IMALRQGGLV LQNYRLIDTT LYVTFEPCVM   120
CAGAMVHSRI GQLVFGVRNS KRGAAGSLMN VLNYPGMNHR IEFTEGVLRD ECAAMLCDFY   180
RQPRQVFNAL KTGNASGGSS GGSSGSETPG TSESATPESS GGSSGGSMRE LDYRIGLAIG   240
TNSIGWGVIE LSWNKDRERY EKVRIVDQGV RMFDRAEMPK TGASLAEPRR IARSSRRRLN   300
RKSQRKKNIR NLLVQHGVIT QEELDSLYPL SKKSMDIWGI RLDGLDRLLN HFEWARLLIH   360
LAQRRGFKSN RKSELKDTET GKVLSSIQLN EKRLSLYRTV GEMWMKDPDF SKYDRKRNSP   420
NEYVFSVSRA ELEKEIVTLF AAQRRFQSPY ASKDLQETYL QIWTHQLPFA SGNAILNKVG   480
YCSLLKGKER RIPKATYTFQ YFSALDQVNR TRLGPDFQPF TKEQREIILN NMFQRTDYYK   540
KKTIPEVTYY DIRKWLELDE TIQFKGLNYD PNEELKKIEK KPFINLKAFY EINKVVANYS   600
ERTNETFSTL DYDGIGYALT VYKTDKDIRS YLKSSHNLPK RCYDDQLIEE LLSLSYTKFG   660
HLSLKAINHV LSIMQKGNTY KEAVDQLGYD TSGLKKEKRS KFLPPISDEI TNPIVKRALT   720
QARKVVNAII RRHGSPHSVH IELARELSKN HDERTKIVSA QDENYKKNKG AISILSEHGI   780
LNPTGYDIVR YKLWKEQGER CAYSLKEIPA DTFFNELKKE RNGAPILEVD HILPYSQSFI   840
DSYHNKVLVY SDENRKKGNR IPYTYFLETN KDWEAFERYV RSNKFFSKKK REYLLKRAYL   900
PRESELIKER HLNDTRYAST FLKNFIEQNL QFKEAEDNPR KRRVQTVNGV ITAHFRKRWG   960
LEKDRQETYL HHAMDAIIVA CTDHHMVTRV TEYYQIKESN KSVKKPYFPM PWEGFRDELL  1020
SHLASQPIAK KISEELKAGY QSLDYIFVSR MPKRSITGAA HKQTIMRKGG IDKKGKTIII  1080
ERLHLKDIKF DENGDFKMVG KEQDMATYEA IKQRYLEHGK NSKKAFETPL YKPSKKGTGN  1140
LIKRVKVEGQ AKSFVREVNG GVAQNGDLVR VDLFEKDDKY YMVPIYVPDT VCSELPKKVV  1200
ASSKGYEQWL TLDNSFTFKF SLYPYDLVRL VKGDEDRFLY FGTLDIDSDR LNFKDVNKPS  1260
KKNEYRYSLK TIEDLEKYEV GVLGDLRLVR KETRRNFHSG GSKRPAATKK AGQAKKKK    1318

SEQ ID NO: 490          moltype = AA  length = 1323
FEATURE                 Location/Qualifiers
REGION                  1..1323
                        note = source = /note="Description of Artificial Sequence:
                        Syntheticpolypeptide"
REGION                  1..1323
                        note = source = /note="LPG50142-nAPG07433.1protein sequence"
source                  1..1323
                        mol_type = protein
                        organism = synthetic construct
SEQUENCE: 490
MAPKKKRKVD YKDHDGDYKD HDIDYKDDDD KMSIPELNHD VWMRHALTLA KRAREEGEVP    60
VGAVLVLNGQ VIGEGWNRAI GLHDPTAHAE IMALRQGGLV LQNYRLIDTT LYVTFEPCVM   120
CAGAMVHSRI GQLVFGVRNS KRGAAGSLIN VLNYPGMNHR VAITEGVLRE ECAAMLCDFY   180
RQPRQVFNAL KKPAGDINAF SGGSSGGSSG SETPGTSESA TPESSGGSSG GSMRELDYRI   240
```

```
GLAIGTNSIG WGVIELSWNK DRERYEKVRI VDQGVRMFDR AEMPKTGASL AEPRRIARSS  300
RRRLNRKSQR KKNIRNLLVQ HGVITQEELD SLYPLSKKSM DIWGIRLDGL DRLLNHFEWA  360
RLLIHLAQRR GFKSNRKSEL KDTETGKVLS SIQLNEKRLS LYRTVGEMWM KDPDFSKYDR  420
KRNSPNEYVF SVSRAELEKE IVTLFAAQRR FQSPYASKDL QETYLQIWTH QLPFASGNAI  480
LNKVGYCSLL KGKERRIPKA TYTFQYFSAL DQVNRTRLGP DFQPFTKEQR EIILNNMFQR  540
TDYYKKKTIP EVTYYDIRKW LELDETIQFK GLNYDPNEEL KKIEKKPFIN LKAFYEINKV  600
VANYSERTNE TFSTLDYDGI GYALTVYKTD KDIRSYLKSS HNLPKRCYDD QLIEELLSLS  660
YTKFGHLSLK AINHVLSIMQ KGNTYKEAVD QLGYDTSGLK KEKRSKFLPP ISDEITNPIV  720
KRALTQARKV VNAIIRRHGS PHSVHIELAR ELSKNHDERT KIVSAQDENY KKNKGAISIL  780
SEHGILNPTG YDIVRYKLWK EQGERCAYSL KEIPADTFFN ELKKERNGAP ILEVDHILPY  840
SQSFIDSYHN KVLVYSDENR KKGNRIPYTY FLETNKDWEA FERYVRSNKF FSKKKREYLL  900
KRAYLPRESE LIKERHLNDT RYASTFLKNF IEQNLQFKEA EDNPRKRRVQ TVNGVITAHF  960
RKRWGLEKDR QETYLHHAMD AIIVACTDHH MVTRVTEYYQ IKESNKSVKK PYFPMPWEGF 1020
RDELLSHLAS QPIAKKISEE LKAGYQSLDY IFVSRMPKRS ITGAAHKQTI MRKGGIDKKG 1080
KTIIIERLHL KDIKFDENGD FKMVGKEQDM ATYEAIKQRY LEHGKNSKKA FETPLYKPSK 1140
KGTGNLIKRV KVEGQAKSFV REVNGGVAQN GDLVRVDLFE KDDKYYMVPI YVPDTVCSEL 1200
PKKVVASSKG YEQWLTLDNS FTFKFSLYPY DLVRLVKGDE DRFLYFGTLD IDSDRLNFKD 1260
VNKPSKKNEY RYSLKTIEDL EKYEVGVLGD LRLVRKETRR NFHSGGSKRP AATKKAGQAK 1320
KKK                                                              1323

SEQ ID NO: 491           moltype = AA  length = 1326
FEATURE                  Location/Qualifiers
REGION                   1..1326
                         note = source = /note="Description of Artificial Sequence:
                          Syntheticpolypeptide"
REGION                   1..1326
                         note = source = /note="LPG50143-nAPG07433.1protein sequence"
source                   1..1326
                         mol_type = protein
                         organism = synthetic construct
SEQUENCE: 491
MAPKKKRKVD YKDHDGDYKD HDIDYKDDDD KMSNPELNHE YWMRYALTLA KRARDEGEVP   60
VGAVLVLNDQ VIGEGWNRAI GLHDPTAHAE IMALRQGGLV LQNYRLIDTT LYVTFEPCVM  120
CAGAMVHSRI GRLVFGVRNS KRGAAGSLLN VLNYPGMNHR IEMEEGVLRD ECAAMLCDFY  180
RQPRQVFNAL KKSPPDINNL QARSGGSSGG SSSGSETPGTS ESATPESSGG SSGGSMRELD  240
YRIGLAIGTN SIGWGVIELS WNKDRERYEK VRIVDQGVRM FDRAEMPKTG ASLAEPRRIA  300
RSSRRRLNRK SQRKKNIRNL LVQHGVITQE ELDSLYPLSK KSMDIWGIRL DGLDRLLNHF  360
EWARLLIHLA QRRGFKSNRK SELKDTETGK VLSSIQLNEK RLSLYRTVGE MWMKDPDFSK  420
YDRKRNSPNE YVFSVSRAEL EKEIVTLFAA QRRFQSPYAS KDLQETYLQI WTHQLPFASG  480
NAILNKVGYC SLLKGKERRI PKATYTFQYF SALDQVNRTR LGPDFQPFTK EQREIILNNM  540
FQRTDYYKKK TIPEVTYYDI RKWLELDETI QFKGLNYDPN EELKKIEKKP FINLKAFYEI  600
NKVVANYSER TNETFSTLDY DGIGYALTVY KTDKDIRSYL KSSHNLPKRC YDDQLIEELL  660
SLSYTKFGHL SLKAINHVLS IMQKGNTYKE AVDQLGYDTS GLKKEKRSKF LPPISDEITN  720
PIVKRALTQA RKVVNAIIRR HGSPHSVHIE LARELSKNHD ERTKIVSAQD ENYKKNKGAI  780
SILSEHGILN PTGYDIVRYK LWKEQGERCA YSLKEIPADT FFNELKKERN GAPILEVDHI  840
LPYSQSFIDS YHNKVLVYSD ENRKKGNRIP YTYFLETNKD WEAFERYVRS NKFFSKKKRE  900
YLLKRAYLPR ESELIKERHL NDTRYASTFL KNFIEQNLQF KEAEDNPRKR RVQTVNGVIT  960
AHFRKRWGLE KDRQETYLHH AMDAIIVACT DHHMVTRVTE YYQIKESNKS VKKPYFPMPW 1020
EGFRDELLSH LASQPIAKKI SEELKAGYQS LDYIFVSRMP KRSITGAAHK QTIMRKGGID 1080
KKGKTIIIER LHLKDIKFDE NGDFKMVGKE QDMATYEAIK QRYLEHGKNS KKAFETPLYK 1140
PSKKGTGNLI KRVKVEGQAK SFVREVNGGV AQNGDLVRVD LFEKDDKYYM VPIYVPDTVC 1200
SELPKKVVAS SKGYEQWLTL DNSFTFKFSL YPYDLVRLVK GDEDRFLYFG TLDIDSDRLN 1260
FKDVNKPSKK NEYRYSLKTI EDLEKYEVGV LGDLRLVRKE TRRNFHSGGS KRPAATKKAG 1320
QAKKKK                                                            1326

SEQ ID NO: 492           moltype = AA  length = 1323
FEATURE                  Location/Qualifiers
REGION                   1..1323
                         note = source = /note="Description of Artificial Sequence:
                          Syntheticpolypeptide"
REGION                   1..1323
                         note = source = /note="LPG50144-nAPG07433.1protein sequence"
source                   1..1323
                         mol_type = protein
                         organism = synthetic construct
SEQUENCE: 492
MAPKKKRKVD YKDHDGDYKD HDIDYKDDDD KMSNPELTHD HWMRHALTLA QRARNEGEVP   60
VGAVLVLNGQ VIGEGWNRAI GLHDPTAHAE IMALRQGGLV LQNYRLIDTV LYVTFEPCVM  120
CAGAMVHSRI GQLVFGVRNS KRGAAGSLIN VLNYPGMNHR VEIIEGVLRD ECAAMLCDFY  180
RHPRQVFNAL KKNAGTINTQ SGGSSGGSSG SETPGTSESA TPESSGGSSG GSMRELDYRI  240
GLAIGTNSIG WGVIELSWNK DRERYEKVRI VDQGVRMFDR AEMPKTGASL AEPRRIARSS  300
RRRLNRKSQR KKNIRNLLVQ HGVITQEELD SLYPLSKKSM DIWGIRLDGL DRLLNHFEWA  360
RLLIHLAQRR GFKSNRKSEL KDTETGKVLS SIQLNEKRLS LYRTVGEMWM KDPDFSKYDR  420
KRNSPNEYVF SVSRAELEKE IVTLFAAQRR FQSPYASKDL QETYLQIWTH QLPFASGNAI  480
LNKVGYCSLL KGKERRIPKA TYTFQYFSAL DQVNRTRLGP DFQPFTKEQR EIILNNMFQR  540
TDYYKKKTIP EVTYYDIRKW LELDETIQFK GLNYDPNEEL KKIEKKPFIN LKAFYEINKV  600
VANYSERTNE TFSTLDYDGI GYALTVYKTD KDIRSYLKSS HNLPKRCYDD QLIEELLSLS  660
YTKFGHLSLK AINHVLSIMQ KGNTYKEAVD QLGYDTSGLK KEKRSKFLPP ISDEITNPIV  720
KRALTQARKV VNAIIRRHGS PHSVHIELAR ELSKNHDERT KIVSAQDENY KKNKGAISIL  780
```

```
SEHGILNPTG YDIVRYKLWK EQGERCAYSL KEIPADTFFN ELKKERNGAP ILEVDHILPY   840
SQSFIDSYHN KVLVYSDENR KKGNRIPYTY FLETNKDWEA FERYVRSNKF FSKKKREYLL   900
KRAYLPRESE LIKERHLNDT RYASTFLKNF IEQNLQFKEA EDNPRKRRVQ TVNGVITAHF   960
RKRWGLEKDR QETYLHHAMD AIIVACTDHH MVTRVTEYYQ IKESNKSVKK PYFPMPWEGF  1020
RDELLSHLAS QPIAKKISEE LKAGYQSLDY IFVSRMPKRS ITGAAHKQTI MRKGGIDKKG  1080
KTIIIERLHL KDIKFDENGD FKMVGKEQDM ATYEAIKQRY LEHGKNSKKA FETPLYKPSK  1140
KGTGNLIKRV KVEGQAKSFV REVNGGVAQN GDLVRVDLFE KDDKYYMVPI YVPDTVCSEL  1200
PKKVVASSKG YEQWLTLDNS FTFKFSLYPY DLVRLVKGDE DRFLYFGTLD IDSDRLNFKD  1260
VNKPSKKNEY RYSLKTIEDL EKYEVGVLGD LRLVRKETRR NFHSGGSKRP AATKKAGQAK  1320
KKK                                                                1323

SEQ ID NO: 493         moltype = AA  length = 1320
FEATURE                Location/Qualifiers
REGION                 1..1320
                       note = source = /note="Description of Artificial Sequence:
                         Syntheticpolypeptide"
REGION                 1..1320
                       note = source = /note="LPG50145-nAPG07433.1protein sequence"
source                 1..1320
                       mol_type = protein
                       organism = synthetic construct
SEQUENCE: 493
MAPKKKRKVD YKDHDGDYKD HDIDYKDDDD KMSDTELNHE YWMRHALMLA KRARDEGEVP    60
VGAVLVLKNQ VIGEGWNRAI GLHDPTAHAE IMALRQGGLV LQNYRLIDTT LYVTFEPCVM   120
CAGAMVHSRI GNLVFGVRNS KRGAAGSLIN VLNYPGMNHR VEIAEGVLAD ECSAMLCDFY   180
RHPRQVFNAL KQAAKHISGG SSGGSSGSET PGTSESATPE SSGGSSGGSM RELDYRIGLA   240
IGTNSIGWGV IELSWNKDRE RYEKVRIVDQ GVRMFDRAEM PKTGASLAEP RRIARSSRRR   300
LNRKSQRKKN IRNLLVQHGV ITQEELDSLY PLSKKSMDIW GIRLDGLDRL LNHFEWARLL   360
IHLAQRRGFK SNRKSELKDT ETGKVLSSIQ LNEKRLSLYR TVGEMWMKDP DFSKYDRKRN   420
SPNEYVFSVS RAELEKEIVT LFAAQRRFQS PYASKDLQET YLQIWTHQLP FASGNAILNK   480
VGYCSLLKGK ERRIPKATYT FQYFSALDQV NRTRLGPDFQ PFTKEQREII LNNMFQRTDY   540
YKKKTIPEVT YYDIRKWLEL DETIQFKGLN YDPNEELKKI EKKPFINLKA FYEINKVVAN   600
YSERTNETFS TLDYDGIGYA LTVYKTDKDI RSYLKSSHNL PKRCYDDQLI EELLSLSYTK   660
FGHLSLKAIN HVLSIMQKGN TYKEAVDQLG YDTSGLKKEK RSKFLPPISD EITNPIVKRA   720
LTQARKVVNA IIRRHGSPHS VHIELARELS KNHDERTKIV SAQDENYKKN KGAISILSEH   780
GILNPTGYDI VRYKLWKEQG ERCAYSLKEI PADTFFNELK KERNGAPILE VDHILPYSQS   840
FIDSYHNKVL VYSDENRKKG NRIPYTYFLE TNKDWEAFER YVRSNKFFSK KKREYLLKRA   900
YLPRESELIK ERHLNDTRYA STFLKNFIEQ NLQFKEAEDN PRKRRVQTVN GVITAHFRKR   960
WGLEKDRQET YLHHAMDAII VACTDHHMVT RVTEYYQIKE SNKSVKKPYF PMPWEGFRDE  1020
LLSHLASQPI AKKISEELKA GYQSLDYIFV SRMPKRSITG AAHKQTIMRK GGIDKKGKTI  1080
IIERLHLKDI KFDENGDFKM VGKEQDMATY EAIKQRYLEH GKNSKKAFET PLYKPSKKGT  1140
GNLIKRVKVE GQAKSFVREV NGGVAQNGDL VRVDLFEKDD KYYMVPIYVP DTVCSELPKK  1200
VVASSKGYEQ WLTLDNSFTF KFSLYPYDLV RLVKGDEDRF LYFGTLDIDS DRLNFKDVNK  1260
PSKKNEYRYS LKTIEDLEKY EVGVLGDLRL VRKETRRNFH SGGSKRPAAT KKAGQAKKKK  1320

SEQ ID NO: 494         moltype = AA  length = 1325
FEATURE                Location/Qualifiers
REGION                 1..1325
                       note = source = /note="Description of Artificial Sequence:
                         Syntheticpolypeptide"
REGION                 1..1325
                       note = source = /note="LPG50146-nAPG07433.1protein sequence"
source                 1..1325
                       mol_type = protein
                       organism = synthetic construct
SEQUENCE: 494
MAPKKKRKVD YKDHDGDYKD HDIDYKDDDD KMSDIELNHE YWMRHALMLA KRAREEGEVP    60
VGAVLVLNNQ VIGEGWNRAI GLHDPTAHAE IMALRQGGLV LQNYRLIDTT LYVTFEPCVM   120
CAGAMVHSRI GHLVFGVRNS KRGAAGSLIN VLNYPGMNHR IEFTEGVLAD ECSGMLCDFY   180
RYPRQVFNTL KQAAKAINPA AQSGGSSGGS SGSETPGTSE SATPESSGGS SGGSMRELDY   240
RIGLAIGTNS IGWGVIELSW NKDRERYEKV RIVDQGVRMF DRAEMPKTGA SLAEPRRIAR   300
SSRRRLNRKS QRKKNIRNLL VQHGVITQEE LDSLYPLSKK SMDIWGIRLD GLDRLLNHFE   360
WARLLIHLAQ RRGFKSNRKS ELKDTETGKV LSSIQLNEKR LSLYRTVGEM WMKDPDFSKY   420
DRKRNSPNEY VFSVSRAELE KEIVTLFAAQ RRFQSPYASK DLQETYLQIW THQLPFASGN   480
AILNKVGYCS LLKGKERRIP KATYTFQYFS ALDQVNRTRL GPDFQPFTKE QREIILNNMF   540
QRTDYYKKKT IPEVTYYDIR KWLELDETIQ FKGLNYDPNE ELKKIEKKPF INLKAFYEIN   600
KVVANYSERT NETFSTLDYD GIGYALTVYK TDKDIRSYLK SSHNLPKRCY DDQLIEELLS   660
LSYTKFGHLS LKAINHVLSI MQKGNTYKEA VDQLGYDTSG LKKEKRSKFL PPISDEITNP   720
IVKRALTQAR KVVNAIIRRH GSPHSVHIEL ARELSKNHDE RTKIVSAQDE NYKKNKGAIS   780
ILSEHGILNP TGYDIVRYKL WKEQGERCAY SLKEIPADTF FNELKKERNG APILEVDHIL   840
PYSQSFIDSY HNKVLVYSDE NRKKGNRIPY TYFLETNKDW EAFERYVRSN KFFSKKKREY   900
LLKRAYLPRE SELIKERHLN DTRYASTFLK NFIEQNLQFK EAEDNPRKRR VQTVNGVITA   960
HFRKRWGLEK DRQETYLHHA MDAIIVACTD HHMVTRVTEY YQIKESNKSV KKPYFPMPWE  1020
GFRDELLSHL ASQPIAKKIS EELKAGYQSL DYIFVSRMPK RSITGAAHKQ TIMRKGGIDK  1080
KGKTIIIERL HLKDIKFDEN GDFKMVGKEQ DMATYEAIKQ RYLEHGKNSK KAFETPLYKP  1140
SKKGTGNLIK RVKVEGQAKS FVREVNGGVA QNGDLVRVDL FEKDDKYYMV PIYVPDTVCS  1200
ELPKKVVASS KGYEQWLTLD NSFTFKFSLY PYDLVRLVKG DEDRFLYFGT LDIDSDRLNF  1260
KDVNKPSKKN EYRYSLKTIE DLEKYEVGVL GDLRLVRKET RRNFHSGGSK RPAATKKAGQ  1320
AKKKK                                                              1325
```

```
SEQ ID NO: 495          moltype = AA  length = 1327
FEATURE                 Location/Qualifiers
REGION                  1..1327
                        note = source = /note="Description of Artificial Sequence:
                        Syntheticpolypeptide"
REGION                  1..1327
                        note = source = /note="LPG50147-nAPG07433.1protein sequence"
source                  1..1327
                        mol_type = protein
                        organism = synthetic construct
SEQUENCE: 495
MAPKKKRKVD YKDHDGDYKD HDIDYKDDDD KMSIPELNHD VWMRHALTLA KRAREEGEVP    60
VGAVLVLNGQ VIGEGWNRAI GLHDPTAHAE IMALRQGGLV LQNYRLIDTT LYVTFEPCVM   120
CAGAMVHSRI GQLVFGVRNS KRGAAGSLMN VLNYPGMNHR VEITEGVLRD ECAAMLCDFY   180
RQPRQVFNAL KKPAGDINAL QNNRSGGSSG GSSGSETPGT SESATPESSG GSSGGSMREL   240
DYRIGLAIGT NSIGWGVIEL SWNKDRERYE KVRIVDQGVR MFDRAEMPKT GASLAEPRRI   300
ARSSRRRLNR KSQRKKNIRN LLVQHGVITQ EELDSLYPLS KKSMDIWGIR LDGLDRLLNH   360
FEWARLLIHL AQRRGFKSNR KSELKDTETG KVLSSIQLNE KRLSLYRTVG EMWMKDPDFS   420
KYDRKRNSPN EYVFSVSRAE LEKEIVTLFA AQRRFQSPYA SKDLQETYLQ IWTHQLPFAS   480
GNAILNKVGY CSLLKGKERR IPKATYTFQY FSALDQVNRT RLGPDFQPFT KEQREIILNN   540
MFQRTDYYKK KTIPEVTYYD IRKWLELDET IQFKGLNYDP NEELKKIEKK PFINLKAFYE   600
INKVVANYSE RTNETFSTLD YDGIGYALTV YKTDKDIRSY LKSSHNLPKR CYDDQLIEEL   660
LSLSYTKFGH LSLKAINHVL SIMQKGNTYK EAVDQLGYDT SGLKKEKRSK FLPPISDEIT   720
NPIVKRALTQ ARKVVNAIIR RHGSPHSVHI ELARELSKNH DERTKIVSAQ DENYKKNKGA   780
ISILSEHGIL NPTGYDIVRY KLWKEQGERC AYSLKEIPAD TFFNELKKER NGAPILEVDH   840
ILPYSQSFID SYHNKVLVYS DENRKKGNRI PYTYFLETNK DWEAFERYVR SNKFFSKKKR   900
EYLLKRAYLP RESELIKERH LNDTRYASTF LKNFIEQNLQ FKEAEDNPRK RRVQTVNGVI   960
TAHFRKRWGL EKDRQETYLH HAMDAIIVAC TDHHMVTRVT EYYQIKESNK SVKKPYFPMP  1020
WEGFRDELLS HLASQPIAKK ISEELKAGYQ SLDYIFVSRM PKRSITGAAH KQTIMRKGGI  1080
DKKGKTIIIE RLHLKDIKFD ENGDFKMVGK EQDMATYEAI KQRYLEHGKN SKKAFETPLY  1140
KPSKKGTGNL IKRVKVEGQA KSFVREVNGG VAQNGDLVRV DLFEKDDKYY MVPIYVPDTV  1200
CSELPKKVVA SSKGYEQWLT LDNSFTFKFS LYPYDLVRLV KGDEDRFLYF GTLDIDSDRL  1260
NFKDVNKPSK KNEYRYSLKT IEDLEKYEVG VLGDLRLVRK ETRRNFHSGG SKRPAATKKA  1320
GQAKKKK                                                            1327

SEQ ID NO: 496          moltype = AA  length = 1322
FEATURE                 Location/Qualifiers
REGION                  1..1322
                        note = source = /note="Description of Artificial Sequence:
                        Syntheticpolypeptide"
REGION                  1..1322
                        note = source = /note="LPG50148-nAPG07433.1protein sequence"
source                  1..1322
                        mol_type = protein
                        organism = synthetic construct
SEQUENCE: 496
MAPKKKRKVD YKDHDGDYKD HDIDYKDDDD KMSNPEFTHE YWMRHALTLA RRARDEGEVP    60
VGAVLVLNNQ VIGEGWNRAI GLHDPTAHAE IMALRQGGLV LQNYRLIDTT LYVTFEPCVM   120
CSGAMVHSRI GTLVFGVRNS KRGAAGSLMN VLNYPGMNHQ VKTIGGVLAP ECSGLLCDFY   180
RMPRQVFNQQ KAELKSINDS GGSSGGSSGS ETPGTSESAT PESSGGSSGG SMRELDYRIG   240
LAIGTNSIGW GVIELSWNKD RERYEKVRIV DQGVRMFDRA EMPKTGASLA EPRRIARSSR   300
RRLNRKSQRK KNIRNLLVQH GVITQEELDS LYPLSKKSMD IWGIRLDGLD RLLNHFEWAR   360
LLIHLAQRRG FKSNRKSELK DTETGKVLSS IQLNEKRLSL YRTVGEMWMK DPDFSKYDRK   420
RNSPNEYVFS VSRAELEKEI VTLFAAQRRF QSPYASKDLQ ETYLQIWTHQ LPFASGNAIL   480
NKVGYCSLLK GKERRIPKAT YTFQYFSALD QVNRTRLGPD FQPFTKEQRE IILNNMFQRT   540
DYYKKKTIPE VTYYDIRKWL ELDETIQFKG LNYDPNEELK KIEKKPFINL KAFYEINKVV   600
ANYSERTNET FSTLDYDGIG YALTVYKTDK DIRSYLKSSH NLPKRCYDDQ LIEELLSLSY   660
TKFGHLSLKA INHVLSIMQK GNTYKEAVDQ LGYDTSGLKK EKRSKFLPPI SDEITNPIVK   720
RALTQARKVV NAIIRRHGSP HSVHIELARE LSKNHDERTK IVSAQDENYK KNKGAISILS   780
EHGILNPTGY DIVRYKLWKE QGERCAYSLK EIPADTFFNE LKKERNGAPI LEVDHILPYS   840
QSFIDSYHNK VLVYSDENRK KGNRIPYTYF LETNKDWEAF ERYVRSNKFF SKKKREYLLK   900
RAYLPRESEL IKERHLNDTR YASTFLKNFI EQNLQFKEAE DNPRKRRVQT VNGVITAHFR   960
KRWGLEKDRQ ETYLHHAMDA IIVACTDHHM VTRVTEYYQI KESNKSVKKP YPMPWEGFR  1020
DELLSHLASQ PIAKKISEEL KAGYQSLDYI FVSRMPKRSI TGAAHKQTIM RKGGIDKKGK  1080
TIIIERLHLK DIKFDENGDF KMVGKEQDMA TYEAIKQRYL EHGKNSKKAF ETPLYKPSKK  1140
GTGNLIKRVK VEGQAKSFVR EVNGGVAQNG DLVRVDLFEK DDKYYMVPIY VPDTVCSELP  1200
KKVVASSKGY EQWLTLDNSF TFKFSLYPYD LVRLVKGDED RFLYFGTLDI DSDRLNFKDV  1260
NKPSKKNEYR YSLKTIEDLE KYEVGVLGDL RLVRKETRRN FHSGGSKRPA ATKKAGQAKK  1320
KK                                                                1322

SEQ ID NO: 497          moltype = AA  length = 1321
FEATURE                 Location/Qualifiers
REGION                  1..1321
                        note = source = /note="Description of Artificial Sequence:
                        Syntheticpolypeptide"
REGION                  1..1321
                        note = source = /note="LPG50149-nAPG07433.1protein sequence"
```

```
source                    1..1321
                          mol_type = protein
                          organism = synthetic construct
SEQUENCE: 497
MAPKKKRKVD YKDHDGDYKD HDIDYKDDDD KMSDAELTHE YWMRHALTLA QRARDEGEVP    60
VGAVLVLNNQ VIGEGWNRAI GLHDPTAHAE IMALRQGGLV QQNYRLIDTT LYVTFEPCVM   120
CAGAMVHSRI GRLIFGVRNS KRGAAGSLIN VLNYPGMNHR VEVVEGILRD ECAGMLCDFY   180
RQPRQVFNAL KKGATDINSG GSSGGSSGSE TPGTSESATP ESSGGSSGGS MRELDYRIGL   240
AIGTNSIGWG VIELSWNKDR ERYEKVRIVD QGVRMFDRAE MPKTGASLAE PRRIARSSRR   300
RLNRKSQRKK NIRNLLVQHG VITQEELDSL YPLSKKSMDI WGIRLDGLDR LLNHFEWARL   360
LIHLAQRGF KSNRKSELKD TETGKVLSSI QLNEKRLSLY RTVGEMWMKD PDFSKYDRKR   420
NSPNEYVFSV SRAELEKEIV TLFAAQRRFQ SPYASKDLQE TYLQIWTHQL PFASGNAILN   480
KVGYCSLLKG KERRIPKATY TFQYFSALDQ VNRTRLGPDF QPFTKEQREI ILNNMFQRTD   540
YYKKKTIPEV TYYDIRKWLE LDETIQFKGL NYDPNEELKK IEKKPFINLK AFYEINKVVA   600
NYSERTNETF STLDYDGIGY ALTVYKTDKD IRSYLKSSHN LPKRCYDDQL IEELLSLSYT   660
KFGHLSLKAI NHVLSIMQKG NTYKEAVDQL GYDTSGLKKE KRSKFLPPIS DEITNPIVKR   720
ALTQARKVVN AIIRRHGSPH SVHIELAREL SKNHDERTKI VSAQDENYKK NKGAISILSE   780
HGILNPTGYD IVRYKLWKEQ GERCAYSLKE IPADTFFNEL KKERNGAPIL EVDHILPYSQ   840
SFIDSYHNKV LVYSDENRKK GNRIPYTYFL ETNKDWEAFE RYVRSNKFFS KKKREYLLKR   900
AYLPRESELI KERHLNDTRY ASTFLKNFIE QNLQFKEAED NPRKRRVQTV NGVITAHFRK   960
RWGLEKDRQE TYLHHAMDAI IVACTDHHMV TRVTEYYQIK ESNKSVKKPY FPMPWEGFRD  1020
ELLSHLASQP IAKKISEELK AGYQSLDYIF VSRMPKRSLT GAAHKQTIMR KGGIDKKGKT  1080
IIIERLHLKD IKFDENGDFK MVGKEQDMAT YEAIKQRYLE HGKNSKKAFE TPLYKPSKKG  1140
TGNLIKRVKV EGQAKSFVRE VNGGVAQNGD LVRVDLFEKD DKYYMVPIYV PDTVCSELPK  1200
KVVASSKGYE QWLTLDNSFT FKFSLYPYDL VRLVKGDEDR FLYFGTLDID SDRLNFKDVN  1260
KPSKKNEYRY SLKTIEDLEK YEVGVLGDLR LVRKETRRNF HSGGSKRPAA TKKAGQAKKK  1320
K                                                                 1321

SEQ ID NO: 498            moltype = AA   length = 1321
FEATURE                   Location/Qualifiers
REGION                    1..1321
                          note = source = /note="Description of Artificial Sequence:
                          Syntheticpolypeptide"
REGION                    1..1321
                          note = source = /note="LPG50150-nAPG07433.1protein sequence"
source                    1..1321
                          mol_type = protein
                          organism = synthetic construct
SEQUENCE: 498
MAPKKKRKVD YKDHDGDYKD HDIDYKDDDD KMSDAELTHE YWMRHALTLA QRARDEGEVP    60
VGAVLVLNNQ VIGEGWNRAI GLHDPTAHAE IMALRQGGLV QQNYRLLDTT LYVTFEPCVM   120
CAGAMVHSRI GRLIFGVRNS KRGAAGSLIN VLNYPGMNHR VEVVEGILRD ECAGMLCAFY   180
RQPRAVKNAL KKGATDVLSG GSSGGSSGSE TPGTSESATP ESSGGSSGGS MRELDYRIGL   240
AIGTNSIGWG VIELSWNKDR ERYEKVRIVD QGVRMFDRAE MPKTGASLAE PRRIARSSRR   300
RLNRKSQRKK NIRNLLVQHG VITQEELDSL YPLSKKSMDI WGIRLDGLDR LLNHFEWARL   360
LIHLAQRRGF KSNRKSELKD TETGKVLSSI QLNEKRLSLY RTVGEMWMKD PDFSKYDRKR   420
NSPNEYVFSV SRAELEKEIV TLFAAQRRFQ SPYASKDLQE TYLQIWTHQL PFASGNAILN   480
KVGYCSLLKG KERRIPKATY TFQYFSALDQ VNRTRLGPDF QPFTKEQREI ILNNMFQRTD   540
YYKKKTIPEV TYYDIRKWLE LDETIQFKGL NYDPNEELKK IEKKPFINLK AFYEINKVVA   600
NYSERTNETF STLDYDGIGY ALTVYKTDKD IRSYLKSSHN LPKRCYDDQL IEELLSLSYT   660
KFGHLSLKAI NHVLSIMQKG NTYKEAVDQL GYDTSGLKKE KRSKFLPPIS DEITNPIVKR   720
ALTQARKVVN AIIRRHGSPH SVHIELAREL SKNHDERTKI VSAQDENYKK NKGAISILSE   780
HGILNPTGYD IVRYKLWKEQ GERCAYSLKE IPADTFFNEL KKERNGAPIL EVDHILPYSQ   840
SFIDSYHNKV LVYSDENRKK GNRIPYTYFL ETNKDWEAFE RYVRSNKFFS KKKREYLLKR   900
AYLPRESELI KERHLNDTRY ASTFLKNFIE QNLQFKEAED NPRKRRVQTV NGVITAHFRK   960
RWGLEKDRQE TYLHHAMDAI IVACTDHHMV TRVTEYYQIK ESNKSVKKPY FPMPWEGFRD  1020
ELLSHLASQP IAKKISEELK AGYQSLDYIF VSRMPKRSIT GAAHKQTIMR KGGIDKKGKT  1080
IIIERLHLKD IKFDENGDFK MVGKEQDMAT YEAIKQRYLE HGKNSKKAFE TPLYKPSKKG  1140
TGNLIKRVKV EGQAKSFVRE VNGGVAQNGD LVRVDLFEKD DKYYMVPIYV PDTVCSELPK  1200
KVVASSKGYE QWLTLDNSFT FKFSLYPYDL VRLVKGDEDR FLYFGTLDID SDRLNFKDVN  1260
KPSKKNEYRY SLKTIEDLEK YEVGVLGDLR LVRKETRRNF HSGGSKRPAA TKKAGQAKKK  1320
K                                                                 1321

SEQ ID NO: 499            moltype = AA   length = 1323
FEATURE                   Location/Qualifiers
REGION                    1..1323
                          note = source = /note="Description of Artificial Sequence:
                          Syntheticpolypeptide"
REGION                    1..1323
                          note = source = /note="LPG50151-nAPG07433.1protein sequence"
source                    1..1323
                          mol_type = protein
                          organism = synthetic construct
SEQUENCE: 499
MAPKKKRKVD YKDHDGDYKD HDIDYKDDDD KMSDLELNHE YWMRHALQLA QRARDEGEVP    60
VGAVLVYNNQ VIGEGWNRAI GLHDPTAHAE IMALRQGGIV LQNYRLLDTT LYVTFEPCVM   120
CSGAMVHSRI GTLVFGVRNE KRGAAGSLMN VLRYPGMNHQ VQIIDGVLAP ECSGLLCDFY   180
RMPRQQKNQQ KAESTSSPGD SGGSSGGSSG SETPGTSESA TPESSGGSSG GSMRELDYRI   240
GLAIGTNSIG WGVIELSWNK DRERYEKVRI VDQGVRMFDR AEMPKTGASL AEPRRIARSS   300
RRRLNRKSQR KKNIRNLLVQ HGVITQEELD SLYPLSKKSM DIWGIRLDGL DRLLNHFEWA   360
```

```
RLLIHLAQRR GFKSNRKSEL KDTETGKVLS SIQLNEKRLS LYRTVGEMWM KDPDFSKYDR    420
KRNSPNEYVF SVSRAELEKE IVTLFAAQRR FQSPYASKDL QETYLQIWTH QLPFASGNAI    480
LNKVGYCSLL KGKERRIPKA TYTFQYFSAL DQVNRTRLGP DFQPFTKEQR EIILNNMFQR    540
TDYYKKKTIP EVTYYDIRKW LELDETIQFK GLNYDPNEEL KKIEKKPFIN LKAFYEINKV    600
VANYSERTNE TFSTLDYDGI GYALTVYKTD KDIRSYLKSS HNLPKRCYDD QLIEELLSLS    660
YTKFGHLSLK AINHVLSIMQ KGNTYKEAVD QLGYDTSGLK KEKRSKFLPP ISDEITNPIV    720
KRALTQARKV VNAIIRRHGS PHSVHIELAR ELSKNHDERT KIVSAQDENY KKNKGAISIL    780
SEHGILNPTG YDIVRYKLWK EQGERCAYSL KEIPADTFFN ELKKERNGAP ILEVDHILPY    840
SQSFIDSYHN KVLVYSDENR KKGNRIPYTY FLETNKDWEA FERYVRSNKF FSKKKREYLL    900
KRAYLPRESE LIKERHLNDT RYASTFLKNF IEQNLQFKEA EDNPRKRRVQ TVNGVITAHF    960
RKRWGLEKDR QETYLHHAMD AIIVACTDHH MVTRVTEYYQ IKESNKSVKK PYFPMPWEGF   1020
RDELLSHLAS QPIAKKISEE LKAGYQSLDY IFVSRMPKRS ITGAAHKQTI MRKGGIDKKG   1080
KTIIIERLHL KDIKFDENGD FKMVGKEQDM ATYEAIKQRY LEHGKNSKKA FETPLYKPSK   1140
KGTGNLIKRV KVEGQAKSFV REVNGGVAQN GDLVRVDLFE KDDKYYMVPI YVPDTVCSEL   1200
PKKVVASSKG YEQWLTLDNS FTFKFSLYPY DLVRLVKGDE DRFLYFGTLD IDSDRLNFKD   1260
VNKPSKKNEY RYSLKTIEDL EKYEVGVLGD LRLVRKETRR NFHSGGSKRP AATKKAGQAK   1320
KKK                                                                1323

SEQ ID NO: 500         moltype = AA  length = 1321
FEATURE                Location/Qualifiers
REGION                 1..1321
                       note = source = /note="Description of Artificial Sequence:
                        Syntheticpolypeptide"
REGION                 1..1321
                       note = source = /note="LPG50152-nAPG07433.1protein sequence"
source                 1..1321
                       mol_type = protein
                       organism = synthetic construct
SEQUENCE: 500
MAPKKKRKVD YKDHDGDYKD HDIDYKDDDD KMSDNELNHE YWMRHALGLA KRAREEGEVP     60
VGAVLVLNNQ VIGEGWNRAI GLHDPTAHAE IMALRQGGLV LQNYRLTDTT LYVTFEPCVM    120
CAGAMVHSRI GTLVFGVRNS KRGAAGSLMN VLNYPGMNHR VEIVEGILSE SCAAMLCDFY    180
RQPRAVKNAL KKAADPAASG GSSGGSSGSE TPGTSESATP ESSGGSSGGS MRELDYRIGL    240
AIGTNSIGWG VIELSWNKDR ERYEKVRIVD QGVRMFDRAE MPKTGASLAE PRRIARSSRR    300
RLNRKSQRKK NIRNLLVQHG VITQEELDSL YPLSKKSMDI WGIRLDGLDR LLNHFEWARL    360
LIHLAQRGF KSNRKSELKD TETGKVLSSI QLNEKRLSLY RTVGEMWMKD PDFSKYDRKR    420
NSPNEYVFSV SRAELEKEIV TLFAAQRRFQ SPYASKDLQE TYLQIWTHQL PFASGNAILN    480
KVGYCSLLKG KERRIPKATY TFQYFSALDQ VNRTRLGPDF QPFTKEQREI ILNNMFQRTD    540
YYKKKTIPEV TYYDIRKWLE LDETIQFKGL NYDPNEELKK IEKKPFINLK AFYEINKVVA    600
NYSERTNETF STLDYDGIGY ALTVYKTDKD IRSYLKSSHN LPKRCYDDQL IEELLSLSYT    660
KFGHLSLKAI NHVLSIMQKG NTYKEAVDQL GYDTSGLKKE KRSKFLPPIS DEITNPIVKR    720
ALTQARKVVN AIIRRHGSPH SVHIELAREL SKNHDERTKI VSAQDENYKK NKGAISILSE    780
HGILNPTGYD IVRYKLWKEQ GERCAYSLKE IPADTFFNEL KKERNGAPIL EVDHILPYSQ    840
SFIDSYHNKV LVYSDENRKK GNRIPYTYFL ETNKDWEAFE RYVRSNKFFS KKKREYLLKR    900
AYLPRESELI KERHLNDTRY ASTFLKNFIE QNLQFKEAED NPRKRRVQTV NGVITAHFRK    960
RWGLEKDRQE TYLHHAMDAI IVACTDHHMV TRVTEYYQIK ESNKSVKKPY FPMPWEGFRD   1020
ELLSHLASQP IAKKISEELK AGYQSLDYIF VSRMPKRSIT GAAHKQTIMR KGGIDKKGKT   1080
IIIERLHLKD IKFDENGDFK MVGKEQDMAT YEAIKQRYLE HGKNSKKAFE TPLYKPSKKG   1140
TGNLIKRVKV EGQAKSFVRE VNGGVAQNGD LVRVDLFEKD DKYYMVPIYV PDTVCSELPK   1200
KVVASSKGYE QWLTLDNSFT FKFSLYPYDL VRLVKGDEDR FLYFGTLDID SDRLNFKDVN   1260
KPSKKNEYRY SLKTIEDLEK YEVGVLGDLR LVRKETRRNF HSGGSKRPAA TKKAGQAKKK   1320
K                                                                 1321

SEQ ID NO: 501         moltype = AA  length = 1318
FEATURE                Location/Qualifiers
REGION                 1..1318
                       note = source = /note="Description of Artificial Sequence:
                        Syntheticpolypeptide"
REGION                 1..1318
                       note = source = /note="LPG50153-nAPG07433.1protein sequence"
source                 1..1318
                       mol_type = protein
                       organism = synthetic construct
SEQUENCE: 501
MAPKKKRKVD YKDHDGDYKD HDIDYKDDDD KMSDTEFTHE HWMRHALTLA QRARDEGEVP     60
VGAVLVLNNQ VIGEGWNRAI GLHDPTAHAE IMALRQGGLV LQNYRLLDTT LYVTFEPCVM    120
CAGAMVHSRI GHLVFGVRNS KRGAIGSLMN VLGYPGMNHQ VQVSEGVLAT ECSAMLCDFY    180
RAPRLVKNAL KEKARSGGSS GGSSGSETPG TSESATPESS GGSSGGSMRE LDYRIGLAIG    240
TNSIGWGVIE LSWNKDRERY EKVRIVDQGV RMFDRAEMPK TGASLAEPRR IARSSRRRLN    300
RKSQRKKNIR NLLVQHGVIT QEELDSLYPL SKKSMDIWGI RLDGLDRLLN HFEWARLLIH    360
LAQRRGFKSN RKSELKDTET GKVLSSIQLN EKRLSLYRTV GEMWMKDPDF SKYDRKRNSP    420
NEYVFSVSRA ELEKEIVTLF AAQRRFQSPY ASKDLQETYL QIWTHQLPFA SGNAILNKVG    480
YCSLLKGKER RIPKATYTFQ YFSALDQVNR TRLGPDFQPF TKEQREIILN NMFQRTDYYK    540
KKTIPEVTYY DIRKWLELDE TIQFKGLNYD PNEELKKIEK KPFINLKAFY EINKVVANYS    600
ERTNETFSTL DYDGIGYALT VYKTDKDIRS YLKSSHNLPK RCYDDQLIEE LLSLSYTKFG    660
HLSLKAINHV LSIMQKGNTY KEAVDQLGYD TSGLKKEKRS KFLPPISDEI TNPIVKRALT    720
QARKVVNAII RRHGSPHSVH IELARELSKN HDERTKIVSA QDENYKKNKG AISILSEHGI    780
LNPTGYDIVR YKLWKEQGER CAYSLKEIPA DTFFNELKKE RNGAPILEVD HILPYSQSFI    840
DSYHNKVLVY SDENRKKGNR IPYTYFLETN KDWEAFERYV RSNKFFSKKK REYLLKRAYL    900
```

```
PRESELIKER HLNDTRYAST FLKNFIEQNL QFKEAEDNPR KRRVQTVNGV ITAHFRKRWG   960
LEKDRQETYL HHAMDAIIVA CTDHHMVTRV TEYYQIKESN KSVKKPYFPM PWEGFRDELL  1020
SHLASQPIAK KISEELKAGY QSLDYIFVSR MPKRSITGAA HKQTIMRKGG IDKKGKTIII  1080
ERLHLKDIKF DENGDFKMVG KEQDMATYEA IKQRYLEHGK NSKKAFETPL YKPSKKGTGN  1140
LIKRVKVEGQ AKSFVREVNG GVAQNGDLVR VDLFEKDDKY YMVPIYVPDT VCSELPKKVV  1200
ASSKGYEQWL TLDNSFTFKF SLYPYDLVRL VKGDEDRFLY FGTLDIDSDR LNFKDVNKPS  1260
KKNEYRYSLK TIEDLEKYEV GVLGDLRLVR KETRRNFHSG GSKRPAATKK AGQAKKKK    1318

SEQ ID NO: 502           moltype = AA   length = 1325
FEATURE                  Location/Qualifiers
REGION                   1..1325
                         note = source = /note="Description of Artificial Sequence:
                          Syntheticpolypeptide"
REGION                   1..1325
                         note = source = /note="LPG50154-nAPG07433.1protein sequence"
source                   1..1325
                         mol_type = protein
                         organism = synthetic construct
SEQUENCE: 502
MAPKKKRKVD YKDHDGDYKD HDIDYKDDDD KMSESEFTHE HWMRHALTLA RRAREEGEVP    60
VGAVLVLNNQ VIGEGWNRAI GLHDPTAHAE IMALRQGGLV LQNYRLLDST LYVTFEPCVM   120
CAGAMVHGRI GNLVFGVRNS KRGAIGSLMN VVGYPGMNHQ INVIEGVLAE ECSAMLCDFY   180
RAPRLVKNAL KEKARNGNNP NKSGGSSGGS SGSETPGTSE SATPESSGGS SGGSMRELDY   240
RIGLAIGTNS IGWGVIELSW NKDRERYEKV RIVDQGVRMF DRAEMPKTGA SLAEPRRIAR   300
SSRRRLNRKS QRKKNIRNLL VQHGVITQEE LDSLYPLSKK SMDIWGIRLD GLDRLLNHFE   360
WARLLIHLAQ RRGFKSNRKS ELKDTETGKV LSSIQLNEKR LSLYRTVGEM WMKDPDFSKY   420
DRKRNSPNEY VFSVSRAELE KEIVTLFAAQ RRFQSPYASK DLQETYLQIW THQLPFASGN   480
AILNKVGYCS LLKGKERRIP KATYTFQYFS ALDQVNRTRL GPDFQPFTKE QREIILNNMF   540
QRTDYYKKKT IPEVTYYDIR KWLELDETIQ FKGLNYDPNE ELKKIEKKPF INLKAFYEIN   600
KVVANYSERT NETFSTLDYD GIGYALTVYK TDKDIRSYLK SSHNLPKRCY DDQLIEELLS   660
LSYTKFGHLS LKAINHVLSI MQKGNTYKEA VDQLGYDTSG LKKEKRSKFL PPISDEITNP   720
IVKRALTQAR KVVNAIIRRH GSPHSVHIEL ARELSKNHDE RTKIVSAQDE NYKKNKGAIS   780
ILSEHGILNP TGYDIVRYKL WKEQGERCAY SLKEIPADTF FNELKKERNG APILEVDHIL   840
PYSQSFIDSY HNKVLVYSDE NRKKGNRIPY TYFLETNKDW EAFERYVRSN KFFSKKKREY   900
LLKRAYLPRE SELIKERHLN DTRYASTFLK NFIEQNLQFK EAEDNPRKRR VQTVNGVITA   960
HFRKRWGLEK DRQETYLHHA MDAIIVACTD HHMVTRVTEY YQIKESNKSV KKPYFPMPWE  1020
GFRDELLSHL ASQPIAKKIS EELKAGYQSL DYIFVSRMPK RSITGAAHKQ TIMRKGGIDK  1080
KGKTIIIERL HLKDIKFDEN GDFKMVGKEQ DMATYEAIKQ RYLEHGKNSK KAFETPLYKP  1140
SKKGTGNLIK RVKVEGQAKS FVREVNGGVA QNGDLRVRDL FEKDDKYYMV PIYVPDTVCS  1200
ELPKKVVASS KGYEQWLTLD NSFTFKFSLY PYDLVRLVKG DEDRFLYFGT LDIDSDRLNF  1260
KDVNKPSKKN EYRYSLKTIE DLEKYEVGVL GDLRLVRKET RRNFHSGGSK RPAATKKAGQ  1320
AKKKK                                                              1325

SEQ ID NO: 503           moltype = AA   length = 1318
FEATURE                  Location/Qualifiers
REGION                   1..1318
                         note = source = /note="Description of Artificial Sequence:
                          Syntheticpolypeptide"
REGION                   1..1318
                         note = source = /note="LPG50155-nAPG07433.1protein sequence"
source                   1..1318
                         mol_type = protein
                         organism = synthetic construct
SEQUENCE: 503
MAPKKKRKVD YKDHDGDYKD HDIDYKDDDD KMSNPELTHE HWMRYALTLA KRAREEGEVP    60
VGAVLVLNNQ VIGEGWNRAI GLHDPTAHAE IMALRQGGLV LQNYRLIDTT LYVTFEPCVM   120
CAGAMVHSRI GQLVFGVRNS KRGAAGSLMN VLNYPGMNHR IEFTEGVLRD ECAAMLCDFY   180
RQPRLVKNAL KTGNASGGSS GGSSGSETPG TSESATPESS GGSSGGSMRE LDYRIGLAIG   240
TNSIGWGVIE LSWNKDRERY EKVRIVDQGV RMFDRAEMPK TGASLAEPRR IARSSRRRLN   300
RKSQRKKNIR NLLVQHGVIT QEELDSLYPL SKKSMDIWGI RLDGLDRLLN HFEWARLLIH   360
LAQRRGFKSN RKSELKDTET GKVLSSIQLN EKRLSLYRTV GEMWMKDPDF SKYDRKRNSP   420
NEYVFSVSRA ELEKEIVTLF AAQRRFQSPY ASKDLQETYL QIWTHQLPFA SGNAILNKVG   480
YCSLLKGKER RIPKATYTFQ YFSALDQVNR TRLGPDFQPF TKEQREIILN NMFQRTDYYK   540
KKTIPEVTYY DIRKWLELDE TIQFKGLNYD PNEELKKIEK KPFINLKAFY EINKVVANYS   600
ERTNETFSTL DYDGIGYALT VYKTDKDIRS YLKSSHNLPK RCYDDQLIEE LLSLSYTKFG   660
HLSLKAINHV LSIMQKGNTY KEAVDQLGYD TSGLKKEKRS KFLPPISDEI TNPIVKRALT   720
QARKVVNAII RRHGSPHSVH IELARELSKN HDERTKIVSA QDENYKKNKG AISILSEHGI   780
LNPTGYDIVR YKLWKEQGER CAYSLKEIPA DTFFNELKKE RNGAPILEVD HILPYSQSFI   840
DSYHNKVLVY SDENRKKGNR IPYTYFLETN KDWEAFERYV RSNKFFSKKK REYLLKRAYL   900
PRESELIKER HLNDTRYAST FLKNFIEQNL QFKEAEDNPR KRRVQTVNGV ITAHFRKRWG   960
LEKDRQETYL HHAMDAIIVA CTDHHMVTRV TEYYQIKESN KSVKKPYFPM PWEGFRDELL  1020
SHLASQPIAK KISEELKAGY QSLDYIFVSR MPKRSITGAA HKQTIMRKGG IDKKGKTIII  1080
ERLHLKDIKF DENGDFKMVG KEQDMATYEA IKQRYLEHGK NSKKAFETPL YKPSKKGTGN  1140
LIKRVKVEGQ AKSFVREVNG GVAQNGDLVR VDLFEKDDKY YMVPIYVPDT VCSELPKKVV  1200
ASSKGYEQWL TLDNSFTFKF SLYPYDLVRL VKGDEDRFLY FGTLDIDSDR LNFKDVNKPS  1260
KKNEYRYSLK TIEDLEKYEV GVLGDLRLVR KETRRNFHSG GSKRPAATKK AGQAKKKK    1318

SEQ ID NO: 504           moltype = AA   length = 1320
FEATURE                  Location/Qualifiers
```

| | | |
|---|---|---|
| REGION | 1..1320 | |
| | note = source = /note="Description of Artificial Sequence: Syntheticpolypeptide" | |
| REGION | 1..1320 | |
| | note = source = /note="LPG50156-nAPG07433.1protein sequence" | |
| source | 1..1320 | |
| | mol_type = protein | |
| | organism = synthetic construct | |
| SEQUENCE: 504 | | |

```
MAPKKKRKVD YKDHDGDYKD HDIDYKDDDD KMSDPELNHE YWMRHALQLA KRAREEGEVP    60
VGAVLVLNNQ VIGEGWNRAI GLHDPTAHAE IMALRQGGLV LQNYRLLDTT LYVTFEPCVM   120
CSGAMIHSRI GTVVFGVRNE KRGAAGSLLN VLRYPGMNHQ VNVLGGVLAP ACSEMLCEFY   180
RMPRQQKNRQ KAESKLSSGG SSGGSSGSET PGTSESATPE SSGGSSGGSM RELDYRIGLA   240
IGTNSIGWGV IELSWNKDRE RYEKVRIVDQ GVRMFDRAEM PKTGASLAEP RRIARSSRRR   300
LNRKSQRKKN IRNLLVQHGV ITQEELDSLY PLSKKSMDIW GIRLDGLDRL LNHFEWARLL   360
IHLAQRRGFK SNRKSELKDT ETGKVLSSIQ LNEKRLSLYR TVGEMWMKDP DFSKYDRKRN   420
SPNEYVFSVS RAELEKEIVT LFAAQRRFQS PYASKDLQET YLQIWTHQLP FASGNAILNK   480
VGYCSLLKGK ERRIPKATYT FQYFSALDQV NRTRLGPDFQ PFTKEQREII LNNMFQRTDY   540
YKKKTIPEVT YYDIRKWLEL DETIQFKGLN YDPNEELKKI EKKPFINLKA FYEINKVVAN   600
YSERTNETFS TLDYDGIGYA LTVYKTDKDI RSYLKSSHNL PKRCYDDQLI EELLSLSYTK   660
FGHLSLKAIN HVLSIMQKGN TYKEAVDQLG YDTSGLKKEK RSKFLPPISD EITNPIVKRA   720
LTQARKVVNA IIRRHGSPHS VHIELARELS KNHDERTKIV SAQDENYKKN KGAISILSEH   780
GILNPTGYDI VRYKLWKEQG ERCAYSLKEI PADTFFNELK KERNGAPILE VDHILPYSQS   840
FIDSYHNKVL VYSDENRKKG NRIPYTYFLE TNKDWEAFER YVRSNKFFSK KKREYLLKRA   900
YLPRESELIK ERHLNDTRYA STFLKNFIEQ NLQFKEAEDN PRKRRVQTVN GVITAHFRKR   960
WGLEKDRQET YLHHAMDAII VACTDHHMVT RVTEYYQIKE SNKSVKKPYF PMPWEGFRDE  1020
LLSHLASQPI AKKISEELKA GYQSLDYIFV SRMPKRSITG AAHKQTIMRK GGIDKKGKTI  1080
IIERLHLKDI KFDENGDFKM VGKEQDMATY EAIKQRYLEH GKNSKKAFET PLYKPSKKGT  1140
GNLIKRVKVE GQAKSFVREV NGGVAQNGDL VRVDLFEKDD KYYMVPIYVP DTVCSELPKK  1200
VVASSKGYEQ WLTLDNSFTF KFSLYPYDLV RLVKGDEDRF LYFGTLDIDS DRLNFKDVNK  1260
PSKKNEYRYS LKTIEDLEKY EVGVLGDLRL VRKETRRNFH SGGSKRPAAT KKAGQAKKKK  1320
```

| | | |
|---|---|---|
| SEQ ID NO: 505 | moltype = AA  length = 1320 | |
| FEATURE | Location/Qualifiers | |
| REGION | 1..1320 | |
| | note = source = /note="Description of Artificial Sequence: Syntheticpolypeptide" | |
| REGION | 1..1320 | |
| | note = source = /note="LPG50157-nAPG07433.1protein sequence" | |
| source | 1..1320 | |
| | mol_type = protein | |
| | organism = synthetic construct | |
| SEQUENCE: 505 | | |

```
MAPKKKRKVD YKDHDGDYKD HDIDYKDDDD KMSDNELNHE HWMRHALTLA QRAREEGEVP    60
VGAVLVLQNQ VIGEGWNRAI GLHDPTAHAE IMALRQGGMV LQNYRLIDTT LYVTFEPCVM   120
CAGAMVHSRI GQLVFGVRNS KRGAAGSLIN VLNYPGMNHR VEITEGVLAD DCSSMLCDFY   180
RHPREQKNAL KRAAHSNSGG SSGGSSGSET PGTSESATPE SSGGSSGGSM RELDYRIGLA   240
IGTNSIGWGV IELSWNKDRE RYEKVRIVDQ GVRMFDRAEM PKTGASLAEP RRIARSSRRR   300
LNRKSQRKKN IRNLLVQHGV ITQEELDSLY PLSKKSMDIW GIRLDGLDRL LNHFEWARLL   360
IHLAQRRGFK SNRKSELKDT ETGKVLSSIQ LNEKRLSLYR TVGEMWMKDP DFSKYDRKRN   420
SPNEYVFSVS RAELEKEIVT LFAAQRRFQS PYASKDLQET YLQIWTHQLP FASGNAILNK   480
VGYCSLLKGK ERRIPKATYT FQYFSALDQV NRTRLGPDFQ PFTKEQREII LNNMFQRTDY   540
YKKKTIPEVT YYDIRKWLEL DETIQFKGLN YDPNEELKKI EKKPFINLKA FYEINKVVAN   600
YSERTNETFS TLDYDGIGYA LTVYKTDKDI RSYLKSSHNL PKRCYDDQLI EELLSLSYTK   660
FGHLSLKAIN HVLSIMQKGN TYKEAVDQLG YDTSGLKKEK RSKFLPPISD EITNPIVKRA   720
LTQARKVVNA IIRRHGSPHS VHIELARELS KNHDERTKIV SAQDENYKKN KGAISILSEH   780
GILNPTGYDI VRYKLWKEQG ERCAYSLKEI PADTFFNELK KERNGAPILE VDHILPYSQS   840
FIDSYHNKVL VYSDENRKKG NRIPYTYFLE TNKDWEAFER YVRSNKFFSK KKREYLLKRA   900
YLPRESELIK ERHLNDTRYA STFLKNFIEQ NLQFKEAEDN PRKRRVQTVN GVITAHFRKR   960
WGLEKDRQET YLHHAMDAII VACTDHHMVT RVTEYYQIKE SNKSVKKPYF PMPWEGFRDE  1020
LLSHLASQPI AKKISEELKA GYQSLDYIFV SRMPKRSITG AAHKQTIMRK GGIDKKGKTI  1080
IIERLHLKDI KFDENGDFKM VGKEQDMATY EAIKQRYLEH GKNSKKAFET PLYKPSKKGT  1140
GNLIKRVKVE GQAKSFVREV NGGVAQNGDL VRVDLFEKDD KYYMVPIYVP DTVCSELPKK  1200
VVASSKGYEQ WLTLDNSFTF KFSLYPYDLV RLVKGDEDRF LYFGTLDIDS DRLNFKDVNK  1260
PSKKNEYRYS LKTIEDLEKY EVGVLGDLRL VRKETRRNFH SGGSKRPAAT KKAGQAKKKK  1320
```

| | | |
|---|---|---|
| SEQ ID NO: 506 | moltype = AA  length = 1322 | |
| FEATURE | Location/Qualifiers | |
| REGION | 1..1322 | |
| | note = source = /note="Description of Artificial Sequence: Syntheticpolypeptide" | |
| REGION | 1..1322 | |
| | note = source = /note="LPG50158-nAPG07433.1protein sequence" | |
| source | 1..1322 | |
| | mol_type = protein | |
| | organism = synthetic construct | |
| SEQUENCE: 506 | | |

```
MAPKKKRKVD YKDHDGDYKD HDIDYKDDDD KMSNPEHNHE YWMRHALTLA QRARDEGEVP    60
VGAVLVYNNQ VIGEGWNRAI GLHDPTAHAE IMALRQGGLV LQNYRLLDTT LYVTFEPCVM   120
```

```
CSGAMVHSRI GTLVFGVRNE KRGAAGSLMN VLGYPGMNHQ VQTIGGVLAP ECSGLLCDFY 180
RMPRQQKNQQ KAELNQPGDS GGSSGGSSGS ETPGTSESAT PESSGGSSGG SMRELDYRIG 240
LAIGTNSIGW GVIELSWNKD RERYEKVRIV DQGVRMFDRA EMPKTGASLA EPRRIARSSR 300
RRLNRKSQRK KNIRNLLVQH GVITQEELDS LYPLSKKSMD IWGIRLDGLD RLLNHFEWAR 360
LLIHLAQRRG FKSNRKSELK DTETGKVLSS IQLNEKRLSL YRTVGEMWMK DPDFSKYDRK 420
RNSPNEYVFS VSRAELEKEI VTLFAAQRRF QSPYASKDLQ ETYLQIWTHQ LPFASGNAIL 480
NKVGYCSLLK GKERRIPKAT YTFQYFSALD QVNRTRLGPD FQPFTKEQRE IILNNMFQRT 540
DYYKKKTIPE VTYYDIRKWL ELDETIQFKG LNYDPNEELK KIEKKPFINL KAFYEINKVV 600
ANYSERTNET FSTLDYDGIG YALTVYKTDK DIRSYLKSSH NLPKRCYDDQ LIEELLSLSY 660
TKFGHLSLKA INHVLSIMQK GNTYKEAVDQ LGYDTSGLKK EKRSKFLPPI SDEITNPIVK 720
RALTQARKVV NAIIRRHGSP HSVHIELARE LSKNHDERTK IVSAQDENYK KNKGAISILS 780
EHGILNPTGY DIVRYKLWKE QGERCAYSLK EIPADTFFNE LKKERNGAPI LEVDHILPYS 840
QSFIDSYHNK VLVYSDENRK KGNRIPYTYF LETNKDWEAF ERYVRSNKFF SKKKREYLLK 900
RAYLPRESEL IKERHLNDTR YASTFLKNFI EQNLQFKEAE DNPRKRRVQT VNGVITAHFR 960
KRWGLEKDRQ ETYLHHAMDA IIVACTDHHM VTRVTEYYQI KESNKSVKKP YFPMPWEGFR 1020
DELLSHLASQ PIAKKISEEL KAGYQSLDYI FVSRMPKRSI TGAAHKQTIM RKGGIDKKGK 1080
TIIIERLHLK DIKFDENGDF KMVGKEQDMA TYEAIKQRYL EHGKNSKKAF ETPLYKPSKK 1140
GTGNLIKRVK VEGQAKSFVR EVNGGVAQNG DLVRVDLFEK DDKYYMVPIY VPDTVCSELP 1200
KKVVASSKGY EQWLTDNSF TFKFSLYPYD LVRLVKGDED RFLYFGTLDI DSDRLNFKDV 1260
NKPSKKNEYR YSLKTIEDLE KYEVGVLGDL RLVRKETRRN FHSGGSKRPA ATKKAGQAKK 1320
KK                                                                  1322

SEQ ID NO: 507          moltype = AA  length = 1322
FEATURE                 Location/Qualifiers
REGION                  1..1322
                        note = source = /note="Description of Artificial Sequence:
                         Syntheticpolypeptide"
REGION                  1..1322
                        note = source = /note="LPG50159-nAPG07433.1protein sequence"
source                  1..1322
                        mol_type = protein
                        organism = synthetic construct
SEQUENCE: 507
MAPKKKRKVD YKDHDGDYKD HDIDYKDDDD KMSDLELNHE YWMRHALSLA KRARDEGEVP 60
VGAVLVLNNQ VIGEGWNRAI GLHDPTAHAE IMALRQGGLV LQNYRLLDTT LYVTFEPCVM 120
CSGAMVHSRI GTLVYGVRNE KRGAAGSLMN VLGYPGMNHQ VQIIGGVLAP DCSGLLCDFY 180
RMPRQQKNQQ KAELKSSGDS GGSSGGSSGS ETPGTSESAT PESSGGSSGG SMRELDYRIG 240
LAIGTNSIGW GVIELSWNKD RERYEKVRIV DQGVRMFDRA EMPKTGASLA EPRRIARSSR 300
RRLNRKSQRK KNIRNLLVQH GVITQEELDS LYPLSKKSMD IWGIRLDGLD RLLNHFEWAR 360
LLIHLAQRRG FKSNRKSELK DTETGKVLSS IQLNEKRLSL YRTVGEMWMK DPDFSKYDRK 420
RNSPNEYVFS VSRAELEKEI VTLFAAQRRF QSPYASKDLQ ETYLQIWTHQ LPFASGNAIL 480
NKVGYCSLLK GKERRIPKAT YTFQYFSALD QVNRTRLGPD FQPFTKEQRE IILNNMFQRT 540
DYYKKKTIPE VTYYDIRKWL ELDETIQFKG LNYDPNEELK KIEKKPFINL KAFYEINKVV 600
ANYSERTNET FSTLDYDGIG YALTVYKTDK DIRSYLKSSH NLPKRCYDDQ LIEELLSLSY 660
TKFGHLSLKA INHVLSIMQK GNTYKEAVDQ LGYDTSGLKK EKRSKFLPPI SDEITNPIVK 720
RALTQARKVV NAIIRRHGSP HSVHIELARE LSKNHDERTK IVSAQDENYK KNKGAISILS 780
EHGILNPTGY DIVRYKLWKE QGERCAYSLK EIPADTFFNE LKKERNGAPI LEVDHILPYS 840
QSFIDSYHNK VLVYSDENRK KGNRIPYTYF LETNKDWEAF ERYVRSNKFF SKKKREYLLK 900
RAYLPRESEL IKERHLNDTR YASTFLKNFI EQNLQFKEAE DNPRKRRVQT VNGVITAHFR 960
KRWGLEKDRQ ETYLHHAMDA IIVACTDHHM VTRVTEYYQI KESNKSVKKP YFPMPWEGFR 1020
DELLSHLASQ PIAKKISEEL KAGYQSLDYI FVSRMPKRSI TGAAHKQTIM RKGGIDKKGK 1080
TIIIERLHLK DIKFDENGDF KMVGKEQDMA TYEAIKQRYL EHGKNSKKAF ETPLYKPSKK 1140
GTGNLIKRVK VEGQAKSFVR EVNGGVAQNG DLVRVDLFEK DDKYYMVPIY VPDTVCSELP 1200
KKVVASSKGY EQWLTDNSF TFKFSLYPYD LVRLVKGDED RFLYFGTLDI DSDRLNFKDV 1260
NKPSKKNEYR YSLKTIEDLE KYEVGVLGDL RLVRKETRRN FHSGGSKRPA ATKKAGQAKK 1320
KK                                                                  1322

SEQ ID NO: 508          moltype = AA  length = 1320
FEATURE                 Location/Qualifiers
REGION                  1..1320
                        note = source = /note="Description of Artificial Sequence:
                         Syntheticpolypeptide"
REGION                  1..1320
                        note = source = /note="LPG50160-nAPG07433.1protein sequence"
source                  1..1320
                        mol_type = protein
                        organism = synthetic construct
SEQUENCE: 508
MAPKKKRKVD YKDHDGDYKD HDIDYKDDDD KMSDHEFNDE YWMRHALTLA KRAREEGEVP 60
VGAVLVLNNQ VIGEGWNRAI GLHDPTAHAE IMALRQGGLV LQNYRLIDAT LYVTFEPCVM 120
CAGAMVHSRI SRLVFGVRNS KRGAAGSLIN VLNYPGMNHR VEITEGILAE SCSAMLCDFY 180
RWPREVKNAL KKARQEESGG SSGGSSGSET PGTSESATPE SSGGSSGGSM RELDYRIGLA 240
IGTNSIGWGV IELSWNKDRE RYEKVRIVDQ GVRMFDRAEM PKTGASLAEP RRIARSSRRR 300
LNRKSQRKKN IRNLLVQHGV ITQEELDSLY PLSKKSMDIW GIRLDGLDRL LNHFEWARLL 360
IHLAQRRGFK SNRKSELKDT ETGKVLSSIQ LNEKRLSLYR TVGEMWMKDP DFSKYDRKRN 420
SPNEYVFSVS RAELEKEIVT LFAAQRRFQS PYASKDLQET YLQIWTHQLP FASGNAILNK 480
VGYCSLLKGK ERRIPKATYT FQYFSALDQV NRTRLGPDFQ PFTKEQREII LNNMFQRTDY 540
YKKKTIPEVT YYDIRKWLEL DETIQFKGLN YDPNEELKKI EKKPFINLKA FYEINKVVAN 600
YSERTNETFS TLDYDGIGYA LTVYKTDKDI RSYLKSSHNL PKRCYDDQLI EELLSLSYTK 660
```

```
FGHLSLKAIN HVLSIMQKGN TYKEAVDQLG YDTSGLKKEK RSKFLPPISD EITNPIVKRA    720
LTQARKVVNA IIRRHGSPHS VHIELARELS KNHDERTKIV SAQDENYKKN KGAISILSEH    780
GILNPTGYDI VRYKLWKEQG ERCAYSLKEI PADTFFNELK KERNGAPILE VDHILPYSQS    840
FIDSYHNKVL VYSDENRKKG NRIPYTYFLE TNKDWEAFER YVRSNKFFSK KKREYLLKRA    900
YLPRESELIK ERHLNDTRYA STFLKNFIEQ NLQFKEAEDN PRKRRVQTVN GVITAHFRKR    960
WGLEKDRQET YLHHAMDAII VACTDHHMVT RVTEYYQIKE SNKSVKKPYF PMPWEGFRDE   1020
LLSHLASQPI AKKISEELKA GYQSLDYIFV SRMPKRSITG AAHKQTIMRK GGIDKKGKTI   1080
IIERLHLKDI KFDENGDFKM VGKEQDMATY EAIKQRYLEH GKNSKAFET PLYKPSKKGT    1140
GNLIKRVKVE GQAKSFVREV NGGVAQNGDL VRVDLFEKDD KYYMVPIYVP DTVCSELPKK   1200
VVASSKGYEQ WLTLDNSFTF KFSLYPYDLV RLVKGDEDRF LYFGTLDIDS DRLNFKDVNK   1260
PSKKNEYRYS LKTIEDLEKY EVGVLGDLRL VRKETRRNFH SGGSKRPAAT KKAGQAKKKK   1320

SEQ ID NO: 509          moltype = AA  length = 1320
FEATURE                 Location/Qualifiers
REGION                  1..1320
                        note = source = /note="Description of Artificial Sequence:
                         Syntheticpolypeptide"
REGION                  1..1320
                        note = source = /note="LPG50161-nAPG07433.1protein sequence"
source                  1..1320
                        mol_type = protein
                        organism = synthetic construct
SEQUENCE: 509
MAPKKKRKVD YKDHDGDYKD HDIDYKDDDD KMSQTELTHE YWMRHALTLA QRARDEGEVP     60
VGAVLVLNNQ VIGEGWNRAI GLHDPTAHAE IMALRQGGLV LQNYRLLDTT LYVTFEPCVM    120
CAGAMIHGRI GTLVFGVRNS KRGAVGSLMN ITGYPGMNHQ VQVIEGILAT ECSAMLCAFY    180
RQPRLVKNAL KEAAKTASGG SSGGSSGSET PGTSESATPE SSGGSSGGSM RELDYRIGLA    240
IGTNSIGWGV IELSWNKDRE RYEKVRIVDQ GVRMFDRAEM PKTGASLAEP RRIARSSRRR    300
LNRKSQRKKN IRNLLVQHGV ITQEELDSLY PLSKKSMDIW GIRLDGLDRL LNHFEWARLL    360
IHLAQRRGFK SNRKSELKDT ETGKVLSSIQ LNEKRLSLY TVGEMWMKDP DFSKYDRKRN    420
SPNEYVFSVS RAELEKEIVT LFAAQRRFQS PYASKDLQET YLQIWTHQLP FASGNAILNK    480
VGYCSLLKGK ERRIPKATYT FQYFSALDQV NRTRLGPDFQ PFTKEQREII LNNMFQRTDY    540
YKKKTIPEVT YYDIRKWLEL DETIQFKGLN YDPNEELKKI EKKPFINLKA FYEINKVVAN    600
YSERTNETFS TLDYDGIGYA LTVYKTDKDI RSYLKSSHNL PKRCYDDQLI EELLSLSYTK    660
FGHLSLKAIN HVLSIMQKGN TYKEAVDQLG YDTSGLKKEK RSKFLPPISD EITNPIVKRA    720
LTQARKVVNA IIRRHGSPHS VHIELARELS KNHDERTKIV SAQDENYKKN KGAISILSEH    780
GILNPTGYDI VRYKLWKEQG ERCAYSLKEI PADTFFNELK KERNGAPILE VDHILPYSQS    840
FIDSYHNKVL VYSDENRKKG NRIPYTYFLE TNKDWEAFER YVRSNKFFSK KKREYLLKRA    900
YLPRESELIK ERHLNDTRYA STFLKNFIEQ NLQFKEAEDN PRKRRVQTVN GVITAHFRKR    960
WGLEKDRQET YLHHAMDAII VACTDHHMVT RVTEYYQIKE SNKSVKKPYF PMPWEGFRDE   1020
LLSHLASQPI AKKISEELKA GYQSLDYIFV SRMPKRSITG AAHKQTIMRK GGIDKKGKTI   1080
IIERLHLKDI KFDENGDFKM VGKEQDMATY EAIKQRYLEH GKNSKAFET PLYKPSKKGT    1140
GNLIKRVKVE GQAKSFVREV NGGVAQNGDL VRVDLFEKDD KYYMVPIYVP DTVCSELPKK   1200
VVASSKGYEQ WLTLDNSFTF KFSLYPYDLV RLVKGDEDRF LYFGTLDIDS DRLNFKDVNK   1260
PSKKNEYRYS LKTIEDLEKY EVGVLGDLRL VRKETRRNFH SGGSKRPAAT KKAGQAKKKK   1320

SEQ ID NO: 510          moltype = AA  length = 1321
FEATURE                 Location/Qualifiers
REGION                  1..1321
                        note = source = /note="Description of Artificial Sequence:
                         Syntheticpolypeptide"
REGION                  1..1321
                        note = source = /note="LPG50162-nAPG07433.1protein sequence"
source                  1..1321
                        mol_type = protein
                        organism = synthetic construct
SEQUENCE: 510
MAPKKKRKVD YKDHDGDYKD HDIDYKDDDD KMSNPELNHD YWMRHALSLA KRAREEGEVP     60
VGAVLVRNNE VIGEGWNRAI GLHDPTAHAE IMALRQGGMV LQNYRLIDTT LYVTFEPCVM    120
CAGAMVHSRI GQLVFGVRNS KRGAAGSLMN VLNYPGMNHR VEIVEGVLRD ECAGMLCDFY    180
RQPRLVKNAQ KKGAEPLISG GSSGGSSGSE TPGTSESATP ESSGGSSGGS MRELDYRIGL    240
AIGTNSIGWG VIELSWNKDR ERYEKVRIVD QGVRMFDRAE MPKTGASLAE PRRIARSSRR    300
RLNRKSQRKK NIRNLLVQHG VITQEELDSL YPLSKKSMDI WGIRLDGLDR LLNHFEWARL    360
LIHLAQRRGF KSNRKSELKD TETGKVLSSI QLNEKRLSLY RTVGEMWMKD PDFSKYDRKR    420
NSPNEYVFSV SRAELEKEIV TLFAAQRRFQ SPYASKDLQE TYLQIWTHQL PFASGNAILN    480
KVGYCSLLKG KERRIPKATY TFQYFSALDQ VNRTRLGPDF QPPTKEQREI LNNMFQRTD    540
YYKKKTIPEV TYYDIRKWLE LDETIQFKGL NYDPNEELKK IEKKPFINLK AFYEINKVVA    600
NYSERTNETF STLDYDGIGY ALTVYKTDKD IRSYLKSSHN LPKRCYDDQL IEELLSLSYT    660
KFGHLSLKAI NHVLSIMQKG NTYKEAVDQL GYDTSGLKKE KRSKFLPPIS DEITNPIVKR    720
ALTQARKVVN AIIRRHGSPH SVHIELAREL SKNHDERTKI VSAQDENYKK NKGAISILSE    780
HGILNPTGYD IVRYKLWKEQ GERCAYSLKE IPADTFFNEL KKERNGAPIL EVDHILPYSQ    840
SFIDSYHNKV LVYSDENRKK GNRIPYTYFL ETNKDWEAFE RYVRSNKFFS KKKREYLLKR    900
AYLPRESELI KERHLNDTRY ASTFLKNFIE QNLQFKEAED NPRKRRVQTN NGVITAHFRK    960
RWGLEKDRQE TYLHHAMDAI IVACTDHHMV TRVTEYYQIK ESNKSVKKPY FPMPWEGFRD   1020
ELLSHLASQP IAKKISEELK AGYQSLDYIF VSRMPKRSIT GAAHKQTIMR KGGIDKKGKT   1080
IIIERLHLKD IKFDENGDFK MVGKEQDMAT YEAIKQRYLE HGKNSKAFE TPLYKPSKKG   1140
TGNLIKRVKV EGQAKSFVRE VNGGVAQNGD LVRVDLFEKD DKYYMVPIYV PDTVCSELPK   1200
```

```
KVVASSKGYE QWLTLDNSFT FKFSLYPYDL VRLVKGDEDR FLYFGTLDID SDRLNFKDVN   1260
KPSKKNEYRY SLKTIEDLEK YEVGVLGDLR LVRKETRRNF HSGGSKRPAA TKKAGQAKKK   1320
K                                                                  1321

SEQ ID NO: 511            moltype = AA  length = 1326
FEATURE                   Location/Qualifiers
REGION                    1..1326
                          note = source = /note="Description of Artificial Sequence:
                           Syntheticpolypeptide"
REGION                    1..1326
                          note = source = /note="LPG50163-nAPG07433.1protein sequence"
source                    1..1326
                          mol_type = protein
                          organism = synthetic construct
SEQUENCE: 511
MAPKKKRKVD YKDHDGDYKD HDIDYKDDDD KMSNPELNHE YWMRYALTLA KRARDEGEVP    60
VGAVLVYNDQ VIGEGWNRAI GLHDPTAHAE IMALRQGGLV LQNYRLIDTT LYVTFEPCVM   120
CAGAMVHSRI GRLVFGVRNS KRGAAGSLLN VLNYPGMNHH IEMEEGVLRD ECAAMLCDFY   180
RQPRMVKNAL KKSPPDSPNL QARSGGSSGG SSGSETPGTS ESATPESSGG SSGGSMRELD   240
YRIGLAIGTN SIGWGVIELS WNKDRERYEK VRIVDQGVRM FDRAEMPKTG ASLAEPRRIA   300
RSSRRRLNRK SQRKKNIRNL LVQHGVITQE ELDSLYPLSK KSMDIWGIRL DGLDRLLNHF   360
EWARLLIHLA QRRGFKSNRK SELKDTETGK VLSSIQLNEK KSLYRTVGE MWMKDPDFSK    420
YDRKRNSPNE YVFSVSRAEL EKEIVTLFAA QRRFQSPYAS KDLQETYLQI WTHQLPFASG   480
NAILNKVGYC SLLKGKERRI PKATYTFQYF SALDQVNRTR LGPDFQPFTK EQREIILNNM   540
FQRTDYYKKK TIPEVTYYDI RKWLELDETI QFKGLNYDPN EELKKIEKKP FINLKAFYEI   600
NKVVANYSER TNETFSTLDY DGIGYALTVY KTDKDIRSYL KSSHNLPKRC YDDQLIEELL   660
SLSYTKFGHL SLKAINHVLS IMQKGNTYKE AVDQLGYDTS GLKKEKRSKF LPPISDEITN   720
PIVKRALTQA RKVVNAIIRR HGSPHSVHIE LARELSKNHD ERTKIVSAQD ENYKKNKGAI   780
SILSEHGILN PTGYDIVRYK LWKEQGERCA YSLKEIPADT FFNELKKERN GAPILEVDHI   840
LPYSQSFIDS YHNKVLVYSD ENRKKGNRIP YTYFLETNKD WEAFERYVRS NKFFSKKKRE   900
YLLKRAYLPR ESELIKERHL NDTRYASTFL KNFIEQNLQF KEAEDNPRKR RVQTVNGVIT   960
AHFRKRWGLE KDRQETYLHH AMDAIIVACT DHHMVTRVTE YYQIKESNKS VKKPYFPMPW  1020
EGFRDELLSH LASQPIAKKI SEELKAGYQS LDYIFVSRMP KRSITGAAHK QTIMRKGGID  1080
KKGKTIIIER LHLKDIKFDE NGDFKMVGKE QDMATYEAIK QRYLEHGKNS KKAFETPLYK  1140
PSKKGTGNLI KRVKVEGQAK SFVREVNGGV AQNGDLVRVD LFEKDDKYYM VPIYVPDTVC  1200
SELPKKVVAS SKGYEQWLTL DNSFTFKFSL YPYDLVRLVK GDEDRFLYFG TLDIDSDRLN  1260
FKDVNKPSKK NEYRYSLKTI EDLEKYEVGV LGDLRLVRKE TRRNFHSGGS KRPAATKKAG  1320
QAKKKK                                                             1326

SEQ ID NO: 512            moltype = AA  length = 1322
FEATURE                   Location/Qualifiers
REGION                    1..1322
                          note = source = /note="Description of Artificial Sequence:
                           Syntheticpolypeptide"
REGION                    1..1322
                          note = source = /note="LPG50164-nAPG07433.1protein sequence"
source                    1..1322
                          mol_type = protein
                          organism = synthetic construct
SEQUENCE: 512
MAPKKKRKVD YKDHDGDYKD HDIDYKDDDD KMSNPEFTHE YWMRHALTLA RRARDEGEVP    60
VGAVLVLNNQ VIGEGWNRAI GLHDPTAHAE IMALRQGGLV LQNYRLLDTT LYVTFEPCVM   120
CSGAMVHSRI GTLVFGVRNE KRGAAGSLMN VLGYPGMNHQ VKTIGGVLAP ECSGLLCDFY   180
RMPRQQKNQQ KAELKSSGDS GGSSGGSSGS ETPGTSESAT PESSGGSSGG SMRELDYRIG   240
LAIGTNSIGW GVIELSWNKD RERYEKVRIV DQGVRMFDRA EMPKTGASLA EPRRIARSSR   300
RRLNRKSQRK KNIRNLLVQH GVITQEELDS LYPLSKKSMD IWGIRLDGLD RLLNHFEWAR   360
LLIHLAQRRG FKSNRKSELK DTETGKVLSS IQLNEKRLSL YRTVGEMWMK DPDFSKYDRK   420
RNSPNEYVFS VSRAELEKEI VTLFAAQRRF QSPYASKDLQ ETYLQIWTHQ LPFASGNAIL   480
NKVGYCSLLK GKERRIPKAT YTFQYFSALD QVNRTRLGPD FQPFTKEQRE IILNNMFQRT   540
DYYKKKTIPE VTYYDIRKWL ELDETIQFKG LNYDPNEELK KIEKKPFINL KAFYEINKVV   600
ANYSERTNET FSTLDYDGIG YALTVYKTDK DIRSYLKSSH NLPKRCYDDQ LIEELLSLSY   660
TKFGHLSLKA INHVLSIMQK GNTYKEAVDQ LGYDTSGLKK EKRSKFLPPI SDEITNPIVK   720
RALTQARKVV NAIIRRHGSP HSVHIELARE LSKNHDERTK IVSAQDENYK KNKGAISILS   780
EHGILNPTGY DIVRYKLWKE QGERCAYSLK EIPADTFFNE LKKERNGAPI LEVDHILPYS   840
QSFIDSYHNK VLVYSDENRK KGNRIPYTYF LETNKDWEAF ERYVRSNKFF SKKKREYLLK   900
RAYLPRESEL IKERHLNDTR YASTFLKNFI EQNLQFKEAE DNPRKRRVQT VNGVITAHFR   960
KRWGLEKDRQ ETYLHHAMDA IIVACTDHHM VTRVTEYYQI KESNKSVKKP YFPMPWEGFR  1020
DELLSHLASQ PIAKKISEEL KAGYQSLDYI FVSRMPKRSI TGAAHKQTIM RKGGIDKKGK  1080
TIIIERLHLK DIKFDENGDF KMVGKEQDMA TYEAIKQRYL EHGKNSKKAF ETPLYKPSKK  1140
GTGNLIKRVK VEGQAKSFVR EVNGGVAQNG DLVRVDLFEK DDKYYMVPIY VPDTVCSELP  1200
KKVVASSKGY EQWLTLDNSF TFKFSLYPYD LVRLVKGDED RFLYFGTLDI DSDRLNFKDV  1260
NKPSKKNEYR YSLKTIEDLE KYEVGVLGDL RLVRKETRRN FHSGGSKRPA ATKKAGQAKK  1320
KK                                                                 1322

SEQ ID NO: 513            moltype = AA  length = 1319
FEATURE                   Location/Qualifiers
REGION                    1..1319
                          note = source = /note="Description of Artificial Sequence:
                           Syntheticpolypeptide"
```

| | | |
|---|---|---|
| REGION | 1..1319 | |
| | note = source = /note="LPG50165-nAPG07433.1protein sequence" | |
| source | 1..1319 | |
| | mol_type = protein | |
| | organism = synthetic construct | |

SEQUENCE: 513

```
MAPKKKRKVD YKDHDGDYKD HDIDYKDDDD KMSDNEFNHE YWMRHALTLA QRARDEGEVP    60
VGAVLVLDNQ VIGEGWNRAI GLHDPTAHAE IMALRQGGMV LQNYRLINAT LYVTFEPCVM   120
CAGAMVHSRI GHVVFGVRNS KRGAAGSLMN VLNYPGMNHR VEVTEGVLRE QCAGMLCDFY   180
REPREQFNAL RKAQKASGGS SGGSSGSETP GTSESATPES SGGSSGGSMR ELDYRIGLAI   240
GTNSIGWGVI ELSWNKDRER YEKVRIVDQG VRMFDRAEMP KTGASLAEPR RIARSSRRRL   300
NRKSQRKKNI RNLLVQHGVI TQEELDSLYP LSKKSMDIWG IRLDGLDRLL NHFEWARLLI   360
HLAQRRGFKS NRKSELKDTE TGKVLSSIQL NEKRLSLYRT VGEMWMKDPD FSKYDRKRNS   420
PNEYVFSVSR AELEKEIVTL FAAQRRFQSP YASKDLQETY LQIWTHQLPF ASGNAILNKV   480
GYCSLLKGKE RRIPKATYTF QYFSALDQVN RTRLGPDFQP FTKEQREIIL NNMFQRTDYY   540
KKKTIPEVTY YDIRKWLELD ETIQFKGLNY DPNEELKKIE KKPFINLKAF YEINKVVANY   600
SERTNETFST LDYDGIGYAL TVYKTDKDIR SYLKSSHNLP KRCYDDQLIE ELLSLSYTKF   660
GHLSLKAINH VLSIMQKGNT YKEAVDQLGY DTSGLKKEKR SKFLPPISDE ITNPIVKRAL   720
TQARKVVNAI IRRHGSPHSV HIELARELSK NHDERTKIVS AQDENYKKNK GAISILSEHG   780
ILNPTGYDIV RYKLWKEQGE RCAYSLKEIP ADTFFNELKK ERNGAPILEV DHILPYSQSF   840
IDSYHNKVLV YSDENRKKGN RIPYTYFLET NKDWEAFERY VRSNKFFSKK KREYLLKRAY   900
LPRESELIKE RHLNDTRYAS TFLKNFIEQN LQFKEAEDNP RKRRVQTVNG VITAHFRKRW   960
GLEKDRQETY LHHAMDAIIV ACTDHHMVTR VTEYYQIKES NKSVKKPYFP MPWEGFRDEL  1020
LSHLASQPIA KKISEELKAG YQSLDYIFVS RMPKRSITGA AHKQTIMRKG GIDKKGKTII  1080
IERLHLKDIK FDENGDFKMV GKEQDMATYE AIKQRYLEHG KNSKKAFETP LYKPSKKGTG  1140
NLIKRVKVEG QAKSFVREVN GGVAQNGDLV RVDLFEKDDK YYMVPIYVPD TVCSELPKKV  1200
VASSKGYEQW LTLDNSFTFK FSLYPYDLVR LVKGDEDRFL YFGTLDIDSD RLNFKDVNKP  1260
SKKNEYRYSL KTIEDLEKYE VGVLGDLRLV RKETRRNFHS GGSKRPAATK KAGQAKKKK   1319
```

| | | |
|---|---|---|
| SEQ ID NO: 514 | moltype = AA length = 1324 | |
| FEATURE | Location/Qualifiers | |
| REGION | 1..1324 | |
| | note = source = /note="Description of Artificial Sequence: Syntheticpolypeptide" | |
| REGION | 1..1324 | |
| | note = source = /note="LPG50166-nAPG07433.1protein sequence" | |
| source | 1..1324 | |
| | mol_type = protein | |
| | organism = synthetic construct | |

SEQUENCE: 514

```
MAPKKKRKVD YKDHDGDYKD HDIDYKDDDD KMSDNELNHE YWMRHALTLA QRARDEGEVP    60
VGAVLVLNNQ VIGEGWNRAI GLHDPTAHAE IMALRQGGMV LQNYRLIDAT LYVTFEPCIM   120
CAGAMVHSRI GQVVFGVRNS KRGAAGSLIN ILNYPGMNHR VDVTEGVLSE RCANMLCDFY   180
REPRLQFNAQ RKAEKAGNAA ASGGSSGGSS GSETPGTSES ATPESSGGSS GGSMRELDYR   240
IGLAIGTNSI GWGVIELSWN KDRERYEKVR IVDQGVRMFD RAEMPKTGAS LAEPRRIARS   300
SRRRLNRKSQ RKKNIRNLLV QHGVITQEEL DSLYPLSKKS MDIWGIRLDG LDRLLNHFEW   360
ARLLIHLAQR RGFKSNRKSE LKDTETGKVL SSIQLNEKRL SLYRTVGEMW MKDPDFSKYD   420
RKRNSPNEYV FSVSRAELEK EIVTLFAAQR RFQSPYASKD LQETYLQIWT HQLPFASGNA   480
ILNKVGYCSL LKGKERRIPK ATYTFQYFSA LDQVNRTRLG PDFQPFTKEQ REIILNNMFQ   540
RTDYYKKKTI PEVTYYDIRK WLELDETIQF KGLNYDPNEE LKKIEKKPFI NLKAFYEINK   600
VVANYSERTN ETFSTLDYDG IGYALTVYKT DKDIRSYLKS SHNLPKRCYD DQLIEELLSL   660
SYTKFGHLSL KAINHVLSIM QKGNTYKEAV DQLGYDTSGL KKEKRSKFLP PISDEITNPI   720
VKRALTQARK VVNAIIRRHG SPHSVHIELA RELSKNHDER TKIVSAQDEN YKKNKGAISI   780
LSEHGILNPT GYDIVRYKLW KEQGERCAYS LKEIPADTFF NELKKERNGA PILEVDHILP   840
YSQSFIDSYH NKVLVYSDEN RKKGNRIPYT YFLETNKDWE AFERYVRSNK FFSKKKREYL   900
LKRAYLPRES ELIKERHLND TRYASTFLKN FIEQNLQFKE AEDNPRKRRV QTVNGVITAH   960
FRKRWGLEKD RQETYLHHAM DAIIVACTDH HMVTRVTEYY QIKESNKSVK KPYFPMPWEG  1020
FRDELLSHLA SQPIAKKISE ELKAGYQSLD YIFVSRMPKR SITGAAHKQT IMRKGGIDKK  1080
GKTIIIERLH LKDIKFDENG DFKMVGKEQD MATYEAIKQR YLEHGKNSKK AFETPLYKPS  1140
KKGTGNLIKR VKVEGQAKSF VREVNGGVAQ NGDLVRVDLF EKDDKYYMVP IYVPDTVCSE  1200
LPKKVVASSK GYEQWLTLDN SFTFKFSLYP YDLVRLVKGD EDRFLYFGTL DIDSDRLNFK  1260
DVNKPSKKNE YRYSLKTIED LEKYEVGVLG DLRLVRKETR RNFHSGGSKR PAATKKAGQA  1320
KKKK                                                              1324
```

| | | |
|---|---|---|
| SEQ ID NO: 515 | moltype = AA length = 1323 | |
| FEATURE | Location/Qualifiers | |
| REGION | 1..1323 | |
| | note = source = /note="Description of Artificial Sequence: Syntheticpolypeptide" | |
| REGION | 1..1323 | |
| | note = source = /note="LPG50167-nAPG07433.1protein sequence" | |
| source | 1..1323 | |
| | mol_type = protein | |
| | organism = synthetic construct | |

SEQUENCE: 515

```
MAPKKKRKVD YKDHDGDYKD HDIDYKDDDD KMSNPELTHD HWMRHALTLA QRARNEGEVP    60
VGAVLVLNGQ VIGEGWNRAI GLHDPTAHAE IMALRQGGLV LQNYRLIDTV LYVTFEPCVM   120
CAGAMVHSRI GQLVFGVRNS KRGAAGSLIN VLNYPGMNHR VEIIEGVLRD ECAAMLCDFY   180
RHPRLVKNAL KKNAGTSPTQ SGGSSGGSSG SETPGTSESA TPESSGGSSG GSMRELDYRI   240
```

```
                                              -continued
GLAIGTNSIG WGVIELSWNK DRERYEKVRI VDQGVRMFDR AEMPKTGASL AEPRRIARSS  300
RRRLNRKSQR KKNIRNLLVQ HGVITQEELD SLYPLSKKSM DIWGIRLDGL DRLLNHFEWA  360
RLLIHLAQRR GFKSNRKSEL KDTETGKVLS SIQLNEKRLS LYRTVGEMWM KDPDFSKYDR  420
KRNSPNEYVF SVSRAELEKE IVTLFAAQRR FQSPYASKDL QETYLQIWTH QLPFASGNAI  480
LNKVGYCSLL KGKERRIPKA TYTFQYFSAL DQVNRTRLGP DFQPFTKEQR EIILNNMFQR  540
TDYYKKKTIP EVTYYDIRKW LELDETIQFK GLNYDPNEEL KKIEKKPFIN LKAFYEINKV  600
VANYSERTNE TFSTLDYDGI GYALTVYKTD KDIRSYLKSS HNLPKRCYDD QLIEELLSLS  660
YTKFGHLSLK AINHVLSIMQ KGNTYKEAVD QLGYDTSGLK KEKRSKFLPP ISDEITNPIV  720
KRALTQARKV VNAIIRRHGS PHSVHIELAR ELSKNHDERT KIVSAQDENY KKNKGAISIL  780
SEHGILNPTG YDIVRYKLWK EQGERCAYSL KEIPADTFFN ELKKERNGAP ILEVDHILPY  840
SQSFIDSYHN KVLVYSDENR KKGNRIPYTY FLETNKDWEA FERYVRSNKF FSKKKREYLL  900
KRAYLPRESE LIKERHLNDT RYASTFLKNF IEQNLQFKEA EDNPRKRRVQ TVNGVITAHF  960
RKRWGLEKDR QETYLHHAMD AIIVACTDHH MVTRVTEYYQ IKESNKSVKK PYFPMPWEGF 1020
RDELLSHLAS QPIAKKISEE LKAGYQSLDY IFVSRMPKRS ITGAAHKQTI MRKGGIDKKG 1080
KTIIIERLHL KDIKFDENGD FKMVGKEQDM ATYEAIKQRY LEHGKNSKKA FETPLYKPSK 1140
KGTGNLIKRV KVEGQAKSFV REVNGGVAQN GDLVRVDLFE KDDKYYMVPI YVPDTVCSEL 1200
PKKVVASSKG YEQWLTLDNS FTFKFSLYPY DLVRLVKGDE DRFLYFGTLD IDSDRLNFKD 1260
VNKPSKKNEY RYSLKTIEDL EKYEVGVLGD LRLVRKETRR NFHSGGSKRP AATKKAGQAK 1320
KKK                                                              1323

SEQ ID NO: 516         moltype = AA  length = 1320
FEATURE                Location/Qualifiers
REGION                 1..1320
                       note = source = /note="Description of Artificial Sequence:
                       Syntheticpolypeptide"
REGION                 1..1320
                       note = source = /note="LPG50168-nAPG07433.1protein sequence"
source                 1..1320
                       mol_type = protein
                       organism = synthetic construct
SEQUENCE: 516
MAPKKKRKVD YKDHDGDYKD HDIDYKDDDD KMSDTELNHE YWMRHALMLA KRARDEGEVP   60
VGAVLVLKNQ VIGEGWNRAI GLHDPTAHAE IMALRQGGLV LQNYRLIDTT LYVTFEPCVM  120
CAGAMVHSRI GNLVFGVRNS KRGAAGSLIN VLNYPGMNHV VEIAEGVLAD ECSAMLCDFY  180
RHPRQQQNAL KQAAKHDSGG SSGGSSGGSE T PGTSESATPE SSGGSSGGSM RELDYRIGLA  240
IGTNSIGWGV IELSWNKDRE RYEKVRIVDQ GVRMFDRAEM PKTGASLAEP RRIARSSRRR  300
LNRKSQRKKN IRNLLVQHGV ITQEELDSLY PLSKKSMDIW GIRLDGLDRL LNHFEWARLL  360
IHLAQRRGFK SNRKSELKDT ETGKVLSSIQ LNEKRLSLYR TVGEMWMKDP DFSKYDRKRN  420
SPNEYVFSVS RAELEKEIVT LFAAQRRFQS PYASKDLQET YLQIWTHQLP FASGNAILNK  480
VGYCSLLKGK ERRIPKATYT FQYFSALDQV NRTRLGPDFQ PFTKEQREII LNNMFQRTDY  540
YKKKTIPEVT YYDIRKWLEL DETIQFKGLN YDPNEELKKI EKKPFINLKA FYEINKVVAN  600
YSERTNETFS TLDYDGIGYA LTVYKTDKDI RSYLKSSHNL PKRCYDDQLI EELLSLSYTK  660
FGHLSLKAIN HVLSIMQKGN TYKEAVDQLG YDTSGLKKEK RSKFLPPISD EITNPIVKRA  720
LTQARKVVNA IIRRHGSPHS VHIELARELS KNHDERTKIV SAQDENYKKN KGAISILSEH  780
GILNPTGYDI VRYKLWKEQG ERCAYSLKEI PADTFFNELK KERNGAPILE VDHILPYSQS  840
FIDSYHNKVL VYSDENRKKG NRIPYTYFLE TNKDWEAFER YVRSNKFFSK KKREYLLKRA  900
YLPRESELIK ERHLNDTRYA STFLKNFIEQ NLQFKEAEDN PRKRRVQTVN GVITAHFRKR  960
WGLEKDRQET YLHHAMDAII VACTDHHMVT RVTEYYQIKE SNKSVKKPYF PMPWEGFRDE 1020
LLSHLASQPI AKKISEELKA GYQSLDYIFV SRMPKRSITG AAHKQTIMRK GGIDKKGKTI 1080
IIERLHLKDI KFDENGDFKM VGKEQDMATY EAIKQRYLEH GKNSKKAFET PLYKPSKKGT 1140
GNLIKRVKVE GQAKSFVREV NGGVAQNGDL VRVDLFEKDD KYYMVPIYVP DTVCSELPKK 1200
VVASSKGYEQ WLTLDNSFTF KFSLYPYDLV RLVKGDEDRF LYFGTLDIDS DRLNFKDVNK 1260
PSKKNEYRYS LKTIEDLEKY EVGVLGDLRL VRKETRRNFH SGGSKRPAAT KKAGQAKKKK 1320

SEQ ID NO: 517         moltype = AA  length = 1325
FEATURE                Location/Qualifiers
REGION                 1..1325
                       note = source = /note="Description of Artificial Sequence:
                       Syntheticpolypeptide"
REGION                 1..1325
                       note = source = /note="LPG50169-nAPG07433.1protein sequence"
source                 1..1325
                       mol_type = protein
                       organism = synthetic construct
SEQUENCE: 517
MAPKKKRKVD YKDHDGDYKD HDIDYKDDDD KMSDIELNHE YWMRHALMLA KRAREEGEVP   60
VGAVLVLNNQ VIGEGWNRAI GLHDPTAHAE IMALRQGGLV LQNYRLIDTT LYVTFEPCVM  120
CAGAMVHSRI GHLVFGVRNS KRGAAGSLIN VLNYPGMNHV IEFTEGVLAD ECSGMLCDFY  180
RYPRQQQNTL KQAAKANPPA AQSGGSSGGS SGSETPGTSE SATPESSGGS SGGSMRELDY  240
RIGLAIGTNS IGWGVIELSW NKDRERYEKV RIVDQGVRMF DRAEMPKTGA SLAEPRRIAR  300
SSRRRLNRKS QRKKNIRNLL VQHGVITQEE LDSLYPLSKK SMDIWGIRLD GLDRLLNHFE  360
WARLLIHLAQ RRGFKSNRKS ELKDTETGKV LSSIQLNEKR LSLYRTVGEM WMKDPDFSKY  420
DRKRNSPNEY VFSVSRAELE KEIVTLFAAQ RRFQSPYASK DLQETYLQIW THQLPFASGN  480
AILNKVGYCS LLKGKERRIP KATYTFQYFS ALDQVNRTRL GPDFQPFTKE QREIILNNMF  540
QRTDYYKKKT IPEVTYYDIR KWLELDETIQ FKGLNYDPNE ELKKIEKKPF INLKAFYEIN  600
KVVANYSERT NETFSTLDYD GIGYALTVYK TDKDIRSYLK SSHNLPKRCY DDQLIEELLS  660
LSYTKFGHLS LKAINHVLSI MQKGNTYKEA VDQLGYDTSG LKKEKRSKFL PPISDEITNP  720
IVKRALTQAR KVVNAIIRRH GSPHSVHIEL ARELSKNHDE RTKIVSAQDE NYKKNKGAIS  780
ILSEHGILNP TGYDIVRYKL WKEQGERCAY SLKEIPADTF FNELKKERNG APILEVDHIL  840
```

```
PYSQSFIDSY HNKVLVYSDE NRKKGNRIPY TYFLETNKDW EAFERYVRSN KFFSKKKREY     900
LLKRAYLPRE SELIKERHLN DTRYASTFLK NFIEQNLQFK EAEDNPRKRR VQTVNGVITA     960
HFRKRWGLEK DRQETYLHHA MDAIIVACTD HHMVTRVTEY YQIKESNKSV KKPYFPMPWE    1020
GFRDELLSHL ASQPIAKKIS EELKAGYQSL DYIFVSRMPK RSITGAAHKQ TIMRKGGIDK    1080
KGKTIIIERL HLKDIKFDEN GDFKMVGKEQ DMATYEAIKQ RYLEHGKNSK KAFETPLYKP    1140
SKKGTGNLIK RVKVEGQAKS FVREVNGGVA QNGDLVRVDL FEKDDKYYMV PIYVPDTVCS    1200
ELPKKVVASS KGYEQWLTLD NSFTFKFSLY PYDLVRLVKG DEDRFLYFGT LDIDSDRLNF    1260
KDVNKPSKKN EYRYSLKTIE DLEKYEVGVL GDLRLVRKET RRNFHSGGSK RPAATKKAGQ    1320
AKKKK                                                                1325

SEQ ID NO: 518           moltype = AA  length = 1319
FEATURE                  Location/Qualifiers
REGION                   1..1319
                         note = source = /note="Description of Artificial Sequence:
                         Syntheticpolypeptide"
REGION                   1..1319
                         note = source = /note="LPG50170-nAPG07433.1protein sequence"
source                   1..1319
                         mol_type = protein
                         organism = synthetic construct
SEQUENCE: 518
MAPKKKRKVD YKDHDGDYKD HDIDYKDDDD KMSDNELNHE RWMRHALTLA QRARDEGEVP      60
VGAVLVYQNQ VIGEGWNRAI GLHDPTAHAE IMALRQGGLV LQNYRLIDTT LYVTFEPCVM     120
CAGAMVHSRI GQLVFGVRNS KRGAAGSLIN VLNYPGMNHR VAITEGVLAE SCSAMLCDFY     180
RHPREQKNAL RRAAQSSGGS SGGSSGSETP GTSESATPES SGGSSGGSMR ELDYRIGLAI     240
GTNSIGWGVI ELSWNKDRER YEKVRIVDQG VRMFDRAEMP KTGASLAEPR RIARSSRRRL     300
NRKSQRKKNI RNLLVQHGVI TQEELDSLYP LSKKSMDIWG IRLDGLDRLL NHFEWARLLI     360
HLAQRRGFKS NRKSELKDTE TGKVLSSIQL NEKRLSLYRT VGEMWMKPD PD FSKYDRKRNS    420
PNEYVFSVSR AELEKEIVTL FAAQRRFQSP YASKDLQETY LQIWTHQLPF ASGNAILNKV     480
GYCSLLKGKE RRIPKATYTF QYFSALDQVN RTRLGPDFQP FTKEQREIIL NNMFQRTDYY     540
KKKTIPEVTY YDIRKWLELD ETIQFKGLNY DPNEELKKIE KKPFINLKAF YEINKVVANY     600
SERTNETFST LDYDGIGYAL TVYKTDKDIR SYLKSSHNLP KRCYDDQLIE ELLSLSYTKF     660
GHLSLKAINH VLSIMQKGNT YKEAVDQLGY DTSGLKKEKR SKFLPPISDE ITNPIVKRAL     720
TQARKVVNAI IRRHGSPHSV HIELARELSK NHDERTKIVS AQDENYKKNK GAISILSEHQ     780
ILNPTGYDIV RYKLWKEQGE RCAYSLKEIP ADTFFNELKK ERNGAPILEV DHILPYSQSF     840
IDSYHNKVLV YSDENRKKGN RIPYTYFLET NKDWEAFERY VRSNKFFSKK KREYLLKRAY     900
LPRESELIKE RHLNDTRYAS TFLKNFIEQN LQFKEAEDNP RKRRVQTVNG VITAHFRKRW     960
GLEKDRQETY LHHAMDAIIV ACTDHHMVTR VTEYYQIKES NKSVKKPYFP MPWEGFRDEL    1020
LSHLASQPIA KKISEELKAG YQSLDYIFVS RMPKRSITGA AHKQTIMRKG GIDKKGKTII    1080
IERLHLKDIK FDENGDFKMV GKEQDMATYE AIKQRYLEHG KNSKKAFETP LYKPSKKGTG    1140
NLIKRVKVEG QAKSFVREVN GGVAQNGDLV RVDLFEKDDK YYMVPIYVPD TVCSELPKKV    1200
VASSKGYEQW LTLDNSFTFK FSLYPYDLVR LVKGDEDRFL YFGTLDIDSD RLNFKDVNKP    1260
SKKNEYRYSL KTIEDLEKYE VGVLGDLRLV RKETRRNFHS GGSKRPAATK KAGQAKKKK     1319

SEQ ID NO: 519           moltype = AA  length = 1320
FEATURE                  Location/Qualifiers
REGION                   1..1320
                         note = source = /note="Description of Artificial Sequence:
                         Syntheticpolypeptide"
REGION                   1..1320
                         note = source = /note="LPG50171-nAPG07433.1protein sequence"
source                   1..1320
                         mol_type = protein
                         organism = synthetic construct
SEQUENCE: 519
MAPKKKRKVD YKDHDGDYKD HDIDYKDDDD KMSDLELNDE YWMRHALTLA KRAREEGEVP      60
VGAVLVLNNQ VIGEGWNRAI GLHDPTAHAE IMALRQGGLV LQNYRLIDAT LYVTFEPCVM     120
CAGAMVHSRI ARLVFGVRNS KRGAAGSLMN VLNYPGMNHR VEISEGVLAE SCSAMLCDFY     180
RWPREVKNAL KKAREQNSGG SSGGSSGSET PGTSESATPE SSGGSSGGSM RELDYRIGLA     240
IGTNSIGWGV IELSWNKDRE RYEKVRIVDQ GVRMFDRAEM PKTGASLAEP RRIARSSRRR     300
LNRKSQRKKN IRNLLVQHGV ITQEELDSLY PLSKKSMDIW GIRLDGLDRL LNHFEWARLL     360
IHLAQRRGFK SNRKSELKDT ETGKVLSSIQ LNEKRLSLYR TVGEMWMKDP DFSKYDRKRN     420
SPNEYVFSVS RAELEKEIVT LFAAQRRFQS PYASKDLQET YLQIWTHQLP FASGNAILNK     480
VGYCSLLKGK ERRIPKATYT FQYFSALDQV NRTRLGPDFQ PFTKEQREII LNNMFQRTDY     540
YKKKTIPEVT YYDIRKWLEL DETIQFKGLN YDPNEELKKI EKKPFINLKA FYEINKVVAN     600
YSERTNETFS TLDYDGIGYA LTVYKTDKDI RSYLKSSHNL PKRCYDDQLI EELLSLSYTK     660
FGHLSLKAIN HVLSIMQKGN TYKEAVDQLG YDTSGLKKEK RSKFLPPISD EITNPIVKRA     720
LTQARKVVNA IIRRHGSPHS VHIELARELS KNHDERTKIV SAQDENYKKN KGAISILSEH     780
QILNPTGYDI VRYKLWKEQG ERCAYSLKEI PADTFFNELK KERNGAPILE VDHILPYSQS     840
FIDSYHNKVL VYSDENRKKG NRIPYTYFLE TNKDWEAFER YVRSNKFFSK KKREYLLKRA     900
YLPRESELIK ERHLNDTRYA STFLKNFIEQ NLQFKEAEDN PRKRRVQTVN GVITAHFRKR     960
WGLEKDRQET YLHHAMDAII VACTDHHMVT RVTEYYQIKE SNKSVKKPYF PMPWEGFRDE    1020
LLSHLASQPI AKKISEELKA GYQSLDYIFV SRMPKRSITG AAHKQTIMRK GGIDKKGKTI    1080
IIERLHLKDI KFDENGDFKM VGKEQDMATY EAIKQRYLEH GKNSKKAFET PLYKPSKKGT    1140
GNLIKRVKVE GQAKSFVREV NGGVAQNGDL VRVDLFEKDD KYYMVPIYVP DTVCSELPKK    1200
VVASSKGYEQ WLTLDNSFTF KFSLYPYDLV RLVKGDEDRF LYFGTLDIDS DRLNFKDVNK    1260
PSKKNEYRYS LKTIEDLEKY EVGVLGDLRL VRKETRRNFH SGGSKRPAAT KKAGQAKKKK    1320

SEQ ID NO: 520           moltype = AA  length = 1323
```

```
FEATURE                 Location/Qualifiers
REGION                  1..1323
                        note = source = /note="Description of Artificial Sequence:
                          Syntheticpolypeptide"
REGION                  1..1323
                        note = source = /note="LPG50172-nAPG07433.1protein sequence"
source                  1..1323
                        mol_type = protein
                        organism = synthetic construct
SEQUENCE: 520
MAPKKKRKVD YKDHDGDYKD HDIDYKDDDD KMSDLELDHE YWMRHALLLA KRARDEGEVP    60
VGAVLVLNNQ VIGEGWNRAI GLHDPTAHAE IMALRQGGLV LQNYRLLDTT LYVTFEPCVM   120
CSGAMVHSRI GTLVYGVRNE KRGAAGSLMN VLGYPGMNHQ VQVIDGVLAP ECSGLLCDFY   180
RMPRQQKNQQ KAESTSSRGD SGGSSGGSSG SETPGTSESA TPESSGGSSG GSMRELDYRI   240
GLAIGTNSIG WGVIELSWNK DRERYEKVRI VDQGVRMFDR AEMPKTGASL AEPRRIARSS   300
RRRLNRKSQR KKNIRNLLVQ HGVITQEELD SLYPLSKKSM DIWGIRLDGL DRLLNHFEWA   360
RLLIHLAQRR GFKSNRKSEL KDTETGKVLS SIQLNEKRLS LYRTVGEMWM KDPDFSKYDR   420
KRNSPNEYVF SVSRAELEKE IVTLFAAQRR FQSPYASKDL QETYLQIWTH QLPFASGNAI   480
LNKVGYCSLL KGKERRIPKA TYTFQYFSAL DQVNRTRLGP DFQPFTKEQR EIILNNMFQR   540
TDYYKKKTIP EVTYYDIRKW LELDETIQFK GLNYDPNEEL KKIEKKPFIN LKAFYEINKV   600
VANYSERTNE TFSTLDYDGI GYALTVYKTD KDIRSYLKSS HNLPKRCYDD QLIEELLSLS   660
YTKFGHLSLK AINHVLSIMQ KGNTYKEAVD QLGYDTSGLK KEKRSKFLPP ISDEITNPIV   720
KRALTQARKV VNAIIRRHGS PHSVHIELAR ELSKNHDERT KIVSAQDENY KKNKGAISIL   780
SEHGILNPTG YDIVRYKLWK EQGERCAYSL KEIPADTFFN ELKKERNGAP ILEVDHILPY   840
SQSFIDSYHN KVLVYSDENR KKGNRIPYTY FLETNKDWEA FERYVRSNKF FSKKKREYLL   900
KRAYLPRESE LIKERHLNDT RYASTFLKNF IEQNLQFKEA EDNPRKRRVQ TVNGVITAHF   960
RKRWGLEKDR QETYLHHAMD AIIVACTDHH MVTRVTEYYQ IKESNKSVKK PYFPMPWEGF  1020
RDELLSHLAS QPIAKKISEE LKAGYQSLDY IFVSRMPKRS ITGAAHKQTI MRKGGIDKKG  1080
KTIIIERLHL KDIKFDENGD FKMVGKEQDM ATYEAIKQRY LEHGKNSKKA FETPLYKPSK  1140
KGTGNLIKRV KVEGQAKSFV REVNGGVAQN GDLVRVDLFE KDDKYYMVPI YVPDTVCSEL  1200
PKKVVASSKG YEQWLTLDNS FTFKFSLYPY DLVRLVKGDE DRFLYFGTLD IDSDRLNFKD  1260
VNKPSKKNEY RYSLKTIEDL EKYEVGVLGD LRLVRKETRR NFHSGGSKRP AATKKAGQAK  1320
KKK                                                                1323

SEQ ID NO: 521          moltype = AA   length = 1316
FEATURE                 Location/Qualifiers
REGION                  1..1316
                        note = source = /note="Description of Artificial Sequence:
                          Syntheticpolypeptide"
REGION                  1..1316
                        note = source = /note="LPG50173-nAPG07433.1protein sequence"
source                  1..1316
                        mol_type = protein
                        organism = synthetic construct
SEQUENCE: 521
MAPKKKRKVD YKDHDGDYKD HDIDYKDDDD KMSDTELTHE YWMRHALMLA QRARDEGEVP    60
VGAVLVLNNR VIGEGWNRAI GLHDPTAHAE IMALRQGGLV LQNYRLLDTT LYVTFEPCVM   120
CAGAMVHGRI GTLVFGVRNL KRGAAGSLMN VLNYPGMNHR VEIVEGTLSD ECSGMLCEFY   180
RQPRLAFNAQ KQASGGSSGG SSGSETPGTS ESATPESSGG SSGGSMRELD YRIGLAIGTN   240
SIGWGVIELS WNKDRERYEK VRIVDQGVRM FDRAEMPKTG ASLAEPRRIA RSSRRRLNRK   300
SQRKKNIRNL LVQHGVITQE ELDSLYPLSK KSMDIWGIRL DGLDRLLNHF EWARLLIHLA   360
QRRGFKSNRK SELKDTETGK VLSSIQLNEK RLSLYRTVGE MWMKDPDFSK YDRKRNSPNE   420
YVFSVSRAEL EKEIVTLFAA QRRFQSPYAS KDLQETYLQI WTHQLPFASG NAILNKVGYC   480
SLLKGKERRI PKATYTFQYF SALDQVNRTR LGPDFQPFTK EQREIILNNM FQRTDYKKK   540
TIPEVTYYDI RKWLELDETI QFKGLNYDPN EELKKIEKKP FINLKAFYEI NKVVANYSER   600
TNETFSTLDY DGIGYALTVY KTDKDIRSYL KSSHNLPKRC YDDQLIEELL SLSYTKFGHL   660
SLKAINHVLS IMQKGNTYKE AVDQLGYDTS GLKKEKRSKF LPPISDEITN PIVKRALTQA   720
RKVVNAIIRR HGSPHSVHIE LARELSKNHD ERTKIVSAQD ENYKKNKGAI SILSEHGILN   780
PTGYDIVRYK LWKEQGERCA YSLKEIPADT FFNELKKERN GAPILEVDHI LPYSQSFIDS   840
YHNKVLVYSD ENRKKGNRIP YTYFLETNKD WEAFERYVRS NKFFSKKKRE YLLKRAYLPR   900
ESELIKERHL NDTRYASTFL KNFIEQNLQF KEAEDNPRKR RVQTVNGVIT AHFRKRWGLE   960
KDRQETYLHH AMDAIIVACT DHHMVTRVTE YYQIKESNKS VKKPYFPMPW EGFRDELLSH  1020
LASQPIAKKI SEELKAGYQS LDYIFVSRMP KRSITGAAHK QTIMRKGGID KKGKTIIIER  1080
LHLKDIKFDE NGDFKMVGKE QDMATYEAIK QRYLEHGKNS KKAFETPLYK PSKKGTGNLI  1140
KRVKVEGQAK SFVREVNGGV AQNGDLVRVD LFEKDDKYYM VPIYVPDTVC SELPKKVVAS  1200
SKGYEQWLTL DNSFTFKFSL YPYDLVRLVK GDEDRFLYFG TLDIDSDRLN FKDVNKPSKK  1260
NEYRYSLKTI EDLEKYEVGV LGDLRLVRKE TRRNFHSGGS KRPAATKKAG QAKKKK      1316

SEQ ID NO: 522          moltype = AA   length = 1327
FEATURE                 Location/Qualifiers
REGION                  1..1327
                        note = source = /note="Description of Artificial Sequence:
                          Syntheticpolypeptide"
REGION                  1..1327
                        note = source = /note="LPG50174-nAPG07433.1protein sequence"
source                  1..1327
                        mol_type = protein
                        organism = synthetic construct
```

```
SEQUENCE: 522
MAPKKKRKVD YKDHDGDYKD HDIDYKDDDD KMSIPELNHD VWMRHALTLA KRAREEGEVP    60
VGAVLVLNGQ VIGEGWNRAI GLHDPTAHAE IMALRQGGLV LQNYRLIDTT LYVTFEPCVM   120
CAGAMVHSRI GQLVFGVRNS KRGAAGSLMN VLNYPGMNHR VEITEGVLRD ECAAMLCDFY   180
RQPRLVKNAL KKPAGDPSAL QNNRSGGSSG GSSSGSETPGT SESATPESSG GSSGGSMREL  240
DYRIGLAIGT NSIGWGVIEL SWNKDRERYE KVRIVDQGVR MFDRAEMPKT GASLAEPRRI   300
ARSSRRRLNR KSQRKKNIRN LLVQHGVITQ EELDSLYPLS KKSMDIWGIR LDGLDRLLNH   360
FEWARLLIHL AQRRGFKSNR KSELKDTETG KVLSSIQLNE KRLSLYRTVG EMWMKDPDFS   420
KYDRKRNSPN EYVFSVSRAE LEKEIVTLFA AQRRFQSPYA SKDLQETYLQ IWTHQLPFAS   480
GNAILNKVGY CSLLKGKERR IPKATYTFQY FSALDQVNRT RLGPDFQPFT KEQREIILNN   540
MFQRTDYYKK KTIPEVTYYD IRKWLELDET IQFKGLNYDP NEELKKIEKK PFINLKAFYE   600
INKVVANYSE RTNETFSTLD YDGIGYALTV YKTDKDIRSY LKSSHNLPKR CYDDQLIEEL   660
LSLSYTKFGH LSLKAINHVL SIMQKGNTYK EAVDQLGYDT SGLKKEKRSK FLPPISDEIT   720
NPIVKRALTQ ARKVVNAIIR RHGSPHSVHI ELARELSKNH DERTKIVSAQ DENYKKNKGA   780
ISILSEHGIL NPTGYDIVRY KLWKEQGERC AYSLKEIPAD TFFNELKKER NGAPILEVDH   840
ILPYSQSFID SYHNKVLVYS DENRKKGNRI PYTYFLETNK DWEAFERYVR SNKFFSKKKR   900
EYLLKRAYLP RESELIKERH LNDTRYASTF LKNFIEQNLQ FKEAEDNPRK RRVQTVNGVI   960
TAHFRKRWGL EKDRQETYLH HAMDAIIVAC TDHHMVTRVT EYYQIKESNK SVKKPYFPMP  1020
WEGFRDELLS HLASQPIAKK ISEELKAGYQ SLDYIFVSRM PKRSITGAAH KQTIMRKGGI  1080
DKKGKTIIIE RLHLKDIKFD ENGDFKMVGK EQDMATYEAI KQRYLEHGKN SKKAFETPLY  1140
KPSKKGTGNL IKRVKVEGQA KSFVREVNGG VAQNGDLVRV DLFEKDDKYY MVPIYVPDTV  1200
CSELPKKVVA SSKGYEQWLT LDNSPTFKFS LYPYDLVRLV KGDEDRFLYF GTLDIDSDRL  1260
NFKDVNKPSK KNEYRYSLKT IEDLEKYEVG VLGDLRLVRK ETRRNFHSGG SKRPAATKKA  1320
GQAKKKK                                                            1327

SEQ ID NO: 523         moltype = AA  length = 1320
FEATURE                Location/Qualifiers
REGION                 1..1320
                       note = source = /note="Description of Artificial Sequence:
                        Syntheticpolypeptide"
REGION                 1..1320
                       note = source = /note="LPG50175-nAPG07433.1protein sequence"
source                 1..1320
                       mol_type = protein
                       organism = synthetic construct
SEQUENCE: 523
MAPKKKRKVD YKDHDGDYKD HDIDYKDDDD KMSDLELNDE YWMRHALTLA KRAREEGEVP    60
VGAVLVLNNQ VIGEGWNRAI GLHDPTAHAE IMALRQGGLV LQNYRLIDAT LYVTFEPCVM   120
CAGAMVHSRI ARLVFGVRNS KRGAAGSLMN VLNYPGMNHR VEISEGVLAG SCSAMLCDFY   180
RWPREVKNAL KKAREQNSGG SSGGSSGSET PGTSESATPE SSGGSSGGSM RELDYRIGLA   240
IGTNSIGWGV IELSWNKDRE RYEKVRIVDQ GVRMFDRAEM PKTGASLAEP RRIARSSRRR   300
LNRKSQRKKN IRNLLVQHGV ITQEELDSLY PLSKKSMDIW GIRLDGLDRL LNHFEWARLL   360
IHLAQRRGFK SNRKSELKDT ETGKVLSSIQ LNEKRLSLYR TVGEMWMKDP DFSKYDRKRN   420
SPNEYVFSVS RAELEKEIVT LFAAQRRFQS PYASKDLQET YLQIWTHQLP FASGNAILNK   480
VGYCSLLKGK ERRIPKATYT FQYFSALDQV NRTRLGPDFQ PFTKEQREII LNNMFQRTDY   540
YKKKTIPEVT YYDIRKWLEL DETIQFKGLN YDPNEELKKI EKKPFINLKA FYEINKVVAN   600
YSERTNETFS TLDYDGIGYA LTVYKTDKDI RSYLKSSHNL PKRCYDDQLI EELLSLSYTK   660
FGHLSLKAIN HVLSIMQKGN TYKEAVDQLG YDTSGLKKEK RSKFLPPISD EITNPIVKRA   720
LTQARKVVNA IIRRHGSPHS VHIELARELS KNHDERTKIV SAQDENYKKN KGAISILSEH   780
GILNPTGYDI VRYKLWKEQG ERCAYSLKEI PADTFFNELK KERNGAPILE VDHILPYSQS   840
FIDSYHNKVL VYSDENRKKG NRIPYTYFLE TNKDWEAFER YVRSNKFFSK KKREYLLKRA   900
YLPRESELIK ERHLNDTRYA STFLKNFIEQ NLQFKEAEDN PRKRRVQTVN GVITAHFRKR   960
WGLEKDRQET YLHHAMDAII VACTDHHMVT RVTEYYQIKE SNKSVKKPYF PMPWEGFRDE  1020
LLSHLASQPI AKKISEELKA GYQSLDYIFV SRMPKRSITG AAHKQTIMRK GGIDKKGKTI  1080
IIERLHLKDI KFDENGDFKM VGKEQDMATY EAIKQRYLEH GKNSKKAFET PLYKPSKKGT  1140
GNLIKRVKVE GQAKSFVREV NGGVAQNGDL VRVDLFEKDD KYYMVPIYVP DTVCSELPKK  1200
VVASSKGYEQ WLTLDNSFTF KFSLYPYDLV RLVKGDEDRF LYFGTLDIDS DRLNFKDVNK  1260
PSKKNEYRYS LKTIEDLEKY EVGVLGDLRL VRKETRRNFH SGGSKRPAAT KKAGQAKKKK  1320

SEQ ID NO: 524         moltype = AA  length = 1307
FEATURE                Location/Qualifiers
REGION                 1..1307
                       note = source = /note="Description of Artificial Sequence:
                        Syntheticpolypeptide"
REGION                 1..1307
                       note = source = /note="LPG50176-nAPG07433.1protein sequence"
source                 1..1307
                       mol_type = protein
                       organism = synthetic construct
SEQUENCE: 524
MAPKKKRKVD YKDHDGDYKD HDIDYKDDDD KMSDIEQNHE YWMRHALVLA KRAREEGEVP    60
VGAVLVLNNQ VIGEGWNRAI GLHDPTAHAE IMALRQGGLV LQNYRLIDTT LYVTFEPCVM   120
CAGAMVHGRI GSLVFGVRNS KRGAAGSLIN VLNYPGMNHR VEMTEGVLAD ECSAMLCDFY   180
RHPRSGGSSG GSSGSETPGT SESATPESSG GSSGGSMREL DYRIGLAIGT NSIGWGVIEL   240
SWNKDRERYE KVRIVDQGVR MFDRAEMPKT GASLAEPRRI ARSSRRRLNR KSQRKKNIRN   300
LLVQHGVITQ EELDSLYPLS KKSMDIWGIR LDGLDRLLNH FEWARLLIHL AQRRGFKSNR   360
KSELKDTETG KVLSSIQLNE KRLSLYRTVG EMWMKDPDFS KYDRKRNSPN EYVFSVSRAE   420
LEKEIVTLFA AQRRFQSPYA SKDLQETYLQ IWTHQLPFAS GNAILNKVGY CSLLKGKERR   480
IPKATYTFQY FSALDQVNRT RLGPDFQPFT KEQREIILNN MFQRTDYYKK KTIPEVTYYD   540
IRKWLELDET IQFKGLNYDP NEELKKIEKK PFINLKAFYE INKVVANYSE RTNETFSTLD   600
```

-continued

```
YDGIGYALTV YKTDKDIRSY LKSSHNLPKR CYDDQLIEEL LSLSYTKFGH LSLKAINHVL    660
SIMQKGNTYK EAVDQLGYDT SGLKKEKRSK FLPPISDEIT NPIVKRALTQ ARKVVNAIIR    720
RHGSPHSVHI ELARELSKNH DERTKIVSAQ DENYKKNKGA ISILSEHGIL NPTGYDIVRY    780
KLWKEQGERC AYSLKEIPAD TFFNELKKER NGAPILEVDH ILPYSQSFID SYHNKVLVYS    840
DENRKKGNRI PYTYFLETNK DWEAFERYVR SNKFFSKKKR EYLLKRAYLP RESELIKERH    900
LNDTRYASTF LKNFIEQNLQ FKEAEDNPRK RRVQTVNGVI TAHFRKRWGL EKDRQETYLH    960
HAMDAIIVAC TDHHMVTRVT EYYQIKESNK SVKKPYFPMP WEGFRDELLS HLASQPIAKK   1020
ISEELKAGYQ SLDYIFVSRM PKRSITGAAH KQTIMRKGGI DKKGKTIIIE RLHLKDIKFD   1080
ENGDFKMVGK EQDMATYEAI KQRYLEHGKN SKKAFETPLY KPSKKGTGNL IKRVKVEGQA   1140
KSFVREVNGG VAQNGDLVRV DLFEKDDKYY MVPIYVPDTV CSELPKKVVA SSKGYEQWLT   1200
LDNSFTKFFS LYPYDLVRLV KGDEDRFLYF GTLDIDSDRL NFKDVNKPSK KNEYRYSLKT   1260
IEDLEKEYEVG VLGDLRLVRK ETRRNFHSGG SKRPAATKKA GQAKKKK               1307

SEQ ID NO: 525          moltype = AA   length = 1322
FEATURE                 Location/Qualifiers
REGION                  1..1322
                        note = source = /note="Description of Artificial Sequence:
                        Syntheticpolypeptide"
REGION                  1..1322
                        note = source = /note="LPG50177-nAPG07433.1protein sequence"
source                  1..1322
                        mol_type = protein
                        organism = synthetic construct
SEQUENCE: 525
MAPKKKRKVD YKDHDGDYKD HDIDYKDDDD KMCNPERDHE YWMRHALTLA QRARDEGEVP     60
VGAVLVLNNQ VIGEGWNRAI GLHDPTAHAE IMALRQGGLV LQNYRLLDTT LYVTFEPCVM    120
CSGAMVHSRI GTLVFGVRNE KRGAAGSLLN VLGYPGMNHQ VKTIGGVLAP ACSALLCDFY    180
RMPRQQKNQQ KAELKLSNDS GGSSGGSSGS ETPGTSESAT PESSGGSSGG SMRELDYRIG    240
LAIGTNSIGW GVIELSWNKD RERYEKVRIV DQGVRMFDRA EMPKTGASLA EPRRIARSSR    300
RRLNRKSQRK KNIRNLLVQH GVITQEELDS LYPLSKKSMD IWGIRLDGLD RLLNHFEWAR    360
LLIHLAQRRG FKSNRKSELK DTETGKVLSS IQLNEKRLSL YRTVGEMWMK DPDFSKYDRK    420
RNSPNEYVFS VSRAELEKEI VTLFAAQRRF QSPYASKDLQ ETYLQIWTHQ LPFASGNAIL    480
NKVGYCSLLK GKERRIPKAT YTFQYFSALD QVNRTRLGPD FQPFTKEQRE IILNNMFQRT    540
DYYKKKTIPE VTYYDIRKWL ELDETIQFKG LNYDPNEELK KIEKKPFINL KAFYEINKVV    600
ANYSERTNET FSTLDYDGIG YALTVYKTDK DIRSYLKSSH NLPKRCYDDQ LIEELLSLSY    660
TKFGHLSLKA INHVLSIMQK GNTYKEAVDQ LGYDTSGLKK EKRSKFLPPI SDEITNPIVK    720
RALTQARKVV NAIIRRHGSP HSVHIELARE LSKNHDERTK IVSAQDENYK KNKGAISILS    780
EHGILNPTGY DIVRYKLWKE QGERCAYSLK EIPADTFFNE LKKERNGAPI LEVDHILPYS    840
QSFIDSYHNK VLVYSDENRK KGNRIPYTYF LETNKDWEAF ERYVRSNKFF SKKKREYLLK    900
RAYLPRESEL IKERHLNDTR YASTFLKNFI EQNLQFKEAE DNPRKRRVQT VNGVITAHFR    960
KRWGLEKDRQ ETYLHHAMDA IIVACTDHHM VTRVTEYYQI KESNKSVKKP YFPMPWEGFR   1020
DELLSHLASQ PIAKKISEEL KAGYQSLDYI FVSRMPKRSI TGAAHKQTIM RKGGIDKKGK   1080
TIIIERLHLK DIKFDENGDF KMVGKEQDMA TYEAIKQRYL EHGKNSKKAF ETPLYKPSKK   1140
GTGNLIKRVK VEGQAKSFVR EVNGGVAQNG DLVRVDLFEK DDKYYMVPIY VPDTVCSELP   1200
KKVVASSKGY EQWLTLDNSF TKFSLYPYD LVRLVKGDED RFLYFGTLDI DSDRLNFKDV   1260
NKPSKKNEYR YSLKTIEDLE KYEVGVLGDL RLVRKETRRN FHSGGSKRPA ATKKAGQAKK   1320
KK                                                                  1322

SEQ ID NO: 526          moltype = AA   length = 1316
FEATURE                 Location/Qualifiers
REGION                  1..1316
                        note = source = /note="Description of Artificial Sequence:
                        Syntheticpolypeptide"
REGION                  1..1316
                        note = source = /note="LPG50178-nAPG07433.1protein sequence"
source                  1..1316
                        mol_type = protein
                        organism = synthetic construct
SEQUENCE: 526
MAPKKKRKVD YKDHDGDYKD HDIDYKDDDD KMSAIELNHE YWMRHALGLA QRARDEGEVP     60
VGAVLVYQNQ VIGEGWNRAI GLHDPTAHAE IMALRQGGLV LQNYRLIDTT LYVTFEPCVM    120
CAGAMVHSRI GRVVFGVRNS KRGAAGSLMN VLNYPGMNHR VEVTEGVLAG ECSAMLCDFY    180
RAPRAQFNAQ KRPSGGSSGG SSGSETPGTS ESATPESSGG SSGSMRELD YRIGLAIGTN    240
SIGWGVIELS WNKDRERYEK VRIVDQGVRM FDRAEMPKTG ASLAEPRRIA RSSRRRLNRK    300
SQRKKNIRNL LVQHGVITQE ELDSLYPLSK KSMDIWGIRL DGLDRLLNHF EWARLLIHLA    360
QRRGFKSNRK SELKDTETGK VLSSIQLNEK RLSLYRTVGE MWMKDPDFSK YDRKRNSPNE    420
YVFSVSRAEL EKEIVTLFAA QRRFQSPYAS KDLQETYLQI WTHQLPFASG NAILNKVGYC    480
SLLKGKERRI PKATYTFQYF SALDQVNRTR LGPDFQPFTK EQREIILNNM FQRTDYYKKK    540
TIPEVTYYDI RKWLELDETI QFKGLNYDPN EELKKIEKKP FINLKAFYEI NKVVANYSER    600
TNETFSTLDY DGIGYALTVY KTDKDIRSYL KSSHNLPKRC YDDQLIEELL SLSYTKFGHL    660
SLKAINHVLS IMQKGNTYKE AVDQLGYDTS GLKKEKRSKF LPPISDEITN PIVKRALTQA    720
RKVVNAIIRR HGSPHSVHIE LARELSKNHD ERTKIVSAQD ENYKKNKGAI SILSEHGILN    780
PTGYDIVRYK LWKEQGERCA YSLKEIPADT FFNELKKERN GAPILEVDHI LPYSQSFIDS    840
YHNKVLVYSD ENRKKGNRIP YTYFLETNKD WEAFERYVRS NKFFSKKKRE YLLKRAYLPR    900
ESELIKERHL NDTRYASTFL KNFIEQNLQF KEAEDNPRKR RVQTVNGVIT AHFRKRWGLE    960
KDRQETYLHH AMDAIIVACT DHHMVTRVTE YYQIKESNKS VKKPYFPMPW EGFRDELLSH   1020
LASQPIAKKI SEELKAGYQS LDYIFVSRMP KRSITGAAHK QTIMRKGGID KKGKTIIIER   1080
LHLKDIKFDE NGDFKMVGKE QDMATYEAIK QRYLEHGKNS KKAFETPLYK PSKKGTGNLI   1140
KRVKVEGQAK SFVREVNGGV AQNGDLVRVD LFEKDDKYY VPIYVPDTVC SELPKKVVAS   1200
```

```
SKGYEQWLTL DNSFTFKFSL YPYDLVRLVK GDEDRFLYFG TLDIDSDRLN FKDVNKPSKK 1260
NEYRYSLKTI EDLEKYEVGV LGDLRLVRKE TRRNFHSGGS KRPAATKKAG QAKKKK     1316

SEQ ID NO: 527          moltype = AA  length = 1323
FEATURE                 Location/Qualifiers
REGION                  1..1323
                        note = source = /note="Description of Artificial Sequence:
                         Syntheticpolypeptide"
REGION                  1..1323
                        note = source = /note="LPG50179-nAPG07433.1protein sequence"
source                  1..1323
                        mol_type = protein
                        organism = synthetic construct
SEQUENCE: 527
MAPKKKRKVD YKDHDGDYKD HDIDYKDDDD KMSNPELNHE YWMRYALTLA KRAREEGEVP  60
VGAVLVLNER VIGEGWNRAI GLHDPTAHAE IMALRQGGMV LQNYRLIDTT LYVTFEPCVM 120
CAGAMVHSRI GHLVFGVRNS KRGAAGSLMN VLNYPGMNHR VAITEGVLRD ECAAMLCDFY 180
RQPRQVKNAL KKTLSDSQEQ SGGSSGGSSG SETPGTSESA TPESSGGSSG GSMRELDYRI 240
GLAIGTNSIG WGVIELSWNK DRERYEKVRI VDQGVRMFDR AEMPKTGASL AEPRRIARSS 300
RRRLNRKSQR KKNIRNLLVQ HGVITQEELD SLYPLSKKSM DIWGIRLDGL DRLLNHFEWA 360
RLLIHLAQRR GFKSNRKSEL KDTETGKVLS SIQLNEKRLS LYRTVGEMWM KDPDFSKYDR 420
KRNSPNEYVF SVSRAELEKE IVTLFAAQRR FQSPYASKDL QETYLQIWTH QLPFASGNAI 480
LNKVGYCSLL KGKERRIPKA TYTFQYFSAL DQVNRTRLGP DFQPFTKEQR EIILNNMFQR 540
TDYYKKKTIP EVTYYDIRKW LELDETIQFK GLNYDPNEEL KKIEKKPFIN LKAFYEINKV 600
VANYSERTNE TFSTLDYDGI GYALTVYKTD KDIRSYLKSS HNLPKRCYDD QLIEELLSLS 660
YTKFGHLSLK AINHVLSIMQ KGNTYKEAVD QLGYDTSGLK KEKRSKFLPP ISDEITNPIV 720
KRALTQARKV VNAIIRRHGS PHSVHIELAR ELSKNHDERT KIVSAQDENY KKNKGAISIL 780
SEHGILNPTG YDIVRYKLWK EQGERCAYSL KEIPADTFFN ELKKERNGAP ILEVDHILPY 840
SQSFIDSYHN KVLVYSDENR KKGNRIPYTY FLETNKDWEA FERYVRSNKF FSKKKREYLL 900
KRAYLPRESE LIKERHLNDT RYASTFLKNF IEQNLQFKEA EDNPRKRRVQ TVNGVITAHF 960
RKRWGLEKDR QETYLHHAMD AIIVACTDHH MVTRVTEYYQ IKESNKSVKK PYFPMPWEGF 1020
RDELLSHLAS QPIAKKISEE LKAGYQSLDY IFVSRMPKRS ITGAAHKQTI MRKGGIDKKG 1080
KTIIIERLHL KDIKFDENGD FKMVGKEQDM ATYEAIKQRY LEHGKNSKKA FETPLYKPSK 1140
KGTGNLIKRV KVEGQAKSFV REVNGGVAQN GDLVRVDLFE KDDKYYMVPI YVPDTVCSEL 1200
PKKVVASSKG YEQWLTLDNS FTFKFSLYPY DLVRLVKGDE DRFLYFGTLD IDSDRLNFKD 1260
VNKPSKKNEY RYSLKTIEDL EKYEVGVLGD LRLVRKETRR NFHSGGSKRP AATKKAGQAK 1320
KKK                                                              1323

SEQ ID NO: 528          moltype = AA  length = 1322
FEATURE                 Location/Qualifiers
REGION                  1..1322
                        note = source = /note="Description of Artificial Sequence:
                         Syntheticpolypeptide"
REGION                  1..1322
                        note = source = /note="LPG50180-nAPG07433.1protein sequence"
source                  1..1322
                        mol_type = protein
                        organism = synthetic construct
SEQUENCE: 528
MAPKKKRKVD YKDHDGDYKD HDIDYKDDDD KMSNPEHDHE YWMRHALNLA QRARDEGEVP  60
VGAVLVLNNQ VIGEGWNRAI GLHDPTAHAE IMALRQGGLV LQNYRLLDTT LYVTFEPCVM 120
CSGAMVHSRI GTLVYGVRNE KRGAAGSLMN VLGYPGMNHQ VNVIGGVLAQ DCSARLCDFY 180
RMPRQQKNQQ RAELKAQGDS GGSSGGSSGS ETPGTSESAT PESSGGSSGG SMRELDYRIG 240
LAIGTNSIGW GVIELSWNKD RERYEKVRIV DQGVRMFDRA EMPKTGASLA EPRRIARSSR 300
RRLNRKSQRK KNIRNLLVQH GVITQEELDS LYPLSKKSMD IWGIRLDGLD RLLNHFEWAR 360
LLIHLAQRRG FKSNRKSELK DTETGKVLSS IQLNEKRLSL YRTVGEMWMK DPDFSKYDRK 420
RNSPNEYVFS VSRAELEKEI VTLFAAQRRF QSPYASKDLQ ETYLQIWTHQ LPFASGNAIL 480
NKVGYCSLLK GKERRIPKAT YTFQYFSALD QVNRTRLGPD FQPFTKEQRE IILNNMFQRT 540
DYYKKKTIPE VTYYDIRKWL ELDETIQFKG LNYDPNEELK KIEKKPFINL KAFYEINKVV 600
ANYSERTNET FSTLDYDGIG YALTVYKTDK DIRSYLKSSH NLPKRCYDDQ LIEELLSLSY 660
TKFGHLSLKA INHVLSIMQK GNTYKEAVDQ LGYDTSGLKK EKRSKFLPPI SDEITNPIVK 720
RALTQARKVV NAIIRRHGSP HSVHIELARE LSKNHDERTK IVSAQDENYK KNKGAISILS 780
EHGILNPTGY DIVRYKLWKE QGERCAYSLK EIPADTFFNE LKKERNGAPI LEVDHILPYS 840
QSFIDSYHNK VLVYSDENRK KGNRIPYTYF LETNKDWEAF ERYVRSNKFF SKKKREYLLK 900
RAYLPRESEL IKERHLNDTR YASTFLKNFI EQNLQFKEAE DNPRKRRVQT VNGVITAHFR 960
KRWGLEKDRQ ETYLHHAMDA IIVACTDHHM VTRVTEYYQI KESNKSVKKP YFPMPWEGFR 1020
DELLSHLASQ PIAKKISEEL KAGYQSLDYI FVSRMPKRSI TGAAHKQTIM RKGGIDKKGK 1080
TIIIERLHLK DIKFDENGDF KMVGKEQDMA TYEAIKQRYL EHGKNSKKAF ETPLYKPSKK 1140
GTGNLIKRVK VEGQAKSFVR EVNGGVAQNG DLVRVDLFEK DDKYYMVPIY VPDTVCSELP 1200
KKVVASSKGY EQWLTLDNSF TFKFSLYPYD LVRLVKGDED RFLYFGTLDI DSDRLNFKDV 1260
NKPSKKNEYR YSLKTIEDLE KYEVGVLGDL RLVRKETRRN FHSGGSKRPA ATKKAGQAKK 1320
KK                                                               1322

SEQ ID NO: 529          moltype = AA  length = 1322
FEATURE                 Location/Qualifiers
REGION                  1..1322
                        note = source = /note="Description of Artificial Sequence:
                         Syntheticpolypeptide"
```

```
REGION                       1..1322
                             note = source = /note="LPG50181-nAPG07433.1protein sequence"
source                       1..1322
                             mol_type = protein
                             organism = synthetic construct
SEQUENCE: 529
MAPKKKRKVD YKDHDGDYKD HDIDYKDDDD KMSDPELNHE YWMRHALQLA QRARDEGEVP    60
VGAVLVLNNQ VIGEGWNRAI GLHDPTAHAE IMALRQGGLV LQNYRLLDTT LYVTFEPCVM   120
CSGAMIHSRI GTVVYGVRNE KRGAAGSLLN VLSYPGMNHQ VKVIGEVLAP ACSAMLCDFY   180
RMPRQQKNQQ KAEWKLSGES GGSSGGSSGS ETPGTSESAT PESSGGSSGG SMRELDYRIG   240
LAIGTNSIGW GVIELSWNKD RERYEKVRIV DQGVRMFDRA EMPKTGASLA EPRRIARSSR   300
RRLNRKSQRK KNIRNLLVQH GVITQEELDS LYPLSKKSMD IWGIRLDGLD RLLNHFEWAR   360
LLIHLAQRRG FKSNRKSELK DTETGKVLSS IQLNEKRLSL YRTVGEMWMK DPDFSKYDRK   420
RNSPNEYVFS VSRAELEKEI VTLFAAQRRF QSPYASKDLQ ETYLQIWTHQ LPFASGNAIL   480
NKVGYCSLLK GKERRIPKAT YTFQYFSALD QVNRTRLGPD FQPFTKEQRE IILNNMFQRT   540
DYYKKKTIPE VTYYDIRKWL ELDETIQFKG LNYDPNEELK KIEKKPFINL KAFYEINKVV   600
ANYSERTNET FSTLDYDGIG YALTVYKTDK DIRSYLKSSH NLPKRCYDDQ LIEELLSLSY   660
TKFGHLSLKA INHVLSIMQK GNTYKEAVDQ LGYDTSGLKK EKRSKFLPPI SDEITNPIVK   720
RALTQARKVV NAIIRRHGSP HSVHIELARE LSKNHDERTK IVSAQDENYK KNKGAISILS   780
EHGILNPTGY DIVRYKLWKE QGERCAYSLK EIPADTFFNE LKKERNGAPI LEVDHILPYS   840
QSFIDSYHNK VLVYSDENRK KGNRIPYTYF LETNKDWEAF ERYVRSNKFF SKKKREYLLK   900
RAYLPRESEL IKERHLNDTR YASTFLKNFI EQNLQFKEAE DNPRKRRVQT VNGVITAHFR   960
KRWGLEKDRQ ETYLHHAMDA IIVACTDHHM VTRVTEYYQI KESNKSVKKP YFPMPWEGFR  1020
DELLSHLASQ PIAKKISEEL KAGYQSLDYI FVSRMPKRSI TGAAHKQTIM RKGGIDKKGK  1080
TIIIERLHLK DIKFDENGDF KMVGKEQDMA TYEAIKQRYL EHGKNSKKAF ETPLYKPSKK  1140
GTGNLIKRVK VEGQAKSFVR EVNGGVAQNG DLVRVDLFEK DDKYYMVPIY VPDTVCSELP  1200
KKVVASSKGY EQWLTLDNSF TFKFSLYPYD LVRLVKGDED RFLYFGTLDI DSDRLNFKDV  1260
NKPSKKNEYR YSLKTIEDLE KYEVGVLGDL RLVRKETRRN FHSGGKRPA ATKKAGQAKK  1320
KK                                                                1322

SEQ ID NO: 530               moltype = AA  length = 1325
FEATURE                      Location/Qualifiers
REGION                       1..1325
                             note = source = /note="Description of Artificial Sequence:
                              Syntheticpolypeptide"
REGION                       1..1325
                             note = source = /note="LPG50182-nAPG07433.1protein sequence"
source                       1..1325
                             mol_type = protein
                             organism = synthetic construct
SEQUENCE: 530
MAPKKKRKVD YKDHDGDYKD HDIDYKDDDD KMSNPELNHE YWMRYALTLA KRARDEGEVP    60
VGAVLVYHDQ VIGEGWNRAI GLHDPTAHAE IMALRQGGLV LQNYRLIDTT LYVTFEPCVM   120
CAGAMVHSRI GRLVFGVRNS KRGAAGSLLN VLNYPGMNHQ IDMEEGVLRD ECAAMLCDFY   180
RLPRIVKNAL KQSPPDSTNL HASGGSSGGS SGSETPGTSE SATPESSGGS SGGSMRELDY   240
RIGLAIGTNS IGWGVIELSW NKDRERYEKV RIVDQGVRMF DRAEMPKTGA SLAEPRRIAR   300
SSRRLNRKS QRKKNIRNLL VQHGVITQEE LDSLYPLSKK SMDIWGIRLD GLDRLLNHFE   360
WARLLIHLAQ RRGFKSNRKS ELKDTETGKV LSSIQLNEKR LSLYRTVGEM WMKDPDFSKY   420
DRKRNSPNEY VFSVSRAELE KEIVTLFAAQ RRFQSPYASK DLQETYLQIW THQLPFASGN   480
AILNKVGYCS LLKGKERRIP KATYTFQYFS ALDQVNRTRL GPDFQPFTKE QREIILNNMF   540
QRTDYYKKKT IPEVTYYDIR KWLELDETIQ FKGLNYDPNE ELKKIEKKPF INLKAFYEIN   600
KVVANYSERT NETFSTLDYD GIGYALTVYK TDKDIRSYLK SSHNLPKRCY DDQLIEELLS   660
LSYTKFGHLS LKAINHVLSI MQKGNTYKEA VDQLGYDTSG LKKEKRSKFL PPISDEITNP   720
IVKRALTQAR KVVNAIIRRH GSPHSVHIEL ARELSKNHDE RTKIVSAQDE NYKKNKGAIS   780
ILSEHGILNP TGYDIVRYKL WKEQGERCAY SLKEIPADTF FNELKKERNG APILEVDHIL   840
PYSQSFIDSY HNKVLVYSDE NRKKGNRIPY TYFLETNKDW EAFERYVRSN KFFSKKKREY   900
LLKRAYLPRE SELIKERHLN DTRYASTFLK NFIEQNLQFK EAEDNPRKRR VQTVNGVITA   960
HFRKRWGLEK DRQETYLHHA MDAIIVACTD HHMVTRVTEY YQIKESNKSV KKPYFPMPWE  1020
GFRDELLSHL ASQPIAKKIS EELKAGYQSL DYIFVSRMPK RSITGAAHKQ TIMRKGGIDK  1080
KGKTIIIERL HLKDIKFDEN GDFKMVGKEQ DMATYEAIKQ RYLEHGKNSK KAFETPLYKP  1140
SKKGTGNLIK RVKVEGQAKS FVREVNGGVA QNGDLVRVDL FEKDDKYYMV PIYVPDTVCS  1200
ELPKKVVASS KGYEQWLTLD NSFTFKFSLY PYDLVRLVKG DEDRFLYFGT LDIDSDRLNF  1260
KDVNKPSKKN EYRYSLKTIE DLEKYEVGVL GDLRLVRKET RRNFHSGGSK RPAATKKAGQ  1320
AKKKK                                                             1325

SEQ ID NO: 531               moltype = RNA  length = 130
FEATURE                      Location/Qualifiers
misc_feature                 1..130
                             note = source = /note="Description of Artificial Sequence:
                              Syntheticpolynucleotide"
misc_feature                 1..130
                             note = source = /note="SGN000139"
source                       1..130
                             mol_type = other RNA
                             organism = synthetic construct
SEQUENCE: 531
aggttttaat ggcccagcct gtcatagttc cattaaagcc aaaagtggct tgatgtttc    60
tatgataagg gtttcgaccc gtggcgtcgg ggatcgcctg cccattgaaa tgggcttctc   120
cccatttatt                                                         130
```

| | |
|---|---|
| SEQ ID NO: 532 | moltype = RNA  length = 130 |
| FEATURE | Location/Qualifiers |
| misc_feature | 1..130 |
| | note = source = /note="Description of Artificial Sequence: Syntheticpolynucleotide" |
| misc_feature | 1..130 |
| | note = source = /note="SGN000143" |
| source | 1..130 |
| | mol_type = other RNA |
| | organism = synthetic construct |

SEQUENCE: 532
catggcagta cattagagca gtcatagttc cattaaagcc aaaagtggct ttgatgtttc   60
tatgataagg gtttcgaccc gtggcgtcgg ggatcgcctg cccattgaaa tgggcttctc  120
cccatttatt                                                         130

| | |
|---|---|
| SEQ ID NO: 533 | moltype = RNA  length = 130 |
| FEATURE | Location/Qualifiers |
| misc_feature | 1..130 |
| | note = source = /note="Description of Artificial Sequence: Syntheticpolynucleotide" |
| misc_feature | 1..130 |
| | note = source = /note="SGN000186" |
| source | 1..130 |
| | mol_type = other RNA |
| | organism = synthetic construct |

SEQUENCE: 533
ggacagtgcg catctccctg gtcatagttc cattaaagcc aaaagtggct ttgatgtttc   60
tatgataagg gtttcgaccc gtggcgtcgg ggatcgcctg cccattgaaa tgggcttctc  120
cccatttatt                                                         130

| | |
|---|---|
| SEQ ID NO: 534 | moltype = RNA  length = 130 |
| FEATURE | Location/Qualifiers |
| misc_feature | 1..130 |
| | note = source = /note="Description of Artificial Sequence: Syntheticpolynucleotide" |
| misc_feature | 1..130 |
| | note = source = /note="SGN000194" |
| source | 1..130 |
| | mol_type = other RNA |
| | organism = synthetic construct |

SEQUENCE: 534
gccgcacagc attcaggtcg gtcatagttc cattaaagcc aaaagtggct ttgatgtttc   60
tatgataagg gtttcgaccc gtggcgtcgg ggatcgcctg cccattgaaa tgggcttctc  120
cccatttatt                                                         130

| | |
|---|---|
| SEQ ID NO: 535 | moltype = RNA  length = 135 |
| FEATURE | Location/Qualifiers |
| misc_feature | 1..135 |
| | note = source = /note="Description of Artificial Sequence: Syntheticpolynucleotide" |
| misc_feature | 1..135 |
| | note = source = /note="SGN000930" |
| source | 1..135 |
| | mol_type = other RNA |
| | organism = synthetic construct |

SEQUENCE: 535
gaacaactca aatggaaatg aatatgtcat agttccatga agccaaaag tggctttgat    60
gtttctatga taagggtttc ggcccgtggc gtcgggatc gcctgcccat tcgatgggc   120
ttctccccat ttatt                                                   135

| | |
|---|---|
| SEQ ID NO: 536 | moltype = RNA  length = 130 |
| FEATURE | Location/Qualifiers |
| misc_feature | 1..130 |
| | note = source = /note="Description of Artificial Sequence: Syntheticpolynucleotide" |
| misc_feature | 1..130 |
| | note = source = /note="SGN001681" |
| source | 1..130 |
| | mol_type = other RNA |
| | organism = synthetic construct |

SEQUENCE: 536
ccgtgccttg acctaccctg gtcatagttc cattaaagcc aaaagtggct ttgatgtttc   60
tatgataagg gtttcgaccc gtggcgtcgg ggatcgcctg cccattgaaa tgggcttctc  120
cccatttatt                                                         130

| | |
|---|---|
| SEQ ID NO: 537 | moltype = DNA  length = 20 |
| FEATURE | Location/Qualifiers |

```
misc_feature        1..20
                    note = source = /note="Description of Artificial Sequence:
                     Syntheticoligonucleotide"
misc_feature        1..20
                    note = source = /note="SGN000139 target sequence"
source              1..20
                    mol_type = other DNA
                    organism = synthetic construct
SEQUENCE: 537
aggttttaat ggcccagcct                                                      20

SEQ ID NO: 538      moltype = DNA   length = 20
FEATURE             Location/Qualifiers
misc_feature        1..20
                    note = source = /note="Description of Artificial Sequence:
                     Syntheticoligonucleotide"
misc_feature        1..20
                    note = source = /note="SGN000143 target sequence"
source              1..20
                    mol_type = other DNA
                    organism = synthetic construct
SEQUENCE: 538
catggcagta cattagagca                                                      20

SEQ ID NO: 539      moltype = DNA   length = 20
FEATURE             Location/Qualifiers
misc_feature        1..20
                    note = source = /note="Description of Artificial Sequence:
                     Syntheticoligonucleotide"
misc_feature        1..20
                    note = source = /note="SGN000186 target sequence"
source              1..20
                    mol_type = other DNA
                    organism = synthetic construct
SEQUENCE: 539
ggacagtgcg catctccctg                                                      20

SEQ ID NO: 540      moltype = DNA   length = 20
FEATURE             Location/Qualifiers
misc_feature        1..20
                    note = source = /note="Description of Artificial Sequence:
                     Syntheticoligonucleotide"
misc_feature        1..20
                    note = source = /note="SGN000194 target sequence"
source              1..20
                    mol_type = other DNA
                    organism = synthetic construct
SEQUENCE: 540
gccgcacagc attcaggtcg                                                      20

SEQ ID NO: 541      moltype = DNA   length = 25
FEATURE             Location/Qualifiers
misc_feature        1..25
                    note = source = /note="Description of Artificial Sequence:
                     Syntheticoligonucleotide"
misc_feature        1..25
                    note = source = /note="SGN000930 target sequence"
source              1..25
                    mol_type = other DNA
                    organism = synthetic construct
SEQUENCE: 541
gaacaactca aatggaaatg aatat                                                25

SEQ ID NO: 542      moltype = DNA   length = 20
FEATURE             Location/Qualifiers
misc_feature        1..20
                    note = source = /note="Description of Artificial Sequence:
                     Syntheticoligonucleotide"
misc_feature        1..20
                    note = source = /note="SGN001681 target sequence"
source              1..20
                    mol_type = other DNA
                    organism = synthetic construct
SEQUENCE: 542
ccgtgccttg acctaccctg                                                      20

SEQ ID NO: 543      moltype = DNA   length = 53
FEATURE             Location/Qualifiers
```

| | |
|---|---|
| misc_feature | 1..53 |
| | note = source = /note="Description of Artificial Sequence: Syntheticoligonucleotide" |
| misc_feature | 1..53 |
| | note = source = /note="SGN000139 forward primer" |
| source | 1..53 |
| | mol_type = other DNA |
| | organism = synthetic construct |

SEQUENCE: 543
tcgtcggcag cgtcagatgt gtataagaga cagcttgtag ctggaggtcc atc          53

| | |
|---|---|
| SEQ ID NO: 544 | moltype = DNA length = 52 |
| FEATURE | Location/Qualifiers |
| misc_feature | 1..52 |
| | note = source = /note="Description of Artificial Sequence: Syntheticoligonucleotide" |
| misc_feature | 1..52 |
| | note = source = /note="SGN000143 forward primer" |
| source | 1..52 |
| | mol_type = other DNA |
| | organism = synthetic construct |

SEQUENCE: 544
tcgtcggcag cgtcagatgt gtataagaga cagacatttg acgagcagcg aa           52

| | |
|---|---|
| SEQ ID NO: 545 | moltype = DNA length = 53 |
| FEATURE | Location/Qualifiers |
| misc_feature | 1..53 |
| | note = source = /note="Description of Artificial Sequence: Syntheticoligonucleotide" |
| misc_feature | 1..53 |
| | note = source = /note="SGN000186 forward primer" |
| source | 1..53 |
| | mol_type = other DNA |
| | organism = synthetic construct |

SEQUENCE: 545
tcgtcggcag cgtcagatgt gtataagaga cagtggcccc tatgtggaga tca          53

| | |
|---|---|
| SEQ ID NO: 546 | moltype = DNA length = 53 |
| FEATURE | Location/Qualifiers |
| misc_feature | 1..53 |
| | note = source = /note="Description of Artificial Sequence: Syntheticoligonucleotide" |
| misc_feature | 1..53 |
| | note = source = /note="SGN000194 forward primer" |
| source | 1..53 |
| | mol_type = other DNA |
| | organism = synthetic construct |

SEQUENCE: 546
tcgtcggcag cgtcagatgt gtataagaga cagatgacat tcaggccaca gtg          53

| | |
|---|---|
| SEQ ID NO: 547 | moltype = DNA length = 53 |
| FEATURE | Location/Qualifiers |
| misc_feature | 1..53 |
| | note = source = /note="Description of Artificial Sequence: Syntheticoligonucleotide" |
| misc_feature | 1..53 |
| | note = source = /note="SGN000930 forward primer" |
| source | 1..53 |
| | mol_type = other DNA |
| | organism = synthetic construct |

SEQUENCE: 547
tcgtcggcag cgtcagatgt gtataagaga caggacagcc aagaggtttt gcc          53

| | |
|---|---|
| SEQ ID NO: 548 | moltype = DNA length = 53 |
| FEATURE | Location/Qualifiers |
| misc_feature | 1..53 |
| | note = source = /note="Description of Artificial Sequence: Syntheticoligonucleotide" |
| misc_feature | 1..53 |
| | note = source = /note="SGN001681 forward primer" |
| source | 1..53 |
| | mol_type = other DNA |
| | organism = synthetic construct |

SEQUENCE: 548
tcgtcggcag cgtcagatgt gtataagaga cagtggtgga actggacggg gat          53

| | |
|---|---|
| SEQ ID NO: 549 | moltype = DNA length = 54 |
| FEATURE | Location/Qualifiers |

| | |
|---|---|
| misc_feature | 1..54 |
| | note = source = /note="Description of Artificial Sequence: Syntheticoligonucleotide" |
| misc_feature | 1..54 |
| | note = source = /note="SGN000139 reverse primer" |
| source | 1..54 |
| | mol_type = other DNA |
| | organism = synthetic construct |

SEQUENCE: 549
gtctcgtggg ctcggagatg tgtataagag acagtgttgg caaatctagt ctcg      54

| | |
|---|---|
| SEQ ID NO: 550 | moltype = DNA  length = 54 |
| FEATURE | Location/Qualifiers |
| misc_feature | 1..54 |
| | note = source = /note="Description of Artificial Sequence: Syntheticoligonucleotide" |
| misc_feature | 1..54 |
| | note = source = /note="SGN000143 reverse primer" |
| source | 1..54 |
| | mol_type = other DNA |
| | organism = synthetic construct |

SEQUENCE: 550
gtctcgtggg ctcggagatg tgtataagag acagggcccc tggagaggtt ttaa      54

| | |
|---|---|
| SEQ ID NO: 551 | moltype = DNA  length = 54 |
| FEATURE | Location/Qualifiers |
| misc_feature | 1..54 |
| | note = source = /note="Description of Artificial Sequence: Syntheticoligonucleotide" |
| misc_feature | 1..54 |
| | note = source = /note="SGN000186 reverse primer" |
| source | 1..54 |
| | mol_type = other DNA |
| | organism = synthetic construct |

SEQUENCE: 551
gtctcgtggg ctcggagatg tgtataagag acagggcaga gctcagcctc atag      54

| | |
|---|---|
| SEQ ID NO: 552 | moltype = DNA  length = 54 |
| FEATURE | Location/Qualifiers |
| misc_feature | 1..54 |
| | note = source = /note="Description of Artificial Sequence: Syntheticoligonucleotide" |
| misc_feature | 1..54 |
| | note = source = /note="SGN000194 reverse primer" |
| source | 1..54 |
| | mol_type = other DNA |
| | organism = synthetic construct |

SEQUENCE: 552
gtctcgtggg ctcggagatg tgtataagag acagcttcct cctattcagg ccca      54

| | |
|---|---|
| SEQ ID NO: 553 | moltype = DNA  length = 54 |
| FEATURE | Location/Qualifiers |
| misc_feature | 1..54 |
| | note = source = /note="Description of Artificial Sequence: Syntheticoligonucleotide" |
| misc_feature | 1..54 |
| | note = source = /note="SGN000930 reverse primer" |
| source | 1..54 |
| | mol_type = other DNA |
| | organism = synthetic construct |

SEQUENCE: 553
gtctcgtggg ctcggagatg tgtataagag acagctgtcc cttgcagctt ctgt      54

| | |
|---|---|
| SEQ ID NO: 554 | moltype = DNA  length = 54 |
| FEATURE | Location/Qualifiers |
| misc_feature | 1..54 |
| | note = source = /note="Description of Artificial Sequence: Syntheticoligonucleotide" |
| misc_feature | 1..54 |
| | note = source = /note="SGN001681 reverse primer" |
| source | 1..54 |
| | mol_type = other DNA |
| | organism = synthetic construct |

SEQUENCE: 554
gtctcgtggg ctcggagatg tgtataagag acagcagctt gtgcccagg atgt      54

| | |
|---|---|
| SEQ ID NO: 555 | moltype = AA  length = 1368 |
| FEATURE | Location/Qualifiers |
| REGION | 1..1368 |
| | note = source = /note="Streptococcus pyogenes Cas9" |

| source | 1..1368 |
| --- | --- |
| | mol_type = protein |
| | organism = Streptococcus pyogenes |

SEQUENCE: 555

```
MDKKYSIGLD IGTNSVGWAV ITDDYKVPSK KLKGLGNTDR HGIKKNLIGA LLFDSGETAE    60
ATRLKRTARR RYTRRKNRIC YLQEIFSNEM AKVDDSFFHR LEESFLVEED KKHERHPIFG   120
NIVDEVAYHE KYPTIYHLRK KLADSTDKVD LRLIYLALAH MIKFRGHFLI EGDLNPDNSD   180
VDKLFIQLVQ TYNQLFEENP INASRVDAKA ILSARLSKSR RLENLIAQLP GEKKNGLFGN   240
LIALSLGLTP NFKSNFDLAE DAKLQLSKDT YDDDLDNLLA QIGDQYADLF LAAKNLSDAT   300
LLSDILRVNS EITKAPLSAS MIKRYDEHHQ DLTLLKALVR QQLPEKYKEI FFDQSKNGYA   360
GYIDGGASQE EFYKFIKPIL EKMDGTEELL AKLNREDLLR KQRTFDNGSI PYQIHLGELH   420
AILRRQEDFY PFLKDNREKI EKILTFRIPY YVGPLARGNS RFAWMTRKSE ETITPWNFEE   480
VVDKGASAQS FIERMTNFDK NLPNEKVLPK HSLLYEYFTV YNELTKVKYV TEGMRKPAFL   540
SGEQKKAIVD LLFKTNRKVT VKQLKEDYFK KIECFDSVEI SGVEDRFNAS LGTYHDLLKI   600
IKDKDFLDNE ENEDILEDIV LTLTLFEDRE MIEERLKTYA HLFDDKVMKQ LKRRRYTGWG   660
RLSRKLINGI RDKQSGKTIL DFLKSDGFAN RNFMQLIHDD SLTFKEDIQK AQVSGQGDSL   720
HEHIANLAGS PAIKKGILQT VKVVDELVKV MGRHKPENIV IEMARENQTT QKGQKNSRER   780
MKRIEEGIKE LGSQILKEYP VENTQLQNEK LYLYYLQNGR DMYVDQELDI NRLSDYDVDH   840
IVPQSFLKDD SIDNKVLTRS DKNRGKSDNV PSEEVVKKMK NYWRQLLNAK LITQRKFDNL   900
TKAERGGLSE LDKVGFIKRQ LVETRQITKH VAQILDSRMN TKYDENDKLI REVRVITLKS   960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV RKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGD              1368
```

| SEQ ID NO: 556 | moltype = AA  length = 1368 |
| --- | --- |
| FEATURE | Location/Qualifiers |
| REGION | 1..1368 |
| | note = source = /note="Description of Artificial Sequence: Syntheticpolypeptide" |
| REGION | 1..1368 |
| | note = source = /note="Streptococcus pyogenes Cas9 D10A nickase" |
| source | 1..1368 |
| | mol_type = protein |
| | organism = synthetic construct |

SEQUENCE: 556

```
MDKKYSIGLA IGTNSVGWAV ITDDYKVPSK KLKGLGNTDR HGIKKNLIGA LLFDSGETAE    60
ATRLKRTARR RYTRRKNRIC YLQEIFSNEM AKVDDSFFHR LEESFLVEED KKHERHPIFG   120
NIVDEVAYHE KYPTIYHLRK KLADSTDKVD LRLIYLALAH MIKFRGHFLI EGDLNPDNSD   180
VDKLFIQLVQ TYNQLFEENP INASRVDAKA ILSARLSKSR RLENLIAQLP GEKKNGLFGN   240
LIALSLGLTP NFKSNFDLAE DAKLQLSKDT YDDDLDNLLA QIGDQYADLF LAAKNLSDAT   300
LLSDILRVNS EITKAPLSAS MIKRYDEHHQ DLTLLKALVR QQLPEKYKEI FFDQSKNGYA   360
GYIDGGASQE EFYKFIKPIL EKMDGTEELL AKLNREDLLR KQRTFDNGSI PYQIHLGELH   420
AILRRQEDFY PFLKDNREKI EKILTFRIPY YVGPLARGNS RFAWMTRKSE ETITPWNFEE   480
VVDKGASAQS FIERMTNFDK NLPNEKVLPK HSLLYEYFTV YNELTKVKYV TEGMRKPAFL   540
SGEQKKAIVD LLFKTNRKVT VKQLKEDYFK KIECFDSVEI SGVEDRFNAS LGTYHDLLKI   600
IKDKDFLDNE ENEDILEDIV LTLTLFEDRE MIEERLKTYA HLFDDKVMKQ LKRRRYTGWG   660
RLSRKLINGI RDKQSGKTIL DFLKSDGFAN RNFMQLIHDD SLTFKEDIQK AQVSGQGDSL   720
HEHIANLAGS PAIKKGILQT VKVVDELVKV MGRHKPENIV IEMARENQTT QKGQKNSRER   780
MKRIEEGIKE LGSQILKEYP VENTQLQNEK LYLYYLQNGR DMYVDQELDI NRLSDYDVDH   840
IVPQSFLKDD SIDNKVLTRS DKNRGKSDNV PSEEVVKKMK NYWRQLLNAK LITQRKFDNL   900
TKAERGGLSE LDKVGFIKRQ LVETRQITKH VAQILDSRMN TKYDENDKLI REVRVITLKS   960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV RKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGD              1368
```

| SEQ ID NO: 557 | moltype = AA  length = 1388 |
| --- | --- |
| FEATURE | Location/Qualifiers |
| REGION | 1..1388 |
| | note = source = /note="Streptococcus thermophilus Cas9" |
| source | 1..1388 |
| | mol_type = protein |
| | organism = Streptococcus thermophilus |

SEQUENCE: 557

```
MTKPYSIGLD IGTNSVGWAV TTDNYKVPSK KMKVLGNTSK KYIKKNLLGV LLFDSGITAE    60
GRRLKRTARR RYTRRRNRIL YLQEIFSTEM ATLDDAFFQR LDDSFLVPDD KRDSKYPIFG   120
NLVEEKAYHD EFPTIYHLRK YLADSTKKAD LRLVYLALAH MIKYRGHFLI EGEFNSKNND   180
IQKNFQDFLD TYNAIFESDL SLENSKQLEE IVKDKISKLE KKDRILKLFP GEKNSGIFSE   240
FLKLIVGNQA DFRKCFNLDE KASLHFSKES YDEDLETLLG YIGDDYSDVF LKAKKLYDAI   300
LLSGFLTVTD NETEAPLSSA MIKRYNEHKE DLALLKEYIR NISLKTYNEV FKDDTKNGYA   360
GYIDGKTNQE DFYVYLKKLL AEFEGADYFL EKIDREDFLR KQRTFDNGSI PYQIHLQEMR   420
```

```
AILDKQAKFY PFLAKNKERI EKILTFRIPY YVGPLARGNS DFAWSIRKRN EKITPWNFED    480
VIDKESSAEA FINRMTSFDL YLPEEKVLPK HSLLYETFNV YNELTKVRFI AESMRDYQFL    540
DSKQKKDIVR LYFKDKRKVT DKDIIEYLHA IYGYDGIELK GIEKQFNSSL STYHDLLNII    600
NDKEFLDDSS NEAIIEEIIH TLTIFEDREM IKQRLSKFEN IFDKSVLKKL SRRHYTGWGK    660
LSAKLINGIR DEKSGNTILD YLIDDGISNR NFMQLIHDDA LSFKKKIQKA QIIGDEDKGN    720
IKEVVKSLPG SPAIKKGILQ SIKIVDELVK VMGGRKPESI VVEMARENQY TNQGKSNSQQ    780
RLKRLEKSLK ELGSKILKEN IPAKLSKIDN NALQNDRLYL YYLQNGKDMY TGDDLDIDRL    840
SNYDIDHIIP QAFLKDNSID NKVLVSSASN RGKSDDVPSL EVVKKRKTFW YQLLKSKLIS    900
QRKFDNLTKA ERGGLSPEDK AGFIQRQLVE TRQITKHVAR LLDEKFNNKK DENNRAVRTV    960
KIITLKSTLV SQFRKDFELY KVREINDFHH AHDAYLNAVV ASALLKKYPK LEPEFVYGDY   1020
PKYNSFRERK SATEKVYFYS NIMNIFKKSI SLADGRVIER PLIEVNEETG ESVWNKESDL   1080
ATVRRVLSYP QVNVVKKVEE QNHGLDRGKP KGLFNANLSS KPKPNSNENL VGAKEYLDPK   1140
KYGGYAGISN SFTVLVKGTI EKGAKKKITN VLEFQGISIL DRINYRKDKL NFLLEKGYKD   1200
IELIIELPKY SLFELSDGSR RMLASILSTN NKRGEIHKGN QIFLSQKFVK LLYHAKRISN   1260
TINENHRKYV ENHKKEFEEL FYYILEFNEN YVGAKKNGKL LNSAFQSWQN HSIDELCSSF   1320
IGPTGSERKG LFELTSRGSA ADFEFLGVKI PRYRDYTPSS LLKDATLIHQ SVTGLYETRI   1380
DLAKLGEG                                                           1388

SEQ ID NO: 558          moltype = AA  length = 1388
FEATURE                 Location/Qualifiers
REGION                  1..1388
                        note = source = /note="Description of Artificial Sequence:
                         Syntheticpolypeptide"
REGION                  1..1388
                        note = source = /note="Streptococcus thermophilus Cas9 D10A
                         nickase"
source                  1..1388
                        mol_type = protein
                        organism = synthetic construct
SEQUENCE: 558
MTKPYSIGLA IGTNSVGWAV TTDNYKVPSK KMKVLGNTSK KYIKKNLLGV LLFDSGITAE     60
GRRLKRTARR RYTRRRNRIL YLQEIFSTEM ATLDDAFFQR LDDSFLVPDD KRDSKYPIFG    120
NLVEEKAYHD EFPTIYHLRK YLADSTKKAD LRLVYLALAH MIKYRGHFLI EGEFNSKNND    180
IQKNFQDFLD TYNAIFESDL SLENSKQLEE IVKDKISKLE KDRILKLFP GEKNSGIFSE    240
FLKLIVGNQA DFRKCFNLDE KASLHFSKES YDEDLETLLG YIGDDYSDVF LKAKKLYDAI    300
LLSGFLTVTD NETEAPLSSA MIKRYNEHKE DLALLKEYIR NISLKTYNEV FKDDTKNGYA    360
GYIDGKTNQE DFYVYLKKLL AEFEGADYFL EKIDREDFLR KQRTFDNGSI PYQIHLQEMR    420
AILDKQAKFY PFLAKNKERI EKILTFRIPY YVGPLARGNS DFAWSIRKRN EKITPWNFED    480
VIDKESSAEA FINRMTSFDL YLPEEKVLPK HSLLYETFNV YNELTKVRFI AESMRDYQFL    540
DSKQKKDIVR LYFKDKRKVT DKDIIEYLHA IYGYDGIELK GIEKQFNSSL STYHDLLNII    600
NDKEFLDDSS NEAIIEEIIH TLTIFEDREM IKQRLSKFEN IFDKSVLKKL SRRHYTGWGK    660
LSAKLINGIR DEKSGNTILD YLIDDGISNR NFMQLIHDDA LSFKKKIQKA QIIGDEDKGN    720
IKEVVKSLPG SPAIKKGILQ SIKIVDELVK VMGGRKPESI VVEMARENQY TNQGKSNSQQ    780
RLKRLEKSLK ELGSKILKEN IPAKLSKIDN NALQNDRLYL YYLQNGKDMY TGDDLDIDRL    840
SNYDIDHIIP QAFLKDNSID NKVLVSSASN RGKSDDVPSL EVVKKRKTFW YQLLKSKLIS    900
QRKFDNLTKA ERGGLSPEDK AGFIQRQLVE TRQITKHVAR LLDEKFNNKK DENNRAVRTV    960
KIITLKSTLV SQFRKDFELY KVREINDFHH AHDAYLNAVV ASALLKKYPK LEPEFVYGDY   1020
PKYNSFRERK SATEKVYFYS NIMNIFKKSI SLADGRVIER PLIEVNEETG ESVWNKESDL   1080
ATVRRVLSYP QVNVVKKVEE QNHGLDRGKP KGLFNANLSS KPKPNSNENL VGAKEYLDPK   1140
KYGGYAGISN SFTVLVKGTI EKGAKKKITN VLEFQGISIL DRINYRKDKL NFLLEKGYKD   1200
IELIIELPKY SLFELSDGSR RMLASILSTN NKRGEIHKGN QIFLSQKFVK LLYHAKRISN   1260
TINENHRKYV ENHKKEFEEL FYYILEFNEN YVGAKKNGKL LNSAFQSWQN HSIDELCSSF   1320
IGPTGSERKG LFELTSRGSA ADFEFLGVKI PRYRDYTPSS LLKDATLIHQ SVTGLYETRI   1380
DLAKLGEG                                                           1388

SEQ ID NO: 559          moltype = AA  length = 1368
FEATURE                 Location/Qualifiers
REGION                  1..1368
                        note = source = /note="Staphylococcus aureus Cas9"
source                  1..1368
                        mol_type = protein
                        organism = Staphylococcus aureus
SEQUENCE: 559
MDKKYSIGLD IGTNSVGWAV ITDEYKVPSK KFKVLGNTDR HSIKKNLIGA LLFDSGETAE     60
ATRLKRTARR RYTRRKNRIC YLQEIFSNEM AKVDDSFFHR LEESFLVEED KKHERHPIFG    120
NIVDEVAYHE KYPTIYHLRK KLVDSTDKAD LRLIYLALAH MIKFRGHFLI EGDLNPDNSD    180
VDKLFIQLVQ TYNQLFEENP INASGVDAKA ILSARLSKSR RLENLIAQLP GEKKNGLFGN    240
LIALSLGLTP NFKSNFDLAE DAKLQLSKDT YDDDLDNLLA QIGDQYADLF LAAKNLSDAI    300
LLSDILRVNT EITKAPLSAS MIKRYDEHHQ DLTLLKALVR QQLPEKYKEI FFDQSKNGYA    360
GYIDGGASQE EFYKFIKPIL EKMDGTEELL VKLNREDLLR KQRTFDNGSI PHQIHLGELH    420
AILRRQEDFY PFLKDNREKI EKILTFRIPY YVGPLARGNS RFAWMTRKSE ETITPWNFEE    480
VVDKGASAQS FIERMTNFDK NLPNEKVLPK HSLLYEYFTV YNELTKVKYV TEGMRKPAFL    540
SGEQKKAIVD LLFKTNRKVT VKQLKEDYFK KIECFDSVEI SGVEDRFNAS LGTYHDLLKI    600
IKDKDFLDNE ENEDILEDIV LTLTLFEDRE MIEEERLKTYA HLFDDKVMKQ LKRRRYTGWG   660
RLSRKLINGI RDKQSGKTIL DFLKSDGFAN RNFMQLIHDD SLTFKEDIQK AQVSGQGDSL    720
HEHIANLAGS PAIKKGILQT VKVVDELVKV MGRHKPENIV IEMARENQTT QKGQKNSRER    780
MKRIEEGIKE LGSQILKEHP VENTQLQNEK LYLYYLQNGR DMYVDQELDI NRLSDYDVDH    840
IVPQSFLKDD SIDNKVLTRS DKNRGKSDNV PSEEVVKKMK NYWRQLLNAK LITQRKFDNL    900
TKAERGGLSE LDKAGFIKRQ LVETRQITKH VAQILDSRMN TKYDENDKLI REVKVITLKS    960
```

```
KLVSDFRKDF QFYKVREINN YHHAHDAYLN AVVGTALIKK YPKLESEFVY GDYKVYDVRK   1020
MIAKSEQEIG KATAKYFFYS NIMNFFKTEI TLANGEIRKR PLIETNGETG EIVWDKGRDF   1080
ATVRKVLSMP QVNIVKKTEV QTGGFSKESI LPKRNSDKLI ARKKDWDPKK YGGFDSPTVA   1140
YSVLVVAKVE KGKSKKLKSV KELLGITIME RSSFEKNPID FLEAKGYKEV KKDLIIKLPK   1200
YSLFELENGR KRMLASAGEL QKGNELALPS KYVNFLYLAS HYEKLKGSPE DNEQKQLFVE   1260
QHKYLDEII  EQISEFSKRV ILADANLDKV LSAYNKHRDK PIREQAENII HLFTLTNLGA   1320
PAAFKYFDTT IDRKRYTSTK EVLDATLIHQ SITGLYETRI DLSQLGGD               1368

SEQ ID NO: 560          moltype = AA  length = 1368
FEATURE                 Location/Qualifiers
REGION                  1..1368
                        note = source = /note="Description of Artificial Sequence:
                        Syntheticpolypeptide"
REGION                  1..1368
                        note = source = /note="Staphylococcus aureus Cas9 D10A
                        nickase"
source                  1..1368
                        mol_type = protein
                        organism = synthetic construct
SEQUENCE: 560
MDKKYSIGLA IGTNSVGWAV ITDEYKVPSK KFKVLGNTDR HSIKKNLIGA LLFDSGETAE    60
ATRLKRTARR RYTRRKNRIC YLQEIFSNEM AKVDDSFFHR LEESFLVEED KKHERHPIFG   120
NIVDEVAYHE KYPTIYHLRK KLVDSTDKAD LRLIYLALAH MIKFRGHFLI EGDLNPDNSD   180
VDKLFIQLVQ TYNQLFEENP INASGVDAKA ILSARLSKSR RLENLIAQLP GEKKNGLFGN   240
LIALSLGLTP NFKSNFDLAE DAKLQLSKDT YDDDLDNLLA QIGDQYADLF LAAKNLSDAI   300
LLSDILRVNT EITKAPLSAS MIKRYDEHHQ DLTLLKALVR QQLPEKYKEI FFDQSKNGYA   360
GYIDGGASQE EFYKFIKPIL EKMDGTEELL VKLNREDLLR KQRTFDNGSI PHQIHLGELH   420
AILRRQEDFY PFLKDNREKI EKILTFRIPY YVGPLARGNS RFAWMTRKSE ETITPWNFEE   480
VVDKGASAQS FIERMTNFDK NLPNEKVLPK HSLLYEYFTV YNELTKVKYV TEGMRKPAFL   540
SGEQKKAIVD LLFKTNRKVT VKQLKEDYFK KIECFDSVEI SGVEDRFNAS LGTYHDLLKI   600
IKDKDFLDNE ENEDILEDIV LTLTLFEDRE MIEERLKTYA HLFDDKVMKQ LKRRRYTGWG   660
RLSRKLINGI RDKQSGKTIL DFLKSDGFAN RNFMQLIHDD SLTFKEDIQK AQVSGQGDSL   720
HEHIANLAGS PAIKKGILQT VKVVDELVKV MGRHKPENIV IEMARENQTT QKGQKNSRER   780
MKRIEEGIKE LGSQILKEHP VENTQLQNEK LYLYYLQNGR DMYVDQELDI NRLSDYDVDH   840
IVPQSFLKDD SIDNKVLTRS DKNRGKSDNV PSEEVVKKMK NYWRQLLNAK LITQRKFDNL   900
TKAERGGLSE LDKAGFIKRQ LVETRQITKH VAQILDSRMN TKYDENDKLI REVKVITLKS   960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKYLDEII  EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGD              1368

SEQ ID NO: 561          moltype = AA  length = 1300
FEATURE                 Location/Qualifiers
REGION                  1..1300
                        note = source = /note="Francisella novicida Cas12a"
source                  1..1300
                        mol_type = protein
                        note = novicida
                        organism = Francisella sp.
SEQUENCE: 561
MSIYQEFVNK YSLSKTLRFE LIPQGKTLEN IKARGLILDD EKRAKDYKKA KQIIDKYHQF    60
FIEEILSSVC ISEDLLQNYS DVYFKLKKSD DDNLQKDFKS AKDTIKKQIS EYIKDSEKFK   120
NLFNQNLIDA KKGQESDLIL WLKQSKDNGI ELFKANSDIT DIDEALEIIK SFKGWTTYFK   180
GFHENRKNVY SSNDIPTSII YRIVDDNLPK FLENKAKYES ILDKAPEAIN YEQIKKDLAE   240
ELTFDIDYKT SEVNQRVFSL DEVFEIANFN NYLNQSGITK FNTIIGGKFV NGENTKRKGI   300
NEYINLYSQQ INDKTLKKYK MSVLFKQILS DTESKSFVID KLEDDSDVVT TMQSFYEQIA   360
AFKTVEEKSI KETLSLLFDD LKAQKLDLSK IYFKNDKSLT DLSQQVFDDY SVIGTAVLEY   420
ITQQIAPKNL DNPSKKEQEL IAKKTEKAKY LSLETIKLAL EEFNKHRDID KQCRFEEILA   480
NFAAIPMIFD EIAQNKDNLA QISIKYQNQG KKDLLQASAE DDVKAIKDLL DQTNNLLHKL   540
KIFHISQSED KANILDKDEH FYLVFEECYF ELANIVPLYN KIRNYITQKP YSDEKFKLNF   600
ENSTLANGWD KNKEPDNTAI LFIKDDKYYL GVMNKKNNKI FDDKAIKENK GEGYKKIVYK   660
LLPGANKMLP KVFFSAKSIK FYNPSEDILR IRNHSTHTKN GSPQKGYEKF EFNIEDCRKF   720
IDFYKQSISK HPEWKDFGFR FSDTQRYNSI DEFYREVENQ GYKLTFENIS ESYIDSVVNQ   780
GKLYLFQIYN KDFSAYSKGR PNLHTLYWKA LFDERNLQDV VYKLNGEAEL FYRKQSIPKK   840
ITHPAKEAIA NKNKDNPKKE SVFEYDLIKD KRFTEDKFFF HCPITINFKS SGANKFNDEI   900
NLLLKEKAND VHILSIDRGE RHLAYYTLVD GKGNIIKQDT FNIIGNDRMK TNYHDKLAAI   960
EKDRDSARKD WKKINNIKEM KEGYLSQVVH EIAKLVIEYN AIVVFEDLNF GFKRGRFKVE  1020
KQVYQKLEKM LIEKLNYLVF KDNEFDKTGG VLRAYQLTAP FETFKKMGKQ TGIIYYVPAG  1080
FTSKICPVTG FVNQLYPKYE SVSKSQEFFS KFDKICYNLD KYFEFSFDY  KNFGDKAAKG  1140
KWTIASFGSR LINFRNSDKN HNWDTREVYP TKELEKLLKD YSIEYGHGEC IKAAICGESD  1200
KKFFAKLTSV LNTILQMRNS KTGTELDYLI SPVADVNGNF FDSRQAPKNM PQDADANGAY  1260
HIGLKGLMLL GRIKNNQEGK KLNLVIKNEE YFEFVQNRNN                        1300

SEQ ID NO: 562          moltype = DNA  length = 65
FEATURE                 Location/Qualifiers
```

```
misc_feature         1..65
                     note = source = /note="Description of Artificial Sequence:
                     Syntheticoligonucleotide"
misc_feature         1..65
                     note = source = /note="SGN001101 genetic locus"
source               1..65
                     mol_type = other DNA
                     organism = synthetic construct
SEQUENCE: 562
accaaagatg atattttctt taatggtgcc aggcataatc caggaaaact gagaacagaa    60
tgaaa                                                                65

SEQ ID NO: 563       moltype = DNA  length = 25
FEATURE              Location/Qualifiers
misc_feature         1..25
                     note = source = /note="Description of Artificial Sequence:
                     Syntheticoligonucleotide"
misc_feature         1..25
                     note = source = /note="SGN001101 target sequence"
source               1..25
                     mol_type = other DNA
                     organism = synthetic construct
SEQUENCE: 563
atattttctt taatggtgcc aggca                                          25

SEQ ID NO: 564       moltype = RNA  length = 130
FEATURE              Location/Qualifiers
misc_feature         1..130
                     note = source = /note="Description of Artificial Sequence:
                     Syntheticpolynucleotide"
misc_feature         1..130
                     note = source = /note="SGN001101 sgRNA sequence"
source               1..130
                     mol_type = other RNA
                     organism = synthetic construct
SEQUENCE: 564
atattttctt taatggtgcc aggcagtcat agttccatta aagccaaaag tggctttgat    60
gtttctatga taagggtttc gacccgtggc gtcgggatc gcctgcccat tgaaatgggc   120
ttctccccat                                                          130
```

DNA MODIFYING ENZYMES AND ACTIVE FRAGMENTS AND VARIANTS THEREOF AND METHODS OF USE

CROSS-REFERENCE TO RELATED APPLICATIONS

This application is a divisional of U.S. application Ser. No. 17/929,162, filed Sep. 1, 2022, now U.S. Pat. No. 11,981,940, which is a continuation of U.S. application Ser. No. 17/851,880 filed Jun. 28, 2022, which is a continuation of International Application No. PCT/US2021/049853, filed Sep. 10, 2021, which claims priority to U.S. Provisional Application Nos. 63/077,089, filed Sep. 11, 2020, and 63/146,840, filed Feb. 8, 2021, each of which application is incorporated by reference herein in its entirety.

STATEMENT REGARDING THE SEQUENCE LISTING

The Sequence Listing associated with this application is provided in ST.26 (XML) format in lieu of a paper copy, and is hereby incorporated by reference into the specification. The XML copy named L103438_1230US_Seq_List.xml is 1,159,840 bytes in size, was created on Jun. 28, 2024, and is being submitted electronically via EFS-Web.

FIELD OF THE INVENTION

The present invention relates to the field of molecular biology and gene editing.

BACKGROUND OF THE INVENTION

Targeted genome editing or modification is rapidly becoming an important tool for basic and applied research. Initial methods involved engineering nucleases such as meganucleases, zinc finger fusion proteins or TALENs, requiring the generation of chimeric nucleases with engineered, programmable, sequence-specific DNA-binding domains specific for each particular target sequence. RNA-guided nucleases (RGNs), such as the Clustered Regularly Interspaced Short Palindromic Repeats (CRISPR)-associated (Cas) proteins of the CRISPR-Cas bacterial system, allow for the targeting of specific sequences by complexing the nucleases with guide RNA that specifically hybridizes with a particular target sequence. Producing target-specific guide RNAs is less costly and more efficient than generating chimeric nucleases for each target sequence. Such RNA-guided nucleases can be used to edit genomes through the introduction of a sequence-specific, double-stranded break that is repaired via error-prone non-homologous end-joining (NHEJ) to introduce a mutation at a specific genomic location.

Additionally, RGNs are useful for targeted DNA editing approaches. Targeted editing of nucleic acid sequences, for example targeted cleavage, to allow for introduction of a specific modification into genomic DNA, enables a highly nuanced approach to studying gene function and gene expression. RGNs may also be used to generate chimeric proteins which use the RNA-guided activity of the RGN in combination with a DNA modifying enzyme, such as a deaminase, for targeted base editing. Targeted editing may be deployed for targeting genetic diseases in humans or for introducing agronomically beneficial mutations in the genomes of crop plants. The development of genome editing tools provides new approaches to gene editing-based mammalian therapeutics and agrobiotechnology.

BRIEF SUMMARY OF THE INVENTION

Compositions and methods for modifying a target DNA molecule are provided. The compositions find use in modifying a target DNA molecule of interest. Compositions provided comprise deaminase polypeptides. Also provided are fusion proteins comprising a nucleic acid molecule-binding polypeptide (e.g., DNA-binding polypeptide) and a deaminase polypeptide, and ribonucleoprotein complexes comprising a fusion protein comprising an RNA-guided nuclease and a deaminase polypeptide and ribonucleic acids. Compositions provided also include nucleic acid molecules encoding the deaminase polypeptides or the fusion proteins, and vectors and host cells comprising the nucleic acid molecules. The methods disclosed herein are drawn to binding a target sequence of interest within a target DNA molecule of interest and modifying the target DNA molecule of interest.

DETAILED DESCRIPTION

Many modifications and other embodiments of the inventions set forth herein will come to mind to one skilled in the art to which these inventions pertain having the benefit of the teachings presented in the foregoing descriptions. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

I. Overview

This disclosure provides novel adenine deaminases and fusion proteins that comprise a nucleic acid molecule-binding polypeptide, such as a DNA-binding polypeptide, and a novel deaminase polypeptide. In certain embodiments, the DNA-binding polypeptide is a sequence-specific DNA-binding polypeptide, in that the DNA-binding polypeptide binds to a target sequence at a greater frequency than binding to a randomized background sequence. In some embodiments, the DNA-binding polypeptide is or is derived from a meganuclease, zinc finger fusion protein, or TALEN. In some embodiments, the fusion protein comprises an RNA-guided DNA-binding polypeptide and a deaminase polypeptide. In some embodiments, the RNA-guided DNA-binding polypeptide is an RNA-guided nuclease, such as a Cas9 polypeptide domain that binds to a guide RNA (also referred to as gRNA), which, in turn, binds a target nucleic acid sequence via strand hybridization.

The deaminase polypeptides disclosed herein can deaminate a nucleobase, such as, for example, adenine. The deamination of a nucleobase by a deaminase can lead to a point mutation at the respective residue, which is referred to herein as "nucleic acid editing", or "base editing". Fusion proteins comprising an RNA-guided nuclease (RGN) polypeptide and a deaminase can thus be used for the targeted editing of nucleic acid sequences.

Such fusion proteins are useful for targeted editing of DNA in vitro, e.g., for the generation of genetically modified cells. These genetically modified cells may be plant cells or animal cells. Such fusion proteins may also be useful for the introduction of targeted mutations, e.g., for the correction of genetic defects in mammalian cells ex vivo, e.g., in cells obtained from a subject that are subsequently re-introduced into the same or another subject; and for the introduction of targeted mutations, e.g., the correction of genetic defects or the introduction of deactivating mutations in disease-associated genes in a mammalian subject. Such fusion proteins may also be useful for the introduction of targeted mutations in plant cells, e.g., for the introduction of beneficial or agronomically valuable traits or alleles.

The terms "protein," "peptide," and "polypeptide" are used interchangeably herein, and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof.

Any of the proteins provided herein may be produced by any method known in the art. For example, the proteins provided herein may be produced via recombinant protein expression and purification, which is especially suited for fusion proteins comprising a peptide linker. Methods for recombinant protein expression and purification are well known, and include those described by Green and Sambrook, *Molecular Cloning: A Laboratory Manual* (4th ed., Cold Spring Harbor Laboratory Press, Cold Spring Harbor, N.Y. (2012)), the entire contents of which are incorporated herein by reference.

II. Deaminases

The term "deaminase" refers to an enzyme that catalyzes a deamination reaction. The deaminases of the invention are nucleobase deaminases and the terms "deaminase" and "nucleobase deaminase" are used interchangeably herein. The deaminase may be a naturally-occurring deaminase enzyme or an active fragment or variant thereof. A deaminase may be active on single-stranded nucleic acids, such as ssDNA or ssRNA, or on double-stranded nucleic acids, such as dsDNA or dsRNA. In some embodiments, the deaminase is only capable of deaminating ssDNA and does not act on dsDNA.

The presently disclosed methods and compositions comprise an adenine deaminase. In some embodiments, the deaminase is an ADAT family deaminase or a variant thereof. Deamination of adenine, adenosine, or deoxyadenosine yields inosine, which is treated as guanine by polymerases. To date there are no known naturally occurring adenine deaminases that deaminate adenine in DNA. Several methods have been employed to evolve and optimize adenine deaminase acting on tRNA (ADAT) proteins to be active on DNA molecules in mammalian cells (Gaudelli et al, 2017; Koblan, L. W. et al, 2018, *Nat Biotechnol* 36, 843-846; Richter, M. F. et al, 2020, *Nat Biotechnol*, doi: 10.1038/s41587-020-0562-8, each of which are incorporated by reference in their entirety herein). One such method uses a bacterial selection assay where only cells with the ability to activate antibiotic resistance through A:T>G:C conversions are able to survive.

The present invention relates to novel adenine deaminase polypeptides which were produced through evolution and optimization of bacterial deaminases. Novel adenine deaminases are presently disclosed and set forth as SEQ ID NOs: 1-10 and 399-441. The deaminases of the invention may be used for editing of DNA or RNA molecules. In some embodiments, the deaminases of the invention may be used for editing of ssDNA or ssRNA molecules. The adenine deaminases described herein are useful as deaminases alone or as components in fusion proteins. A fusion protein comprising a DNA-targeting polypeptide and an adenine deaminase polypeptide is referred to herein as an "A-based editor", "adenine base editor", or an "ABE" and can be used for the targeted editing of nucleic acid sequences.

"Base editors" are fusion proteins comprising a DNA-targeting polypeptide, such as an RGN, and a deaminase. Adenine base editors (ABEs) comprise a DNA-targeting protein, such as an RGN, and an adenine deaminase. ABEs function through the deamination of adenine into inosine on a DNA target molecule (Gaudelli, N. M. et al. 2017). Inosine is recognized as a guanine by polymerases and allows for the incorporation of a cytosine on the complementary DNA strand across from the inosine. After a round of replication post-deamination, there is a resulting A:T to G:C base pair change in the genome. In some embodiments, the presently disclosed adenine deaminases or active variants or fragments thereof introduce A>N mutations in a DNA molecule, wherein N is C, G, or T. In further embodiments, they introduce A>G mutations in a DNA molecule.

In those embodiments wherein the deaminase has been targeted to a specific region of a nucleic acid molecule via fusion with a DNA-binding polypeptide, the mutation rate of adenines within or adjacent to the target sequence to which the DNA-binding polypeptide binds can be measured using any method known in the art, including polymerase chain reaction (PCR), restriction fragment length polymorphism (RFLP), or DNA sequencing.

The presently disclosed novel deaminases or active variants or fragments thereof that retain deaminase activity may be introduced into the cell as part of a deaminase-DNA-binding polypeptide fusion, and/or may be co-expressed with a DNA-binding polypeptide-deaminase fusion, to increase the efficiency of introducing the desired A>G mutation in a target DNA molecule. The presently disclosed deaminases have the amino acid sequence of any of SEQ ID NOs: 1-10 and 399-441 or a variant or fragment thereof retaining deaminase activity. In some embodiments, the deaminase has an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity to the amino acid sequence of any of SEQ ID NOs: 1-10 and 399-441. In particular embodiments, the deaminase comprises an amino acid sequence having at least 80% sequence identity to any one of SEQ ID NOs: 407, 405, 399, 1-10, 400-404, 406, and 408-441. In some embodiments, the deaminase comprises an amino acid sequence having at least 80% sequence identity to SEQ ID NO: 407. For example, the deaminase comprises an amino acid sequence having at least about 80% identity, at least about 90% identity, at least about 95% identity, at least about 96% identity, at least about 97% identity, at least about 98% identity, at least about 99% identity, at least about 99.5% identity, or at least about 99.9% identity to SEQ ID NO: 407. In some embodiments, the deaminase comprises an amino acid sequence having at least 80% identity, at least 90% identity, at least 95% identity, at least 96% identity, at least 97% identity, at least 98% identity, at least 99% identity, at least 99.5% identity, or at least 99.9% identity to SEQ ID NO: 407. In some embodiments, the deaminase comprises the amino acid sequence of SEQ ID NO: 407. In some embodiments, the deaminase comprises an amino acid sequence having at least 80% sequence identity to SEQ ID NO: 399. For example, the deaminase comprises an amino acid sequence having at least about 80% identity, at least about 90% identity, at least about 95% identity, at least about 96% identity, at least about 97% identity, at least about 98% identity, at least about 99% identity, at least about 99.5% identity, or at least about 99.9% identity to SEQ ID NO: 399. In some embodiments, the deaminase comprises an amino acid sequence having at least 80% identity, at least 90% identity, at least 95% identity, at least 96% identity, at least 97% identity, at least 98% identity, at least 99% identity, at least 99.5% identity, or at least 99.9% identity to SEQ ID NO: 399. In some embodiments, the deaminase comprises the amino acid sequence of SEQ ID NO: 399. In some embodiments, the deaminase comprises an amino acid sequence having at least 80% sequence identity to SEQ ID NO: 405. For example, the deaminase comprises an amino acid sequence having at least about 80% identity, at least about 90% identity, at least about 95% identity, at least about 96% identity, at least about 97% identity, at least about 98% identity, at least about 99% identity, at least about 99.5% identity, or at least about 99.9% identity to SEQ ID NO: 405. In some embodiments, the deaminase comprises an amino acid sequence having at least 80% identity, at least 90% identity, at least 95% identity, at least 96% identity, at least 97% identity, at least 98% identity, at least 99% identity, at least 99.5% identity, or at least 99.9% identity to SEQ ID NO: 405. In some embodiments, the deaminase comprises the amino acid sequence of SEQ ID NO: 405.

III. Nucleic Acid Molecule-Binding Polypeptides

Some aspects of this disclosure provide fusion proteins that comprise a nucleic acid molecule-binding polypeptide and a deaminase polypeptide. While binding to and targeted editing of RNA molecules is contemplated by the present invention, in some embodiments, the nucleic acid molecule-binding polypeptide of the fusion protein is a DNA-binding polypeptide. Such fusion proteins are useful for targeted editing of DNA in vitro, ex vivo, or in vivo. These novel fusion proteins are active in mammalian cells and are useful for targeted editing of DNA molecules.

The term "fusion protein" as used herein refers to a hybrid polypeptide which comprises protein domains from at least two different proteins. A fusion protein may comprise more than one different domain, for example, a DNA-binding domain and a deaminase. In some embodiments, a fusion protein is in a complex with, or is in association with, a nucleic acid, e.g., RNA.

In some embodiments, the presently disclosed fusion proteins comprise a DNA-binding polypeptide. As used herein, the term "DNA-binding polypeptide" refers to any polypeptide which is capable of binding to DNA. In certain embodiments, the DNA-binding polypeptide portion of the presently disclosed fusion proteins binds to double-stranded DNA. In particular embodiments, the DNA-binding polypeptide binds to DNA in a sequence-specific manner. As used herein, the terms "sequence-specific" or "sequence-specific manner" refer to the selective interaction with a specific nucleotide sequence.

Two polynucleotide sequences can be considered to be substantially complementary when the two sequences hybridize to each other under stringent conditions. Likewise, a DNA-binding polypeptide is considered to bind to a particular target sequence in a sequence-specific manner if the DNA-binding polypeptide binds to its sequence under stringent conditions. By "stringent conditions" or "stringent hybridization conditions" is intended conditions under which the two polynucleotide sequences (or the polypeptide binds to its specific target sequence) will bind to each other to a detectably greater degree than to other sequences (e.g., at least 2-fold over background). Stringent conditions are sequence-dependent and will be different in different circumstances. Typically, stringent conditions will be those in which the salt concentration is less than 1.5 M Na ion, typically about 0.01 to 1.0 M Na ion concentration (or other salts) at pH 7.0 to 8.3, and the temperature is at least 30° C. for short sequences (e.g., 10 to 50 nucleotides) and at least 60° C. for long sequences (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

The Tm is the temperature (under defined ionic strength and pH) at which 50% of a complementary target sequence hybridizes to a perfectly matched sequence. For DNA-DNA hybrids, the Tm can be approximated from the equation of Meinkoth and Wahl (1984) Anal. Biochem. 138:267-284: Tm=81.5° C. +16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. An extensive guide to the hybridization of nucleic acids is found in Tijssen (1993) Laboratory Techniques in Biochemistry and Molecular Biology-Hybridization with Nucleic Acid Probes, Part I, Chapter 2 (Elsevier, New York); and Ausubel et al., eds. (1995) Current Protocols in Molecular Biology, Chapter 2 (Greene Publishing and Wiley-Interscience, New York). See Sambrook et al. (1989) Molecular Cloning: A Laboratory Manual (2d ed., Cold Spring Harbor Laboratory Press, Plainview, New York).

In certain embodiments, the sequence-specific DNA-binding polypeptide is an RNA-guided, DNA-binding polypeptide (RGDBP). As used herein, the terms "RNA-guided, DNA-binding polypeptide" and "RGDBP" refer to polypeptides capable of binding to DNA through the hybridization of an associated RNA molecule with the target DNA sequence.

In some embodiments, the DNA-binding polypeptide of the fusion protein is a nuclease, such as a sequence-specific nuclease. As used herein, the term "nuclease" refers to an enzyme that catalyzes the cleavage of phosphodiester bonds between nucleotides in a nucleic acid molecule. In some embodiments, the DNA-binding polypeptide is an endonuclease, which is capable of cleaving phosphodiester bonds between nucleotides within a nucleic acid molecule, whereas in certain embodiments, the DNA-binding polypeptide is an exonuclease that is capable of cleaving the nucleotides at either end (5' or 3') of a nucleic acid molecule. In some embodiments, the sequence-specific nuclease is selected from the group consisting of a meganuclease, a zinc finger nuclease, a TAL-effector DNA binding domain-nuclease fusion protein (TALEN), and an RNA-guided nuclease (RGN) or variants thereof wherein the nuclease activity has been reduced or inhibited.

As used herein, the term "meganuclease" or "homing endonuclease" refers to endonucleases that bind a recognition site within double-stranded DNA that is 12 to 40 bp in length. Non-limiting examples of meganucleases are those that belong to the LAGLIDADG family that comprise the conserved amino acid motif LAGLIDADG (SEQ ID NO: 49). The term "meganuclease" can refer to a dimeric or single-chain meganuclease.

As used herein, the term "zinc finger nuclease" or "ZFN" refers to a chimeric protein comprising a zinc finger DNA-binding domain and a nuclease domain.

As used herein, the term "TAL-effector DNA binding domain-nuclease fusion protein" or "TALEN" refers to a chimeric protein comprising a TAL effector DNA-binding domain and a nuclease domain.

As used herein, the term "RNA-guided nuclease" or "RGN" refers to an RNA-guided, DNA-binding polypeptide that has nuclease activity. RGNs are considered "RNA-guided" because guide RNAs form a complex with the RNA-guided nucleases to direct the RNA-guided nuclease to bind to a target sequence and in some embodiments, introduce a single-stranded or double-stranded break at the target sequence. The RGN may be a CasX, a CasY, a C2c1, a C2c2, a C2c3, a GeoCas9, aSpCas9, a SaCas9, a Nme2Cas9, a CjCas9, a Cas12a (formerly known as Cpf1), a Cas12b, a Cas12g, a Cas12h, a Cas12i, aLbCas12a, a AsCas12a, a CasMINI, a Cas13b, a Cas13c, a Cas13d, a Cas14, a Csn2, an xCas9, an SpCas9-NG, an LbCas12a, an AsCas12a, a Cas9-KKH, a circularly permuted Cas9, an Argonaute (Ago), a SmacCas9, or a Spy-macCas9, a Spy-macCas9 domain, or a RGN with an amino acid sequence set forth in any one of SEQ ID NOs: 41, 60, 366, or 368. In some embodiments, as described below, the RGNs provided herein are RGN nickases.

According to the present invention, an RGN protein that has been mutated to become nuclease-inactive or "dead", such as for example dCas9, can be referred to as an RNA-guided, DNA-binding polypeptide or a nuclease-inactive RGN or nuclease-dead RGN. Additionally, suitable nuclease-inactive Cas9 domains of other known RNA guided nucleases (RGNs) can be determined (for example, a nuclease-inactive variant of the RGN APG08290.1 disclosed in U.S. Patent Publication No. 2019/0367949, the entire contents of which are incorporated herein by reference herein).

In some embodiments, the fusion protein comprises an RGN fused to a deaminase described herein. In those embodiments of fusion proteins described above, the deaminase is selected from deaminases comprising an amino acid sequence having at least 80% sequence identity to any one of SEQ ID NOs: 1-10 and 399-441. In some embodiments, the deaminase comprises an amino acid sequence having at least 80% sequence identity to SEQ ID NO: 407. In some embodiments, the deaminase comprises an amino acid sequence having at least 80% sequence identity to SEQ ID NO: 399. In some embodiments, the deaminase comprises an amino acid sequence having at least 80% sequence identity to SEQ ID NO: 405. In those embodiments of fusion proteins described above, the RGN is selected from a CasX, a CasY, a C2c1, a C2c2, a C2c3, a GeoCas9, aSpCas9, a SaCas9, a Nme2Cas9, a CjCas9, a Cas12a (formerly known as Cpf1), a Cas12b, a Cas12g, a Cas12h, a Cas12i, aLbCas12a, a AsCas12a, a CasMINI, a Cas13b, a Cas13c, a Cas13d, a Cas14, a Csn2, an xCas9, an SpCas9-NG, an LbCas12a, an AsCas12a, a Cas9-KKH, a circularly permuted Cas9, an Argonaute (Ago), a SmacCas9, a Spy-macCas9, a Spy-macCas9 domain, or an RGN with an amino acid sequence set forth in any one of SEQ ID NOs: 41, 60, 366, or 368. In particular embodiments, the fusion protein comprises a Cas9 nickase fused to a deaminase comprising an amino acid sequence having at least 80% sequence identity to SEQ ID NO: 407. In some embodiments, the fusion protein comprises a Cas9 nickase fused to a deaminase comprising an amino acid sequence having at least 80% sequence identity to SEQ ID NO: 399. In particular embodiments, the fusion protein comprises a Cas9 nickase fused to a deaminase comprising an amino acid sequence having at least 80% sequence identity to SEQ ID NO: 405. The Cas9 nickase, can be any Cas9 nickase disclosed in PCT Patent Publication No. WO2020181195, the entire contents of which is incorporated herein by reference herein.

The term "RGN polypeptide" encompasses RGN polypeptides that only cleave a single strand of a target nucleotide sequence, which is referred to herein as a nickase. Such RGNs have a single functioning nuclease domain. RGN nickases can be naturally-occurring nickases or can be RGN proteins that naturally cleave both strands of a double-stranded nucleic acid molecule that have been mutated within one or more nuclease domains such that the nuclease activity of these mutated domains is reduced or eliminated, to become a nickase. In some embodiments, the nickase RGN of the fusion protein comprises a mutation (e.g., a D10A mutation) which renders the RGN capable of cleaving only the non-base edited, target strand (the strand which comprises the PAM and is base paired to a gRNA) of a nucleic acid duplex. This D10A mutation mutates the first aspartic acid residue in the split RuvC nuclease domain of the RGN. The present application discloses several D10A nickase variants or homologous nickase variants of described RGNs (see Example 4). nAPG07433.1 and nAPG08290.1 (set forth as SEQ ID NOs: 42 and 61, respectively) are nickase variants of APG07433.1 and APG08290.1, which are set forth as SEQ ID NO: 41 and 60, respectively, and are described in WO 2019/236566 (incorporated by reference in its entirety herein). nAPG00969 (set for as SEQ ID NO: 52) and nAPG09748 (set forth as SEQ ID NO: 54) are nickase variants of APG00969 and APG09748, respectively, which are described in WO 2020/139783 (incorporated by reference in its entirety herein). nAPG06646 (set forth as SEQ ID NO: 53) and nAPG09882 (set forth as SEQ ID NO: 55) are nickase variants of APG06646 and APG09882, respectively, which are described in PCT publication WO 2021/030344 (incorporated by reference in its entirety herein). nAPG03850, nAPG07553, nAPG055886, and nAPG01604 are set forth as SEQ ID NOs: 56-59, respectively, and are nickase variants of APG03850, APG07553, APG055886, and APG01604 which are described in the pending PCT Application No. PCT/US2021/028843 (incorporated by reference in its entirety herein). Various RGN nickases, their variants and their sequences are disclosed in PCT Patent Publication No. WO2020181195, the entire contents of which are incorporated herein by reference herein. One exemplary suitable nuclease-inactive Cas9 is the D10A/H840A Cas9 mutant (see, e.g., Qi et al., *Cell*. 2013; 152(5): 1173-83, the entire contents of which are incorporated herein by reference).

In some embodiments, the nickase RGN of the fusion protein comprises a mutation (e.g., a H840A mutation), which renders the RGN capable of cleaving only the base-edited, non-targeted strand (the strand which does not comprise the PAM and is not base paired to a gRNA) of a nucleic acid duplex. The H840A mutation mutates the first histidine of the HNH nuclease domain. A nickase RGN comprising an H840A mutation, or an equivalent mutation, has an inactivated HNH domain. A nickase RGN with an H840A mutation cleaves the non-targeted strand. A nickase comprising a D10A mutation, or an equivalent mutation, has an inactivated RuvC nuclease domain and cleaves the targeted strand. D10A nickases are not able to cleave the non-targeted strand of the DNA, i.e., the strand where base editing is desired.

Other additional exemplary suitable nuclease inactive Cas9 domains include, but are not limited to, D10A/D839A/H840A, and D10A/D839A/H840A/N863A mutant domains (See, e.g., Mali et al., *Nature Biotechnology*. 2013; 31(9): 833-838, the entire contents of which are incorporated herein by reference). Additional suitable RGN proteins mutated to be nickases will be apparent to those of skill in the art based on this disclosure and knowledge in the field (such as for example the RGNs disclosed in PCT Publication Nos. WO 2019/236566, WO2020181195, which are herein incorporated by reference in their entirety) and are within the scope of this disclosure. In preferred embodiments, an RGN which has nickase activity on the target strand nicks the target strand, while the complementary, non-target strand is modified by the deaminase. Cellular DNA-repair machinery may repair the nicked, target strand using the modified non-target strand as a template, thereby introducing a mutation in the DNA.

In some embodiments the RGN nickase retaining nickase activity comprises an amino acid sequence that has at least 60%, at least 65%, at least 70%, at least 75%, at least 80%, at least 85%, at least 90%, at least 95%, at least 96%, at least 97%, at least 98%, at least 99%, or at least 99.5% identity to SEQ ID NO: 42 or any one of SEQ ID NOs: 52-59, 61, 397, and 398.

Any method known in the art for introducing mutations into an amino acid sequence, such as PCR-mediated mutagenesis and site-directed mutagenesis, can be used for generating nickases or nuclease-dead RGNs. See, e.g., U.S. Publ. No. 2014/0068797 and U.S. Pat. No. 9,790,490; each of which is incorporated herein by reference in its entirety. RNA-guided nucleases (RGNs) allow for the targeted manipulation of a single site within a genome and are useful in the context of gene targeting for therapeutic and research applications. In a variety of organisms, including mammals, RNA-guided nucleases have been used for genome engineering by stimulating either non-homologous end joining or homologous recombination. RGNs include CRISPR-Cas proteins, which are RNA-guided nucleases directed to the target sequence by a guide RNA (gRNA) as part of a Clustered Regularly Interspaced Short Palindromic Repeats (CRISPR) RNA-guided nuclease system, or active variants or fragments thereof.

Further provided herein are RGN polypeptides (and nucleic acid molecules encoding RGN polypeptides) that comprise the amino acid sequence set forth as SEQ ID NO: 41 or 60, but lacking amino acid residues 590 to 597 of SEQ ID NO: 41 or 60, or an active variant or fragment thereof. In certain embodiments, the RGN polypeptide comprises the amino acid sequence set forth as SEQ ID NO: 366, 368, 397, or 398 or an active variant or fragment thereof.

Some aspects of this disclosure provide fusion proteins that comprise an RNA-guided DNA-binding polypeptide and a deaminase polypeptide, specifically an adenine deaminase polypeptide. In some embodiments, the RNA-guided DNA-binding polypeptide is an RNA-guided nuclease. In further embodiments, the RNA-guided nuclease is a naturally-occurring CRISPR-Cas protein or an active variant or fragment thereof. CRISPR-Cas systems are classified into Class 1 or Class 2 systems. Class 2 systems comprise a single effector nuclease and include Types II, V, and VI. The Class 1 and 2 systems are subdivided into types (Types I, II, III, IV, V, VI), with some types further divided into subtypes (e.g., Type II-A, Type II-B, Type II-C, Type V-A, Type V-B).

In certain embodiments, the CRISPR-Cas protein is a naturally-occurring Type II CRISPR-Cas protein or an active variant or fragment thereof. As used herein, the term "Type II CRISPR-Cas protein," "Type II CRISPR-Cas effector protein," or "Cas9" refers to a CRISPR-Cas effector protein that requires a trans-activating RNA (tracrRNA) and comprises two nuclease domains (i.e., RuvC and HNH), each of which is responsible for cleaving a single strand of a double-stranded DNA molecule. In some embodiments, the present invention provides a fusion protein comprising a presently disclosed deaminase fused to *Streptococcus pyogenes* Cas9 (SpCas9) or a SpCas9 nickase, the sequences of which are set forth as SEQ ID NOs: 555 and 556, respectively, and are described in U.S. Pat. Nos. 10,000,772 and 8,697,359, each of which is herein incorporated by reference in its entirety. In some embodiments, the present invention provides a fusion protein comprising a presently disclosed deaminase fused to *Streptococcus thermophilus* Cas9 (StCas9) or a StCas9 nickase, the sequences of which are set forth as SEQ ID NOs: 557 and 558, respectively, and are disclosed in U.S. Pat. No. 10,113,167, which is herein incorporated by reference in its entirety. In some embodiments, the present invention provides a fusion protein comprising a presently disclosed deaminase fused to *Streptococcus aureus* Cas9 (SaCas9) or a SaCas9 nickase, the sequences of which are set forth as SEQ ID NOs: 559 and 560, respectively, and are disclosed in U.S. Pat. No. 9,752,132, which is herein incorporated by reference in its entirety.

In some embodiments, the CRISPR-Cas protein is a naturally-occurring Type V CRISPR-Cas protein or an active variant or fragment thereof. As used herein, the term "Type V CRISPR-Cas protein," "Type V CRISPR-Cas effector protein," or "Cas12" refers to a CRISPR-Cas effector protein that cleaves dsDNA and comprises a single RuvC nuclease domain or a split-RuvC nuclease domain and lacks an HNH domain (Zetsche et al 2015, *Cell* doi:10.1016/j.cell.2015.09.038; Shmakov et al 2017, *Nat Rev Microbiol* doi:10.1038/nrmicro.2016.184; Yan et al 2018, *Science* doi:10.1126/science.aav7271; Harrington et al 2018, *Science* doi:10.1126/science.aav4294). It is to be noted that Cas12a is also referred to as Cpf1, and does not require a tracrRNA, although other Type V CRISPR-Cas proteins, such as Cas12b, do require a tracrRNA. Most Type V effectors can also target ssDNA (single-stranded DNA), often without a PAM requirement (Zetsche et al 2015; Yan et al 2018; Harrington et al 2018). The term "Type V CRISPR-Cas protein" encompasses the unique RGNs comprising split RuvC nuclease domains, such as those disclosed in U.S. Provisional Appl. Nos. 62/955,014 filed Dec. 30, 2019 and 63/058,169 filed Jul. 29, 2020, and PCT International Appl. No. PCT/US2020/067138 filed Dec. 28, 2020, the contents of each of which are incorporated herein by reference in its entirety. In some embodiments, the present invention provides a fusion protein comprising a presently disclosed deaminase fused to *Francisella novicida* Cas12a (FnCas12a), the sequence of which is set forth as SEQ ID NOs: 561 and is disclosed in U.S. Pat. No. 9,790,490, which is herein incorporated by reference in its entirety, or any of the nuclease-inactivating mutants of FnCas12a disclosed within U.S. Pat. No. 9,790,490.

In some embodiments, the CRISPR-Cas protein is a naturally-occurring Type VI CRISPR-Cas protein or an active variant or fragment thereof. As used herein, the term "Type VI CRISPR-Cas protein," "Type VI CRISPR-Cas effector protein," or "Cas13" refers to a CRISPR-Cas effector protein that does not require a tracrRNA and comprises two HEPN domains that cleave RNA.

The term "guide RNA" refers to a nucleotide sequence having sufficient complementarity with a target nucleotide sequence to hybridize with the target sequence and direct sequence-specific binding of an associated RGN to the target nucleotide sequence. For CRISPR-Cas RGNs, the respective guide RNA is one or more RNA molecules (generally, one or two), that can bind to the RGN and guide the RGN to bind to a particular target nucleotide sequence, and in those instances wherein the RGN has nickase or nuclease activity, also cleave the target nucleotide sequence. A guide RNA comprises a CRISPR RNA (crRNA) and in some embodiments, a trans-activating CRISPR RNA (tracrRNA).

A CRISPR RNA comprises a spacer sequence and a CRISPR repeat sequence. The "spacer sequence" is the nucleotide sequence that directly hybridizes with the target nucleotide sequence of interest. The spacer sequence is engineered to be fully or partially complementary with the target sequence of interest. In various embodiments, the spacer sequence comprises from about 8 nucleotides to about 30 nucleotides, or more. For example, the spacer sequence can be about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, or more nucleotides in length. In some embodiments, the spacer sequence is 8, 9, 10, 11, 12, 13, 14, 15, 16, 17, 18, 19, 20, 21, 22, 23, 24, 25, 26, 27, 28, 29, 30, or more nucleotides in length. In some embodiments, the spacer sequence is about 10 to about 26 nucleotides in length, or about 12 to about 30 nucleotides in length. In some embodiments, the spacer sequence is 10 to 26 nucleotides in length, or 12 to 30 nucleotides in length. In particular embodiments, the spacer sequence is about 30 nucleotides in length. In particular embodiments, the spacer sequence is 30 nucleotides in length. In some embodiments, the degree of complementarity between a spacer sequence and its corresponding target sequence, when optimally aligned using a suitable alignment algorithm, is between 50% and 99% or more, including but not limited to about or more than about 50%, about 60%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or more. In particular embodiments, the degree of complementarity between a spacer sequence and its corresponding target sequence, when optimally aligned using a suitable alignment algorithm, is 50%, 60%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or more. In particular embodiments, the spacer sequence is free of secondary structure, which can be predicted using any suitable polynucleotide folding algorithm known in the art, including but not limited to mFold (see, e.g., Zuker and Stiegler (1981) *Nucleic Acids Res.* 9:133-148) and RNAfold (see, e.g., Gruber et al. (2008) *Cell* 106(1):23-24).

The CRISPR RNA repeat sequence comprises a nucleotide sequence that forms a structure, either on its own or in concert with a hybridized tracrRNA, that is recognized by the RGN molecule. In various embodiments, the CRISPR RNA repeat sequence comprises from about 8 nucleotides to about 30 nucleotides, or more. In particular embodiments, the CRISPR RNA repeat sequence comprises from 8 nucleotides to 30 nucleotides, or more. For example, the CRISPR repeat sequence can be about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, or more nucleotides in length. In particular embodiments, the CRISPR repeat sequence is 8, 9, 10, 11, 12, 13, 14, 15, 16, 17, 18, 19, 20, 21, 22, 23, 24, 25, 26, 27, 28, 29, 30, or more nucleotides in length. In some embodiments, the degree of complementarity between a CRISPR repeat sequence and its corresponding tracrRNA sequence, when optimally aligned using a suitable alignment algorithm, is between 50% and 99%, or more, including but not limited to about or more than about 50%, about 60%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or more. In particular embodiments, the degree of complementarity between a CRISPR repeat sequence and its corresponding tracrRNA sequence, when optimally aligned using a suitable alignment algorithm, is 50%, 60%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or more.

In some embodiments, the guide RNA further comprises a tracrRNA molecule. A trans-activating CRISPR RNA or tracrRNA molecule comprises a nucleotide sequence comprising a region that has sufficient complementarity to hybridize to a CRISPR repeat sequence of a crRNA, which is referred to herein as the anti-repeat region. In some embodiments, the tracrRNA molecule further comprises a region with secondary structure (e.g., stem-loop) or forms secondary structure upon hybridizing with its corresponding crRNA. In particular embodiments, the region of the tracrRNA that is fully or partially complementary to a CRISPR repeat sequence is at the 5' end of the molecule and the 3' end of the tracrRNA comprises secondary structure. This region of secondary structure generally comprises several hairpin structures, including the *nexus* hairpin, which is found adjacent to the anti-repeat sequence. There are often terminal hairpins at the 3' end of the tracrRNA that can vary in structure and number, but often comprise a GC-rich Rho-independent transcriptional terminator hairpin followed by a string of Us at the 3' end. See, for example, Briner et al. (2014) *Molecular Cell* 56:333-339, Briner and Barrangou (2016) *Cold Spring Harb Protoc*; doi: 10.1101/pdb.top090902, and U.S. Publication No. 2017/0275648, each of which is herein incorporated by reference in its entirety.

In various embodiments, the anti-repeat region of the tracrRNA that is fully or partially complementary to the CRISPR repeat sequence comprises from about 6 nucleotides to about 30 nucleotides, or more. For example, the region of base pairing between the tracrRNA anti-repeat sequence and the CRISPR repeat sequence can be about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, or more nucleotides in length. In particular embodiments, the region of base pairing between the tracrRNA anti-repeat sequence and the CRISPR repeat sequence is 6, 7, 8, 9, 10, 11, 12, 13, 14, 15, 16, 17, 18, 19, 20, 21, 22, 23, 24, 25, 26, 27, 28, 29, 30, or more nucleotides in length. In particular embodiments, the anti-repeat region of the tracrRNA that is fully or partially complementary to a CRISPR repeat sequence is about 10 nucleotides in length. In particular embodiments, the anti-repeat region of the tracrRNA that is fully or partially complementary to a CRISPR repeat sequence is 10 nucleotides in length. In some embodiments, the degree of complementarity between a CRISPR repeat sequence and its corresponding tracrRNA anti-repeat sequence, when optimally aligned using a suitable alignment algorithm, is between 50% and 99% or more, including but not limited to about or more than about 50%, about 60%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or more. In particular embodiments, the degree of complementarity between a CRISPR repeat sequence and its corresponding tracrRNA anti-repeat sequence, when optimally aligned using a suitable alignment algorithm, is 50%, 60%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or more.

In various embodiments, the entire tracrRNA comprises from about 60 nucleotides to more than about 210 nucleotides. In particular embodiments, the entire tracrRNA comprises from 60 nucleotides to more than 210 nucleotides. For example, the tracrRNA can be about 60, about 65, about 70, about 75, about 80, about 85, about 90, about 95, about 100, about 105, about 110, about 115, about 120, about 125, about 130, about 135, about 140, about 150, about 160, about 170, about 180, about 190, about 200, about 210 or more nucleotides in length. In particular embodiments, the tracrRNA is 60, 65, 70, 75, 80, 85, 90, 95, 100, 105, 110, 115, 120, 125, 130, 135, 140, 150, 160, 170, 180, 190, 200, 210 or more nucleotides in length. In particular embodiments, the tracrRNA is about 100 to about 210 nucleotides in length, including about 95, about 96, about 97, about 98, about 99, about 100, about 105, about 106, about 107, about 108, about 109, and about 100 nucleotides in length. In particular embodiments, the tracrRNA is 100 to 110 nucleotides in length, including 95, 96, 97, 98, 99, 100, 105, 106, 107, 108, 109, and 110 nucleotides in length.

Guide RNAs form a complex with an RNA-guided, DNA-binding polypeptide or an RNA-guided nuclease to direct the RNA-guided nuclease to bind to a target sequence. If the guide RNA complexes with an RGN, the bound RGN introduces a single-stranded or double-stranded break at the target sequence. After the target sequence has been cleaved, the break can be repaired such that the DNA sequence of the target sequence is modified during the repair process. Provided herein are methods for using mutant variants of RNA-guided nucleases, which are either nuclease inactive or nickases, which are linked to deaminases to modify a target sequence in the DNA of host cells. The mutant variants of RNA-guided nucleases in which the nuclease activity is inactivated or significantly reduced may be referred to as RNA-guided, DNA-binding polypeptides, as the polypeptides are capable of binding to, but not necessarily cleaving, a target sequence. RNA-guided nucleases only capable of cleaving a single strand of a double-stranded nucleic acid molecule are referred to herein as nickases.

A target nucleotide sequence is bound by an RNA-guided, DNA-binding polypeptide and hybridizes with the guide RNA associated with the RGDBP. The target sequence can then be subsequently cleaved if the RGDBP possesses nuclease activity (i.e., is an RGN), which encompasses activity as a nickase.

The guide RNA can be a single guide RNA or a dual-guide RNA system. A single guide RNA comprises the crRNA and optionally tracrRNA on a single molecule of RNA, whereas a dual-guide RNA system comprises a crRNA and a tracrRNA present on two distinct RNA molecules, hybridized to one another through at least a portion of the CRISPR repeat sequence of the crRNA and at least a portion of the tracrRNA, which may be fully or partially complementary to the CRISPR repeat sequence of the crRNA. In some of those embodiments wherein the guide RNA is a single guide RNA, the crRNA and optionally tracrRNA are separated by a linker nucleotide sequence.

In general, the linker nucleotide sequence is one that does not include complementary bases in order to avoid the formation of secondary structure within or comprising nucleotides of the linker nucleotide sequence. In some embodiments, the linker nucleotide sequence between the crRNA and tracrRNA is at least 3, at least 4, at least 5, at least 6, at least 7, at least 8, at least 9, at least 10, at least 11, at least 12, or more nucleotides in length. In particular embodiments, the linker nucleotide sequence between the crRNA and tracrRNA is 3, 4, 5, 6, 7, 8, 9, 10, 11, 12, or more nucleotides in length. In particular embodiments, the linker nucleotide sequence of a single guide RNA is at least 4 nucleotides in length. In particular embodiments, the linker nucleotide sequence of a single guide RNA is 4 nucleotides in length.

In certain embodiments, the guide RNA can be introduced into a target cell, organelle, or embryo as an RNA molecule. The guide RNA can be transcribed in vitro or chemically synthesized. In some embodiments, a nucleotide sequence encoding the guide RNA is introduced into the cell, organelle, or embryo. In some embodiments, the nucleotide sequence encoding the guide RNA is operably linked to a promoter (e.g., an RNA polymerase III promoter). The promoter can be a native promoter or heterologous to the guide RNA-encoding nucleotide sequence.

In various embodiments, the guide RNA can be introduced into a target cell, organelle, or embryo as a ribonucleoprotein complex, as described herein, wherein the guide RNA is bound to an RNA-guided nuclease polypeptide.

The guide RNA directs an associated RNA-guided nuclease to a particular target nucleotide sequence of interest through hybridization of the guide RNA to the target nucleotide sequence. A target nucleotide sequence can comprise DNA, RNA, or a combination of both and can be single-stranded or double-stranded. A target nucleotide sequence can be genomic DNA (i.e., chromosomal DNA), plasmid DNA, or an RNA molecule (e.g., messenger RNA, ribosomal RNA, transfer RNA, micro RNA, small interfering RNA). The target nucleotide sequence can be bound (and in some embodiments, cleaved) by an RNA-guided, DNA-binding polypeptide in vitro or in a cell. The chromosomal sequence targeted by the RGDBP can be a nuclear, plastid or mitochondrial chromosomal sequence. In some embodiments, the target nucleotide sequence is unique in the target genome.

In some embodiments, the target nucleotide sequence is adjacent to a protospacer adjacent motif (PAM). A PAM is generally within about 1 to about 10 nucleotides from the target nucleotide sequence, including about 1, about 2, about 3, about 4, about 5, about 6, about 7, about 8, about 9, or about 10 nucleotides from the target nucleotide sequence. In particular embodiments, a PAM is within 1 to 10 nucleotides from the target nucleotide sequence, including 1, 2, 3, 4, 5, 6, 7, 8, 9, or 10 nucleotides from the target nucleotide sequence. The PAM can be 5' or 3' of the target sequence. In some embodiments, the PAM is 3' of the target sequence. Generally, the PAM is a consensus sequence of about 2-6 nucleotides, but in particular embodiments, is 1, 2, 3, 4, 5, 6, 7, 8, 9, or more nucleotides in length.

The PAM restricts which sequences a given RGDBP or RGN can target, as its PAM needs to be proximal to the target nucleotide sequence. Upon recognizing its corresponding PAM sequence, the RGN can cleave the target nucleotide sequence at a specific cleavage site. As used herein, a cleavage site is made up of the two particular nucleotides within a target nucleotide sequence between which the nucleotide sequence is cleaved by an RGN. The cleavage site can comprise the $1^{st}$ and $2^{nd}$, $2^{nd}$ and $3^{rd}$, $3^{rd}$ and $4^{th}$, $4^{th}$ and $5^{th}$, $5^{th}$ and $6^{th}$, $7^{th}$ and $8^{th}$ or $8^{th}$ and $9^{th}$ nucleotides from the PAM in either the 5' or 3' direction. As RGNs can cleave a target nucleotide sequence resulting in staggered ends, in some embodiments, the cleavage site is defined based on the distance of the two nucleotides from the PAM on the positive (+) strand of the polynucleotide and the distance of the two nucleotides from the PAM on the negative (−) strand of the polynucleotide.

RGDBPs and RGNs can be used to deliver a fused polypeptide, polynucleotide, or small molecule payload to a particular genomic location.

In those embodiments wherein the DNA-binding polypeptide comprises a meganuclease, a target sequence can comprise a pair of inverted, 9 basepair "half sites" which are separated by four basepairs. In the case of a single-chain meganuclease, the N-terminal domain of the protein contacts a first half-site and the C-terminal domain of the protein contacts a second half-site. Cleavage by a meganuclease produces four basepair 3' overhangs. In those embodiments wherein the DNA-binding polypeptide comprises a compact TALEN, the recognition sequence comprises a first CNNNGN sequence that is recognized by the I-TevI domain, followed by a non-specific spacer 4-16 basepairs in length, followed by a second sequence 16-22 bp in length that is recognized by the TAL-effector domain (this sequence typically has a 5' T base). In those embodiments wherein the DNA-binding polypeptide comprises a zinc finger, the DNA binding domains typically recognize an 18-bp recognition sequence comprising a pair of nine base-pair "half-sites" separated by 2-10 basepairs and cleavage by the nuclease creates a blunt end or a 5' overhang of variable length (frequently four basepairs).

IV. Fusion Proteins

In some embodiments, a DNA-binding polypeptide (e.g., nuclease-inactive or a nickase RGN) is operably linked to a deaminase of the invention. In some embodiments, a DNA-binding polypeptide (e.g., nuclease inactive RGN or nickase RGN) fused to a deaminase of the invention can be targeted to a particular location of a nucleic acid molecule (i.e., target nucleic acid molecule), which in some embodiments is a particular genomic locus, to alter the expression of a desired sequence. In some embodiments, the binding of a fusion protein to a target sequence results in deamination of a nucleobase, resulting in conversion from one nucleobase to another. In some embodiments, the binding of this fusion protein to a target sequence results in deamination of a nucleobase adjacent to the target sequence. The nucleobase adjacent to the target sequence that is deaminated and mutated using the presently disclosed compositions and methods may be 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 base pairs from the 5' or 3' end of the target sequence (bound by the gRNA) within the target nucleic acid molecule. Some aspects of this disclosure provide fusion proteins comprising (i) a DNA-binding polypeptide (e.g., a nuclease-inactive or nickase RGN polypeptide); (ii) a deaminase polypeptide; and optionally (iii) a second deaminase. The second deaminase may be the same deaminase as the first or may be a different deaminase. In some embodiments, both the first and the second deaminase are adenine deaminases of the invention.

The instant disclosure provides fusion proteins of various configurations. In some embodiments, the deaminase polypeptide is fused to the N-terminus of the DNA-binding polypeptide (e.g., RGN polypeptide). In some embodiments, the deaminase polypeptide is fused to the C-terminus of the DNA-binding polypeptide (e.g., RGN polypeptide).

In some embodiments, the deaminase and DNA-binding polypeptide (e.g., RNA-guided, DNA-binding polypeptide) are fused to each other via a peptide linker. The linker between the deaminase and DNA-binding polypeptide (e.g., RNA-guided, DNA-binding polypeptide) can determine the editing window of the fusion protein, thereby increasing deaminase specificity and reducing off-target mutations. Various linker lengths and flexibilities can be employed, ranging from very flexible linkers of the form (GGGGS)$_n$ and (G)$_n$ to more rigid linkers of the form (EAAAK)$_n$ and (XP)$_n$, to achieve the optimal length and rigidity for deaminase activity for the specific applications. The term "linker," as used herein, refers to a chemical group or a molecule linking two molecules or moieties, e.g., a binding domain and a cleavage domain of a nuclease.

In some embodiments, a linker joins an RNA guided nuclease and a deaminase. In some embodiments, a linker joins a dead or inactive RGN and a deaminase. In further embodiments, a linker joins two deaminases. Typically, the linker is positioned between, or flanked by, two groups, molecules, or other moieties and connected to each one via a covalent bond, thus connecting the two. In some embodiments, the linker is an amino acid or a plurality of amino acids (e.g., a peptide or protein). In some embodiments, the linker is an organic molecule, group, polymer, or chemical moiety. In some embodiments, the linker is 3-100 amino acids in length, for example, 3, 4, 5, 6, 7, 8, 9, 10, 11, 12, 13, 14, 15, 16, 17, 18, 19, 20, 21, 22, 23, 24, 25, 26, 27, 28, 29, 30, 30-35, 35-40, 40-45, 45-50, 50-60, 60-70, 70-80, 80-90, 90-100, 100-150, or 150-200 amino acids in length. Longer or shorter linkers are also contemplated. In some embodiments, a shorter linker is preferred to decrease the overall size or length of the fusion protein or its coding sequence.

In some embodiments, the linker comprises a $(GGGGS)_n$, a $(G)_n$, an $(EAAAK)_n$, or an $(XP)_n$ motif, or a combination of any of these, wherein n is independently an integer between 1 and 30. In some embodiments, n is independently 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, or, if more than one linker or more than one linker motif is present, any combination thereof. Additional suitable linker motifs and linker configurations will be apparent to those of skill in the art. In some embodiments, suitable linker motifs and configurations include those described in Chen et al., 2013 (*Adv Drug Deliv Rev.* 65(10):1357-69, the entire contents of which are incorporated herein by reference). Additional suitable linker sequences will be apparent to those of skill in the art. In some embodiments, the linker sequence comprises the amino acid sequence set forth as SEQ ID NO: 45 or 442.

In some embodiments, the general architecture of exemplary fusion proteins provided herein comprises the structure: [NH₂]-[deaminase]-[DBP]—[COOH]; [NH₂]-[DBP]-[deaminase]-[COOH]; [NH₂]-[DBP]-[deaminase]-[deaminase]-[COOH]; [NH₂]-[deaminase]-[DBP]-[deaminase]-[COOH]; or [NH₂]-[deaminase]-[deaminase]-[DBP]—[COOH], wherein DBP is a DNA-binding polypeptide, NH₂ is the N-terminus of the fusion protein and COOH is the C-terminus of the fusion protein. In some embodiments, the fusion protein comprises more than two deaminase polypeptides.

In certain embodiments, the general architecture of exemplary fusion proteins provided herein comprises the structure: [NH₂]-[deaminase]-[RGN]—[COOH]; [NH₂]—[RGN]-[deaminase]-[COOH]; [NH₂]—[RGN]-[deaminase]-[deaminase]-[COOH]; [NH₂]-[deaminase]-[RGN]-[deaminase]-[COOH]; or [NH₂]-[deaminase]-[deaminase]-[RGN]—[COOH], wherein NH₂ is the N-terminus of the fusion protein and COOH is the C-terminus of the fusion protein. In some embodiments, the fusion protein comprises more than two deaminase polypeptides.

In some embodiments, the fusion protein comprises the structure: [NH₂]-[deaminase]-[nuclease-inactive RGN]—[COOH]; [NH₂]-[deaminase]-[deaminase]-[nuclease-inactive RGN]—[COOH]; [NH₂]-[nuclease-inactive RGN]-[deaminase]-[COOH]; [NH₂]-[deaminase]-[nuclease-inactive RGN]-[deaminase]-[COOH]; or [NH₂]-[nuclease-inactive RGN]-[deaminase]-[deaminase]-[COOH]. It should be understood that "nuclease-inactive RGN" represents any RGN, including any CRISPR-Cas protein, which has been mutated to be nuclease-inactive. In some embodiments, the fusion protein comprises more than two deaminase polypeptides.

In some embodiments, the fusion protein comprises the structure: [NH₂]-[deaminase]-[RGN nickase]-[COOH]; [NH₂]-[deaminase]-[deaminase]-[RGN nickase]-[COOH]; [NH₂]—[RGN nickase]-[deaminase]-[COOH]; [NH₂]-[deaminase]-[RGN nickase]-[deaminase]-[COOH]; or [NH₂]-[RGN nickase]-[deaminase]-[deaminase]-[COOH]. It should be understood that "RGN nickase" represents any RGN, including any CRISPR-Cas protein, which has been mutated to be active as a nickase.

In some embodiments, the "-" used in the general architecture above indicates the presence of an optional linker sequence. In some embodiments, the fusion proteins provided herein do not comprise a linker sequence. In some embodiments, at least one of the optional linker sequences are present.

Other exemplary features that may be present are localization sequences, such as nuclear localization sequences, cytoplasmic localization sequences, export sequences, such as nuclear export sequences, or other localization sequences, as well as sequence tags that are useful for solubilization, purification or detection of the fusion proteins. Suitable localization signal sequences and sequences of protein tags that are provided herein, and include, but are not limited to, biotin carboxylase carrier protein (BCCP) tags, myc-tags, calmodulin-tags, FLAG-tags, hemagglutinin (HA)-tags, polyhistidine tags, also referred to as histidine tags or His-tags, maltose binding protein (MBP)-tags, nus-tags, glutathione-S-transferase (GST)-tags, green fluorescent protein (GFP)-tags, thioredoxin-tags, S-tags, Softags (e.g., Softag 1, Softag 3), streptags, biotin ligase tags, FlAsH tags, V5 tags, and SBP-tags. Additional suitable sequences will be apparent to those of skill in the art.

In certain embodiments, the presently disclosed fusion proteins comprise at least one cell-penetrating domain that facilitates cellular uptake of the fusion protein. Cell-penetrating domains are known in the art and generally comprise stretches of positively charged amino acid residues (i.e., polycationic cell-penetrating domains), alternating polar amino acid residues and non-polar amino acid residues (i.e., amphipathic cell-penetrating domains), or hydrophobic amino acid residues (i.e., hydrophobic cell-penetrating domains) (see, e.g., Milletti F. (2012) *Drug Discov Today* 17:850-860). A non-limiting example of a cell-penetrating domain is the trans-activating transcriptional activator (TAT) from the human immunodeficiency virus 1.

In some embodiments, deaminases or fusion proteins provided herein further comprise a nuclear localization sequence (NLS). The nuclear localization signal, plastid localization signal, mitochondrial localization signal, dual-targeting localization signal, and/or cell-penetrating domain can be located at the amino-terminus (N-terminus), the carboxyl-terminus (C-terminus), or in an internal location of the fusion protein.

In some embodiments, the NLS is fused to the N-terminus of the fusion protein or deaminase. In some embodiments, the NLS is fused to the C-terminus of the fusion protein or deaminase. In some embodiments, the NLS is fused to the N-terminus of the deaminase of the fusion protein. In some embodiments, the NLS is fused to the C-terminus of the deaminase of the fusion protein. In some embodiments, the NLS is fused to the N-terminus of the DNA-binding polypeptide (e.g., RGN polypeptide) of the fusion protein. In some embodiments, the NLS is fused to the C-terminus of the DNA-binding polypeptide (e.g., RGN polypeptide) of the fusion protein. In some embodiments, the NLS is fused to the N-terminus of the deaminase polypeptide of the fusion protein. In some embodiments, the NLS is fused to the C-terminus of the deaminase polypeptide of the fusion protein. In some embodiments, the NLS is fused to the fusion protein via one or more linkers. In some embodiments, the NLS is fused to the fusion protein without a linker. In some embodiments, the NLS comprises an amino acid sequence of any one of the NLS sequences provided or referenced herein. In some embodiments, the NLS comprises an amino acid sequence as set forth in SEQ ID NO: 43 or SEQ ID NO: 46. In some embodiments, the fusion protein or deaminase comprises SEQ ID NO: 43 on its N-terminus and SEQ ID NO: 46 on its C-terminus.

In some embodiments, fusion proteins as provided herein comprise the full-length sequence of a deaminase, e.g., any one of SEQ ID NO: 1-10 and 399-441. In some embodiments, however, fusion proteins as provided herein do not comprise a full-length sequence of a deaminase, but only a fragment thereof. For example, in some embodiments, a fusion protein provided herein further comprises a DNA-binding polypeptide (e.g., an RNA-guided, DNA-binding) domain and a deaminase domain.

In some embodiments, a fusion protein of the invention comprises a DNA-binding polypeptide (e.g., an RGN) and a deaminase, wherein the deaminase has an amino acid sequence having at least 50%, at least 55%, at least 60%, at least 65%, at least 70%, at least 75%, at least 80%, at least 85%, at least 90%, at least 95%, at least 96%, at least 97%, at least 98%, at least 99%, or 100% identity to any of SEQ ID NOs: 1-10 and 399-441. Examples of such fusion proteins are described in the Examples section herein.

In some embodiments, the fusion protein comprises one deaminase polypeptide. In some embodiments, the fusion protein comprises at least two deaminase polypeptides, operably linked either directly or via a peptide linker. In some embodiments, the fusion protein comprises one deaminase polypeptide, and a second deaminase polypeptide is co-expressed with the fusion protein.

Also provided herein is a ribonucleoprotein complex comprising a fusion protein comprising a deaminase and an RGDBP and the guide RNA, either as a single guide or as a dual guide RNA (also collectively referred to as gRNA).

V. Nucleotides Encoding Deaminases, Fusion Proteins, and or gRNA

The present disclosure provides polynucleotides (SEQ ID NOs: 11-20 and 443-485) encoding the presently disclosed deaminase polypeptides. The present disclosure further provides polynucleotides encoding for fusion proteins which comprise a deaminase and DNA-binding polypeptide, for example a meganuclease, a zinc finger fusion protein, or a TALEN. The present disclosure further provides polynucleotides encoding for fusion proteins which comprise a deaminase domain and an RNA-guided, DNA-binding polypeptide. Such RNA-guided, DNA-binding polypeptides may be an RGN or RGN variant. The protein variant may be nuclease-inactive or a nickase. The RGN may be a CRISPR-Cas protein or active variant or fragment thereof. SEQ ID NOs: 41 and 42 are non-limiting examples of an RGN and a nickase RGN variant, respectively. Examples of CRISPR-Cas nucleases are well-known in the art, and similar corresponding mutations can create mutant variants which are also nickases or are nuclease inactive.

An embodiment of the invention provides a polynucleotide encoding a fusion protein which comprises an RGDBP and a deaminase described herein (SEQ ID NO: 1-10 and 399-441, or a variant thereof). In some embodiments, a second polynucleotide encodes the guide RNA required by the RGDBP for targeting to the nucleotide sequence of interest. In some embodiments, the guide RNA and the fusion protein are encoded by the same polynucleotide.

The use of the term "polynucleotide" is not intended to limit the present disclosure to polynucleotides comprising DNA, though such DNA polynucleotides are contemplated. Those of ordinary skill in the art will recognize that polynucleotides can comprise ribonucleotides (RNA) and combinations of ribonucleotides and deoxyribonucleotides. Such deoxyribonucleotides and ribonucleotides include both naturally occurring molecules and synthetic analogues. The polynucleotides disclosed herein also encompass all forms of sequences including, but not limited to, single-stranded forms, double-stranded forms, stem-and-loop structures, circular forms (e.g., including circular RNA), and the like.

An embodiment of the invention is a nucleic acid molecule comprising a sequence having at least 50%, at least 55%, at least 60%, at least 65%, at least 70%, at least 75%, at least 80%, at least 85%, at least 90%, at least 95%, at least 96%, at least 97%, at least 98%, at least 99% or 100% identity to any of SEQ ID NOs: 11-20 and 443-485, wherein the nucleic acid molecule encodes a deaminase having adenine deaminase activity. The nucleic acid molecule may further comprise a heterologous promoter or terminator. The nucleic acid molecule may encode a fusion protein, where the encoded deaminase is operably linked to a DNA-binding polypeptide, and optionally a second deaminase. In some embodiments, the nucleic acid molecule encodes a fusion protein, where the encoded deaminase is operably linked to an RGN and optionally a second deaminase.

In some embodiments, nucleic acid molecules comprising a polynucleotide which encodes a deaminase of the invention are codon optimized for expression in an organism of interest. A "codon-optimized" coding sequence is a polynucleotide coding sequence having its frequency of codon usage designed to mimic the frequency of preferred codon usage or transcription conditions of a particular host cell. Expression in the particular host cell or organism is enhanced as a result of the alteration of one or more codons at the nucleic acid level such that the translated amino acid sequence is not changed. Nucleic acid molecules can be codon optimized, either wholly or in part. Codon tables and other references providing preference information for a wide range of organisms are available in the art (see, e.g., Campbell and Gown (1990) *Plant Physiol.* 92:1-11 for a discussion of plant-preferred codon usage). Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

In some embodiments, polynucleotides encoding the deaminases, fusion proteins, and/or gRNAs described herein are provided in expression cassettes for in vitro expression or expression in a cell, organelle, embryo, or organism of interest. The cassette may include 5' and 3' regulatory sequences operably linked to a polynucleotide encoding a deaminase and/or a fusion protein comprising a deaminase, an RNA-guided DNA-binding polypeptide and optionally a second deaminase, and/or gRNA provided herein that allows for expression of the polynucleotide. The cassette may additionally contain at least one additional gene or genetic element to be cotransformed into the organism. Where additional genes or elements are included, the components are operably linked. The term "operably linked" is intended to mean a functional linkage between two or more elements. For example, an operable linkage between a promoter and a coding region of interest (e.g., a region coding for a deaminase, RNA-guided DNA-binding polypeptide, and/or gRNA) is a functional link that allows for expression of the coding region of interest. Operably linked elements may be contiguous or non-contiguous. When used to refer to the joining of two protein coding regions, by operably linked is intended that the coding regions are in the same reading frame. In some embodiments, the additional gene(s) or element(s) are provided on multiple expression cassettes. For example, the nucleotide sequence encoding a presently disclosed deaminase, either alone or as a component of a fusion protein, can be present on one expression cassette, whereas the nucleotide sequence encoding a gRNA can be on a separate expression cassette. Another example may have the nucleotide sequence encoding a presently disclosed deaminase alone on a first expression cassette, a second expression cassette encoding a fusion protein comprising a deaminase, and a nucleotide sequence encoding a gRNA on third expression cassette. Such an expression cassette is provided with a plurality of restriction sites and/or recombination sites for insertion of the polynucleotides to be under the transcriptional regulation of the regulatory regions. Expression cassettes which comprise a selectable marker gene may also be present.

The expression cassette may include in the 5'-3' direction of transcription, a transcriptional (and, in some embodiments, translational) initiation region (i.e., a promoter), a deaminase-encoding polynucleotide of the invention, and a transcriptional (and in some embodiments, translational) termination region (i.e., termination region) functional in the organism of interest. The promoters of the invention are capable of directing or driving expression of a coding sequence in a host cell. The regulatory regions (e.g., promoters, transcriptional regulatory regions, and translational termination regions) may be endogenous or heterologous to the host cell or to each other. As used herein, "heterologous" in reference to a sequence is a sequence that originates from a foreign species, or, if from the same species, is substantially modified from its native form in composition and/or genomic locus by deliberate human intervention. As used herein, a chimeric gene comprises a coding sequence operably linked to a transcription initiation region that is heterologous to the coding sequence.

Convenient termination regions are available from the T1-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Additional regulatory signals include, but are not limited to, transcriptional initiation start sites, operators, activators, enhancers, other regulatory elements, ribosomal binding sites, an initiation codon, termination signals, and the like. See, for example, U.S. Pat. Nos. 5,039,523 and 4,853,331; EPO 0480762A2; Sambrook et al. (1992) *Molecular Cloning: A Laboratory Manual*, ed. Maniatis et al. (Cold Spring Harbor Laboratory Press, Cold Spring Harbor, N.Y.), hereinafter "Sambrook 11"; Davis et al., eds. (1980) *Advanced Bacterial Genetics* (Cold Spring Harbor Laboratory Press), Cold Spring Harbor, N.Y., and the references cited therein.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, inducible, growth stage-specific, cell type-specific, tissue-preferred, tissue-specific, or other promoters for expression in the organism of interest. See, for example, promoters set forth in WO 99/43838 and in U.S. Pat. Nos. 8,575,425; 7,790,846; 8,147,856; 8,586832; 7,772,369; 7,534,939; 6,072,050; 5,659,026; 5,608,149; 5,608,144; 5,604,121; 5,569,597; 5,466,785; 5,399,680; 5,268,463; 5,608,142; and 6,177,611; herein incorporated by reference.

For expression in plants, constitutive promoters also include CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); and MAS (Velten et al. (1984) *EMBO J* 3:2723-2730).

Examples of inducible promoters are the Adh1 promoter which is inducible by hypoxia or cold stress, the Hsp70 promoter which is inducible by heat stress, the PPDK promoter and the pepcarboxylase promoter which are both inducible by light. Also useful are promoters which are chemically inducible, such as the In2-2 promoter which is safener induced (U.S. Pat. No. 5,364,780), the Axig1 promoter which is auxin induced and tapetum specific but also active in callus (PCT USO1/22169), the steroid-responsive promoters (see, for example, the ERE promoter which is estrogen induced, and the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

In some embodiments, tissue-specific or tissue-preferred promoters are utilized to target expression of an expression construct within a particular tissue. In certain embodiments, the tissue-specific or tissue-preferred promoters are active in plant tissue. Examples of promoters under developmental control in plants include promoters that initiate transcription preferentially in certain tissues, such as leaves, roots, fruit, seeds, or flowers. A "tissue specific" promoter is a promoter that initiates transcription only in certain tissues. Unlike constitutive expression of genes, tissue-specific expression is the result of several interacting levels of gene regulation. As such, promoters from homologous or closely related plant species can be preferable to use to achieve efficient and reliable expression of transgenes in particular tissues. In some embodiments, the expression comprises a tissue-preferred promoter. A "tissue preferred" promoter is a promoter that initiates transcription preferentially, but not necessarily entirely or solely in certain tissues.

In some embodiments, the nucleic acid molecules encoding a deaminase described herein comprise a cell type-specific promoter. A "cell type specific" promoter is a promoter that primarily drives expression in certain cell types in one or more organs. Some examples of plant cells in which cell type specific promoters functional in plants may be primarily active include, for example, BETL cells, vascular cells in roots, leaves, stalk cells, and stem cells. The nucleic acid molecules can also include cell type preferred promoters. A "cell type preferred" promoter is a promoter that primarily drives expression mostly, but not necessarily entirely or solely in certain cell types in one or more organs. Some examples of plant cells in which cell type preferred promoters functional in plants may be preferentially active include, for example, BETL cells, vascular cells in roots, leaves, stalk cells, and stem cells.

In some embodiments, the nucleic acid sequences encoding the deaminases, fusion proteins, and/or gRNAs are operably linked to a promoter sequence that is recognized by a phage RNA polymerase for example, for in vitro mRNA synthesis. In such embodiments, the in vitro-transcribed RNA can be purified for use in the methods described herein. For example, the promoter sequence can be a T7, T3, or SP6 promoter sequence or a variation of a T7, T3, or SP6 promoter sequence. In such embodiments, the expressed protein and/or RNAs can be purified for use in the methods of genome modification described herein.

In certain embodiments, the polynucleotide encoding the deaminase, fusion protein, and/or gRNA is linked to a polyadenylation signal (e.g., SV40 polyA signal and other signals functional in plants) and/or at least one transcriptional termination sequence. In some embodiments, the sequence encoding the deaminase or fusion protein is linked to sequence(s) encoding at least one nuclear localization signal, at least one cell-penetrating domain, and/or at least one signal peptide capable of trafficking proteins to particular subcellular locations, as described elsewhere herein.

In some embodiments, the polynucleotide encoding the deaminase, fusion protein, and/or gRNA is present in a vector or multiple vectors. A "vector" refers to a polynucleotide composition for transferring, delivering, or introducing a nucleic acid into a host cell. Suitable vectors include plasmid vectors, phagemids, cosmids, artificial/mini-chromosomes, transposons, and viral vectors (e.g., lentiviral vectors, adeno-associated viral vectors, baculoviral vector). In some embodiments, the vector comprises additional expression control sequences (e.g., enhancer sequences, Kozak sequences, polyadenylation sequences, transcriptional termination sequences), selectable marker sequences (e.g., antibiotic resistance genes), origins of replication, and the like. Additional information can be found in "Current Protocols in Molecular Biology" Ausubel et al., John Wiley & Sons, New York, 2003 or "Molecular Cloning: A Laboratory Manual" Sambrook & Russell, Cold Spring Harbor Press, Cold Spring Harbor, N.Y., $3^{rd}$ edition, 2001.

In some embodiments, the vector comprises a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D).

In some embodiments, the expression cassette or vector comprising the sequence encoding a fusion protein comprising an RNA-guided DNA-binding polypeptide, such as an RGN, further comprises a sequence encoding a gRNA. In some embodiments, the sequence(s) encoding the gRNA are operably linked to at least one transcriptional control sequence for expression of the gRNA in the organism or host cell of interest. For example, the polynucleotide encoding the gRNA can be operably linked to a promoter sequence that is recognized by RNA polymerase III (Pol III). Examples of suitable Pol III promoters include, but are not limited to, mammalian U6, U3, H1, and 7SL RNA promoters and rice U6 and U3 promoters.

As indicated, expression constructs comprising nucleotide sequences encoding the deaminases, fusion proteins, and/or gRNAs can be used to transform organisms of interest. Methods for transformation involve introducing a nucleotide construct into an organism of interest. By "introducing" is intended to introduce the nucleotide construct to the host cell in such a manner that the construct gains access to the interior of the host cell. The methods of the invention do not require a particular method for introducing a nucleotide construct to a host organism, only that the nucleotide construct gains access to the interior of at least one cell of the host organism. The host cell can be a eukaryotic or prokaryotic cell. In particular embodiments, the eukaryotic host cell is a plant cell, a mammalian cell, or an insect cell. Methods for introducing nucleotide constructs into plants and other host cells are known in the art including, but not limited to, stable transformation methods, transient transformation methods, and virus-mediated methods.

The methods result in a transformed organism, such as a plant, including whole plants, as well as plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen).

"Transgenic organisms" or "transformed organisms" or "stably transformed" organisms or cells or tissues refers to organisms that have incorporated or integrated a polynucleotide encoding a deaminase of the invention. It is recognized that other exogenous or endogenous nucleic acid sequences or DNA fragments may also be incorporated into the host cell. *Agrobacterium*- and biolistic-mediated transformation remain the two predominantly employed approaches for transformation of plant cells. However, transformation of a host cell may be performed by infection, transfection, microinjection, electroporation, microprojection, biolistics or particle bombardment, electroporation, silica/carbon fibers, ultrasound mediated, PEG mediated, calcium phosphate co-precipitation, polycation DMSO technique, DEAE dextran procedure, and viral mediated, liposome mediated and the like. Viral-mediated introduction of a polynucleotide encoding a deaminase, fusion protein, and/or gRNA includes retroviral, lentiviral, adenoviral, and adeno-associated viral mediated introduction and expression, as well as the use of Caulimoviruses (e.g., cauliflower mosaic virus), Geminiviruses (e.g., bean golden yellow mosaic virus or maize streak virus), and RNA plant viruses (e.g., tobacco mosaic virus).

Transformation protocols as well as protocols for introducing polypeptides or polynucleotide sequences into plants may vary depending on the type of host cell (e.g., monocot or dicot plant cell) targeted for transformation. Methods for transformation are known in the art and include those set forth in U.S. Pat. Nos. 8,575,425; 7,692,068; 8,802,934; 7,541,517; each of which is herein incorporated by reference. See, also, Rakoczy-Trojanowska, M. (2002) *Cell Mol Biol Lett.* 7:849-858; Jones et al. (2005) *Plant Methods* 1:5; Rivera et al. (2012) *Physics of Life Reviews* 9:308-345; Bartlett et al. (2008) *Plant Methods* 4:1-12; Bates, G. W. (1999) *Methods in Molecular Biology* 111:359-366; Binns and Thomashow (1988) *Annual Reviews in Microbiology* 42:575-606; Christou, P. (1992) *The Plant Journal* 2:275-281; Christou, P. (1995) *Euphytica* 85:13-27; Tzfira et al. (2004) *TRENDS in Genetics* 20:375-383; Yao et al. (2006) *Journal of Experimental Botany* 57:3737-3746; Zupan and Zambryski (1995) *Plant Physiology* 107:1041-1047; Jones et al. (2005) *Plant Methods* 1:5;

Transformation may result in stable or transient incorporation of the nucleic acid into the cell. "Stable transformation" is intended to mean that the nucleotide construct introduced into a host cell integrates into the genome of the host cell and is capable of being inherited by the progeny thereof "Transient transformation" is intended to mean that a polynucleotide is introduced into the host cell and does not integrate into the genome of the host cell.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

The cells that have been transformed may be grown into a transgenic organism, such as a plant, in accordance with conventional ways. See, for example, McCormick et al. (1986) *Plant Cell Reports* 5:81-84. These plants may then be grown, and either pollinated with the same transformed strain or different strains, and the resulting hybrid having the deaminase or fusion protein polynucleotide identified. Two or more generations may be grown to ensure that the deaminase or fusion protein polynucleotide is stably maintained and inherited and the seeds harvested to ensure the presence of the deaminase or fusion protein polynucleotide. In this manner, the present invention provides transformed seed (also referred to as "transgenic seed") having a nucleotide construct of the invention, for example, an expression cassette of the invention, stably incorporated into their genome.

In some embodiments, cells that have been transformed are introduced into an organism. These cells could have originated from the organism, wherein the cells are transformed in an ex vivo approach.

The sequences provided herein may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, *papaya*, cashew, macadamia, almond, oats, vegetables, ornamentals, and conifers.

Vegetables include, but are not limited to, tomatoes, lettuce, green beans, lima beans, peas, and members of the genus Curcumis such as cucumber, cantaloupe, and musk melon. Ornamentals include, but are not limited to, azalea, *hydrangea*, hibiscus, roses, tulips, daffodils, petunias, carnation, poinsettia, and *chrysanthemum*. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape, etc.).

As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides. Further provided is a processed plant product or byproduct that retains the sequences disclosed herein, including for example, soymeal.

In some embodiments, the polynucleotides encoding the deaminases, fusion proteins, and/or gRNAs are used to transform any eukaryotic species, including but not limited to animals (e.g., mammals, insects, fish, birds, and reptiles), fungi, amoeba, algae, and yeast. In some embodiments, the polynucleotides encoding the deaminases, fusion proteins, and/or gRNAs are used to transform any prokaryotic species, including but not limited to, archaea and bacteria (e.g., *Bacillus* spp., *Klebsiella* spp. *Streptomyces* spp., *Rhizobium* spp., *Escherichia* spp., *Pseudomonas* spp., *Salmonella* spp., *Shigella* spp., *Vibrio* spp., *Yersinia* spp., *Mycoplasma* spp., *Agrobacterium* spp., and *Lactobacillus* spp.).

In some embodiments, conventional viral and non-viral based gene transfer methods are used to introduce nucleic acids in mammalian cells or target tissues. Such methods can be used to administer nucleic acids encoding a deaminase or fusion protein of the invention and optionally a gRNA to cells in culture, or in a host organism. Non-viral vector delivery systems include DNA plasmids, RNA (e.g., a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. Non-limiting examples include vectors utilizing Caulimoviruses (e.g., cauliflower mosaic virus), Geminiviruses (e.g., bean golden yellow mosaic virus or maize steak virus), and RNA plant viruses (e.g., tobacco mosaic virus). For a review of gene therapy procedures, see Anderson, *Science* 256: 808-813 (1992); Nabel & Feigner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10): 1149-1154 (1988); Vigne, *Restorative Neurology and Neuroscience* 8:35-36 (1995); Kremer & Perricaudet, *British Medical Bulletin* 51(1):31-44 (1995); Haddada et al., in Current Topics in Microbiology and Immunology, Doerfler and Bohm (eds) (1995); and Yu et al., *Gene Therapy* 1:13-26 (1994).

Methods of non-viral delivery of nucleic acids include lipofection, *Agrobacterium*-mediated transformation, nucleofection, microinjection, biolistics, virosomes, liposomes, immunoliposomes, polycation or lipid: nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO 91/17424; WO 91/16024. Delivery can be to cells (e.g. in vitro or ex vivo administration) or target tissues (e.g. in vivo administration). The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids takes advantage of highly evolved processes for targeting a virus to specific cells in the body and trafficking the viral payload to the nucleus. Viral vectors can be administered directly to patients (in vivo) or they can be used to treat cells in vitro, and the modified cells may optionally be administered to patients (ex vivo). Conventional viral based systems could include retroviral, lentivirus, adenoviral, adeno-associated and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., *J. Virol.* 66:2731-2739 (1992); Johann et al., *J. Virol.* 66:1635-1640 (1992); Sommnerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications where transient expression is preferred, adenoviral based systems may be used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors may also be used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Katin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); *Hermonat* & Muzyczka, *PNAS* 81:6466-6470 (1984); and Samulski et al., *J. Virol.* 63:03822-3828 (1989). Packaging cells are typically used to form virus particles that are capable of infecting a host cell. Such cells include 293 cells, which package adenovirus, and ψJ2 cells or PA317 cells, which package retrovirus.

Viral vectors used in gene therapy are usually generated by producing a cell line that packages a nucleic acid vector into a viral particle. The vectors typically contain the minimal viral sequences required for packaging and subsequent integration into a host, other viral sequences being replaced by an expression cassette for the polynucleotide(s) to be expressed. The missing viral functions are typically supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences.

The cell line may also be infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. Additional methods for the delivery of nucleic acids to cells are known to those skilled in the art. See, for example, US20030087817, incorporated herein by reference.

In some embodiments, a host cell is transiently or non-transiently transfected with one or more vectors described herein. In some embodiments, a cell is transfected as it naturally occurs in a subject. In some embodiments, a cell that is transfected is taken from a subject.

In some embodiments, a cell that is transfected is a eukaryotic cell. In some embodiments, the eukaryotic cell is an animal cell (e.g., mammals, insects, fish, birds, and reptiles). In some embodiments, a cell that is transfected is a human cell. In some embodiments, a cell that is transfected is a cell of hematopoietic origin, such as an immune cell (i.e., a cell of the innate or adaptive immune system) including but not limited to a B cell, a T cell, a natural killer (NK) cell, a pluripotent stem cell, an induced pluripotent stem cell, a chimeric antigen receptor T (CAR-T) cell, a monocyte, a macrophage, and a dendritic cell.

In some embodiments, the cell is derived from cells taken from a subject, such as a cell line. In some embodiments, the cell or cell line is prokaryotic. In some embodiments, the cell or cell line is eukaryotic. In further embodiments, the cell or cell line is derived from insect, avian, plant, or fungal species. In some embodiments, the cell or cell line may be mammalian, such as for example human, monkey, mouse, cow, swine, goat, hamster, rat, cat, or dog. A wide variety of cell lines for tissue culture are known in the art. Examples of cell lines include, but are not limited to, C8161, CCRF-CEM, MOLT, mIMCD-3, NHDF, HeLaS3, Huh1, Huh4, Huh7, HUVEC, HASMC, HEKn, HEKa, MiaPaCell, Panel, PC-3, TF1, CTLL-2, CIR, Rat6, CVI, RPTE, A10, T24, 182, A375, ARH-77, Calul, SW480, SW620, SKOV3, SK-UT, CaCo2, P388D1, SEM-K2, WEHI-231, HB56, TIB55, lurkat, 145.01, LRMB, Bcl-1, BC-3, IC21, DLD2, Raw264.7, NRK, NRK-52E, MRC5, MEF, Hep G2, HeLa B, HeLa T4. COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, 721, 9L, A2780, A2780ADR, A2780cis, A172, A20, A253, A431, A-549, ALC, B16, B35, BCP-I cells, BEAS-2B, bEnd.3, BHK-21, BR 293, BxPC3, C3H-10T1/2, C6/36, Cal-27, CHO, CHO-7, CHO-IR, CHO-K1, CHO-K2, CHO-T, CHO Dhfr-/-. COR-L23, COR-L23/CPR, COR-L235010, CORL23/R23, COS-7, COV-434, CML T1, CMT, CT26, D17, DH82, DU145, DuCaP, EL4, EM2, EM3, EMT6/AR1, EMT6/AR10.0, FM3, H1299, H69, HB54, HB55, HCA2, HEK-293, HeLa, Hepalclc7, HL-60, HMEC, HT-29, lurkat, IY cells, K562 cells, Ku812, KCL22, KGl, KYOl, LNCap, Ma-Mel 1-48, MC-38, MCF-7, MCF-10A, MDA-MB-231, MDA-MB-468, MDA-MB-435, MDCKII, MDCKII, MOR/0.2R, MONO-MAC 6, MTD-IA, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-IA/PNT 2, RenCa, RIN-5F, RMA/RMAS, Saos-2 cells, Sf-9, SkBr3, T2, T-47D, T84, THPI cell line, U373, U87, U937, VCaP, Vero cells, WM39, WT-49, X63, YAC-1, YAR, and transgenic varieties thereof. Cell lines are available from a variety of sources known to those with skill in the art (see, e.g., the American Type Culture Collection (ATCC) (Manassas, Va.)).

In some embodiments, a cell transfected with one or more vectors described herein is used to establish a new cell line comprising one or more vector-derived sequences. In some embodiments, a cell transiently transfected with a fusion protein of the invention and optionally a gRNA, or with a ribonucleoprotein complex of the invention, and modified through the activity of a fusion protein or ribonucleoprotein complex, is used to establish a new cell line comprising cells containing the modification but lacking any other exogenous sequence. In some embodiments, cells transiently or non-transiently transfected with one or more vectors described herein, or cell lines derived from such cells are used in assessing one or more test compounds.

In some embodiments, one or more vectors described herein are used to produce a non-human transgenic animal or transgenic plant. In some embodiments, the transgenic animal is an insect. In further embodiments, the insect is an insect pest, such as a mosquito or tick. In some embodiments, the insect is a plant pest, such as a corn rootworm or a fall armyworm. In some embodiments, the transgenic animal is a bird, such as a chicken, turkey, goose, or duck. In some embodiments, the transgenic animal is a mammal, such as a human, mouse, rat, hamster, monkey, ape, rabbit, swine, cow, horse, goat, sheep, cat, or dog.

VI. Variants and Fragments of Polypeptides and Polynucleotides

The present disclosure provides novel adenine deaminases which are active on DNA molecules, the amino acid sequence of which are set forth as SEQ ID NO: 1-10 and 399-441, active variants or fragments thereof, and polynucleotides encoding the same.

While the activity of a variant or fragment may be altered compared to the polynucleotide or polypeptide of interest, the variant and fragment should retain the functionality of the polynucleotide or polypeptide of interest. For example, a variant or fragment may have increased activity, decreased activity, different spectrum of activity or any other alteration in activity when compared to the polynucleotide or polypeptide of interest.

Fragments and variants of deaminases of the invention which have adenine deaminase activity will retain said activity if they are part of a fusion protein further comprising a DNA-binding polypeptide or a fragment thereof.

The term "fragment" refers to a portion of a polynucleotide or polypeptide sequence of the invention. "Fragments" or "biologically active portions" include polynucleotides comprising a sufficient number of contiguous nucleotides to retain the biological activity (i.e., deaminase activity on nucleic acids). "Fragments" or "biologically active portions" include polypeptides comprising a sufficient number of contiguous amino acid residues to retain the biological activity. Fragments of the deaminases disclosed herein include those that are shorter than the full-length sequences due to the use of an alternate downstream start site. In some embodiments, a biologically active portion of a deaminase is a polypeptide that comprises, for example, 10, 20, 30, 40, 50, 60, 70, 80, 90, 100, 110, 120, 130, 140, 150, 160, or more contiguous amino acid residues of any of SEQ ID NOs: 1-10 and 399-441, or a variant thereof. Such biologically active portions can be prepared by recombinant techniques and evaluated for activity.

In general, "variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a "native" or "wild type" polynucleotide or polypeptide comprises a naturally occurring nucleotide sequence or amino acid sequence, respectively. For polynucleotides, conservative variants include those sequences that, because of the degeneracy of the genetic code, encode the native amino acid sequence of the gene of interest. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis but which still encode the polypeptide or the polynucleotide of interest. Generally, variants of a particular polynucleotide disclosed herein will have at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or more sequence identity to that particular polynucleotide as determined by sequence alignment programs and parameters described elsewhere herein.

Variants of a particular polynucleotide disclosed herein (i.e., the reference polynucleotide) can also be evaluated by comparison of the percent sequence identity between the polypeptide encoded by a variant polynucleotide and the polypeptide encoded by the reference polynucleotide. Percent sequence identity between any two polypeptides can be calculated using sequence alignment programs and parameters described elsewhere herein. Where any given pair of polynucleotides disclosed herein is evaluated by comparison of the percent sequence identity shared by the two polypeptides they encode, the percent sequence identity between the two encoded polypeptides is at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or more sequence identity.

In particular embodiments, the presently disclosed polynucleotides encode an adenine deaminase comprising an amino acid sequence having at least 40%, at least 45%, at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or greater identity to an amino acid sequence of any of SEQ ID NOs: 1-10 and 399-441.

A biologically active variant of an adenine deaminase of the invention may differ by as few as 1-15 amino acid residues, as few as 1-10, such as 6-10, as few as 5, as few as 4, as few as 3, as few as 2, or as few as 1 amino acid residue. In specific embodiments, the polypeptides comprise an N-terminal or a C-terminal truncation, which can comprise at least a deletion of 5, 10, 15, 20, 25, 30, 35, 40, 45, 50, 55, 60 amino acids or more from either the N or C terminus of the polypeptide. In some embodiments, the polypeptides comprise an internal deletion which can comprise at least a deletion of 1, 2, 3, 4, 5, 6, 7, 8, 9, 10, 11, 12, 13, 14, 15, 16, 17, 18, 19, 20, 25, 30, 35, 40, 45, 50, 55, 60 amino acids or more.

It is recognized that modifications may be made to the deaminases provided herein creating variant proteins and polynucleotides. Changes designed by man may be introduced through the application of site-directed mutagenesis techniques. In some embodiments, native, as yet-unknown or as yet unidentified polynucleotides and/or polypeptides structurally and/or functionally-related to the sequences disclosed herein may also be identified that fall within the scope of the present invention. Conservative amino acid substitutions may be made in nonconserved regions that do not alter the function of the polypeptide as an adenine deaminase. In some embodiments, modifications are made that improve the adenine deaminase activity of the deaminase.

Variant polynucleotides and proteins also encompass sequences and proteins derived from a mutagenic and recombinogenic procedure such as DNA shuffling. With such a procedure, one or more different deaminases disclosed herein (e.g., SEQ ID NO: 1-10 and 399-441) is manipulated to create a new adenine deaminase possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the deaminase sequences provided herein and other subsequently identified deaminase genes to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) Proc. *P Natl. Acad. Sci. USA* 94:4504-4509; Crameri et al. (1998) *Nature* 391:288-291; and U.S. Pat. Nos. 5,605,793 and 5,837,458. A "shuffled" nucleic acid is a nucleic acid produced by a shuffling procedure such as any shuffling procedure set forth herein. Shuffled nucleic acids are produced by recombining (physically or virtually) two or more nucleic acids (or character strings), for example in an artificial, and optionally recursive, fashion. Generally, one or more screening steps are used in shuffling processes to identify nucleic acids of interest; this screening step can be performed before or after any recombination step. In some (but not all) shuffling embodiments, it is desirable to perform multiple rounds of recombination prior to selection to increase the diversity of the pool to be screened. The overall process of recombination and selection are optionally repeated recursively. Depending on context, shuffling can refer to an overall process of recombination and selection, or, alternately, can simply refer to the recombinational portions of the overall process.

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, California).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

Two sequences are "optimally aligned" when they are aligned for similarity scoring using a defined amino acid substitution matrix (e.g., BLOSUM62), gap existence penalty and gap extension penalty so as to arrive at the highest score possible for that pair of sequences. Amino acid substitution matrices and their use in quantifying the similarity between two sequences are well-known in the art and described, e.g., in Dayhoff et al. (1978) "A model of evolutionary change in proteins." In "Atlas of Protein Sequence and Structure," Vol. 5, Suppl. 3 (ed. M. O. Dayhoff), pp. 345-352. Natl. Biomed. Res. Found., Washington, D.C. and Henikoff et al. (1992) Proc. Natl. Acad. Sci. USA 89:10915-10919. The BLOSUM62 matrix is often used as a default scoring substitution matrix in sequence alignment protocols. The gap existence penalty is imposed for the introduction of a single amino acid gap in one of the aligned sequences, and the gap extension penalty is imposed for each additional empty amino acid position inserted into an already opened gap. The alignment is defined by the amino acids positions of each sequence at which the alignment begins and ends, and optionally by the insertion of a gap or multiple gaps in one or both sequences, so as to arrive at the highest possible score. While optimal alignment and scoring can be accomplished manually, the process is facilitated by the use of a computer-implemented alignment algorithm, e.g., gapped BLAST 2.0, described in Altschul et al. (1997) *Nucleic Acids Res.* 25:3389-3402, and made available to the public at the National Center for Biotechnology Information Website (World Wide Web at ncbi.nlm.nih.gov). Optimal alignments, including multiple alignments, can be prepared using, e.g., PSI-BLAST, available through World Wide Web at ncbi.nlm.nih.gov and described by Altschul et al. (1997) *Nucleic Acids Res.* 25:3389-3402.

With respect to an amino acid sequence that is optimally aligned with a reference sequence, an amino acid residue "corresponds to" the position in the reference sequence with which the residue is paired in the alignment. The "position" is denoted by a number that sequentially identifies each amino acid in the reference sequence based on its position relative to the N-terminus. Owing to deletions, insertion, truncations, fusions, etc., that must be taken into account when determining an optimal alignment, in general the amino acid residue number in a test sequence as determined by simply counting from the N-terminal will not necessarily be the same as the number of its corresponding position in the reference sequence. For example, in a case where there is a deletion in an aligned test sequence, there will be no amino acid that corresponds to a position in the reference sequence at the site of deletion. Where there is an insertion in an aligned reference sequence, that insertion will not correspond to any amino acid position in the reference sequence. In the case of truncations or fusions there can be stretches of amino acids in either the reference or aligned sequence that do not correspond to any amino acid in the corresponding sequence.

VII. Antibodies

Antibodies to the deaminases, fusion proteins, or ribonucleoproteins comprising the deaminases of the present invention, including those having the amino acid sequence set forth as any one of SEQ ID NOs: 1-10 and 399-441 or active variants or fragments thereof, are also encompassed. Methods for producing antibodies are well known in the art (see, for example, Harlow and Lane (1988) Antibodies: A Laboratory Manual, Cold Spring Harbor Laboratory, Cold Spring Harbor, N.Y.; and U.S. Pat. No. 4,196,265). These antibodies can be used in kits for the detection and isolation of deaminases or fusion proteins or ribonucleoproteins comprising deaminases described herein. Thus, this disclosure provides kits comprising antibodies that specifically bind to the polypeptides or ribonucleoproteins described herein, including, for example, polypeptides comprising a sequence of at least 85% identity to any of SEQ ID NOs: 1-10 and 399-441.

VIII. Systems and Ribonucleoprotein Complexes for Binding and or Modifying a Target Sequence of Interest and Methods of Making the Same The present disclosure provides a system which targets to a nucleic acid sequence and modifies a target nucleic acid sequence. In some embodiments, an RNA-guided, DNA-binding polypeptide, such as an RGN, and the gRNA are responsible for targeting the ribonucleoprotein complex to a nucleic acid sequence of interest; the deaminase polypeptide fused to the RGDBP is responsible for modifying the targeted nucleic acid sequence from A>N. In some embodiments, the deaminase converts A>G. The guide RNA hybridizes to the target sequence of interest and also forms a complex with the RNA-guided, DNA-binding polypeptide, thereby directing the RNA-guided, DNA-binding polypeptide to bind to the target sequence. The RNA-guided, DNA-binding polypeptide is one domain of a fusion protein; the second domain is a deaminase described herein. In some embodiments, the RNA-guided, DNA-binding polypeptide is an RGN, such as a Cas9. Other examples of RNA-guided, DNA-binding polypeptides include RGNs such as those described in International Patent Application Publication Nos. WO 2019/236566 and WO 2020/139783. In some embodiments, the RNA-guided, DNA-binding polypeptide is a Type II CRISPR-Cas polypeptide, or an active variant or fragment thereof. In some embodiments, the RNA-guided, DNA-binding polypeptide is a Type V CRISPR-Cas polypeptide, or an active variant or fragment thereof. In some embodiments, the RNA-guided, DNA-binding polypeptide is a Type VI CRISPR-Cas polypeptide. In some embodiments, the DNA-binding domain of the fusion protein does not require an RNA guide, such as a zinc finger nuclease, TALEN, or meganuclease polypeptide. In some embodiments, the nuclease activity of a DNA-binding domain has been partially or completely inactivated. In further embodiments, the RNA-guided, DNA-binding polypeptide comprises an amino acid sequence of an RGN, such as for example APG07433.1 (SEQ ID NO: 41), or an active variant or fragment thereof such as nickase nAPG07433.1 (SEQ ID NO: 42) or other nickase RGN variants described in the Examples (SEQ ID NOs: 52-59, 61, 397, and 398).

In some embodiments, the system for binding and modifying a target sequence of interest provided herein is a ribonucleoprotein complex, which is at least one molecule of an RNA bound to at least one protein. The ribonucleoprotein complexes provided herein comprise at least one guide RNA as the RNA component and a fusion protein comprising a deaminase of the invention and an RNA-guided, DNA-binding polypeptide as the protein component. In some embodiments, the ribonucleoprotein complex is purified from a cell or organism that has been transformed with polynucleotides that encode the fusion protein and a guide RNA and cultured under conditions to allow for the expression of the fusion protein and guide RNA.

In various embodiments, ribonucleoprotein complexes comprising any of the fusion proteins described herein and a guide RNA bound to the DNA-binding polypeptide of the fusion protein, are provided. For example, provided herein is a ribonucleoprotein complex comprising a fusion protein with a deaminase comprising an amino acid sequence having at least 80% sequence identity to SEQ ID NO: 407. In another instance, a ribonucleoprotein complex comprising a fusion protein with a deaminase comprising an amino acid sequence having at least 80% sequence identity to SEQ ID NO: 399, is provided. In yet another example, a ribonucleoprotein complex comprising a fusion protein with a deaminase comprising an amino acid sequence having at least 80% sequence identity to SEQ ID NO: 405, is provided. In some of those embodiments of the ribonucleoprotein complexes described above, the fusion protein comprises an RGN selected from a CasX, a CasY, a C2c1, a C2c2, a C2c3, a GeoCas9, aSpCas9, a SaCas9, a Nme2Cas9, a CjCas9, a Cas12a (formerly known as Cpf1), a Cas12b, a Cas12g, a Cas12h, a Cas12i, aLbCas12a, a AsCas12a, a CasMINI, a Cas13b, a Cas13c, a Cas13d, a Cas14, a Csn2, an xCas9, an SpCas9-NG, an LbCas12a, an AsCas12a, a Cas9-KKH, a circularly permuted Cas9, an Argonaute (Ago), a SmacCas9, a Spy-macCas9 domain, or an RGN with an amino acid sequence set forth in any one of SEQ ID NOs: 41, 60, 366, or 368. In some embodiments, the ribonucleoprotein complex comprises a nickase having an amino acid sequence with at least 95% sequence identity to any one of SEQ ID NOs: 42, 52-59, 61, 397, and 398, fused to a deaminase comprising an amino acid sequence having at least 80% sequence identity to SEQ ID NO: 407. In some embodiments, the ribonucleoprotein complex comprises a nickase having an amino acid sequence with at least 95% sequence identity to any one of SEQ ID NOs: 42, 52-59, 61, 397, and 398, fused to a deaminase comprising an amino acid sequence having at least 80% sequence identity to SEQ ID NO: 399. In some embodiments, the ribonucleoprotein complex comprises a nickase having an amino acid sequence with at least 95% sequence identity to any one of SEQ ID NOs: 42, 52-59, 61, 397, and 398, fused to a deaminase comprising an amino acid sequence having at least 80% sequence identity to SEQ ID NO: 405. In some embodiments, the ribonucleoprotein complex comprises a Cas9 nickase fused to a deaminase comprising an amino acid sequence having at least 80% sequence identity to SEQ ID NO: 407. In some embodiments, the ribonucleoprotein complex comprises a Cas9 nickase fused to a deaminase comprising an amino acid sequence having at least 80% sequence identity to SEQ ID NO: 399. In some embodiments, the ribonucleoprotein complex comprises a Cas9 nickase fused to a deaminase comprising an amino acid sequence having at least 80% sequence identity to SEQ ID NO: 405. The Cas9 nickase, can be any Cas9 nickase disclosed in PCT Patent Publication No. WO2020181195, the entire contents of which is incorporated herein by reference herein. In various embodiments described herein, the ribonucleoprotein complex may also contain the gRNAs described herein.

Methods are provided for making a deaminase, a fusion protein, or a fusion protein ribonucleoprotein complex. Such methods comprise culturing a cell comprising a nucleotide sequence encoding a deaminase, a fusion protein, and in some embodiments a nucleotide sequence encoding a guide RNA, under conditions in which the deaminase or fusion protein (and in some embodiments, the guide RNA) is expressed. The deaminase, fusion protein, or fusion ribonucleoprotein can then be purified from a lysate of the cultured cells.

Methods for purifying a deaminase, fusion protein, or fusion ribonucleoprotein complex from a lysate of a biological sample are known in the art (e.g., size exclusion and/or affinity chromatography, 2D-PAGE, HPLC, reversed-phase chromatography, immunoprecipitation). In particular methods, the deaminase or fusion protein is recombinantly produced and comprises a purification tag to aid in its purification, including but not limited to, glutathione-S-transferase (GST), chitin binding protein (CBP), maltose binding protein, thioredoxin (TRX), poly(NANP), tandem affinity purification (TAP) tag, myc, AcV5, AU1, AU5, E, ECS, E2, FLAG, HA, nus, Softag 1, Softag 3, Strep, SBP, Glu-Glu, HSV, KT3, S, S1, T7, V5, VSV-G, 6xHis, biotin carboxyl carrier protein (BCCP), and calmodulin. Generally, the tagged deaminase, fusion protein, or fusion ribonucleoprotein complex is purified using immunoprecipitation or other similar methods known in the art.

An "isolated" or "purified" polypeptide, or biologically active portion thereof, is substantially or essentially free from components that normally accompany or interact with the polypeptide as found in its naturally occurring environment. Thus, an isolated or purified polypeptide is substantially free of other cellular material, or culture medium when produced by recombinant techniques, or substantially free of chemical precursors or other chemicals when chemically synthesized. A protein that is substantially free of cellular material includes preparations of protein having less than 30%, less than 20%, less than 10%, less than 5%, or less than 1% (by dry weight) of contaminating protein. When the protein of the invention or biologically active portion thereof is recombinantly produced, optimally culture medium represents less than 30%, less than 20%, less than 10%, less than 5%, or less than 1% (by dry weight) of chemical precursors or non-protein-of-interest chemicals.

Particular methods provided herein for binding and/or cleaving a target sequence of interest involve the use of a ribonucleoprotein complex. In some embodiments, the ribonucleoprotein complex is assembled in vitro. In vitro assembly of a ribonucleoprotein complex can be performed using any method known in the art in which an RGDBP polypeptide or a fusion protein comprising the same is contacted with a guide RNA under conditions to allow for binding of the RGDBP polypeptide or fusion protein comprising the same to the guide RNA. As used herein, "contact", "contacting", "contacted," refer to placing the components of a desired reaction together under conditions suitable for carrying out the desired reaction. In some embodiments of the described methods for modifying a target DNA molecule, the step of contacting is performed in vitro. In some embodiments, the step of contacting is performed in vivo. In some embodiments, the step of contacting is performed in a subject (e.g., a human subject or a non-human animal subject). In some embodiments, the step of contacting is performed in a cell, such as a human or non-human animal cell. The RGDBP polypeptide or fusion protein comprising the same can be purified from a biological sample, cell lysate, or culture medium, produced via in vitro translation, or chemically synthesized. The guide RNA can be purified from a biological sample, cell lysate, or culture medium, transcribed in vitro, or chemically synthesized. The RGDBP polypeptide or fusion protein comprising the same and guide RNA can be brought into contact in solution (e.g., buffered saline solution) to allow for in vitro assembly of the ribonucleoprotein complex.

IX. Methods of Modifying a Target Sequence

The present disclosure provides methods for modifying a target nucleic acid molecule (e.g., target DNA molecule) of interest. The methods include delivering a fusion protein comprising a DNA-binding polypeptide and at least one deaminase of the invention or a polynucleotide encoding the same to a target sequence or a cell, organelle, or embryo comprising a target sequence. In certain embodiments, the methods include delivering a system comprising at least one guide RNA or a polynucleotide encoding the same, and at least one fusion protein comprising at least one deaminase of the invention and an RNA-guided, DNA-binding polypeptide or a polynucleotide encoding the same to the target sequence or a cell, organelle, or embryo comprising the target sequence. In some embodiments, the fusion protein comprises any one of the amino acid sequences of SEQ ID NOs: 1-10 and 399-441, or an active variant or fragment thereof.

In some embodiments, the methods comprise contacting a DNA molecule with (a) a fusion protein comprising a deaminase and an RNA-guided, DNA-binding polypeptide, such as for example a nuclease-inactive or a nickase Cas9 domain; and (b) a gRNA targeting the fusion protein of (a) to a target nucleotide sequence of the DNA molecule; wherein the DNA molecule is contacted with the fusion protein and the gRNA in an amount effective and under conditions suitable for the deamination of a nucleobase. In some embodiments, the target DNA molecule comprises a sequence associated with a disease or disorder, and wherein the deamination of the nucleobase results in a sequence that is not associated with a disease or disorder. In some embodiments, the disease or disorder affects animals. In further embodiments, the disease or disorder affects mammals, such as humans, cows, horses, dogs, cats, goats, sheep, swine, monkeys, rats, mice, or hamsters. In some embodiments, the target DNA sequence resides in an allele of a crop plant, wherein the particular allele of the trait of interest results in a plant of lesser agronomic value. The deamination of the nucleobase results in an allele that improves the trait and increases the agronomic value of the plant.

In those embodiments wherein the method comprises delivering a polynucleotide encoding a guide RNA and/or a fusion protein, the cell or embryo can then be cultured under conditions in which the guide RNA and/or fusion protein are expressed. In various embodiments, the method comprises contacting a target sequence with a ribonucleoprotein complex comprising a gRNA and a fusion protein (which comprises a deaminase of the invention and an RNA-guided DNA-binding polypeptide). In certain embodiments, the method comprises introducing into a cell, organelle, or embryo comprising a target sequence a ribonucleoprotein complex of the invention. The ribonucleoprotein complex of the invention can be one that has been purified from a biological sample, recombinantly produced and subsequently purified, or in vitro-assembled as described herein. In those embodiments wherein the ribonucleoprotein complex that is contacted with the target sequence or a cell organelle, or embryo has been assembled in vitro, the method can further comprise the in vitro assembly of the complex prior to contact with the target sequence, cell, organelle, or embryo.

A purified or in vitro assembled ribonucleoprotein complex of the invention can be introduced into a cell, organelle, or embryo using any method known in the art, including, but not limited to electroporation. In some embodiments, a fusion protein comprising a deaminase of the invention and an RNA-guided, DNA-binding polypeptide, and a polynucleotide encoding or comprising the guide RNA is introduced into a cell, organelle, or embryo using any method known in the art (e.g., electroporation).

Upon delivery to or contact with the target sequence or cell, organelle, or embryo comprising the target sequence, the guide RNA directs the fusion protein to bind to the target sequence in a sequence-specific manner. The target sequence can subsequently be modified via the deaminase domain of the fusion protein. In some embodiments, the binding of this fusion protein to a target sequence results in modification of a nucleotide adjacent to the target sequence. The nucleobase adjacent to the target sequence that is modified by the deaminase may be 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 base pairs from the 5' or 3' end of the target sequence. A fusion protein comprising a deaminase of the invention and an RNA-guided, DNA-binding polypeptide can introduce targeted A>N, and preferably targeted A>G, mutations in the targeted DNA molecule.

In some embodiments of the described methods for modifying a target DNA molecule, the step of contacting is performed in vitro. In particular embodiments, the step of contacting is performed in vivo. In some embodiments, the step of contacting is performed in a subject (e.g., a human subject or a non-human animal subject). In some embodiments, the step of contacting is performed in a cell, such as a human or non-human animal cell.

Methods to measure binding of the fusion protein to a target sequence are known in the art and include chromatin immunoprecipitation assays, gel mobility shift assays, DNA pull-down assays, reporter assays, microplate capture and detection assays. Likewise, methods to measure cleavage or modification of a target sequence are known in the art and include in vitro or in vivo cleavage assays wherein cleavage is confirmed using PCR, sequencing, or gel electrophoresis, with or without the attachment of an appropriate label (e.g., radioisotope, fluorescent substance) to the target sequence to facilitate detection of degradation products. In some embodiments, the nicking triggered exponential amplification reaction (NTEXPAR) assay is used (see, e.g., Zhang et al. (2016) *Chem. Sci.* 7:4951-4957). In vivo cleavage can be evaluated using the Surveyor assay (Guschin et al. (2010) *Methods Mol Biol* 649:247-256).

In some embodiments, the methods involve the use of an RNA-binding, DNA-guided domain, as part of the fusion protein, complexed with more than one guide RNA. The more than one guide RNA can target different regions of a single gene or can target multiple genes. This multiple targeting enables the deaminase domain of the fusion protein to modify nucleic acids, thereby introducing multiple mutations in the target nucleic acid molecule (e.g., genome) of interest.

In those embodiments wherein the method involves the use of an RNA-guided nuclease (RGN), such as a nickase RGN (i.e., is only able to cleave a single strand of a double-stranded polynucleotide, for example nAPG07433.1 (SEQ ID NO: 42 or SEQ ID NOs: 50-57), the method can comprise introducing two different RGNs or RGN variants that target identical or overlapping target sequences and cleave different strands of the polynucleotide. For example, an RGN nickase that only cleaves the positive (+) strand of a double-stranded polynucleotide can be introduced along with a second RGN nickase that only cleaves the negative (−) strand of a double-stranded polynucleotide. In some embodiments, two different fusion proteins are provided, where each fusion protein comprises a different RGN with a different PAM recognition sequence, so that a greater diversity of nucleotide sequences may be targeted for mutation.

One of ordinary skill in the art will appreciate that any of the presently disclosed methods can be used to target a single target sequence or multiple target sequences. Thus, methods comprise the use of a fusion protein comprising a single RNA-guided, DNA-binding polypeptide in combination with multiple, distinct guide RNAs, which can target multiple, distinct sequences within a single gene and/or multiple genes. The deaminase domain of the fusion protein would then introduce mutations at each of the targeted sequences. Also encompassed herein are methods wherein multiple, distinct guide RNAs are introduced in combination with multiple, distinct RNA-guided, DNA binding polypeptides. Such RNA-guided, DNA-binding polypeptides may be multiple RGN or RGN variants. These guide RNAs and guide RNA/fusion protein systems can target multiple, distinct sequences within a single gene and/or multiple genes.

In some embodiments, a fusion protein comprising an RNA-guided, DNA-binding polypeptide and a deaminase polypeptide of the invention may be used for generating mutations in a targeted gene or targeted region of a gene of interest. In some embodiments, a fusion protein of the invention may be used for saturation mutagenesis of a targeted gene or region of a targeted gene of interest followed by high-throughput forward genetic screening to identify novel mutations and/or phenotypes. In some embodiments, a fusion protein described herein may be used for generating mutations in a targeted genomic location, which may or may not comprise coding DNA sequence. Libraries of cell lines generated by the targeted mutagenesis described above may also be useful for study of gene function or gene expression.

X. Target Polynucleotides

In one aspect, the invention provides for methods of modifying a target polynucleotide in a eukaryotic cell, which may be in vivo, ex vivo or in vitro. In some embodiments, the method comprises sampling a cell or population of cells from a human or non-human animal or plant (including microalgae) and modifying the cell or cells. Culturing may occur at any stage ex vivo. The cell or cells may even be re-introduced into the human, non-human animal or plant (including micro-algae).

Using natural variability, plant breeders combine most useful genes for desirable qualities, such as yield, quality, uniformity, hardiness, and resistance against pests. These desirable qualities also include growth, day length preferences, temperature requirements, initiation date of floral or reproductive development, fatty acid content, insect resistance, disease resistance, nematode resistance, fungal resistance, herbicide resistance, tolerance to various environmental factors including drought, heat, wet, cold, wind, and adverse soil conditions including high salinity. The sources of these useful genes include native or foreign varieties, heirloom varieties, wild plant relatives, and induced mutations, e.g., treating plant material with mutagenic agents. Using the present invention, plant breeders are provided with a new tool to induce mutations. Accordingly, one skilled in the art can employ the present invention to induce the rise of useful genes, with more precision than previous mutagenic agents and hence accelerate and improve plant breeding programs.

The target polynucleotide of a deaminase or a fusion protein of the invention can be any polynucleotide endogenous or exogenous to the eukaryotic cell. For example, the target polynucleotide can be a polynucleotide residing in the nucleus of the eukaryotic cell. In some embodiments, the target polynucleotide is a sequence coding a gene product (e.g., a protein) or a non-coding sequence (e.g., a regulatory polynucleotide or a junk DNA). In some embodiments, the target sequence for a fusion protein of the invention is associated with a PAM (protospacer adjacent motif); that is, a short sequence recognized by the RNA-guided DNA-binding polypeptide. The precise sequence and length requirements for the PAM differ depending on the RNA-guided DNA-binding polypeptide used, but PAMs are typically 2-5 base pair sequences adjacent the protospacer (that is, the target sequence).

The target polynucleotide of a fusion protein of the invention may include a number of disease-associated genes and polynucleotides as well as signaling biochemical pathway-associated genes and polynucleotides. Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non-disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease (e.g., a causal mutation). The transcribed or translated products may be known or unknown, and further may be at a normal or abnormal level.

Non-limiting examples of disease-associated genes that can be targeted using the presently disclosed methods and compositions are provided in Table 34. In some embodiments, the disease-associated gene that is targeted are those disclosed in Table 34 having a G>A mutation. Additional examples of disease-associated genes and polynucleotides are available from McKusick-Nathans Institute of Genetic Medicine, Johns Hopkins University (Baltimore, Md.) and National Center for Biotechnology Information, National Library of Medicine (Bethesda, Md.), available on the World Wide Web.

In some embodiments, the target polynucleotide comprises a cystic fibrosis transmembrane conductance regulator (5) gene.

As used herein, the term "cystic fibrosis transmembrane conductance regulator" or "CFTR" refers to a cAMP regulated chloride channel located in the apical membrane of epithelial cells that catalyze the passage of small ions through the membrane. A non-limiting example of a CFTR gene is set forth as SEQ ID NO: 51.

As used herein, the term "target" or "targets," in relation to a spacer sequence and a target sequence, refers to the localization of an RNA-guided nuclease to a target sequence based on the ability of a spacer sequence within an associated guide RNA to hybridize sufficiently with a target sequence.

CRISPR RNAs (crRNAs) or nucleic acid molecules encoding the same, wherein the crRNA comprises a spacer sequence that targets a CFTR target sequence are provided. Guide RNAs comprising such crRNAs, one or more nucleic acid molecules encoding a guide RNA comprising such crRNAs, vectors comprising one or more nucleic acid molecules encoding a guide RNA comprising such crRNAs, and systems comprising such crRNAs are also provided. Methods of using such crRNAs or nucleic molecules encoding the same, guide RNAs comprising such crRNAs, one or more nucleic acid molecules encoding a guide RNA comprising such crRNAs, vectors comprising one or more nucleic acid molecules encoding a guide RNA comprising such crRNAs, and systems comprising such crRNAs to bind to, cleave, and/or modulate the target sequence are also provided.

In some embodiments, the CFTR target sequence of a crRNA or a guide RNA has the sequence set forth in any one of SEQ ID NOs: 98-115, 140-151, 186-202, 235-250, 287-304, 345-364, 562, and 563, or the complement thereof. In some embodiments, a single guide RNA (sgRNA) comprising a crRNA having a spacer sequence that targets a CFTR target sequence has at least 40%, 45%, 50%, 55%, 60%, 65%, 70%, 75%, 80%, 85%, 90%, 91%, 92%, 93%, 94%, 95%, 96%, 97%, 98%, 99% or more sequence identity to any one of SEQ ID NOs: 98-115, 140-151, 186-202, 235-250, 287-304, 345-364, and 564.

In some embodiments, the CFTR target sequence of a crRNA or a guide RNA has the sequence set forth in any one of SEQ ID NOs: 62-68, 80-85, 116-119, 128-131, 163, 164, 180, 181, 203-209, 219-225, 256-258, 274-276, 310-313, and 330-333, or the complement thereof, and the associated RGN polypeptide has an amino acid sequence having at least 40%, 45%, 50%, 55%, 60%, 65%, 70%, 75%, 80%, 85%, 90%, 91%, 92%, 93%, 94%, 95%, 96%, 97%, 98%, 99% or more sequence identity to SEQ ID NO: 53. In some embodiments, a sgRNA comprising a crRNA having a spacer sequence that targets a CFTR target sequence has at least 40%, 45%, 50%, 55%, 60%, 65%, 70%, 75%, 80%, 85%, 90%, 91%, 92%, 93%, 94%, 95%, 96%, 97%, 98%, 99% or more sequence identity to any one of SEQ ID NOs: 98-104, 140-143, 197, 198, 235-241, 292-294, and 350-353, and the associated RGN polypeptide has an amino acid sequence having at least 40%, 45%, 50%, 55%, 60%, 65%, 70%, 75%, 80%, 85%, 90%, 91%, 92%, 93%, 94%, 95%, 96%, 97%, 98%, 99% or more sequence identity to SEQ ID NO: 53.

In some embodiments, the CFTR target sequence of a crRNA or a guide RNA has the sequence set forth in any one of SEQ ID NOs: 68-71, 86-89, 120-122, 132-134, 152-156, 169-173, 213-215, 229-231, 251-255, 269-273, 305-309, and 325-329, or the complement thereof and the associated RGN polypeptide has an amino acid sequence having at least 40%, 45%, 50%, 55%, 60%, 65%, 70%, 75%, 80%, 85%, 90%, 91%, 92%, 93%, 94%, 95%, 96%, 97%, 98%, 99% or more sequence identity to SEQ ID NO: 55. In some embodiments, a sgRNA comprising a crRNA having a spacer sequence that targets a CFTR target sequence has at least 40%, 45%, 50%, 55%, 60%, 65%, 70%, 75%, 80%, 85%, 90%, 91%, 92%, 93%, 94%, 95%, 96%, 97%, 98%, 99% or more sequence identity to any one of SEQ ID NOs: 104-107, 144-146, 186-190, 245-247, 287-291, and 345-349, and the associated RGN polypeptide has an amino acid sequence having at least 40%, 45%, 50%, 55%, 60%, 65%, 70%, 75%, 80%, 85%, 90%, 91%, 92%, 93%, 94%, 95%, 96%, 97%, 98%, 99% or more sequence identity to SEQ ID NO: 55.

In some embodiments, the CFTR target sequence of a crRNA or a guide RNA has the sequence set forth in any one of SEQ ID NOs: 72, 73, 90, 91, 161, 162, 178, 179, 265, 266, 283, and 284, or the complement thereof and the associated RGN polypeptide has an amino acid sequence having at least 40%, 45%, 50%, 55%, 60%, 65%, 70%, 75%, 80%, 85%, 90%, 91%, 92%, 93%, 94%, 95%, 96%, 97%, 98%, 99% or more sequence identity to SEQ ID NO: 52. In some embodiments, a sgRNA comprising a crRNA having a spacer sequence that targets a CFTR target sequence has at least 40%, 45%, 50%, 55%, 60%, 65%, 70%, 75% 80%, 85%, 90%, 91%, 92%, 93%, 94%, 95%, 96%, 97%, 98%, 99% or more sequence identity to any one of SEQ ID NOs: 108, 109, 195, 196, 301, and 302, and the associated RGN polypeptide has an amino acid sequence having at least 40%, 45%, 50%, 55%, 60%, 65%, 70%, 75% 80%, 85%, 90%, 91%, 92%, 93%, 94%, 95%, 96%, 97%, 98%, 99% or more sequence identity to SEQ ID NO: 52.

In some embodiments, the CFTR target sequence of a crRNA or a guide RNA has the sequence set forth in any one of SEQ ID NOs: 74, 75, 92, 93, 123, 124, 135, 136, 167, 184, 216-218, 232-234, 259-261, 277-279, 314-317, and 334-337, or the complement thereof and the associated RGN polypeptide has an amino acid sequence having at least 40%, 45%, 50%, 55%, 60%, 65%, 70%, 75%, 80%, 85%, 90%, 91%, 92%, 93%, 94%, 95%, 96%, 97%, 98%, 99% or more sequence identity to SEQ ID NO: 56. In some embodiments, a sgRNA comprising a crRNA having a spacer sequence that targets a CFTR target sequence has at least 40%, 45%, 50%, 55%, 60%, 65%, 70%, 75%, 80%, 85%, 90%, 91%, 92%, 93%, 94%, 95%, 96%, 97%, 98%, 99% or more sequence identity to any one of SEQ ID NOs: 110, 111, 147, 148, 201, 248-250, 295-297, and 354-357, and the associated RGN polypeptide has an amino acid sequence having at least 40%, 45%, 50%, 55%, 60%, 65%, 70%, 75%, 80%, 85%, 90%, 91%, 92%, 93%, 94%, 95%, 96%, 97%, 98%, 99% or more sequence identity to SEQ ID NO: 56.

In some embodiments, the CFTR target sequence of a crRNA or a guide RNA has the sequence set forth in any one of SEQ ID NOs: 76, 94, 210-212, 226-228, 322, 342, 562, and 563, or the complement thereof and the associated RGN polypeptide has an amino acid sequence having at least 40%, 45%, 50%, 55%, 60%, 65%, 70%, 75%, 80%, 85%, 90%, 91%, 92%, 93%, 94%, 95%, 96%, 97%, 98%, 99% or more sequence identity to SEQ ID NO: 42. In some embodiments, a sgRNA comprising a crRNA having a spacer sequence that targets a CFTR target sequence has at least 40%, 45%, 50%, 55%, 60%, 65%, 70%, 75%, 80%, 85%, 90%, 91%, 92%, 93%, 94%, 95%, 96%, 97%, 98%, 99% or more sequence identity to any one of SEQ ID NOs: 112, 242-244, 362, and 564, and the associated RGN polypeptide has an amino acid sequence having at least 40%, 45%, 50%, 55%, 60%, 65%, 70%, 75%, 80%, 85%, 90%, 91%, 92%, 93%, 94%, 95%, 96%, 97%, 98%, 99% or more sequence identity to SEQ ID NO: 42.

In some embodiments, the CFTR target sequence of a crRNA or a guide RNA has the sequence set forth in any one of SEQ ID NOs: 77, 95, 125, 137, 157-160, 174-177, 323, and 343, or the complement thereof and the associated RGN polypeptide has an amino acid sequence having at least 40%, 45%, 50%, 55%, 60%, 65%, 70%, 75%, 80%, 85%, 90%, 91%, 92%, 93%, 94%, 95%, 96%, 97%, 98%, 99% or more sequence identity to SEQ ID NO: 54. In some embodiments, a sgRNA comprising a crRNA having a spacer sequence that targets a CFTR target sequence has at least 40%, 45%, 50%, 55%, 60%, 65%, 70%, 75%, 80%, 85%, 90%, 91%, 92%, 93%, 94%, 95%, 96%, 97%, 98%, 99% or more sequence identity to any one of SEQ ID NOs: 113, 149, 191-194, and 363, and the associated RGN polypeptide has an amino acid sequence having at least 40%, 45%, 50%, 55%, 60%, 65%, 70%, 75%, 80%, 85%, 90%, 91%, 92%, 93%, 94%, 95%, 96%, 97%, 98%, 99% or more sequence identity to SEQ ID NO: 54.

In some embodiments, the CFTR target sequence of a crRNA or a guide RNA has the sequence set forth in any one of SEQ ID NOs: 78, 96, 126, 138, 168, 185, 267, 285, 318, 319, 338, and 339, or the complement thereof and the associated RGN polypeptide has an amino acid sequence having at least 40%, 45%, 50%, 55%, 60%, 65%, 70%, 75%, 80%, 85%, 90%, 91%, 92%, 93%, 94%, 95%, 96%, 97%, 98%, 99% or more sequence identity to SEQ ID NO: 57. In some embodiments, a sgRNA comprising a crRNA having a spacer sequence that targets a CFTR target sequence has at least 40%, 45%, 50%, 55%, 60%, 65%, 70%, 75%, 80%, 85%, 90%, 91%, 92%, 93%, 94%, 95%, 96%, 97%, 98%, 99% or more sequence identity to any one of SEQ ID NOs: 114, 150, 202, 303, 358, and 359, and the associated RGN polypeptide has an amino acid sequence having at least 40%, 45%, 50%, 55%, 60%, 65%, 70%, 75%, 80%, 85%, 90%, 91%, 92%, 93%, 94%, 95%, 96%, 97%, 98%, 99% or more sequence identity to SEQ ID NO: 57.

In some embodiments, the CFTR target sequence of a crRNA or a guide RNA has the sequence set forth in any one of SEQ ID NOs: 79, 97, 127, 139, 262-264, 280-282, 324, and 344, or the complement thereof and the associated RGN polypeptide has an amino acid sequence having at least 40%, 45%, 50%, 55%, 60%, 65%, 70%, 75%, 80%, 85%, 90%, 91%, 92%, 93%, 94%, 95%, 96%, 97%, 98%, 99% or more sequence identity to SEQ ID NO: 58. In some embodiments, a sgRNA comprising a crRNA having a spacer sequence that targets a CFTR target sequence has at least 40%, 45%, 50%, 55%, 60%, 65%, 70%, 75%, 80%, 85%, 90%, 91%, 92%, 93%, 94%, 95%, 96%, 97%, 98%, 99% or more sequence identity to any one of SEQ ID NOs: 115, 151, 298-300, and 364, and the associated RGN polypeptide has an amino acid sequence having at least 40%, 45%, 50%, 55%, 60%, 65%, 70%, 75%, 80%, 85%, 90%, 91%, 92%, 93%, 94%, 95%, 96%, 97%, 98%, 99% or more sequence identity to SEQ ID NO: 58.

In some embodiments, the CFTR target sequence of a crRNA or a guide RNA has the sequence set forth in any one of SEQ ID NOs: 165, 166, 182, 183, 268, 286, 320, 321, 340, and 341, or the complement thereof and the associated RGN polypeptide has an amino acid sequence having at least 40%, 45%, 50%, 55%, 60%, 65%, 70%, 75%, 80%, 85%, 90%, 91%, 92%, 93%, 94%, 95%, 96%, 97%, 98%, 99% or more sequence identity to SEQ ID NO: 59. In some embodiments, a sgRNA comprising a crRNA having a spacer sequence that targets a CFTR target sequence has at least 40%, 45%, 50%, 55%, 60%, 65%, 70%, 75%, 80%, 85%, 90%, 91%, 92%, 93%, 94%, 95%, 96%, 97%, 98%, 99% or more sequence identity to any one of SEQ ID NOs: 199, 200, 304, 360, and 361, and the associated RGN polypeptide has an amino acid sequence having at least 40%, 45%, 50%, 55%, 60%, 65%, 70%, 75%, 80%, 85%, 90%, 91%, 92%, 93%, 94%, 95%, 96%, 97%, 98%, 99% or more sequence identity to SEQ ID NO: 59.

In some embodiments, the methods comprise contacting a DNA molecule comprising a target DNA sequence with a DNA-binding polypeptide-deaminase fusion protein of the invention, wherein the DNA molecule is contacted with the fusion protein in an amount effective and under conditions suitable for the deamination of a nucleobase. In certain embodiments, the methods comprise contacting a DNA molecule comprising a target DNA sequence with (a) an RGN-deaminase fusion protein of the invention; and (b) a gRNA targeting the fusion protein of (a) to a target nucleotide sequence of the DNA strand; wherein the DNA molecule is contacted with the fusion protein and the gRNA in an amount effective and under conditions suitable for the deamination of a nucleobase. In some embodiments, the target DNA sequence comprises a sequence associated with a disease or disorder, and wherein the deamination of the nucleobase results in a sequence that is not associated with a disease or disorder. In some embodiments, the target DNA sequence resides in an allele of a crop plant, wherein the particular allele of the trait of interest results in a plant of lesser agronomic value. The deamination of the nucleobase results in an allele that improves the trait and increases the agronomic value of the plant.

In some embodiments, the target DNA sequence comprises a G>A point mutation associated with a disease or disorder, and wherein the deamination of the mutant A base results in a sequence that is not associated with a disease or disorder. In some embodiments, the deamination corrects a point mutation in the sequence associated with the disease or disorder. In some embodiments, the sequence associated with the disease or disorder encodes a protein, and the deamination introduces a stop codon into the sequence associated with the disease or disorder, resulting in a truncation of the encoded protein. In some embodiments, the contacting is performed in vivo in a subject susceptible to having, having, or diagnosed with the disease or disorder. In some embodiments, the disease or disorder is a disease associated with a point mutation, or a single-base mutation, in the genome. In some embodiments, the disease is a genetic disease, a cancer, a metabolic disease, or a lysosomal storage disease.

XI. Pharmaceutical Compositions and Methods of Treatment

Methods of treating a disease in a subject in need thereof are provided herein. The methods comprise administering to a subject in need thereof an effective amount of a presently disclosed fusion protein or a polynucleotide encoding the same, a presently disclosed gRNA or a polynucleotide encoding the same, a presently disclosed fusion protein system, a presently disclosed ribonucleoprotein complex, or a cell modified by or comprising any one of these compositions.

In some embodiments, the treatment comprises in vivo gene editing by administering to a subject in need thereof a presently disclosed fusion protein, gRNA, or a presently disclosed fusion protein system or polynucleotide(s) encoding the same. In some embodiments, the treatment comprises ex vivo gene editing wherein cells are genetically modified ex vivo with a presently disclosed fusion protein, gRNA, or a presently disclosed fusion protein system or polynucleotide(s) encoding the same and then the modified cells are administered to a subject. In some embodiments, the genetically modified cells originate from the subject that is then administered the modified cells, and the transplanted cells are referred to herein as autologous. In some embodiments, the genetically modified cells originate from a different subject (i.e., donor) within the same species as the subject that is administered the modified cells (i.e., recipient), and the transplanted cells are referred to herein as allogeneic. In some examples described herein, the cells can be expanded in culture prior to administration to a subject in need thereof.

For example, in some embodiments, a method is provided that comprises administering to a subject having such a disease, e.g., a genetic defect associated with the CFTR gene, an effective amount of ribonucleoprotein complex comprising a fusion protein with a deaminase having an amino acid sequence that is at least 80% identical to sequence set forth in any one of the SEQ ID NOs: 399, and 405-407. In the embodiments described herein, the administration of the ribonucleoprotein complex corrects the point mutation or introduces a deactivating mutation into a disease-associated CFTR gene. Other diseases that can be treated by correcting a point mutation or introducing a deactivating mutation into a disease-associated gene will be known to those of skill in the art, and the disclosure is not limited in this respect.

In some embodiments, the disease to be treated with the presently disclosed compositions is one that can be treated with immunotherapy, such as with a chimeric antigen receptor (CAR) T cell. Such diseases include but are not limited to cancer.

In some embodiments, the deamination of the target nucleobase results in the correction of a genetic defect, e.g., to correct the CFTR gene, or in the correction of a point mutation that leads to a loss of function in a gene product. In some embodiments, the genetic defect is associated with a disease or disorder, e.g., a lysosomal storage disorder or a metabolic disease, such as, for example, type I diabetes. Thus, in some embodiments, the disease to be treated with the presently disclosed compositions is associated with a sequence (i.e., the sequence is causal for the disease or disorder or causal for symptoms associated with the disease or disorder) that is mutated in order to treat the disease or disorder or the reduction of symptoms associated with the disease or disorder.

In some embodiments, the disease to be treated with the presently disclosed compositions is associated with a causal mutation. As used herein, a "causal mutation" refers to a particular nucleotide, nucleotides, or nucleotide sequence in the genome that contributes to the severity or presence of a disease or disorder in a subject. The correction of the causal mutation leads to the improvement of at least one symptom resulting from a disease or disorder. In some embodiments, the correction of the causal mutation leads to the improvement of at least one symptom resulting from a disease or disorder. In some embodiments, the causal mutation is adjacent to a PAM site recognized by the RGDBP (e.g., RGN) fused to a deaminase disclosed herein. The causal mutation can be corrected with a fusion polypeptide comprising a RGDBP (e.g., RGN) and a presently disclosed deaminase. Non-limiting examples of diseases associated with a causal mutation include cystic fibrosis, Hurler syndrome, Friedreich's Ataxia, Huntington's Disease, and sickle cell disease. Additional non-limiting examples of disease-associated genes and mutations are available from McKusick-Nathans Institute of Genetic Medicine, Johns Hopkins University (Baltimore, Md.) and National Center for Biotechnology Information, National Library of Medicine (Bethesda, Md.), available on the World Wide Web.

In some embodiments, the methods provided herein are used to introduce a deactivating point mutation into a gene or allele that encodes a gene product that is associated with a disease or disorder. For example, in some embodiments, methods are provided herein that employ a fusion protein to introduce a deactivating point mutation into an oncogene (e.g., in the treatment of a proliferative disease). A deactivating mutation may, in some embodiments, generate a premature stop codon in a coding sequence, which results in the expression of a truncated gene product, e.g., a truncated protein lacking the function of the full-length protein. In some embodiments, the purpose of the methods provided herein is to restore the function of a dysfunctional gene via genome editing. The fusion proteins provided herein can be validated for gene editing-based human therapeutics in vitro, e.g., by correcting a disease associated mutation in human cell culture. It will be understood by the skilled artisan that the fusion proteins provided herein, e.g., the fusion proteins comprising an RNA-guided, DNA-binding polypeptide and deaminase polypeptide can be used to correct any single point G>A mutation. Deamination of the mutant A to G leads to a correction of the mutation.

As used herein, "treatment" or "treating," or "palliating" or "ameliorating" are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested. In some embodiments, treatment may be administered after one or more symptoms have developed and/or after a disease has been diagnosed. In particular embodiments, treatment may be administered in the absence of symptoms, e.g., to prevent or delay onset of a symptom or inhibit onset or progression of a disease. For example, treatment may be administered to a susceptible individual prior to the onset of symptoms (e.g., in light of a history of symptoms and/or in light of genetic or other susceptibility factors). Treatment may also be continued after symptoms have resolved, for example, to prevent or delay their prevention or recurrence.

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The specific dose may vary depending on one or more of: the particular agent chosen, the dosing regimen to be followed, whether it is administered in combination with other compounds, timing of administration, and the delivery system in which it is carried.

The term "administering" refers to the placement of an active ingredient into a subject, by a method or route that results in at least partial localization of the introduced active ingredient at a desired site, such as a site of injury or repair, such that a desired effect(s) is produced. In some embodiments, the disclosure provides methods comprising delivering any of the isolated polypeptides, nucleic acid molecules fusion proteins, ribonucleoprotein complexes, vectors, pharmaceutical compositions and/or gRNAs described herein. In some embodiments, the disclosure further provides cells produced by such methods, and organisms (such as animals or plants) comprising or produced from such cells. In some embodiments, a deaminase, fusion protein and/or nucleic acid molecules as described herein in combination with (and optionally complexed with) a guide sequence is delivered to a cell.

In some embodiments, the administering comprises administering by viral delivery. Viral vectors comprising a nucleic acid encoding the fusion proteins, ribonucleoprotein complexes, or vectors disclosed herein may be administered directly to patients (i.e., in vivo) or they may be used to treat cells in vitro, and the modified cells may optionally be administered to patients (i.e., ex vivo). Conventional viral based systems may include, without limitation, retroviral, lentivirus, adenoviral, adeno-associated and herpes simplex virus vectors for gene transfer. Integration in the host genome is possible with the retrovirus, lentivirus, and adeno-associated virus gene transfer methods, often resulting in long term expression of the inserted transgene. Lentiviral vectors are retroviral vectors that are able to transduce or infect non-dividing cells and typically produce high viral titers. In applications where transient expression is preferred, adenoviral based systems may be used. Adenoviral based vectors are capable of very high transduction efficiency in many cell types and do not require cell division.

In some embodiments, the administering comprises administering by electroporation. In some embodiments, the administering comprises administering by nanoparticle delivery. In some embodiments, the administering comprises administering by liposome delivery. Any effective route of administration can be used to administer an effective amount of a pharmaceutical composition described herein.

In some embodiments, the administering comprises administering by other non-viral delivery of nucleic acids. Exemplary non-viral delivery methods, without limitation, include RNP complexes, lipofection, nucleofection, microinjection, biolistics, virosomes, liposomes, immunoliposomes, polycation or lipidmucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO1991/17424; WO 1991/16024. Delivery can be to cells (e.g. in vitro or ex vivo administration) or target tissues (e.g. in vivo administration).

As used herein, the term "subject" refers to any individual for whom diagnosis, treatment or therapy is desired. In some embodiments, the subject is an animal. In some embodiments, the subject is a mammal. In some embodiments, the subject is a human being.

The efficacy of a treatment can be determined by the skilled clinician. However, a treatment is considered an "effective treatment," if any one or all of the signs or symptoms of a disease or disorder are altered in a beneficial manner (e.g., decreased by at least 10%), or other clinically accepted symptoms or markers of disease are improved or ameliorated. Efficacy can also be measured by failure of an individual to worsen as assessed by hospitalization or need for medical interventions (e.g., progression of the disease is halted or at least slowed). Methods of measuring these indicators are known to those of skill in the art. Treatment includes: (1) inhibiting the disease, e.g., arresting, or slowing the progression of symptoms; or (2) relieving the disease, e.g., causing regression of symptoms; and (3) preventing or reducing the likelihood of the development of symptoms.

Pharmaceutical compositions comprising the presently disclosed RGN polypeptides or polynucleotides encoding the same, the presently disclosed gRNAs or polynucleotides encoding the same, the presently disclosed deaminases or polynucleotides encoding the same, the presently disclosed fusion proteins, the presently disclosed systems (such as those comprising a fusion protein), the presently disclosed ribonucleoprotein complex or cells comprising any of the RGN polypeptides or RGN-encoding polynucleotides, gRNA or gRNA-encoding polynucleotides, fusion protein-encoding polynucleotides, or the systems, and a pharmaceutically acceptable carrier are provided.

As used herein, a "pharmaceutically acceptable carrier" refers to a material that does not cause significant irritation to an organism and does not abrogate the activity and properties of the active ingredient (e.g., a deaminase or fusion protein or nucleic acid molecule encoding the same). Carriers must be of sufficiently high purity and of sufficiently low toxicity to render them suitable for administration to a subject being treated. The carrier can be inert, or it can possess pharmaceutical benefits. In some embodiments, a pharmaceutically acceptable carrier comprises one or more compatible solid or liquid filler, diluents or encapsulating substances which are suitable for administration to a human or other vertebrate animal. In some embodiments, the pharmaceutical composition comprises a pharmaceutically acceptable carrier that is non-naturally occurring. In some embodiments, the pharmaceutically acceptable carrier and the active ingredient are not found together in nature and are thus, heterologous.

Pharmaceutical compositions used in the presently disclosed methods can be formulated with suitable carriers, excipients, and other agents that provide suitable transfer, delivery, tolerance, and the like. A multitude of appropriate formulations are known to those skilled in the art. See, e.g., Remington, The Science and Practice of Pharmacy (21st ed. 2005). Non-limiting examples include a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. Administered intravenously, particular carriers are physiological saline or phosphate buffered saline (PBS). Pharmaceutical compositions for oral or parenteral use may be prepared into dosage forms in a unit dose suited to fit a dose of the active ingredients. Such dosage forms in a unit dose include, for example, tablets, pills, capsules, injections (ampoules), suppositories, etc. These compositions also may contain adjuvants including preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It also may be desirable to include isotonic agents, for example, sugars, sodium chloride and the like. Prolonged absorption of the injectable pharmaceutical form may be brought about by the use of agents delaying absorption, for example, aluminum monostearate and gelatin.

In some embodiments wherein cells comprising or modified with the presently disclosed RGNs, gRNAs, deaminases, fusion proteins, systems (including those comprising fusion proteins) or polynucleotides encoding the same are administered to a subject, the cells are administered as a suspension with a pharmaceutically acceptable carrier. One of skill in the art will recognize that a pharmaceutically acceptable carrier to be used in a cell composition will not include buffers, compounds, cryopreservation agents, preservatives, or other agents in amounts that substantially interfere with the viability of the cells to be delivered to the subject. A formulation comprising cells can include e.g., osmotic buffers that permit cell membrane integrity to be maintained, and optionally, nutrients to maintain cell viability or enhance engraftment upon administration. Such formulations and suspensions are known to those of skill in the art and/or can be adapted for use with the cells described herein using routine experimentation.

A cell composition can also be emulsified or presented as a liposome composition, provided that the emulsification procedure does not adversely affect cell viability. The cells and any other active ingredient can be mixed with excipients that are pharmaceutically acceptable and compatible with the active ingredient, and in amounts suitable for use in the therapeutic methods described herein.

Additional agents included in a cell composition can include pharmaceutically acceptable salts of the components therein. Pharmaceutically acceptable salts include the acid addition salts (formed with the free amino groups of the polypeptide) that are formed with inorganic acids, such as, for example, hydrochloric or phosphoric acids, or such organic acids as acetic, tartaric, mandelic and the like. Salts formed with the free carboxyl groups can also be derived from inorganic bases, such as, for example, sodium, potassium, ammonium, calcium or ferric hydroxides, and such organic bases as isopropylamine, trimethylamine, 2-ethylamino ethanol, histidine, procaine and the like.

Suitable routes of administrating the pharmaceutical composition described herein include, without limitation: topical, subcutaneous, transdermal, intradermal, intralesional, intraarticular, intraperitoneal, intravesical, transmucosal, gingival, intradental, intracochlear, transtympanic, intraorgan, epidural, intrathecal, intramuscular, intravenous, intravascular, intraosseus, periocular, intratumoral, intracerebral, and intracerebroventricular administration.

In some embodiments, the pharmaceutical composition described herein is administered locally to a diseased site (e.g., the lung). In some embodiments, the pharmaceutical composition described herein is administered to a subject by injection, inhalation (e.g., of an aerosol), by means of a catheter, by means of a suppository, or by means of an implant, the implant being of a porous, non-porous, or gelatinous material, including a membrane, such as a sialastic membrane, or a fiber. In some embodiments, the pharmaceutical composition is formulated for delivery to a subject, e.g., for gene editing.

In some embodiments, the pharmaceutical composition is formulated in accordance with routine procedures as a composition adapted for intravenous or subcutaneous administration to a subject, e.g., a human. In some embodiments, pharmaceutical composition for administration by injection are solutions in sterile isotonic aqueous buffer. Where necessary, the pharmaceutical can also include a solubilizing agent and a local anesthetic such as lignocaine to ease pain at the site of the injection. Generally, the ingredients are supplied either separately or mixed together, for example, as a dry lyophilized powder or water free concentrate in a hermetically sealed container such as an ampoule or sachette indicating the quantity of active agent. Where the pharmaceutical is to be administered by infusion, it can be dispensed with an infusion bottle containing sterile pharmaceutical grade water or saline. Where the pharmaceutical composition is administered by injection, an ampoule of sterile water for injection or saline can be provided so that the ingredients can be mixed prior to administration.

In some embodiments, the pharmaceutical composition can be contained within a lipid particle or vesicle, such as a liposome or microcrystal, which is also suitable for parenteral administration.

Although the descriptions of pharmaceutical compositions provided herein are principally directed to pharmaceutical compositions which are suitable for administration to humans, it will be understood by the skilled artisan that such compositions are generally suitable for administration to animals or organisms of all sorts.

Modifying Causal Mutations Using Base-Editing

An example of a genetically inherited disease which could be corrected using an approach that relies on an RGN-deaminase fusion protein of the invention is Cystic Fibrosis. Cystic fibrosis (CF) is an autosomal recessive disease caused by mutations in the cystic fibrosis transmembrane regulator (CFTR) gene (set forth as SEQ ID NO: 51). CFTR encodes for a cAMP regulated chloride channel located in the apical membrane of epithelial cells that catalyze the passage of small ions through the membrane. Dysregulation of this mechanism causes an impairment of salt and fluid homeostasis that results in multiorgan dysfunctions and ultimately mortality from respiratory failure.

Almost 2,000 mutations in the CFTR gene have been found to cause CF. CFTR mutations are divided into six classes based on the functional defect in either CFTR protein synthesis, trafficking, function, or stability, although it is acknowledged that many CFTR mutants present multiple defects. Class I mutations lead to severely defective protein production. They are primarily nonsense or frameshift mutations which introduce a premature termination codon (PTC), leading to unstable messenger RNA (mRNA) degraded by the mRNA decay pathway (NMD). Nonsense mutations due to single nucleotide changes comprise a major subset of Class I mutations (Marangi, M. and Pistritto, G, 2018, *Front Pharmacol* 9, 396, doi:10.3389/fphar.2018.00396; Pranke, I., et al., 2019, *Front Pharmacol* 10, 121, doi:10.3389/fphar.2019.00121, both of which are incorporated by reference herein). Treatment for patients with Class I cystic fibrosis can be difficult, as no functional CFTR protein is produced. Notably, a significant fraction of these nonsense mutations are potentially addressable with A to G base editors (Geurts, M. H. et al, 2020, *Cell Stem Cell* 26, 503-510 e507, doi:10.1016/j.stem.2020.01.019 incorporated by reference herein).

Geurts et al. were the first group to perform precise base editing in cultured lung epithelial cells with Class I mutations from cystic fibrosis patients, using a fusion protein comprising an adenine deaminase operably linked an RGN, namely either SpyCas9 or the xSpyCas9 variant. SpyCas9 recognizes a 5'-nGG-3'PAM, while the xSpyCas9 variant recognized the reduced 5'-nG-3'. The authors state that a major limitation of the base editing technology is the PAM requirement of the Cas protein being used. They find that the majority of nonsense mutations identified in the CFTR gene are not in the required targeting window for a fusion protein comprising the RGN SpyCas9. The PAM is a short motif, generally one to four nucleotides, on the target DNA sequence that is recognized by the RGN. The PAM sequence is intrinsic to each RGN protein, such that an RGN can only access the genomic space around a suitable PAM. Additionally, the base editing window for base editors is limited, frequently to just a portion of the nucleotides in the target sequence. If the nucleotide of interest is too close to the PAM, the RGN blocks access to the nucleotide. If the nucleotide is too far away from the PAM, the deaminase tethered to the RGN is unable to reach the nucleotide. Also, the amount of ssDNA exposed by the R-loop limits the accessibility of the deaminases. The present invention includes RGN-deaminase fusion proteins where the RGN recognizes a PAM which is proximal to a Class I mutation of the CFTR gene and the deaminase is able to successfully modify the targeted causal mutation.

Another limitation to RGN-deaminase fusion proteins known in the art is that the vector construct encoding for the fusion protein is too large for methods of in vivo delivery. AAV delivery of these fusion proteins is not an option for SpyCas9-based fusion proteins because their size exceeds the limit for efficient AAV packaging. The RGN component of the fusion proteins described herein are smaller in size and are therefore viable candidates for AAV vector delivery strategies. The present invention also discloses guide RNAs which are specific for the RGNs described herein and which guide the fusion proteins of the invention to target sites of nonsense mutations in the CFTR gene which were previously unreachable. The present invention also teaches methods of using said fusion proteins for targeted base editing through in vivo AAV vector delivery.

Ideally, the coding sequence of an RGN-deaminase fusion protein of the invention and a corresponding guide RNA for targeting the fusion protein to the CFTR gene may all be packaged into a single AAV vector. The generally accepted size limit for AAV vectors is 4.7 kb, although larger sizes may be contemplated at the expense of reduced packing efficiency. The RGN nickases in Table 28 have a coding sequence length of about 3.15-3.45 kB. To ensure that the expression cassettes for both the fusion protein and its corresponding guide RNA could fit into an AAV vector, novel, active deletion variants of RGNs are described herein. In addition to shortening the amino acid sequence and therefore the coding sequence of the RGN of the fusion protein, the peptide linker which links the RGN and the deaminase may also be shortened. Finally, the genetic elements, such as the promoters, enhancers, and/or terminators, may also be engineered via deletion analysis to determine the minimal size required for each to be functional.

Some embodiments of the disclosure provide methods for editing a nucleic acid using the deaminases or the RGN complexes described herein to achieve the nucleobase change, e.g., an A:T base pair to G:C base pair. In some embodiments, the method is a method for editing a nucleobase of a nucleic acid (e.g., a base pair of a double-stranded DNA sequence). In some embodiments, the deaminases or the RGN complexes described herein are used to introduce a point mutation into a nucleic acid by deaminating and excising a target "A" nucelobase. In some embodiments, the deamination-and-excision of the target nucleobase results in the correction of a genetic defect, e.g., in the correction of a point mutation in a CFTR gene. In some embodiments, the genetic defect is associated with a disease, disorder, or condition, e.g., Cystic Fibrosis. For example, in some embodiments, methods are provided herein employ a base editing RGN complexes comprising a fusion protein with a deaminase having an amino acid sequence that is at least 80% identical to sequence set forth in any one of the SEQ ID NOs: 399, and 405-407, to correct a gene associated with a genetic defect, e.g., to correct a point mutation in a CFTR gene (e.g., in the treatment of a proliferative disease). In specific embodiments, the target sequence in the CFTR gene is 62-97, 116-139, 152-185, 203-234, 251-286, 305-344, 562, or 563.

In some embodiments, the purpose of the methods provided herein is to restore the function of a dysfunctional gene via genome editing. The base editor proteins provided herein may be validated for gene editing-based human therapeutics in vitro, e.g., by correcting a disease-associated mutation in human cell culture. It will be understood by the skilled artisan that the fusion proteins and/or the RGN complexes provided herein comprising a nucleic acid binding protein (e.g., nCas9) and a nucleobase modification domain (e.g., deaminase with an amino acid sequence set forth in SEQ ID NO.: 407, 399, or 405 may be used to correct any single point of T to G or change a pairing of T:A to G:C.

In some embodiments, provided herein are the methods for the treatment of a subject diagnosed with a disease associated with or caused by a point mutation (e.g., mutation in CFTR gene) that can be corrected by a fusion protein or the RGN complexes described herein. For example, in some embodiments, a method is provided that comprises administering to a subject having such a disease, e.g., cystic fibrosis, an effective amount of a fusion protein or RGN complex disclosed herein that corrects the point mutation or introduces a deactivating mutation into a disease-associated gene. In some embodiments, a method is provided that comprises administering to a subject having such a disease, e.g., a cancer associated with a point mutation as described above, an effective amount of a fusion protein, RGN complex, or pharmaceutical composition disclosed herein that corrects the point mutation or introduces a deactivating mutation into a disease-associated gene. In specific embodiments, methods of treating cystic fibrosis are provided along with methods of reducing at least one symptom of cystic fibrosis by administering an effective amount of a pharmaceutical composition disclosed herein. An effective amount of a pharmaceutical composition for treating or reducing a symptom of cystic fibrosis can reduce a symptom (i.e., treat) of cystic fibrosis by about 5%, 10%, 15%20%, 25%, 30%, 40%, 50%, 60%, 70%, 80%, 90%, 95%, or more; or about 10-20%, 15-25%, 20-40%, 30-50%, 40-60%, 50-70%, 60-80%, 70-90%, 80-95%, or 90-95% when compared to a control patient. In specific embodiments, the control patient can be the same patient before administration of the effective amount of the pharmaceutical composition disclosed herein. Symptoms of cystic fibrosis can include, but are not limited to: sneezing, a persistent cough that produces mucus or phlegm, shortness of breath, especially when exercising, recurrent lung infections, a stuffy nose, stuffy sinuses, greasy foul-smelling stools, constipation, nausea, swollen abdomen, loss of appetite, among others. Methods of identifying and measuring symptoms of cystic fibrosis are known in the art.

In some embodiments of the described methods for modifying a target DNA molecule, the step of contacting is performed in vitro. In particular embodiments, the step of contacting is performed in vivo. In some embodiments, the step of contacting is performed in a subject (e.g., a human subject or a non-human animal subject). In some embodiments, the step of contacting is performed in a cell, such as a human or non-human animal cell.

XII. Cells Comprising a Polynucleotide Genetic Modification

Provided herein are cells and organisms comprising a target nucleic acid molecule of interest that has been modified using a process mediated by a fusion protein, optionally with a gRNA, as described herein. In some embodiments, the fusion protein comprises a deaminase polypeptide comprising an amino acid sequence of any of SEQ ID NOs: 1-10 and 399-441, or an active variant or fragment thereof. In some embodiments, the fusion protein comprises an adenine deaminase comprising an amino acid sequence having at least 50%, at least 55%, at least 60%, at least 65%, at least 70%, at least 75%, at least 80%, at least 85%, at least 90%, at least 95%, at least 96%, at least 97%, at least 98%, or at least 99% identity to any of SEQ ID NOs: 1-10 and 399-441. In some embodiments, the fusion protein comprises a deaminase and a DNA-binding polypeptide (e.g., an RNA-guided, DNA-binding polypeptide). In further embodiments, the fusion protein comprises a deaminase and an RGN or a variant thereof, such as for example APG07433.1 (SEQ ID NO: 41) or its nickase variant nAPG07433.1 (SEQ ID NO: 42). In some embodiments, the fusion protein comprises a deaminase and a Cas9 or a variant thereof, such as for example dCas9 or nickase Cas9. In some embodiments, the fusion protein comprises a nuclease-inactive or nickase variant of a Type II CRISPR-Cas polypeptide. In some embodiments, the fusion protein comprises a nuclease-inactive or nickase variant of a Type V CRISPR-Cas polypeptide. In some embodiments, the fusion protein comprises a nuclease-inactive or nickase variant of a Type VI CRISPR-Cas polypeptide.

The modified cells can be eukaryotic (e.g., mammalian, plant, insect, avian cell) or prokaryotic. Also provided are organelles and embryos comprising at least one nucleotide sequence that has been modified by a process utilizing a fusion protein as described herein. The genetically modified cells, organisms, organelles, and embryos can be heterozygous or homozygous for the modified nucleotide sequence. The mutation(s) introduced by the deaminase domain of the fusion protein can result in altered expression (up-regulation or down-regulation), inactivation, or the expression of an altered protein product or an integrated sequence. In those instances wherein the mutation(s) results in either the inactivation of a gene or the expression of a non-functional protein product, the genetically modified cell, organism, organelle, or embryo is referred to as a "knock out". The knock out phenotype can be the result of a deletion mutation (i.e., deletion of at least one nucleotide), an insertion mutation (i.e., insertion of at least one nucleotide), or a nonsense mutation (i.e., substitution of at least one nucleotide such that a stop codon is introduced).

In some embodiments, the mutation(s) introduced by the deaminase domain of the fusion protein results in the production of a variant protein product. The expressed variant protein product can have at least one amino acid substitution and/or the addition or deletion of at least one amino acid. The variant protein product can exhibit modified characteristics or activities when compared to the wild-type protein, including but not limited to altered enzymatic activity or substrate specificity.

In some embodiments, the mutation(s) introduced by the deaminase domain of the fusion protein result in an altered expression pattern of a protein. As a non-limiting example, mutation(s) in the regulatory regions controlling the expression of a protein product can result in the overexpression or downregulation of the protein product or an altered tissue or temporal expression pattern.

The cells that have been modified can be grown into an organism, such as a plant, in accordance with conventional ways. See, for example, McCormick et al. (1986) *Plant Cell Reports* 5:81-84. These plants may then be grown, and either pollinated with the same modified strain or different strains, and the resulting hybrid having the genetic modification. The present invention provides genetically modified seed. Progeny, variants, and mutants of the regenerated plants are also included within the scope of the invention, provided that these parts comprise the genetic modification. Further provided is a processed plant product or byproduct that retains the genetic modification, including for example, soymeal.

The methods provided herein may be used for modification of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, *papaya*, cashew, macadamia, almond, oats, vegetables, ornamentals, and conifers.

Vegetables include, but are not limited to, tomatoes, lettuce, green beans, lima beans, peas, and members of the genus Curcumis such as cucumber, cantaloupe, and musk melon. Ornamentals include, but are not limited to, azalea, *hydrangea*, hibiscus, roses, tulips, daffodils, petunias, carnation, poinsettia, and *chrysanthemum*. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape, etc.).

The methods provided herein can also be used to genetically modify any prokaryotic species, including but not limited to, archaea and bacteria (e.g., *Bacillus* sp., *Klebsiella* sp. *Streptomyces* sp., *Rhizobium* sp., *Escherichia* sp., *Pseudomonas* sp., *Salmonella* sp., *Shigella* sp., *Vibrio* sp., *Yersinia* sp., *Mycoplasma* sp., *Agrobacterium, Lactobacillus* sp.).

The methods provided herein can be used to genetically modify any eukaryotic species or cells therefrom, including but not limited to animals (e.g., mammals, insects, fish, birds, and reptiles), fungi, amoeba, algae, and yeast. In some embodiments, the cell that is modified by the presently disclosed methods include cells of hematopoietic origin, such as immune cells (i.e., a cell of the innate or adaptive immune system) including but not limited to B cells, T cells, natural killer (NK) cells, pluripotent stem cells, induced pluripotent stem cells, chimeric antigen receptor T (CAR-T) cells, monocytes, macrophages, and dendritic cells.

Cells that have been modified may be introduced into an organism. These cells could have originated from the same organism (e.g., person) in the case of autologous cellular transplants, wherein the cells are modified in an ex vivo approach. In some embodiments, the cells originated from another organism within the same species (e.g., another person) in the case of allogeneic cellular transplants.

XIII. Kits

Some aspects of this disclosure provide kits comprising a deaminase of the invention. In certain embodiments, the disclosure provides kits comprising a fusion protein comprising a deaminase of the invention and a DNA-binding polypeptide (e.g., an RNA-guided, DNA-binding polypeptide, such as an RGN polypeptide, for example a nuclease-inactive Cas9 domain), and, optionally, a linker positioned between the DNA-binding polypeptide domain and the deaminase. In addition, in some embodiments, the kit comprises suitable reagents, buffers, and/or instructions for using the fusion protein, e.g., for in vitro or in vivo DNA or RNA editing. In some embodiments, the kit comprises instructions regarding the design and use of suitable gRNAs for targeted editing of a nucleic acid sequence.

In some embodiments, the pharmaceutical composition may be provided as a pharmaceutical kit comprising (a) a container containing a composition of the disclosure in lyophilized form and (b) a second container containing a pharmaceutically acceptable diluent (e.g., sterile water) for injection. The pharmaceutically acceptable diluent can be used for reconstitution or dilution of the lyophilized compound of the disclosure. Optionally associated with such container(s) can be a notice in the form prescribed by a governmental agency regulating the manufacture, use or sale of pharmaceuticals or biological products, which notice reflects approval by the agency of manufacture, use or sale for human administration.

The article "a" and "an" are used herein to refer to one or more than one (i.e., to at least one) of the grammatical object of the article. By way of example, "a polypeptide" means one or more polypeptides.

All publications and patent applications mentioned in the specification are indicative of the level of those skilled in the art to which this disclosure pertains. All publications and patent applications are herein incorporated by reference to the same extent as if each individual publication or patent application was specifically and individually indicated to be incorporated herein by reference.

Although the foregoing invention has been described in some detail by way of illustration and example for purposes of clarity of understanding, it will be obvious that certain changes and modifications may be practiced within the scope of the appended claims.

Non-limiting embodiments include:

1. An isolated polypeptide comprising an amino acid sequence having at least 90% sequence identity to any one of SEQ ID NOs: 407, 405, 399, 1-10, 400-404, 406, and 408-441, wherein said polypeptide has deaminase activity.
2. The isolated polypeptide of embodiment 1, comprising an amino acid sequence having at least 95% sequence identity to any one of SEQ ID NOs: 407, 405, 399, 1-10, 400-404, 406, and 408-441.
3. The isolated polypeptide of embodiment 1, comprising an amino acid sequence having 100% sequence identity to any one of SEQ ID NOs: 407, 405, 399, 1-10, 400-404, 406, and 408-441.

4. A nucleic acid molecule comprising a polynucleotide encoding a deaminase polypeptide, wherein the deaminase is encoded by a nucleotide sequence that:
a) has at least 80% sequence identity to any one of SEQ ID NOs: 451, 449, 443, 11-20, 444-448, 450, and 452-485, or
b) encodes an amino acid sequence having at least 90% sequence identity to any one of SEQ ID NOs: 407, 405, 399, 1-10, 400-404, 406, and 408-441.

5. The nucleic acid molecule of embodiment 4, wherein the deaminase is encoded by a nucleotide sequence that has at least 90% sequence identity to any one of SEQ ID NOs: 451, 449, 443, 11-20, 444-448, 450, and 452-485.

6. The nucleic acid molecule of embodiment 4, wherein the deaminase is encoded by a nucleotide sequence that has at least 95% sequence identity to any one of SEQ ID NOs: 451, 449, 443, 11-20, 444-448, 450, and 452-485.

7. The nucleic acid molecule of embodiment 4, wherein the deaminase is encoded by a nucleotide sequence that has 100% sequence identity to any one of SEQ ID NOs: 451, 449, 443, 11-20, 444-448, 450, and 452-485.

8. The nucleic acid molecule of embodiment 4, wherein the deaminase polypeptide has an amino acid sequence having at least 95% sequence identity to any one of SEQ ID NOs: 407, 405, 399, 1-10, 400-404, 406, and 408-441.

9. The nucleic acid molecule of embodiment 4, wherein the deaminase polypeptide has an amino acid sequence having 100% sequence identity to any one of SEQ ID NOs: 407, 405, 399, 1-10, 400-404, 406, and 408-441.

10. The nucleic acid molecule of any one of embodiments 4-9, wherein said nucleic acid molecule further comprises a heterologous promoter operably linked to said polynucleotide.

11. A pharmaceutical composition comprising a pharmaceutically acceptable carrier and the polypeptide of any one of embodiments of 1-3 or the nucleic acid molecule of any one of embodiments 4-10.

12. The pharmaceutical composition of embodiment 11, wherein the pharmaceutically acceptable carrier is heterologous to said polypeptide or said nucleic acid molecule.

13. The pharmaceutical composition of embodiment 11 or 12, wherein the pharmaceutically acceptable carrier is not naturally-occurring.

14. A fusion protein comprising a DNA-binding polypeptide and a deaminase having at least 90% sequence identity to any one of SEQ ID NOs: 407, 405, 399, 1-10, 400-404, 406, and 408-441.

15. The fusion protein of embodiment 14, wherein said deaminase has at least 95% sequence identity to any one of SEQ ID NOs: 407, 405, 399, 1-10, 400-404, 406, and 408-441.

16. The fusion protein of embodiment 14, wherein said deaminase has 100% sequence identity to any one of SEQ ID NOs: 407, 405, 399, 1-10, 400-404, 406, and 408-441.

17. The fusion protein of any one of embodiments 14-16, wherein the deaminase is an adenine deaminase.

18. The fusion protein of any one of embodiments 14-17, wherein the DNA-binding polypeptide is a meganuclease, zinc finger fusion protein, or a TALEN.

19. The fusion protein of any one of embodiments 14-17, wherein the DNA-binding polypeptide is an RNA-guided, DNA-binding polypeptide.

20. The fusion protein of embodiment 19, wherein the RNA-guided, DNA-binding polypeptide is an RNA-guided nuclease (RGN) polypeptide.

21. The fusion protein of embodiment 20, wherein the RGN is a Type II CRISPR-Cas polypeptide.

22. The fusion protein of embodiment 20, wherein the RGN is a Type V CRISPR-Cas polypeptide.

23. The fusion protein of any one of embodiments 20-22, wherein the RGN is an RGN nickase.

24. The fusion protein of embodiment 20, wherein the RGN has an amino acid sequence having at least 95% sequence identity to any one of SEQ ID NOs: 41, 60, 366, and 368.

25. The fusion protein of embodiment 20, wherein the RGN has an amino acid sequence of any one of SEQ ID NOs: 41, 60, 366, and 368.

26. The fusion protein of embodiment 23, wherein the RGN nickase is any one of SEQ ID NOs: 42, 52-59, 61, 397, and 398.

27. The fusion protein of any of embodiments 14-26, wherein the fusion protein further comprises at least one nuclear localization signal (NLS).

28. A nucleic acid molecule comprising a polynucleotide encoding a fusion protein comprising a DNA-binding polypeptide and a deaminase, wherein the deaminase is encoded by a nucleotide sequence that:
a) has at least 80% sequence identity to any one of SEQ ID NOs: 451, 449, 443, 11-20, 444-448, 450, and 452-485, or
b) encodes an amino acid sequence having at least 90% sequence identity to any one of SEQ ID NOs: 407, 405, 399, 1-10, 400-404, 406, and 408-441.

29. The nucleic acid molecule of embodiment 28, wherein said nucleotide sequence has at least 90% sequence identity to any one of SEQ ID NOs: 451, 449, 443, 11-20, 444-448, 450, and 452-485.

30. The nucleic acid molecule of embodiment 28, wherein said nucleotide sequence has at least 95% sequence identity to any one of SEQ ID NOs: 451, 449, 443, 11-20, 444-448, 450, and 452-485.

31. The nucleic acid molecule of embodiment 28, wherein said nucleotide sequence has 100% sequence identity to any one of SEQ ID NOs: 451, 449, 443, 11-20, 444-448, 450, and 452-485.

32. The nucleic acid molecule of embodiment 28, wherein said nucleotide sequence encodes an amino acid sequence having at least 95% sequence identity to any one of SEQ ID NOs 407, 405, 399, 1-10, 400-404, 406, and 408-441.

33. The nucleic acid molecule of embodiment 28, wherein said nucleotide sequence encodes an amino acid sequence having 100% sequence identity to any one of SEQ ID NOs: 407, 405, 399, 1-10, 400-404, 406, and 408-441.

34. The nucleic acid molecule of any one of embodiments 28-33, wherein the deaminase is an adenine deaminase.

35. The nucleic acid molecule of any one of embodiments 28-34, wherein the DNA-binding polypeptide is a meganuclease, zinc finger fusion protein, or a TALEN.

36. The nucleic acid molecule of any one of embodiments 28-34-, wherein the DNA-binding polypeptide is an RNA-guided, DNA-binding polypeptide.

37. The nucleic acid molecule of embodiment 36, wherein the RNA-guided, DNA-binding polypeptide is an RNA-guided nuclease (RGN) polypeptide.

38. The nucleic acid molecule of embodiment 37, wherein the RGN is a Type II CRISPR-Cas polypeptide.

39. The nucleic acid molecule of embodiment 37, wherein the RGN is a Type V CRISPR-Cas polypeptide.

40. The nucleic acid molecule of any one of embodiments 37-39, wherein the RGN is an RGN nickase.

41. The nucleic acid molecule of embodiment 37, wherein the RGN has an amino acid sequence having at least 95% sequence identity to any one of SEQ ID NOs: 41, 60, 366, and 368.

42. The nucleic acid molecule of embodiment 37, wherein the RGN is SEQ ID NO: 41, 60, 366, or 368.

43. The nucleic acid molecule of embodiment 40, wherein the RGN nickase is any one of SEQ ID NOs: 42, 52-59, 61, 397, and 398.

44. The nucleic acid molecule of any of embodiments 28-43, wherein the polynucleotide encoding the fusion protein is operably linked at its 5' end to a heterologous promoter.

45. The nucleic acid molecule of any of embodiments 28-44, wherein the polynucleotide encoding the fusion protein is operably linked at its 3' end to a heterologous terminator.

46. The nucleic acid molecule of any of embodiments 28-45, wherein the fusion protein comprises one or more nuclear localization signals.

47. The nucleic acid molecule of any of embodiments 28-46, wherein the fusion protein is codon optimized for expression in a eukaryotic cell.

48. The nucleic acid molecule of any of embodiments 28-46, wherein the fusion protein is codon optimized for expression in a prokaryotic cell.

49. A vector comprising the nucleic acid molecule of any one of embodiments 28-48.

50. A vector comprising the nucleic acid molecule of any one of embodiments 28-48, further comprising at least one nucleotide sequence encoding a guide RNA (gRNA) capable of hybridizing to a target sequence.

51. The vector of embodiment 50, wherein the gRNA is a single guide RNA.

52. The vector of embodiment 50, wherein the gRNA is a dual guide RNA.

53. A cell comprising the fusion protein of any of embodiments 14-27.

54. A cell comprising the fusion protein of any one of embodiments 14-27, wherein the cell further comprises a guide RNA.

55. A cell comprising the nucleic acid molecule of any one of embodiments 28-48.

56. A cell comprising the vector of embodiments of any one of embodiments 49-52.

57. The cell of any one of embodiments 53-56, wherein the cell is a prokaryotic cell.

58. The cell of any one of embodiments 53-56, wherein the cell is a eukaryotic cell.

59. The cell of embodiment 58, wherein the eukaryotic cell is a mammalian cell.

60. The cell of embodiment 59, wherein the mammalian cell is a human cell.

61. The cell of embodiment 60, wherein the human cell is an immune cell.

62. The cell of embodiment 61, wherein the immune cell is a stem cell.

63. The cell of embodiment 62, wherein the stem cell is an induced pluripotent stem cell.

64. The cell of embodiment 58, wherein the eukaryotic cell is an insect or avian cell.

65. The cell of embodiment 58, wherein the eukaryotic cell is a fungal cell.

66. The cell of embodiment 58, wherein the eukaryotic cell is a plant cell.

67. A plant comprising the cell of embodiment 66.

68. A seed comprising the cell of embodiment 66.

69. A pharmaceutical composition comprising a pharmaceutically acceptable carrier and the fusion protein of any one of embodiments 14-27, the nucleic acid molecule of any one of embodiments 28-48, the vector of any one of embodiments 49-52, or the cell of any one of embodiments 59-63.

70. A method for making a fusion protein comprising culturing the cell of any one of embodiments 53-66 under conditions in which the fusion protein is expressed.

71. A method for making a fusion protein comprising introducing into a cell the nucleic acid molecule of any of embodiments 28-48 or a vector of any one of embodiments 49-52 and culturing the cell under conditions in which the fusion protein is expressed.

72. The method of embodiment 70 or 71, further comprising purifying said fusion protein.

73. A method for making an RGN fusion ribonucleoprotein complex, comprising introducing into a cell the nucleic acid molecule of any one of embodiments 37-43 and a nucleic acid molecule comprising an expression cassette encoding for a guide RNA, or the vector of any of embodiments 50-52, and culturing the cell under conditions in which the fusion protein and the gRNA are expressed and form an RGN fusion ribonucleoprotein complex.

74. The method of embodiment 73, further comprising purifying said RGN fusion ribonucleoprotein complex.

75. A system for modifying a target DNA molecule comprising a target DNA sequence, said system comprising:
a) a fusion protein comprising an RNA-guided nuclease polypeptide (RGN) and a deaminase, wherein the deaminase has an amino acid sequence having at least 90% sequence identity to any one of SEQ ID NOs: 407, 405, 399, 1-10, 400-404, 406, and 408-441, or a nucleotide sequence encoding said fusion protein; and
b) one or more guide RNAs capable of hybridizing to said target DNA sequence or one or more nucleotide sequences encoding the one or more guide RNAs (gRNAs); and
wherein the one or more guide RNAs are capable of forming a complex with the fusion protein in order to direct said fusion protein to bind to said target DNA sequence and modify the target DNA molecule.

76. The system of embodiment 75, wherein said deaminase has an amino acid sequence having at least 95% sequence identity to any one of SEQ ID NOs: 407, 405, 399, 1-10, 400-404, 406, and 408-441.

77. The system of embodiment 75, wherein said deaminase has an amino acid sequence having 100% sequence identity to any one of SEQ ID NOs: 407, 405, 399, 1-10, 400-404, 406, and 408-441.

78. The system of any one of embodiments 75-77, wherein at least one of said nucleotide sequence encoding the one or more guide RNAs and said nucleotide sequence encoding the fusion protein is operably linked to a promoter heterologous to said nucleotide sequence.

79. The system of any one of embodiments 75-78, wherein the target DNA sequence is a eukaryotic target DNA sequence.

80. The system of any one of embodiments 75-79, wherein the target DNA sequence is located adjacent to a protospacer adjacent motif (PAM) that is recognized by the RGN.

81. The system of any one of embodiments 75-80, wherein the target DNA molecule is within a cell.

82. The system of embodiment 81, wherein the cell is a eukaryotic cell.

83. The system of embodiment 82, wherein the eukaryotic cell is a plant cell.

84. The system of embodiment 82, wherein the eukaryotic cell is a mammalian cell.

85. The system of embodiment 84, wherein the mammalian cell is a human cell.

86. The system of embodiment 85, wherein the human cell is an immune cell.

87. The system of embodiment 86, wherein the immune cell is a stem cell.

88. The system of embodiment 87, wherein the stem cell is an induced pluripotent stem cell.

89. The system of embodiment 82, wherein the eukaryotic cell is an insect cell.

90. The system of embodiment 81, wherein the cell is a prokaryotic cell.

91. The system of any one of embodiments 75-90, wherein the RGN of the fusion protein is a Type II CRISPR-Cas polypeptide.

92. The system of any one of embodiments 75-90, wherein the RGN of the fusion protein is a Type V CRISPR-Cas polypeptide.

93. The system of any one of embodiments 75-90, wherein the RGN of the fusion protein has an amino acid sequence having at least 95% sequence identity to SEQ ID NO: 41, 60, 366, or 368.

94. The system of any one of embodiments 75-90, wherein the RGN of the fusion protein has an amino acid sequence of any one of SEQ ID NOs: 41, 60, 366, and 368.

95. The system of any one of embodiments 75-90, wherein the RGN of the fusion protein is an RGN nickase.

96. The system of embodiment 95, wherein the RGN nickase is any one of SEQ ID NOs: 42, 52-59, 61, 397, and 398.

97. The system of any of embodiments 75-96, wherein the fusion protein comprises one or more nuclear localization signals.

98. The system of any of embodiments 75-97, wherein the fusion protein is codon optimized for expression in a eukaryotic cell.

99. The system of any of embodiments 75-98, wherein nucleotide sequences encoding the one or more guide RNAs and the nucleotide sequence encoding a fusion protein are located on one vector.

100. A pharmaceutical composition comprising a pharmaceutically acceptable carrier and the system of any one of embodiments 75-99.

101. A method for modifying a target DNA molecule comprising a target DNA sequence, said method comprising delivering a system according to any one of embodiments 75-99 to said target DNA molecule or a cell comprising the target DNA molecule.

102. The method of embodiment 101, wherein said modified target DNA molecule comprises an A>N mutation of at least one nucleotide within the target DNA molecule, wherein N is C, G, or T.

103. The method of embodiment 102, wherein said modified target DNA molecule comprises an A>G mutation of at least one nucleotide within the target DNA molecule.

104. A method for modifying a target DNA molecule comprising a target sequence comprising:
a) assembling an RGN-deaminase ribonucleotide complex in vitro by combining:
i) one or more guide RNAs capable of hybridizing to the target DNA sequence; and
ii) a fusion protein comprising an RNA-guided nuclease polypeptide (RGN), and at least one deaminase, wherein the deaminase has an amino acid sequence having at least 90% sequence identity to any one of SEQ ID NOs: 407, 405, 399, 1-10, 400-404, 406, and 408-441;
under conditions suitable for formation of the RGN-deaminase ribonucleotide complex; and
b) contacting said target DNA molecule or a cell comprising said target DNA molecule with the in vitro-assembled RGN-deaminase ribonucleotide complex;
wherein the one or more guide RNAs hybridize to the target DNA sequence, thereby directing said fusion protein to bind to said target DNA sequence and modification of the target DNA molecule occurs.

105. The method of embodiment 104, wherein said deaminase has an amino acid sequence having at least 95% sequence identity to any one of SEQ ID NOs: 407, 405, 399, 1-10, 400-404, 406, and 408-441.

106. The method of embodiment 104, wherein said deaminase has an amino acid sequence having 100% sequence identity to any one of SEQ ID NOs: 407, 405, 399, 1-10, 400-404, 406, and 408-441.

107. The method of any one of embodiments 104-106, wherein said modified target DNA molecule comprises an A>N mutation of at least one nucleotide within the target DNA molecule, wherein N is C, G, or T.

108. The method of embodiment 107, wherein said modified target DNA molecule comprises an A>G mutation of at least one nucleotide within the target DNA molecule.

109. The method of any one of embodiments 104-108, wherein the RGN of the fusion protein is a Type II CRISPR-Cas polypeptide.

110. The method of any of embodiments 104-108, wherein the RGN of the fusion protein is a Type V CRISPR-Cas polypeptide.

111. The method of any of embodiments 104-108, wherein the RGN of the fusion protein has an amino acid sequence having at least 95% sequence identity to SEQ ID NO: 41, 60, 366, or 368.

112. The method of any of embodiments 104-108, wherein the RGN of the fusion protein has an amino acid sequence of any one of SEQ ID NOs: 41, 60, 366, and 368.

113. The method of any of embodiments 104-108, wherein the RGN of the fusion protein is an RGN nickase.

114. The method of embodiment 113, wherein the RGN nickase is any one of SEQ ID NOs: 42, 52-59, 61, 397, and 398.

115. The method of any of embodiments 104-114, wherein the fusion protein comprises one or more nuclear localization signals.

116. The method of any of embodiments 104-115, wherein the fusion protein is codon optimized for expression in a eukaryotic cell.
117. The method of any one of embodiments 104-116, wherein said target DNA sequence is a eukaryotic target DNA sequence.
118. The method of any of embodiments 104-117, wherein said target DNA sequence is located adjacent to a protospacer adjacent motif (PAM).
119. The method of any of embodiments 104-118, wherein the target DNA molecule is within a cell.
120. The method of embodiment 119, wherein the cell is a eukaryotic cell.
121. The method of embodiment 120, wherein the eukaryotic cell is a plant cell.
122. The method of embodiment 120, wherein the eukaryotic cell is a mammalian cell.
123. The method of embodiment 122, wherein the mammalian cell is a human cell.
124. The method of embodiment 123, wherein the human cell is an immune cell.
125. The method of embodiment 124, wherein the immune cell is a stem cell.
126. The method of embodiment 125, wherein the stem cell is an induced pluripotent stem cell.
127. The method of embodiment 120, wherein the eukaryotic cell is an insect cell.
128. The method of embodiment 119, wherein the cell is a prokaryotic cell.
129. The method of any one of embodiments 119-128, further comprising selecting a cell comprising said modified DNA molecule.
130. A cell comprising a modified target DNA sequence according to the method of embodiment 129.
131. The cell of embodiment 130, wherein the cell is a eukaryotic cell.
132. The cell of embodiment 131, wherein the eukaryotic cell is a plant cell.
133. A plant comprising the cell of embodiment 132.
134. A seed comprising the cell of embodiment 132.
135. The cell of embodiment 131, wherein the eukaryotic cell is a mammalian cell.
136. The cell of embodiment 135, wherein the mammalian cell is a human cell.
137. The cell of embodiment 136, wherein the human cell is an immune cell.
138. The cell of embodiment 137, wherein the immune cell is a stem cell.
139. The cell of embodiment 138, wherein the stem cell is an induced pluripotent stem cell.
140. The cell of embodiment 131, wherein the eukaryotic cell is an insect cell.
141. The cell of embodiment 130, wherein the cell is a prokaryotic cell.
142. A pharmaceutical composition comprising the cell of any one of embodiments 135-139, and a pharmaceutically acceptable carrier.
143. A method for producing a genetically modified cell with a correction in a causal mutation for a genetically inherited disease, the method comprising introducing into the cell:
a) a fusion protein comprising an RNA-guided nuclease polypeptide (RGN) and a deaminase, wherein the deaminase has an amino acid sequence having at least 90% sequence identity to any one of SEQ ID NOs: 407, 405, 399, 1-10, 400-404, 406, and 408-441, or a polynucleotide encoding said fusion protein, wherein said polynucleotide encoding the fusion protein is operably linked to a promoter to enable expression of the fusion protein in the cell; and
b) one or more guide RNAs (gRNA) capable of hybridizing to a target DNA sequence, or a polynucleotide encoding said gRNA, wherein said polynucleotide encoding the gRNA is operably linked to a promoter to enable expression of the gRNA in the cell;
whereby the fusion protein and gRNA target to the genomic location of the causal mutation and modify the genomic sequence to remove the causal mutation.
144. The method of embodiment 143, wherein said deaminase has an amino acid sequence having at least 95% sequence identity to any one of SEQ ID NOs: 407, 405, 399, 1-10, 400-404, 406, and 408-441.
145. The method of embodiment 143, wherein said deaminase has an amino acid sequence having 100% sequence identity to any one of SEQ ID NOs: 407, 405, 399, 1-10, 400-404, 406, and 408-441.
146. The method of any one of embodiments 143-145, wherein said RGN of the fusion protein is an RGN nickase.
147. The method of embodiment 146, wherein the RGN nickase is any one of SEQ ID NOs: 42, 52-59, 61, 397, and 398.
148. The method of any one of embodiments 143-147, wherein the genome modification comprises introducing an A>G mutation of at least one nucleotide within the target DNA sequence.
149. The method of any of embodiments 143-148, wherein the cell is an animal cell.
150. The method of embodiment 149, wherein the animal cell is a mammalian cell.
151. The method of embodiment 150, wherein the cell is derived from a dog, cat, mouse, rat, rabbit, horse, sheep, goat, cow, pig, or human.
152. The method of any one of embodiments 143-151, wherein the correction of the causal mutation comprises correcting a nonsense mutation.
153. The method of embodiment 149, wherein the genetically inherited disease is a disease listed in Table 34.
154. The method of embodiment 149, wherein the genetically inherited disease is cystic fibrosis.
155. The method of embodiment 154, wherein the gRNA further comprises a spacer sequence that targets any one of SEQ ID NOs: 62-97, 116-139, 152-185, 203-234, 251-286, 305-344, 562, and 563, or the complement thereof.
156. The method of embodiment 155, wherein the gRNA comprises any one of SEQ ID NOs: 98-115, 140-151, 186-202, 235-250, 287-304, 345-364, and 564.
157. A CRISPR RNA (crRNA) or a nucleic acid molecule encoding the same, wherein said CRISPR RNA comprises a spacer sequence that targets a target DNA sequence within a cystic fibrosis transmembrane conductance regulator (CFTR) gene, wherein said target sequence has the sequence set forth as any one of SEQ ID NOs: 98-115, 140-151, 186-202, 235-250, 287-304, 345-364, 562, and 563, or the complement thereof.
158. A guide RNA comprising the crRNA of embodiment 157.
159. The guide RNA of embodiment 158, wherein said guide RNA is a dual-guide RNA.
160. The guide RNA of embodiment 158, wherein said guide RNA is a single guide RNA (sgRNA).

161. The guide RNA of embodiment 160, wherein said sgRNA has at least 90% sequence identity to any one of SEQ ID NOs: 98-115, 140-151, 186-202, 235-250, 287-304, 345-364, and 564.

162. The guide RNA of embodiment 160, wherein said sgRNA has at least 95% sequence identity to any one of SEQ ID NOs: 98-115, 140-151, 186-202, 235-250, 287-304, 345-364, and 564.

163. The guide RNA of embodiment 160, wherein said sgRNA has the sequence set forth as any one of SEQ ID NOs: 98-115, 140-151, 186-202, 235-250, 287-304, 345-364, and 564.

164. A vector comprising one or more nucleic acid molecules encoding said guide RNA of any one of embodiments 158-163.

165. A system for binding a target DNA sequence of a DNA molecule, said system comprising:
a) one or more guide RNAs capable of hybridizing to said target DNA sequence or one or more polynucleotides comprising one or more nucleotide sequences encoding the one or more guide RNAs (gRNAs); and
b) a fusion protein comprising an RNA-guided nuclease polypeptide (RGN) and an adenine deaminase, or a polynucleotide comprising a nucleotide sequence encoding the fusion protein;
wherein the one or more guide RNAs are capable of hybridizing to the target DNA sequence,
wherein the one or more guide RNAs are capable of forming a complex with the RGN polypeptide in order to direct said RGN polypeptide to bind to said target DNA sequence of the DNA molecule, and
wherein at least one guide RNA comprises a CRISPR RNA (crRNA) comprising a spacer sequence that targets a target DNA sequence within a cystic fibrosis transmembrane conductance regulator (CFTR) gene, wherein said target sequence has the sequence set forth as any one of SEQ ID NOs: 98-115, 140-151, 186-202, 235-250, 287-304, 345-364, 562, and 563, or the complement thereof.

166. The system of embodiment 165, wherein at least one of said nucleotide sequences encoding the one or more guide RNAs and said nucleotide sequence encoding the fusion protein is operably linked to a promoter heterologous to said nucleotide sequence.

167. A system for binding a target DNA sequence of a DNA molecule, said system comprising:
a) one or more guide RNAs capable of hybridizing to said target DNA sequence or one or more polynucleotides comprising one or more nucleotide sequences encoding the one or more guide RNAs (gRNAs); and
b) a fusion protein comprising an RNA-guided nuclease polypeptide (RGN) and an adenine deaminase;
wherein the one or more guide RNAs are capable of hybridizing to the target DNA sequence,
wherein the one or more guide RNAs are capable of forming a complex with the RGN polypeptide in order to direct said RGN polypeptide to bind to said target DNA sequence of the DNA molecule, and
wherein at least one guide RNA comprises a CRISPR RNA (crRNA) comprising a spacer sequence that targets a target DNA sequence within a cystic fibrosis transmembrane conductance regulator (CFTR) gene, wherein said target sequence has the sequence set forth as any one of SEQ ID NOs: 98-115, 140-151, 186-202, 235-250, 287-304, 345-364, 562, and 563, or the complement thereof.

168. The system of embodiment 167, wherein at least one of said nucleotide sequences encoding the one or more guide RNAs is operably linked to a promoter heterologous to said nucleotide sequence.

169. The system of any one of embodiments 165-168, wherein the deaminase has an amino acid sequence having at least 90% sequence identity to any one of SEQ ID NOs: 1-10 and 399-441.

170. The system of any one of embodiments 165-168, wherein the deaminase has an amino acid sequence having at least 95% sequence identity to any one of SEQ ID NOs: 1-10 and 399-441.

171. The system of any one of embodiments 165-168, wherein the deaminase has an amino acid sequence having the sequence set forth in any one of SEQ ID NOs: 1-10 and 399-441.

172. The system of any one of embodiments 165-171, wherein said RGN polypeptide and said one or more guide RNAs are not found complexed to one another in nature.

173. The system of any one of embodiments 165-172, wherein:
a) said target DNA sequence has the sequence set forth as any one of SEQ ID NOs: 62-68, 80-85, 116-119, 128-131, 163, 164, 180, 181, 203-209, 219-225, 256-258, 274-276, 310-313, and 330-333, or the complement thereof, and wherein said RGN polypeptide has a sequence having at least 90% sequence identity to SEQ ID NO: 53;
b) said target DNA sequence has the sequence set forth as any one of SEQ ID NOs: 68-71, 86-89, 120-122, 132-134, 152-156, 169-173, 213-215, 229-231, 251-255, 269-273, 305-309, and 325-329, or the complement thereof, and wherein said RGN polypeptide has a sequence having at least 90% sequence identity to SEQ ID NO: 55;
c) said target DNA sequence has the sequence set forth as any one of SEQ ID NOs: 72, 73, 90, 91, 161, 162, 178, 179, 265, 266, 283, and 284 or the complement thereof, and wherein said RGN polypeptide has a sequence having at least 90% sequence identity to SEQ ID NO: 52;
d) said target DNA sequence has the sequence set forth as any one of SEQ ID NOs: 74, 75, 92, 93, 123, 124, 135, 136, 167, 184, 216-218, 232-234, 259-261, 277-279, 314-317, and 334-337, or the complement thereof, and wherein said RGN polypeptide has a sequence having at least 90% sequence identity to SEQ ID NO: 56;
e) said target DNA sequence has the sequence set forth as any one of SEQ ID NOs: 76, 94, 210-212, 226-228, 322, 342, 562, and 563, or the complement thereof, and wherein said RGN polypeptide has a sequence having at least 90% sequence identity to SEQ ID NO: 42;
f) said target DNA sequence has the sequence set forth as any one of SEQ ID NOs: 77, 95, 125, 137, 157-160, 174-177, 323, and 343, or the complement thereof, and wherein said RGN polypeptide has a sequence having at least 90% sequence identity to SEQ ID NO: 54;
g) said target DNA sequence has the sequence set forth as any one of SEQ ID NOs: 78, 96, 126, 138, 168, 185, 267, 285, 318, 319, 338, and 339, or the complement thereof, and wherein said RGN polypeptide has a sequence having at least 90% sequence identity to SEQ ID NO: 57;
h) said target DNA sequence has the sequence set forth as any one of SEQ ID NOs: 79, 97, 127, 139, 262-264, 280-282, 324, and 344, or the complement thereof, and wherein said RGN polypeptide has a sequence having at least 90% sequence identity to SEQ ID NO: 58; and
i) said target DNA sequence has the sequence set forth as any one of SEQ ID NOs: 165, 166, 182, 183, 268, 286, 320, 321, 340, and 341, or the complement thereof, and wherein said RGN polypeptide has a sequence having at least 90% sequence identity to SEQ ID NO: 59.

174. The system of any one of embodiments 165-172, wherein:
a) said target DNA sequence has the sequence set forth as any one of SEQ ID NOs: 62-68, 80-85, 116-119, 128-131, 163, 164, 180, 181, 203-209, 219-225, 256-258, 274-276, 310-313, and 330-333, or the complement thereof, and wherein said RGN polypeptide has a sequence having at least 95% sequence identity to SEQ ID NO: 53;
b) said target DNA sequence has the sequence set forth as any one of SEQ ID NOs: 68-71, 86-89, 120-122, 132-134, 152-156, 169-173, 213-215, 229-231, 251-255, 269-273, 305-309, and 325-329, or the complement thereof, and wherein said RGN polypeptide has a sequence having at least 95% sequence identity to SEQ ID NO: 55;
c) said target DNA sequence has the sequence set forth as any one of SEQ ID NOs: 72, 73, 90, 91, 161, 162, 178, 179, 265, 266, 283, and 284 or the complement thereof, and wherein said RGN polypeptide has a sequence having at least 95% sequence identity to SEQ ID NO: 52;
d) said target DNA sequence has the sequence set forth as any one of SEQ ID NOs: 74, 75, 92, 93, 123, 124, 135, 136, 167, 184, 216-218, 232-234, 259-261, 277-279, 314-317, and 334-337, or the complement thereof, and wherein said RGN polypeptide has a sequence having at least 95% sequence identity to SEQ ID NO: 56;
e) said target DNA sequence has the sequence set forth as any one of SEQ ID NOs: 76, 94, 210-212, 226-228, 322, 342, 562, and 563, or the complement thereof, and wherein said RGN polypeptide has a sequence having at least 95% sequence identity to SEQ ID NO: 42;
f) said target DNA sequence has the sequence set forth as any one of SEQ ID NOs: 77, 95, 125, 137, 157-160, 174-177, 323, and 343, or the complement thereof, and wherein said RGN polypeptide has a sequence having at least 95% sequence identity to SEQ ID NO: 54;
g) said target DNA sequence has the sequence set forth as any one of SEQ ID NOs: 78, 96, 126, 138, 168, 185, 267, 285, 318, 319, 338, and 339, or the complement thereof, and wherein said RGN polypeptide has a sequence having at least 95% sequence identity to SEQ ID NO: 57;
h) said target DNA sequence has the sequence set forth as any one of SEQ ID NOs: 79, 97, 127, 139, 262-264, 280-282, 324, and 344, or the complement thereof, and wherein said RGN polypeptide has a sequence having at least 95% sequence identity to SEQ ID NO: 58; and
i) said target DNA sequence has the sequence set forth as any one of SEQ ID NOs: 165, 166, 182, 183, 268, 286, 320, 321, 340, and 341, or the complement thereof, and wherein said RGN polypeptide has a sequence having at least 95% sequence identity to SEQ ID NO: 59.

175. The system of any one of embodiments 165-172, wherein:
a) said target DNA sequence has the sequence set forth as any one of SEQ ID NOs: 62-68, 80-85, 116-119, 128-131, 163, 164, 180, 181, 203-209, 219-225, 256-258, 274-276, 310-313, and 330-333, or the complement thereof, and wherein said RGN polypeptide has a sequence having 100% sequence identity to SEQ ID NO: 53;
b) said target DNA sequence has the sequence set forth as any one of SEQ ID NOs: 68-71, 86-89, 120-122, 132-134, 152-156, 169-173, 213-215, 229-231, 251-255, 269-273, 305-309, and 325-329, or the complement thereof, and wherein said RGN polypeptide has a sequence having 100% sequence identity to SEQ ID NO: 55;
c) said target DNA sequence has the sequence set forth as any one of SEQ ID NOs: 72, 73, 90, 91, 161, 162, 178, 179, 265, 266, 283, and 284 or the complement thereof, and wherein said RGN polypeptide has a sequence having 100% sequence identity to SEQ ID NO: 52;
d) said target DNA sequence has the sequence set forth as any one of SEQ ID NOs: 74, 75, 92, 93, 123, 124, 135, 136, 167, 184, 216-218, 232-234, 259-261, 277-279, 314-317, and 334-337, or the complement thereof, and wherein said RGN polypeptide has a sequence having 100% sequence identity to SEQ ID NO: 56;
e) said target DNA sequence has the sequence set forth as any one of SEQ ID NOs: 76, 94, 210-212, 226-228, 322, 342, 562, and 563, or the complement thereof, and wherein said RGN polypeptide has a sequence having 100% sequence identity to SEQ ID NO: 42;
f) said target DNA sequence has the sequence set forth as any one of SEQ ID NOs: 77, 95, 125, 137, 157-160, 174-177, 323, and 343, or the complement thereof, and wherein said RGN polypeptide has a sequence having 100% sequence identity to SEQ ID NO: 54;
g) said target DNA sequence has the sequence set forth as any one of SEQ ID NOs: 78, 96, 126, 138, 168, 185, 267, 285, 318, 319, 338, and 339, or the complement thereof, and wherein said RGN polypeptide has a sequence having 100% sequence identity to SEQ ID NO: 57;
h) said target DNA sequence has the sequence set forth as any one of SEQ ID NOs: 79, 97, 127, 139, 262-264, 280-282, 324, and 344, or the complement thereof, and wherein said RGN polypeptide has a sequence having 100% sequence identity to SEQ ID NO: 58; and
i) said target DNA sequence has the sequence set forth as any one of SEQ ID NOs: 165, 166, 182, 183, 268, 286, 320, 321, 340, and 341, or the complement thereof, and wherein said RGN polypeptide has a sequence having 100% sequence identity to SEQ ID NO: 59.

176. The system of any one of embodiments 165-175, wherein at least one guide RNA is a dual-guide RNA.

177. The system of any one of embodiments 165-175, wherein at least one guide RNA is a single guide RNA (sgRNA).

178. The system of embodiment 177, wherein:
a) said sgRNA has at least 90% sequence identity to any one of SEQ ID NOs: 98-104, 140-143, 197, 198, 235-241, 292-294, and 350-353, and wherein said RGN polypeptide has a sequence having at least 90% sequence identity to SEQ ID NO: 53;
b) said sgRNA has at least 90% sequence identity to any one of SEQ ID NOs: 104-107, 144-146, 186-190, 245-247, 287-291, and 345-349, and wherein said RGN polypeptide has a sequence having at least 90% sequence identity to SEQ ID NO: 55;
c) said sgRNA has at least 90% sequence identity to any one of SEQ ID NOs: 108, 109, 195, 196, 301, and 302, and wherein said RGN polypeptide has a sequence having at least 90% sequence identity to SEQ ID NO: 52;
d) said sgRNA has at least 90% sequence identity to any one of SEQ ID NOs: 110, 111, 147, 148, 201, 248-250, 295-297, and 354-357, and wherein said RGN polypeptide has a sequence having at least 90% sequence identity to SEQ ID NO: 56;
e) said sgRNA has at least 90% sequence identity to any one of SEQ ID NOs: 112, 242-244, 362, and 564, and wherein said RGN polypeptide has a sequence having at least 90% sequence identity to SEQ ID NO: 42;
f) said sgRNA has at least 90% sequence identity to any one of SEQ ID NOs: 113, 149, 191-194, and 363, and wherein said RGN polypeptide has a sequence having at least 90% sequence identity to SEQ ID NO: 54;
g) said sgRNA has at least 90% sequence identity to any one of SEQ ID NOs: 114, 150, 202, 303, 358, and 359, and wherein said RGN polypeptide has a sequence having at least 90% sequence identity to SEQ ID NO: 57;
h) said sgRNA has at least 90% sequence identity to any one of SEQ ID NOs: 115, 151, 298-300, and 364, and wherein said RGN polypeptide has a sequence having at least 90% sequence identity to SEQ ID NO: 58; and
i) said sgRNA has at least 90% sequence identity to any one of SEQ ID NOs: 199, 200, 304, 360, and 361, and wherein said RGN polypeptide has a sequence having at least 90% sequence identity to SEQ ID NO: 59.

179. The system of embodiment 177, wherein:
a) said sgRNA has at least 95% sequence identity to any one of SEQ ID NOs: 98-104, 140-143, 197, 198, 235-241, 292-294, and 350-353, and wherein said RGN polypeptide has a sequence having at least 95% sequence identity to SEQ ID NO: 53;
b) said sgRNA has at least 95% sequence identity to any one of SEQ ID NOs: 104-107, 144-146, 186-190, 245-247, 287-291, and 345-349, and wherein said RGN polypeptide has a sequence having at least 95% sequence identity to SEQ ID NO: 55;
c) said sgRNA has at least 95% sequence identity to any one of SEQ ID NOs: 108, 109, 195, 196, 301, and 302, and wherein said RGN polypeptide has a sequence having at least 95% sequence identity to SEQ ID NO: 52;
d) said sgRNA has at least 95% sequence identity to any one of SEQ ID NOs: 110, 111, 147, 148, 201, 248-250, 295-297, and 354-357, and wherein said RGN polypeptide has a sequence having at least 95% sequence identity to SEQ ID NO: 56;
e) said sgRNA has at least 95% sequence identity to any one of SEQ ID NOs: 112, 242-244, 362, and 564, and wherein said RGN polypeptide has a sequence having at least 95% sequence identity to SEQ ID NO: 42;
f) said sgRNA has at least 95% sequence identity to any one of SEQ ID NOs: 113, 149, 191-194, and 363, and wherein said RGN polypeptide has a sequence having at least 95% sequence identity to SEQ ID NO: 54;
g) said sgRNA has at least 95% sequence identity to any one of SEQ ID NOs: 114, 150, 202, 303, 358, and 359, and wherein said RGN polypeptide has a sequence having at least 95% sequence identity to SEQ ID NO: 57;
h) said sgRNA has at least 95% sequence identity to any one of SEQ ID NOs: 115, 151, 298-300, and 364, and wherein said RGN polypeptide has a sequence having at least 95% sequence identity to SEQ ID NO: 58; and
i) said sgRNA has at least 95% sequence identity to any one of SEQ ID NOs: 199, 200, 304, 360, and 361, and wherein said RGN polypeptide has a sequence having at least 95% sequence identity to SEQ ID NO: 59.

180. The system of embodiment 177, wherein:
a) said sgRNA has 100% sequence identity to any one of SEQ ID NOs: 98-104, 140-143, 197, 198, 235-241, 292-294, and 350-353, and wherein said RGN polypeptide has a sequence having 100% sequence identity to SEQ ID NO: 53;
b) said sgRNA has 100% sequence identity to any one of SEQ ID NOs: 104-107, 144-146, 186-190, 245-247, 287-291, and 345-349, and wherein said RGN polypeptide has a sequence having 100% sequence identity to SEQ ID NO: 55;
c) said sgRNA has 100% sequence identity to any one of SEQ ID NOs: 108, 109, 195, 196, 301, and 302, and wherein said RGN polypeptide has a sequence having 100% sequence identity to SEQ ID NO: 52;
d) said sgRNA has 100% sequence identity to any one of SEQ ID NOs: 110, 111, 147, 148, 201, 248-250, 295-297, and 354-357, and wherein said RGN polypeptide has a sequence having 100% sequence identity to SEQ ID NO: 56;
e) said sgRNA has 100% sequence identity to any one of SEQ ID NOs: 112, 242-244, 362, and 564, and wherein said RGN polypeptide has a sequence having 100% sequence identity to SEQ ID NO: 42;
f) said sgRNA has 100% sequence identity to any one of SEQ ID NOs: 113, 149, 191-194, and 363, and wherein said RGN polypeptide has a sequence having 100% sequence identity to SEQ ID NO: 54;
g) said sgRNA has 100% sequence identity to any one of SEQ ID NOs: 114, 150, 202, 303, 358, and 359, and wherein said RGN polypeptide has a sequence having 100% sequence identity to SEQ ID NO: 57;
h) said sgRNA has 100% sequence identity to any one of SEQ ID NOs: 115, 151, 298-300, and 364, and wherein said RGN polypeptide has a sequence having 100% sequence identity to SEQ ID NO: 58; and
i) said sgRNA has 100% sequence identity to any one of SEQ ID NOs: 199, 200, 304, 360, and 361, and wherein said RGN polypeptide has a sequence having 100% sequence identity to SEQ ID NO: 59.

181. A cell comprising the crRNA or nucleic acid molecule of embodiment 157, the guide RNA of any one of embodiments 158-163, the vector of embodiment 164 or the system of any one of embodiments 165-180.

182. A pharmaceutical composition comprising the crRNA or nucleic acid molecule of embodiment 157, the guide RNA of any one of embodiments 158-163, the vector of embodiment 164, the cell of embodiment 181, or the system of any one of embodiments 165-180, and a pharmaceutically acceptable carrier.

183. A composition comprising:
a) a fusion protein comprising a DNA-binding polypeptide and an adenine deaminase, or a nucleic acid molecule encoding the fusion protein; and
b) a second adenine deaminase having at least 90% sequence identity to any one of SEQ ID NOs: 407, 405, 399, 1-10, 400-404, 406, and 408-441; or a nucleic acid molecule encoding the deaminase.

184. The composition of embodiment 183, wherein said second adenine deaminase has at least 90% sequence identity to any one of SEQ ID NOs: 407, 405, 399, 1-10, 400-404, 406, and 408-441.

185. The composition of embodiment 183, wherein said second adenine deaminase has 100% sequence identity to any one of SEQ ID NOs: 407, 405, 399, 1-10, 400-404, 406, and 408-441.

186. The composition of any one of embodiments 183-185, wherein the first adenine deaminase has at least 90% sequence identity to any one of SEQ ID NOs: 407, 405, 399, 1-10, 400-404, 406, and 408-441.

187. The composition of any one of embodiments 183-186, wherein the first adenine deaminase has at least 95% sequence identity to any one of SEQ ID NOs: 407, 405, 399, 1-10, 400-404, 406, and 408-441.

188. The composition of any one of embodiments 183-186, wherein the first adenine deaminase has 100% sequence identity to any one of SEQ ID NOs: 407, 405, 399, 1-10, 400-404, 406, and 408-441.

189. The composition of any one of embodiments 183-188, wherein the DNA-binding polypeptide is a meganuclease, zinc finger fusion protein, or a TALEN.

190. The composition of any one of embodiments 183-189, wherein the DNA-binding polypeptide is an RNA-guided, DNA-binding polypeptide.

191. The composition of embodiment 190, wherein the RNA-guided, DNA-binding polypeptide is an RNA-guided nuclease (RGN) polypeptide.

192. The composition of embodiment 191, wherein the RGN is an RGN nickase.

193. A vector comprising a nucleic acid molecule encoding a fusion protein and a nucleic acid molecule encoding a second deaminase, wherein said fusion protein comprises a DNA-binding polypeptide and a first adenine deaminase, and wherein said second adenine deaminase has at least 90% sequence identity to any one of SEQ ID NOs: 407, 405, 399, 1-10, 400-404, 406, and 408-441.

194. The vector of embodiment 193, wherein said second adenine deaminase has at least 90% sequence identity to any one of SEQ ID NOs: 407, 405, 399, 1-10, 400-404, 406, and 408-441.

195. The vector of embodiment 193, wherein said second adenine deaminase has 100% sequence identity to any one of SEQ ID NOs: 407, 405, 399, 1-10, 400-404, 406, and 408-441.

196. The vector of any one of embodiments 193-195, wherein the first adenine deaminase has at least 90% sequence identity to any one of SEQ ID NOs: 407, 405, 399, 1-10, 400-404, 406, and 408-441.

197. The vector of any one of embodiments 193-195, wherein the first adenine deaminase has at least 95% sequence identity to any one of SEQ ID NOs: 407, 405, 399, 1-10, 400-404, 406, and 408-441.

198. The vector of any one of embodiments 193-195, wherein the first adenine deaminase has 100% sequence identity to any one of SEQ ID NOs: 407, 405, 399, 1-10, 400-404, 406, and 408-441.

199. The vector of any one of embodiments 193-198, wherein the DNA-binding polypeptide is a meganuclease, zinc finger fusion protein, or a TALEN.

200. The vector of any one of embodiments 193-198, wherein the DNA-binding polypeptide is an RNA-guided, DNA-binding polypeptide.

201. The vector of embodiment 200, wherein the RNA-guided, DNA-binding polypeptide is an RNA-guided nuclease (RGN) polypeptide.

202. The vector of embodiment 201, wherein the RGN is an RGN nickase.

203. A cell comprising the vector of any one of embodiments 193-202.

204. A cell comprising:
a) a fusion protein comprising a DNA-binding polypeptide and a first adenine deaminase; or a nucleic acid molecule encoding the fusion protein; and
b) a second adenine deaminase having at least 90% sequence identity to any one of SEQ ID NOs: 407, 405, 399, 1-10, 400-404, 406, and 408-441; or a nucleic acid molecule encoding the second adenine deaminase.

205. The cell of embodiment 204, wherein said second adenine deaminase has at least 90% sequence identity to any one of SEQ ID NOs: 407, 405, 399, 1-10, 400-404, 406, and 408-441.

206. The cell of embodiment 204, wherein said second adenine deaminase has 100% sequence identity to any one of SEQ ID NOs: 407, 405, 399, 1-10, 400-404, 406, and 408-441.

207. The cell of any one of embodiments 204-206, wherein the first adenine deaminase has at least 90% sequence identity to any one of SEQ ID NOs: 407, 405, 399, 1-10, 400-404, 406, and 408-441.

208. The cell of any one of embodiments 204-206, wherein the first adenine deaminase has at least 95% sequence identity to any one of SEQ ID NOs: 407, 405, 399, 1-10, 400-404, 406, and 408-441.

209. The cell of any one of embodiments 204-206, wherein the first adenine deaminase has 100% sequence identity to any one of SEQ ID NOs: 407, 405, 399, 1-10, 400-404, 406, and 408-441.

210. The cell of any one of embodiments 204-209, wherein the DNA-binding polypeptide is a meganuclease, zinc finger fusion protein, or a TALEN.

211. The cell of any one of embodiments 204-209, wherein the DNA-binding polypeptide is an RNA-guided, DNA-binding polypeptide.

212. The cell of embodiment 211, wherein the RNA-guided, DNA-binding polypeptide is an RNA-guided nuclease (RGN) polypeptide.

213. The cell of embodiment 212, wherein the RGN is an RGN nickase.

214. A pharmaceutical composition comprising a pharmaceutically acceptable carrier and the composition of any one of embodiments 183-192, the vector of any one of embodiments 193-202, or the cell of any one of embodiments 203-213.

215. A method for treating a disease, said method comprising administering to a subject in need thereof an effective amount of a pharmaceutical composition of any one of embodiments 69, 100, 142, and 214.

216. The method of embodiment 215, wherein said disease is associated with a causal mutation and said effective amount of said pharmaceutical composition corrects said causal mutation.

217. Use of the fusion protein of any one of embodiments 14-27, the nucleic acid molecule of any one of embodiments 28-48, the vector of any one of embodiments 49-52 and 193-202, the cell of any one of embodiments 59-63, 135-139, and 203-213, the system of any one of embodiments 75-99, or the composition of any one of embodiments 183-192 for the treatment of a disease in a subject.

218. The use of embodiment 217, wherein said disease is associated with a causal mutation and said treating comprises correcting said causal mutation.

219. Use of the fusion protein of any one of embodiments 14-27, the nucleic acid molecule of any one of embodiments 28-48, the vector of any one of embodiments 49-52 and 193-202, the cell of any one of embodiments 59-63, 135-139, and 203-213, the system of any one of embodiments 75-99, or the composition of any one of embodiments 183-192 for the manufacture of a medicament useful for treating a disease.

220. The use of embodiment 219, wherein said disease is associated with a causal mutation and an effective amount of said medicament corrects said causal mutation.

221. A nucleic acid molecule comprising a polynucleotide encoding an RNA-guided nuclease (RGN) polypeptide, wherein said polynucleotide comprises a nucleotide sequence encoding an RGN polypeptide comprising an amino acid sequence having at least 95% sequence identity to SEQ ID NO: 41 or 60, but lacking amino acid residues 590 to 597 of SEQ ID NO: 41 or 60; wherein said RGN polypeptide is capable of binding a target DNA sequence in an RNA-guided sequence specific manner when bound to a guide RNA (gRNA) capable of hybridizing to said target DNA sequence.

222. The nucleic acid molecule of embodiment 221, wherein said polynucleotide encoding an RGN polypeptide is operably linked to a promoter heterologous to said polynucleotide.

223. The nucleic acid molecule of embodiment 221 or 222, wherein said RGN polypeptide comprises an amino acid sequence having at least 95% sequence identity to SEQ ID NO: 366 or 368.

224. The nucleic acid molecule of embodiment 221 or 222, wherein said RGN polypeptide comprises an amino acid sequence of SEQ ID NO: 366 or 368.

225. The nucleic acid molecule of any one of embodiments 221-223, wherein said RGN polypeptide is nuclease dead or functions as a nickase.

226. The nucleic acid molecule of embodiment 225, wherein said nickase has the amino acid sequence set forth in SEQ ID NO: 397 or 398.

227. The nucleic acid molecule of any one of embodiments 221-226, wherein the RGN polypeptide is operably fused to a base-editing polypeptide.

228. A vector comprising the nucleic acid molecule of any one of claims 221-227.

229. An isolated polypeptide comprising an amino acid sequence having at least 95% sequence identity to SEQ ID NO: 41 or 60, but lacking amino acid residues 590 to 597 of SEQ ID NO: 41 or 60, wherein said polypeptide is an RNA-guided nuclease.

230. The isolated polypeptide of embodiment 229, wherein said RGN polypeptide comprises an amino acid sequence having at least 95% sequence identity to SEQ ID NO: 366 or 368.

231. The isolated polypeptide of embodiment 230, wherein said RGN polypeptide comprises an amino acid sequence of SEQ ID NO: 366 or 368.

232. The isolated polypeptide of embodiment 229 or 230, wherein said RGN polypeptide is nuclease dead or functions as a nickase.

233. The isolated polypeptide of embodiment 232, wherein said nickase has the amino acid sequence set forth in SEQ ID NO: 397 or 398.

234. The isolated polypeptide of any one of embodiments 229-233, wherein the RGN polypeptide is operably fused to a base-editing polypeptide.

235. A cell comprising the nucleic acid molecule of any one of embodiments 221-227, the vector of claim 228, or the polypeptide of any one of claims 229-234.

236. An isolated polypeptide comprising an amino acid sequence having at least 90% sequence identity to SEQ ID NO: 407, wherein said polypeptide has deaminase activity.

237. The isolated polypeptide of embodiment 236 comprising an amino acid sequence having at least 95% sequence identity to SEQ ID NO: 407, wherein said polypeptide has deaminase activity.

238. The isolated polypeptide of embodiment 236, wherein the polypeptide comprises an amino acid sequence set forth in SEQ ID NO: 407.

239. A nucleic acid molecule comprising a polynucleotide encoding a deaminase polypeptide, wherein the deaminase is encoded by a nucleotide sequence that:

a) has at least 80% sequence identity to SEQ ID NO: 451, or b) encodes an amino acid sequence having at least 90% sequence identity to any one of SEQ ID NO: 407.

240. The nucleic acid molecule of embodiment 239, wherein the deaminase is encoded by a nucleotide sequence that has at least 90% sequence identity to SEQ ID NO: 451.

241. The nucleic acid molecule of embodiment 239, wherein the deaminase is encoded by a nucleotide sequence that has at least 95% sequence identity to SEQ ID NO: 451.

242. The nucleic acid molecule of embodiment 239, wherein the deaminase is encoded by a nucleotide sequence that has at least 100% sequence identity to SEQ ID NO: 451.

243. The nucleic acid molecule of embodiments 239-242, wherein said nucleic acid molecule further comprises a heterologous promoter operably linked to said polynucleotide.

244. A pharmaceutical composition comprising a pharmaceutically acceptable carrier and the polypeptide of any one of embodiments 236-238 or the nucleic acid molecule of any one of embodiments 239-242.

245. A fusion protein comprising a DNA-binding polypeptide and a deaminase having at least 90% sequence identity to SEQ ID NO: 407.

246. A fusion protein of embodiment 245 comprising a DNA-binding polypeptide and a deaminase having at least 95% sequence identity to SEQ ID NO: 407.

247. A fusion protein of embodiment 245 comprising a DNA-binding polypeptide and a deaminase having 100% sequence identity to SEQ ID NO: 407.

248. The fusion protein of any one of embodiments 245-247, wherein the DNA-binding polypeptide is a RNA-guided nuclease (RGN) polypeptide.

249. The fusion protein of embodiment 248, wherein the RGN polypeptide is a Type II CRISPR-Cas polypeptide or a Type V CRISPR-Cas polypeptide.

250. The fusion protein of any one of embodiments 248-249, wherein the RGN polypeptide is a Cas9, a CasX, a CasY, a Cpf1, a C2c1, a C2c2, a C2c3, a GeoCas9, a CjCas9, a Cas12a, a Cas12b, a Cas12g, a Cas12h, a Cas12i, a Cas13b, a Cas13c, a Cas13d, a Cas14, a Csn2, an xCas9, an SpCas9-NG, an LbCas12a, an AsCas12a, a Cas9-KKH, a circularly permuted Cas9, an Argonaute (Ago), a SmacCas9, a Spy-macCas9 domain, or a RGN polypeptide with an amino acid sequence set forth in any one of SEQ ID NOs: 41, 60, 366, or 368.

251. The fusion protein of any one of embodiments 248-250, wherein the RGN polypeptide is a nickase.

252. The fusion protein of embodiment 251, wherein the nickase has an amino acid sequence having at least 95% sequence identity to any one of SEQ ID NOs: 42, 52-59, 61, 397, and 398.

253. The fusion protein of embodiment 251, wherein the nickase has an amino acid sequence having 100% sequence identity to any one of SEQ ID NOs: 42, 52-59, 61, 397, and 398.

254. A nucleic acid molecule comprising a polynucleotide encoding a fusion protein comprising a DNA-binding polypeptide and a deaminase, wherein the deaminase is encoded by a nucleotide sequence that:
a) has at least 80% sequence identity to SEQ ID NO: 451, or
b) encodes an amino acid sequence having at least 90% sequence identity to SEQ ID NO: 407.

255. The nucleic acid molecule of embodiment 254, wherein the deaminase is encoded by a nucleotide sequence that has at least 90% sequence identity to SEQ ID NO: 451.

256. The nucleic acid molecule of embodiment 254, wherein the deaminase is encoded by a nucleotide sequence that has at least 95% sequence identity to SEQ ID NO: 451.

257. The nucleic acid molecule of embodiment 254, wherein the deaminase is encoded by a nucleotide sequence that has at least 100% sequence identity to SEQ ID NO: 451.

258. The nucleic acid molecule of any one of embodiments 254-257, wherein the DNA-binding polypeptide is a RGN polypeptide.

259. The nucleic acid molecule of embodiment 258, wherein the RGN is a Type II CRISPR-Cas polypeptide or a Type V CRISPR-Cas polypeptide.

260. The nucleic acid molecule of any one of embodiments 258-259, wherein the RGN polypeptide is a Cas9, a CasX, a CasY, a Cpf1, a C2c1, a C2c2, a C2c3, a GeoCas9, a CjCas9, a Cas12a, a Cas12b, a Cas12g, a Cas12h, a Cas12i, a Cas13b, a Cas13c, a Cas13d, a Cas14, a Csn2, an xCas9, an SpCas9-NG, an LbCas12a, an AsCas12a, a Cas9-KKH, a circularly permuted Cas9, an Argonaute (Ago), a SmacCas9, a Spy-macCas9 domain, or a RGN polypeptide with an amino acid sequence set forth in any one of SEQ ID NOs: 41, 60, 366, or 368.

261. The nucleic acid molecule of any one of embodiments 258-260, wherein the RGN polypeptide is a nickase.

262. The nucleic acid molecule of embodiment 261, wherein the nickase has an amino acid sequence having at least 95% sequence identity to any one of SEQ ID NOs: 42, 52-59, 61, 397, and 398.

263. The nucleic acid molecule of embodiment 262, wherein the nickase has an amino acid sequence having 100% sequence identity to any one of SEQ ID NOs: 42, 52-59, 61, 397, and 398.

264. A vector comprising the nucleic acid molecule of any one of embodiments 254-263.

265. The vector of embodiment 264, further comprising at least one nucleotide sequence encoding a guide RNA (gRNA) capable of hybridizing to a target sequence.

266. A ribonucleoprotein (RNP) complex comprising the fusion protein of any one of embodiments 245-253 and a guide RNA bound to the DNA-binding polypeptide of the fusion protein.

267. A cell comprising the fusion protein of any of embodiments 245-253, the nucleic acid molecule of any one of embodiments 254-263, the vector of any one of embodiments 264-265, or the RNP complex of embodiment 266.

268. A system for modifying a target DNA molecule comprising a target DNA sequence, said system comprising:
a) a fusion protein comprising an RNA-guided nuclease (RGN) polypeptide and a deaminase, wherein the deaminase has an amino acid sequence having at least 90% sequence identity to SEQ ID NO: 407, or a nucleotide sequence encoding said fusion protein; and
b) one or more guide RNAs capable of hybridizing to said target DNA sequence or one or more nucleotide sequences encoding the one or more guide RNAs (gRNAs); and
wherein the one or more guide RNAs are capable of forming a complex with the fusion protein in order to direct said fusion protein to bind to said target DNA sequence and modify the target DNA molecule.

269. The system of embodiment 268, wherein said deaminase has an amino acid sequence having at least 95% sequence identity to SEQ ID NO: 407.

270. The system of embodiment 268, wherein said deaminase has an amino acid sequence having 100% sequence identity to SEQ ID NO: 407.

271. The system of any one of embodiments 268-270, wherein at least one of said nucleotide sequence encoding the one or more guide RNAs and said nucleotide sequence encoding the fusion protein is operably linked to a promoter heterologous to said nucleotide sequence.

272. The system of any one of embodiments 268-271, wherein the target DNA sequence is located adjacent to a protospacer adjacent motif (PAM) that is recognized by the RGN polypeptide.

273. The system of any one of embodiments 268-272, wherein the target DNA sequence comprises a nucleic acid sequence selected from the group consisting of SEQ ID NOs:
62-97, 116-139, 152-185, 203-234, 251-286, 305-344, 562, and 563, or the complement thereof.

274. The system of any one of embodiments 268-273, wherein the gRNA sequence comprises a nucleic acid sequence selected from the group consisting of SEQ ID NOs: 98-115, 140-151, 186-202, 235-250, 287-304, 345-364, and 564.

275. The system of any one of embodiments 268-274, wherein the RGN polypeptide of the fusion protein is a Type II CRISPR-Cas polypeptide or a Type V CRISPR-Cas polypeptide.

276. The system of any one of embodiments 272-275, wherein the RGN polypeptide is a Cas9, a CasX, a CasY, a Cpf1, a C2c1, a C2c2, a C2c3, a GeoCas9, a CjCas9, a Cas12a, a Cas12b, a Cas12g, a Cas12h, a Cas12i, a Cas13b, a Cas13c, a Cas13d, a Cas14, a Csn2, an xCas9, an SpCas9-NG, an LbCas12a, an AsCas12a, a Cas9-KKH, a circularly permuted Cas9, an Argonaute (Ago), a SmacCas9, a Spy-macCas9 domain, or a RGN with an amino acid sequence set forth in any one of SEQ ID NOs: 41, 60, 366, or 368.

277. The system of embodiment 276, wherein the RGN polypeptide is a nickase.

278. The system of embodiment 277, wherein the nickase has an amino acid sequence having at least 95% sequence identity to any one of SEQ ID NOs: 42, 52-59, 61, 397, and 398.

279. A pharmaceutical composition comprising a pharmaceutically acceptable carrier and the fusion protein of any of embodiments 245-253, the nucleic acid molecule of any one of embodiments 254-263, the vector of any one of embodiments 264-265, the RNP complex of embodiment 266, the cell of embodiment 267, or the system of any one of embodiments 268-28.

280. A method for modifying a target DNA molecule comprising a target sequence comprising:
a) assembling an RGN-deaminase ribonucleotide complex by combining:
i) one or more guide RNAs capable of hybridizing to the target DNA sequence; and
ii) a fusion protein comprising an RNA-guided nuclease polypeptide (RGN), and at least one deaminase, wherein the deaminase has an amino acid sequence having at least 90% sequence identity to SEQ ID NO: 407; under conditions suitable for formation of the RGN-deaminase ribonucleotide complex; and
b) contacting said target DNA molecule or a cell comprising said target DNA molecule with the assembled RGN-deaminase ribonucleotide complex;
wherein the one or more guide RNAs hybridize to the target DNA sequence, thereby directing said fusion protein to bind to said target DNA sequence and modification of the target DNA molecule occurs.

281. The method of embodiment 280, wherein the target DNA sequence comprises a nucleic acid sequence selected from the group consisting of SEQ ID NOs: 62-97, 116-139, 152-185, 203-234, 251-286, 305-344, 562, and 563, or the complement thereof.

282. The method of any one of embodiments 280-281, wherein the gRNA sequence comprises a nucleic acid sequence selected from the group consisting of SEQ ID NOs: 98-115, 140-151, 186-202, 235-250, 287-304, 345-364, and 564.

283. The method of any one of embodiments 280-283, wherein the method is performed in vitro, in vivo, or ex vivo.

284. A method of treating a subject having or at risk of developing a disease, disorder, or condition, the method comprising:
administering to the subject the fusion protein of any of embodiments 245-253, the nucleic acid molecule of any one of embodiments 254-263, the vector of any one of embodiments 264-265, the RNP complex of embodiment 266, the cell of embodiment 267, the system of any one of embodiments 268-28, or the pharmaceutical composition of embodiment 279.

285. The method of embodiment 284, further comprising administering any one of a gRNA comprising a nucleic acid sequence selected from the group consisting of SEQ ID NOs:
98-115, 140-151, 186-202, 235-250, 287-304, 345-364, and 564.

286. An isolated polypeptide comprising an amino acid sequence having at least 90% sequence identity to SEQ ID NO: 405, wherein said polypeptide has deaminase activity.

287. The isolated polypeptide of embodiment 286 comprising an amino acid sequence having at least 95% sequence identity to SEQ ID NO: 405, wherein said polypeptide has deaminase activity.

288. The isolated polypeptide of embodiment 286, wherein the polypeptide comprises an amino acid sequence set forth in SEQ ID NO: 407.

289. A nucleic acid molecule comprising a polynucleotide encoding a deaminase polypeptide, wherein the deaminase is encoded by a nucleotide sequence that:
a) has at least 80% sequence identity to SEQ ID NO: 449, or
b) encodes an amino acid sequence having at least 90% sequence identity to any one of SEQ ID NO: 405.

290. The nucleic acid molecule of embodiment 289, wherein the deaminase is encoded by a nucleotide sequence that has at least 90% sequence identity to SEQ ID NO: 449.

291. The nucleic acid molecule of embodiment 289, wherein the deaminase is encoded by a nucleotide sequence that has at least 95% sequence identity to SEQ ID NO: 449.

292. The nucleic acid molecule of embodiment 289, wherein the deaminase is encoded by a nucleotide sequence that has at least 100% sequence identity to SEQ ID NO: 449.

293. The nucleic acid molecule of embodiments 289-292, wherein said nucleic acid molecule further comprises a heterologous promoter operably linked to said polynucleotide.

294. A pharmaceutical composition comprising a pharmaceutically acceptable carrier and the polypeptide of any one of embodiments 286-288 or the nucleic acid molecule of any one of embodiments 289-293.

295. A fusion protein comprising a DNA-binding polypeptide and a deaminase having at least 90% sequence identity to SEQ ID NO: 405.

296. A fusion protein of embodiment 295 comprising a DNA-binding polypeptide and a deaminase having at least 95% sequence identity to SEQ ID NO: 405.

297. A fusion protein of embodiment 295 comprising a DNA-binding polypeptide and a deaminase having 100% sequence identity to SEQ ID NO: 405.

298. The fusion protein of any one of embodiments 295-297, wherein the DNA-binding polypeptide is a RNA-guided nuclease (RGN) polypeptide.

299. The fusion protein of embodiment 298, wherein the RGN polypeptide is a Type II CRISPR-Cas polypeptide or a Type V CRISPR-Cas polypeptide.

300. The fusion protein of any one of embodiments 298-299, wherein the RGN polypeptide is a Cas9, a CasX, a CasY, a Cpf1, a C2c1, a C2c2, a C2c3, a GeoCas9, a CjCas9, a Cas12a, a Cas12b, a Cas12g, a Cas12h, a Cas12i, a Cas13b, a Cas13c, a Cas13d, a Cas14, a Csn2, an xCas9, an SpCas9-NG, an LbCas12a, an AsCas12a, a Cas9-KKH, a circularly permuted Cas9, an Argonaute (Ago), a SmacCas9, a Spy-macCas9 domain, or a RGN polypeptide with an amino acid sequence set forth in any one of SEQ ID NOs: 41, 60, 366, or 368.

301. The fusion protein of any one of embodiments 298-300, wherein the RGN polypeptide is a nickase.

302. The fusion protein of embodiment 301, wherein the nickase has an amino acid sequence having at least 95% sequence identity to any one of SEQ ID NOs: 42, 52-59, 61, 397, and 398.

303. The fusion protein of embodiment 301, wherein the nickase has an amino acid sequence having 100% sequence identity to any one of SEQ ID NOs: 42, 52-59, 61, 397, and 398.

304. A nucleic acid molecule comprising a polynucleotide encoding a fusion protein comprising a DNA-binding polypeptide and a deaminase, wherein the deaminase is encoded by a nucleotide sequence that:

a) has at least 80% sequence identity to SEQ ID NO: 449, or
b) encodes an amino acid sequence having at least 90% sequence identity to SEQ ID NO: 405.

305. The nucleic acid molecule of embodiment 304, wherein the deaminase is encoded by a nucleotide sequence that has at least 90% sequence identity to SEQ ID NO: 449.

306. The nucleic acid molecule of embodiment 304, wherein the deaminase is encoded by a nucleotide sequence that has at least 95% sequence identity to SEQ ID NO: 449.

307. The nucleic acid molecule of embodiment 304, wherein the deaminase is encoded by a nucleotide sequence that has at least 100% sequence identity to SEQ ID NO: 449.

308. The nucleic acid molecule of any one of embodiments 304-307, wherein the DNA-binding polypeptide is a RGN polypeptide.

309. The nucleic acid molecule of embodiment 308, wherein the RGN is a Type II CRISPR-Cas polypeptide or a Type V CRISPR-Cas polypeptide.

310. The nucleic acid molecule of any one of embodiments 308-309, wherein the RGN polypeptide is a Cas9, a CasX, a CasY, a Cpf1, a C2c1, a C2c2, a C2c3, a GeoCas9, a CjCas9, a Cas12a, a Cas12b, a Cas12g, a Cas12h, a Cas12i, a Cas13b, a Cas13c, a Cas13d, a Cas14, a Csn2, an xCas9, an SpCas9-NG, an LbCas12a, an AsCas12a, a Cas9-KKH, a circularly permuted Cas9, an Argonaute (Ago), a SmacCas9, a Spy-macCas9 domain, or a RGN polypeptide with an amino acid sequence set forth in any one of SEQ ID NOs: 41, 60, 366, or 368.

311. The nucleic acid molecule of any one of embodiments 308-310, wherein the RGN polypeptide is a nickase.

312. The nucleic acid molecule of embodiment 311, wherein the nickase has an amino acid sequence having at least 95% sequence identity to any one of SEQ ID NOs: 42, 52-59, 61, 397, and 398.

313. The nucleic acid molecule of embodiment 312, wherein the nickase has an amino acid sequence having 100% sequence identity to any one of SEQ ID NOs: 42, 52-59, 61, 397, and 398.

314. A vector comprising the nucleic acid molecule of any one of embodiments 304-313.

315. The vector of embodiment 314, further comprising at least one nucleotide sequence encoding a guide RNA (gRNA) capable of hybridizing to a target sequence.

316. A ribonucleoprotein (RNP) complex comprising the fusion protein of any one of embodiments 295-303 and a guide RNA bound to the DNA-binding polypeptide of the fusion protein.

317. A cell comprising the fusion protein of any of embodiments 295-303, the nucleic acid molecule of any one of embodiments 304-313, the vector of any one of embodiments 314-315, or the RNP complex of embodiment 316.

318. A system for modifying a target DNA molecule comprising a target DNA sequence, said system comprising:
a) a fusion protein comprising an RNA-guided nuclease (RGN) polypeptide and a deaminase, wherein the deaminase has an amino acid sequence having at least 90% sequence identity to SEQ ID NO: 405, or a nucleotide sequence encoding said fusion protein; and
b) one or more guide RNAs capable of hybridizing to said target DNA sequence or one or more nucleotide sequences encoding the one or more guide RNAs (gRNAs); and
wherein the one or more guide RNAs are capable of forming a complex with the fusion protein in order to direct said fusion protein to bind to said target DNA sequence and modify the target DNA molecule.

319. The system of embodiment 318, wherein said deaminase has an amino acid sequence having at least 95% sequence identity to SEQ ID NO: 405.

320. The system of embodiment 318, wherein said deaminase has an amino acid sequence having 100% sequence identity to SEQ ID NO: 405.

321. The system of any one of embodiments 318-320, wherein at least one of said nucleotide sequence encoding the one or more guide RNAs and said nucleotide sequence encoding the fusion protein is operably linked to a promoter heterologous to said nucleotide sequence.

322. The system of any one of embodiments 318-321, wherein the target DNA sequence is located adjacent to a protospacer adjacent motif (PAM) that is recognized by the RGN polypeptide.

323. The system of any one of embodiments 318-322, wherein the target DNA sequence comprises a nucleic acid sequence selected from the group consisting of SEQ ID NOs: 62-97, 116-139, 152-185, 203-234, 251-286, 305-344, 562, and 563, or the complement thereof.

324. The system of any one of embodiments 318-323, wherein the gRNA sequence comprises a nucleic acid sequence selected from the group consisting of SEQ ID NOs: 98-115, 140-151, 186-202, 235-250, 287-304, 345-364, and 564. 325. The system of any one of embodiments 318-324, wherein the RGN polypeptide of the fusion protein is a Type II CRISPR-Cas polypeptide or a Type V CRISPR-Cas polypeptide.

326. The system of any one of embodiments 322-325, wherein the RGN polypeptide is a Cas9, a CasX, a CasY, a Cpf1, a C2c1, a C2c2, a C2c3, a GeoCas9, a CjCas9, a Cas12a, a Cas12b, a Cas12g, a Cas12h, a Cas12i, a Cas13b, a Cas13c, a Cas13d, a Cas14, a Csn2, an xCas9, an SpCas9-NG, an LbCas12a, an AsCas12a, a Cas9-KKH, a circularly permuted Cas9, an Argonaute (Ago), a SmacCas9, a Spy-macCas9 domain, or a RGN with an amino acid sequence set forth in any one of SEQ ID NOs: 41, 60, 366, or 368.

327. The system of embodiment 326, wherein the RGN polypeptide is a nickase.

328. The system of embodiment 327, wherein the nickase has an amino acid sequence having at least 95% sequence identity to any one of SEQ ID NOs: 42, 52-59, 61, 397, and 398.

329. A pharmaceutical composition comprising a pharmaceutically acceptable carrier and the fusion protein of any of embodiments 295-303, the nucleic acid molecule of any one of embodiments 304-313, the vector of any one of embodiments 314-315, the RNP complex of embodiment 316, the cell of embodiment 317, or the system of any one of embodiments 318-328.

330. A method for modifying a target DNA molecule comprising a target sequence comprising:
a) assembling an RGN-deaminase ribonucleotide complex by combining:
i) one or more guide RNAs capable of hybridizing to the target DNA sequence; and ii) a fusion protein comprising an RNA-guided nuclease polypeptide (RGN), and at least one deaminase, wherein the deaminase has an amino acid sequence having at least 90% sequence identity to SEQ ID NO: 405;
under conditions suitable for formation of the RGN-deaminase ribonucleotide complex; and
b) contacting said target DNA molecule or a cell comprising said target DNA molecule with the assembled RGN-deaminase ribonucleotide complex;
wherein the one or more guide RNAs hybridize to the target DNA sequence, thereby directing said fusion protein to bind to said target DNA sequence and modification of the target DNA molecule occurs.

331. The method of embodiment 330, wherein the target DNA sequence comprises a nucleic acid sequence selected from the group consisting of SEQ ID NOs: 62-97, 116-139, 152-185, 203-234, 251-286, 305-344, 562, and 563, or the complement thereof.

332. The method of any one of embodiments 330-331, wherein the gRNA sequence comprises a nucleic acid sequence selected from the group consisting of SEQ ID NOs: 98-115, 140-151, 186-202, 235-250, 287-304, 345-364, and 564.

333. The method of any one of embodiments 330-332, wherein the method is performed in vitro, in vivo, or ex vivo.

334. A method of treating a subject having or at risk of developing a disease, disorder, or condition, the method comprising:
administering to the subject the fusion protein of any of embodiments 295-303, the nucleic acid molecule of any one of embodiments 304-313, the vector of any one of embodiments 314-315, the RNP complex of embodiment 316, the cell of embodiment 317, the system of any one of embodiments 318-328, or the pharmaceutical composition of embodiment 329.

335. The method of embodiment 334, further comprising administering any one of a gRNA comprising a nucleic acid sequence selected from the group consisting of SEQ ID NOs: 98-115, 140-151, 186-202, 235-250, 287-304, 345-364, and 564.

336. An isolated polypeptide comprising an amino acid sequence having at least 90% sequence identity to SEQ ID NO: 399, wherein said polypeptide has deaminase activity.

337. The isolated polypeptide of embodiment 336 comprising an amino acid sequence having at least 95% sequence identity to SEQ ID NO: 399, wherein said polypeptide has deaminase activity.

338. The isolated polypeptide of embodiment 336, wherein the polypeptide comprises an amino acid sequence set forth in SEQ ID NO: 399.

339. A nucleic acid molecule comprising a polynucleotide encoding a deaminase polypeptide, wherein the deaminase is encoded by a nucleotide sequence that:
a) has at least 80% sequence identity to SEQ ID NO: 443, or
b) encodes an amino acid sequence having at least 90% sequence identity to any one of SEQ ID NO: 399.

340. The nucleic acid molecule of embodiment 339, wherein the deaminase is encoded by a nucleotide sequence that has at least 90% sequence identity to SEQ ID NO: 443.

341. The nucleic acid molecule of embodiment 339, wherein the deaminase is encoded by a nucleotide sequence that has at least 95% sequence identity to SEQ ID NO: 443.

342. The nucleic acid molecule of embodiment 339, wherein the deaminase is encoded by a nucleotide sequence that has at least 100% sequence identity to SEQ ID NO: 443.

343. The nucleic acid molecule of embodiments 339-342, wherein said nucleic acid molecule further comprises a heterologous promoter operably linked to said polynucleotide.

344. A pharmaceutical composition comprising a pharmaceutically acceptable carrier and the polypeptide of any one of embodiments 336-338 or the nucleic acid molecule of any one of embodiments 339-342.

345. A fusion protein comprising a DNA-binding polypeptide and a deaminase having at least 90% sequence identity to SEQ ID NO: 399.

346. A fusion protein of embodiment 345 comprising a DNA-binding polypeptide and a deaminase having at least 95% sequence identity to SEQ ID NO: 399.

347. A fusion protein of embodiment 345 comprising a DNA-binding polypeptide and a deaminase having 100% sequence identity to SEQ ID NO: 399.

348. The fusion protein of any one of embodiments 345-347, wherein the DNA-binding polypeptide is a RNA-guided nuclease (RGN) polypeptide.

349. The fusion protein of embodiment 348, wherein the RGN polypeptide is a Type II CRISPR-Cas polypeptide or a Type V CRISPR-Cas polypeptide.

350. The fusion protein of any one of embodiments 348-349, wherein the RGN polypeptide is a Cas9, a CasX, a CasY, a Cpf1, a C2c1, a C2c2, a C2c3, a GeoCas9, a CjCas9, a Cas12a, a Cas12b, a Cas12g, a Cas12h, a Cas12i, a Cas13b, a Cas13c, a Cas13d, a Cas14, a Csn2, an xCas9, an SpCas9-NG, an LbCas12a, an AsCas12a, a Cas9-KKH, a circularly permuted Cas9, an Argonaute (Ago), a SmacCas9, a Spy-macCas9 domain, or a RGN polypeptide with an amino acid sequence set forth in any one of SEQ ID NOs: 41, 60, 366, or 368.

351. The fusion protein of any one of embodiments 348-350, wherein the RGN polypeptide is a nickase.

352. The fusion protein of embodiment 351, wherein the nickase has an amino acid sequence having at least 95% sequence identity to any one of SEQ ID NOs: 42, 52-59, 61, 397, and 398.

353. The fusion protein of embodiment 351, wherein the nickase has an amino acid sequence having 100% sequence identity to any one of SEQ ID NOs: 42, 52-59, 61, 397, and 398.

354. A nucleic acid molecule comprising a polynucleotide encoding a fusion protein comprising a DNA-binding polypeptide and a deaminase, wherein the deaminase is encoded by a nucleotide sequence that:
a) has at least 80% sequence identity to SEQ ID NO: 443, or
b) encodes an amino acid sequence having at least 90% sequence identity to SEQ ID NO: 399.

355. The nucleic acid molecule of embodiment 354, wherein the deaminase is encoded by a nucleotide sequence that has at least 90% sequence identity to SEQ ID NO: 443.

356. The nucleic acid molecule of embodiment 354, wherein the deaminase is encoded by a nucleotide sequence that has at least 95% sequence identity to SEQ ID NO: 443.

357. The nucleic acid molecule of embodiment 354, wherein the deaminase is encoded by a nucleotide sequence that has at least 100% sequence identity to SEQ ID NO: 443.

358. The nucleic acid molecule of any one of embodiments 354-357, wherein the DNA-binding polypeptide is a RGN polypeptide.

359. The nucleic acid molecule of embodiment 358, wherein the RGN is a Type II CRISPR-Cas polypeptide or a Type V CRISPR-Cas polypeptide.

360. The nucleic acid molecule of any one of embodiments 358-359, wherein the RGN polypeptide is a Cas9, a CasX, a CasY, a Cpf1, a C2c1, a C2c2, a C2c3, a GeoCas9, a CjCas9, a Cas12a, a Cas12b, a Cas12g, a Cas12h, a Cas12i, a Cas13b, a Cas13c, a Cas13d, a Cas14, a Csn2, an xCas9, an SpCas9-NG, an LbCas12a, an AsCas12a, a Cas9-KKH, a circularly permuted Cas9, an Argonaute (Ago), a SmacCas9, a Spy-macCas9 domain, or a RGN polypeptide with an amino acid sequence set forth in any one of SEQ ID NOs: 41, 60, 366, or 368.

361. The nucleic acid molecule of any one of embodiments 358-360, wherein the RGN polypeptide is a nickase.

362. The nucleic acid molecule of embodiment 361, wherein the nickase has an amino acid sequence having at least 95% sequence identity to any one of SEQ ID NOs: 42, 52-59, 61, 397, and 398.

363. The nucleic acid molecule of embodiment 362, wherein the nickase has an amino acid sequence having 100% sequence identity to any one of SEQ ID NOs: 42, 52-59, 61, 397, and 398.

364. A vector comprising the nucleic acid molecule of any one of embodiments 354-363.

365. The vector of embodiment 364, further comprising at least one nucleotide sequence encoding a guide RNA (gRNA) capable of hybridizing to a target sequence.

366. A ribonucleoprotein (RNP) complex comprising the fusion protein of any one of embodiments 345-353 and a guide RNA bound to the DNA-binding polypeptide of the fusion protein.

367. A cell comprising the fusion protein of any of embodiments 345-353, the nucleic acid molecule of any one of embodiments 354-363, the vector of any one of embodiments 364-365, or the RNP complex of embodiment 366.

368. A system for modifying a target DNA molecule comprising a target DNA sequence, said system comprising:
a) a fusion protein comprising an RNA-guided nuclease (RGN) polypeptide and a deaminase, wherein the deaminase has an amino acid sequence having at least 90% sequence identity to SEQ ID NO: 399, or a nucleotide sequence encoding said fusion protein; and
b) one or more guide RNAs capable of hybridizing to said target DNA sequence or one or more nucleotide sequences encoding the one or more guide RNAs (gRNAs); and
wherein the one or more guide RNAs are capable of forming a complex with the fusion protein in order to direct said fusion protein to bind to said target DNA sequence and modify the target DNA molecule.

369. The system of embodiment 368, wherein said deaminase has an amino acid sequence having at least 95% sequence identity to SEQ ID NO: 399.

370. The system of embodiment 368, wherein said deaminase has an amino acid sequence having 100% sequence identity to SEQ ID NO: 399.

371. The system of any one of embodiments 368-370, wherein at least one of said nucleotide sequence encoding the one or more guide RNAs and said nucleotide sequence encoding the fusion protein is operably linked to a promoter heterologous to said nucleotide sequence.

372. The system of any one of embodiments 368-371, wherein the target DNA sequence is located adjacent to a protospacer adjacent motif (PAM) that is recognized by the RGN polypeptide.

373. The system of any one of embodiments 368-372, wherein the target DNA sequence comprises a nucleic acid sequence selected from the group consisting of SEQ ID NOs: 62-97, 116-139, 152-185, 203-234, 251-286, 305-344, 562, and 563, or the complement thereof.

374. The system of any one of embodiments 368-373, wherein the gRNA sequence comprises a nucleic acid sequence selected from the group consisting of SEQ ID NOs: 98-115, 140-151, 186-202, 235-250, 287-304, 345-364, and 564.

375. The system of any one of embodiments 368-374, wherein the RGN polypeptide of the fusion protein is a Type II CRISPR-Cas polypeptide or a Type V CRISPR-Cas polypeptide.

376. The system of any one of embodiments 372-375, wherein the RGN polypeptide is a Cas9, a CasX, a CasY, a Cpf1, a C2c1, a C2c2, a C2c3, a GeoCas9, a CjCas9, a Cas12a, a Cas12b, a Cas12g, a Cas12h, a Cas12i, a Cas13b, a Cas13c, a Cas13d, a Cas14, a Csn2, an xCas9, an SpCas9-NG, an LbCas12a, an AsCas12a, a Cas9-KKH, a circularly permuted Cas9, an Argonaute (Ago), a SmacCas9, a Spy-macCas9 domain, or a RGN with an amino acid sequence set forth in any one of SEQ ID NOs: 41, 60, 366, or 368.

377. The system of embodiment 376, wherein the RGN polypeptide is a nickase.

378. The system of embodiment 377, wherein the nickase has an amino acid sequence having at least 95% sequence identity to any one of SEQ ID NOs: 42, 52-59, 61, 397, and 398.

379. A pharmaceutical composition comprising a pharmaceutically acceptable carrier and the fusion protein of any of embodiments 345-353, the nucleic acid molecule of any one of embodiments 354-363, the vector of any one of embodiments 364-365, the RNP complex of embodiment 366, the cell of embodiment 367, or the system of any one of embodiments 368-378.

380. A method for modifying a target DNA molecule comprising a target sequence comprising:
a) assembling an RGN-deaminase ribonucleotide complex by combining:
i) one or more guide RNAs capable of hybridizing to the target DNA sequence; and
ii) a fusion protein comprising an RNA-guided nuclease polypeptide (RGN), and at least one deaminase, wherein the deaminase has an amino acid sequence having at least 90% sequence identity to SEQ ID NO: 399;
under conditions suitable for formation of the RGN-deaminase ribonucleotide complex; and b) contacting said target DNA molecule or a cell comprising said target DNA molecule with the assembled RGN-deaminase ribonucleotide complex;
wherein the one or more guide RNAs hybridize to the target DNA sequence, thereby directing said fusion protein to bind to said target DNA sequence and modification of the target DNA molecule occurs.

381. The method of embodiment 380, wherein the target DNA sequence comprises a nucleic acid sequence selected from the group consisting of SEQ ID NOs: 62-97, 116-139, 152-185, 203-234, 251-286, 305-344, 562, and 563, or the complement thereof.

382. The method of any one of embodiments 380-381, wherein the gRNA sequence comprises a nucleic acid sequence selected from the group consisting of SEQ ID NOs: 98-115, 140-151, 186-202, 235-250, 287-304, 345-364, and 564.

383. The method of any one of embodiments 380-382, wherein the method is performed in vitro, in vivo, or ex vivo.

384. A method of treating a subject having or at risk of developing a disease, disorder, or condition, the method comprising:
administering to the subject the fusion protein of any of embodiments 345-353, the nucleic acid molecule of any one of embodiments 354-363, the vector of any one of embodiments 364-365, the RNP complex of embodiment 366, the cell of embodiment 367, the system of any one of embodiments 368-378, or the pharmaceutical composition of embodiment 379.

385. The method of embodiment 384, further comprising administering any one of a gRNA comprising a nucleic acid sequence selected from the group consisting of SEQ ID NOs:
98-115, 140-151, 186-202, 235-250, 287-304, 345-364, and 564.

386. A method for producing a treating or reducing at least one symptom of cystic fibrosis, the method comprising administering to a subject in need thereof an effective amount of:
a) a fusion protein comprising an RNA-guided nuclease polypeptide (RGN) and a deaminase, wherein the deaminase has an amino acid sequence having at least 90% sequence identity to any one of SEQ ID NOs: 407, 405, 399, 1-10, 400-404, 406, and 408-441, or a polynucleotide encoding said fusion protein, wherein said polynucleotide encoding the fusion protein is operably linked to a promoter to enable expression of the fusion protein in the cell; and
b) one or more guide RNAs (gRNA) capable of hybridizing to a target DNA sequence, or a polynucleotide encoding said gRNA, wherein said polynucleotide encoding the gRNA is operably linked to a promoter to enable expression of the gRNA in the cell; whereby the fusion protein and gRNA target to the genomic location of the causal mutation and modify the genomic sequence to remove the causal mutation.

387. The method of embodiment 386, wherein the gRNA comprises a spacer sequence that targets any one of SEQ ID NOs: 62-97, 116-139, 152-185, 203-234, 251-286, 305-344, 562, and 563, or the complement thereof.

388. The method of embodiments 386 or 387, wherein the gRNA comprises any one of SEQ ID NOs: 98-115, 140-151, 186-202, 235-250, 287-304, 345-364, and 564.

389. The method of any one of claims 386-388, wherein said the RGN has an amino acid sequence having at least 90% sequence identity to any one of SEQ ID NOs: 41, 60, 366, and 368.

390. The method of any one of claims 386-389, wherein said the RGN has an amino acid sequence having at least 90% sequence identity to any one of SEQ ID NOs: 42, 52-59, 61, 397, and 398.

The following examples are offered by way of illustration and not by way of limitation.

EXPERIMENTAL

Example 1: Demonstration of Base Editing in Mammalian Cells

The deaminases shown in Table 1 below were produced based on naturally occurring deaminases which were then mutated and selected for adenine deaminase activity in prokaryotic cells.

TABLE 1

Deaminase sequences

| Deaminase | SEQ ID NO. |
|---|---|
| APG09982 | 1 |
| APG03724 | 2 |
| APG09949 | 3 |
| APG08196 | 4 |
| APG06333 | 5 |
| APG06489 | 6 |
| APG08449 | 7 |
| APG05174 | 8 |
| APG09102 | 9 |
| APG05723 | 10 |

To determine if the deaminases of Table 1 are able to perform adenine base editing in mammalian cells, each deaminase was operably fused to an RGN nickase to produce a fusion protein. Residues predicted to deactivate the RuvC domain of the RGN APG07433.1 (set forth as SEQ ID NO: 41; described in PCT publication WO 2019/236566, incorporated by reference herein) were identified and the RGN was modified to a nickase variant (nAPG07433.1; SEQ ID NO: 42). A nickase variant of an RGN is referred to herein as "nRGN". It should be understood that any nickase variant of an RGN may be used to produce a fusion protein of the invention.

Deaminase and nRGN nucleotide sequences codon optimized for mammalian expression were synthesized as fusion proteins with an N-terminal nuclear localization tag and cloned into the pTwist CMV (Twist Biosciences) expression plasmid. Each fusion protein comprises, starting at the amino terminus, the SV40 NLS (SEQ ID NO: 43) operably linked at the C-terminal end to 3× FLAG Tag (SEQ ID NO: 44), operably linked at the C-terminal end to a deaminase, operably linked at the C-terminal end to a peptide linker (SEQ ID NO: 45), operably linked at the C-terminal end to an nRGN (for example, nAPG07433.1, which is SEQ ID NO: 42), finally operably linked at the C-terminal end to the nucleoplasmin NLS (SEQ ID NO: 45). All fusion proteins comprise at least one NLS and a 3× FLAG Tag, as described above.

Expression plasmids comprising an expression cassette encoding a sgRNA expressed by a human U6 promoter (SEQ ID NO: 50) were also produced. Human genomic target sequences and the sgRNA sequences for guiding the fusion proteins to the genomic targets are indicated in Table 2.

TABLE 2

Guide RNA sequences

| sgRNA ID | Target sequence | sgRNA sequence | Forward Primer for amplification | Reverse Primer for amplification |
|---|---|---|---|---|
| SGN000930 | 21 | 26 | 31 | 32 |
| SGN000186 | 22 | 27 | 33 | 34 |
| SGN000194 | 23 | 28 | 35 | 36 |
| SGN000143 | 24 | 29 | 37 | 38 |
| SGN000139 | 25 | 30 | 39 | 40 |

500 ng of plasmid comprising an expression cassette comprising a coding sequence for a fusion protein for each deaminase described in Table 1 and 500 ng of plasmid comprising an expression cassette encoding an sgRNA shown in Table 2 were co-transfected into HEK293FT cells at 75-90% confluency in 24-well plates using Lipofectamine 2000 reagent (Life Technologies). Cells were then incubated at 37° C. for 72 h. Following incubation, genomic DNA was then extracted using NucleoSpin 96 Tissue (Macherey-Nagel) following the manufacturer's protocol. The genomic region flanking the targeted genomic site was PCR amplified using the primers in Table 2 and products were purified using ZR-96 DNA Clean and Concentrator (Zymo Research) following the manufacturer's protocol. The purified PCR products underwent Next Generation Sequencing on Illumina MiSeq. Typically, 100,000 of 250 bp paired-end reads (2×100,000 reads) are generated per amplicon. The reads were analyzed using CRISPResso (Pinello, et al. 2016 *Nature Biotech*, 34:695-697) to calculate the rates of editing. Output alignments were analyzed for INDEL formation or introduction of specific adenine mutations. Tables 3 through 7 show adenine base editing for each fusion protein comprising nAPG07433.1 and a deaminase from Table 1 and a guide RNA from Table 2. The deaminase component of each fusion protein is indicated. The editing rate for adenines within or proximal to the target sequence is indicated. "A5" indicates, for example, an adenine at position 5 of the target sequence. The position of each nucleotide in the target sequence was determined by numbering the first nucleotide in the target sequence closest to the PAM as position 1, and the position number increases in the 3' direction away from the PAM sequence. The tables also show which nucleotide the adenine was changed to, and at what rate. For example, Table 3 shows that for the APG09982-nAPG07433.1 fusion protein, the adenine at position 13 was mutated to a guanine at a rate of 1.2%.

TABLE 3

A > N Editing Rate using guide SGN000139

| Deaminase | | A5 | A12 | A13 | A20 | A22 |
|---|---|---|---|---|---|---|
| APG09982 | C | 0 | 0 | 0 | 0.3 | 0 |
|  | G | 0 | 0.5 | 1.2 | 0 | 0 |
|  | T | 0 | 0 | 0 | 0 | 0 |
| APG03724 | C | 0 | 0 | 0 | 0.3 | 0 |
|  | G | 0 | 0.7 | 0.7 | 0.1 | 0 |
|  | T | 0 | 0 | 0 | 0 | 0 |
| APG09949 | C | 0 | 0 | 0 | 0.3 | 0.1 |
|  | G | 0.1 | 0.6 | 0.7 | 0 | 0 |
|  | T | 0 | 0 | 0 | 0 | 0 |
| APG08196 | C | 0 | 0 | 0 | 0.6 | 0.1 |

TABLE 3-continued

A > N Editing Rate using guide SGN000139

| Deaminase | | A5 | A12 | A13 | A20 | A22 |
|---|---|---|---|---|---|---|
|  | G | 0 | 0.6 | 0.6 | 0 | 0 |
|  | T | 0 | 0 | 0 | 0 | 0 |
| APG06333 | C | 0 | 0 | 0 | 0.2 | 0 |
|  | G | 0 | 0.5 | 1 | 0 | 0 |
|  | T | 0 | 0 | 0 | 0 | 0 |
| APG06489 | C | 0 | 0 | 0 | 0.2 | 0 |
|  | G | 0 | 0.6 | 0.4 | 0 | 0 |
|  | T | 0 | 0 | 0 | 0 | 0 |
| APG08449 | C | 0 | 0 | 0 | 0.3 | 0.1 |
|  | G | 0 | 0.8 | 0.8 | 0 | 0 |
|  | T | 0 | 0 | 0 | 0 | 0 |
| APG05174 | C | 0 | 0 | 0 | 0.6 | 0.1 |
|  | G | 0 | 0.6 | 0.7 | 0 | 0 |
|  | T | 0 | 0 | 0 | 0 | 0 |
| APG09102 | C | 0 | 0 | 0 | 0.1 | 0 |
|  | G | 0 | 0.6 | 0.6 | 0 | 0 |
|  | T | 0 | 0 | 0 | 0 | 0 |
| APG05723 | C | 0 | 0 | 0 | 0.1 | 0 |
|  | G | 0 | 0.4 | 0.5 | 0.1 | 0 |
|  | T | 0 | 0 | 0 | 0 | 0 |

All fusion proteins showed detectable A>G conversion at positions A12 and A13. APG09982 and APG06333 showed at least 1% editing at position A13.

TABLE 4

A > N Editing Rate using guide SGN000143

| Deaminase | | A1 | A4 | A6 | A9 | A11 | A14 | A19 | A30 |
|---|---|---|---|---|---|---|---|---|---|
| APG09982 | C | 0 | 0 | 0 | 0 | 0 | 0 | 0 | 0 |
|  | G | 0 | 0 | 0 | 0.1 | 4.5 | 1.7 | 0 | 0 |
|  | T | 0 | 0 | 0 | 0 | 0 | 0 | 0 | 0 |
| APG03724 | C | 0 | 0 | 0 | 0 | 0 | 0 | 0 | 0 |
|  | G | 0 | 0 | 0.1 | 0.1 | 1.3 | 1.1 | 0 | 0 |
|  | T | 0 | 0 | 0 | 0 | 0 | 0 | 0 | 0 |
| APG09949 | C | 0 | 0 | 0 | 0 | 0 | 0 | 0 | 0.1 |
|  | G | 0 | 0 | 0 | 0.1 | 0.8 | 0.7 | 0 | 0 |
|  | T | 0 | 0 | 0 | 0 | 0 | 0 | 0 | 0 |
| APG08196 | C | 0 | 0 | 0 | 0 | 0 | 0 | 0 | 0 |
|  | G | 0 | 0 | 0 | 0.4 | 0.7 | 0.5 | 0.1 | 0 |
|  | T | 0 | 0 | 0 | 0 | 0 | 0 | 0 | 0 |
| APG06333 | C | 0 | 0 | 0 | 0 | 0 | 0 | 0 | 0 |
|  | G | 0 | 0 | 0 | 0 | 1.3 | 0.8 | 0.1 | 0 |
|  | T | 0 | 0 | 0 | 0 | 0 | 0 | 0 | 0 |
| APG06489 | C | 0 | 0 | 0 | 0 | 0 | 0 | 0 | 0 |
|  | G | 0 | 0 | 0.1 | 0.6 | 1.8 | 0.8 | 0.1 | 0 |
|  | T | 0 | 0 | 0 | 0 | 0 | 0 | 0 | 0 |
| APG08449 | C | 0 | 0 | 0 | 0 | 0 | 0 | 0 | 0.1 |
|  | G | 0 | 0 | 0 | 0 | 2.4 | 1.2 | 0 | 0 |
|  | T | 0 | 0 | 0 | 0 | 0 | 0 | 0 | 0 |
| APG05174 | C | 0 | 0 | 0 | 0 | 0 | 0 | 0 | 0 |
|  | G | 0 | 0 | 0 | 0 | 1.5 | 0.7 | 0 | 0 |
|  | T | 0 | 0 | 0 | 0 | 0 | 0 | 0 | 0 |
| APG09102 | C | 0 | 0 | 0 | 0 | 0 | 0 | 0 | 0 |
|  | G | 0 | 0 | 0 | 0 | 2.6 | 1.6 | 0 | 0 |
|  | T | 0 | 0 | 0 | 0 | 0 | 0 | 0 | 0 |
| APG05723 | C | 0 | 0 | 0 | 0 | 0.1 | 0 | 0 | 0 |
|  | G | 0 | 0 | 0.1 | 0.1 | 1.1 | 0.5 | 0 | 0 |
|  | T | 0 | 0 | 0 | 0 | 0 | 0 | 0 | 0 |

All fusion proteins showed A>G conversion at positions A11 and A14. APG09982 showed 4.5% conversion of A 11 to G and 1.7% conversion of A14 to G.

TABLE 5

A > N Editing Rate using guide SGN000186

| Deaminase | | A9 | A16 | A18 | A22 | A25 | A28 | A30 |
|---|---|---|---|---|---|---|---|---|
| APG09982 | C | 0 | 0 | 0 | 0 | 0 | 0 | 0 |
| | G | 1.7 | 4.5 | 2 | 0 | 0 | 0 | 0 |
| | T | 0 | 0 | 0 | 0 | 0 | 0 | 0 |
| APG03724 | C | 0 | 0 | 0 | 0 | 0.1 | 0 | 0 |
| | G | 0.7 | 4.1 | 1.4 | 0 | 0 | 0 | 0 |
| | T | 0 | 0 | 0 | 0 | 0 | 0 | 0 |
| APG09949 | C | 0 | 0 | 0.1 | 0 | 0.1 | 0 | 0 |
| | G | 0.6 | 3.4 | 1.1 | 0 | 0 | 0 | 0 |
| | T | 0 | 0 | 0 | 0 | 0.1 | 0 | 0 |
| APG08196 | C | 0 | 0 | 0.1 | 0 | 0.1 | 0 | 0 |
| | G | 1 | 3.3 | 1.4 | 0 | 0 | 0.1 | 0 |
| | T | 0 | 0 | 0 | 0 | 0.1 | 0 | 0 |
| APG06333 | C | 0 | 0 | 0 | 0 | 0 | 0 | 0 |
| | G | 1.4 | 4.2 | 1.9 | 0 | 0 | 0 | 0 |
| | T | 0 | 0 | 0 | 0 | 0 | 0 | 0 |
| APG06489 | C | 0 | 0 | 0 | 0 | 0 | 0 | 0 |
| | G | 1.7 | 2.5 | 1.4 | 0 | 0 | 0 | 0.1 |
| | T | 0 | 0 | 0 | 0 | 0 | 0 | 0 |
| APG08449 | C | 0 | 0 | 0.1 | 0 | 0.1 | 0 | 0 |
| | G | 1.5 | 5.3 | 1.6 | 0 | 0 | 0 | 0 |
| | T | 0 | 0 | 0 | 0 | 0.1 | 0 | 0 |
| APG05174 | C | 0 | 0 | 0.1 | 0 | 0 | 0 | 0 |
| | G | 0.9 | 3.2 | 1 | 0 | 0 | 0.1 | 0 |
| | T | 0 | 0 | 0 | 0 | 0.1 | 0 | 0 |
| APG09102 | C | 0 | 0 | 0 | 0 | 0 | 0 | 0 |
| | G | 2.3 | 6.2 | 2.1 | 0 | 0 | 0 | 0 |
| | T | 0 | 0 | 0 | 0 | 0 | 0 | 0 |
| APG05723 | C | 0 | 0 | 0 | 0 | 0 | 0 | 0 |
| | G | 1.1 | 1.9 | 1.2 | 0 | 0 | 0 | 0 |
| | T | 0 | 0 | 0 | 0 | 0 | 0 | 0 |

All fusion proteins showed base editing of over 100 at multiple locations in target SGN000186. APG09102 showed 6.2% A>G conversion at position A 16; it also showed over 2% base editing at positions A9 and A18. For all fusion proteins tested, position A16 was the most highly edited.

TABLE 6

A > N Editing Rate using guide SGN000194

| Deaminase | | A6 | A10 | A13 | A15 | A21 | A23 | A26 | A27 |
|---|---|---|---|---|---|---|---|---|---|
| APG09982 | C | 0 | 0 | 0 | 0 | 0 | 0 | 0 | 0 |
| | G | 0 | 0.3 | 0.6 | 1.5 | 0 | 0 | 0 | 0 |
| | T | 0 | 0 | 0 | 0 | 0 | 0 | 0 | 0 |
| APG03724 | C | 0 | 0 | 0 | 0 | 0 | 0 | 0 | 0 |
| | G | 0 | 0.1 | 0.3 | 1 | 0 | 0 | 0 | 0 |
| | T | 0 | 0 | 0 | 0 | 0 | 0 | 0 | 0 |
| APG09949 | C | 0 | 0 | 0 | 0 | 0 | 0 | 0 | 0 |
| | G | 0 | 0.2 | 0.3 | 1.6 | 0 | 0 | 0 | 0 |
| | T | 0 | 0 | 0 | 0 | 0 | 0 | 0 | 0 |
| APG08196 | C | 0 | 0 | 0 | 0 | 0 | 0 | 0 | 0 |
| | G | 0.1 | 0.4 | 0.1 | 0.9 | 0 | 0 | 0 | 0 |
| | T | 0 | 0 | 0 | 0 | 0 | 0 | 0 | 0 |
| APG06333 | C | 0 | 0 | 0 | 0 | 0 | 0 | 0 | 0 |
| | G | 0 | 0.2 | 0.3 | 1 | 0 | 0 | 0 | 0 |
| | T | 0 | 0 | 0 | 0 | 0 | 0 | 0 | 0 |
| APG06489 | C | 0 | 0 | 0 | 0 | 0 | 0 | 0 | 0 |
| | G | 0 | 0.4 | 0.2 | 1.1 | 0 | 0 | 0 | 0 |
| | T | 0 | 0 | 0 | 0 | 0 | 0 | 0 | 0 |
| APG08449 | C | 0 | 0 | 0 | 0 | 0 | 0 | 0 | 0 |
| | G | 0.1 | 0.3 | 0.4 | 1.8 | 0 | 0 | 0 | 0 |
| | T | 0 | 0 | 0 | 0 | 0 | 0 | 0 | 0 |
| APG05174 | C | 0 | 0 | 0 | 0 | 0 | 0 | 0 | 0 |
| | G | 0.1 | 0.1 | 0.3 | 0.9 | 0 | 0 | 0 | 0 |
| | T | 0 | 0 | 0 | 0 | 0 | 0 | 0 | 0 |
| APG09102 | C | 0 | 0 | 0 | 0 | 0 | 0 | 0 | 0 |
| | G | 0 | 0.2 | 0.7 | 1.6 | 0 | 0 | 0 | 0 |
| | T | 0 | 0 | 0 | 0 | 0 | 0 | 0 | 0 |
| APG05723 | C | 0 | 0 | 0 | 0 | 0 | 0 | 0 | 0 |
| | G | 0 | 0 | 0.1 | 0.9 | 0 | 0 | 0 | 0 |
| | T | 0 | 0 | 0 | 0 | 0 | 0 | 0 | 0 |

With SGN00194, all fusion proteins showed 0.9%-~1.8% A>G editing at position A15. No detectable editing was seen in positions A21, A23, A26 and A27.

TABLE 7

A > N Editing Rate using guide SGN000930

| Deaminase | | A2 | A4 | A5 | A8 | A9 | A10 | A14 | A15 | A16 | A20 | A21 | A23 | A24 | A26 | A27 | A29 | A30 |
|---|---|---|---|---|---|---|---|---|---|---|---|---|---|---|---|---|---|---|
| APG09982 | C | 0 | 0 | 0 | 0 | 0 | 0 | 0 | 0 | 0 | 0 | 0 | 0 | 0 | 0 | 0 | 0 | 0 |
| | G | 0 | 0 | 0 | 0 | 0 | 0.3 | 0.7 | 0.1 | 0.2 | 0.5 | 0.2 | 0 | 0 | 0 | 0 | 0 | 0 |
| | T | 0 | 0 | 0 | 0 | 0 | 0 | 0 | 0 | 0 | 0 | 0 | 0 | 0 | 0 | 0 | 0 | 0 |
| APG03724 | C | 0 | 0 | 0 | 0 | 0 | 0 | 0 | 0 | 0 | 0 | 0 | 0 | 0 | 0 | 0 | 0 | 0 |
| | G | 0 | 0 | 0 | 0.1 | 0.1 | 0.4 | 0.5 | 0.2 | 0.2 | 0.3 | 0.1 | 0 | 0 | 0 | 0 | 0 | 0 |
| | T | 0 | 0 | 0 | 0 | 0 | 0 | 0 | 0 | 0 | 0 | 0 | 0 | 0 | 0 | 0 | 0 | 0 |
| APG09949 | C | 0 | 0 | 0 | 0 | 0 | 0 | 0 | 0 | 0 | 0 | 0 | 0 | 0 | 0 | 0 | 0 | 0 |
| | G | 0 | 0 | 0 | 0 | 0 | 0.1 | 0.5 | 0.3 | 0.3 | 0.4 | 0 | 0 | 0 | 0 | 0 | 0 | 0 |
| | T | 0 | 0 | 0 | 0 | 0 | 0 | 0 | 0 | 0 | 0 | 0 | 0 | 0 | 0 | 0 | 0 | 0 |
| APG08196 | C | 0 | 0 | 0 | 0 | 0 | 0 | 0 | 0 | 0 | 0 | 0 | 0 | 0 | 0 | 0 | 0 | 0 |
| | G | 0 | 0 | 0 | 0.1 | 0 | 0.2 | 0.7 | 0.3 | 0.2 | 0.4 | 0.1 | 0 | 0 | 0 | 0 | 0 | 0 |
| | T | 0 | 0 | 0 | 0 | 0 | 0 | 0 | 0 | 0 | 0 | 0 | 0 | 0 | 0 | 0 | 0 | 0 |
| APG06333 | C | 0 | 0 | 0 | 0 | 0 | 0 | 0 | 0 | 0 | 0 | 0 | 0 | 0 | 0 | 0 | 0 | 0 |
| | G | 0 | 0 | 0 | 0.1 | 0.1 | 0.3 | 0.4 | 0.3 | 0.9 | 0.2 | 0.1 | 0.1 | 0 | 0 | 0 | 0 | 0 |
| | T | 0 | 0 | 0 | 0 | 0 | 0 | 0 | 0 | 0 | 0 | 0 | 0 | 0 | 0 | 0 | 0 | 0 |
| APG06489 | C | 0 | 0 | 0 | 0 | 0 | 0 | 0 | 0 | 0 | 0 | 0 | 0 | 0 | 0 | 0 | 0 | 0 |
| | G | 0 | 0 | 0 | 0.3 | 0.1 | 0.2 | 0.8 | 0.3 | 0.4 | 0.6 | 0 | 0.1 | 0 | 0 | 0 | 0 | 0 |
| | T | 0 | 0 | 0 | 0 | 0 | 0 | 0 | 0 | 0 | 0 | 0 | 0 | 0 | 0 | 0 | 0 | 0 |
| APG08449 | C | 0 | 0 | 0 | 0 | 0 | 0 | 0 | 0 | 0 | 0 | 0 | 0 | 0 | 0 | 0 | 0 | 0 |
| | G | 0 | 0 | 0 | 0.1 | 0.1 | 0.3 | 0.6 | 0.4 | 0.2 | 0.4 | 0.1 | 0 | 0 | 0 | 0 | 0 | 0 |
| | T | 0 | 0 | 0 | 0 | 0 | 0 | 0 | 0 | 0 | 0 | 0 | 0 | 0 | 0 | 0 | 0 | 0 |
| APG05174 | C | 0 | 0 | 0 | 0 | 0 | 0 | 0 | 0 | 0 | 0 | 0 | 0 | 0 | 0 | 0 | 0 | 0 |
| | G | 0 | 0 | 0 | 0 | 0.1 | 0.2 | 0.8 | 0.3 | 0.4 | 0.2 | 0.2 | 0 | 0 | 0 | 0 | 0 | 0 |
| | T | 0 | 0 | 0 | 0 | 0 | 0 | 0 | 0 | 0 | 0 | 0 | 0 | 0 | 0 | 0 | 0 | 0 |
| APG09102 | C | 0 | 0 | 0 | 0 | 0 | 0 | 0 | 0 | 0 | 0 | 0 | 0 | 0 | 0 | 0 | 0 | 0 |
| | G | 0 | 0 | 0 | 0 | 0 | 0 | 0.9 | 0.1 | 0.1 | 0.6 | 0.3 | 0 | 0 | 0 | 0 | 0 | 0 |
| | T | 0 | 0 | 0 | 0 | 0 | 0 | 0 | 0 | 0 | 0 | 0 | 0 | 0 | 0 | 0 | 0 | 0 |
| APG05723 | C | 0 | 0 | 0 | 0 | 0 | 0 | 0 | 0 | 0 | 0 | 0 | 0 | 0 | 0 | 0 | 0 | 0 |
| | G | 0 | 0 | 0 | 0 | 0.1 | 0.1 | 1.2 | 0.6 | 0.2 | 0.5 | 0 | 0 | 0 | 0 | 0 | 0 | 0 |
| | T | 0 | 0 | 0 | 0 | 0 | 0 | 0 | 0 | 0 | 0 | 0 | 0 | 0 | 0 | 0 | 0 | 0 |

A14 was the most highly edited position in SGN000930 with all fusion proteins tested. The editing rate ranged from 0.3%-1.2% for A>G conversions.

Example 2: Fluorescence Assay for Targeted Adenine Base Editing

A vector harboring Enhanced Green Fluorescent Protein (EGFP) containing a W58X mutation which causes a premature stop codon (GFP-STOP, SEQ ID NO: 47) was constructed such that the W58 codon can be reverted from a stop codon (TGA) to the wild-type tryptophan (TOO) residue using an adenine deaminase to alter the third position A to G. Successful A to G Conversion results in the expression ofEGFP which can be quantified. A second vector capable of expressing a guide RNA which targets the dearinase-RGN fusion protein to the region around the W58X mutation (SEQ ID NO: 48) was also produced This GFP-STOP reporter vector, along with the vectors capable of expressing a deaminase-nRGN fusion protein and the corresponding guide RNA, were transfected into HEK293T cells, using either lipofection or electroporation. For lipofection, cells were seeded at 1×10$^5$ cells/well in 24-well plates the day prior to transfection in growth medium (DMEFM+10% Fetal Bovine Serum+1% Penicillin/streptomycin). 500 ng each of the GFP-STOP reporter vector, deaminase-RGN expression vector, and guide RNA expression vector were transfected using Lipofectamine® 3000 reagent (Thermo Fisher Scientific) following manufacturer's instructions. For electroporation, cells were electroporated using the Neon® Transfection System (Thermo Fisher Scientific) following manufacturer's instructions, In addition to transient transfection of the fluorescent GFP-STOP reporter, a stable cell line harboring a chromosomally integrated GFP-STOP cassette was generated. Once the stable line was established, for transfection, cells were seeded at 1×10$^5$ cells/well in 24-well plates the day prior to transfection in growth medium (DMEM+10% Fetal Bovine Serum +1% Penicillin/streptomycin). 500 ng each of the deaminnase-nRGN expression vector and guide RNA expression vector were transfected using Lipofectamine® 3000 reagent (Thermo Fisher Scientific) following manufacturer's instructions. For electroporation, cells were electroporated using the Neon® Transfection System (Thermo Fisher Scientific) following manufacturer's instructions.

24-48 hours after lipofection or electroporation, the expression of GFP was determined by microscopically surveying the cells for the presence of GFP+ cells. Following visual inspection, the proportion of GFP+ cells versus GFP− cells may be determined. Fluorescence was observed in mammalian cells expressing each of the deaminase-nRGN fusion proteins, indicating the fusion protein successfully targeted to the GFP-STOP mutation and edited the mutation to restore fluorescence of the GFP protein.

Following microscopic analysis, the cells were lysed in RTPA buffer and the resulting lysate was analyzed on a fluorescence plate reader to determine the fluorescence intensity of GFP (Table 8). A person of skill in the art will appreciate that the cells may be analyzed by flow cytometry or fluorescence activated cell sorting to determine the exact proportions of GFP+ and GFP− cells.

TABLE 8

GFP-STOP assay results

| Deaminase of fusion protein | GFP+ cells detected |
|---|---|
| APG09982 | ++ |
| APG03724 | ++ |
| APG09949 | ++ |
| APG08196 | ++ |
| APG06333 | +++ |
| APG06489 | ++ |
| APG08449 | ++ |
| APG05174 | +++ |
| APG09102 | ++ |
| APG05723 | ++ |

N.D = None Detected;
+ = few GFP+ cells detected;
++ = several GFP+ cells detected;
+++ = many GFP+ cells detected Example 3: Demonstration of a Base Editing in Mammalian Cells The deaminases shown in Table 9 below were produced based on naturally occurring deaminases which were then mutated and selected for adenine deaminase activity in prokaryotic cells.

TABLE 9

Deaminase sequences

| Deaminase | SEQ ID NO. |
|---|---|
| LPG50140 | 399 |
| LPG50141 | 400 |
| LPG50142 | 401 |
| LPG50143 | 402 |
| LPG50144 | 403 |
| LPG50145 | 404 |
| LPG50146 | 405 |
| LPG50147 | 406 |
| LPG50148 | 407 |
| LPG50149 | 408 |
| LPG50150 | 409 |
| LPG50151 | 410 |
| LPG50152 | 411 |
| LPG50153 | 412 |
| LPG50154 | 413 |
| LPG50155 | 414 |
| LPG50156 | 415 |
| LPG50157 | 416 |
| LPG50158 | 417 |
| LPG50159 | 418 |
| LPG50160 | 419 |
| LPG50161 | 420 |
| LPG50162 | 421 |
| LPG50163 | 422 |
| LPG50164 | 423 |
| LPG50165 | 424 |
| LPG50166 | 425 |
| LPG50167 | 426 |
| LPG50168 | 427 |
| LPG50169 | 428 |
| LPG50170 | 429 |
| LPG50171 | 430 |
| LPG50172 | 431 |
| LPG50173 | 432 |
| LPG50174 | 433 |
| LPG50175 | 434 |
| LPG50176 | 435 |
| LPG50177 | 436 |
| LPG50178 | 437 |
| LPG50179 | 438 |
| LPG50180 | 439 |

TABLE 9-continued

Deaminase sequences

| Deaminase | SEQ ID NO. |
|---|---|
| LPG50181 | 440 |
| LPG50182 | 441 |

To determine if the deaminases of Table 9 are able to perform adenine base editing in mammalian cells, each deaminase was operably fused to an RGN nickase to produce a fusion protein. Residues predicted to deactivate the RuvC domain of the RGN APG07433.1 (set forth as SEQ ID NO: 41; described in PCT publication WO 2019/236566, incorporated by reference herein) were identified and the RGN was modified to a nickase variant (nAPG07433.1; SEQ ID NO: 42). A nickase variant of an RGN is referred to herein as "nRGN". It should be understood that any nickase variant of an RGN may be used to produce a fusion protein of the invention.

Deaminase and nRGN nucleotide sequences codon optimized for mammalian expression were synthesized as fusion proteins with an N-terminal nuclear localization tag and cloned into the pTwist CMV (Twist Biosciences) expression plasmid. Each fusion protein comprises, starting at the amino terminus, the SV40 NLS (SEQ ID NO: 43) operably linked at the C-terminal end to 3X FLAG Tag (SEQ ID NO: 44), operably linked at the C-terminal end to a deaminase, operably linked at the C-terminal end to a peptide linker (SEQ ID NO: 442), operably linked at the C-terminal end to an nRGN (for example, nAPG07433.1, which is SEQ ID NO: 42), finally operably linked at the C-terminal end to the nucleoplasmin NLS (SEQ ID NO: 46). The nAPG07433.1 and peptide linker nucleotide sequences codon optimized for mammalian expression are set forth as SEQ ID NOs: 486 and 487, respectively. Table 10 shows the fusion proteins produced and tested for activity. All fusion proteins comprise at least one NLS and a 3X FLAG Tag, as described above.

TABLE 10

Fusion protein sequences with N-terminus SV40 NLS, 3X FLAG Tag and C-terminus Nucleoplasmin NLS

| Fusion Protein | SEQ ID |
|---|---|
| LPG50140-nAPG07433.1 | 488 |
| LPG50141-nAPG07433.1 | 489 |
| LPG50142-nAPG07433.1 | 490 |
| LPG50143-nAPG07433.1 | 491 |
| LPG50144-nAPG07433.1 | 492 |
| LPG50145-nAPG07433.1 | 493 |
| LPG50146-nAPG07433.1 | 494 |
| LPG50147-nAPG07433.1 | 495 |
| LPG50148-nAPG07433.1 | 496 |
| LPG50149-nAPG07433.1 | 497 |
| LPG50150-nAPG07433.1 | 498 |
| LPG50151-nAPG07433.1 | 499 |
| LPG50152-nAPG07433.1 | 500 |
| LPG50153-nAPG07433.1 | 501 |
| LPG50154-nAPG07433.1 | 502 |
| LPG50155-nAPG07433.1 | 503 |
| LPG50156-nAPG07433.1 | 504 |
| LPG50157-nAPG07433.1 | 505 |
| LPG50158-nAPG07433.1 | 506 |
| LPG50159-nAPG07433.1 | 507 |
| LPG50160-nAPG07433.1 | 508 |
| LPG50161-nAPG07433.1 | 509 |
| LPG50162-nAPG07433.1 | 510 |

TABLE 10-continued

Fusion protein sequences with N-terminus SV40 NLS, 3X FLAG Tag and C-terminus Nucleoplasmin NLS

| Fusion Protein | SEQ ID |
|---|---|
| LPG50163-nAPG07433.1 | 511 |
| LPG50164-nAPG07433.1 | 512 |
| LPG50165-nAPG07433.1 | 513 |
| LPG50166-nAPG07433.1 | 514 |
| LPG50167-nAPG07433.1 | 515 |
| LPG50168-nAPG07433.1 | 516 |
| LPG50169-nAPG07433.1 | 517 |
| LPG50170-nAPG07433.1 | 518 |
| LPG50171-nAPG07433.1 | 519 |
| LPG50172-nAPG07433.1 | 520 |
| LPG50173-nAPG07433.1 | 521 |
| LPG50174-nAPG07433.1 | 522 |
| LPG50175-nAPG07433.1 | 523 |
| LPG50176-nAPG07433.1 | 524 |
| LPG50177-nAPG07433.1 | 525 |
| LPG50178-nAPG07433.1 | 526 |
| LPG50179-nAPG07433.1 | 527 |
| LPG50180-nAPG07433.1 | 528 |
| LPG50181-nAPG07433.1 | 529 |
| LPG50182-nAPG07433.1 | 530 |

Expression plasmids comprising an expression cassette encoding for a sgRNA were also produced. Human genomic target sequences and the sgRNA sequences for guiding the fusion proteins to the genomic targets are indicated in Table 11.

TABLE 11

Guide RNA sequences

| sgRNA ID | Target sequence | sgRNA sequence | Forward Primer for amplification | Reverse Primer for amplification |
|---|---|---|---|---|
| SGN000139 | 537 | 531 | 543 | 549 |
| SGN000143 | 538 | 532 | 544 | 550 |
| SGN000186 | 539 | 533 | 545 | 551 |
| SGN000194 | 540 | 534 | 546 | 552 |
| SGN000930 | 541 | 535 | 547 | 553 |
| SGN001681 | 542 | 536 | 548 | 554 |

500 ng of plasmid comprising an expression cassette comprising a coding sequence for a fusion protein shown in Table 10 and 500 ng of plasmid comprising an expression cassette encoding for an sgRNA shown in Table 11 were co-transfected into HEK293FT cells at 75-90% confluency in 24-well plates using Lipofectamine 2000 reagent (Life Technologies). Cells were then incubated at 37° C. for 72 h. Following incubation, genomic DNA was then extracted using NucleoSpin 96 Tissue (Macherey-Nagel) following the manufacturer's protocol. The genomic region flanking the targeted genomic site was PCR amplified using the primers in Table 11 and products were purified using ZR-96 DNA Clean and Concentrator (Zymo Research) following the manufacturer's protocol. The purified PCR products underwent Next Generation Sequencing on Illumina MiSeq. Typically, 100,000 of 250 bp paired-end reads (2×100,000 reads) are generated per amplicon. The reads were analyzed using CRISPResso (Pinello, et al. 2016 Nature Biotech, 34:695-697) to calculate the rates of editing. Output alignments were analyzed for IN4DEL formation or introduction of specific adenine mutations.

Table 12 shows all of the adenine base editing for each adenine deaminase fusion in Table 10 and a guide RNA from Table 12. Tables 13-27 show the specific nucleotide mutation profile for select exemplary samples. The editing rate for adenines within or proximal to the target sequence is indicated. "A5" indicates, for example, an adenine at position 5 of the target sequence. The position of each nucleotide in the target sequence was determined by numbering the first nucleotide in the target sequence closest to the PAM (which is 3' of the target for APG07433.1) as position 1, and the position number increases in the 5' direction away from the PAM sequence. The tables also show which nucleotide the adenine was changed to, and at what rate. For example, Table 13 shows that for the LPG50148-nAPG07433.1 fusion protein, the adenine at position 13 was mutated to a guanine at a rate of 9.7%.

TABLE 12

Estimate of base editing rates for each adenine deaminase

| Deaminase | SGN | % Mutated Reads | Deaminase | SGN | % Mutated Reads |
|---|---|---|---|---|---|
| LPG50140 | SGN001681 | 30.01% | LPG50161 | SGN000930 | 0% |
| LPG50140 | SGN000139 | 6.91% | LPG50162 | SGN001681 | 21.73% |
| LPG50140 | SGN000143 | 16.09% | LPG50162 | SGN000139 | 2% |
| LPG50140 | SGN000186 | 18.76% | LPG50162 | SGN000143 | 5% |
| LPG50140 | SGN000194 | 9.77% | LPG50162 | SGN000186 | 14% |
| LPG50140 | SGN000930 | 3.51% | LPG50162 | SGN000194 | 6% |
| LPG50141 | SGN001681 | 21.37% | LPG50162 | SGN000930 | 5% |
| LPG50141 | SGN000139 | 2.43% | LPG50163 | SGN001681 | 12.80% |
| LPG50141 | SGN000143 | 6.93% | LPG50163 | SGN000139 | 0% |
| LPG50141 | SGN000186 | 9.79% | LPG50163 | SGN000143 | 2% |
| LPG50141 | SGN000194 | 4.45% | LPG50163 | SGN000186 | 10% |
| LPG50141 | SGN000930 | 5.29% | LPG50163 | SGN000194 | 4% |
| LPG50142 | SGN001681 | 34.19% | LPG50163 | SGN000930 | 3% |
| LPG50142 | SGN000139 | 3.10% | LPG50164 | SGN001681 | 4.28% |
| LPG50142 | SGN000143 | 8.67% | LPG50164 | SGN000139 | 0% |
| LPG50142 | SGN000186 | 14.12% | LPG50164 | SGN000143 | 3.36% |
| LPG50142 | SGN000194 | 10.04% | LPG50164 | SGN000186 | 7.38% |
| LPG50142 | SGN000930 | 6.78% | LPG50164 | SGN000194 | 2.73% |
| LPG50143 | SGN001681 | 20.62% | LPG50164 | SGN000930 | 1.47% |
| LPG50143 | SGN000139 | 1.99% | LPG50165 | SGN001681 | 25.66% |
| LPG50143 | SGN000143 | 6.09% | LPG50165 | SGN000139 | 2% |
| LPG50143 | SGN000186 | 10.58% | LPG50165 | SGN000143 | 5.11% |
| LPG50143 | SGN000194 | 5.60% | LPG50165 | SGN000186 | 9.88% |
| LPG50143 | SGN000930 | 3.98% | LPG50165 | SGN000194 | 3.97% |
| LPG50144 | SGN001681 | 28.26% | LPG50165 | SGN000930 | 3.18% |
| LPG50144 | SGN000139 | 3.55% | LPG50166 | SGN000139 | 2% |
| LPG50144 | SGN000143 | 5.77% | LPG50166 | SGN000143 | 4% |
| LPG50144 | SGN000186 | 12.22% | LPG50166 | SGN000186 | 8% |
| LPG50144 | SGN000194 | 6.40% | LPG50166 | SGN000194 | 2% |
| LPG50144 | SGN000930 | 5.81% | LPG50166 | SGN000930 | 4% |
| LPG50145 | SGN001681 | 29.23% | LPG50167 | SGN001681 | 20.56% |
| LPG50145 | SGN000139 | 2.53% | LPG50167 | SGN000139 | 2% |
| LPG50145 | SGN000143 | 3.75% | LPG50167 | SGN000143 | 4% |
| LPG50145 | SGN000186 | 9.93% | LPG50167 | SGN000186 | 8% |
| LPG50145 | SGN000194 | 3.98% | LPG50167 | SGN000194 | 5% |
| LPG50145 | SGN000930 | 3.84% | LPG50167 | SGN000930 | 4% |
| LPG50146 | SGN001681 | 32.53% | LPG50168 | SGN001681 | 13.81% |
| LPG50146 | SGN000139 | 5.95% | LPG50168 | SGN000139 | 2% |
| LPG50146 | SGN000143 | 11.30% | LPG50168 | SGN000143 | 3% |
| LPG50146 | SGN000186 | 17.78% | LPG50168 | SGN000186 | 7% |
| LPG50146 | SGN000194 | 7.38% | LPG50168 | SGN000194 | 2% |
| LPG50146 | SGN000930 | 7.13% | LPG50168 | SGN000930 | 3% |
| LPG50147 | SGN001681 | 49.10% | LPG50169 | SGN001681 | 25.73% |
| LPG50147 | SGN000139 | 3.26% | LPG50169 | SGN000139 | 4% |
| LPG50147 | SGN000143 | 8.59% | LPG50169 | SGN000143 | 8% |
| LPG50147 | SGN000186 | 12.61% | LPG50169 | SGN000186 | 13% |
| LPG50147 | SGN000194 | 8.80% | LPG50169 | SGN000194 | 9% |
| LPG50147 | SGN000930 | 4.96% | LPG50169 | SGN000930 | 8% |
| LPG50148 | SGN001681 | 49.39% | LPG50170 | SGN001681 | 12.87% |
| LPG50148 | SGN000139 | 10.80% | LPG50170 | SGN000139 | 1.50% |
| LPG50148 | SGN000143 | 12.49% | LPG50170 | SGN000143 | 3.14% |
| LPG50148 | SGN000186 | 32.65% | LPG50170 | SGN000186 | 12.16% |
| LPG50148 | SGN000194 | 16.60% | LPG50170 | SGN000194 | 2.76% |
| LPG50148 | SGN000930 | 7.61% | LPG50170 | SGN000930 | 4.10% |
| LPG50149 | SGN001681 | 27.62% | LPG50171 | SGN001681 | 27.16% |
| LPG50149 | SGN000139 | 2.83% | LPG50171 | SGN000139 | 1.75% |

TABLE 12-continued

Estimate of base editing rates for each adenine deaminase

| Deaminase | SGN | % Mutated Reads | Deaminase | SGN | % Mutated Reads |
|---|---|---|---|---|---|
| LPG50149 | SGN000143 | 9.33% | LPG50171 | SGN000143 | 6.14% |
| LPG50149 | SGN000186 | 22.12% | LPG50171 | SGN000186 | 12.65% |
| LPG50149 | SGN000194 | 7.94% | LPG50171 | SGN000194 | 5.60% |
| LPG50149 | SGN000930 | 7.06% | LPG50171 | SGN000930 | 4.55% |
| LPG50150 | SGN001681 | 28.46% | LPG50172 | SGN001681 | 1.78% |
| LPG50150 | SGN000139 | 3.06% | LPG50172 | SGN000139 | 0% |
| LPG50150 | SGN000143 | 6.00% | LPG50172 | SGN000143 | 0% |
| LPG50150 | SGN000186 | 23.67% | LPG50172 | SGN000186 | 0% |
| LPG50150 | SGN000194 | 9.47% | LPG50172 | SGN000194 | 0% |
| LPG50150 | SGN000930 | 5.41% | LPG50172 | SGN000930 | 0% |
| LPG50151 | SGN001681 | 3.01% | LPG50173 | SGN001681 | 12.64% |
| LPG50151 | SGN000139 | 0% | LPG50173 | SGN000139 | 1.00% |
| LPG50151 | SGN000143 | 1.53% | LPG50173 | SGN000143 | 3.23% |
| LPG50151 | SGN000186 | 7.76% | LPG50173 | SGN000186 | 7.88% |
| LPG50151 | SGN000194 | 1.43% | LPG50173 | SGN000194 | 2.66% |
| LPG50151 | SGN000930 | 0% | LPG50173 | SGN000930 | 1.77% |
| LPG50152 | SGN001681 | 26.06% | LPG50174 | SGN001681 | 14.11% |
| LPG50152 | SGN000139 | 2% | LPG50174 | SGN000139 | 0% |
| LPG50152 | SGN000143 | 3% | LPG50174 | SGN000143 | 3% |
| LPG50152 | SGN000186 | 18% | LPG50174 | SGN000186 | 8% |
| LPG50152 | SGN000194 | 3% | LPG50174 | SGN000194 | 2% |
| LPG50152 | SGN000930 | 6% | LPG50174 | SGN000930 | 3% |
| LPG50153 | SGN001681 | 1.12% | LPG50175 | SGN001681 | 22.29% |
| LPG50153 | SGN000139 | 0% | LPG50175 | SGN000139 | 4% |
| LPG50153 | SGN000143 | 0% | LPG50175 | SGN000143 | 9% |
| LPG50153 | SGN000186 | 0% | LPG50175 | SGN000186 | 14% |
| LPG50153 | SGN000194 | 1% | LPG50175 | SGN000194 | 13% |
| LPG50153 | SGN000930 | 0% | LPG50175 | SGN000930 | 5% |
| LPG50154 | SGN001681 | 2.26% | LPG50176 | SGN001681 | 9.52% |
| LPG50154 | SGN000139 | 0% | LPG50176 | SGN000139 | 0% |
| LPG50154 | SGN000143 | 0% | LPG50176 | SGN000143 | 2% |
| LPG50154 | SGN000186 | 0% | LPG50176 | SGN000186 | 7% |
| LPG50154 | SGN000194 | 1% | LPG50176 | SGN000194 | 2% |
| LPG50154 | SGN000930 | 0% | LPG50176 | SGN000930 | 0% |
| LPG50155 | SGN001681 | 14.91% | LPG50177 | SGN001681 | 7.98% |
| LPG50155 | SGN000139 | 2% | LPG50177 | SGN000139 | 2% |
| LPG50155 | SGN000143 | 4% | LPG50177 | SGN000143 | 4% |
| LPG50155 | SGN000186 | 17% | LPG50177 | SGN000186 | 11% |
| LPG50155 | SGN000194 | 7% | LPG50177 | SGN000194 | 3% |
| LPG50155 | SGN000930 | 5% | LPG50177 | SGN000930 | 9% |
| LPG50156 | SGN001681 | 11.19% | LPG50178 | SGN000139 | 2.00% |
| LPG50156 | SGN000139 | 3.79% | LPG50178 | SGN000143 | 6.19% |
| LPG50156 | SGN000143 | 6.44% | LPG50178 | SGN000186 | 12.94% |
| LPG50156 | SGN000186 | 12.69% | LPG50178 | SGN000194 | 5.51% |
| LPG50156 | SGN000194 | 6.87% | LPG50178 | SGN000930 | 3.95% |
| LPG50156 | SGN000930 | 4.10% | LPG50179 | SGN001681 | 23.35% |
| LPG50157 | SGN001681 | 20.66% | LPG50179 | SGN000139 | 2.00% |
| LPG50157 | SGN000139 | 3.37% | LPG50179 | SGN000143 | 5.08% |
| LPG50157 | SGN000143 | 6.91% | LPG50179 | SGN000186 | 12.50% |
| LPG50157 | SGN000186 | 12.15% | LPG50179 | SGN000194 | 4.49% |
| LPG50157 | SGN000194 | 9.98% | LPG50179 | SGN000930 | 4.62% |
| LPG50157 | SGN000930 | 5.55% | LPG50180 | SGN001681 | 1.80% |
| LPG50158 | SGN001681 | 1.56% | LPG50180 | SGN000139 | 0% |
| LPG50158 | SGN000139 | 0% | LPG50180 | SGN000143 | 0% |
| LPG50158 | SGN000143 | 1.15% | LPG50180 | SGN000186 | 0% |
| LPG50158 | SGN000186 | 4.91% | LPG50180 | SGN000194 | 0% |
| LPG50158 | SGN000194 | 1.73% | LPG50180 | SGN000930 | 0% |
| LPG50158 | SGN000930 | 0% | LPG50181 | SGN001681 | 7.93% |
| LPG50159 | SGN001681 | 5.85% | LPG50181 | SGN000139 | 2.88% |
| LPG50159 | SGN000139 | 0% | LPG50181 | SGN000143 | 3.78% |
| LPG50159 | SGN000143 | 2.78% | LPG50181 | SGN000186 | 12.56% |
| LPG50159 | SGN000186 | 6.99% | LPG50181 | SGN000194 | 3.39% |
| LPG50159 | SGN000194 | 4.40% | LPG50181 | SGN000930 | 1.20% |
| LPG50159 | SGN000930 | 2.60% | LPG50182 | SGN001681 | 16.49% |
| LPG50160 | SGN001681 | 22.20% | LPG50182 | SGN000139 | 1.00% |
| LPG50160 | SGN000139 | 4% | LPG50182 | SGN000143 | 5% |
| LPG50160 | SGN000143 | 8% | LPG50182 | SGN000186 | 9% |
| LPG50160 | SGN000186 | 16% | LPG50182 | SGN000194 | 6% |
| LPG50160 | SGN000194 | 5% | LPG50182 | SGN000930 | 3% |
| LPG50160 | SGN000930 | 6% | | | |
| LPG50161 | SGN001681 | 1.47% | | | |

TABLE 12-continued

Estimate of base editing rates for each adenine deaminase

| Deaminase | SGN | % Mutated Reads | Deaminase | SGN | % Mutated Reads |
|---|---|---|---|---|---|
| LPG50161 | SGN000139 | 0% | | | |
| LPG50161 | SGN000143 | 0% | | | |
| LPG50161 | SGN000186 | 0% | | | |
| LPG50161 | SGN000194 | 0% | | | |

TABLE 13

A > N Editing Rate using deaminase LPG50148 and guide SGN000139

| | | \multicolumn{5}{c}{SGN000139} |
|---|---|---|---|---|---|---|
| | | A5 | A12 | A13 | A20 | A22 |
| LPG50148 | C | 0 | 0 | 0 | 0.1 | 0 |
| | G | 0 | 2.2 | 9.7 | 0.2 | 0 |
| | T | 0 | 0 | 0 | 0 | 0 |

LPG50140, LPG50146, and LPG50148 showed detectable A>G conversion at positions A12 and A13. LPG50148 showed over 9% editing at position A13.

TABLE 14

A > N Editing Rate using deaminase LPG50148 and guide SGN000143

| | | SGN000143 | | | | | | | |
|---|---|---|---|---|---|---|---|---|---|
| | | A1 | A4 | A6 | A9 | A11 | A14 | A19 | A30 |
| LPG50148 | C | 0 | 0 | 0 | 0 | 0 | 0 | 0 | 0 |
| | G | 0 | 0 | 0.1 | 1.2 | 11 | 6.7 | 0.1 | 0 |
| | T | 0 | 0 | 0 | 0 | 0 | 0 | 0 | 0 |

LPG50140, LPG50146, and LPG50148 showed detectable A>G conversion at positions A9, A11 and A14. LPG50148 showed over 11% editing at position A11.

TABLE 15

A > N Editing Rate using deaminase LPG50148 and guide SGN000186

| | | SGN000186 | | | | | | |
|---|---|---|---|---|---|---|---|---|
| | | A9 | A16 | A18 | A22 | A25 | A28 | A30 |
| LPG50148 | C | 0 | 0 | 0 | 0 | 0.4 | 0 | 0 |
| | G | 23.7 | 29.2 | 4.1 | 0.2 | 0 | 0 | 0 |
| | T | 0 | 0 | 0 | 0 | 0 | 0 | 0 |

LPG50140, LPG50146, and LPG50148 showed detectable A>G conversion at positions A9, A16 and A18. LPG50148 showed over 23% editing at positions A9 and A16.

TABLE 16

A > N Editing Rate using deaminase LPG50148 and guide SGN000194

| | | SGN000194 | | | | | | |
|---|---|---|---|---|---|---|---|---|
| | | A6 | A10 | A13 | A15 | A21 | A23 | A26 | A27 |
| LPG50148 | C | 0 | 0 | 0 | 0 | 0 | 0 | 0 | 0 |
| | G | 0.3 | 5.3 | 13 | 14 | 0 | 0 | 0 | 0 |
| | T | 0 | 0 | 0 | 0 | 0 | 0 | 0 | 0 |

LPG50140, LPG50146, and LPG50148 showed detectable A>G conversion at positions A13 and A15. LPG50148 showed over 12% editing at positions A13 and A15.

TABLE 17

A > N Editing Rate using deaminase LPG50148 and guide SGN000930

| | | SGN000930 | | | | | | | | | | | | | | | |
|---|---|---|---|---|---|---|---|---|---|---|---|---|---|---|---|---|---|
| | | A2 | A4 | A5 | A8 | A9 | A10 | A14 | A15 | A16 | A20 | A21 | A23 | A24 | A26 | A27 | A29 | A30 |
| LPG50148 | C | 0 | 0 | 0 | 0 | 0 | 0 | 0 | 0 | 0 | 0 | 0 | 0 | 0 | 0 | 0 | 0 | 0 |
| | G | 0 | 0 | 0 | 0 | 0.2 | 2 | 2.2 | 1.1 | 2.2 | 2.2 | 2.5 | 0 | 0 | 0 | 0 | 0 | 0 |
| | T | 0 | 0 | 0 | 0 | 0 | 0 | 0 | 0 | 0 | 0 | 0 | 0 | 0 | 0 | 0 | 0 | 0 |

LPG50140, LPG50146, and LPG50148 showed detectable A>G conversion at positions A10, A14, A15, A16, A20 and A21. LPG50148 showed over 2% editing at positions A10, A14, A16, A20 and A21.

TABLE 18

A > N Editing Rate using deaminase LPG50146 and guide SGN000139

| | | SGN000139 | | | | |
|---|---|---|---|---|---|---|
| | | A5 | A12 | A13 | A20 | A22 |
| LPG50146 | C | 0 | 0 | 0 | 0.4 | 0.1 |
| | G | 0 | 2.1 | 4.1 | 0 | 0 |
| | T | 0 | 0 | 0 | 0 | 0 |

LPG50140, LPG50146, and LPG50148 showed detectable A>G conversion at positions A12 and A13. LPG50146 showed over 4% editing at position A13.

TABLE 19

A > N Editing Rate using deaminase LPG50146 and guide SGN000143

| | | \multicolumn{8}{c}{SGN000143} | | | | | | | |
|---|---|---|---|---|---|---|---|---|---|
| | | A1 | A4 | A6 | A9 | A11 | A14 | A19 | A30 |
| LPG50146 | C | 0 | 0 | 0 | 0 | 0 | 0 | 0 | 0 |
| | G | 0 | 0 | 0 | 0.8 | 8.4 | 5 | 0 | 0 |
| | T | 0 | 0 | 0 | 0 | 0 | 0 | 0 | 0 |

LPG50140, LPG50146, and LPG50148 showed detectable A>G conversion at positions A9, A11 and A14. LPG50146 showed over 8% editing at position A11.

TABLE 20

A > N Editing Rate using deaminase LPG50146 and guide SGN000186

| | | SGN000186 | | | | | | |
|---|---|---|---|---|---|---|---|---|
| | | A9 | A16 | A18 | A22 | A25 | A28 | A30 |
| LPG50146 | C | 0 | 0 | 0 | 0 | 0.2 | 0 | 0 |
| | G | 7.4 | 13.4 | 3.1 | 0.1 | 0 | 0 | 0 |
| | T | 0 | 0 | 0 | 0 | 0 | 0 | 0 |

LPG50140, LPG50146, and LPG50148 showed detectable A>G conversion at positions A9, A16 and A18. LPG50146 showed over 13% editing at position A16.

TABLE 21

A > N Editing Rate using deaminase LPG50146 and guide SGN000194

| | | SGN000194 | | | | | | |
|---|---|---|---|---|---|---|---|---|
| | | A6 | A10 | A13 | A15 | A21 | A23 | A26 | A27 |
| LPG50146 | C | 0 | 0 | 0 | 0 | 0 | 0 | 0 | 0 |
| | G | 0 | 1.8 | 3.2 | 4.5 | 0 | 0 | 0 | 0 |
| | T | 0 | 0 | 0 | 0 | 0 | 0 | 0 | 0 |

LPG50140, LPG50146, and LPG50148 showed detectable A>G conversion at positions A13 and A15. LPG50146 showed over 3% editing at positions A13 and A15.

TABLE 22

A > N Editing Rate using deaminase LPG50146 and guide SGN000930

| | | SGN000930 | | | | | | | | | | | | | | | |
|---|---|---|---|---|---|---|---|---|---|---|---|---|---|---|---|---|---|
| | | A2 | A4 | A5 | A8 | A9 | A10 | A14 | A15 | A16 | A20 | A21 | A23 | A24 | A26 | A27 | A29 | A30 |
| LPG50146 | C | 0 | 0 | 0 | 0 | 0 | 0 | 0 | 0 | 0 | 0 | 0 | 0 | 0 | 0 | 0 | 0 | 0 |
| | G | 0 | 0 | 0 | 0.1 | 0.1 | 0.7 | 2.9 | 2.6 | 2.4 | 1 | 0.8 | 0 | 0 | 0 | 0 | 0 | 0 |
| | T | 0 | 0 | 0 | 0 | 0 | 0 | 0 | 0 | 0 | 0 | 0 | 0 | 0 | 0 | 0 | 0 | 0 |

LPG50140, LPG50146, and LPG50148 showed detectable A>G conversion at positions A10, A14, A15, A16, A20 and A21. LPG50146 showed over 2% editing at positions A14 and A16.

TABLE 23

A > N Editing Rate using deaminase LPG50140 and guide SGN000139

| | | SGN000139 | | | | |
|---|---|---|---|---|---|---|
| | | A5 | A12 | A13 | A20 | A22 |
| LPG50140 | C | 0 | 0 | 0 | 0.4 | 0 |
| | G | 0 | 0.5 | 5.5 | 0 | 0 |
| | T | 0 | 0 | 0 | 0 | 0 |

LPG50140, LPG50146, and LPG50148 showed detectable A>G conversion at positions A12 and A13. LPG50140 showed over 5% editing at position A13.

TABLE 24

A > N Editing Rate using deaminase LPG50140 and guide SGN000143

| | | SGN000143 | | | | | | | |
|---|---|---|---|---|---|---|---|---|---|
| | | A1 | A4 | A6 | A9 | A11 | A14 | A19 | A30 |
| LPG50140 | C | 0 | 0 | 0 | 0 | 0 | 0 | 0 | 0 |
| | G | 0 | 0 | 0 | 1.2 | 14 | 5.6 | 0 | 0 |
| | T | 0 | 0 | 0 | 0 | 0 | 0 | 0 | 0 |

LPG50140, LPG50146, and LPG50148 showed detectable A>G conversion at positions A9, A11 and A14. LPG50140 showed 14% editing at position A11.

TABLE 25

A > N Editing Rate using deaminase LPG50140 and guide SGN000186

| | | SGN000186 | | | | | | |
|---|---|---|---|---|---|---|---|---|
| | | A9 | A16 | A18 | A22 | A25 | A28 | A30 |
| LPG50140 | C | 0 | 0 | 0 | 0 | 0.2 | 0 | 0 |
| | G | 9.4 | 15 | 1.7 | 0 | 0 | 0 | 0 |
| | T | 0 | 0 | 0 | 0 | 0 | 0 | 0 |

LPG50140, LPG50146, and LPG50148 showed detectable A>G conversion at positions A9, A16 and A18. LPG50140 showed over 9% editing at positions A9 and A16.

TABLE 26

A > N Editing Rate using deaminase LPG50140 and guide SGN000194

| | | \multicolumn{8}{c}{SGN000194} | | | | | | | |
|---|---|---|---|---|---|---|---|---|---|
| | | A6 | A10 | A13 | A15 | A21 | A23 | A26 | A27 |
| LPG50140 | C | 0 | 0 | 0 | 0 | 0 | 0 | 0 | 0 |
| | G | 0 | 0 | 6.7 | 7.8 | 0 | 0 | 0 | 0 |
| | T | 0 | 0 | 0 | 0 | 0 | 0 | 0 | 0 |

LPG50140, LPG50146, and LPG50148 showed detectable A>G conversion at positions A13 and A15. LPG50140 showed over 6% editing at positions A13 and A15.

TABLE 27

A > N Editing Rate using deaminase LPG50140 and guide SGN000930

| | | A2 | A4 | A5 | A8 | A9 | A10 | A14 | A15 | A16 | A20 | A21 | A23 | A24 | A26 | A27 | A29 | A30 |
|---|---|---|---|---|---|---|---|---|---|---|---|---|---|---|---|---|---|---|
| LPG50140 | C | 0 | 0 | 0 | 0 | 0 | 0 | 0 | 0 | 0 | 0 | 0 | 0 | 0 | 0 | 0 | 0 | 0 |
| | G | 0 | 0 | 0 | 0 | 0 | 0.4 | 1.4 | 0.6 | 1.1 | 0.4 | 0.5 | 0 | 0 | 0 | 0 | 0 | 0 |
| | T | 0 | 0 | 0 | 0 | 0 | 0 | 0 | 0 | 0 | 0 | 0 | 0 | 0 | 0 | 0 | 0 | 0 |

LPG50140, LPG50146, and LPG50148 showed detectable A>G conversion at positions A10, A14, A15, A16, A20 and A21. LPG50140 showed over 10% editing at positions A14 and A16.

Table 28 below shows the average editing rates for LPG50148-nAPG07433.1 at several guides tested in HEK293T cells by lipofection of two plasmids. The base editor was encoded on one plasmid and the guide RNA was encoded on a second plasmid. Total substitution rate in the target is used to measure the base editing rate.

TABLE 28

Average Editing Rate for LPG50148-nAPG07433.1

| Gene | SGN | Average % Substitution rate | N |
|---|---|---|---|
| Gene A | SGN000139 | 10.8 | 1 |
| Gene A | SGN000143 | 29.65 | 2 |
| Gene B | SGN000487 | 34.68 | 2 |
| Gene B | SGN000488 | 39.94 | 1 |
| Gene B | SGN001061 | 9.18 | 2 |
| Gene B | SGN001062 | 32.77 | 1 |
| Gene B | SGN001270 | 8.34 | 3 |
| Gene B | SGN001946 | 5.1 | 1 |
| Gene B | SGN001947 | 16.43 | 1 |
| Gene B | SGN001948 | 0.46 | 1 |
| Gene B | SGN001949 | 1.44 | 1 |
| Gene B | SGN001950 | 10.96 | 1 |
| Gene B | SGN001951 | 5.38 | 1 |
| Gene B | SGN001952 | 6.29 | 1 |
| Gene B | SGN001953 | 5.28 | 1 |
| Gene B | SGN001954 | 7.95 | 1 |
| Gene B | SGN001955 | 7.83 | 1 |
| Gene B | SGN001956 | 4.78 | 1 |
| Gene B | SGN001959 | 1.43 | 1 |
| Gene B | SGN001960 | 17.4 | 1 |
| Gene B | SGN001961 | 1.46 | 1 |
| Gene B | SGN001962 | 1.62 | 1 |
| Gene B | SGN001963 | 11.31 | 1 |
| Gene B | SGN001964 | 2.03 | 1 |
| Gene B | SGN001965 | 9.3 | 1 |
| Gene B | SGN001966 | 1.51 | 1 |
| CFTR | SGN001101 | 17.06 | 1 |
| Gene D | SGN001196 | 14.58 | 1 |
| Gene D | SGN001199 | 42.05 | 1 |
| Gene E | SGN001681 | 48.85 | 1 |
| Gene F | SGN000169 | 55.13 | 2 |
| Gene F | SGN000173 | 47.13 | 1 |
| Gene G | SGN000412 | 16.58 | 1 |
| Gene G | SGN000414 | 14.5 | 2 |
| Gene G | SGN001259 | 24.16 | 1 |
| Gene G | SGN001274 | 10.45 | 2 |
| Gene G | SGN001275 | 5.25 | 1 |
| Gene H | SGN000186 | 32.65 | 1 |
| Gene I | SGN000754 | 30.76 | 1 |
| Gene I | SGN000909 | 21.57 | 2 |
| Gene I | SGN000927 | 3.8 | 1 |
| Gene I | SGN000928 | 28.77 | 1 |
| Gene I | SGN000929 | 17.58 | 2 |
| Gene I | SGN000949 | 26.43 | 1 |
| Gene I | SGN001268 | 16.64 | 2 |
| Gene I | SGN001269 | 6.42 | 1 |
| Gene I | SGN001967 | 1.45 | 1 |
| Gene I | SGN001968 | 5.61 | 1 |
| Gene I | SGN001973 | 5.14 | 1 |
| Gene I | SGN001975 | 0.16 | 1 |
| Gene I | SGN001976 | 0.62 | 1 |
| Gene I | SGN001977 | 0.65 | 1 |
| Gene I | SGN001978 | 3.09 | 1 |
| Gene I | SGN001981 | 2.34 | 1 |

LPG50148-nAPG07433.1 shows editing at many different guides across the genome.

Table 29 shows the editing rates of adenine bases in each guide from LPG50148-nAPG07433.1. Only the adenine positions are shown below. The rate of adenine conversion is the average of multiple experiments when appropriate.

TABLE 29

Editing rate of A nucleotides in mammalian cells for top 10 guides

| SGN | A1 | A3 | A4 | A5 | A6 | A7 | A8 | A9 | A10 | A11 | A13 |
|---|---|---|---|---|---|---|---|---|---|---|---|
| SGN001681 | | | | | 13 | | | | 47 | | |
| SGN000169 | | | | 0.2 | | 1.3 | 17 | | | 22 | |
| SGN001199 | | | | | | 3.5 | | | | | 42 |
| SGN000186 | | | | | | | | 24 | | | |
| SGN000754 | | | | 0 | | 0 | | 1.3 | | | |
| SGN000143 | 0 | | 0 | | 0.4 | | | 4.4 | | 27 | |
| SGN000928 | 0.3 | | | 0.2 | 0.3 | | 6.1 | | | | |
| SGN000487 | 0.2 | 0.2 | | | | | | | 12 | | |
| SGN001259 | | | 0 | | | | | | 12 | | |
| SGN001062 | | | 0 | | 0.7 | | | 0 | | | |

Editing rate of A nucleotides in mammalian cells for top 10 guides

| SGN | A14 | A15 | A16 | A17 | A18 | A19 | A20 | A21 | A22 | A24 | A25 |
|---|---|---|---|---|---|---|---|---|---|---|---|
| SGN001681 | | | | | | | | | | | |
| SGN000169 | | | | 43 | | 11 | | | 1.7 | | |
| SGN001199 | | | | | | | | | | | |
| SGN000186 | | | 29 | | 4.1 | | | | 0.2 | | 0.4 |
| SGN000754 | 6.1 | | | 29 | | | | | | | |
| SGN000143 | 17 | | | | | 0.3 | | | | | |
| SGN000928 | | | | | | 26 | | | | | |
| SGN000487 | 25 | | 8.7 | | 7.6 | | | 14 | | | |
| SGN001259 | | | | 16 | | | | | | 1 | |
| SGN001062 | | 10 | | | 5.8 | | 13 | | 2.4 | 0.1 | 0 |

LPG50148-nAPG07433.1 shows adenine base editing in positions 6 through 21 in the target region depending on the guide RNA used. Editing rates vary by guide RNAs used.

Example 4: Correction of Class I Cystic Fibrosis Nonsense Mutations

Example 4.1: Identification of RGNs and Guide RNAs

Cystic fibrosis is generally caused by deleterious mutations in the CFTR gene (SEQ ID NO: 51). Six of the most common nonsense mutations are G542X, W1282X, R553X, R1162X, E60X, R785X, and Q493X. Each of these stop mutations could be edited to restore a coding codon by an RGN-deaminase fusion protein described herein. To target each mutation, the following must be determined: 1) an RGN which has a PAM recognition site proximal to the nonsense mutation; and 2) a guide RNA which optimally targets the RGN-deaminase fusion protein to the target DNA. Table 30 below shows nickase variants of RGNs which possess PAMs that are proximal to each of the six nonsense mutations and the number of guide RNAs which can be used for each RGN. Table 31 describes the genetic loci for each guide RNA. The PAM recognition site for each genetic locus is underlined. The target sequence for the guide RNA and the guide RNA sequence itself are also indicated.

TABLE 30

RGN nickases and number of guide RNAs for nonsense mutations in CFTR

| RGN nickase | SEQ ID NO. for RGN nickase | E60X | G542X | Q493X | R1162X | R553X | W1282X |
|---|---|---|---|---|---|---|---|
| nAPG00969 | 52 | | 2 | | 2 | 2 | |
| nAPG07433.1 | 42 | 1 | | | | 3 | 1 |
| nAPG06646 | 53 | 6 | 4 | 2 | 3 | 7 | 4 |
| nAPG09748 | 54 | 1 | 1 | 4 | | | 1 |
| nAPG09882 | 55 | 4 | 3 | 5 | 5 | 3 | 5 |
| nAPG03850 | 56 | 2 | 2 | 1 | 3 | 3 | 4 |
| nAPG07553 | 57 | 1 | 1 | 1 | 1 | 1 | 2 |
| nAPG05586 | 58 | 1 | 1 | | 3 | | 1 |
| nAPG01604 | 59 | | | 2 | 1 | | 2 |

TABLE 31 guide RNAs for nonsense mutations in CFTR

| Guide ID | Genetic locus | Genetic locus (SEQ ID NO.) | Target (SEQ ID NO.) | gRNA (SEQ ID NO.) |
|---|---|---|---|---|
| E60X nAPG06646 Target 1 | AATGAGTTTAGGATTTTCTTTGAAGCCAGCTATCTATCCCATTCTCTGCAAAAGAATAAAAAGT | 62 | 80 | 98 |
| E60X nAPG06646 Target 2 | ATTAATGAGTTTAGGATTTTTCTTTGAAGCCAGCTATCTATCCCATTCTCTGCAAAAGAATAAAA | 63 | 81 | 99 |
| E60X nAPG06646 Target 3 | GCATTAATGAGTTTAGGATTTTTCTTTGAAGCCAGCTATCTATCCCATTCTCTGCAAAAGAATAA | 64 | 82 | 100 |
| E60X nAPG06646 Target 4 | AAGGGCATTAATGAGTTTAGGATTTTTCTTTGAAGCCAGCTATCTATCCCATTCTCTGCAAAAGA | 65 | 83 | 101 |
| E60X nAPG06646 Target 5 | GAAGGGCATTAATGAGTTTAGGATTTTTCTTTGAAGCCAGCTATCTATCCCATTCTCTGCAAAAG | 66 | 84 | 102 |
| E60X nAPG06646 Target 6 | CGAAGGGCATTAATGAGTTTAGGATTTTTCTTTGAAGCCAGCTATCTATCCCATTCTCTGCAAAA | 67 | 85 | 103 |
| E60X nAPG09882 Target 1 | GAGTTTAGGATTTTTCTTTGAAGCCAGCTATCTATCCCATTCTCTGCAAAAGAATAAAAAGTGGG | 68 | 86 | 104 |
| E60X nAPG09882 Target 2 | TGAGTTTAGGATTTTTCTTTGAAGCCAGCTATCTATCCCATTCTCTGCAAAAGAATAAAAAGTGG | 69 | 87 | 105 |
| E60X nAPG09882 Target 3 | ATGAGTTTAGGATTTTTCTTTGAAGCCAGCTATCTATCCCATTCTCTGCAAAAGAATAAAAAGTG | 70 | 88 | 106 |
| E60X nAPG09882 Target 4 | AGGGCATTAATGAGTTTAGGATTTTTCTTTGAAGCCAGCTATCTATCCCATTCTCTGCAAAAGAA | 71 | 89 | 107 |
| E60X nAPG00969 Target 1 | GTTTAGGATTTTTCTTTGAAGCCAGCTATCTATCCCATTCTCTGCAAAAGAATAAAAAGTGGGAC | 72 | 90 | 108 |
| E60X nAPG00969 Target 2 | AGTTTAGGATTTTTCTTTGAAGCCAGCTATCTATCCCATTCTCTGCAAAAGAATAAAAAGTGGGA | 73 | 91 | 109 |
| E60X nAPG03850 Target 1 | GGATTTTTCTTTGAAGCCAGCTATCTATCCCATTCTCTGCAAAAGAATAAAAAGTGGGAC | 74 | 92 | 110 |
| E60X nAPG03850 Target 2 | AGTTTAGGATTTTTCTTTGAAGCCAGCTATCTATCCCATTCTCTGCAAAAGAATAAAAAG | 75 | 93 | 111 |
| E60X nAPG07433.1 Target 1 | GAAGGGCATTAATGAGTTTAGGATTTTTCTTTGAAGCCAGCTATCTATCCCATTCTCTGCAAAAG | 76 | 94 | 112 |
| E60X nAPG09748 Target 1 | GTCCCACTTTTTATTCTTTTGCAGAGAATGGGATAGATAGCTGGCTTCAAAGAAAAATCC | 77 | 95 | 113 |
| E60X nAPG07553 Target 1 | AGTTTAGGATTTTTCTTTGAAGCCAGCTATCTATCCCATTCTCTGCAAAAGAATAAAAAG | 78 | 96 | 114 |
| E60X nAPG05586 Target 1 | TTTAGGATTTTTCTTTGAAGCCAGCTATCTATCCCATTCTCTGCAAAAGAATAAAAAGTG | 79 | 97 | 115 |
| G542X nAPG06646 Target 1 | CGTTGACCTCCACTCAGTGTGATTCCACCTTCTCAAAGAACTATATTGTCTTTCTCTGCAAACTT | 116 | 128 | 140 |
| G542X nAPG06646 Target 2 | GACCTCCACTCAGTGTGATTCCACCTTCTCAAAGAACTATATTGTCTTTCTCTGCAAACTTGGAG | 117 | 129 | 141 |
| G542X nAPG06646 Target 3 | CCTCCACTCAGTGTGATTCCACCTTCTCAAAGAACTATATTGTCTTTCTCTGCAAACTTGGAGAT | 118 | 130 | 142 |
| G542X nAPG06646 Target 4 | CCACTCAGTGTGATTCCACCTTCTCAAAGAACTATATTGTCTTTCTCTGCAAACTTGGAGATGTC | 119 | 131 | 143 |
| G542X nAPG09882 Target 1 | TCTTGCTCGTTGACCTCCACTCAGTGTGATTCCACCTTCTCAAAGAACTATATTGTCTTTCTCTG | 120 | 132 | 144 |
| G542X nAPG09882 Target 2 | TTGCTCGTTGACCTCCACTCAGTGTGATTCCACCTTCTCAAAGAACTATATTGTCTTTCTCTGCA | 121 | 133 | 145 |

TABLE 31-continued guide RNAs for nonsense mutations in CFTR

| Guide ID | Genetic locus | Genetic locus (SEQ ID NO.) | Target (SEQ ID NO.) | gRNA (SEQ ID NO.) |
|---|---|---|---|---|
| G542X nAPG09882 Target 3 | CACTCAGTGTGATTCCACCTTCTCAAAGAACTATATTGTCTTTC TCTGCAAACTTGGAGATGTCC | 122 | 134 | 146 |
| G542X nAPG03850 Target 1 | TGACCTCCACTCAGTGTGATTCCACCTTCTCAAAGAACTATATT GTCTTTCTCTGCAAAC | 123 | 135 | 147 |
| G542X nAPG03850 Target 2 | TCAGTGTGATTCCACCTTCTCAAAGAACTATATTGTCTTTCTCT GCAAACTTGGAGATGT | 124 | 136 | 148 |
| G542X nAPG09748 Target 1 | AGAGAAAGACAATATAGTTCTTTGAGAAGGTGGAATCACACTGA GTGGAGGTCAACGAGC | 125 | 137 | 149 |
| G542X nAPG07553 Target 1 | TCAGTGTGATTCCACCTTCTCAAAGAACTATATTGTCTTTCTCT GCAAACTTGGAGATGT | 126 | 138 | 150 |
| G542X nAPG05586 Target 1 | CGTTGACCTCCACTCAGTGTGATTCCACCTTCTCAAAGAACTAT ATTGTCTTTCTCTGCA | 127 | 139 | 151 |
| Q493X nAPG09882 Target 1 | GATATTTCTTTAATGGTGCCAGGCATAATCCAGGAAAACTAAG AACAGAATGAAATTCTTCCAC | 152 | 169 | 186 |
| Q493X nAPG09882 Target 2 | ATATTTCTTTAATGGTGCCAGGCATAATCCAGGAAAACTAAGA ACAGAATGAAATTCTTCCACT | 153 | 170 | 187 |
| Q493X nAPG09882 Target 3 | TTTTCTTTAATGGTGCCAGGCATAATCCAGGAAAACTAAGAACA GAATGAAATTCTTCCACTGTG | 154 | 171 | 188 |
| Q493X nAPG09882 Target 4 | TTTCTTTAATGGTGCCAGGCATAATCCAGGAAAACTAAGAACAG AATGAAATTCTTCCACTGTGC | 155 | 172 | 189 |
| Q493X nAPG09882 Target 5 | TTCTTTAATGGTGCCAGGCATAATCCAGGAAAACTAAGAACAGA ATGAAATTCTTCCACTGTGCT | 156 | 173 | 190 |
| Q493X nAPG09748 Target 1 | TAAGCACAGTGGAAGAATTTCATTCTGTTCTTAGTTTTCCTGGA TTATGCCTGGCACCAT | 157 | 174 | 191 |
| Q493X nAPG09748 Target 2 | AAGCACAGTGGAAGAATTTCATTCTGTTCTTAGTTTTCCTGGAT TATGCCTGGCACCATT | 158 | 175 | 192 |
| Q493X nAPG09748 Target 3 | ACAGTGGAAGAATTTCATTCTGTTCTTAGTTTTCCTGGATTATG CCTGGCACCATTAAAG | 159 | 176 | 193 |
| Q02VAPC007/0+A | GGAAGAATTTCATTCTGTTCTTAGTTTTCCTGGATTATGCCTGG CACCATTAAAGAAAAT | 160 | 177 | 194 |
| Q493X nAPG00969 Target 1 | GATATTTCTTTAATGGTGCCAGGCATAATCCAGGAAAACTAAG AACAGAATGAAATTCTTCC AC | 161 | 178 | 195 |
| Q493X nAPG00969 Target 2 | TTCTTTAATGGTGCCAGGCATAATCCAGGAAAACTAAGAACAGA ATGAAATTCTTCCACTGTG CT | 162 | 179 | 196 |
| Q493X nAPG06646 Target 1 | TTTAATGGTGCCAGGCATAATCCAGGAAAACTAAGAACAGAATG AAATTCTTCCACTGTGCTT AA | 163 | 180 | 197 |
| Q493X nAPG06646 Target 2 | AATGGTGCCAGGCATAATCCAGGAAAACTAAGAACAGAATGAAA TTCTTCCACTGTGCTTAAT TT | 164 | 181 | 198 |
| Q493X nAPG01604 Target 1 | TTCTTTAATGGTGCCAGGCATAATCCAGGAAAACTAAGAACAGA ATGAAATTCTTCCACT | 165 | 182 | 199 |
| Q493X nAPG01604 Target 2 | TTAATGGTGCCAGGCATAATCCAGGAAAACTAAGAACAGAATGA AATTCTTCCACTGTGC | 166 | 183 | 200 |
| Q493X nAPG03850 Target 1 | CTTTAATGGTGCCAGGCATAATCCAGGAAAACTAAGAACAGAAT GAAATTCTTCCACTGT | 167 | 184 | 201 |
| Q493X nAPG07553 Target 1 | CTTTAATGGTGCCAGGCATAATCCAGGAAAACTAAGAACAGAAT GAAATTCTTCCACTGT | 168 | 185 | 202 |

TABLE 31-continued guide RNAs for nonsense mutations in CFTR

| Guide ID | Genetic locus | Genetic locus (SEQ ID NO.) | Target (SEQ ID NO.) | gRNA (SEQ ID NO.) |
|---|---|---|---|---|
| R553X nAPG06646 Target 1 | CCAATAATTAGTTATTCACCTTGCTAAAGAAATTCTTGCTCATTGACCTCCACTCAGTGTGATTC | 203 | 219 | 235 |
| R553X nAPG06646 Target 2 | CAATAATTAGTTATTCACCTTGCTAAAGAAATTCTTGCTCATTGACCTCCACTCAGTGTGATTCC | 204 | 220 | 236 |
| R553X nAPG06646 Target 3 | ATAATTAGTTATTCACCTTGCTAAAGAAATTCTTGCTCATTGACCTCCACTCAGTGTGATTCCAC | 205 | 221 | 237 |
| R553X nAPG06646 Target 4 | AATTAGTTATTCACCTTGCTAAAGAAATTCTTGCTCATTGACCTCCACTCAGTGTGATTCCACCT | 206 | 222 | 238 |
| R553X nAPG06646 Target 5 | TCACCTTGCTAAAGAAATTCTTGCTCATTGACCTCCACTCAGTGTGATTCCACCTTCTCCAAGA | 207 | 223 | 239 |
| R553X nAPG06646 Target 6 | CACCTTGCTAAAGAAATTCTTGCTCATTGACCTCCACTCAGTGTGATTCCACCTTCTCCAAGAAC | 208 | 224 | 240 |
| R553X nAPG06646 Target 7 | CCTTGCTAAAGAAATTCTTGCTCATTGACCTCCACTCAGTGTGATTCCACCTTCTCCAAGAACTA | 209 | 225 | 241 |
| R553X nAPG07433.1 Target 1 | CCAATAATTAGTTATTCACCTTGCTAAAGAAATTCTTGCTCATTGACCTCCACTCAGTGTGATTC | 210 | 226 | 242 |
| R553X nAPG07433.1 Target 2 | TCACCTTGCTAAAGAAATTCTTGCTCATTGACCTCCACTCAGTGTGATTCCACCTTCTCCAAGA | 211 | 227 | 243 |
| R553X nAPG07433.1 Target 3 | CCTTGCTAAAGAAATTCTTGCTCATTGACCTCCACTCAGTGTGATTCCACCTTCTCCAAGAACTA | 212 | 228 | 244 |
| R553X nAPG09882 Target 1 | AATAATTAGTTATTCACCTTGCTAAAGAAATTCTTGCTCATTGACCTCCACTCAGTGTGATTCCA | 213 | 229 | 245 |
| R553X nAPG09882 Target 2 | ATTAGTTATTCACCTTGCTAAAGAAATTCTTGCTCATTGACCTCCACTCAGTGTGATTCCACCT | 214 | 230 | 246 |
| R553X nAPG09882 Target 3 | TATTCACCTTGCTAAAGAAATTCTTGCTCATTGACCTCCACTCAGTGTGATTCCACCTTCTCCAA | 215 | 231 | 247 |
| R553X nAPG03850 Target 1 | TATTCACCTTGCTAAAGAAATTCTTGCTCATTGACCTCCACTCAGTGTGATTCCACCTTC | 216 | 232 | 248 |
| R553X nAPG03850 Target 2 | TTCACCTTGCTAAAGAAATTCTTGCTCATTGACCTCCACTCAGTGTGATTCCACCTTCTC | 217 | 233 | 249 |
| R553X nAPG03850 Target 3 | CACCTTGCTAAAGAAATTCTTGCTCATTGACCTCCACTCAGTGTGATTCCACCTTCTCCA | 218 | 234 | 250 |
| R1162X nAPG09882 Target 1 | GGTTTACCTTCTGTTGGCATGTCAATGAACTTAAAGACTCAGCTCACAGATCGCATCTGAAATAA | 251 | 269 | 287 |
| R1162X nAPG09882 Target 2 | ACCTTCTGTTGGCATGTCAATGAACTTAAAGACTCAGCTCACAGATCGCATCTGAAATAAAAATA | 252 | 270 | 288 |

TABLE 31-continued guide RNAs for nonsense mutations in CFTR

| Guide ID | Genetic locus | Genetic locus (SEQ ID NO.) | Target (SEQ ID NO.) | gRNA (SEQ ID NO.) |
|---|---|---|---|---|
| R1162X nAPG09882 Target 3 | CTGTTGGCATGTCAATGAACTTAAAGACTCAGCTCACAGATCGC ATCTGAAATAAAAATAACA AC | 253 | 271 | 289 |
| R1162X nAPG09882 Target 4 | TGTTGGCATGTCAATGAACTTAAAGACTCAGCTCACAGATCGCA TCTGAAATAAAAATAACAA CA | 254 | 272 | 290 |
| R1162X nAPG09882 Target 5 | GTTGGCATGTCAATGAACTTAAAGACTCAGCTCACAGATCGCAT CTGAAATAAAAATAACAAC AT | 255 | 273 | 291 |
| R1162X nAPG06646 Target 1 | TTTACCTTCTGTTGGCATGTCAATGAACTTAAAGACTCAGCTCA CAGATCGCATCTGAAATAA AA | 256 | 274 | 292 |
| R1162X nAPG06646 Target 2 | TACCTTCTGTTGGCATGTCAATGAACTTAAAGACTCAGCTCACA GATCGCATCTGAAATAAAA AT | 257 | 275 | 293 |
| R1162X nAPG06646 Target 3 | TGGCATGTCAATGAACTTAAAGACTCAGCTCACAGATCGCATCT GAAATAAAAATAACAA | 258 | 276 | 294 |
| R1162X nAPG03850 Target 1 | TACCTTCTGTTGGCATGTCAATGAACTTAAAGACTCAGCTCACA GATCGCATCTGAAATA | 259 | 277 | 295 |
| R1162X nAPG03850 Target 2 | TTCTGTTGGCATGTCAATGAACTTAAAGACTCAGCTCACAGATC GCATCTGAAATAAAAA | 260 | 278 | 296 |
| R1162X nAPG03850 Target 3 | TGGCATGTCAATGAACTTAAAGACTCAGCTCACAGATCGCATCT GAAATAAAAATAACAA | 261 | 279 | 297 |
| R1162X nAPG05586 Target 1 | TTACCTTCTGTTGGCATGTCAATGAACTTAAAGACTCAGCTCAC AGATCGCATCTGAAAT | 262 | 280 | 298 |
| R1162X nAPG05586 Target 2 | CTGTTGGCATGTCAATGAACTTAAAGACTCAGCTCACAGATCGC ATCTGAAATAAAAATA | 263 | 281 | 299 |
| R1162X nAPG05586 Target 3 | TGTCAATGAACTTAAAGACTCAGCTCACAGATCGCATCTGAAAT AAAAATAACAACATTT | 264 | 282 | 300 |
| R1162X nAPG00969 Target 1 | GGTTTACCTTCTGTTGGCATGTCAATGAACTTAAAGACTCAGCT CACAGATCGCATCTGAAAT AA | 265 | 283 | 301 |
| R1162X nAPG00969 Target 2 | GTTGGCATGTCAATGAACTTAAAGACTCAGCTCACAGATCGCAT CTGAAATAAAAATAACAAC AT | 266 | 284 | 302 |
| R1162X nAPG07553 Target 1 | TGGCATGTCAATGAACTTAAAGACTCAGCTCACAGATCGCATCT GAAATAAAAATAACAA | 267 | 285 | 303 |
| R1162X nAPG01604 Target 1 | GCATGTCAATGAACTTAAAGACTCAGCTCACAGATCGCATCTGA AATAAAAATAACAACA | 268 | 286 | 304 |
| W1282X nAPG09882 Target 1 | GTGTGTCTTGGGATTCAATAACTTTGCAACAGTGAAGGAAAGCC TTTGGAGTGATACCACAGG TG | 305 | 325 | 345 |
| W1282X nAPG09882 Target 2 | GTCTTGGGATTCAATAACTTTGCAACAGTGAAGGAAAGCCTTTG GAGTGATACCACAGGTGAG CA | 306 | 326 | 346 |
| W1282X nAPG09882 Target 3 | CTTGGGATTCAATAACTTTGCAACAGTGAAGGAAAGCCTTTGGA GTGATACCACAGGTGAGCA AA | 307 | 327 | 347 |
| W1282X nAPG09882 Target 4 | GGGATTCAATAACTTTGCAACAGTGAAGGAAAGCCTTTGGAGTG ATACCACAGGTGAGCAAA AGG | 308 | 328 | 348 |

TABLE 31-continued guide RNAs for nonsense mutations in CFTR

| Guide ID | Genetic locus | Genetic locus (SEQ ID NO.) | Target (SEQ ID NO.) | gRNA (SEQ ID NO.) |
|---|---|---|---|---|
| W1282X nAPG09882 Target 5 | GATTCAATAACTTTGCAACAGTGAAGGAAAGCCTTTGGAGTGATACCACAGGTGAGCAAAAGGAC | 309 | 329 | 349 |
| W1282X nAPG06646 Target 1 | TCGATGGTGTGTCTTGGGATTCAATAACTTTGCAACAGTGAAGGAAAGCCTTTGGAGTGATACCA | 310 | 330 | 350 |
| W1282X nAPG06646 Target 2 | TTGGGATTCAATAACTTTGCAACAGTGAAGGAAAGCCTTTGGAGTGATACCACAGGTGAGCAAAA | 311 | 331 | 351 |
| W1282X nAPG06646 Target 3 | TGGGATTCAATAACTTTGCAACAGTGAAGGAAAGCCTTTGGAGTGATACCACAGGTGAGCAAAAG | 312 | 332 | 352 |
| W1282X nAPG06646 Target 4 | GGATTCAATAACTTTGCAACAGTGAAGGAAAGCCTTTGGAGTGATACCACAGGTGAGCAAAAGGA | 313 | 333 | 353 |
| W1282X nAPG03850 Target 1 | TGTCTTGGGATTCAATAACTTTGCAACAGTGAAGGAAAGCCTTTGGAGTGATACCACAGG | 314 | 334 | 354 |
| W1282X nAPG03850 Target 2 | GTCTTGGGATTCAATAACTTTGCAACAGTGAAGGAAAGCCTTTGGAGTGATACCACAGGT | 315 | 335 | 355 |
| W1282X nAPG03850 Target 3 | CTTGGGATTCAATAACTTTGCAACAGTGAAGGAAAGCCTTTGGAGTGATACCACAGGTGA | 316 | 336 | 356 |
| W1282X nAPG03850 Target 4 | TGGGATTCAATAACTTTGCAACAGTGAAGGAAAGCCTTTGGAGTGATACCACAGGTGAGC | 317 | 337 | 357 |
| W1282X nAPG07553 Target 1 | CTTGGGATTCAATAACTTTGCAACAGTGAAGGAAAGCCTTTGGAGTGATACCACAGGTGA | 318 | 338 | 358 |
| W1282X nAPG07553 Target 2 | TGGGATTCAATAACTTTGCAACAGTGAAGGAAAGCCTTTGGAGTGATACCACAGGTGAGC | 319 | 339 | 359 |
| W1282X nAPG01604 Target 1 | TCTTGGGATTCAATAACTTTGCAACAGTGAAGGAAAGCCTTTGGAGTGATACCACAGGTG | 320 | 340 | 360 |
| W1282X nAPG01604 Target 2 | CTTGGGATTCAATAACTTTGCAACAGTGAAGGAAAGCCTTTGGAGTGATACCACAGGTGA | 321 | 341 | 361 |
| W1282X nAPG07433.1 Target 1 | TTGGGATTCAATAACTTTGCAACAGTGAAGGAAAGCCTTTGGAGTGATACCACAGGTGAGCAAAA | 322 | 342 | 362 |
| W1282X nAPG09748 Target 1 | GTATCACTCCAAAGGCTTTCCTTCACTGTTGCAAAGTTATTGAATCCCAAGACACACCAT | 323 | 343 | 363 |
| W1282X nAPG05586 Target 1 | GATTCAATAACTTTGCAACAGTGAAGGAAAGCCTTTGGAGTGATACCACAGGTGAGCAAA | 324 | 344 | 364 |
| F508de nAPG07433.1 SGN001101 Target1 | ACCAAAGATGATATTTTCTTTAATGGTGCCAGGCATAATCCAGGAAAACTGAGAACAGAATGAAA | 562 | 563 | 564 |

Table 28 in Example 3 provides editing data for the SGN001101 sgRNA targeting CFTR.

To assay for activity of the other guide RNAs, a guide RNA of Table 31 is provided with the corresponding nickase variant of each RGN described in Table 30, which is operably linked to a deaminase of the invention to produce a fusion protein. It is recognized that nuclease inactive variants of each RGN may be tested similarly as well. Each guide and fusion protein combination is assayed for the ability to edit at the target location in 16HBE14o-immortalized bronchial epithelial cells. Currently, three HBE cell lines containing the CFTR nonsense mutations are available (Cystic Fibrosis Foundation, Lexington, MA). These cell lines are used to assay the G542X, W1282X, and RI 162X nonsense mutation targets and compared to the 16HBE14o-line. The fusion protein and guide RNA is delivered to the cells as ribonucleoproteins (RNPs), which are nucleofected into the 16HBE14o-cell line following culturing and transformation methods provided in Valley et al (Valley et al, 2019. J Cyst Fibros 18, 476-483, incorporated by reference herein). The guide RNA is provided as a single guide RNA or as a 1:1 or 1:1.2 molar ratio of tracrRNA:crRNA duplex with RGN proteins. Nucleofection of RNPs into cells is performed on a Lonza 4D-Nucleofector. Cells are then incubated at 37° C. for 72 h. In some embodiments, the fusion protein and gRNA are delivered to the cells as RNA molecules, with the fusion protein encoded in an mRNA.

Because there are no cell lines available for the E60X, R553X, and Q493X, these mutations are assayed in HEK293 cells using a modification of the GFP restoration assay described in Example 2, where the mutant locus containing the nonsense mutation is cloned into the GFP reading frame 2.

Following incubation, genomic DNA is then extracted using NucleoSpin 96 Tissue (Macherey-Nagel) following the manufacturer's protocol. The genomic region flanking the targeted genomic site is PCR amplified and products are purified using ZR-96 DNA Clean and Concentrator (Zymo Research) following the manufacturer's protocol. The purified PCR products are then sent for Next Generation Sequencing on Illumina MiSeq. Typically, 100,000 of 250 bp paired-end reads (2×100,000 reads) are generated per amplicon. The reads are analyzed using CRISPResso (Pinello, et al. 2016) to calculate the rates of editing. Output alignments are hand-curated to confirm introduction of the base-edited mutations of interest and also to screen for undesirable INDEL formation.

In addition to efficiency of base editing, the protein product of the base-edited CFTR gene is evaluated for function. For two of the nonsense mutations, Glu60X and Gly542X, the base edited change of adenine to guanine does not restore the wildtype sequence, as these mutations are caused by guanine to thymine transversions. The targeted activity of the fusion protein changes the Glu60X to Glu60Gln and Gly452X to Gly542Arg. While these mutations do allow for a full-length protein to be made, the stability and functionality of the CFTR protein is also confirmed.

Example 4.2: Engineering RGNs for Decreased Size

Ideally, the coding sequence of an RGN-deaminase fusion protein of the invention and a corresponding guide RNA for targeting the fusion protein to the CFTR gene is all packaged into a single AAV vector. The generally accepted size limit for AAV vectors is 4.7 kb, although larger sizes may be contemplated at the expense of reduced packing efficiency. The RGN nickases in Table 30 have a coding sequence length of about 3.15-3.45 kB. To ensure that the expression cassettes for both the fusion protein and its corresponding guide RNA could fit into an AAV vector, shortening the length of RGN amino acid and its corresponding nucleic acid coding sequence is desirable.

Through alignment with closely related homologs, a unique 8 amino acid region at positions 590-597 was identified in APG07433.1 and its close homolog APG08290.1 (described in WO 2019/236566 and set forth herein as SEQ ID NO: 60). This region, set forth as SEQ ID NO: 365 for APG07433.1 and SEQ ID NO: 367 for APG08290.1, was removed from both proteins, resulting in variant RGNs APG07433.1-del (SEQ ID NO: 366) and APG08290.1-del (SEQ ID NO: 368). These deletion variants and their corresponding wild-type RGNs were assayed for editing activity in HEK293T cells using the guide RNAs indicated in Tables 32 and 33 following methods similar to those described in Example 1. Rates of editing of the target sequences are shown in Tables 32 and 33 below.

TABLE 32

Editing Rate for APG07433.1 Protein Deletion Variants

| guide RNA | Target (SEQ ID NO.) | sgRNA (SEQ ID NO.) | APG07433.1 | APG07433.1-del |
|---|---|---|---|---|
| SGN000139 | 369 | 383 | 11.09% | 1.00% |
| SGN000143 | 370 | 384 | 2.68% | 0.71% |
| SGN000169 | 371 | 385 | 13.37% | 15.48% |
| SGN000173 | 372 | 386 | 13.65% | 15.37% |
| SGN000186 | 373 | 387 | 14.72% | 15.16% |
| SGN000194 | 374 | 388 | 11.91% | 7.66% |
| SGN000927 | 376 | 390 | 9.53% | 11.47% |
| SGN000929 | 378 | 392 | 6.14% | 13.10% |
| SGN000930 | 379 | 393 | 7.52% | 9.51% |
| SGN000935 | 381 | 395 | 11.08% | 15.99% |
| SGN001101 | 382 | 396 | 6.16% | 6.75% |

For targets SGN000169, SGN000173, SGN000186, SGN000927, SGN000930, and SGN001101, the editing rate of the wild type APG07433.1 protein and the engineered variant was similar. For targets SGN000139, SGN000143, and SGN000194, the editing rate is decreased when the engineered variant was used compared to the wild type protein. With SGN000929 and SGN000935, the editing rate increased with the engineered APG07433.1 variant compared to the wild type sequence.

TABLE 33

Editing Rate for APG08290.1 Protein Deletion Variants

| sgRNA ID | Target (SEQ ID NO.) | sgRNA (SEQ ID NO.) | APG08290.1 | APG08290.1-del |
|---|---|---|---|---|
| SGN000926 | 375 | 389 | N.D. | 6.47% |
| SGN000929 | 378 | 392 | 1.83% | 0.61% |
| SGN000930 | 379 | 393 | 9.93% | 6.47% |
| SGN000928 | 377 | 391 | N.D. | 0.13% |
| SGN000931 | 380 | 394 | 0% | 0% |

N.D. = Not determined

The APG08290.1 deletion variant showed editing in all samples where the wild type APG08290.1 protein also showed editing. The lowest editing rate detected was 0.13% with the engineered protein. Target SGN000926 showed the highest editing rate: 9.17%.

Fusion proteins comprising APG07433.1-del or APG08290.1-del and a deaminase of the invention are produced and assayed for base editing activity using methods similar to Example 1.

A fusion protein comprises an RGN and a deaminase linked by a flexible peptide linker, such as that set forth as SEQ ID NO: 45. The linker of SEQ ID NO: 45 is 16 amino acids in length; this size may be reduced to reduce the size of the coding sequence of the fusion protein. Peptide linkers of less than 16 amino acids can be produced and operably link RGNs APG07433.1-del or APG08290.1-del and a deaminase of the invention and tested for base editing activity using methods similar to Example 1. Because the peptide linker between the RGN and the deaminase can determine the editing window of the fusion protein, testing of alternative linkers with different lengths and rigidity may also lead to improvements in editing efficiency while reducing off-target mutations. Therefore, fusion proteins with the highest editing rate are then assayed following methods similar to Example 4.1 to determine editing efficiency for each of the CFTR target sequences. Fusion protein-gRNA combinations with the highest editing efficiency are selected as the preferred guide for editing at that location and are used for AAV vector design.

Example 4.3: AAV Delivery

The coding sequences for validated fusion protein/gRNA combinations with the highest editing rate are packaged into AAV vectors. AAV delivery has a number of benefits including a lack of pathogenicity, low immunogenicity, high transduction rates, and a defined path to manufacturing. Also, AAV dosing of the lungs has been shown to be safe and at least to some degree, efficacious with both single and repeat dosing (Guggino et al., 2017, Expert Opin Biol Ther 17, 1265-1273). After a fusion protein/gRNA combination has been cloned into an AAV vector, it may be packaged into several different serotypes to optimize tissue specific infectivity. For treatment of CF, the target for base editing is progenitor apical epithelium cells of the lungs, which will allow the correction to persist throughout cell turnover. To target respiratory epithelium, the capsid for serotypes AAV1, AAV5 or AAV6 are utilized, as these serotypes have been shown to have high infectivity in respiratory epithelium cells (Zabner et al., 2000, J Virol 74, 3852-3858).

Once the AAV vectors are produced, they are transduced into human airway epithelial cells in culture. The three HBE cell lines containing the CFTR G542X, RI 162X, and W1282X nonsense mutation targets are used to validate the constructs for correction of those mutations. The 16HBE14o-line is used to test the constructs correcting the other nonsense mutations. A range of multiplicities of infection (MOIs) are tested. In either case, reversion of the nonsense mutation to the wild type CFTR sequence is assessed. After 2-3 days in culture, genomic DNA is harvested, amplicons around the targeted sites are generated by PCR, and NGS is performed to determine editing rates at each locus similar to the methods described in Example 1. Because airway epithelial cells are used, AAV introduction and editing rates are as similar to an in vivo treatment as possible while using a cultured cell system. AAVs with different serotypes are compared to determine which serotype is optimal for delivery of the fusion protein/gRNA into airway cells. The editing rates achieved by AAV introduction of these systems are compared with the RNP editing rates observed in Example 4.2.

Because cell lines for the nonsense mutations R553X, E60X, and Q493X are not available, fusion protein/gRNA systems targeting these mutations are evaluated in wild type 16HBE14o-cells to assay for AAV introduction, base editor expression, and off-target editing rates at the location of interest. To determine the rate of stop codon correction, the mutant locus is cloned into GFP for a GFP restoration assay as described in Example 4.1.

In parallel with determining editing rates by NGS, total protein lysates from cells harboring CFTR mutations edited with fusion protein/gRNA systems are collected and the levels of full-length CFTR protein assessed by western blotting. To test whether functional CFTR protein is formed, forskolin activation assays are performed using methods similar to those described by Devor et al (2000, Am J Physiol Cell Physiol 279, C461-479, incoparated by reference herein) and/or Dousmais et al (2002, J Gen Physiol 119, 545-559, incorporated by reference herein). In these experiments, edited CFTR mutant cells are treated with forskolin, an activator of adenylate cyclase, to increase intracellular levels of cAMP. Elevated cAMP levels then activate CFTR, and the influx of Cl⁻ is measured by either a genetically-encoded yellow fluorescent protein based Cl⁻ sensor or a small molecule fluorescent indicator of chloride such as MQAE. The G542X, RI 162X, and W1282X edited cell lines are tested in this assay.

To determine the rate of off-target mutations, a bioinformatic approach which is customized with information about the seed region and flexible off-target PAM recognition space of each specific nuclease is used. These pieces of information have been determined bioinformatically for each protein and are used to rank the likelihood of off-target activity for each protein.

To complement bioinformatic prediction of off targets, biochemical detection of off-targets via a modified SITE-seq protocol (Cameron et al., 2017, Nat Methods 14, 600-606, herein incorporated by reference) is also performed. Briefly, genomic DNA from human airway epithelial cells is obtained. This DNA is then treated with the RGN of interest at several different concentrations. Any DNA double stranded breaks are labelled, selectively isolated, and PCR amplified with adapter sequences that allow for NGS. Sequencing reads are then mapped to the genome and "pileups" of reads are identified at sites of double stranded breaks, marking putative off target locations. In a subsequent set of experiments, cells are edited with the RGN or RGN-deaminase fusion protein of interest and these putative sites are individually sequenced to confirm if they are bona fide off-targets. Since chromatin context, DNA accessibility, and other factors can impact the efficiency of genome editors in living cells, biochemical methods typically overestimate the number of off-targets. Therefore, both bioinformatic and biochemical methods together provide complementary methods to identify putative off-target sites, but these sites must be verified by amplicon sequencing to get an accurate assessment of off-target editing.

Once putative off-target sites are identified, amplicon sequencing on 16HBE airway epithelial cells edited with the same optimized fusion protein and guide(s) ensures that the off-target profile established for these systems matches the expected profile in patient lungs as closely as possible.

To determine if the fusion proteins described herein induce changes in cellular RNA, careful analysis of the cellular transcriptome following editing is necessary. Fortunately, RNA-seq techniques to assess adenine base-editing off-target effects have become routine (Grunewald et al, 2017, Nature 569, 433-437; Zhou et al, Nature 571, 275-278, both incorporated by reference herein). Briefly, after editing cells with the fusion protein/gRNA systems determined in Example 4.2, total cellular mRNA is collected and subjected to RNA-seq. Transcriptomes from edited cells are compared to cells transfected with the ABE alone, and significant differences in RNA sequence are identified.

Example 5: Targeted Base-Editing for Correction of Causal Disease Mutations

A database of clinical variants was obtained from NCBI ClinVar database, which is available through the world wide web at the NCBI ClinVar website. Pathogenic Single Nucleotide Polymorphisms (SNPs) were identified from this list. Using the genomic locus information, CRISPR targets in the region overlapping and surrounding each SNP were identified. A selection of SNPs that can be corrected using base editing in combination with an RGN, such as for example an RGN listed in Table 30 or a variant thereof, to target the causal mutation ("Casl Mut.") is listed in Table 34. In Table 34 below, only one alias of each disease is listed. The "RS #" corresponds to the RS accession number through the SNP database at the NCBI website. The "AlleleID" corresponds to a causal allele accession number. The "Name" column contains the genetic locus identifier, the gene name, the location of the mutation in the gene, and the change resulting from the mutation.

TABLE 34

Disease Targets for Base Editing

| RS# | Allele ID | Name | GeneSymbol |
|---|---|---|---|
| 36053993 | 20333 | NM_001128425.1(MUTYH): c.1187G>A (p.Gly396Asp) | MUTYH |
| 41293455 | 32714 | NM_007294.3(BRCA1): c.4327C>T (p.Arg1443Ter) | BRCA1 |
| 62625308 | 32710 | NM_007294.3(BRCA1): c.3607C>T (p.Arg1203Ter) | BRCA1 |
| 41293465 | 70268 | NM_007294.3(BRCA1): c.5503C>T (p.Arg1835Ter) | BRCA1 |
| 80357123 | 70147 | NM_007294.3(BRCA1): c.5251C>T (p.Arg1751Ter) | BRCA1 |
| 137929307 | 171217 | NM_000527.4(LDLR): c.1775G>A (p.Gly592Glu) | LDLR |
| 80356898 | 45982 | NM_007294.3(BRCA1): c.1687C>T (p.Gln563Ter) | BRCA1 |
| 28936415 | 22745 | NM_000303.2(PMM2): c.422G>A (p.Arg141His) | PMM2 |
| 11555217 | 34125 | NM_001360.2(DHCR7): c.452C>T (p.Trp151Ter) | DHCR7 |
| 55770810 | 70063 | NM_007294.3(BRCA1): c.5095C>T (p.Arg1699Trp) | BRCA1 |
| 28934906 | 26850 | NM_004992.3(MECP2): c.473C>T (p.Thr158Met) | MECP2 |
| 28929474 | 33006 | NM_001127701.1(SERPINA1): c.1096G>A (p.Glu366Lys) | SERPINA1 |
| 371898076 | 52045 | NM_000257.4(MYH7): c.1988G>A (p.Arg663His) | MYH7 |
| 5030858 | 15616 | NM_000277.3(PAH): c.1222C>T (p.Arg408Trp) | PAH |
| 80356945 | 69207 | NM_007294.3(BRCA1): c.2338C>T (p.Gln780Ter) | BRCA1 |
| 1800553 | 22927 | NM_000350.2(ABCA4): c.5882G>A (p.Gly1961Glu) | ABCA4 |
| 80356962 | 70247 | NM_007294.3(BRCA1): c.5444G>A (p.Trp1815Ter) | BRCA1 |
| 104894396 | 32041 | NM_004004.6(GJB2): c.71G>A (p.Trp24Ter) | GJB2 |
| 113994095 | 28535 | NM_002693.2(POLG): c.1399G>A (p.Ala467Thr) | POLG |
| 61749721 | 26868 | NM_004992.3(MECP2): c.763C>T (p.Arg255Ter) | MECP2 |
| 137852700 | 23943 | NM_000310.3(PPT1): c.451C>T (p.Arg151Ter) | PPT1 |
| 75527207 | 22159 | NM_000492.3(CFTR): c.1652G>A (p.Gly551Asp) | CFTR |
| 78655421 | 22148 | NM_000492.3(CFTR): c.350G>A (p.Arg117His) | CFTR |
| 80356885 | 69888 | NM_007294.3(BRCA1): c.4524G>A (p.Trp1508Ter) | BRCA1 |
| 113994098 | 28541 | NM_002693.2(POLG): c.2542G>A (p.Gly848Ser) | POLG |
| 61750240 | 26854 | NM_004992.3(MECP2): c.808C>T (p.Arg270Ter) | MECP2 |
| 61751362 | 26858 | NM_001110792.1(MECP2): c.916C>T (p.Arg306Ter) | MECP2 |
| 80357260 | 69792 | NM_007294.3(BRCA1): c.4183C>T (p.Gln1395Ter) | BRCA1 |
| 80359071 | 67203 | NM_000059.3(BRCA2): c.8243G>A (p.Gly2748Asp) | BRCA2 |
| 62625307 | 69596 | NM_007294.3(BRCA1): c.3598C>T (p.Gln1200Ter) | BRCA1 |
| 76992529 | 28465 | NM_000371.3(TTR): c.424G>A (p.Val142Ile) | TTR |
| 77010898 | 22168 | NM_000492.3(CFTR): c.3846G>A (p.Trp1282Ter) | CFTR |
| 80359003 | 67069 | NM_000059.3(BRCA2): c.7757G>A (p.Trp2586Ter) | BRCA2 |
| 61750420 | 22555 | NM_000466.2(PEX1): c.2528G>A (p.Gly843Asp) | PEX1 |

TABLE 34-continued

Disease Targets for Base Editing

| RS# | Allele ID | Name | GeneSymbol |
|---|---|---|---|
| 80357284 | 46214 | NM_007294.3(BRCA1): c.5346G>A (p.Trp1782Ter) | BRCA1 |
| 200411226 | 174776 | NM_000256.3(MYBPC3): c.1484G>A (p.Arg495Gln) | MYBPC3 |
| 5030857 | 98638 | NM_000277.3(PAH): c.1208C>T (p.Ala403 Val) | PAH |
| 28935468 | 26863 | NM_004992.3(MECP2): c.916C>T (p.Arg306Cys) | MECP2 |
| 62642937 | 15667 | NM_000277.3(PAH): c.1139C>T (p.Thr380Met) | PAH |
| 80356989 | 69812 | NM_007294.3(BRCA1): c.4222C>T (D.Gln1408Ter) | BRCA1 |
| 28942080 | 18735 | NM_000527.4(LDLR): c.1567G>A (p.Val523Met) | LDLR |
| 121908039 | 18778 | NM_000527.4(LDLR): c.551G>A (p.Cys184Tyr) | LDLR |
| 267607213 | 18780 | NM_000527.4(LDLR): c.131G>A (p.Trp44Ter) | LDLR |
| 3218716 | 52071 | NM_000257.3(MYH7): c.2389G>A (p.Ala797Thr) | MYH7 |
| 104895097 | 17588 | NM_000243.2(MEFV): c.2282G>A (p.Arg761His) | MEFV |
| 397516074 | 51962 | NM_000256.3(MYBPC3): c.772G>A (p.Glu258Lys) | MYBPC3 |
| 119455955 | 17682 | NM_000391.3(TPP1): c.622C>T (p.Arg208Ter) | TPP1 |
| 75184679 | 16301 | NM_024570.3(RNASEH2B): c.529G>A (p.Ala177Thr) | RNASEH2B |
| 80338901 | 26909 | NM_000137.2(FAH): c.1062+5G>A | FAH |
| 119450941 | 17501 | NM_000026.3(ADSL): c.1277G>A (p.Arg426His) | ADSL |
| 121965019 | 26947 | NM_000203.4(IDUA): c.1205G>A (p.Trp402Ter) | IDUA |
| 141659620 | 21858 | NM_003119.3(SPG7): c.1045G>A (p.Gly349Ser) | SPG7 |
| 41276738 | 15335 | NM_000552.4(VWF): c.2561G>A (p.Arg854Gln) | VWF |
| 80338940 | 32068 | NM_004004.5(GJB2): c.-23+1G>A | GJB2 |
| 80357292 | 46268 | NM_007294.3(BRCA1): c.962G>A (p.Trp321Ter) | BRCA1 |
| 121913627 | 29130 | NM_000257.3(MYH7): c.1816G>A (p.Val606Met) | MYH7 |
| 137854601 | 24416 | NM_198056.2(SCN5A): c.5350G>A (p.Glu1784Lys) | SCN5A |
| 80338933 | 17521 | NM_024577.3(SH3TC2): c.2860C>T (p.Arg954Ter) | SH3TC2 |
| 80338948 | 32048 | NM_004004.5(GJB2): c.427C>T (p.Arg143Trp) | GJB2 |
| 80356903 | 69645 | NM_007294.3(BRCA1): c.3718C>T (p.Gln1240Ter) | BRCA1 |
| 80356969 | 70213 | NM_007294.3(BRCA1): c.5353C>T (p.Gln1785Ter) | BRCA1 |
| 80357010 | 45971 | NM_007294.3(BRCA1): c.1480C>T (p.Gln494Ter) | BRCA1 |
| 116987552 | 17337 | NM_005609.3(PYGM): c.148C>T (p.Arg50Ter) | PYGM |
| 121913625 | 29128 | NM_000257.4(MYH7): c.1357C>T (p.Arg453Cys) | MYH7 |
| 387907267 | 45725 | NM_000256.3(MYBPC3): c.2827C>T (p.Arg943Ter) | MYBPC3 |
| 28934897 | 26968 | NM_000431.3(MVK): c.1129G>A (p.Val377Ile) | MVK |
| 76713772 | 22151 | NM_000492.3(CFTR): c.1585-1G>A | CFTR |
| 137852959 | 19587 | NM_153638.3(PANK2): c.1561G>A (p.Gly521Arg) | PANK2 |
| 199682486 | 101428 | NM_013339.4(ALG6): c.257+5G>A | ALG6 |
| 397507389 | 46666 | NM_000059.3(BRCA2): c.7618-1G>A | BRCA2 |
| 769370816 | 228176 | NM_000527.4(LDLR): c.1618G>A (p.Ala540Thr) | LDLR |

TABLE 34-continued

Disease Targets for Base Editing

| RS# | Allele ID | Name | GeneSymbol |
|---|---|---|---|
| 36211715 | 29159 | NM_000257.4(MYH7): c.2609G>A (p.Arg870His) | MYH7 |
| 76434661 | 53916 | NM_004004.5(GJB2): c.416G>A (p.Ser139Asn) | GJB2 |
| 104894368 | 29104 | NM_000432.3(MYL2): c.64G>A (p.Glu22Lys) | MYL2 |
| 104894635 | 20146 | NM_000199.3(SGSH): c.734G>A (p.Arg245His) | SGSH |
| 121913628 | 29131 | NM_000257.3(MYH7): c.2770G>A (p.Glu924Lys) | MYH7 |
| 193922390 | 45304 | NM_000257.4(MYH7): c.5135G>A (p.Arg1712Gln) | MYH7 |
| 397515757 | 51454 | NM_000138.4(FBN1): c.1468+5G>A | FBN1 |
| 11549407 | 30441 | NM_000518.5(HBB): c.118C>T (p.Gln40Ter) | HBB |
| 61751374 | 22933 | NM_000350.2(ABCA4): c.3113C>T (p.Ala1038Val) | ABCA4 |
| 121434420 | 21793 | NM_004572.3(PKP2): c.235C>T (p.Arg79Ter) | PKP2 |
| 137853007 | 20631 | NM_007194.4(CHEK2): c.433C>T (p.Arg145Trp) | CHEK2 |
| 1137887 | 18083 | NM_000051.3(ATM): c.2250G>A (p.Lys750=) | ATM |
| 28934872 | 27436 | NM_000548.3(TSC2): c.1832G>A (p.Arg611Gln) | TSC2 |
| 80224560 | 47062 | NM_000492.3(CFTR): c.2657+5G>A | CFTR |
| 80359004 | 46672 | NM_000059.3(BRCA2): c.7758G>A (p.Trp2586Ter) | BRCA2 |
| 121434274 | 18627 | NM_000016.5(ACADM): c.799G>A (p.Gly267Arg) | ACADM |
| 121908529 | 38436 | NM_000030.2(AGXT): c.508G>A (p.Gly170Arg) | AGXT |
| 121918007 | 28709 | NM_000478.4(ALPL): c.571G>A (p.Glu191Lys) | ALPL |
| 121918243 | 16464 | NM_015506.2(MMACHC): c.482G>A (p.Arg161Gln) | MMACHC |
| 397518423 | 94255 | NM_005026.4(PIK3CD): c.3061G>A (p.Glu1021Lys) | PIK3CD |
| 587781629 | 150997 | NM_000059.3(BRCA2): c.1909+1G>A | BRCA2 |
| 765696008 | 228162 | NM_000527.4(LDLR): c.1187-10G>A | LDLR |
| 3218713 | 29127 | NM_000257.3(MYH7): c.746G>A (p.Arg249Gln) | MYH7 |
| 5030855 | 15646 | NM_000277.3(PAH): c.1066-11G>A | PAH |
| 55851803 | 69067 | NM_007294.3(BRCA1): c.191G>A (p.Cys64Tyr) | BRCA1 |
| 62508698 | 15619 | NM_000277.1(PAH): c.838G>A (p.Glu280Lys) | PAH |
| 62516152 | 108520 | NM_000277.3(PAH): c.688G>A (p.Val230Ile) | PAH |
| 62644499 | 15656 | NM_000277.3(PAH): c.1243G>A (p.Asp415Asn) | PAH |
| 80338815 | 18090 | NM_000487.5(ARSA): c.465+1G>A | ARSA |
| 121908987 | 21885 | NM_016203.3(PRKAG2): c.905G>A (p.Arg302Gln) | PRKAG2 |
| 121964962 | 15156 | NM_000071.2(CBS): c.919G>A (p.Gly307Ser) | CBS |
| 5030851 | 15628 | NM_000277.3(PAH): c.842C>T (p.Pro281Leu) | PAH |
| 63750871 | 24273 | NM_000535.6(PMS2): c.400C>T (p.Arg134Ter) | PMS2 |
| 80338853 | 21822 | NM_001360.2(DHCR7): c.278C>T (p.Thr93Met) | DHCR7 |
| 80356893 | 68976 | NM_007294.3(BRCA1): c.1612C>T (p.Gln538Ter) | BRCA1 |
| 80357131 | 46031 | NM_007294.3(BRCA1): c.2563C>T (p.Gln855Ter) | BRCA1 |
| 80357223 | 69350 | NM_007294.3(BRCA1): c.2800C>T (p.Gln934Ter) | BRCA1 |
| 80357318 | 46112 | NM_007294.3(BRCA1): c.3937C>T (p.Gln1313Ter) | BRCA1 |
| 104886457 | 27086 | NM_000136.2(FANCC): c.1642C>T (p.Arg548Ter) | FANCC |
| 137852944 | 19147 | NM_138694.3(PKHD1): c.107C>T (p.Thr36Met) | PKHD1 |
| 180177083 | 132139 | NM_024675.3(PALB2): c.196C>T (p.Gln66Ter) | PALB2 |
| 180177110 | 152117 | NM_024675.3(PALB2): c.2257C>T (p.Arg753Ter) | PALB2 |
| 199475575 | 108459 | NM_000277.3(PAH): c.526C>T (p.Arg176Ter) | PAH |
| 387906843 | 39241 | NM_002878.3(RAD51D): c.556C>T (p.Arg186Ter) | RAD51D |
| 529008617 | 152318 | NM_001128425.1(MUTYH): c.1214C>T (p.Pro405Leu) | MUTYH |
| 587780021 | 133177 | NM_000465.3(BARD1): c.1690C>T (p.Gln564Ter) | BARD1 |
| 34637584 | 16979 | NM_198578.3(LRRK2): c.6055G>A (p.Gly2019Ser) | LRRK2 |
| 78802634 | 22233 | NM_000492.3(CFTR): c.3266G>A (p.Trp1089Ter) | CFTR |
| 80358809 | 66611 | NM_000059.3(BRCA2): c.581G>A (p.Trp194Ter) | BRCA2 |
| 80359011 | 46678 | NM_000059.3(BRCA2): c.7857G>A (p.Trp2619Ter) | BRCA2 |
| 104894503 | 27495 | NM_001018005.1(TPM1): c.523G>A (p.Asp175Asn) | TPM1 |
| 121908641 | 21368 | NM_000050.4(ASS1): c.1168G>A (p.Gly390Arg) | ASS1 |
| 121918593 | 28009 | NM_000540.2(RYR1): c.7300G>A (p.Gly2434Arg) | RYR1 |
| 140108514 | 100191 | NM_003494.3(DYSF): c.2643+1G>A | DYSF |
| 145138923 | 98271 | NM_000048.3(ASL): c.35G>A (p.Arg12Gln) | ASL |
| 150726175 | 45795 | NM_022787.3(NMNAT1): c.769G>A (p.Glu257Lys) | NMNAT1 |
| 267607578 | 45138 | NM_170707.3(LMNA): c.1412G>A (p.Arg471His) | LMNA |
| 376607329 | 48992 | NM_002834.4(PTPN11): c.794G>A (p.Arg265Gln) | PTPN11 |
| 587776934 | 48407 | NM_005027.3(PIK3R2): c.1117G>A (p.Gly373Arg) | PIK3R2 |
| 62508588 | 15630 | NM_000277.1(PAH): c.728G>A (p.Arg243Gln) | PAH |
| 62637014 | 20604 | NM_014336.4(AIPL1): c.834G>A (p.Trp278Ter) | AIPL1 |
| 80356860 | 46194 | NM_007294.3(BRCA1): c.5117G>A (p.Gly1706Glu) | BRCA1 |
| 80357268 | 70265 | NM_007294.3(BRCA1): c.5497G>A (p.Val1833Met) | BRCA1 |
| 80357418 | 70077 | NM_007294.3(BRCA1): c.5136G>A (p.Trp1712Ter) | BRCA1 |
| 80358145 | 46229 | NM_007294.3(BRCA1): c.5467+1G>A | BRCA1 |
| 121918166 | 15994 | NM_000275.2(OCA2): c.1327G>A (p.Val443Ile) | OCA2 |
| 140342925 | 150591 | NM_001128425.1(MUTYH): c.734G>A (p.Arg245His) | MUTYH |
| 148660051 | 195093 | NM_206933.2(USH2A): c.10073G>A (p.Cys3358Tyr) | USH2A |
| 193922672 | 45341 | NM_004572.3(PKP2): c.1613G>A (p.Trp538Ter) | PKP2 |
| 267607144 | 20039 | NM_021625.4(TRPV4): c.806G>A (p.Arg269His) | TRPV4 |
| 397516083 | 51977 | NM_000256.3(MYBPC3): c.927-9G>A | MYBPC3 |
| 397516357 | 52565 | NM_000363.4(TNNI3): c.557G>A (p.Arg186Gln) | TNNI3 |
| 587782958 | 165560 | NM_000256.3(MYBPC3): c.3190+5G>A | MYBPC3 |
| 28934907 | 26853 | NM_004992.3(MECP2): c.316C>T (p.Arg106Trp) | MECP2 |

TABLE 34-continued

Disease Targets for Base Editing

| RS# | Allele ID | Name | GeneSymbol |
|---|---|---|---|
| 28934908 | 26862 | NM_004992.3(MECP2): c.419C>T (p.Ala140Val) | MECP2 |
| 28940893 | 18091 | NM_000487.5(ARSA): c.1283C>T (p.Pro428Leu) | ARSA |
| 63751422 | 96795 | NM_000535.5(PMS2): c.1927C>T (p.Gln643Ter) | PMS2 |
| 74315366 | 27817 | NM_003000.2(SDHB): c.268C>T (p.Arg90Ter) | SDHB |
| 80338856 | 34127 | NM_001360.2(DHCR7): c.724C>T (p.Arg242Cys) | DHCR7 |
| 80357038 | 69707 | NM_007294.3(BRCA1): c.3895C>T (p.Gln1299Ter) | BRCA1 |
| 80357136 | 69535 | NM_007294.3(BRCA1): c.3403C>T (p.Gln1135Ter) | BRCA1 |
| 80357208 | 69682 | NM_007294.3(BRCA1): c.3817C>T (p.Gln1273Ter) | BRCA1 |
| 80357234 | 69166 | NM_007294.3(BRCA1): c.220C>T (p.Gln74Ter) | BRCA1 |
| 80357262 | 69729 | NM_007294.3(BRCA1): c.3967C>T (p.Gln1323Ter) | BRCA1 |
| 80357305 | 69822 | NM_007294.3(BRCA1): c.4258C>T (p.Gln1420Ter) | BRCA1 |
| 80357350 | 69232 | NM_007294.3(BRCA1): c.241C>T (p.Gln81Ter) | BRCA1 |
| 104894636 | 20147 | NM_000199.3(SGSH): c.220C>T (p.Arg74Cys) | SGSH |
| 111401431 | 44742 | NM_000138.4(FBN1): c.4588C>T (p.Arg1530Cys) | FBN1 |
| 121918624 | 27928 | NM_006920.5(SCN1A): c.664C>T (p.Arg222Ter) | SCN1A |
| 137852981 | 19794 | NM_014795.3(ZEB2): c.2083C>T (p.Arg695Ter) | ZEB2 |
| 137854476 | 31491 | NM_000138.4(FBN1): c.1585C>T (p.Arg529Ter) | FBN1 |
| 137854480 | 31500 | NM_000138.4(FBN1): c.718C>T (p.Arg240Cys) | FBN1 |
| 180177100 | 133574 | NM_024675.3(PALB2): c.1240C>T (p.Arg414Ter) | PALB2 |
| 193922109 | 44392 | NM_000053.3(ATP7B): c.3955C>T (p.Arg1319Ter) | ATP7B |
| 200640585 | 96857 | NM_000535.6(PMS2): c.943C>T (p.Arg315Ter) | PMS2 |
| 201431517 | 48426 | NM_139242.3(MTFMT): c.626C>T (p.Ser209Leu) | MTFMT |
| 397516037 | 51905 | NM_000256.3(MYBPC3): c.3697C>T (p.Gln1233Ter) | MYBPC3 |
| 587780104 | 133350 | NM_002878.3(RAD51D): c.694C>T (p.Arg232Ter) | RAD51D |
| 765123255 | 181726 | NM_001128425.1(MUTYH): c.325C>T (p.Arg109Trp) | MUTYH |
| 63751657 | 95331 | NM_000249.3(MLH1): c.1731G>A (p.Ser577=) | MLH1 |
| 75549581 | 22162 | NM_000492.3(CFTR): c.1675G>A (p.Ala559Thr) | CFTR |
| 80338851 | 16303 | NM_194318.3(B3GLCT): c.660+1G>A | B3GLCT |
| 80358544 | 46368 | NM_000059.3(BRCA2): c.2979G>A (p.Trp993Ter) | BRCA2 |
| 111033178 | 52388 | NM_000260.3(MYO7A): c.3719G>A (p.Arg1240Gln) | MYO7A |
| 121908188 | 19535 | NM_020451.2(SELENON): c.943G>A (p.Gly315Ser) | SELENON |
| 139770721 | 180483 | NM_000051.3(ATM): c.6095G>A (p.Arg2032Lys) | ATM |
| 199476315 | 40542 | NM_001018005.1(TPM1): c.574G>A (p.Glu192Lys) | TPM1 |
| 267607004 | 15310 | NM_001134363.2(RBM20): c.1907G>A (p.Arg636His) | RBM20 |
| 267608122 | 94980 | NM_000179.2(MSH6): c.4001G>A (p.Arg1334Gln) | MSH6 |
| 377349459 | 150947 | NM_000051.3(ATM): c.7913G>A (p.Trp2638Ter) | ATM |
| 387906303 | 18745 | NM_000527.4(LDLR): c.670G>A (p.Asp224Asn) | LDLR |
| 587779227 | 94719 | NM_000179.2(MSH6): c.2057G>A (p.Gly686Asp) | MSH6 |
| 587780290 | 134019 | NM_000070.2(CAPN3): c.2243G>A (p.Arg748Gln) | CAPN3 |
| 727504317 | 49251 | NM_002755.3(MAP2K1): c.199G>A (p.Asp67Asn) | MAP2K1 |
| 5030869 | 25402 | NM_000402.4(G6PD): c.1093G>A (p.Ala365Thr) | G6PD |
| 9332964 | 18390 | NM_000348.3(SRD5A2): c.680G>A (p.Arg227Gln) | SRD5A2 |
| 36211723 | 45266 | NM_000256.3(MYBPC3): c.2308G>A (p.Asp770Asn) | MYBPC3 |
| 72549410 | 78547 | NM_000335.4(SCN5A): c.1231G>A (p.Val411Met) | SCN5A |
| 80357498 | 45948 | NM_007294.3(BRCA1): c.116C>A (p.Cys39Tyr) | BRCA1 |
| 80358079 | 70118 | NM_007294.3(BRCA1): c.5194-12G>A | BRCA1 |
| 121434529 | 33201 | NM_000262.2(NAGA): c.973G>A (p.Glu325Lys) | NAGA |
| 121908627 | 21067 | NM_005476.5(GNE): c.2086G>A (p.Val696Met) | GNE |
| 387906592 | 38552 | NM_001613.2(ACTA2): c.536G>A (p.Arg179His) | ACTA2 |
| 397515907 | 51711 | NM_000256.3(MYBPC3): c.1505G>A (p.Arg502Gln) | MYBPC3 |
| 397516089 | 51992 | NM_000257.4(MYH7): c.1106G>A (p.Arg369Gln) | MYH7 |
| 397516248 | 52239 | NM_000257.4(MYH7): c.5401G>A (p.Glu1801Lys) | MYH7 |
| 397516349 | 52554 | NM_000363.4(TNNI3): c.434G>A (p.Arg145Gln) | TNNI3 |
| 5030846 | 15627 | NM_000277.3(PAH): c.727C>T (p.Arg243Ter) | PAH |
| 28941784 | 18134 | NM_052845.3(MMAB): c.556C>T (p.Arg186Trp) | MMAB |
| 34126013 | 181693 | NM_001128425.1(MUTYH): c.721C>T (p.Arg241 Trp) | MUTYH |
| 62541771 | 21074 | NM_001128227.2(GNE): c.1985C>T (p.Ala662Val) | GNE |
| 62625303 | 68931 | NM_007294.3(BRCA1): c.1471C>T (p.Gln491Ter) | BRCA1 |
| 74315379 | 27453 | NM_001001430.2(TNNT2): c.421C>T (p.Arg141Trp) | TNNT2 |
| 76687508 | 108539 | NM_000277.3(PAH): c.721C>T (p.Arg241Cys) | PAH |
| 80338794 | 20654 | NM_012434.4(SLC17A5): c.115C>T (p.Arg39Cys) | SLC17A5 |
| 80356866 | 69689 | NM_007294.3(BRCA1): c.3841C>T (p.Gln1281Ter) | BRCA1 |
| 80357134 | 69569 | NM_007294.3(BRCA1): c.34C>T (p.Gln12Ter) | BRCA1 |
| 80357229 | 69904 | NM_007294.3(BRCA1): c.4609C>T (p.Gln1537Ter) | BRCA1 |
| 111033260 | 19972 | NM_033056.3(PCDH15): c.733C>T (p.Arg245Ter) | PCDH15 |
| 121909398 | 17403 | NM_201548.4(CERKL): c.769C>T (p.Arg257Ter) | CERKL |
| 121913637 | 29143 | NM_000257.4(MYH7): c.2155C>T (p.Arg719Trp) | MYH7 |
| 200495564 | 50200 | NM_001128425.1(MUTYH): c.733C>T (p.Arg245Cys) | MUTYH |
| 267607203 | 20760 | NM_194456.1(KRIT1): c.1363C>T (p.Gln455Ter) | KRIT1 |
| 587776527 | 132239 | NM_024675.3(PALB2): c.3256C>T (p.Arg1086Ter) | PALB2 |
| 587777219 | 125784 | NM_172107.3(KCNQ2): c.794C>T (p.Ala265Val) | KCNQ2 |
| 587778617 | 96774 | NM_000535.5(PMS2): c.1261C>T (p.Arg421Ter) | PMS2 |
| 587783057 | 166274 | NM_001128425.1(MUTYH): c.1171C>T (p.Gln391Ter) | MUTYH |
| 730880099 | 178699 | NM_000138.4(FBN1): c.1633C>T (p.Arg545Cys) | FBN1 |

TABLE 34-continued

Disease Targets for Base Editing

| RS# | Allele ID | Name | GeneSymbol |
|---|---|---|---|
| 2309689 | 33868 | NM 000018.3(ACADVL): c.1322G>A (p.Gly441Asp) | ACADVL |
| 28933093 | 29543 | NM 170707.3(LMNA): c.481G>A (p.Glu161Lys) | LMNA |
| 28937873 | 20571 | NM_014249.3(NR2E3): c.932G>A (p.Arg311Gln) | NR2E3 |
| 59332535 | 77828 | NM_170707.3(LMNA): c.746G>A (p.Arg249Gln) | LMNA |
| 62645748 | 48213 | NM_201253.2(CRB1): c.2843G>A (p.Cys948Tyr) | CRB1 |
| 63750828 | 96748 | NM_000251.2(MSH2): c.998G>A (p.Cys333Tyr) | MSH2 |
| 80358456 | 65843 | NM_000059.3(BRCA2): c.1689G>A (p.Trp563Ter) | BRCA2 |
| 80359101 | 67273 | NM_000059.3(BRCA2): c.8489G>A (p.Trp2830Ter) | BRCA2 |
| 80359148 | 131733 | NM_000059.3(BRCA2): c.8969G>A (p.Trp2990Ter) | BRCA2 |
| 80359149 | 67384 | NM_000059.3(BRCA2): c.8970G>A (p.Trp2990Ter) | BRCA2 |
| 80359211 | 46791 | NM 000059.3(BRCA2): c.9380G>A (p.Trp3127Ter) | BRCA2 |
| 111033565 | 26915 | NM 002769.4(PRSS1): c.365G>A (p.Arg122His) | PRSS1 |
| 113994205 | 19482 | NM 004937.2(CTNS): c.414G>A (p.Trp138Ter) | CTNS |
| 116840778 | 23322 | NM 033337.2(CAV3): c.80G>A (p.Arg27Gln) | CAV3; SSUH2 |
| 118192158 | 76835 | NM 000540.2(RYR1): c.14818G>A (p.Ala4940Thr) | RYR1 |
| 121434278 | 18633 | NM_000016.5(ACADM): c.583G>A (p.Gly195Arg) | ACADM |
| 121434346 | 17058 | NM_001003841.2(SLC6A19): c.517G>A (p.Asp173Asn) | SLC6A19 |
| 121908011 | 18814 | NM_000372.4(TYR): c.1147G>A (p.Asp383Asn) | TYR |
| 121908638 | 21365 | NM_000050.4(ASS1): c.539G>A (p.Ser180Asn) | ASS1 |
| 121912938 | 32219 | NM_001848.2(COL6A1): c.850G>A (p.Gly284Arg) | COL6A1 |
| 137853096 | 22694 | NM_000414.3(HSD17B4): c.46G>A (p.Gly16Ser) | HSD17B4 |
| 151344631 | 45847 | NM_000218.2(KCNQ1): c.613G>A (p.Val205Met) | KCNQ1 |
| 192838388 | 98283 | NM_000050.4(ASS1): c.787G>A (p.Val263Met) | ASS1 |
| 267607768 | 95759 | NM 000249.3(MLH1): c.588+5G>A | MLH1 |
| 376107921 | 213634 | NM 000070.2(CAPN3): c.1319G>A (p.Arg440Gln) | CAPN3 |
| 397507981 | 67234 | NM 000059.3(BRCA2): c.8364G>A (p.Trp2788Ter) | BRCA2 |
| 398124321 | 101692 | NM 017780.3(CHD7): c.5405-7G>A | CHD7 |
| 730882246 | 181441 | NM_194279.3(ISCA2): c.229G>A (p.Gly77Ser) | ISCA2 |
| 778906552 | 195186 | NM_000016.5(ACADM): c.443G>A (p.Arg148Lys) | ACADM |
| 139428292 | 39421 | NM_005105.4(RBM8A): c.- 21G>A | RBM8A |
| 28934891 | 15165 | NM_000071.2(CBS): c.1330G>A (p.Asp444Asn) | CBS |
| 28937316 | 24408 | NM_198056.2(SCN5A): c.4931G>A (p.Arg1644His) | SCN5A |
| 33930165 | 30165 | NM_000518.4(HBB): c.19G>A (p.Glu7Lys) | HBB |
| 35004220 | 30493 | NM 000518.5(HBB): c.-93-21G>A | HBB |
| 45546039 | 48043 | NM 198056.2(SCN5A): c.665G>A (p.Arg222Gln) | SCN5A |
| 61751402 | 105177 | NM 000350.2(ABCA4): c.4469G>A (p.Cys1490Tyr) | ABCA4 |
| 72549387 | 22776 | NM 000104.3(CYP1B1): c.171G>A (p.Trp57Ter) | CYP1B1 |
| 75822236 | 19350 | NM 000157.3(GBA): c.1604G>A (p.Arg535His) | GBA |
| 79389353 | 20821 | NM 014270.4(SLC7A9): c.544G>A (p.Ala182Thr) | SLC7A9 |
| 80338862 | 34124 | NM_001360.2(DHCR7): c.1228G>A (p.Gly410Ser) | DHCR7 |
| 80338892 | 27366 | NM_199292.2(TH): c.698G>A (p.Arg233His) | TH |
| 80356935 | 68777 | NM_007294.3(BRCA1): c.1059G>A (p.Trp353Ter) | BRCA1 |
| 80357468 | 68802 | NM_007294.3(BRCA1): c.1116G>A (p.Trp372Ter) | BRCA1 |
| 104894365 | 27628 | NM_004985.4(KRAS): c.40G>A (p.Val14Ile) | KRAS |
| 104894639 | 20153 | NM_000199.3(SGSH): c.1339G>A (p.Glu447Lys) | SGSH |
| 111033364 | 17396 | NM_206933.2(USH2A): c.11864G>A (p.Trp3955Ter) | USH2A |
| 119103251 | 17338 | NM_005609.3(PYGM): c.613G>A (p.Gly205Ser) | PYGM |
| 119455954 | 17681 | NM 000391.3(TPP1): c.1094G>A (p.Cys365Tyr) | TPP1 |
| 121913638 | 29144 | NM 000257.4(MYH7): c.2146G>A (p.Gly716Arg) | MYH7 |
| 137854478 | 31496 | NM 000138.4(FBN1): c.3217G>A (p.Glu1073Lys) | FBN1 |
| 143353451 | 179937 | NM 001128425.1(MUTYH): c.545G>A (p.Arg182His) | MUTYH |
| 151045328 | 20182 | NM 005709.3(USH1C): c.216G>A (p.Val72=) | USH1C |
| 151344623 | 24127 | NM_001287174.1(ABCC8): c.3992-9G>A | ABCC8 |
| 193922204 | 44739 | NM_000138.4(FBN1): c.4460-8G>A | FBN1 |
| 193922219 | 51564 | NM_000138.4(FBN1): c.5788+5G>A | FBN1 |
| 193922680 | 33370 | NM_005159.4(ACTC1): c.301G>A (p.Glu101Lys) | ACTC1 |
| 267608172 | 96804 | NM_000535.5(PMS2): c.2174+1G>A | PMS2 |
| 397516202 | 52163 | NM_000257.4(MYH7): c.4135G>A (p.Ala1379Thr) | MYH7 |
| 397516209 | 52176 | NM 000257.4(MYH7): c.428G>A (p.Arg143Gln) | MYH7 |
| 397517159 | 49176 | NM 005633.3(SOS1): c.2536G>A (p.Glu846Lys) | SOS1 |
| 587776576 | 18532 | NM 024426.5(WT1): c.1447+5G>A | WT1 |
| 727503246 | 175600 | NM 000257.4(MYH7): c.4066G>A (p.Glu1356Lys) | MYH7 |
| 730881687 | 181107 | NM 007194.4(CHEK2): c.793-1G>A | CHEK2 |
| 748170941 | 181727 | NM_001128425.1(MUTYH): c.309G>A (p.Trp103Ter) | MUTYH |
| 140583 | 260073 | NM_000138.4(FBN1): c.2581C>T (p.Arg861Ter) | FBN1 |
| 2754158 | 175617 | NM_000257.3(MYH7): c.2572C>T (p.Arg858Cys) | MYH7 |
| 28931570 | 33013 | NM_001127701.1(SERPINA1): c.187C>T (p.Arg63Cys) | SERPINA1 |
| 34424986 | 22089 | NM_004562.2(PRKN): c.823C>T (p.Arg275Trp) | PRKN |
| 61750130 | 22943 | NM_000350.2(ABCA4): c.4139C>T (p.Pro1380Leu) | ABCA4 |
| 61750200 | 22937 | NM_000350.2(ABCA4): c.634C>T (p.Arg212Cys) | ABCA4 |
| 63750451 | 24281 | NM_000535.5(PMS2): c.1882C>T (p.Arg628Ter) | PMS2 |
| 72653706 | 21598 | NM 001171.5(ABCC6): c.3421C>T (p.Arg1141Ter) | ABCC6 |
| 74503222 | 108557 | NM 000277.3(PAH): c.745C>T (p.Leu249Phe) | PAH |
| 76296470 | 15620 | NM 000277.3(PAH): c.331C>T (p.Arg111Ter) | PAH |

TABLE 34-continued

Disease Targets for Base Editing

| RS# | Allele ID | Name | GeneSymbol |
|---|---|---|---|
| 80338860 | 21826 | NM_001360.2(DHCR7): c.1054C>T (p.Arg352Trp) | DHCR7 |
| 80356682 | 29578 | NM_000228.2(LAMB3): c.1903C>T (p.Arg635Ter) | LAMB3 |
| 80356771 | 19334 | NM_001005741.2(GBA): c.1504C>T (p.Arg502Cys) | GBA |
| 80356904 | 68978 | NM_007294.3(BRCA1): c.1621C>T (p.Gln541Ter) | BRCA1 |
| 80356932 | 69850 | NM_007294.3(BRCA1): c.4372C>T (p.Gln1458Ter) | BRCA1 |
| 80356947 | 70087 | NM_007294.3(BRCA1): c.514C>T (p.Gln172Ter) | BRCA1 |
| 80356992 | 69906 | NM_007294.3(BRCA1): c.4612C>T (p.Gln1538Ter) | BRCA1 |
| 80357133 | 70034 | NM_007294.3(BRCA1): c.505C>T (p.Gln169Ter) | BRCA1 |
| 80357215 | 68781 | NM_007294.3(BRCA1): c.1066C>T (p.Gln356Ter) | BRCA1 |
| 104894419 | 22712 | NM_002312.3(LIG4): c.2440C>T (p.Arg814Ter) | LIG4 |
| 113871094 | 44746 | NM_000138.4(FBN1): c.4786C>T (p.Arg1596Ter) | FBN1 |
| 118203682 | 58105 | NM_000368.4(TSC1): c.2356C>T (p.Arg786Ter) | TSC1 |
| 121908177 | 19611 | NM_031885.3(BBS2): c.823C>T (p.Arg275Ter) | BBS2 |
| 121908715 | 16998 | NM_000022.2(ADA): c.986C>T (p.Ala329Val) | ADA |
| 121909122 | 22411 | NM_001083962.1(TCF4): c.1153C>T (p.Arg385Ter) | TCF4 |
| 121917901 | 16740 | NM_000124.3(ERCC6): c.2203C>T (p.Arg735Ter) | ERCC6 |
| 121964964 | 15158 | NM_000071.2(CBS): c.341C>T (p.Ala114Val) | CBS |
| 137852924 | 18422 | NM_147127.4(EVC2): c.1195C>T (p.Arg399Ter) | EVC2 |
| 137854466 | 31478 | NM_000138.4(FBN1): c.8326C>T (p.Arg2776Ter) | FBN1 |
| 137854467 | 31479 | NM_000138.4(FBN1): c.364C>T (p.Arg122Cys) | FBN1 |
| 137854604 | 24422 | NM_000335.4(SCN5A): c.5126C>T (p.Ser1709Leu) | SCN5A |
| 150518260 | 51200 | NM_000232.4(SGCB): c.341C>T (p.Ser114Phe) | SGCB |
| 200432447 | 133521 | NM_007194.4(CHEK2): c.1555C>T (p.Arg519Ter) | CHEK2 |
| 201587138 | 176561 | NM_144612.6(LOXHD1): c.4480C>T (p.Arg1494Ter) | LOXHD1 |
| 367543286 | 70502 | NM_002609.3(PDGFRB): c.1681C>T (p.Arg561Cys) | PDGFRB |
| 372827156 | 54183 | NM_004572.3(PKP2): c.1237C>T (p.Arg413Ter) | PKP2 |
| 374950566 | 181683 | NM_001128425.1(MUTYH): c.884C>T (p.Pro295Leu) | MUTYH |
| 397514558 | 48266 | NM_000138.4(FBN1): c.2920C>T (p.Arg974Cys) | FBN1 |
| 397515992 | 51839 | NM_000256.3(MYBPC3): c.2905C>T (p.Gln969Ter) | MYBPC3 |
| 397516456 | 52796 | NM_000364.3(TNNT2): c.304C>T (p.Arg102Trp) | TNNT2 |
| 587780082 | 133292 | NM_001128425.1(MUTYH): c.1012C>T (p.Gln338Ter) | MUTYH |
| 587782705 | 152480 | NM_000546.5(TP53): c.455C>T (p.Pro152Leu) | TP53 |
| 727503974 | 177432 | NM_172107.3(KCNQ2): c.821C>T (p.Thr274Met) | KCNQ2 |
| 730881864 | 180279 | NM_002485.4(NBN): c.2140C>T (p.Arg714Ter) | NBN |
| 767215758 | 188057 | NM_002485.4(NBN): c.1030C>T (p.Gln344Ter) | NBN |
| 45517259 | 27442 | NM_000548.3(TSC2): c.2714G>A (p.Arg905Gln) | TSC2 |
| 61195471 | 57234 | NM_170707.3(LMNA): c.607G>A (p.Glu203Lys) | LMNA |
| 61753185 | 18815 | NM_000372.4(TYR): c.230G>A (p.Arg77Gln) | TYR |
| 63749869 | 28021 | NM_000540.2(RYR1): c.14582G>A (p.Arg4861His) | RYR1 |
| 63749939 | 32145 | NM_000249.3(MLH1): c.200G>A (p.Gly67Glu) | MLH1 |
| 63750119 | 150580 | NM_000179.2(MSH6): c.3725G>A (p.Arg1242His) | MSH6 |
| 72554308 | 26053 | NM_000531.5(OTC): c.119G>A (p.Arg40His) | OTC |
| 79891110 | 32671 | NM_000719.6(CACNA1C): c.1216G>A (p.Gly406Arg) | CACNA1C |
| 80338707 | 22758 | NM_000303.2(PMM2): c.691G>A (p.Val231Met) | PMM2 |
| 80338802 | 32652 | NM_000070.2(CAPN3): c.2306G>A (p.Arg769Gln) | CAPN3 |
| 80356700 | 32571 | NM_000083.2(CLCN1): c.689G>A (p.Gly230Glu) | CLCN1 |
| 80359803 | 67339 | NM_000059.3(BRCA2): c.8754G>A (p.Glu2918=) | BRCA2 |
| 81002809 | 67078 | NM_000059.3(BRCA2): c.7805+1G>A | BRCA2 |
| 104886142 | 35796 | NM_000495.4(COL4A5): c.1871G>A (p.Gly624Asp) | COL4A5 |
| 104894423 | 17048 | NM_000231.2(SGCG): c.787G>A (p.Glu263Lys) | SGCG |
| 104894525 | 22747 | NM_000303.2(PMM2): c.385G>A (p.Val129Met) | PMM2 |
| 113994049 | 20984 | NM_003907.3(EIF2B5): c.338G>A (p.Arg113His) | EIF2B5 |
| 121434372 | 17127 | NM_000159.3(GCDH): c.1198G>A (p.Val400Met) | GCDH |
| 121908099 | 19299 | NM_000784.3(CYP27A1): c.1214G>A (p.Arg405Gln) | CYP27A1 |
| 121908192 | 23730 | NM_005262.2(GFER): c.581G>A (p.Arg194His) | GFER |
| 121908753 | 22237 | NM_000492.3(CFTR): c.1055G>A (p.Arg352Gln) | CFTR |
| 121918013 | 28716 | NM_000478.4(ALPL): c.346G>A (p.Ala116Thr) | ALPL |
| 139729994 | 68418 | NM_000492.3(CFTR): c.3468G>A (p.Leu1156=) | CFTR |
| 142637046 | 98272 | NM_000048.3(ASL): c.446+1G>A | ASL |
| 142761835 | 177782 | NM_002225.3(IVD): c.367G>A (p.Gly123Arg) | IVD |
| 146015592 | 46845 | NM_000060.4(BTD): c.470G>A (p.Arg157His) | BTD |
| 150877497 | 226470 | NM_003494.3(DYSF): c.3113G>A (p.Arg1038Gln) | DYSF |
| 199472815 | 67686 | NM_000218.2(KCNQ1): c.1781G>A (p.Arg594Gln) | KCNQ1 |
| 199474738 | 79199 | NM_001042492.2(NF1): c.1885G>A (p.Gly629Arg) | NF1 |
| 199476112 | 24747 | NC_012920.1: m.11778G>A | MT-ND4 |
| 199476317 | 40544 | NM_001018005.1(TPM1): c.688G>A (p.Asp230Asn) | TPM1 |
| 201540674 | 51186 | RTEL1: c.2402G>A (p.Arg801His) | RTEL1 |
| 267606640 | 16147 | NM_000642.2(AGL): c.3980G>A (p.Trp1327Ter) | AGL |
| 386834233 | 76679 | NM_183050.3(BCKDHB): c.832G>A (p.Gly278Ser) | BCKDHB |
| 397515355 | 19301 | NM_000784.3(CYP27A1): c.1263+1G>A | CYP27A1 |
| 397515404 | 48194 | NM_020822.2(KCNT1): c.1421G>A (p.Arg474His) | KCNT1 |
| 398123787 | 100221 | NM_003494.3(DYSF): c.4253G>A (p.Gly1418Asp) | DYSF |
| 398124641 | 44139 | NM_024531.4(SLC52A2): c.916G>A (p.Gly306Arg) | SLC52A2 |
| 587776783 | 132342 | NM_000321.2(RB1): c.1215+1G>A | RB1 |

TABLE 34-continued

Disease Targets for Base Editing

| RS# | Allele ID | Name | GeneSymbol |
|---|---|---|---|
| 587776889 | 39757 | NM_015506.2(MMACHC): c.609G>A (p.Trp203Ter) | MMACHC |
| 587777721 | 165903 | NM_014191.3(SCN8A): c.4850G>A (p.Arg1617Gln) | SCN8A |
| 587779818 | 132798 | NM_000051.3(ATM): c.170G>A (p.Trp57Ter) | ATM |
| 587780537 | 136457 | NM_004360.4(CDH1): c.715G>A (p.Gly239Arg) | CDH1 |
| 587783050 | 166264 | NM_004360.5(CDH1): c.1137G>A (p.Thr379=) | CDH1 |
| 751995154 | 200340 | NM_000018.4(ACADVL): c.1376G>A (p.Arg459Gln) | ACADVL |
| 781404312 | 186796 | NM_000051.3(ATM): c.3G>A (p.Met1Ile) | ATM |
| 786202112 | 184694 | NM_001042492.2(NF1): c.5609G>A (p.Arg1870Gln) | NF1 |
| 794727152 | 191718 | NM_021007.2(SCN2A): c.2558G>A (p.Arg853Gln) | SCN2A |
| 796051858 | 18086 | NM_000051.3(ATM): c.496+5G>A | ATM |
| 796052505 | 201880 | NM_000816.3(GABRG2): c.316G>A (p.Ala106Thr) | GABRG2 |
| 863223408 | 210238 | NM_000020.2(ACVRL1): c.1451G>A (p.Arg484Gln) | ACVRL1 |
| 863225082 | 188114 | NM_006245.3(PPP2R5D): c.592G>A (p.Glu198Lys) | PPP2R5D |
| 875989911 | 228151 | NM_000527.4(LDLR): c.938G>A (p.Cys313Tyr) | LDLR |
| 5030852 | 15638 | NM_000277.3(PAH): c.842+1G>A | PAH |
| 5030859 | 15651 | NM_000277.3(PAH): c.1223G>A (p.Arg408Gln) | PAH |
| 28930068 | 32662 | NM_000069.2(CACNA1S): c.3716G>A (p.Arg1239His) | CACNA1S |
| 56264519 | 55267 | NM_024022.2(TMPRSS3): c.1276G>A (p.Ala426Thr) | TMPRSS3 |
| 61750641 | 105317 | NM_000350.2(ABCA4): c.6089G>A (p.Arg2030Gln) | ABCA4 |
| 61751276 | 104715 | NM_000329.2(RPE65): c.11+5G>A | RPE65 |
| 62507336 | 108472 | NM_000277.3(PAH): c.561G>A (p.Trp187Ter) | PAH |
| 62508613 | 108291 | NM_000277.2(PAH): c.1199+17G>A | PAH |
| 72645357 | 32351 | NM_000088.3(COL1A1): c.994G>A (p.Gly332Arg) | COL1A1 |
| 80338777 | 32664 | NM_000069.2(CACNA1S): c.1583G>A (p.Arg528His) | CACNA1S |
| 80356908 | 68776 | NM_007294.3(BRCA1): c.1058G>A (p.Trp353Ter) | BRCA1 |
| 80357093 | 69031 | NM_007294.3(BRCA1): c.182G>A (p.Cys61Tyr) | BRCA1 |
| 80357219 | 70211 | NM_007294.3(BRCA1): c.5345G>A (p.Trp1782Ter) | BRCA1 |
| 104886460 | 99352 | NM_001005741.2(GBA): c.115+1G>A | GBA |
| 104894129 | 27501 | NM_003289.3(TPM2): c.349G>A (p.Glu117Lys) | TPM2 |
| 104894401 | 32056 | NM_004004.5(GJB2): c.428G>A (p.Arg143Gln) | GJB2 |
| 104895085 | 17592 | NM_000243.2(MEFV): c.1958G>A (p.Arg653His) | MEFV |
| 111033299 | 53902 | NM_004004.5(GJB2): c.283G>A (p.Val95Met) | GJB2 |
| 113994139 | 33347 | NM_139276.2(STAT3): c.1909G>A (p.Val637Met) | STAT3 |
| 120074135 | 18010 | NM_000271.4(NPC1): c.2848G>A (p.Val950Met) | NPC1 |
| 121909334 | 23512 | NM_007126.4(VCP): c.572G>A (p.Arg191Gln) | VCP |
| 121918491 | 28307 | NM_000141.4(FGFR2): c.1032G>A (p.Ala344=) | FGFR2 |
| 137852314 | 25406 | NM_000402.4(G6PD): c.577G>A (p.Gly193Ser) | G6PD |
| 137852327 | 25425 | NM_000402.4(G6PD): c.961G>A (p.Val321Met) | G6PD |
| 137853285 | 166061 | NM_000053.3(ATP7B): c.2128G>A (p.Gly710Ser) | ATP7B |
| 138213197 | 133488 | NM_006361.5(HOXB13): c.251G>A (p.Gly84Glu) | HOXB13 |
| 148311934 | 44907 | NM_000162.5(GCK): c.676G>A (p.Val226Met) | GCK |
| 199473684 | 25807 | NM_000169.2(GLA): c.639+919G>A | GLA |
| 200482683 | 131950 | NM_014625.3(NPHS2): c.868G>A (p.Val290Met) | NPHS2 |
| 371418985 | 232124 | NM_007194.4(CHEK2): c.1232G>A (p.Trp411Ter) | CHEK2 |
| 387907281 | 45778 | NM_152296.4(ATP1A3): c.2443G>A (p.Glu815Lys) | ATP1A3 |
| 397509284 | 70248 | NM_007294.3(BRCA1): c.5445G>A (p.Trp1815Ter) | BRCA1 |
| 397514495 | 152034 | NM_000546.5(TP53): c.542G>A (p.Arg181His) | TP53 |
| 397514581 | 48359 | NM_172107.3(KCNQ2): c.638G>A (p.Arg213Gln) | KCNQ2 |
| 397516101 | 52008 | NM_000257.4(MYH7): c.1358G>A (p.Arg453His) | MYH7 |
| 397516264 | 52270 | NM_000257.3(MYH7): c.715G>A (p.Asp239Asn) | MYH7 |
| 398122822 | 48057 | NM_001111.5(ADAR): c.3019G>A (p.Gly1007Arg) | ADAR |
| 587777446 | 141325 | NM_022168.4(IFIH1): c.2336G>A (p.Arg779His) | IFIH1 |
| 587782962 | 165566 | NM_000257.4(MYH7): c.3158G>A (p.Arg1053Gln) | MYH7 |
| 606231435 | 170985 | NM_152296.4(ATP1A3): c.2267G>A (p.Arg756His) | ATP1A3 |
| 727504247 | 172354 | NM_001001430.2(TNNT2): c.860G>A (p.Trp287Ter) | TNNT2 |
| 730881833 | 179933 | NM_001128425.1(MUTYH): c.857G>A (p.Gly286Glu) | MUTYH |
| 762307622 | 232266 | NM_001128425.1(MUTYH): c.467G>A (p.Trp156Ter) | MUTYH |
| 777759523 | 17038 | NM_199242.2(UNC13D): c.1389+1G>A | UNC13D |
| 794728625 | 197538 | NM_130799.2(MEN1): c.784-9G>A | MEN1 |
| 1060499814 | 389282 | NM_024675.3(PALB2): c.108+1G>A | PALB2 |
| 25403 | 51465 | NM_000138.4(FBN1): c.184C>T (p.Arg62Cys) | FBN1 |
| 28931591 | 32539 | NM_000744.6(CHRNA4): c.851C>T (p.Ser284Leu) | CHRNA4 |
| 28942108 | 18015 | NM_000271.4(NPC1): c.2932C>T (p.Arg978Cys) | NPC1 |
| 61750152 | 105192 | NM_000350.2(ABCA4): c.4577C>T (p.Thr1526Met) | ABCA4 |
| 61750654 | 105349 | NM_000350.2(ABCA4): c.6445C>T (p.Arg2149Ter) | ABCA4 |
| 61751404 | 105219 | NM_000350.2(ABCA4): c.4918C>T (p.Arg1640Trp) | ABCA4 |
| 61751408 | 22921 | NM_000350.2(ABCA4): c.6079C>T (p.Leu2027Phe) | ABCA4 |
| 63751466 | 24276 | NM_000535.5(PMS2): c.2404C>T (p.Arg802Ter) | PMS2 |
| 72552255 | 44374 | NM_000053.3(ATP7B): c.2930C>T (p.Thr977Met) | ATP7B |
| 74315369 | 27822 | NM_003000.2(SDHB): c.79C>T (p.Arg27Ter) | SDHB |
| 80338680 | 16726 | NM_000528.3(MAN2B1): c.2248C>T (p.Arg750Trp) | MAN2B1 |
| 80356952 | 68980 | NM_007294.3(BRCA1): c.1630C>T (p.Gln544Ter) | BRCA1 |
| 80357011 | 69802 | NM_007294.3(BRCA1): c.4186C>T (p.Gln1396Ter) | BRCA1 |
| 80357296 | 69580 | NM_007294.3(BRCA1): c.3544C>T (p.Gln1182Ter) | BRCA1 |

TABLE 34-continued

Disease Targets for Base Editing

| RS# | Allele ID | Name | GeneSymbol |
|---|---|---|---|
| 80357367 | 70140 | NM_007294.3(BRCA1): c.5239C>T (p.Gln1747Ter) | BRCA1 |
| 80357377 | 69340 | NM_007294.3(BRCA1): c.2761C>T (p.Gln921Ter) | BRCA1 |
| 80357471 | 69016 | NM_007294.3(BRCA1): c.178C>T (p.Gln60Ter) | BRCA1 |
| 80357497 | 69389 | NM_007294.3(BRCA1): c.2923C>T (p.Gln975Ter) | BRCA1 |
| 104893950 | 18137 | NM_005670.3(EPM2A): c.721C>T (p.Arg241Ter) | EPM2A |
| 104894787 | 26252 | NM_004006.2(DMD): c.10108C>T (p.Arg3370Ter) | DMD |
| 111231312 | 51536 | NM_000138.4(FBN1): c.4615C>T (p.Arg1539Ter) | FBN1 |
| 112645512 | 178700 | NM_000138.4(FBN1): c.1285C>T (p.Arg429Ter) | FBN1 |
| 113001196 | 51577 | NM_000138.4(FBN1): c.6658C>T (p.Arg2220Ter) | FBN1 |
| 113249837 | 51552 | NM_000138.4(FBN1): c.5368C>T (p.Arg1790Ter) | FBN1 |
| 113812345 | 51455 | NM_000138.4(FBN1): c.1546C>T (p.Arg516Ter) | FBN1 |
| 116100695 | 16552 | NM_000298.5(PKLR): c.1456C>T (p.Arg486Trp) | PKLR |
| 118203631 | 58047 | NM_000368.4(TSC1): c.2074C>T (p.Arg692Ter) | TSC1 |
| 118203963 | 16148 | NM_025137.3(SPG11): c.6100C>T (p.Arg2034Ter) | SPG11 |
| 118204437 | 15739 | NM_000512.4(GALNS): c.1156C>T (p.Arg386Cys) | GALNS |
| 121434526 | 33315 | NM_001613.3(ACTA2): c.445C>T (p.Arg149Cys) | ACTA2 |
| 121908547 | 20943 | NM_000334.4(SCN4A): c.3938C>T (p.Thr1313Met) | SCN4A |
| 121912504 | 29459 | NM_000238.3(KCNH2): c.1682C>T (p.Ala561Val) | KCNH2 |
| 121913120 | 31271 | NM_000143.3(FH): c.301C>T (p.Arg101Ter) | FH |
| 121913122 | 31274 | NM_000143.3(FH): c.1027C>T (p.Arg343Ter) | FH |
| 121917783 | 27083 | NM_000136.2(FANCC): c.553C>T (p.Arg185Ter) | FANCC |
| 121918775 | 79496 | NM_006920.4(SCN1A): c.2803C>T (p.Arg935Cys) | SCN1A |
| 121964972 | 15170 | NM_000071.2(CBS): c.1058C>T (p.Thr353Met) | CBS |
| 128627256 | 26327 | NM_004006.2(DMD): c.8713C>T (p.Arg2905Ter) | DMD |
| 137854613 | 24413 | NM_198056.2(SCN5A): c.4867C>T (p.Arg1623Ter) | SCN5A |
| 137886232 | 39244 | NM_002878.3(RAD51D): c.757C>T (p.Arg253Ter) | RAD51D |
| 138996609 | 181608 | NM_003000.2(SDHB): c.688C>T (p.Arg230Cys) | SDHB |
| 144500145 | 202960 | NM_002693.2(POLG): c.2554C>T (p.Arg852Cys) | POLG |
| 180177111 | 132156 | NM_024675.3(PALB2): c.2323C>T (p.Gln775Ter) | PALB2 |
| 185492864 | 99918 | NM_001918.3(DBT): c.901C>T (p.Arg301Cys) | DBT |
| 193922185 | 44706 | NM_000138.4(FBN1): c.1948C>T (p.Arg650Cys) | FBN1 |
| 199472944 | 38732 | NM_000238.3(KCNH2): c.1841C>T (p.Ala614Val) | KCNH2 |
| 199472990 | 78275 | NM_000238.3(KCNH2): c.2254C>T (p.Arg752Trp) | KCNH2 |
| 199473161 | 78626 | NM_198056.2(SCN5A): c.2440C>T (p.Arg814Trp) | SCN5A |
| 199473524 | 78188 | NM_000238.3(KCNH2): c.1838C>T (p.Thr613Met) | KCNH2 |
| 273898674 | 69115 | NM_007294.3(BRCA1): c.2059C>T (p.Gln687Ter) | BRCA1 |
| 368796923 | 151096 | NM_032043.2(BRIP1): c.1240C>T (p.Gln414Ter) | BRIP1 |
| 376128990 | 215031 | NM_052845.3(MMAB): c.571C>T (p.Arg191Trp) | MMAB |
| 397509283 | 70244 | NM_007294.3(BRCA1): c.5431C>T (p.Gln1811Ter) | BRCA1 |
| 397515812 | 51535 | NM_000138.4(FBN1): c.4567C>T (p.Arg1523Ter) | FBN1 |
| 397516005 | 51860 | NM_000256.3(MYBPC3): c.3181C>T (p.Gln1061Ter) | MYBPC3 |
| 397516042 | 51914 | NM_000256.3(MYBPC3): c.3811C>T (p.Arg1271Ter) | MYBPC3 |
| 397516127 | 52044 | NM_000257.3(MYH7): c.1987C>T (p.Arg663Cys) | MYH7 |
| 397516201 | 52162 | NM_000257.4(MYH7): c.4130C>T (p.Thr1377Met) | MYH7 |
| 397516435 | 52758 | NM_000546.5(TP53): c.586C>T (p.Arg196Ter) | TP53 |
| 397517689 | 56466 | NM_001267550.2(TTN): c.71602C>T (p.Arg23868Ter) | TTN |
| 398123585 | 99539 | NM_001165963.1(SCN1A): c.1837C>T (p.Arg613Ter) | SCN1A |
| 549794342 | 360820 | NM_001271208.1(NEB): c.24094C>T (p.Arg8032Ter) | NEB |
| 574660186 | 178478 | NM_001267550.2(TTN): c.67495C>T (p.Arg22499Ter) | TTN |
| 575822089 | 227149 | NM_001163435.2(TBCK): c.376C>T (p.Arg126Ter) | TBCK |
| 587778618 | 138806 | NM_000535.7(PMS2): c.1687C>T (p.Arg563Ter) | PMS2 |
| 587779343 | 96837 | NM_000535.5(PMS2): c.697C>T (p.Gln233Ter) | PMS2 |
| 587780088 | 133302 | NM_001128425.1(MUTYH): c.55C>T (p.Arg19Ter) | MUTYH |
| 587781269 | 150486 | NM_007194.4(CHEK2): c.283C>T (p.Arg95Ter) | CHEK2 |
| 587781756 | 151166 | NM_002878.3(RAD51D): c.451C>T (p.Gln151Ter) | RAD51D |
| 672601370 | 171771 | NM_001244008.1(KIF1A): c.946C>T (p.Arg316Trp) | KIF1A |
| 727505006 | 176130 | NM_000138.4(FBN1): c.3373C>T (p.Arg1125Ter) | FBN1 |
| 794728165 | 197808 | NM_000138.4(FBN1): c.1090C>T (p.Arg364Ter) | FBN1 |
| 794728228 | 197690 | NM_000138.4(FBN1): c.4621C>T (p.Arg1541Ter) | FBN1 |
| 794728283 | 197585 | NM_000138.4(FBN1): c.8038C>T (p.Arg2680Cys) | FBN1 |
| 879255678 | 247653 | NM_144997.5(FLCN): c.1429C>T (p.Arg477Ter) | FLCN |
| 886041116 | 263863 | NM_015339.4(ADNP): c.2188C>T (p.Arg730Ter) | ADNP |
| 1553547838 | 512805 | NM_001172509.1(SATB2): c.1375C>T (p.Arg459Ter) | SATB2 |
| 45507199 | 59122 | NM_000548.3(TSC2): c.5228G>A (p.Arg1743Gln) | TSC2 |
| 60458016 | 29564 | NM_170707.3(LMNA): c.1072G>A (p.Glu358Lys) | LMNA |
| 61672878 | 29534 | NM_170707.3(LMNA): c.1130G>A (p.Arg377His) | LMNA |
| 61750173 | 24396 | NM_000180.3(GUCY2D): c.2513G>A (p.Arg838His) | GUCY2D |
| 61753180 | 18833 | NM_000372.4(TYR): c.140G>A (p.Gly47Asp) | TYR |
| 61754375 | 18835 | NM_000372.4(TYR): c.896G>A (p.Arg299His) | TYR |
| 62636275 | 20778 | NM_201253.2(CRB1): c.3307G>A (p.Gly1103Arg) | CRB1 |
| 63750453 | 95615 | NM_000249.3(MLH1): c.304G>A (p.Glu102Lys) | MLH1 |
| 63750604 | 95363 | NM_000249.3(MLH1): c.1790G>A (p.Trp597Ter) | MLH1 |
| 63751632 | 95404 | NM_000249.3(MLH1): c.1896G>A (p.Glu632=) | MLH1 |
| 74315205 | 19565 | NM_006005.3(WFS1): c.2590G>A (p.Glu864Lys) | WFS1 |

TABLE 34-continued

Disease Targets for Base Editing

| RS# | Allele ID | Name | GeneSymbol |
|---|---|---|---|
| 74503330 | 22256 | NM_000492.3(CFTR):c.3752G>A (p.Ser1251Asn) | CFTR |
| 80282562 | 57854 | NM_000492.3(CFTR):c.532G>A (p.Gly178Arg) | CFTR |
| 80356702 | 32581 | NM_000083.2(CLCN1):c.950G>A (p.Arg317Gln) | CLCN1 |
| 80358543 | 131539 | NM_000059.3(BRCA2):c.2978G>A (p.Trp993Ter) | BRCA2 |
| 80358810 | 46556 | NM_000059.3(BRCA2):c.582G>A (p.Trp194Ter) | BRCA2 |
| 80358997 | 67062 | NM_000059.3(BRCA2):c.7721G>A (p.Trp2574Ter) | BRCA2 |
| 80359205 | 67482 | NM_000059.3(BRCA2):c.9317G>A (p.Trp3106Ter) | BRCA2 |
| 81002873 | 67120 | NM_000059.3(BRCA2):c.7976+1G>A | BRCA2 |
| 104894317 | 18840 | NM_000372.4(TYR):c.1336G>A (p.Gly446Ser) | TYR |
| 104894590 | 16599 | NM_000263.3(NAGLU):c.2021G>A (p.Arg674His) | NAGLU |
| 111033270 | 19955 | NM_022124.5(CDH23):c.5237G>A (p.Arg1746Gln) | CDH23 |
| 111436401 | 226974 | NM_000540.2(RYR1):c.10347+1G>A | RYR1 |
| 112406105 | 200333 | NM_000018.4(ACADVL):c.1097G>A (p.Arg366His) | ACADVL |
| 113560320 | 15440 | NM_017841.2(SDHAF2):c.232G>A (p.Gly78Arg) | SDHAF2 |
| 113690956 | 16661 | NM_000018.2(ACADVL):c.1182+1G>A | ACADVL |
| 113994171 | 33871 | NM_000018.3(ACADVL):c.1679-6G>A | ACADVL |
| 113994207 | 19490 | NM_004937.2(CTNS):c.589G>A (p.Gly197Arg) | CTNS |
| 114925667 | 260377 | NM_024818.4(UBA5):c.1111G>A (p.Ala371Thr) | UBA5 |
| 118192122 | 76888 | NM_000540.2(RYR1):c.7361G>A (p.Arg2454His) | RYR1 |
| 118192176 | 28015 | NM_000540.2(RYR1):c.6502G>A (p.Val2168Met) | RYR1 |
| 118203982 | 16396 | NM_001080.3(ALDH5A1):c.612G>A (p.Trp204Ter) | ALDH5A1 |
| 119462987 | 18289 | NM_007171.3(POMT1):c.2005G>A (p.Ala669Thr) | POMT1 |
| 120074190 | 18179 | NM_000218.2(KCNQ1):c.1766G>A (p.Gly589Asp) | KCNQ1 |
| 121434544 | 32653 | NM_000070.2(CAPN3):c.1715G>A (p.Arg572Gln) | CAPN3 |
| 121434548 | 32661 | NM_000070.2(CAPN3):c.1469G>A (p.Arg490Gln) | CAPN3; POMT1 |
| 121908153 | 19416 | NM_001243133.1(NLRP3):c.907G>A (p.Asp303Asn) | NLRP3 |
| 121908185 | 19531 | NM_020451.2(SELENON):c.1397G>A (p.Arg466Gln) | SELENON |
| 121908419 | 20395 | NM_014384.2(ACAD8):c.1129G>A (p.Gly377Ser) | ACAD8 |
| 121908759 | 44497 | NM_000492.3(CFTR):c.1865G>A (p.Gly622Asp) | CFTR |
| 121908889 | 21460 | NM_003060.3(SLC22A5):c.506G>A (p.Arg169Gln) | SLC22A5 |
| 121909013 | 22181 | NM_000492.3(CFTR):c.1651G>A (p.Gly551Ser) | CFTR |
| 121909019 | 22197 | NM_000492.3(CFTR):c.3197G>A (p.Arg1066His) | CFTR |
| 121909092 | 22321 | NM_001005360.2(DNM2):c.1102G>A (p.Glu368Lys) | DNM2 |
| 121918009 | 28711 | NM_000478.5(ALPL):c.1001G>A (p.Gly334Asp) | ALPL |
| 121918592 | 28008 | NM_000540.2(RYR1):c.1021G>A (p.Gly341Arg) | RYR1 |
| 137852871 | 17416 | NM_000709.3(BCKDHA):c.868G>A (p.Gly290Arg) | BCKDHA |
| 141158996 | 22214 | NM_000492.3(CFTR):c.2490+1G>A | CFTR |
| 141554661 | 208401 | NM_004287.4(GOSR2):c.336+1G>A | GOSR2 |
| 148032587 | 194820 | NM_000303.2(PMM2):c.442G>A (p.Asp148Asn) | PMM2 |
| 193922503 | 44492 | NM_000492.3(CFTR):c.1585-8G>A | CFTR |
| 199472687 | 77968 | NM_000218.2(KCNQ1):c.421G>A (p.Val141Met) | KCNQ1 |
| 201016593 | 245339 | NM_000527.4(LDLR):c.11G>A (p.Trp4Ter) | LDLR |
| 267606997 | 21861 | NM_058216.2(RAD51C):c.773G>A (p.Arg258His) | RAD51C |
| 267607914 | 96367 | NM_000251.2(MSH2):c.212-1G>A | MSH2 |
| 369560930 | 98197 | NM_000018.4(ACADVL):c.520G>A (p.Val174Met) | ACADVL |
| 370523609 | 227889 | NM_000016.5(ACADM):c.600-18G>A | ACADM |
| 370950728 | 186993 | NM_000152.3(GAA):c.655G>A (p.Gly219Arg) | GAA |
| 374143224 | 187013 | NM_000152.3(GAA):c.1979G>A (p.Arg660His) | GAA |
| 397508045 | 67476 | NM_000059.3(BRCA2):c.92G>A (p.Trp31Ter) | BRCA2 |
| 397508200 | 67910 | NM_000492.3(CFTR):c.1393-1G>A | CFTR |
| 397509418 | 75098 | NM_021942.5(TRAPPC11):c.1287+5G>A | TRAPPC11 |
| 397515330 | 76388 | NM_001098512.2(PRKG1):c.530G>A (p.Arg177Gln) | PRKG1 |
| 398122711 | 97208 | NM_000059.3(BRCA2):c.8633-1G>A | BRCA2 |
| 398123139 | 98311 | NM_000060.4(BTD):c.626G>A (p.Arg209His) | BTD |
| 398123763 | 100162 | NM_003494.3(DYSF):c.1053+1G>A | DYSF |
| 587777057 | 77012 | NM_020988.2(GNAO1):c.607G>A (p.Gly203Arg) | GNAO1 |
| 587777570 | 150453 | NM_004522.2(KIF5C):c.709G>A (p.Glu237Lys) | KIF5C |
| 587778777 | 76741 | NM_000784.3(CYP27A1):c.1184+1G>A | CYP27A1 |
| 587779110 | 96248 | NM_000251.2(MSH2):c.1760-1G>A | MSH2 |
| 587780639 | 139490 | NM_000051.3(ATM):c.7788G>A (p.Glu2596=) | ATM |
| 587781894 | 151348 | NM_000051.3(ATM):c.9023G>A (p.Arg3008His) | ATM |
| 587782719 | 152505 | NM_000051.3(ATM):c.8122G>A (p.Asp2708Asn) | ATM |
| 727503030 | 176785 | NM_001278939.1(ELN):c.1150+1G>A | ELN |
| 730881581 | 180665 | NM_000059.3(BRCA2):c.8174G>A (p.Trp2725Ter) | BRCA2 |
| 730882035 | 180121 | NM_000551.3(VHL):c.482G>A (p.Arg161Gln) | VHL |
| 750663117 | 234071 | NM_000051.3(ATM):c.3078-1G>A | ATM |
| 756039188 | 243266 | NM_000527.4(LDLR):c.12G>A (p.Trp4Ter) | LDLR |
| 796053216 | 202741 | NM_014191.3(SCN8A):c.4423G>A (p.Gly1475Arg) | SCN8A |
| 876661242 | 231905 | NM_000059.3(BRCA2):c.9381G>A (p.Trp3127Ter) | BRCA2 |
| 879254600 | 245669 | NM_000527.4(LDLR):c.626G>A (p.Cys209Tyr) | LDLR |
| 1057519632 | 362622 | NM_003718.4(CDK13):c.2149G>A (p.Gly717Arg) | CDK13 |
| 10250779 | 15457 | NM_000290.3(PGAM2):c.233G>A (p.Trp78Ter) | PGAM2 |
| 28928905 | 29469 | NM_000238.3(KCNH2):c.1468G>A (p.Ala490Thr) | KCNH2 |
| 28931593 | 32066 | NM_004004.5(GJB2):c.224G>A (p.Arg75Gln) | GJB2 |

TABLE 34-continued

Disease Targets for Base Editing

| RS# | Allele ID | Name | GeneSymbol |
|---|---|---|---|
| 28937318 | 24429 | NM 198056.2(SCN5A): c.1100G>A (p.Arg367His) | SCN5A |
| 61749397 | 15329 | NM 000552.4(VWF): c.3946G>A (p.Val1316Met) | VWF |
| 61751403 | 105220 | NM_000350.2(ABCA4): c.4919G>A (p.Arg1640Gln) | ABCA4 |
| 62514907 | 15633 | NM_000277.3(PAH): c.442-1G>A | PAH |
| 62514956 | 98659 | NM_000277.3(PAH): c.912+1G>A | PAH |
| 62516146 | 108608 | NM_000277.1(PAH): c.842+5G>A | PAH |
| 62642939 | 98657 | NM_000277.2(PAH): c.890G>A (p.Arg297His) | PAH |
| 62644503 | 108560 | NM_000277.3(PAH): c.755G>A (p.Arg252Gln) | PAH |
| 63749856 | 21618 | NM_001171.5(ABCC6): c.3904G>A (p.Gly1302Arg) | ABCC6 |
| 63750783 | 30442 | NM_000518.5(HBB): c.47G>A (p.Trp16Ter) | HBB |
| 66555264 | 414003 | NM 000088.3(COL1A1): c.1821+1G>A | COL1A1 |
| 72645321 | 414022 | NM 000088.3(COL1A1): c.769G>A (p.Gly257Arg) | COL1A1 |
| 74315368 | 27820 | NM 003000.2(SDHB): c.725G>A (p.Arg242His) | SDHB |
| 74315471 | 18113 | NM 000487.5(ARSA): c.739G>A (p.Gly247Arg) | ARSA |
| 78973108 | 19367 | NM 001005741.2(GBA): c.887G>A (p.Arg296Gln) | GBA |
| 80338735 | 33917 | NM_000156.5(GAMT): c.327G>A (p.Lys109=) | GAMT |
| 80338857 | 34128 | NM_001360.2(DHCR7): c.725G>A (p.Arg242His) | DHCR7 |
| 80338864 | 21831 | NM_001360.2(DHCR7): c.1342G>A (p.Glu448Lys) | DHCR7 |
| 80338944 | 32040 | NM_004004.5(GJB2): c.231G>A (p.Trp77Ter) | GJB2 |
| 80356914 | 70276 | NM_007294.3(BRCA1): c.5511G>A (p.Trp1837Ter) | BRCA1 |
| 80357212 | 70255 | NM_007294.3(BRCA1): c.5467G>A (p.Ala1823Thr) | BRCA1 |
| 80357307 | 70275 | NM_007294.3(BRCA1): c.5510G>A (p.Trp1837Ter) | BRCA1 |
| 80358252 | 18013 | NM 000271.4(NPC1): c.530G>A (p.Cys177Tyr) | NPC1 |
| 104894103 | 19470 | NM 175073.2(APTX): c.837G>A (p.Trp279Ter) | APTX |
| 104894415 | 20583 | NM 006783.4(GJB6): c.31G>A (p.Gly11Arg) | GJB6 |
| 104894519 | 21096 | NM 004862.3(LITAF): c.334G>A (p.Gly112Ser) | LITAF |
| 104894727 | 27461 | NM 000363.4(TNNI3): c.586G>A (p.Asp196Asn) | TNNI3 |
| 104894828 | 25754 | NM_000169.2(GLA): c.902G>A (p.Arg301Gln) | GLA |
| 111683277 | 175150 | NM_000256.3(MYBPC3): c.3190+1G>A | MYBPC3 |
| 111984349 | 258823 | NM_000138.4(FBN1): c.7828G>A (p.Glu2610Lys) | FBN1 |
| 113403872 | 16550 | NM_000298.5(PKLR): c.1529G>A (p.Arg510Gln) | PKLR |
| 121434249 | 18383 | NM_000348.3(SRD5A2): c.682G>A (p.Ala228Thr) | SRD5A2 |
| 121908216 | 23534 | NM_001127221.1(CACNA1A): c.4982G>A (p.Arg1661His) | CACNA1A |
| 121908551 | 20948 | NM_000334.4(SCN4A): c.3877G>A (p.Val1293Ile) | SCN4A |
| 121908552 | 20949 | NM 000334.4(SCN4A): c.1333G>A (p.Val445Met) | SCN4A |
| 121908557 | 20958 | NM 000334.4(SCN4A): c.2024G>A (p.Arg675Gln) | SCN4A |
| 121908716 | 16996 | NM 000022.2(ADA): c.632G>A (p.Arg211His) | ADA |
| 121908723 | 17007 | NM 000022.3(ADA): c.646G>A (p.Gly216Arg) | ADA |
| 121909768 | 21834 | NM 001360.2(DHCR7): c.1055G>A (p.Arg352Gln) | DHCR7 |
| 121913039 | 31702 | NM_001953.4(TYMP): c.622G>A (p.Val208Met) | TYMP |
| 137853050 | 22116 | NM_006009.3(TUBA1A): c.1265G>A (p.Arg422His) | TUBA1A |
| 137853283 | 166064 | NM_000053.3(ATP7B): c.2336G>A (p.Trp779Ter) | ATP7B |
| 137854612 | 24434 | NM_198056.2(SCN5A): c.4222G>A (p.Gly1408Arg) | SCN5A |
| 139751448 | 187031 | NM_000271.4(NPC1): c.1211G>A (p.Arg404Gln) | NPC1 |
| 150038620 | 187049 | NM_004646.3(NPHS1): c.2335-1G>A | NPHS1 |
| 180177122 | 132185 | NM_024675.3(PALB2): c.2718G>A (p.Trp906Ter) | PALB2 |
| 181087667 | 40103 | NM_007055.3(POLR3A): c.2617-1G>A | POLR3A |
| 193922110 | 44393 | NM 000053.3(ATP7B): c.4058G>A (p.Trp1353Ter) | ATP7B |
| 199473565 | 78528 | NM 198056.2(SCN5A): c.1066G>A (p.Asp356Asn) | SCN5A |
| 199474703 | 40437 | NM 000258.2(MYL3): c.281G>A (p.Arg94His) | MYL3 |
| 199971687 | 216058 | NM 052845.3(MMAB): c.291-1G>A | MMAB |
| 201188361 | 40345 | NM 014714.3(IFT140): c.634G>A (p.Gly212Arg) | IFT140 |
| 202160208 | 75126 | NM_013334.3(GMPPB): c.860G>A (p.Arg287Gln) | GMPPB |
| 281875334 | 38553 | NM_001101.3(ACTB): c.587G>A (p.Arg196His) | ACTB |
| 386134249 | 45185 | NM_000244.3(MEN1): c.1277G>A (p.Cys426Tyr) | MEN1 |
| 387906623 | 38652 | NM_000138.4(FBN1): c.5284G>A (p.Gly1762Ser) | FBN1 |
| 387906905 | 39430 | NM_021625.4(TRPV4): c.947G>A (p.Arg316His) | TRPV4 |
| 397507479 | 48850 | NM_004333.5(BRAF): c.1595G>A (p.Cys532Tyr) | BRAF |
| 397514494 | 48018 | NM_021625.4(TRPV4): c.557G>A (p.Arg186Gln) | TRPV4 |
| 397515854 | 51599 | NM_000138.4(FBN1): c.7606G>A (p.Gly2536Arg) | FBN1 |
| 397515982 | 51820 | NM_000256.3(MYBPC3): c.2670G>A (p.Trp890Ter) | MYBPC3 |
| 397516031 | 51898 | NM_000256.3(MYBPC3): c.3627+1G>A | MYBPC3 |
| 397516471 | 52818 | NM_001001430.2(TNNT2): c.518G>A (p.Arg173Gln) | TNNT2 |
| 398122853 | 38917 | NM_004006.2(DMD): c.9G>A (p.Trp3Ter) | DMD |
| 483352809 | 65656 | NM_006087.3(TUBB4A): c.745G>A (p.Asp249Asn) | TUBB4A |
| 515726205 | 40114 | NM_001031726.3(C19orf12): c.205G>A (p.Gly69Arg) | C19orf12 |
| 564069299 | 200114 | NM_000255.3(MMUT): c.1106G>A (p.Arg369His) | MMUT |
| 574673404 | 182906 | NM_002485.4(NBN): c.37+1G>A | NBN |
| 587780345 | 134590 | NM_000162.3(GCK): c.544G>A (p.Val182Met) | GCK |
| 606231324 | 136674 | NM_000257.3(MYH7): c.1573G>A (p.Glu525Lys) | MYH7 |
| 727504382 | 49283 | NM_030662.3(MAP2K2): c.619G>A (p.Glu207Lys) | MAP2K2 |
| 730880850 | 29166 | NM 000257.3(MYH7): c.732+1G>A | MYH7 |
| 730882175 | 181517 | NM 002238.3(KCNH1): c.1405G>A (p.Gly469Arg) | KCNH1 |
| 751604696 | 425943 | NM 001360.2(DHCR7): c.1337G>A (p.Arg446Gln) | DHCR7 |

TABLE 34-continued

Disease Targets for Base Editing

| RS# | Allele ID | Name | GeneSymbol |
|---|---|---|---|
| 753288303 | 216044 | NM_000255.3(MMUT): c.1280G>A (p.Gly427Asp) | MMUT |
| 767399782 | 213656 | NM_006087.3(TUBB4A): c.763G>A (p.Val255Ile) | TUBB4A |
| 794728208 | 197723 | NM_000138.4(FBN1): c.3712G>A (p.Asp1238Asn) | FBN1 |
| 796756333 | 410338 | NM_024422.4(DSC2): c.943-1G>A | DSC2 |
| 797044872 | 205316 | NM_004977.2(KCNC3): c.1268G>A (p.Arg423His) | KCNC3 |
| 797045586 | 207083 | NM_032682.5(FOXP1): c.1541G>A (p.Arg514His) | FOXP1 |
| 863223403 | 209408 | NM_002140.4(HNRNPK): c.257G>A (p.Arg86His) | HNRNPK |
| 876658367 | 232176 | NM_003000.2(SDHB): c.587G>A (p.Cys196Tyr) | SDHB |
| 1057517585 | 358911 | NM_024675.3(PALB2): c.3G>A (p.Met1Ile) | PALB2 |
| 1555582065 | 431537 | NM_014233.3(UBTF): c.628G>A (p.Glu210Lys) | UBTF |
| 140630 | 197685 | NM_000138.4(FBN1): c.4930C>T (p.Arg1644Ter) | FBN1 |
| 28940869 | 19031 | NM_017739.3(POMGNT1): c.1324C>T (p.Arg442Cys) | POMGNT1 |
| 34451549 | 30497 | NM_000518.5(HBB): c.316-197C>T | HBB |
| 41556519 | 31832 | NM_000400.3(ERCC2): c.2047C>T (p.Arg683Trp) | ERCC2 |
| 45611033 | 175462 | NM_000257.4(MYH7): c.3133C>T (p.Arg1045Cys) | MYH7 |
| 55832599 | 151478 | NM_000546.5(TP53): c.799C>T (p.Arg267Trp) | TP53 |
| 59616921 | 18036 | NM_000226.3(KRT9): c.487C>T (p.Arg163Trp) | KRT9 |
| 60399023 | 29651 | NM_000526.4(KRT14): c.373C>T (p.Arg125Cys) | KRT14 |
| 61749409 | 104973 | NM_000350.2(ABCA4): c.1804C>T (p.Arg602Trp) | ABCA4 |
| 61749423 | 105003 | NM_000350.2(ABCA4): c.2041C>T (p.Arg681Ter) | ABCA4 |
| 61750645 | 105327 | NM_000350.2(ABCA4): c.6229C>T (p.Arg2077Trp) | ABCA4 |
| 61751383 | 22946 | NM_000350.2(ABCA4): c.6088C>T (p.Arg2030Ter) | ABCA4 |
| 61752871 | 28154 | NM_000329.2(RPE65): c.271C>T (p.Arg91Trp) | RPE65 |
| 61757582 | 21827 | NM_001360.2(DHCR7): c.1210C>T (p.Arg404Cys) | DHCR7 |
| 61816761 | 31358 | NM_002016.1(FLG): c.1501C>T (p.Arg501Ter) | FLG |
| 62507344 | 15662 | NM_000277.2(PAH): c.1066-3C>T | PAH |
| 72559722 | 186816 | NM_001287174.1(ABCC8): c.2509C>T (p.Arg837Ter) | ABCC8 |
| 72646846 | 56340 | NM_001256850.1(TTN): c.56953C>T (p.Arg18985Ter) | TTN |
| 72648250 | 225057 | NM_001256850.1(TTN): c.88243C>T (p.Arg29415Ter) | TTN |
| 72650700 | 39295 | NM_001171.5(ABCC6): c.1552C>T (p.Arg518Ter) | ABCC6 |
| 72651642 | 271557 | NM_000088.3(COL1A1): c.2089C>T (p.Arg697Ter) | COL1A1 |
| 72653170 | 32386 | NM_000088.3(COL1A1): c.3040C>T (p.Arg1014Cys) | COL1A1 |
| 74315348 | 20408 | NM_014625.3(NPHS2): c.871C>T (p.Arg291Trp) | NPHS2 |
| 74315391 | 22425 | NM_172107.3(KCNQ2): c.619C>T (p.Arg207Trp) | KCNQ2 |
| 74315442 | 23435 | NM_000100.3(CSTB): c.202C>T (p.Arg68Ter) | CSTB |
| 74315472 | 18114 | NM_000487.5(ARSA): c.827C>T (p.Thr276Met) | ARSA |
| 75166491 | 108429 | NM_000277.3(PAH): c.472C>T (p.Arg158Trp) | PAH |
| 75949023 | 39947 | NM_144612.6(LOXHD1): c.4714C>T (p.Arg1572Ter) | LOXHD1 |
| 78635798 | 16299 | NM_032193.3(RNASEH2C): c.205C>T (p.Arg69Trp) | RNASEH2C |
| 80338652 | 18848 | NM_000081.3(LYST): c.3310C>T (p.Arg1104Ter) | LYST |
| 80338826 | 29117 | NM_002473.5(MYH9): c.2104C>T (p.Arg702Cys) | MYH9 |
| 80338934 | 17522 | NM_024577.3(SH3TC2): c.3325C>T (p.Arg1109Ter) | SH3TC2 |
| 80338957 | 20935 | NM_000334.4(SCN4A): c.2111C>T (p.Thr704Met) | SCN4A |
| 80356680 | 29580 | NM_000228.2(LAMB3): c.124C>T (p.Arg42Ter) | LAMB3 |
| 80356779 | 76552 | NM_001876.3(CPT1A): c.1436C>T (p.Pro479Leu) | CPT1A |
| 80356973 | 69370 | NM_007294.3(BRCA1): c.2869C>T (p.Gln957Ter) | BRCA1 |
| 80356982 | 69227 | NM_007294.3(BRCA1): c.2410C>T (p.Gln804Ter) | BRCA1 |
| 80357067 | 69840 | NM_007294.3(BRCA1): c.4339C>T (p.Gln1447Ter) | BRCA1 |
| 80357089 | 69512 | NM_007294.3(BRCA1): c.3331C>T (p.Gln1111Ter) | BRCA1 |
| 80357352 | 69958 | NM_007294.3(BRCA1): c.4810C>T (p.Gln1604Ter) | BRCA1 |
| 80357485 | 69485 | NM_007294.3(BRCA1): c.3286C>T (p.Gln1096Ter) | BRCA1 |
| 80359818 | 31157 | NM_006516.3(SLC2A1): c.376C>T (p.Arg126Cys) | SLC2A1 |
| 80359826 | 201142 | NM_006516.3(SLC2A1): c.988C>T (p.Arg330Ter) | SLC2A1 |
| 104894003 | 33314 | NM_001101.4(ACTB): c.547C>T (p.Arg183Trp) | ACTB |
| 104894261 | 31727 | NM_130799.2(MEN1): c.1579C>T (p.Arg527Ter) | MEN1 |
| 104894267 | 31731 | NM_130799.2(MEN1): c.1378C>T (p.Arg460Ter) | MEN1 |
| 104894364 | 27627 | NM_004985.4(KRAS): c.173C>T (p.Thr58Ile) | KRAS |
| 104894621 | 23472 | NM_000304.3(PMP22): c.215C>T (p.Ser72Leu) | PMP22 |
| 104894714 | 19826 | NM_181882.2(PRX): c.2857C>T (p.Arg953Ter) | PRX |
| 104894797 | 26321 | NM_004006.2(DMD): c.9568C>T (p.Arg3190Ter) | DMD |
| 111033297 | 53892 | NM_004004.5(GJB2): c.169C>T (p.Gln57Ter) | GJB2 |
| 111033538 | 17382 | NM_032601.3(MCEE): c.139C>T (p.Arg47Ter) | MCEE |
| 111687884 | 51571 | NM_000138.4(FBN1): c.643C>T (p.Arg215Ter) | FBN1 |
| 112901682 | 76366 | NM_001141945.2(ACTA2): c.115C>T (p.Arg39Cys) | ACTA2 |
| 114368325 | 38634 | NM_000782.4(CYP24A1): c.1186C>T (p.Arg396Trp) | CYP24A1 |
| 118192226 | 34614 | NM_172107.3(KCNQ2): c.1342C>T (p.Arg448Ter) | KCNQ2 |
| 118192251 | 34269 | NM_004519.3(KCNQ3): c.988C>T (p.Arg330Cys) | KCNQ3 |
| 118203427 | 58245 | NM_000368.4(TSC1): c.682C>T (p.Arg228Ter) | TSC1 |
| 118203434 | 58253 | NM_000368.4(TSC1): c.733C>T (p.Arg245Ter) | TSC1 |
| 118203542 | 57958 | NM_000368.4(TSC1): c.1525C>T (p.Arg509Ter) | TSC1 |
| 118203999 | 16285 | NM_024675.3(PALB2): c.2962C>T (p.Gln988Ter) | PALB2 |
| 118204429 | 15511 | NM_000035.4(ALDOB): c.178C>T (p.Arg60Ter) | ALDOB |
| 121907916 | 18505 | NM_000280.4(PAX6): c.607C>T (p.Arg203Ter) | PAX6 |
| 121908212 | 23527 | NM_001127221.1(CACNA1A): c.1997C>T (p.Thr666Met) | CACNA1A |

TABLE 34-continued

Disease Targets for Base Editing

| RS# | Allele ID | Name | GeneSymbol |
|---|---|---|---|
| 121908427 | 20365 | NM_133647.1(SLC12A6): c.3031C>T (p.Arg1011Ter) | SLC12A6 |
| 121908489 | 20807 | NM_003919.2(SGCE): c.289C>T (p.Arg97Ter) | SGCE |
| 121912708 | 33034 | NM_001182.4(ALDH7A1): c.328C>T (p.Arg110Ter) | ALDH7A1 |
| 121913344 | 151858 | NM_000546.5(TP53): c.916C>T (p.Arg306Ter) | TP53 |
| 121917784 | 27085 | NM_000136.2(FANCC): c.37C>T (p.Gln13Ter) | FANCC |
| 121918167 | 15995 | NM_000275.2(OCA2): c.2228C>T (p.Pro743Leu) | OCA2 |
| 121918244 | 16869 | NM_001023570.3(IQCB1): c.1381C>T (p.Arg461Ter) | IQCB1 |
| 121918257 | 16926 | NM_000255.3(MMUT): c.322C>T (p.Arg108Cys) | MMUT |
| 122445105 | 26774 | NM_000489.4(ATRX): c.736C>T (p.Arg246Cys) | ATRX |
| 122445108 | 26781 | NM_000489.4(ATRX): c.109C>T (p.Arg37Ter) | ATRX |
| 122453121 | 26733 | NM_004484.3(GPC3): c.1159C>T (p.Arg387Ter) | GPC3 |
| 128626235 | 26264 | NM_004006.2(DMD): c.433C>T (p.Arg145Ter) | DMD |
| 137852897 | 17803 | NM_024312.4(GNPTAB): c.3565C>T (p.Arg1189Ter) | GNPTAB |
| 137852994 | 19999 | NM_018136.4(ASPM): c.9178C>T (p.Gln3060Ter) | ASPM |
| 137853229 | 21102 | NM_004260.3(RECQL4): c.2269C>T (p.Gln757Ter) | RECQL4 |
| 138049878 | 171163 | NM_000257.4(MYH7): c.2608C>T (p.Arg870Cys) | MYH7 |
| 138119149 | 39897 | NM_020745.3(AARS2): c.1774C>T (p.Arg592Trp) | AARS2 |
| 139675596 | 40180 | NM_023073.3(CPLANE1): c.7477C>T (p.Arg2493Ter) | CPLANE1 |
| 140511594 | 39892 | NM_024753.4(TTC21B): c.626C>T (p.Pro209Leu) | TTC21B |
| 143343083 | 169011 | NM_004004.5(GJB2): c.298C>T (p.His100Tyr) | GJB2 |
| 148865119 | 210450 | NM_000071.2(CBS): c.146C>T (p.Pro49Leu) | CBS |
| 180177091 | 132277 | NM_024675.3(PALB2): c.751C>T (p.Gln251Ter) | PALB2 |
| 199422209 | 33004 | NM_001127701.1(SERPINA1): c.1178C>T (p.Pro393Leu) | SERPINA1 |
| 199473556 | 78702 | NM_198056.2(SCN5A): c.361C>T (p.Arg121Trp) | SCN5A |
| 200075782 | 39327 | NM_003560.3(PLA2G6): c.109C>T (p.Arg37Ter) | PLA2G6 |
| 200287925 | 151917 | NM_002485.4(NBN): c.127C>T (p.Arg43Ter) | NBN |
| 200309328 | 176122 | NM_000138.4(FBN1): c.8080C>T (p.Arg2694Ter) | FBN1 |
| 200440128 | 205749 | NM_012160.4(FBXL4): c.64C>T (p.Arg22Ter) | FBXL4 |
| 201632198 | 55279 | NM_024022.2(TMPRSS3): c.325C>T (p.Arg109Trp) | TMPRSS3 |
| 267606919 | 21912 | NM_004646.3(NPHS1): c.3478C>T (p.Arg1160Ter) | NPHS1 |
| 267607143 | 20038 | NM_021625.4(TRPV4): c.943C>T (p.Arg315Trp) | TRPV4 |
| 267607258 | 46918 | NM_002437.5(MPV17): c.293C>T (p.Pro98Leu) | MPV17 |
| 375699023 | 223602 | NM_024675.3(PALB2): c.1042C>T (p.Gln348Ter) | PALB2 |
| 387906799 | 39125 | NM_001244008.1(KIF1A): c.296C>T (p.Thr99Met) | KIF1A |
| 387906904 | 39429 | NM_021625.4(TRPV4): c.694C>T (p.Arg232Cys) | TRPV4 |
| 387907329 | 51081 | NM_007075.3(WDR45): c.700C>T (p.Arg234Ter) | WDR45 |
| 397507215 | 46080 | NM_007294.3(BRCA1): c.3352C>T (p.Gln1118Ter) | BRCA1 |
| 397507447 | 47625 | NM_024312.4(GNPTAB): c.1123C>T (p.Arg375Ter) | GNPTAB |
| 397509002 | 69322 | NM_007294.3(BRCA1): c.2713C>T (p.Gln905Ter) | BRCA1 |
| 397509151 | 69806 | NM_007294.3(BRCA1): c.4201C>T (p.Gln1401Ter) | BRCA1 |
| 397509330 | 70405 | NM_007294.3(BRCA1): c.850C>T (p.Gln284Ter) | BRCA1 |
| 397514477 | 40113 | NM_001031726.3(C19orf12): c.32C>T (p.Thr11Met) | C19orf12 |
| 397515848 | 51592 | NM_000138.4(FBN1): c.7180C>T (p.Arg2394Ter) | FBN1 |
| 397516463 | 52805 | NM_001001430.2(TNNT2): c.388C>T (p.Arg130Cys) | TNNT2 |
| 398123061 | 76995 | NM_012160.4(FBXL4): c.1444C>T (p.Arg482Trp) | FBXL4 |
| 398123168 | 98367 | NM_000143.3(FH): c.952C>T (p.His318Tyr) | FH |
| 398123832 | 100328 | NM_004006.2(DMD): c.10171C>T (p.Arg3391Ter) | DMD |
| 398123929 | 100476 | NM_004006.2(DMD): c.3151C>T (p.Arg1051Ter) | DMD |
| 398124478 | 102281 | NM_138694.3(PKHD1): c.2341C>T (p.Arg781Ter) | PKHD1 |
| 536907995 | 137626 | NM_007194.4(CHEK2): c.58C>T (p.Gln20Ter) | CHEK2 |
| 587776407 | 153707 | NM_024675.3(PALB2): c.451C>T (p.Gln151Ter) | PALB2 |
| 587776935 | 48413 | NM_005465.4(AKT3): c.1393C>T (p.Arg465Trp) | AKT3 |
| 587780062 | 133253 | NM_000535.5(PMS2): c.823C>T (p.Gln275Ter) | PMS2 |
| 587780226 | 133611 | NM_032043.2(BRIP1): c.1315C>T (p.Arg439Ter) | BRIP1 |
| 587781948 | 151416 | NM_000465.3(BARD1): c.1921C>T (p.Arg641Ter) | BARD1 |
| 587783685 | 168920 | NM_003482.3(KMT2D): c.12592C>T (p.Arg4198Ter) | KMT2D |
| 587784339 | 169779 | NM_003560.3(PLA2G6): c.1903C>T (p.Arg635Ter) | PLA2G6 |
| 724159971 | 172085 | NM_152778.2(MFSD8): c.1444C>T (p.Arg482Ter) | MFSD8 |
| 727503504 | 176073 | NM_000363.4(TNNI3): c.508C>T (p.Arg170Trp) | TNNI3 |
| 727503513 | 172503 | NM_001001430.2(TNNT2): c.280C>T (p.Arg94Cys) | TNNT2 |
| 727504136 | 177069 | NM_001165963.1(SCN1A): c.3733C>T (p.Arg1245Ter) | SCN1A |
| 730881422 | 179951 | NM_000465.3(BARD1): c.1996C>T (p.Gln666Ter) | BARD1 |
| 730882029 | 180988 | NM_000546.5(TP53): c.1024C>T (p.Arg342Ter) | TP53 |
| 747604569 | 185305 | NM_032043.2(BRIP1): c.484C>T (p.Arg162Ter) | BRIP1 |
| 750621215 | 184806 | NM_002878.3(RAD51D): c.898C>T (p.Arg300Ter) | RAD51D |
| 753330544 | 195505 | NM_206933.2(USH2A): c.13316C>T (p.Thr4439Ile) | USH2A |
| 761494650 | 185659 | NM_007194.4(CHEK2): c.85C>T (p.Gln29Ter) | CHEK2 |
| 763091520 | 197655 | NM_000138.4(FBN1): c.6169C>T (p.Arg2057Ter) | FBN1 |
| 768933093 | 226933 | NM_024685.4(BBS10): c.145C>T (p.Arg49Trp) | BBS10 |
| 773770609 | 264863 | NM_177550.4(SLC13A5): c.997C>T (p.Arg333Ter) | SLC13A5 |
| 778989252 | 236615 | NM_007194.4(CHEK2): c.1315C>T (p.Gln439Ter) | CHEK2 |
| 786202064 | 184902 | NM_007294.3(BRCA1): c.4834C>T (p.Gln1612Ter) | BRCA1 |
| 786203821 | 184272 | NM_024675.3(PALB2): c.940C>T (p.Gln314Ter) | PALB2 |
| 794726710 | 187772 | NM_001165963.1(SCN1A): c.3637C>T (p.Arg1213Ter) | SCN1A |

TABLE 34-continued

Disease Targets for Base Editing

| RS# | Allele ID | Name | GeneSymbol |
|---|---|---|---|
| 794726730 | 187817 | NM_001165963.1(SCN1A): c.2134C>T (p.Arg712Ter) | SCN1A |
| 794728195 | 197755 | NM_000138.4(FBN1): c.2645C>T (p.Ala882Val) | FBN1 |
| 796051885 | 199890 | NM_003239.4(TGFB3): c.898C>T (p.Arg300Trp) | TGFB3 |
| 797044883 | 205286 | NM_019066.4(MAGEL2): c.1912C>T (p.Gln638Ter) | MAGEL2 |
| 869312892 | 226683 | NM_139276.2(STAT3): c.2147C>T (p.Thr716Met) | STAT3 |
| 876658461 | 232175 | NM_003000.2(SDHB): c.640C>T (p.Gln214Ter) | SDHB |
| 886037684 | 248861 | NM_177438.2(DICER1): c.2062C>T (p.R688*) | DICER1 |
| 886038001 | 249129 | NM_007294.3(BRCA1): c.2599C>T (p.Gln867Ter) | BRCA1 |
| 886039480 | 260102 | NM_024675.3(PALB2): c.2368C>T (p.Gln790Ter) | PALB2 |
| 886040218 | 261660 | NM_007294.3(BRCA1): c.4225C>T (p.Gln1409Ter) | BRCA1 |
| 886041222 | 264422 | NM_000280.4(PAX6): c.781C>T (p.Arg261Ter) | PAX6 |
| 1057521083 | 366251 | NM_015265.3(SATB2): c.1165C>T (p.Arg389Cys) | SATB2 |

Example 6: Demonstration of Gene Editing Activity in Plant Cells

Base-editing activity of an RGN-deaminase fusion protein of the invention is demonstrated in plant cells using protocols adapted from Li, et al., 2013 (*Nat. Biotech.* 31:688-691). Briefly, an expression vector comprising an expression cassette capable of expressing in plant cells an RGN-deaminase fusion protein operably linked to a SV40 nuclear localization signal (SEQ ID NO: 43) and a second expression cassette encoding a guide RNA targeting one or more sites in the plant PDS gene that flank an appropriate PAM sequence are introduced into *Nicotiana benthamiana* mesophyll protoplasts using PEG-mediated transformation. The transformed protoplasts are incubated in the dark for up to 36 hr. Genomic DNA is isolated from the protoplasts using a DNeasy Plant Mini Kit (Qiagen). The genomic region flanking the RGN target site is PCR amplified, products are purified, and the purified PCR products are analyzed using Next Generation Sequencing on Illumina MiSeq. Typically, 100,000 of 250 bp paired-end reads (2×100,000 reads) are generated per amplicon. The reads are analyzed using CRISPResso (Pinello, et al. 2016 *Nature Biotech,* 34:695-697) to calculate the rates of editing. Output alignments are analyzed for INDEL formation or introduction of specific adenine mutations.

Example 7: Testing mRNA Delivery

To determine if the base editors are capable of delivery in different formats, mRNA delivery was tested with primary T-cells. Purified CD3+ T-cells or PBMCs were thawed, activated using CD3/CD28 beads (ThermoFisher) for 3 days, then nucleofected using the Lonza 4D-Nucleofector X unit and Nucleocuvette strips. The P3 Primary Cell kit was used for both mRNA and RNP delivery. Cells were transfected using the EO-115 and EH-115 programs for mRNA and RNP delivery respectively. Cells were cultured in CTS OpTimizer T cell expansion medium (ThermoFisher) containing IL-2, IL-7, and IL-15 (Miltenyi Biotec) for 4 days post nucleofection before being harvested using a Nucleospin Tissue genomic DNA isolation kit (Machery Nagel).

Amplicons surrounding the editing sites were generated by PCR using primers identified in Table 35 and subjected to NGS sequencing using the Illumina Nexterra platform using 2×250 bp paired end sequencing. The estimated base editing rate was determined by calculating the overall substitution rate for each sample. The average and number of samples for each guide tested are shown below.

TABLE 35

Average Editing rate for LPG50148-nAPG07433.1 via mRNA delivery

| SGN | Average % Edit | N |
|---|---|---|
| SGN002352 | 7.84 | 2 |
| SGN002364 | 29.79 | 2 |
| SGN002367 | 0.1 | 2 |
| SGN001061 | 0.37 | 1 |
| SGN001062 | 71.81 | 1 |
| SGN001064 | 3.99 | 1 |
| SGN002254 | 8.92 | 2 |
| SGN002255 | 5.26 | 2 |
| SGN002256 | 8.32 | 2 |
| SGN002290 | 2.88 | 2 |
| SGN002293 | 9.68 | 2 |
| SGN002299 | 27.05 | 2 |
| SGN002132 | 29.11 | 2 |
| SGN002137 | 7.77 | 2 |
| SGN002139 | 6.00 | 2 |
| SGN001770 | 1.22 | 2 |
| SGN001773 | 0.49 | 2 |
| SGN002212 | 29.63 | 2 |
| SGN002216 | 2.58 | 2 |
| SGN002218 | 36.13 | 2 |
| SGN002230 | 14.32 | 2 |
| SGN002231 | 33.18 | 2 |
| SGN000753 | 6.84 | 2 |
| SGN000754 | 26.41 | 1 |
| SGN001856 | 0.5 | 2 |
| SGN002248 | 9.91 | 2 |
| SGN002249 | 40.19 | 2 |

That which is claimed:

1. A fusion protein comprising a Type II CRISPR-Cas protein nickase and a deaminase, wherein said deaminase comprises an amino acid sequence having at least 90% sequence identity to the amino acid sequence of SEQ ID NO: 399 and has adenine deaminase activity, and wherein said nickase
   (a) is a Cas9 nickase; or
   (b) comprises an amino acid sequence having at least 95% sequence identity to any one of SEQ ID NO: 42, 52, 53, 55-59, 61, 397, or 398.

2. The fusion protein of claim 1, wherein said deaminase comprises an amino acid sequence having at least 95% sequence identity to the amino acid sequence of SEQ ID NO: 399 and has adenine deaminase activity.

3. The fusion protein of claim 1, wherein said deaminase comprises the amino acid sequence of SEQ ID NO: 399.

4. The fusion protein of claim 1, wherein the nickase has the amino acid sequence of any one of SEQ ID NO: 42, 52, 53, 55-59, 61, 397, or 398.

5. The fusion protein of claim 1, wherein said fusion protein comprises the amino acid sequence of SEQ ID NO: 488.

6. The fusion protein of claim 1, wherein the fusion protein further comprises at least one nuclear localization signal.

7. The fusion protein of claim 1, wherein the fusion protein further comprises a protein tag or a cell penetrating domain.

8. A cell comprising the fusion protein of claim 1, wherein the cell further comprises a guide RNA.

9. A ribonucleoprotein (RNP) complex comprising the fusion protein of claim 1 and a guide RNA.

10. A system for modifying a target DNA molecule comprising a target DNA sequence, said system comprising:
    a) the fusion protein of claim 1; and
    b) one or more guide RNAs (gRNAs) capable of hybridizing to said target DNA molecule or one or more nucleotide sequences encoding the one or more gRNAs; and
    wherein the one or more gRNAs are capable of forming a complex with the fusion protein in order to direct said fusion protein to bind to and modify said target DNA molecule.

11. The system of claim 10, wherein the nickase has the amino acid sequence of any one of SEQ ID NO: 42, 52, 53, 55-59, 61, 397, or 398.

12. The system of claim 10, wherein at least one of the one or more nucleotide sequences encoding the one or more gRNAs is operably linked to a promoter heterologous to said nucleotide sequence.

13. The system of claim 10, wherein the target DNA is a eukaryotic target DNA.

14. A polypeptide having adenine deaminase activity and comprising an amino acid sequence having at least 90% sequence identity to the amino acid sequence of SEQ ID NO: 399.

15. The polypeptide of claim 14, wherein said polypeptide comprises an amino acid sequence having at least 95% sequence identity to the amino acid sequence of SEQ ID NO: 399.

16. The polypeptide of claim 14, wherein said polypeptide has the amino acid sequence of SEQ ID NO: 399.

17. The polypeptide of claim 14, wherein said polypeptide further comprises at least one nuclear localization signal.

18. An adenine base editor comprising the polypeptide of claim 14 and a Type II CRISPR-Cas nickase, wherein said nickase
   (a) is a Cas9 nickase; or
   (b) comprises an amino acid sequence having at least 95% sequence identity to any one of SEQ ID NOs: 42, 52, 53, 55-59, 61, 397, or 398.

19. The adenine base editor of claim 18, wherein the nickase has the amino acid sequence of any one of SEQ ID NO: 42, 52, 53, 55-59, 61, 397, or 398.

20. The adenine base editor of claim 18, wherein the adenine base editor introduces an A>G mutation in a DNA molecule.

* * * * *